US011345686B2

(12) United States Patent
Kato

(10) Patent No.: US 11,345,686 B2
(45) Date of Patent: May 31, 2022

(54) AROMATIC AMINE DERIVATIVE, AND ORGANIC ELECTROLUMINESCENT ELEMENT

(71) Applicant: IDEMITSU KOSAN CO., LTD., Tokyo (JP)

(72) Inventor: Tomoki Kato, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 283 days.

(21) Appl. No.: 16/275,361

(22) Filed: Feb. 14, 2019

(65) Prior Publication Data

US 2019/0177306 A1 Jun. 13, 2019

Related U.S. Application Data

(63) Continuation of application No. 13/435,965, filed on Mar. 30, 2012, now Pat. No. 10,246,441, which is a continuation of application No. PCT/JP2010/067280, filed on Oct. 1, 2010.

(30) Foreign Application Priority Data

Oct. 2, 2009 (JP) .................................. 2009-230929

(51) Int. Cl.
```
C07D 405/14    (2006.01)
H01L 51/50     (2006.01)
H01L 51/00     (2006.01)
C07D 209/86    (2006.01)
C09K 11/06     (2006.01)
H05B 33/14     (2006.01)
C09B 57/00     (2006.01)
```

(52) U.S. Cl.
CPC ......... *C07D 405/14* (2013.01); *C07D 209/86* (2013.01); *C09B 57/00* (2013.01); *C09B 57/008* (2013.01); *C09K 11/06* (2013.01); *H01L 51/0059* (2013.01); *H01L 51/5056* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1088* (2013.01); *H01L 51/0072* (2013.01)

(58) Field of Classification Search
None
See application file for complete search history.

(56) References Cited

U.S. PATENT DOCUMENTS

```
5,256,945   A       10/1993   Imai et al.
8,394,510   B2 *    3/2013    Mizuki ............... C07D 209/86
                                                            428/690
2002/0158242 A1    10/2002   Son et al.
2004/0241972 A1    12/2004   Stegamat et al.
2006/0147747 A1     7/2006   Yamamoto et al.
2006/0257684 A1 * 11/2006   Arakane ............. H01L 51/0067
                                                            428/690
2008/0014464 A1     1/2008   Kawamura et al.
2008/0124572 A1 *   5/2008   Mizuki ................ C07D 409/10
                                                            428/690
2009/0179554 A1     7/2009   Kuma et al.
2009/0206736 A1     8/2009   Kuma et al.
2009/0243473 A1    10/2009   Iwakuma et al.
2010/0145067 A1     6/2010   Yokota et al.
2010/0245217 A1     9/2010   Nomura et al.
2010/0276673 A1    11/2010   Jung et al.
2011/0278551 A1    11/2011   Yabunouchi et al.
2011/0297924 A1    12/2011   Yabunouchi et al.
2011/0315964 A1    12/2011   Eida et al.
2012/0248426 A1    10/2012   Kato
```

FOREIGN PATENT DOCUMENTS

```
EP      2 502 908 A1       9/2012
JP      2010-254671       11/2010
KR      20090029893 A  *   3/2009
WO      2007/132678 A1    11/2007
WO      2007/132704 A1    11/2007
WO      2008/015949 A1     2/2008
WO      2008/059943 A1     5/2008
```

(Continued)

OTHER PUBLICATIONS

Yu et al., Machine Translation of KR-20090029893-A (2009) pp. 1-7. (Year: 2009).*

(Continued)

*Primary Examiner* — Dylan C Kershner
(74) *Attorney, Agent, or Firm* — Oblon, McClelland, Maier & Neustadt, L.L.P.

(57) ABSTRACT

Provided are: an aromatic amine derivative including a substituent A and a substituent B each represented by the formula (1) or (2) and having an arylene group bound to a carbazole structure, in which the substituent A and the substituent B include groups different from each other in the position at which the arylene group is bonded to the carbazole structure, and the substituent A and the substituent B are bonded to the same nitrogen atom or different nitrogen atoms in the molecule; an organic electroluminescent device including an organic thin-film layer formed of one or more layers including at least a light emitting layer, the organic thin-film layer being interposed between a cathode and a anode, in which at least one layer of the organic thin-film layer contains the aromatic amine derivative, and the molecules are rarely crystallized, the yield upon production of the organic electroluminescent device is improved, the driving voltage for the organic electroluminescent device is low, and the lifetime of the organic electroluminescent device is long; and an aromatic amine derivative which can realize the organic electroluminescent device. (In the formulae, each substituent is as described in claim 1.)

14 Claims, No Drawings

(56) References Cited

FOREIGN PATENT DOCUMENTS

| WO | 2009/035295 | 3/2009 |
| WO | 2009/035296 | 3/2009 |
| WO | 2010/061824 A1 | 6/2010 |
| WO | 2010/103765 A1 | 9/2010 |
| WO | 2010/110553 | 9/2010 |
| WO | 2012/026780 A1 | 3/2012 |

OTHER PUBLICATIONS

Extended Search Report dated Feb. 19, 2013 in European Patent Application No. 10820721.8.
Kuwabara, et al., Thermally Stable Multilayered Organic Electroluminescent Devices Using Novel Starburst Molecules, 4,4',4"-Tri(N-carbazolyl)triphenylamine (TCTA) and 4,4",4"-Tris(3-methylphenylphenyiamin)triphenylamine (m-MTDATA), as Hole-Transport Materials, Advanced Materials, vol. 6, No. 9, pp. 677-679 (1994).
International Search Report dated Dec. 14, 2010 in PCT/JP2010/067280 filed Oct. 1, 2010.

\* cited by examiner

AROMATIC AMINE DERIVATIVE, AND ORGANIC ELECTROLUMINESCENT ELEMENT

CROSS-REFERENCE TO RELATED APPLICATION

This application is a continuation application of PCT/JP10/067280 filed Oct. 1, 2010, the text of which is incorporated by reference, and claims priority to the following application: Japanese Patent Application No. 2009-230929 filed Oct. 2, 2009, the text of which is also incorporated by reference.

TECHNICAL FIELD

The present invention relates to an aromatic amine derivative and an organic electroluminescence (EL) device using the same, and more particularly, to an aromatic amine derivative and an organic EL device using the same, which are capable of providing high efficiency even at high temperatures and increasing a lifetime of the organic EL device by using an aromatic amine derivative having a specific structure as a hole transporting material.

BACKGROUND ART

An organic EL device is a spontaneous light emitting device which utilizes such a principle that a fluorescent substance emits light by virtue of recombination energy of holes injected from an anode and electrons injected from a cathode by an application of an electric field. Since an organic EL device of the laminate type capable of being driven under low electric voltage has been reported by C. W. Tang et al. of Eastman Kodak Company (C. W. Tang and S. A. Vanslyke, Applied Physics Letters, Volume 51, Page 913, 1987, or the like), many studies have been conducted for an organic EL device using an organic material as a constituent material. Tang et al. used tris(8-quinolinolato)aluminum for alight emitting layer and a triphenyldiamine derivative for a hole transporting layer. Advantages of the laminate structure reside in the followings: an efficiency of the hole injection into the light emitting layer can be increased; an efficiency of forming excitons which are formed by blocking and recombining electrons injected from the cathode can be increased; and excitons formed within the light emitting layer can be enclosed. As described above, for the device structure of the organic EL device, a two-layered structure having a hole transporting (injecting) layer and an electron transporting light emitting layer and a three-layered structure having a hole transporting (injecting) layer, a light emitting layer, an electron transporting (injecting) layer, and the like are widely known. In order to increase the efficiency of recombination of injected holes and electrons in such devices of the laminate type, the device structure and the process of forming the device have been studied.

In general, when an organic EL device is driven or stored in an environment of high temperature, there occur adverse affects such as a change in luminescent color, a decrease in emission efficiency, an increase in driving voltage, and a decrease in a lifetime of light emission. In order to prevent the adverse affects, it has been necessary that the glass transition temperature (Tg) of the hole transporting material be elevated. Therefore, it is necessary that many aromatic groups be held within a molecule of the hole transporting material (for example, an aromatic diamine derivative of Patent Literature 1 and an aromatic fused ring diamine derivative of Patent Literature 2), and in general, a structure having 8 to 12 benzene rings is preferably used.

However, in the case of a highly symmetrical compound and a compound high in flatness each having a large number of aromatic groups in a molecule, crystallization is liable to occur upon production of the organic EL device through the formation of a thin film by using those hole transporting materials. As a result, there arises a problem such as clogging of an outlet of a crucible to be used in vapor deposition or a reduction in yields of the organic EL device due to generation of defects of the thin film resulting from the crystallization. In addition, a compound having a large number of aromatic groups in any one of its molecules generally has a high Tg, but has a high sublimation temperature. Accordingly, there arises a problem in that the lifetime of the compound is short probably because a phenomenon such as decomposition at the time of the vapor deposition or the formation of a nonuniform deposition film occurs.

Meanwhile, a large number of reports have been made on amine compounds in each of which N-carbazole is bonded to an amine through an aryl group. Examples of the reports include Patent Literature 3. However, there has been demanded further improvements in the efficiency and lifetime of the organic EL device.

CITATION LIST

Patent Literature

[PTL 1] WO 2009/041635 A1
[PTL 2] JP 2005-290000 A
[PTL 3] WO 2009/020095 A1

SUMMARY OF INVENTION

Technical Problem

The present invention has been made to solve the problems, and an object of the present invention is to provide an organic electroluminescence device, which does not only exert a reducing effect on its driving voltage, but also has a long lifetime, and an aromatic amine derivative for realizing the device.

Solution to Problem

The inventors of the present invention have made extensive studies to achieve the object, and as a result, have found that the problems can be solved by using a novel aromatic amine derivative having a specific substituent including a carbazole structure as a material for an organic EL device, in particular, a hole injecting material or a hole transporting material.

Of such aromatic amine derivatives, an amine compound having such a structure that an N-carbazolyl group was bonded to an amine through an aryl group was able to improve the yield in which an organic EL device was produced because of the following reasons. The compound had steric hindrance and hence showed a small intermolecular interaction. Further, the symmetry of the compound was low and hence its crystallization was suppressed.

In addition, such compound that an N-carbazolyl group was bonded to an amine through an aryl group exerted an improving effect on luminous efficiency because of the following reason. The compound had so large an energy gap (Eg) as to be capable of effectively blocking an electron from a light emitting layer, and hence suppressed the injection of the electron into a hole transporting layer.

Further, an amine compound having such a structure that a 3-carbazolyl group was bonded to an amine through an aryl group was able to improve the yield in which an organic EL device was produced because of the following reasons. The compound had steric hindrance and hence showed a small intermolecular interaction. Further, the symmetry of the compound was low and hence its crystallization was suppressed.

In addition, the amine compound having such a structure that a 3-carbazolyl group was bonded to an amine through an aryl group had a large ionization potential (IP) and excellent property by which a hole was injected into a light emitting layer as compared with an amine compound having such a structure that a 3-carbazolyl group was directly bonded to an amine, and hence exerted a reducing effect on a driving voltage.

In addition, such compound that a 3-carbazolyl group was bonded to an amine through an aryl group had excellent oxidation stability and a lifetime-lengthening effect, and exerted a significant voltage-reducing effect and a significant lifetime-lengthening effect particularly when being combined with a blue light emitting device.

The inventors of the present invention have completed the present invention on the basis of such findings.

That is, the present invention provides an aromatic amine derivative including a substituent A and a substituent B each represented by the following formula (1) or (2) in a molecule thereof, in which: the substituent A and the substituent B include groups different from each other in a position at which $L^1$ in the formula (1) or $L^2$ in the formula (2) is bonded to a carbazole structure; and the substituent A and the substituent B are bonded to the same nitrogen atom, or different nitrogen atoms, in the molecule:

[Chem. 1]

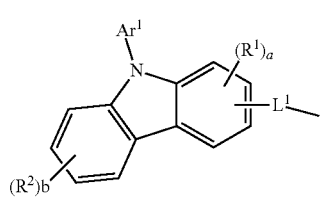

(1)

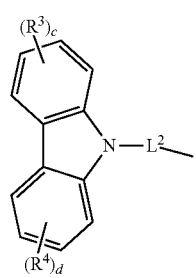

(2)

where: $L^1$ and $L^2$ each represent a substituted or unsubstituted arylene group having 6 to 25 ring carbon atoms, and a substituent which L' may have includes a linear or branched alkyl group having 1 to 15 carbon atoms, a cycloalkyl group having 3 to 15 ring carbon atoms, a trialkylsilyl group having linear or branched alkyl groups each having 1 to 15 carbon atoms, a triarylsilyl group having aryl groups each having 6 to 25 ring carbon atoms, an alkylarylsilyl group having a linear or branched alkyl group having 1 to 15 carbon atoms and an aryl group having 6 to 25 ring carbon atoms, an aryl group having 6 to 25 ring carbon atoms, a halogen atom, or a cyano group;

$Ar^1$ represents a substituted or unsubstituted aryl group having 6 to 25 ring carbon atoms, and a substituent which $Ar^1$ may have, includes a linear or branched alkyl group having 1 to 15 carbon atoms, a cycloalkyl group having 3 to 15 ring carbon atoms, a trialkylsilyl group having linear or branched alkyl groups each having 1 to 15 carbon atoms, a triarylsilyl group having aryl groups each having 6 to 25 ring carbon atoms, an alkylarylsilyl group having a linear or branched alkyl group having 1 to 15 carbon atoms and an aryl group having 6 to 25 ring carbon atoms, an aryl group having 6 to 25 ring carbon atoms, a halogen atom, or a cyano group;

a represents an integer of 0 to 3, and b, c, and d each independently represent an integer of 0 to 4; and $R^1$ to $R^4$ each independently represent a linear or branched alkyl group having 1 to 15 carbon atoms, a cycloalkyl group having 3 to 15 ring carbon atoms, a trialkylsilyl group having linear or branched alkyl groups each having 1 to 15 carbon atoms, a triarylsilyl group having aryl groups each having 6 to 25 ring carbon atoms, an alkylarylsilyl group having a linear or branched alkyl group having 1 to 15 carbon atoms and an aryl group having 6 to 25 ring carbon atoms, an aryl group having 6 to 25 ring carbon atoms, a halogen atom, or a cyano group, and a plurality of $R^1$'s to $R^4$'s adjacent to each other may be bonded to each other to form a saturated or unsaturated, divalent group that forms a ring.

Further, the present invention provides an organic electroluminescence device, including an organic thin-film layer formed of one or more layers including at least a light emitting layer, the organic thin-film layer being interposed between a cathode and an anode, in which at least one layer of the organic thin-film layer contains the aromatic amine derivative of the present invention.

Advantageous Effects of Invention

The aromatic amine derivative of the present invention hardly crystallizes, and the use of the derivative as a material for an organic EL device provides an organic EL device that not only has low driving voltage but also has a long lifetime.

DESCRIPTION OF EMBODIMENTS

The aromatic amine derivative of the present invention is a compound having a substituent A and a substituent B each represented by the following formula (1) or (2) in a molecule thereof, in which: the substituent A and the substituent B are groups different from each other in a position at which $L^1$ in the formula (1) or $L^2$ in the formula (2) is bonded to a carbazole structure; and the substituent A and the substituent B are bonded to the same nitrogen atom, or different nitrogen atoms, in the molecule.

The aromatic amine derivative of the present invention usually refers to an amine compound having a molecular weight of 300 to 2,000 and having a substituent formed of an aromatic compound. The molecular weight is more preferably 400 to 1,500, particularly preferably 500 to 1,200. A molecular weight of 500 to 1,200 is preferred because the device can be produced by a deposition method.

[Chem. 2]

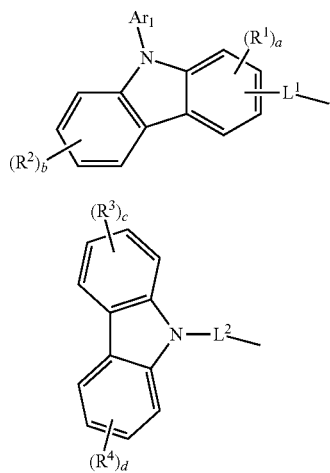

(1)

(2)

Further, the substituent A and the substituent B each represented by the formula (1) or (2) are preferably substituents represented by the formula (2) and one of the following formulae (3) and (4), and the substituent A and the substituent B are more preferably represented by the formula (3):

[Chem. 3]

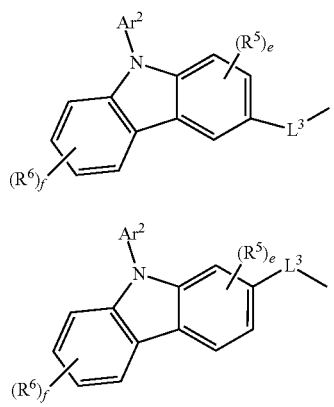

(3)

(4)

where $L^3$ is the same as $L^1$ and $L^2$, $Ar^2$ is the same as $Ar^1$, $R^5$ and $R^6$ are the same as $R^1$ to $R^4$, e represents an integer of 0 to 3, and f represents an integer of 0 to 4.

When the carbazole structure in the formula (1), (3), or (4) is bonded to a nitrogen atom without through the linking group $L^1$ or $L^3$, the use of the aromatic amine derivative of the present invention as a hole transporting material may increase the driving voltage of the device because the electron density of the amine compound increases and its IP reduces. In addition, when carbazole in any one of the formulae (1) to (4) is bonded to a nitrogen atom without through any linking group, the lifetime of the device may shorten because the amine is readily oxidized and hence the compound becomes instable in many cases. In addition, when carbazole in the formula (2) is bonded to a nitrogen atom without through the linking group $L^2$, the compound becomes instable and is hence difficult to synthesize.

In the formulae (1) to (4), $R^1$ to $R^6$ each independently represent a linear or branched alkyl group having 1 to 15, preferably 1 to 6 carbon atoms, a cycloalkyl group having 3 to 15, preferably 5 to 7 ring carbon atoms, a trialkylsilyl group having linear or branched alkyl groups each having 1 to 15, preferably 1 to 6 carbon atoms, a triarylsilyl group having aryl groups each having 6 to 25, preferably 6 to 14 ring carbon atoms, an alkylarylsilyl group having a linear or branched alkyl group having 1 to 15, preferably 1 to 6 carbon atoms and an aryl group having 6 to 25, preferably 6 to 14 ring carbon atoms, an aryl group having 6 to 25, preferably 6 to 14 ring carbon atoms, a halogen atom, or a cyano group. A plurality of $R^1$'s to $R^6$'s themselves adjacent to each other, or $R^1$ and $R^2$, $R^3$ and $R^4$, or $R^5$ and $R^6$ may be bonded to each other to form a saturated or unsaturated, divalent group.

Specific examples of the alkyl group include a methyl group, an ethyl group, a propyl group, an isopropyl group, an n-butyl group, an isobutyl group, a sec-butyl group, a tert-butyl group, an n-pentyl group, an n-hexyl group, an n-heptyl group, and an n-octyl group. Preferred are a methyl group, an ethyl group, a propyl group, an isopropyl group, an n-butyl group, an isobutyl group, a sec-butyl group, and a tert-butyl group.

Specific examples of the cycloalkyl group include a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a 1-adamantyl group, a 2-adamantyl group, a 1-norbornyl group, and a 2-norbornyl group. Preferred are a cyclopentyl group and a cyclohexyl group.

Specific examples of the trialkylsilyl group include a trimethylsilyl group, a vinyldimethylsilyl group, a triethylsilyl group, a tripropylsilyl group, a propyldimethylsilyl group, a tributylsilyl group, a t-butyldimethylsilyl group, a tripentylsilyl group, a triheptylsilyl group, and a trihexylsilyl group. Preferred are a trimethylsilyl group and a triethylsilyl group. A silyl group may be substituted with alkyl groups identical to or different from each other.

Specific examples of the triarylsilyl group include a triphenylsilyl group, a trinaphthylsilyl group, and a trianthrylsilyl group. Preferred is a triphenylsilyl group. A silyl group may be substituted with aryl groups identical to or different from each other.

Specific examples of the alkylarylsilyl group include a dimethylphenylsilyl group, a diethylphenylsilyl group, a dipropylphenylsilyl group, a dibutylphenylsilyl group, a dipentylphenylsilyl group, a diheptylphenylsilyl group, a dihexylphenylsilyl group, a dimethylnaphthylsilyl group, a dipropylnaphthylsilyl group, a dibutylnaphthylsilyl group, a dipentylnaphthylsilyl group, a diheptylnaphthylsilyl group, a dihexylnaphthylsilyl group, a dimethylanthrylsilyl group, a diethylanthrylsilyl group, a dipropylanthrylsilyl group, a dibutylanthrylsilyl group, a dipentylanthrylsilyl group, a diheptylanthrylsilyl group, a dihexylanthrylsilyl group, and a diphenylmethyl group. Preferred are a dimethylphenylsilyl group, a diethylphenylsilyl group, and a diphenylmethyl group.

Specific examples of the aryl group include a phenyl group, a 2-methylphenyl group, a 3-methylphenyl group, a 4-methylphenyl group, a 4-ethylphenyl group, a biphenyl group, a 4-methylbiphenyl group, a 4-ethylbiphenyl group, a 4-cyclohexylbiphenyl group, an anthracenyl group, a naphthacenyl group, a terphenyl group, a triphenylyl group, a 3,5-dichlorophenylyl group, a naphthyl group, a 5-methylnaphthyl group, a phenanthryl group, a chrysenyl group, a benzphenanthryl group, a terphenyl group, a benzanthranyl group, a benzochrysenyl group, a pentacenyl group, a picenyl group, a pentaphenyl group, a pyrenyl group, a benzopyrenyl group, a chrysenyl group, a fluorenyl group, a 9,9-dimethylfluorenyl group, an indenyl group, an acenaphthylenyl group, a fluoranthenyl group, and a perylenyl group. Preferred are a phenyl group, a biphenylyl group, and a naphthyl group.

Specific examples of the halogen atom include fluorine, chlorine, and bromine.

Specific examples of the ring formed by the saturated or unsaturated, divalent group which the plurality of $R^1$'s to $R^6$'s are bonded to themselves, or $R^1$ and $R^2$, $R^3$ and $R^4$, or $R^5$ and $R^6$ are bonded to each other to form include the aryl groups and cycloalkyl groups, and heteroaryl groups.

Examples of the heteroaryl group include a pyrrolyl group, a pyrazinyl group, a pyridinyl group, an indolyl group, an isoindolyl group, a furyl group, a benzofuranyl group, an isobenzofuranyl group, a quinolyl group, an isoquinolyl group, a quinoxalinyl group, a carbazolyl group, a phenanthridinyl group, an acridinyl group, a phenadinyl group, a phenothiadinyl group, a phenoxazinyl group, an oxazolyl group, an oxadiazolyl group, a furazanyl group, a thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl) pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a thiophenyl group, a 1-phenyl thiophenyl group, a 1,4-diphenylthiophenyl group, a benzothiophenyl group, a 1-phenylbenzothiophenyl group, a 1-phenyldibenzothiophenyl group, a dibenzofuranyl group, a 1-phenyldibenzofuranyl group, and a benzothiazolyl group. Of those, a carbazolyl group or a dibenzofuranyl group is preferred.

In the formulae (1) to (4), a and e each independently represent an integer of 0 to 3, and b, c, d, and f each independently represent an integer of 0 to 4.

In the formulae (1) to (4), $L^1$ to $L^3$ each represent a substituted or unsubstituted arylene group having 6 to 25, preferably 6 to 14 ring carbon atoms.

It should be noted that substituents which $L^1$ to $L^3$ may have are each independently a linear or branched alkyl group having 1 to 15, preferably 1 to 6 carbon atoms, a cycloalkyl group having 3 to 15, preferably 5 to 7 ring carbon atoms, a trialkylsilyl group having linear or branched alkyl groups each having 1 to 15, preferably 1 to 6 carbon atoms, a triarylsilyl group having aryl groups each having 6 to 25, preferably 6 to 14 ring carbon atoms, an alkylarylsilyl group having a linear or branched alkyl group having 1 to 15, preferably 1 to 6 carbon atoms and an aryl group having 6 to 25, preferably 6 to 14 ring carbon atoms, an aryl group having 6 to 25, preferably 6 to 14 ring carbon atoms, a halogen atom, or a cyano group.

Specific examples and preferred examples of the alkyl group, the cycloalkyl group, the trialkylsilyl group, the triarylsilyl group, the alkylarylsilyl group, the aryl group, and the halogen atom are the same as those listed in the description of the $R^1$ to the $R^6$.

Specific examples of the arylene group represented by any one of the $L^1$ to the $L^3$ include a phenylene group, a biphenylene group, a terphenylene group, a tetrafluorophenylene group, a dimethylphenylene group, a naphthylene group, an anthranylene group, a phenanthrylene group, a pyrenylene group, a naphthacenylene group, a quaterphenylene group, a pentacenylene group, a perylenylene group, a pyrenylene group, a coronylene group, a fluorenylene group, an acenaphthofluorenylene group, and a 9,9-dimethylfluorenylene group.

In addition, the arylene groups represented by the $L^1$ to the $L^3$ are preferably each independently represented by the following formula (5), and are more preferably each independently represented by any one of the following formulae (6) to (8).

In the case where the aromatic amine derivative of the present invention has a substituent represented by the formula (1), (3), or (4), when the arylene group represented by $L^1$ or $L^3$ is represented by the formula (7), an increase in the electron density of the amine compound is suppressed, and as a result, its IP increases. Accordingly, the use of the derivative as a hole transporting material can be expected to improve the property by which a hole is injected into a light emitting layer and to reduce the driving voltage of the device. In particular, an improvement in the luminous efficiency of the device and the lengthening of its lifetime can be expected from a monoamine derivative because the derivative has a large energy gap and hence can suppress the injection of an electron into a hole transporting layer. It is particularly preferred that: the substituents which the aromatic amine derivative has be each represented by the formula (1), (3), or (4); and the arylene group represented by L' or $L^3$ be represented by the formula (7).

When the substituents are each represented by the formula (2), an improvement in the luminous efficiency of the device and the lengthening of its lifetime can be expected because the amine compound has an enlarged energy gap and hence can suppress the injection of an electron into the hole transporting layer.

In addition, the molecular symmetry of the aromatic amine derivative of the present invention can be additionally reduced and the suppression of its crystallization can be expected because the derivative has two or more substituents each represented by the formula (1) or (2) and the substituents are not identical to each other.

[Chem. 4]

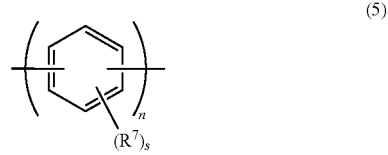

(5)

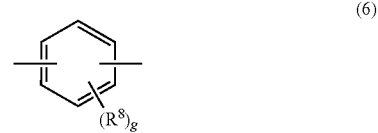

(6)

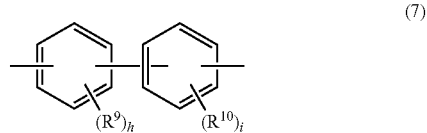

(7)

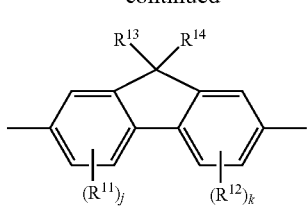

In the formulae (5) to (8), $R^7$ to $R^{12}$ each independently represent a linear or branched alkyl group having 1 to 15, preferably 1 to 6 carbon atoms, a cycloalkyl group having 3 to 15, preferably 5 to 7 ring carbon atoms, a trialkylsilyl group having linear or branched alkyl groups each having 1 to 15, preferably 1 to 6 carbon atoms, a triarylsilyl group having aryl groups each having 6 to 25, preferably 6 to 14 ring carbon atoms, an alkylarylsilyl group having a linear or branched alkyl group having 1 to 15, preferably 1 to 6 carbon atoms and an aryl group having 6 to 25, preferably 6 to 14 ring carbon atoms, an aryl group having 6 to 25, preferably 6 to 14 ring carbon atoms, a halogen atom, or a cyano group.

A plurality of $R^7$'s to $R^{12}$'s adjacent to each other may be bonded to each other to form a saturated or unsaturated, divalent group.

Specific examples and preferred examples of the alkyl group, cycloalkyl group, trialkylsilyl group, triarylsilyl group, alkylarylsilyl group, aryl group, and halogen atom each represented by any one of $R^7$ to $R^{12}$ are the same as those listed in the description of the $R^1$ to the $R^6$. Of those, preferred are a methyl group, an ethyl group, a propyl group, an isopropyl group, an n-butyl group, an isobutyl group, an sec-butyl group, or a tert-butyl group.

Rings formed by the saturated or unsaturated, divalent groups which $R^7$'s to $R^{12}$'s are bonded to each other to form are also the same as those listed in the description of the $R^1$ to the $R^6$.

$R^{13}$ and $R^{14}$ in the formula (8) each independently represent a linear or branched alkyl group having 1 to 25, preferably 1 to 6 carbon atoms, or a cycloalkyl group having 3 to 25, preferably 5 to 7 ring carbon atoms. Specific examples and preferred examples of the alkyl group and the cycloalkyl group are the same as those listed in the description of the $R^1$ to the $R^6$.

n and s in the formula (5) each independently represent an integer of 0 to 4. When n represents 2 to 4, $R^7$'s on different benzene rings may be identical to or different from each other, and respective $R^7$'s present on benzene rings adjacent to each other may be bonded to each other to form a ring.

In the formulae (6) to (8), g, h, and i each independently represent an integer of 0 to 4, preferably an integer of 0 or 1, and j and k each independently represent an integer of 0 to 3, preferably an integer of 0 or 1.

Specifically, for example, each of the formulae (6) to (8) is more preferably a substituted or unsubstituted phenylene, biphenylene, or 9,9-dimethylfluorenylene group.

$Ar^1$ and $Ar^2$ in the formulae (1), (3), and (4) each independently represent a substituted or unsubstituted aryl group having 6 to 25 (preferably 6 to 14) ring carbon atoms.

Specific examples and preferred examples of the aryl group are the same as those listed in the description of the $R^1$ to the $R^6$.

In addition, the substituent of the aryl group is the same as the substituent which any one of the $L^1$ to the $L^3$ may have, and specific examples and preferred examples thereof are the same as those listed in the description of the $R^1$ to the $R^6$.

The aromatic amine derivative of the present invention is represented by preferably any one of the following formulae (9) to (13), more preferably the formula (9) or (10), particularly preferably the formula (9). The purities of a monoamine derivative represented by the formula (9) and a diamine derivative represented by the formula (10) can be expected to improve at low costs because the derivatives are relatively easily synthesized. In addition, the use of each of the monoamine derivative and the diamine derivative as a hole transporting material can be expected to improve the property by which a hole is injected into the light emitting layer and to reduce the driving voltage of the device because the derivatives each have a large IP. In particular, an improvement in the luminous efficiency of the device and the lengthening of its lifetime can be expected from the monoamine derivative because the derivative has a large energy gap and hence can suppress the injection of an electron into the hole transporting layer.

[Chem. 5]

(9)

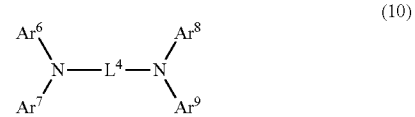

(10)

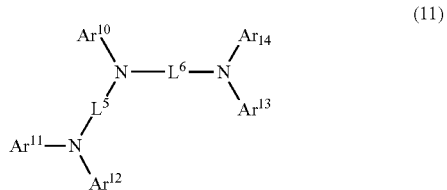

(11)

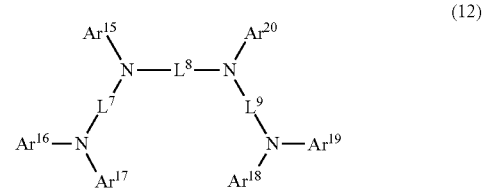

(12)

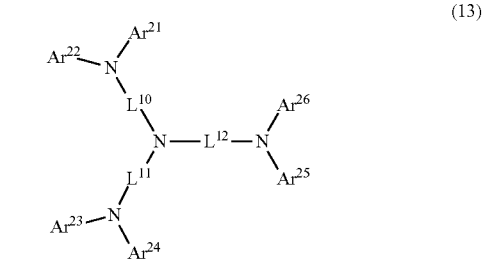

(13)

Next, the compound represented by any one of the formulae (9) to (13) is described.

In the formula (9), at least one of $Ar^3$ to $Ar^5$ represents the substituent A represented by the formula (1) or (2), at least one of $Ar^3$ to $Ar^5$ represents the substituent B represented by the formula (1) or (2), and the substituent A and the substituent B are groups different from each other;

In the formula (10), at least one of $Ar^6$ to $Ar^9$ represents the substituent A represented by the formula (1) or (2), at least one of $Ar^6$ to $Ar^9$ represents the substituent B represented by the formula (1) or (2), and the substituent A and the substituent B are groups different from each other.

In the formula (11), at least one of $Ar^{10}$ to $Ar^{14}$ represents the substituent A represented by the formula (1) or (2), at least one of $Ar^{10}$ to $Ar^{14}$ represents the substituent B represented by the formula (1) or (2), and the substituent A and the substituent B are groups different from each other.

In the formula (12), at least one of $Ar^{15}$ to $Ar^{20}$ represents the substituent A represented by the formula (1) or (2), at least one of $Ar^{15}$ to $Ar^{20}$ represents the substituent B represented by the formula (1) or (2), and the substituent A and the substituent B are groups different from each other.

In the formula (13), at least one of $Ar^{21}$ to $Ar^{26}$ represents the substituent A represented by the formula (1) or (2), at least one of $Ar^{21}$ to $Ar^{26}$ represents the substituent B represented by the formula (1) or (2), and the substituent A and the substituent B are groups different from each other.

In the formulae (9) to (13), groups out of $Ar^3$ to $Ar^{26}$ which are not the substituent A or the substituent B are each independently a substituted or unsubstituted aryl group having 6 to 25, preferably 6 to 14 ring carbon atoms, or a substituted or unsubstituted heteroaryl group having 5 to 25, preferably 5 to 14 ring atoms, and specific examples and preferred examples of the aryl group and the heteroaryl group are the same as those listed in the description of the $R^1$ to the $R^6$. Of those, a terphenyl group is particularly preferred. When the compound has a terphenyl group excellent in reduction stability, the reduction stability of a molecule thereof is improved and hence the compound exerts a lengthening effect on the lifetime of the organic EL device to be obtained. The compound exerts a significant lifetime-lengthening effect particularly when combined with a blue light emitting device.

Specific examples and preferred examples of the substituents of $Ar^3$ to $Ar^{26}$ are the same as those listed in the description of the $R^1$ to the $R^6$.

$L^4$ to $L^{12}$ in the formulae (9) to (13) each independently represent a substituted or unsubstituted arylene group having 6 to 25, preferably 6 to 14 ring carbon atoms. Specific examples and preferred examples of the arylene group represented by any one of $L^4$ to $L^{12}$, and the substituent thereof are the same as those listed in $L^1$ to $L^3$ described for the formulae (1) to (4).

In addition, $L^4$ to $L^{12}$ are each preferably represented by the formula (5), and are each more preferably represented by any one of the formulae (6) to (8).

As described in the foregoing, the formula (9) out of the formulae (9) to (13) is particularly preferred. It is preferred that in the formula (9), $Ar^3$ represent the substituent A, $Ar^4$ represent the substituent B, and $Ar^5$ represent a substituent C represented by the formula (1) or (2). The substituent A, the substituent B, and the substituent C are preferably groups different from one another in the position at which $L^1$ in the formula (1) or $L^2$ in the formula (2) is bonded to the carbazole structure.

Further, in the formula (9), it is preferred that the $Ar^3$ represents the substituent A, the $Ar^4$ represents the substituent B, and the $Ar^5$ represents a substituent C represented by the following formula (14).

[Chem. 6]

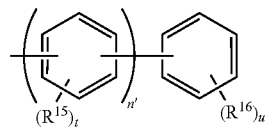

In the formula (14), $R^{15}$ and $R^{16}$ each represent a halogen atom, a linear or branched alkyl group having 1 to 15 carbon atoms, a linear or branched alkenyl group having 2 to 15 carbon atoms, an aryl group having 6 to 25 ring carbon atoms, or a heteroaryl group having 5 to 25 ring atoms.

Specific examples of the alkyl group, the aryl group, and the heteroaryl group include the same examples as those of $R^1$ to $R^6$. In addition, examples of the alkenyl group include an ethenyl group, a propenyl group, and a butenyl group.

A plurality of $R^{15}$'s or $R^{16}$'s adjacent to each other, or $R^{15}$ and $R^{16}$ may be bonded to each other to form a ring, and an oxygen atom or a nitrogen atom may be present in the ring.

n' represents an integer of 0 to 3, t represents an integer of 0 to 4, and u represents an integer of 0 to 5.

Further, in the formula (9), it is preferred that the $Ar^3$ represent the substituent A, the $Ar^4$ represent the substituent B, and the $Ar^5$ represent a substituent C represented by the following formula (15):

[Chem. 7]

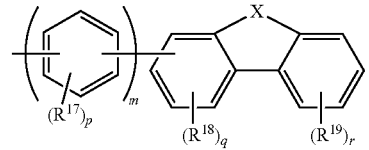

In the formula (15), X represents an oxygen atom or a sulfur atom.

$R^{17}$, $R^{18}$, and $R^{19}$ each independently represent a linear or branched alkyl group having 1 to 15 carbon atoms, a linear or branched alkenyl group having 2 to 15 carbon atoms, a cycloalkyl group having 3 to 15 ring carbon atoms, an aryl group having 6 to 25 ring carbon atoms, a heteroaryl group having 5 to 25 ring atoms, a triarylalkyl group having aryl groups each having 6 to 25 ring carbon atoms, a trialkylsilyl group having alkyl groups each having 1 to 15 carbon atoms, a triarylsilyl group having aryl groups each having 6 to 25 ring carbon atoms, an alkylarylsilyl group having an alkyl group having 1 to 15 carbon atoms and an aryl group having 6 to 25 ring carbon atoms, a halogen atom, or a cyano group.

Specific examples of the groups include the same examples as those of $R^1$ to $R^6$, and $R^{15}$ and $R^{16}$.

Further, a plurality of $R^{17}$'s, $R^{18}$'s, or $R^{19}$'s adjacent to each other, or $R^{18}$ and $R^{19}$ may be bonded to each other to form a ring.

m represents an integer of 0 to 4, and when m represents 2 to 4, $R^{17}$'s on different benzene rings may be identical to or different from each other, and respective $R^{17}$'s present on benzene rings adjacent to each other may be bonded to each other to form a ring.

q represents an integer of 0 to 3, r and p each independently represent an integer of 0 to 4, and when m represents 2 to 4, p's that specify the numbers of $R^{17}$'s on the different benzene rings may have the same value or may have different values.

The formula (15) is preferably the substituent C represented by the following formula (16):

[Chem. 8]

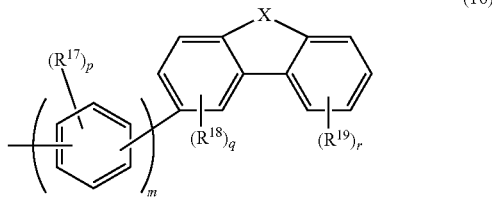

(16)

In the formula (16), X, $R^{17}$ to $R^{19}$, m, p, q, and r are the same as those of the formula (15).

The aromatic amine derivative represented by any one of the formulae (9) to (13) is preferably a compound having any one of the following combinations.

(I) The aromatic amine derivative, in which in the formula (9), the $Ar^3$ is represented by the formula (1), and the $Ar^4$ and the $Ar^5$ are each independently represented by the formula (2).

(II) The aromatic amine derivative, in which in the formula (9), the $Ar^3$ and the $Ar^4$ are each independently represented by the formula (1), and the $Ar^5$ is represented by the formula (2).

(III) The aromatic amine derivative, in which in the formula (9), the $Ar^3$ is represented by the formula (1), the $Ar^4$ is represented by the formula (2), and the $Ar^5$ represents a substituted or unsubstituted aryl group having 6 to 25 ring carbon atoms, provided that a substituent of the $Ar^5$ is an aryl group having 6 to 25 ring carbon atoms, a linear or branched alkyl group having 1 to 15 carbon atoms, a halogen atom, or a cyano group.

(IV) The aromatic amine derivative, in which: the aromatic amine derivative is represented by the formula (10); and the $Ar^6$ and the $Ar^7$ are each independently represented by the formula (1), and the $Ar^8$ and the $Ar^9$ are each independently represented by the formula (2).

(V) The aromatic amine derivative, in which: the aromatic amine derivative is represented by the formula (10); and the $Ar^6$ and the $Ar^8$ are each independently represented by the formula (1), and the $Ar^7$ and the $Ar^9$ are each independently represented by the formula (2).

(VI) The aromatic amine derivative, in which: the aromatic amine derivative is represented by the formula (11); and the $Ar^{10}$ is represented by the formula (1), and the $Ar^{12}$ and the $Ar^{13}$ are each independently represented by the formula (1) or (2).

(VII) The aromatic amine derivative, in which: the aromatic amine derivative is represented by the formula (11); and the $Ar^{12}$ and the $Ar^{13}$ are each independently represented by the formula (1), and the $Ar^{10}$ is represented by the formula (2).

(VIII) The aromatic amine derivative, in which: the aromatic amine derivative is represented by the formula (12); and the $Ar^{15}$ and the $Ar^{20}$ are each independently represented by the formula (1), and the $Ar^{17}$ and the $Ar^{18}$ are each independently represented by the formula (2).

(IX) The aromatic amine derivative, in which: the aromatic amine derivative is represented by the formula (12); and the $Ar^{17}$ and the $Ar^{18}$ are each independently represented by the formula (1), and the $Ar^{15}$ and the $Ar^{20}$ are each independently represented by the formula (2).

(X) The aromatic amine derivative, in which: the aromatic amine derivative is represented by the formula (13); and the $Ar^{21}$, the $Ar^{23}$, and the $Ar^{25}$ are each independently represented by the formula (1), and the $Ar^{22}$, the $Ar^{24}$, and the $Ar^{26}$ are each independently represented by the formula (2).

(XI) The aromatic amine derivative, in which groups out of the $Ar^3$ to $Ar^{26}$ except the substituent A and the substituent B each independently include a phenyl group, a naphthyl group, a biphenyl group, a terphenyl group, or a fluorenyl group.

Specific examples of the aromatic amine derivative represented by any one of the formulae (9) to (13) include the following compounds.

[Chem. 9]

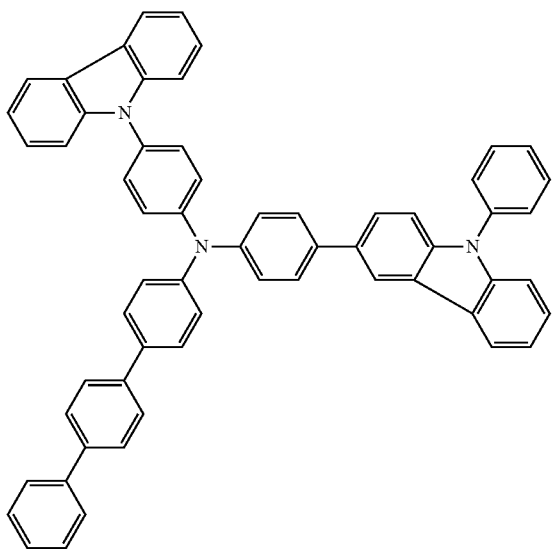

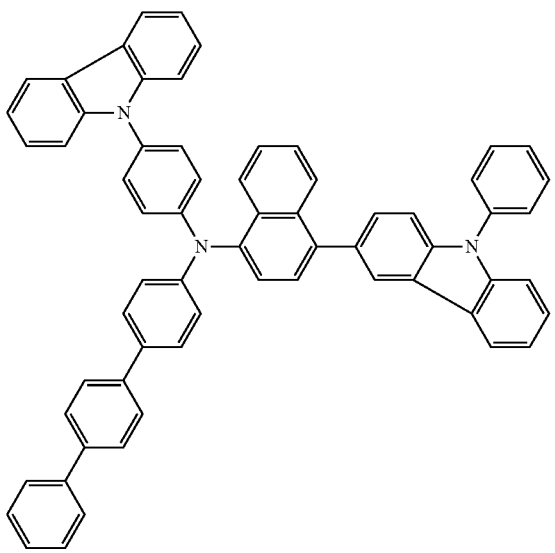

-continued
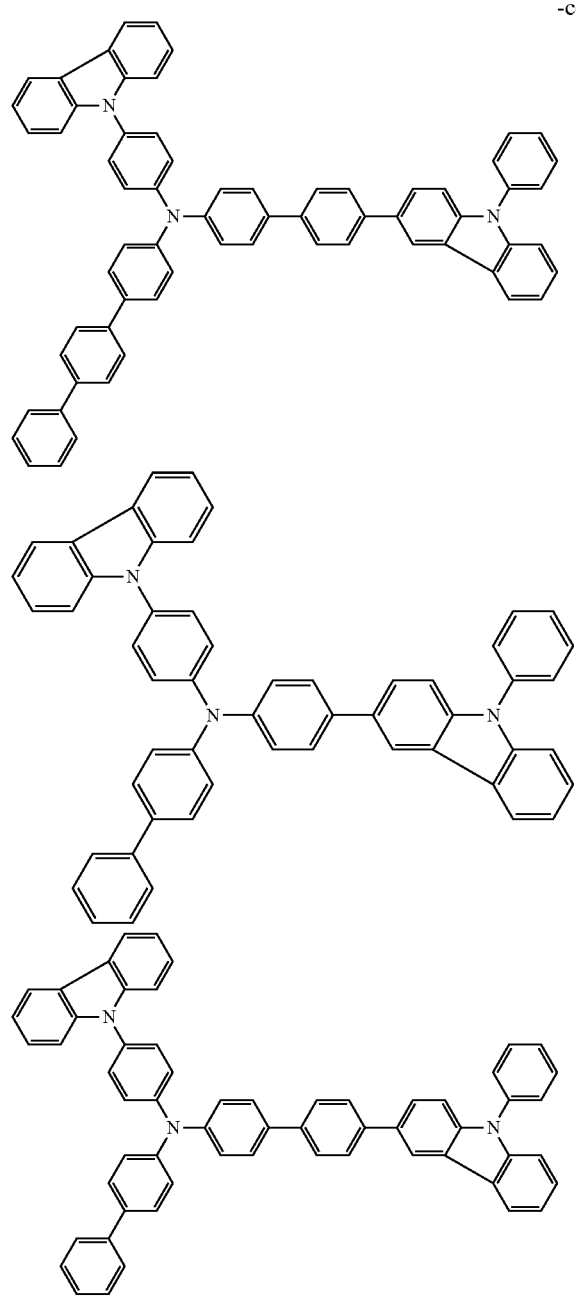
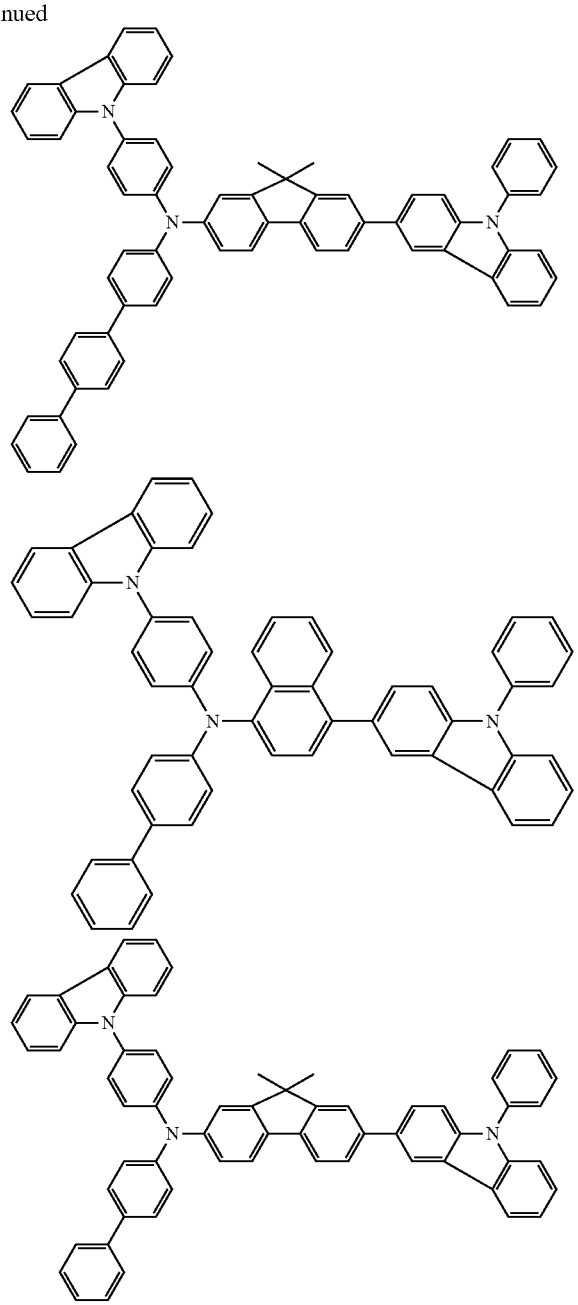
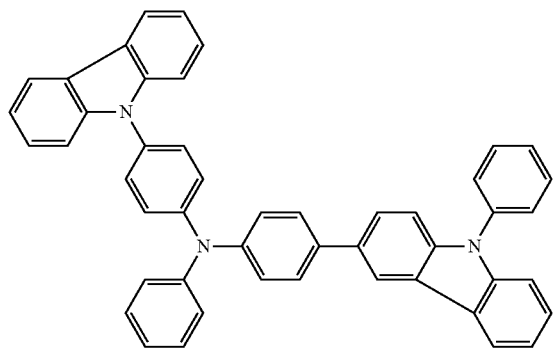
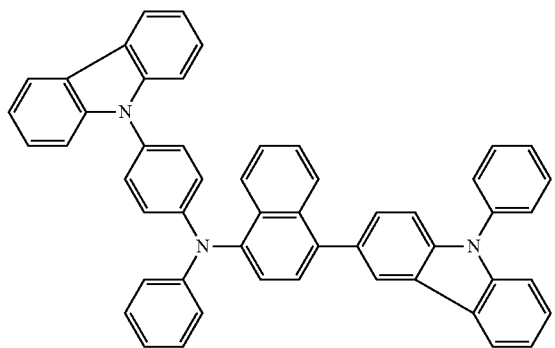

-continued
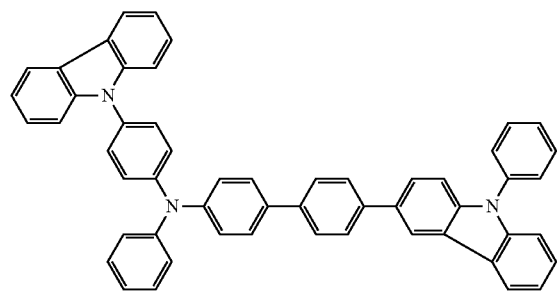
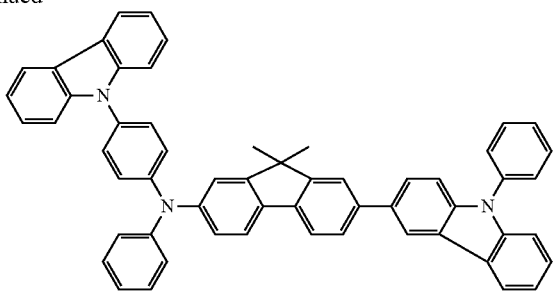
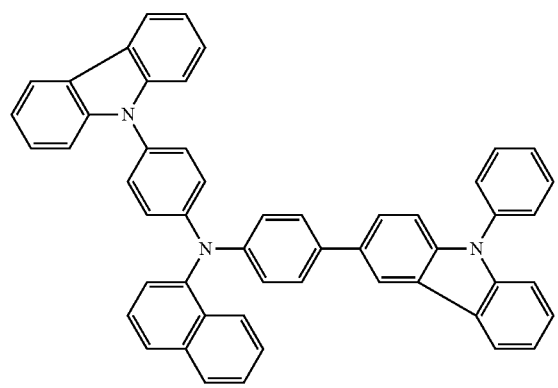
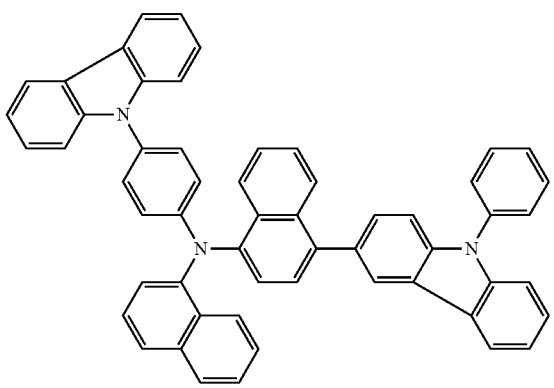
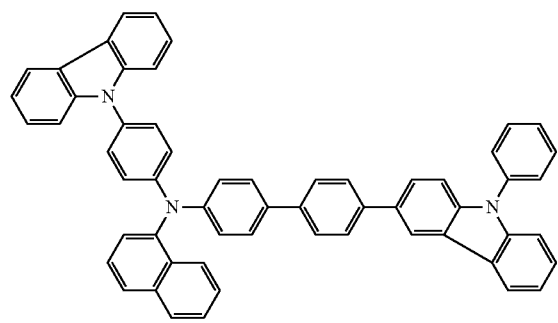
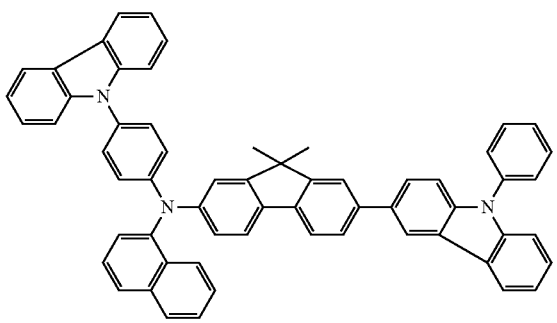

-continued
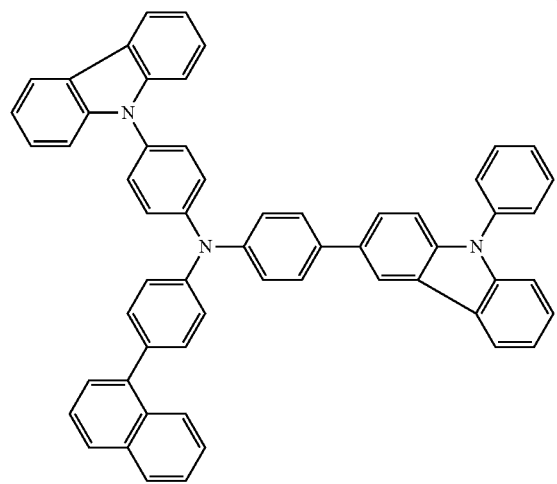
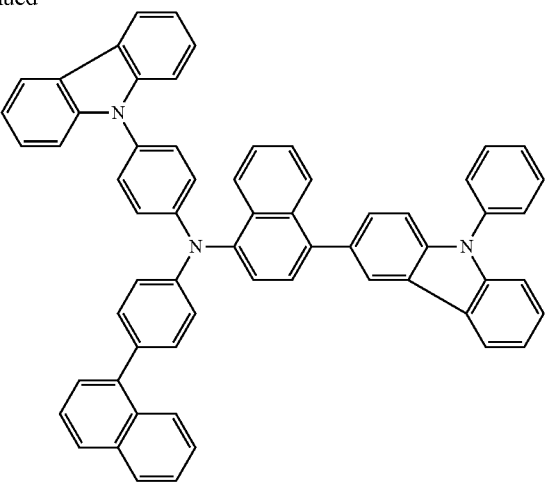
[Chem. 10]
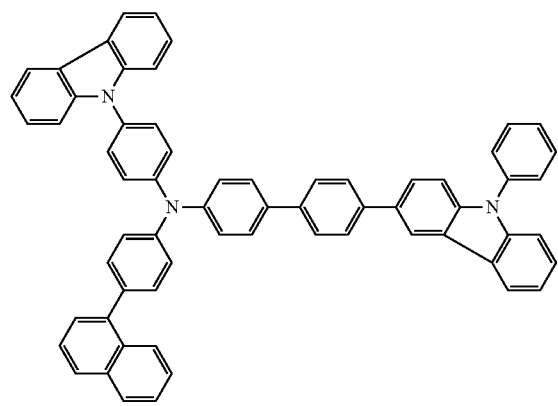
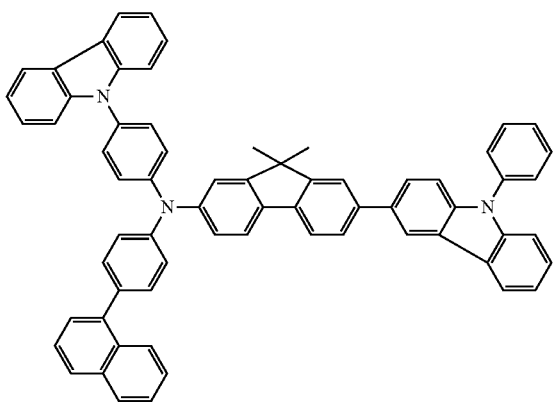
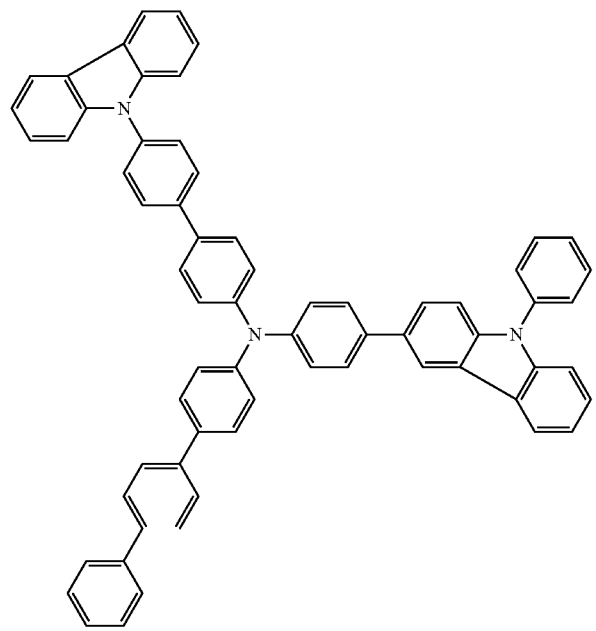
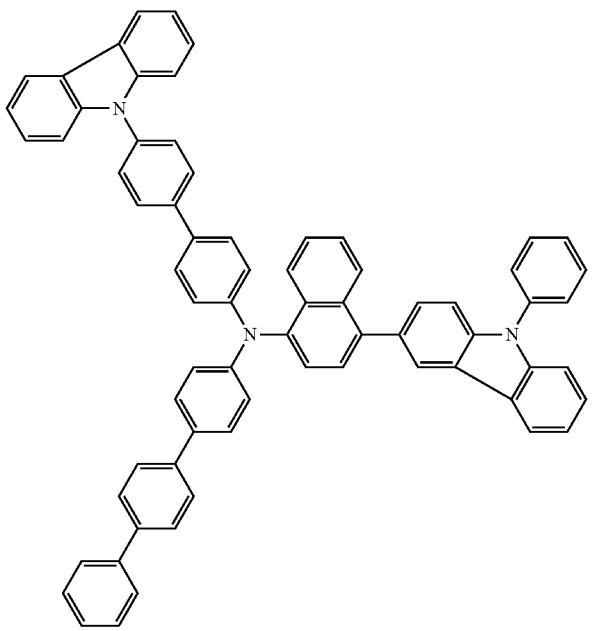


-continued
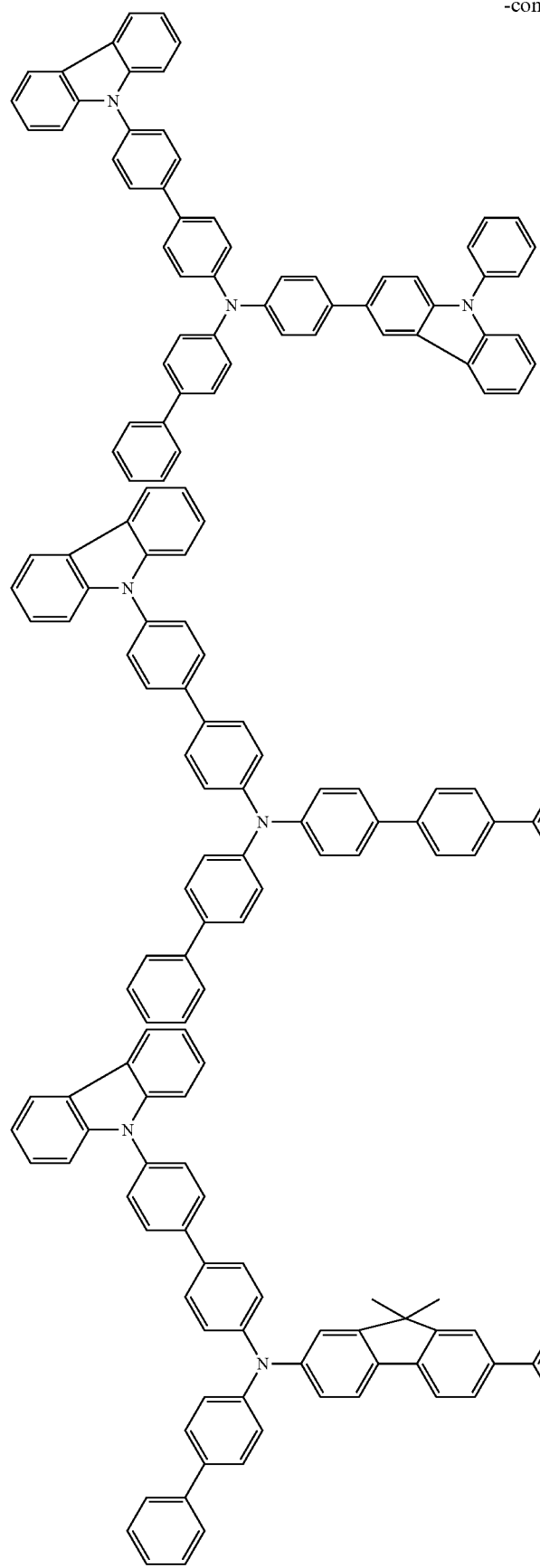
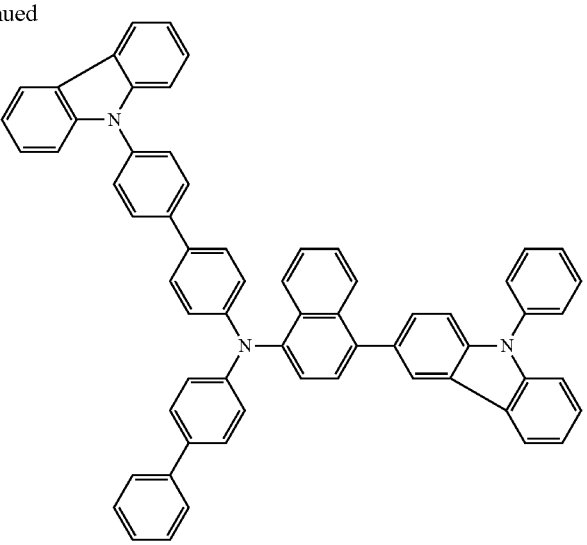

-continued
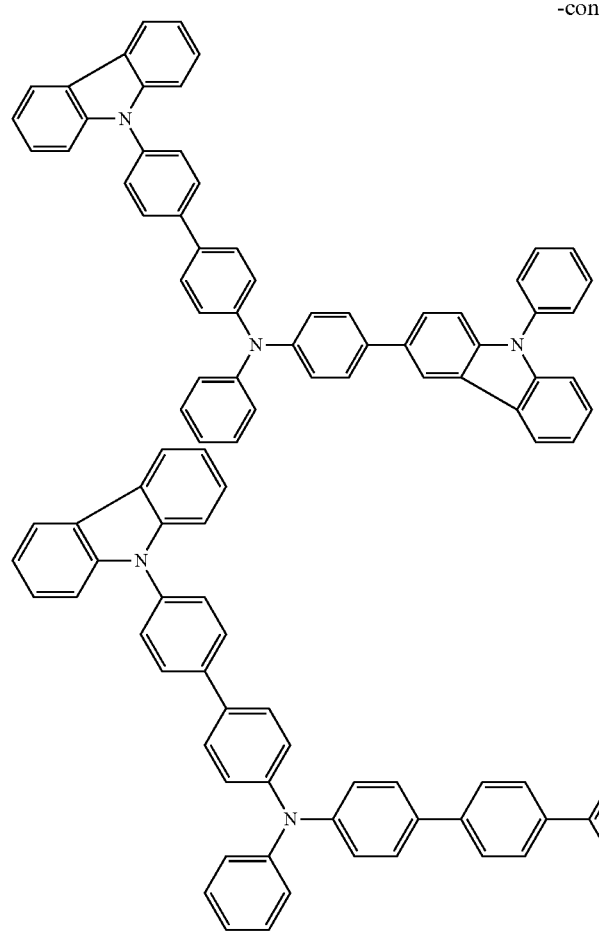
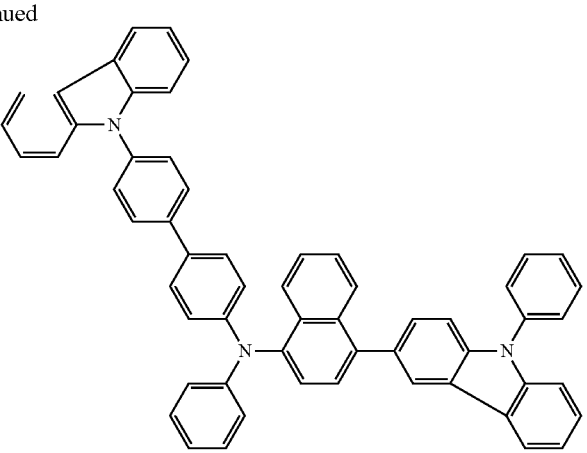
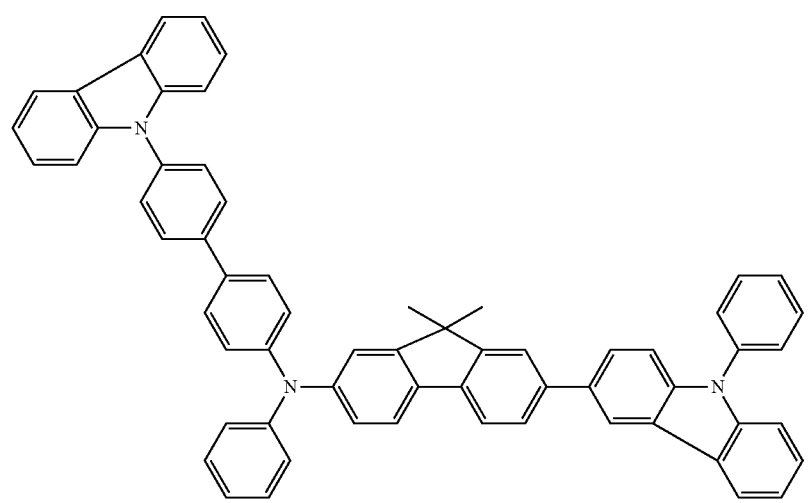

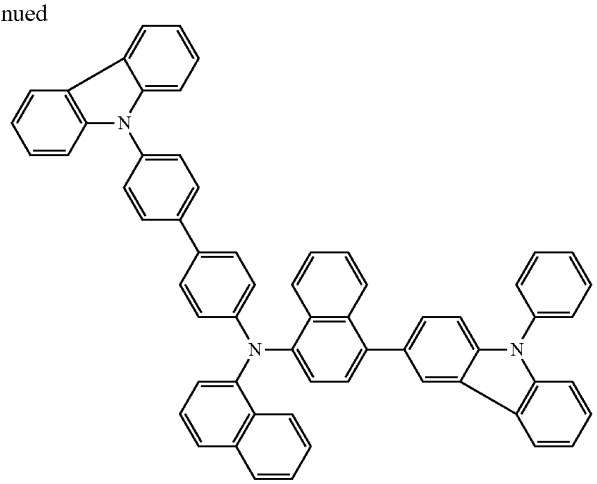
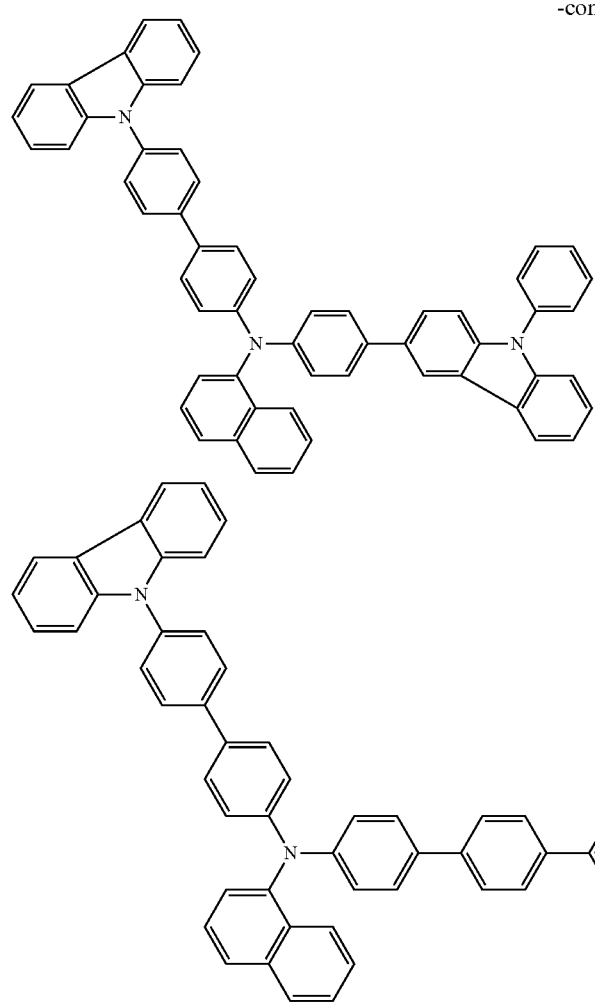
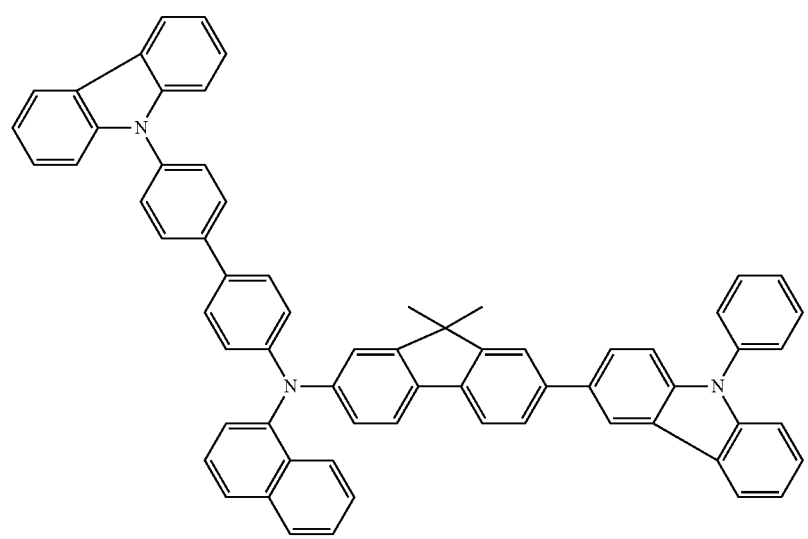

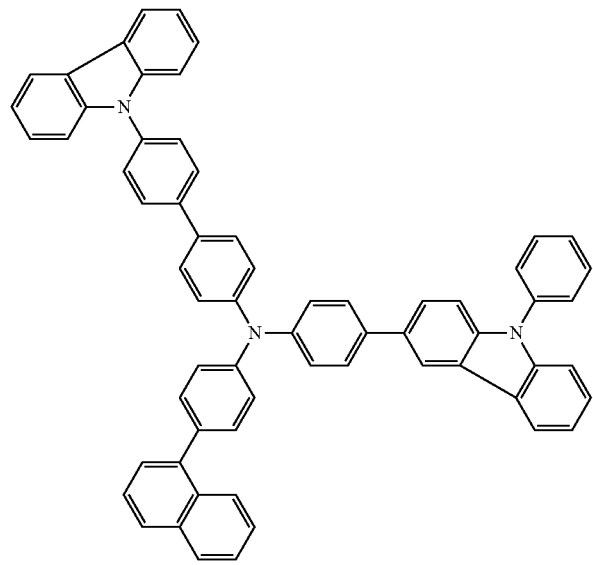
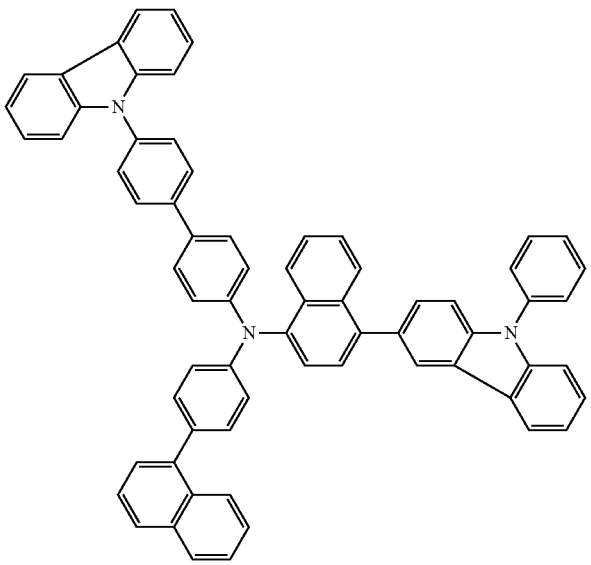
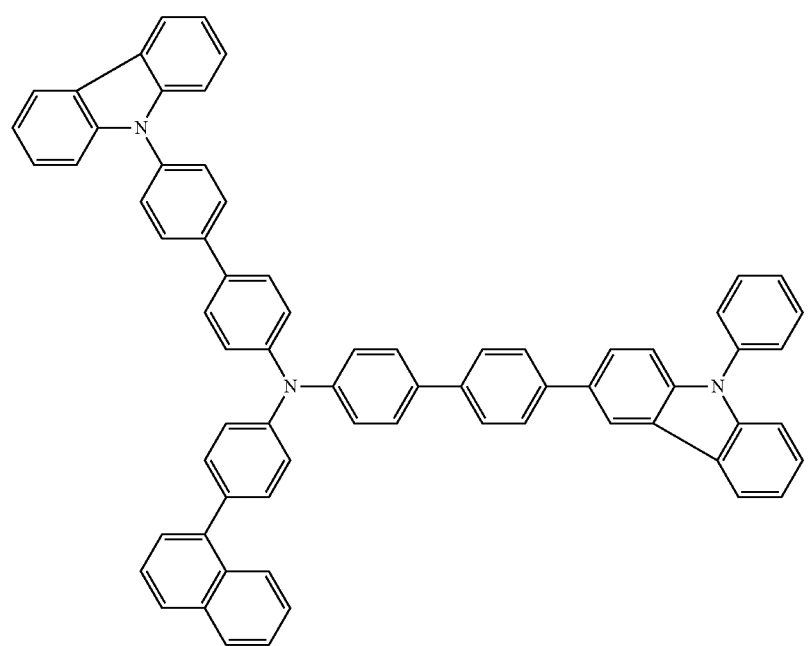

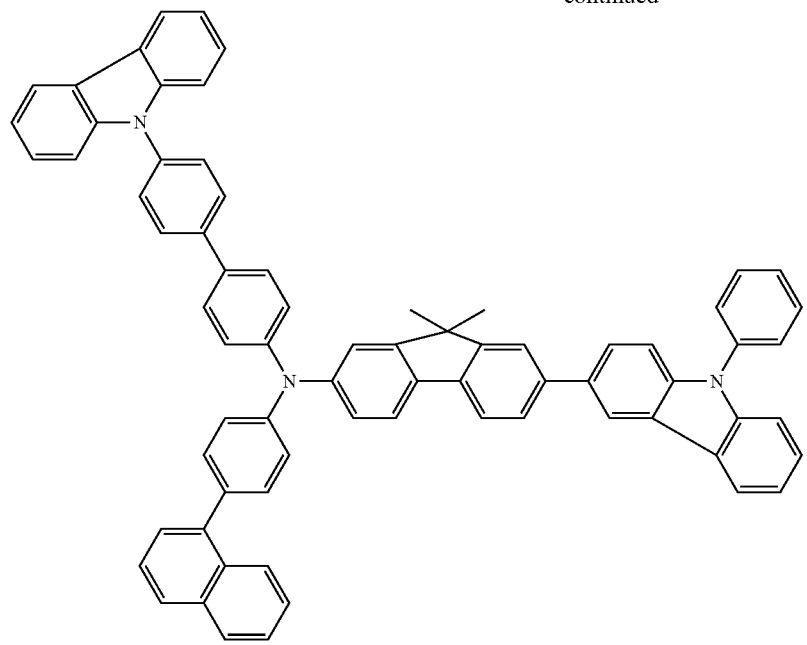
[Chem. 11]
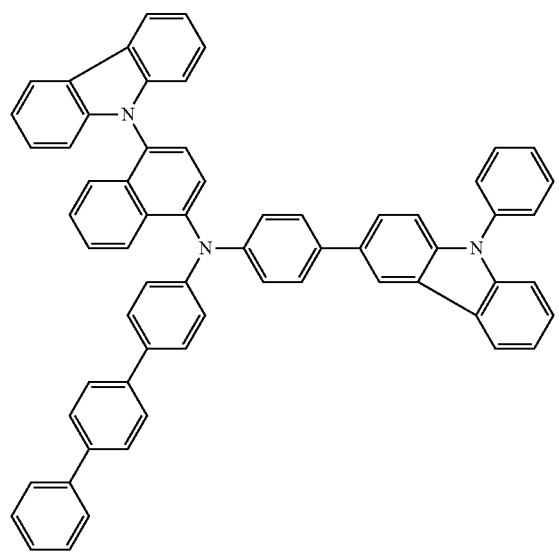
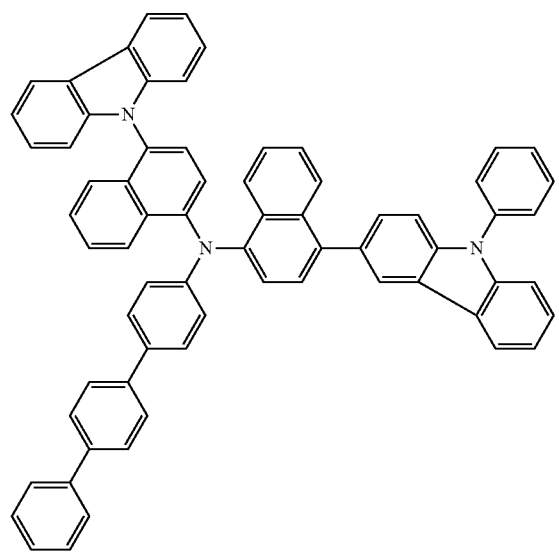
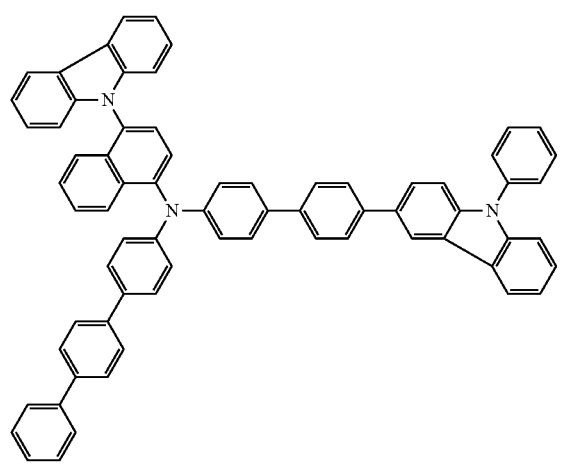
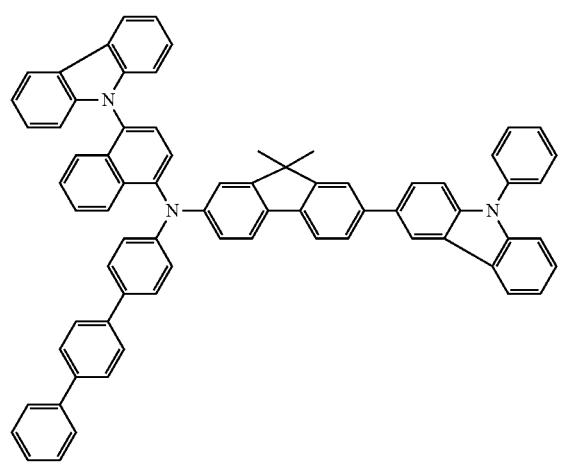

-continued
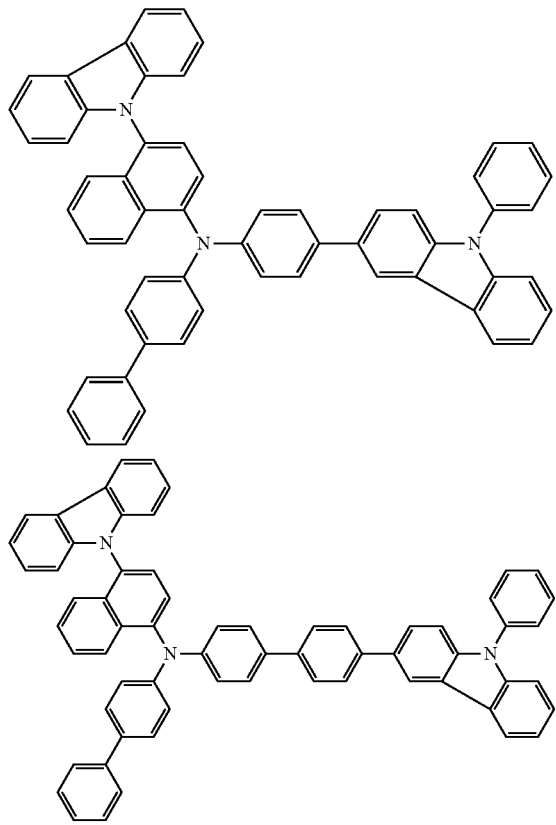
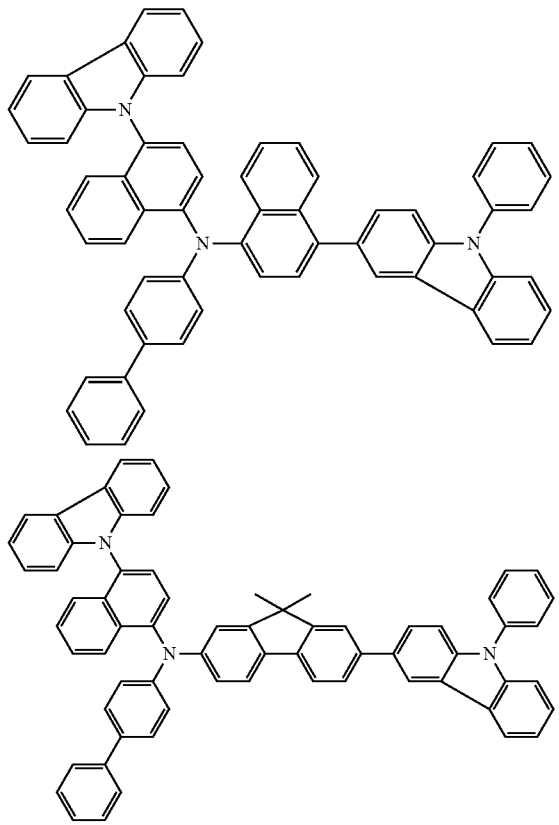
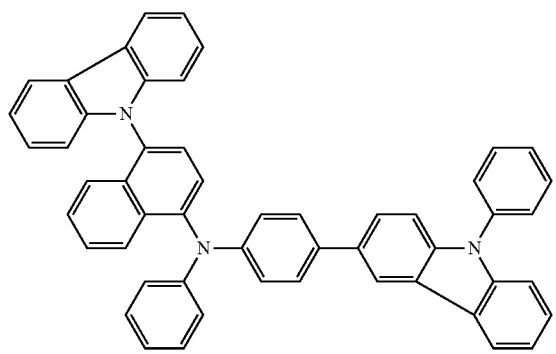
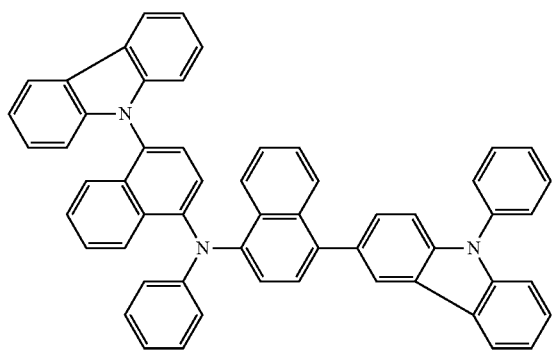
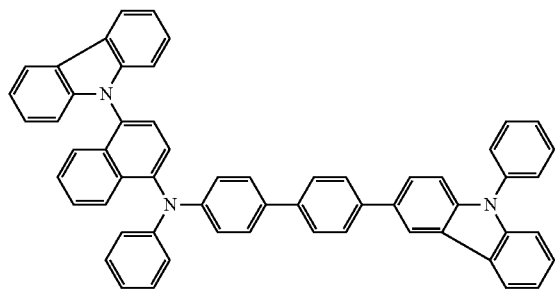
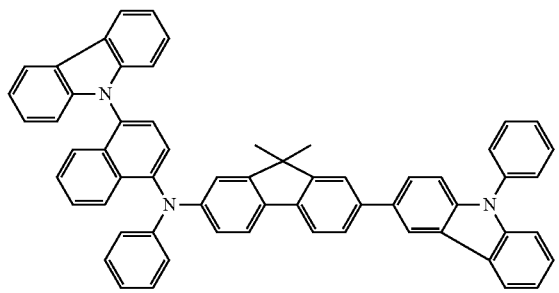

-continued
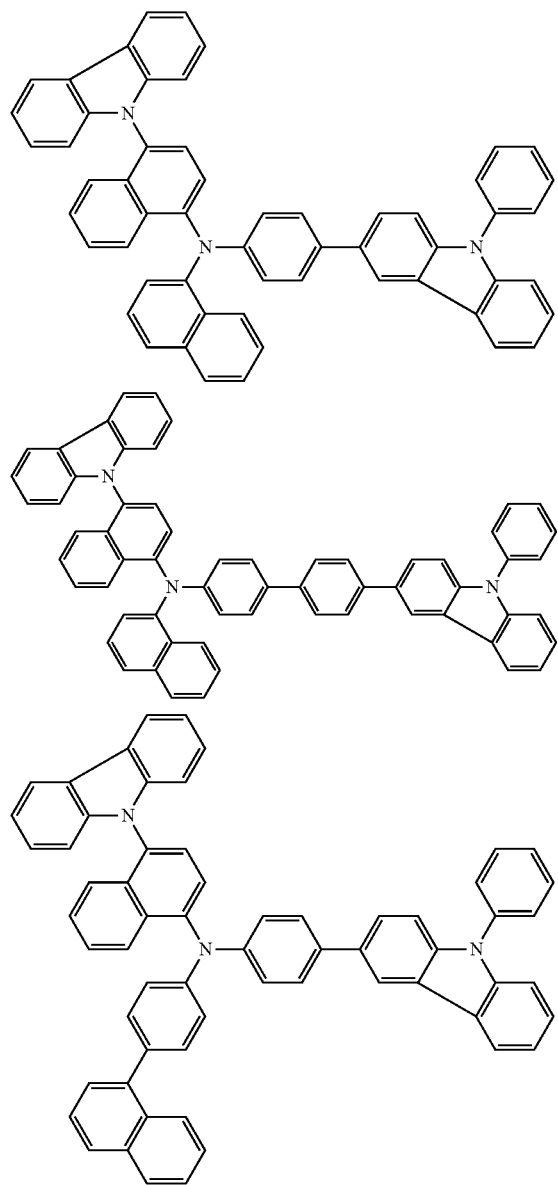
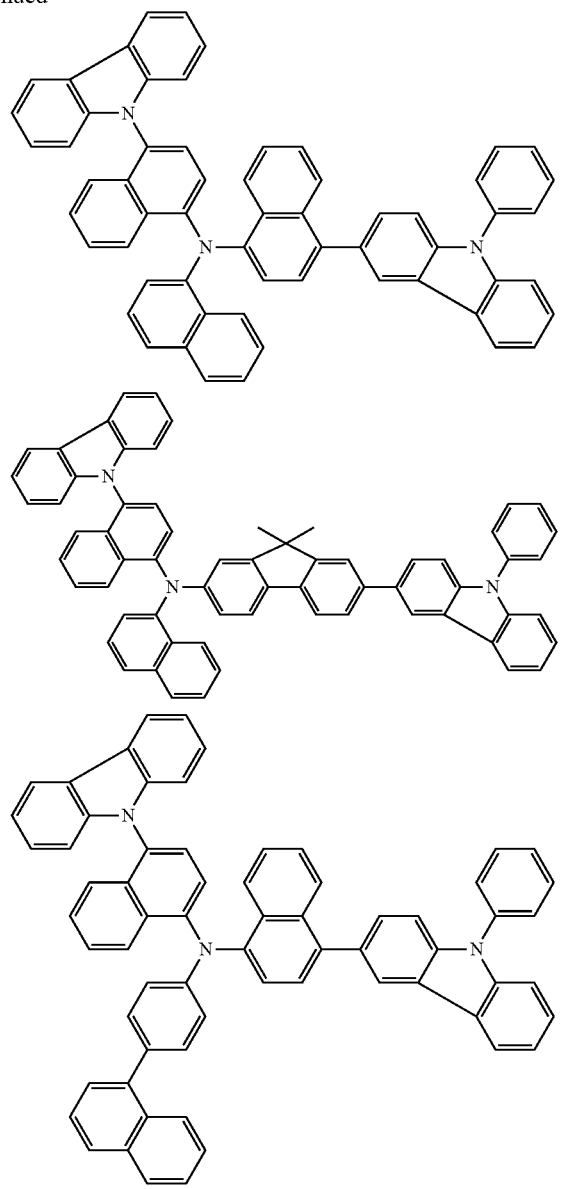
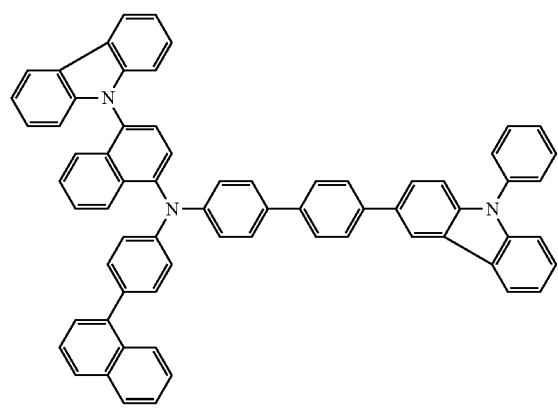
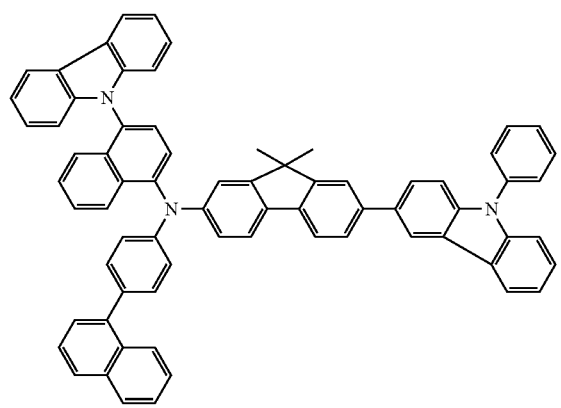

[Chem. 12]
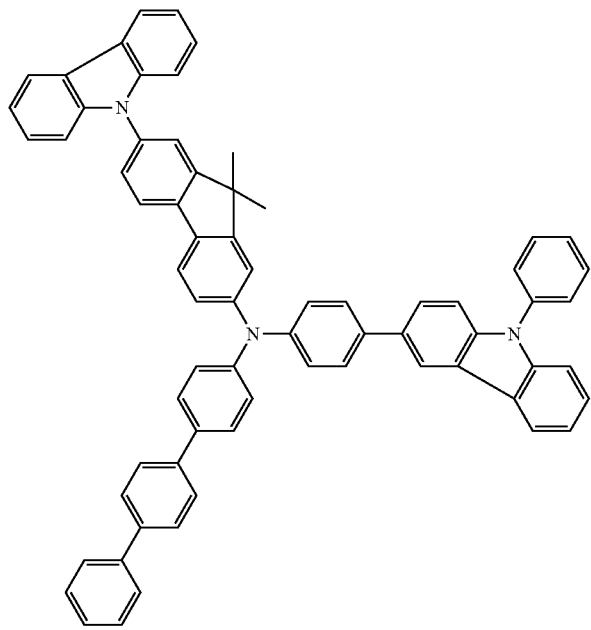
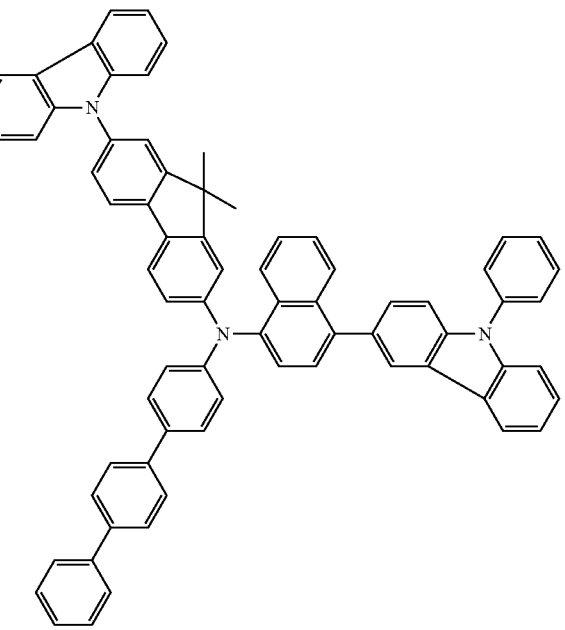
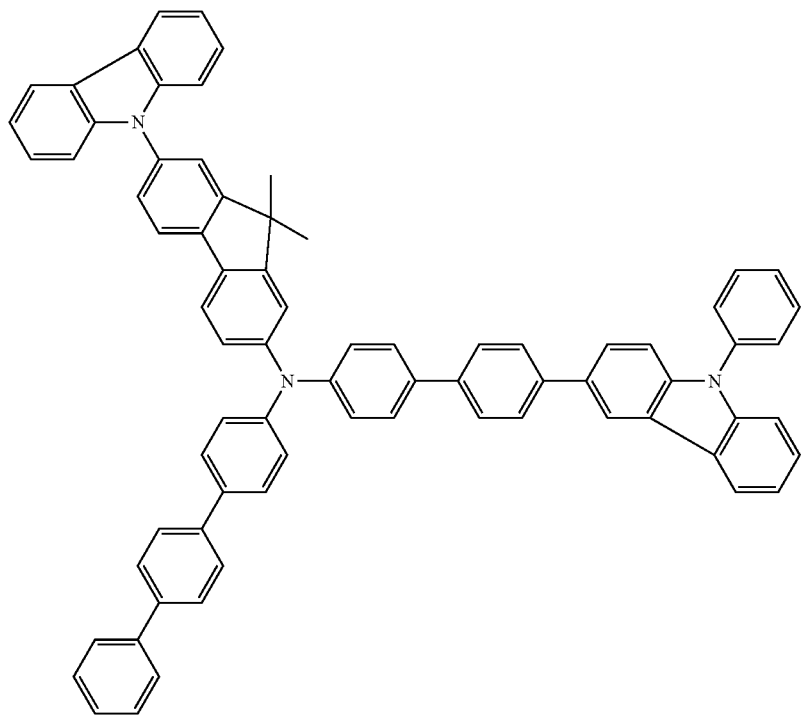

-continued
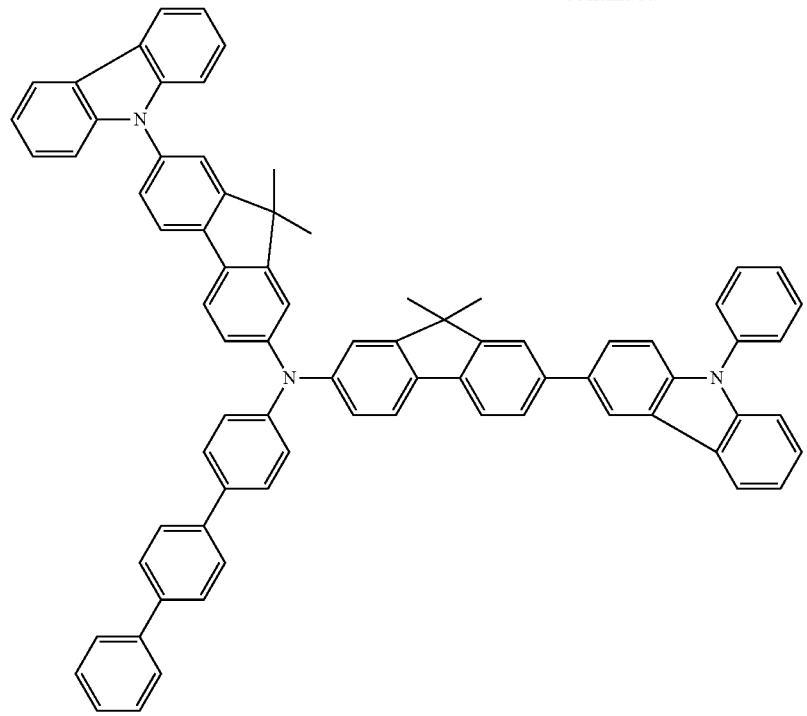
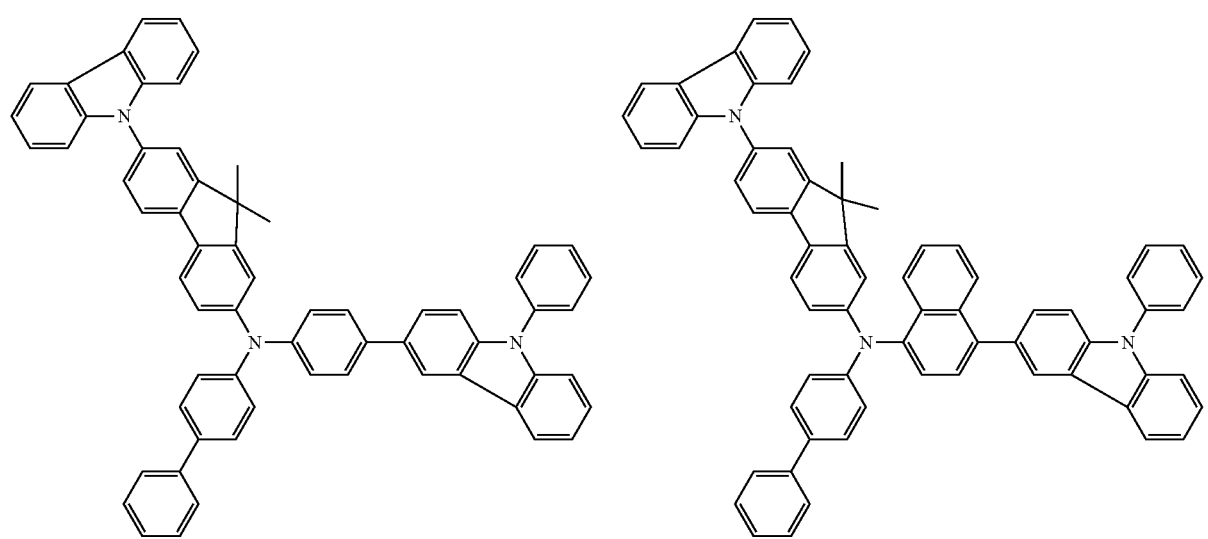

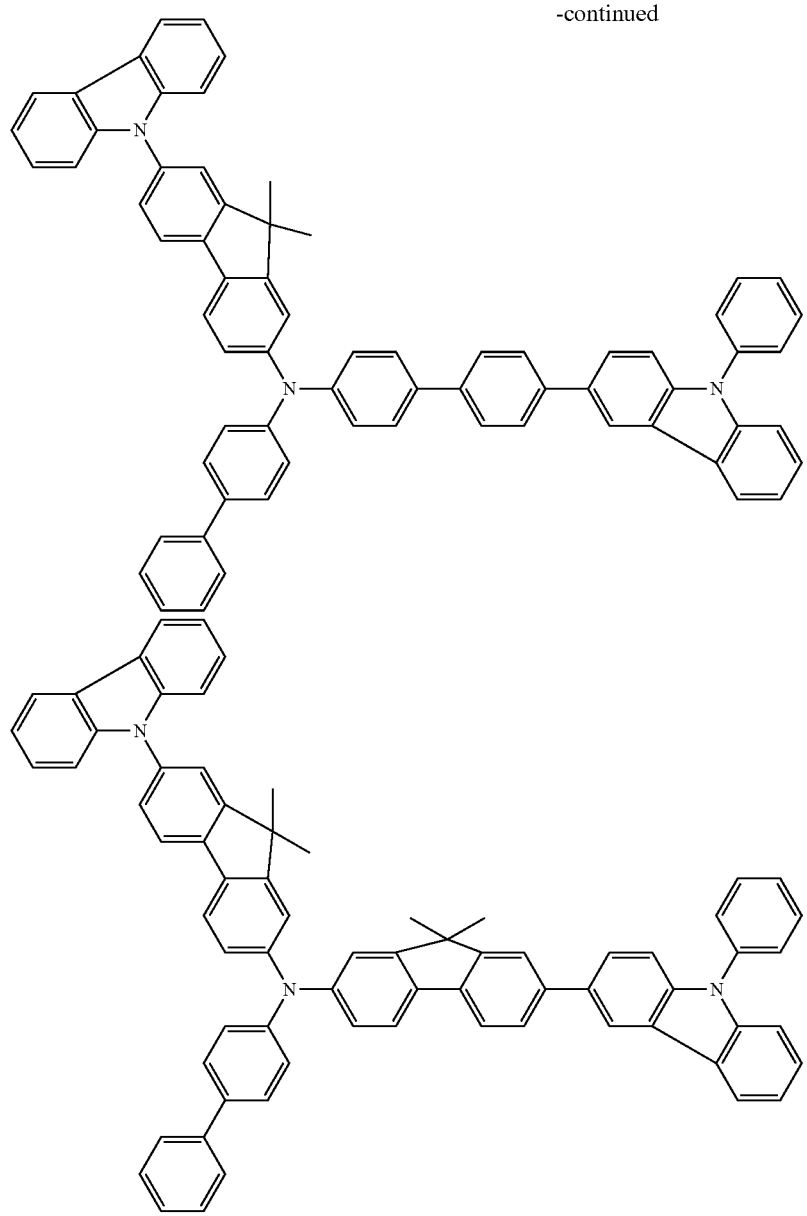
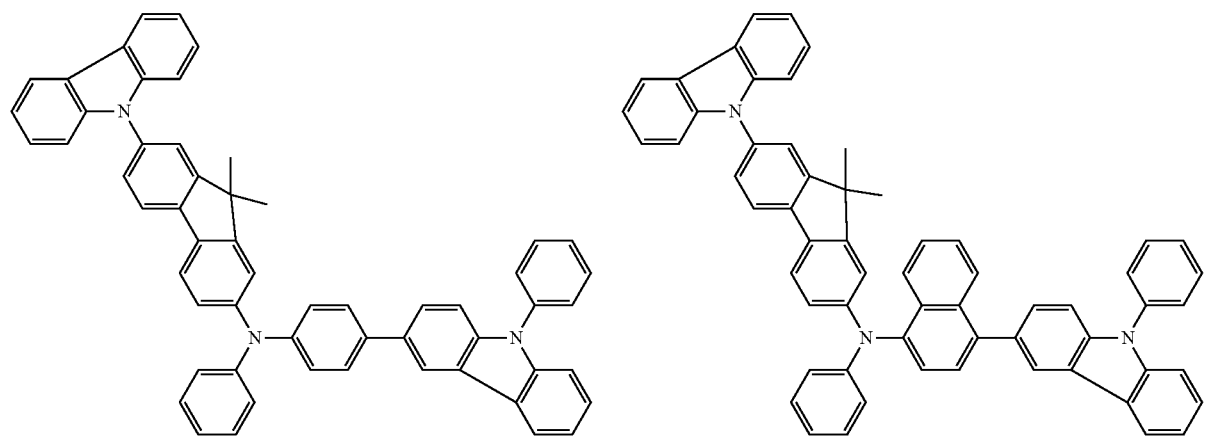

-continued
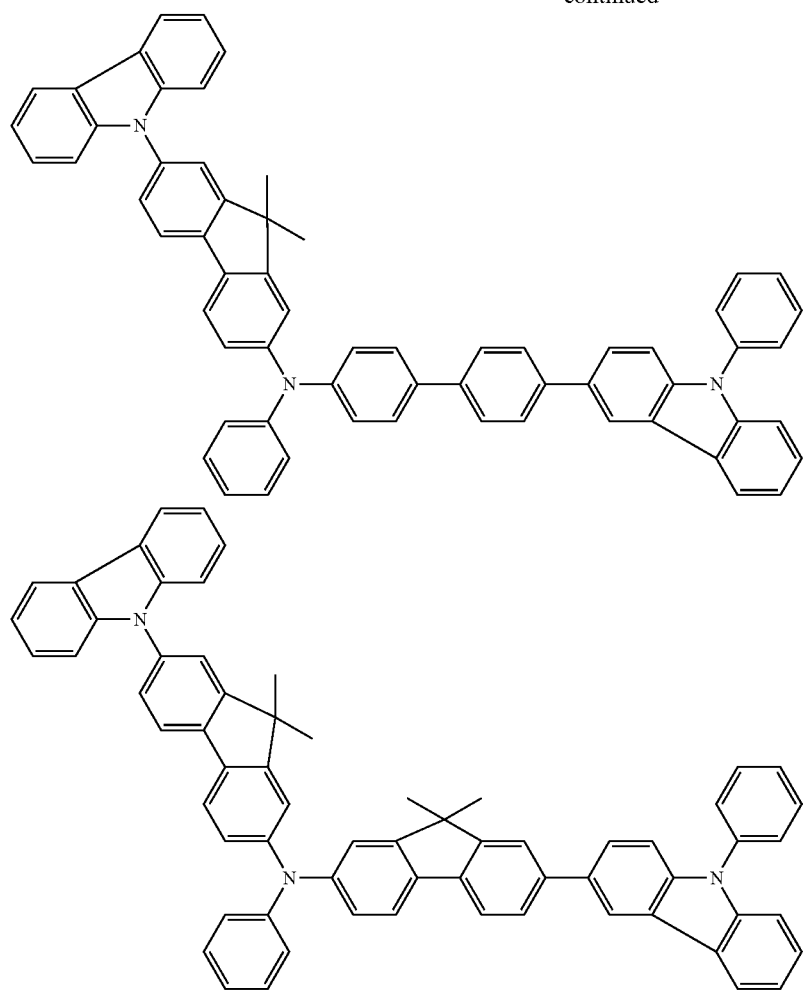
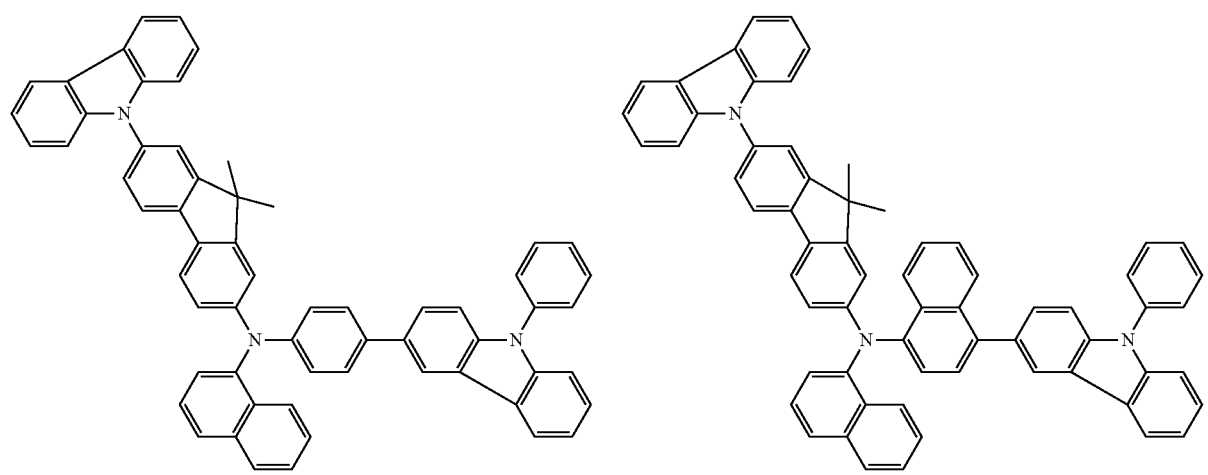

-continued
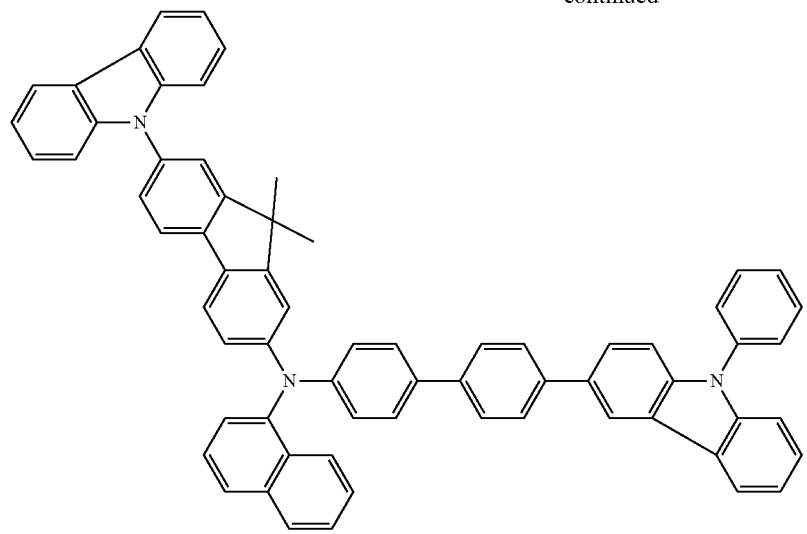
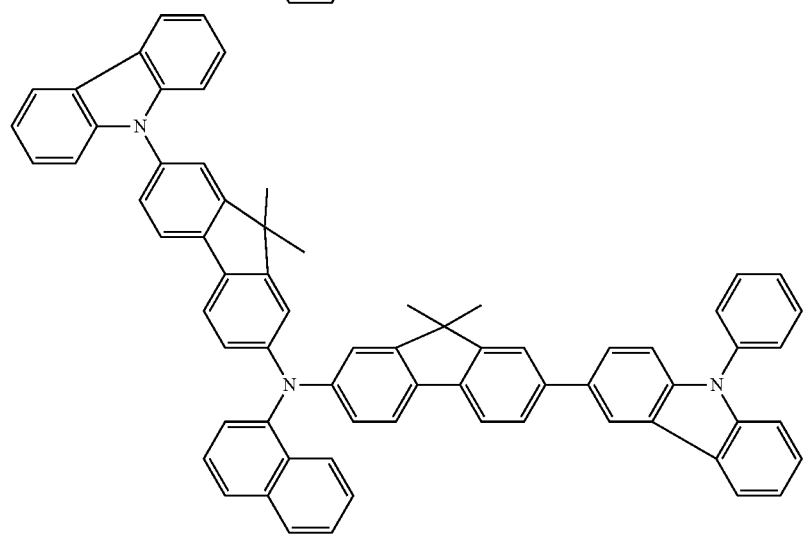
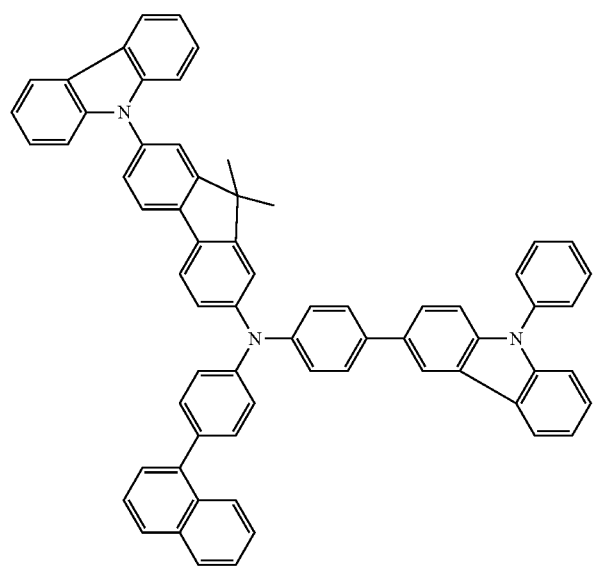
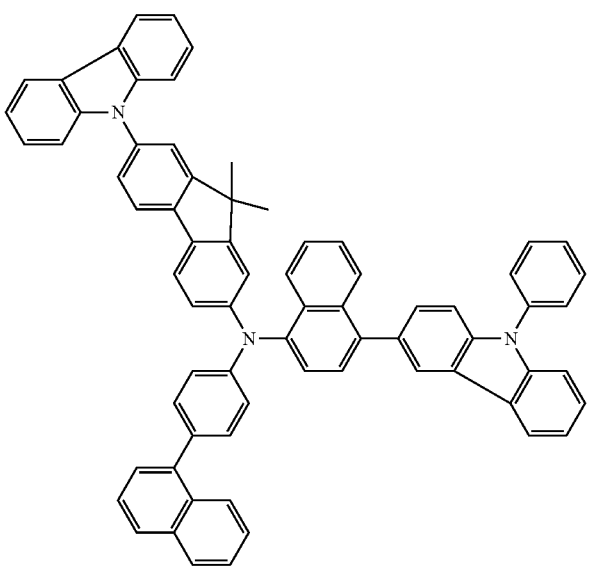

-continued
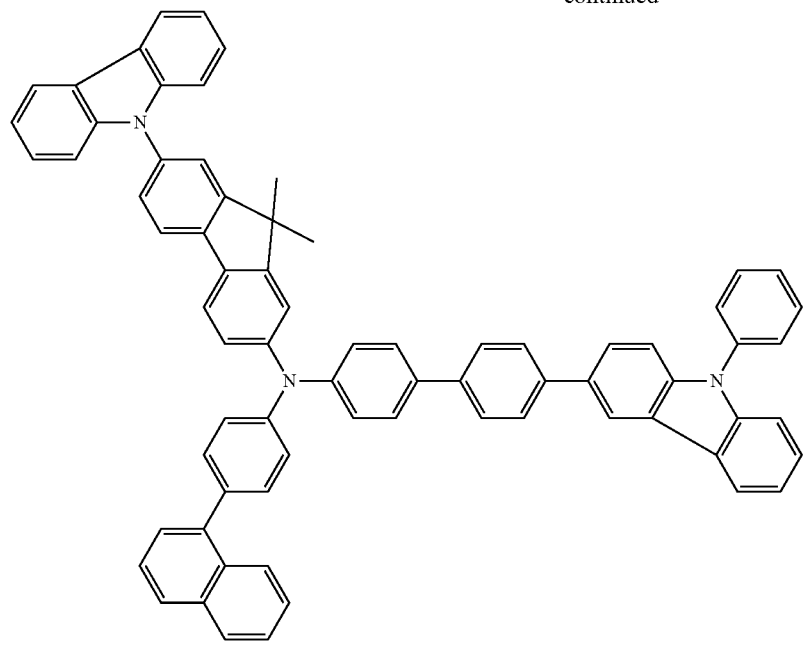
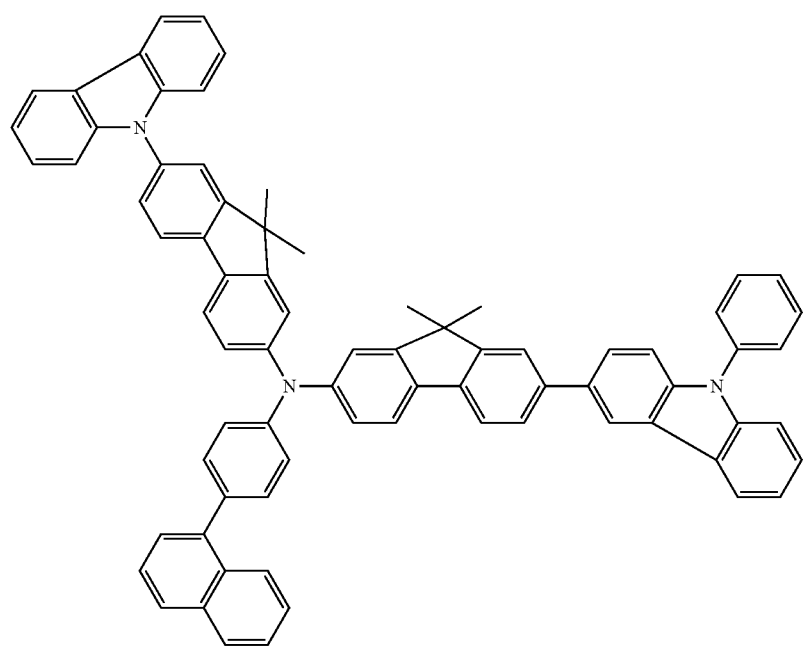

[Chem. 13]
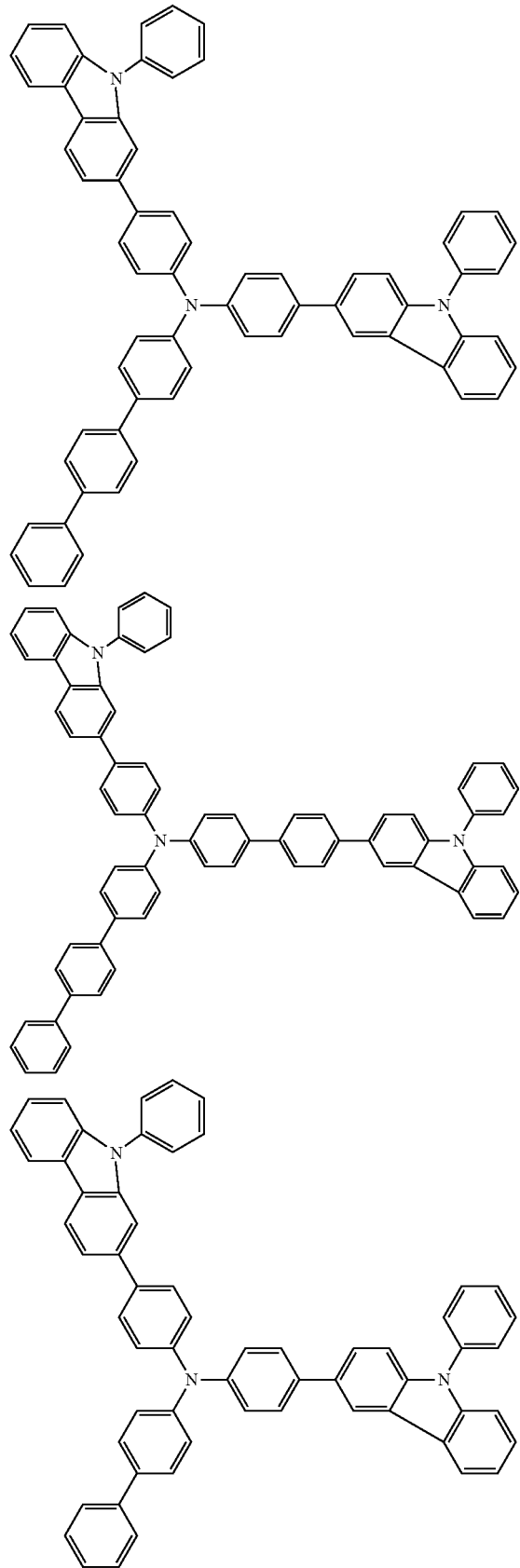
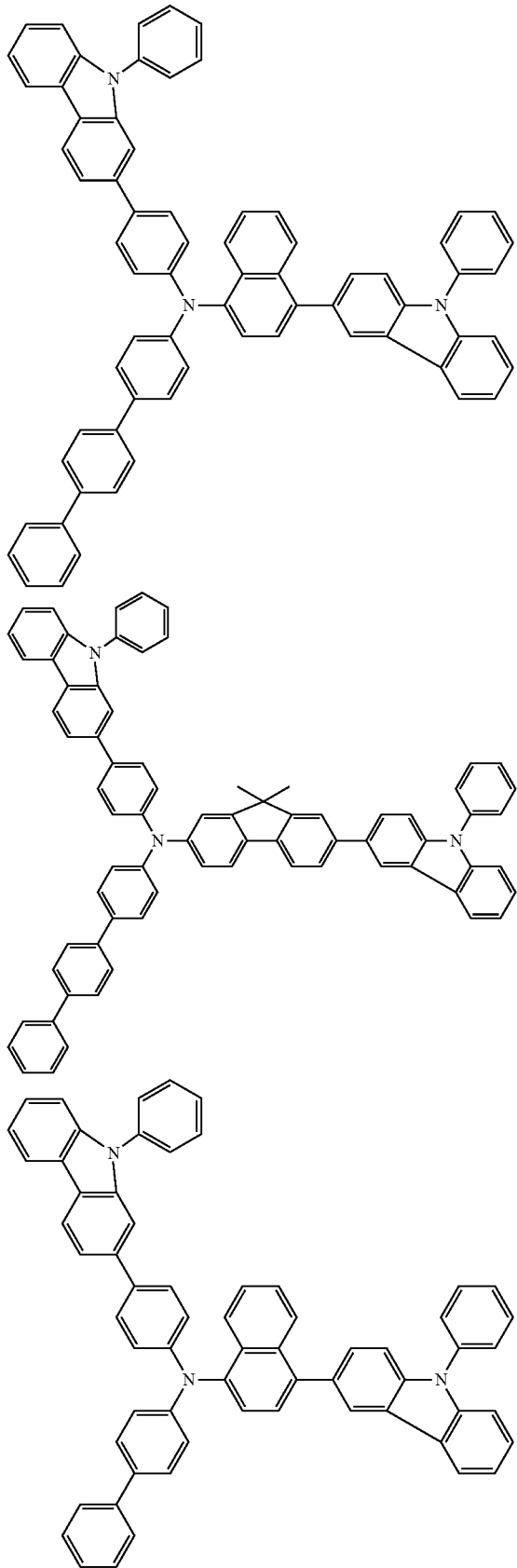

-continued
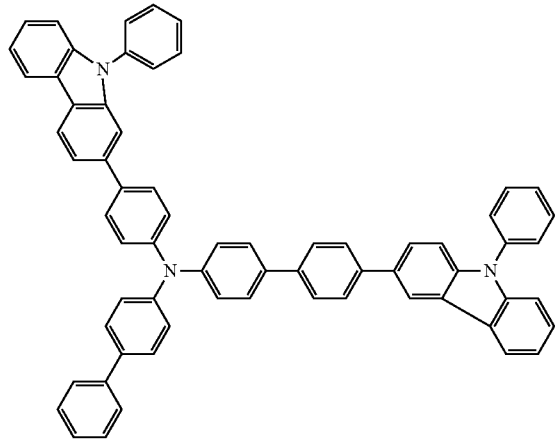
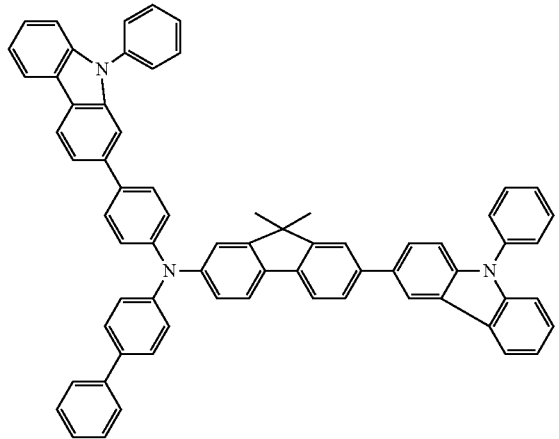
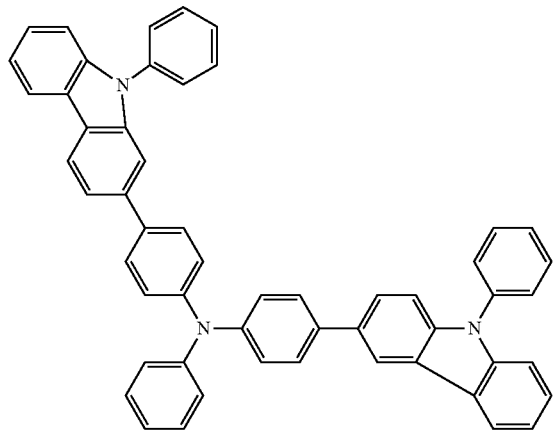
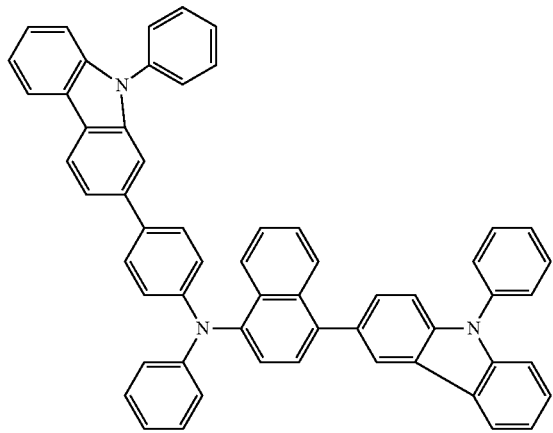
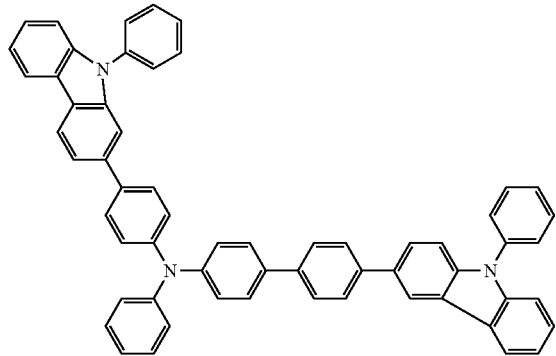
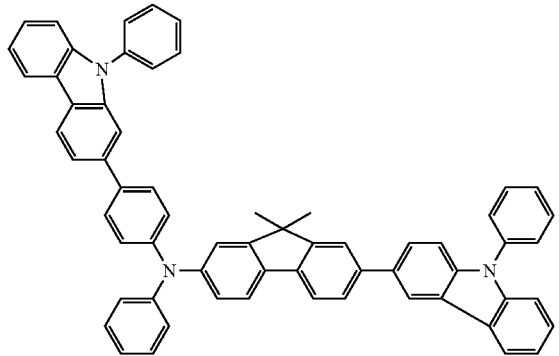
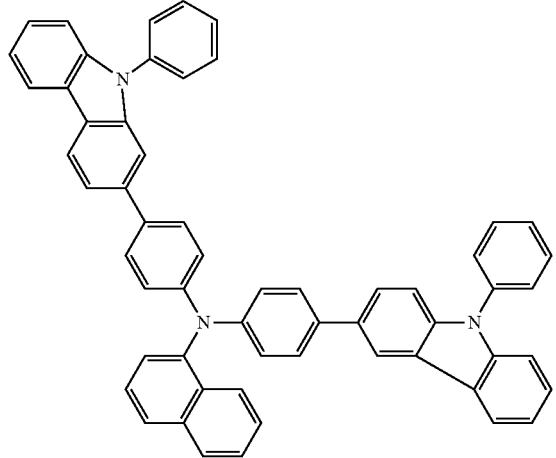
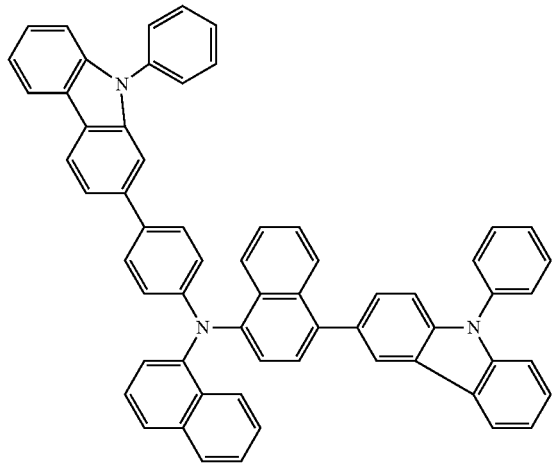

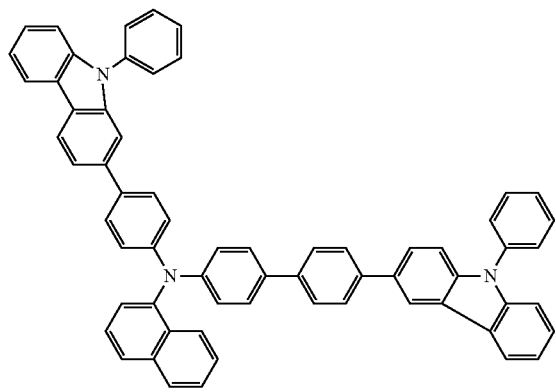
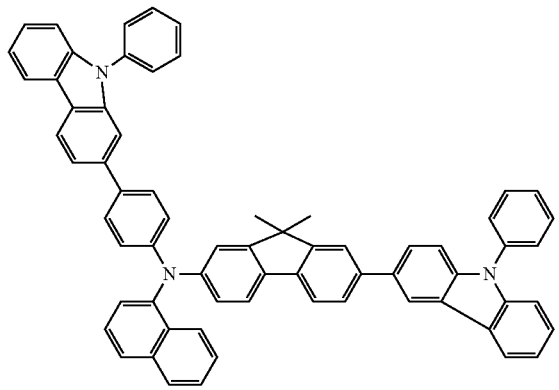
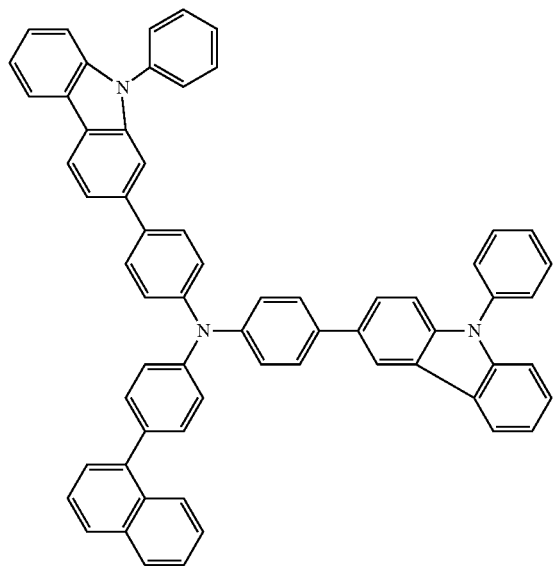
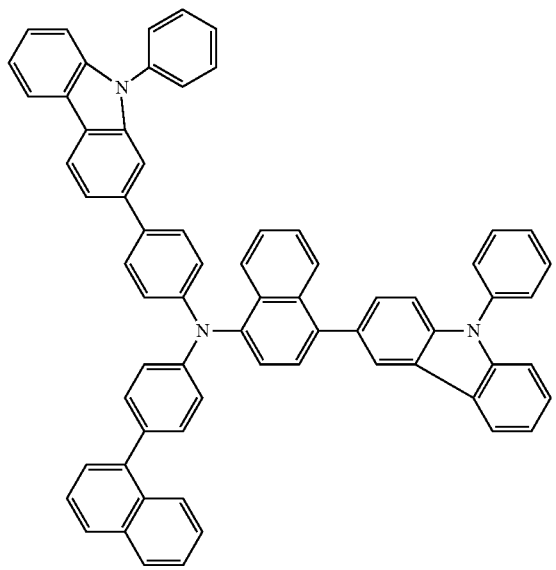
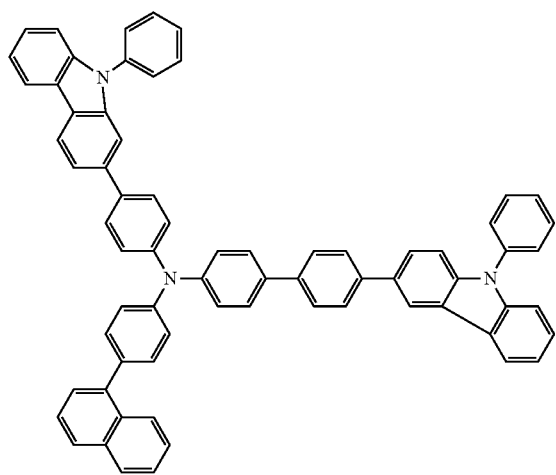
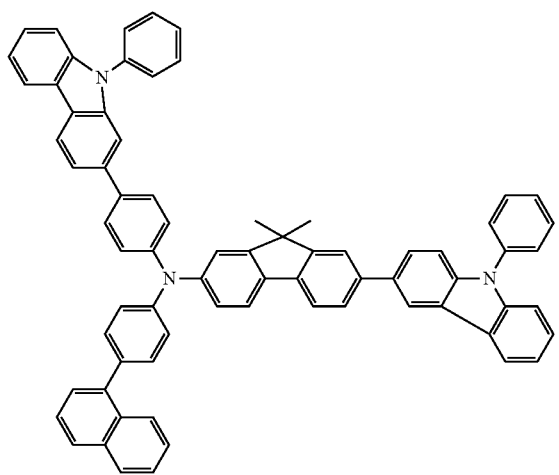

[Chem. 14]
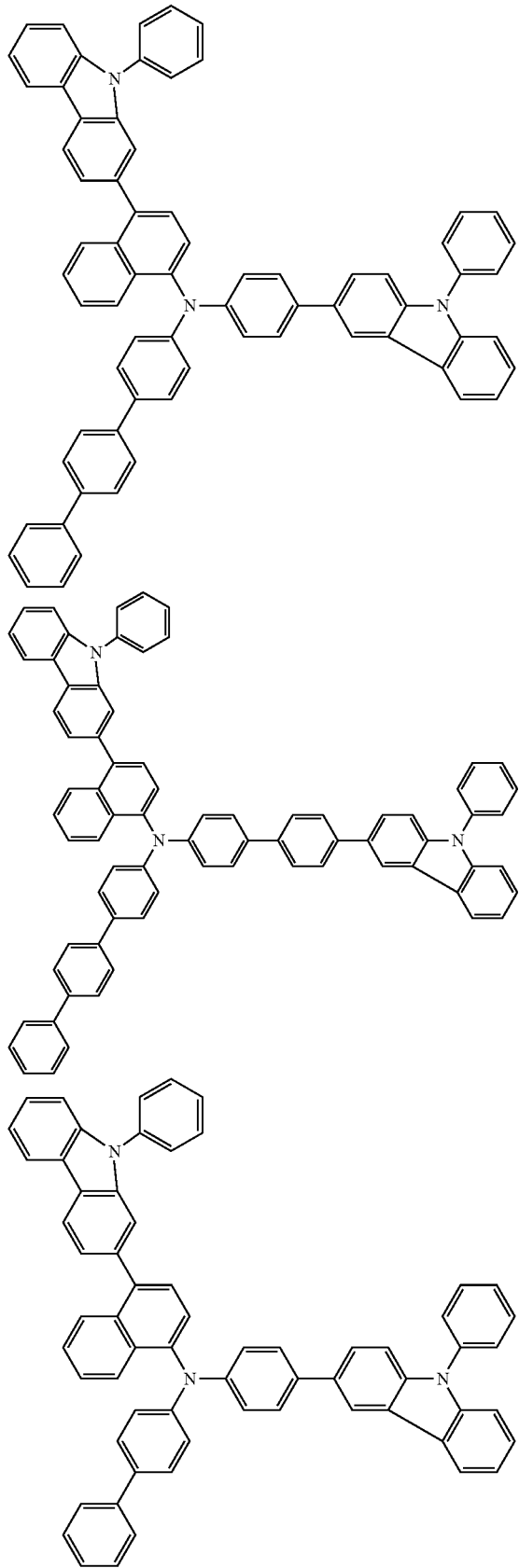
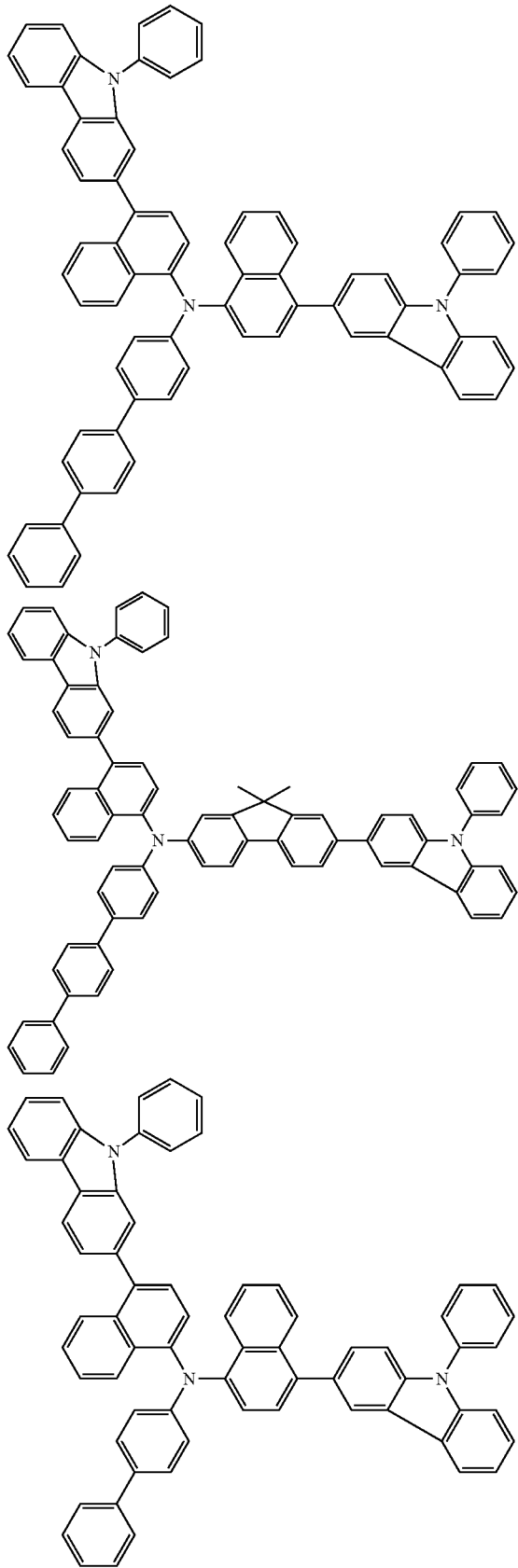

-continued
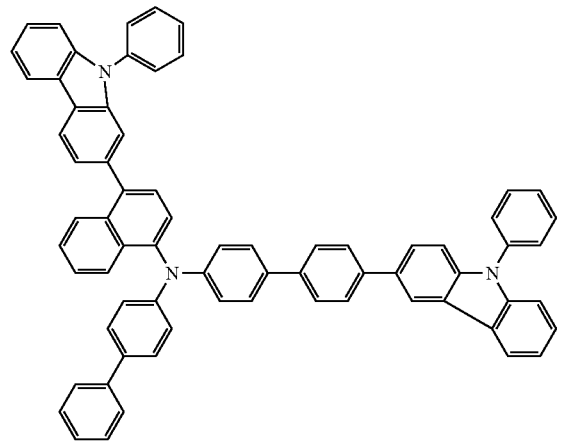
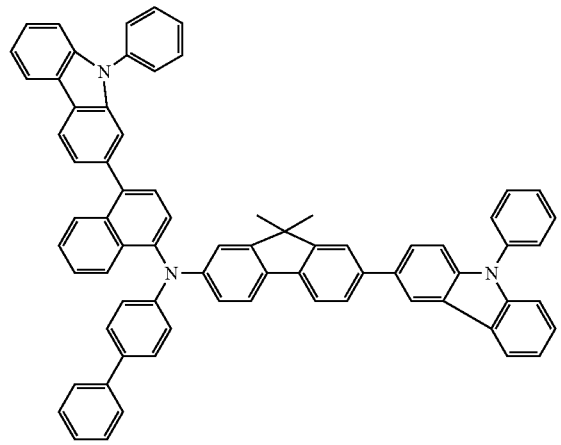
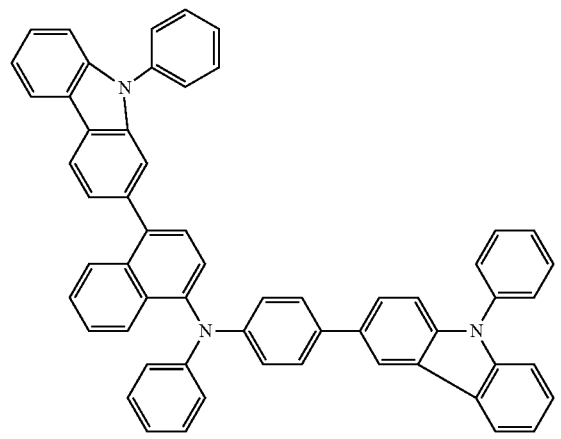
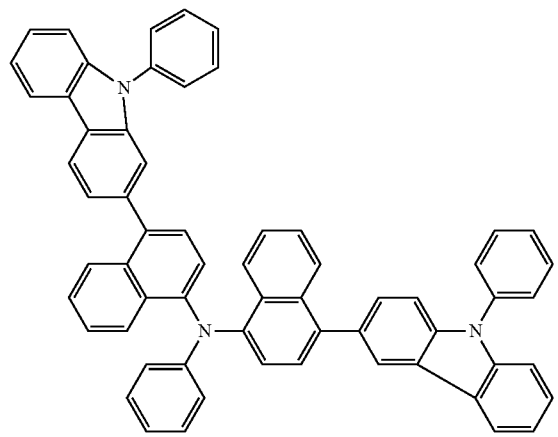
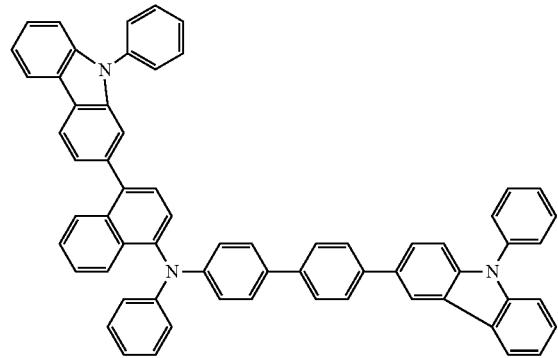
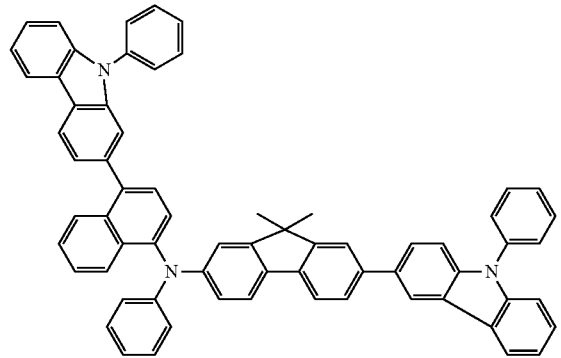
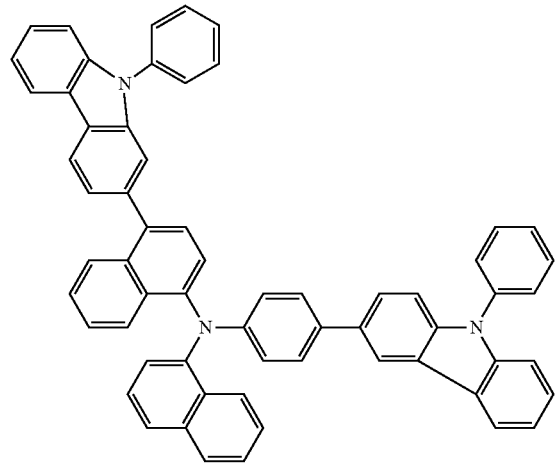
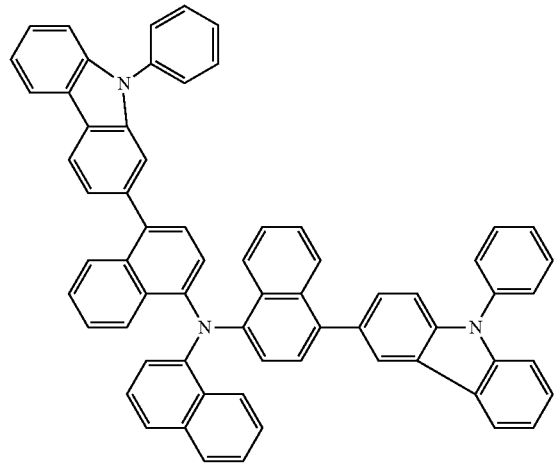

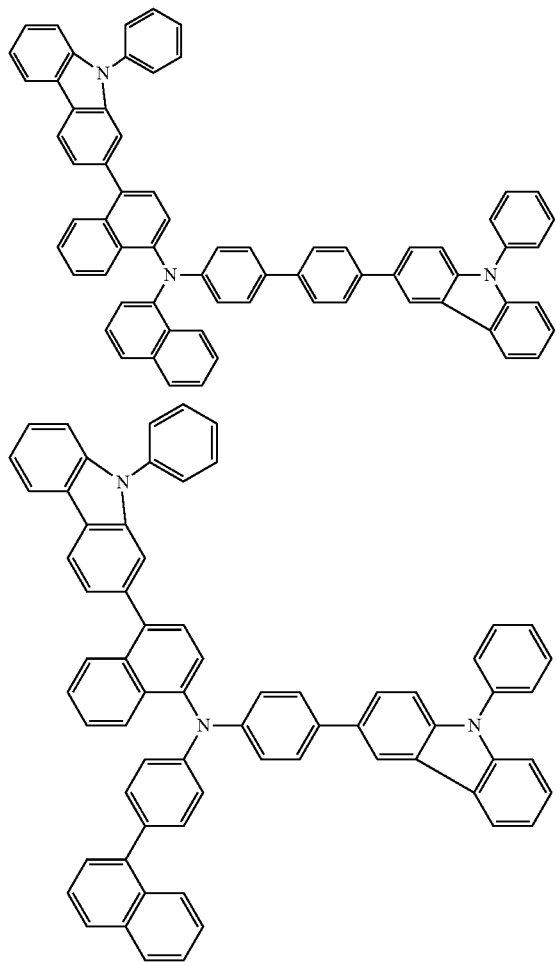
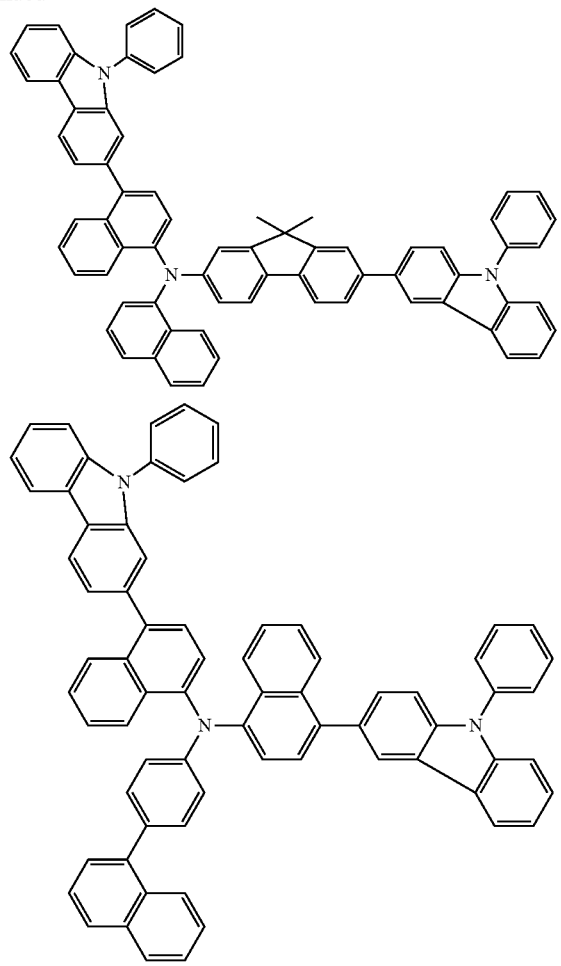
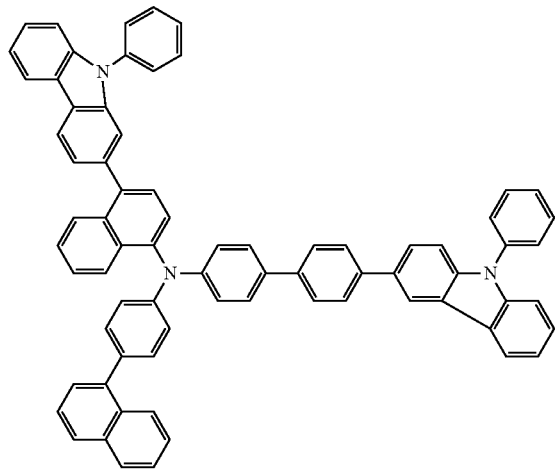
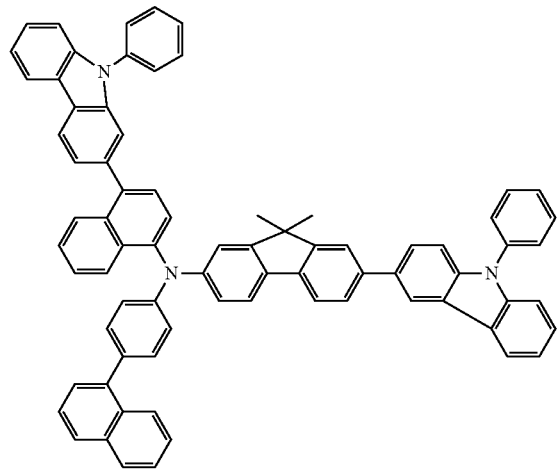

[Chem. 15]
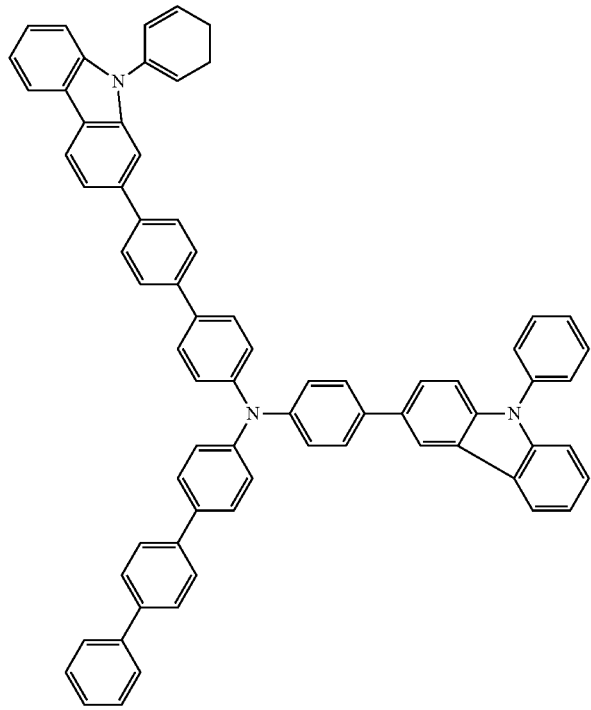
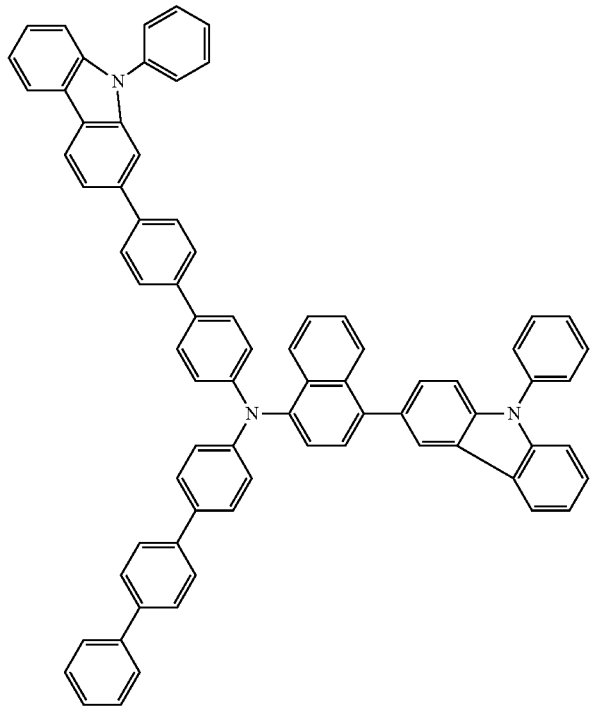
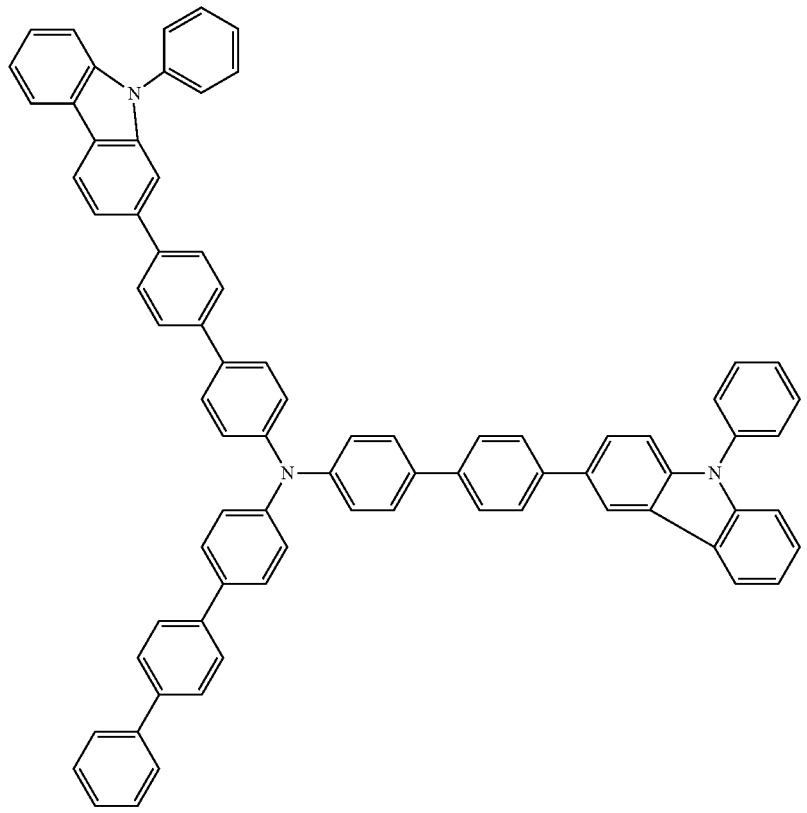

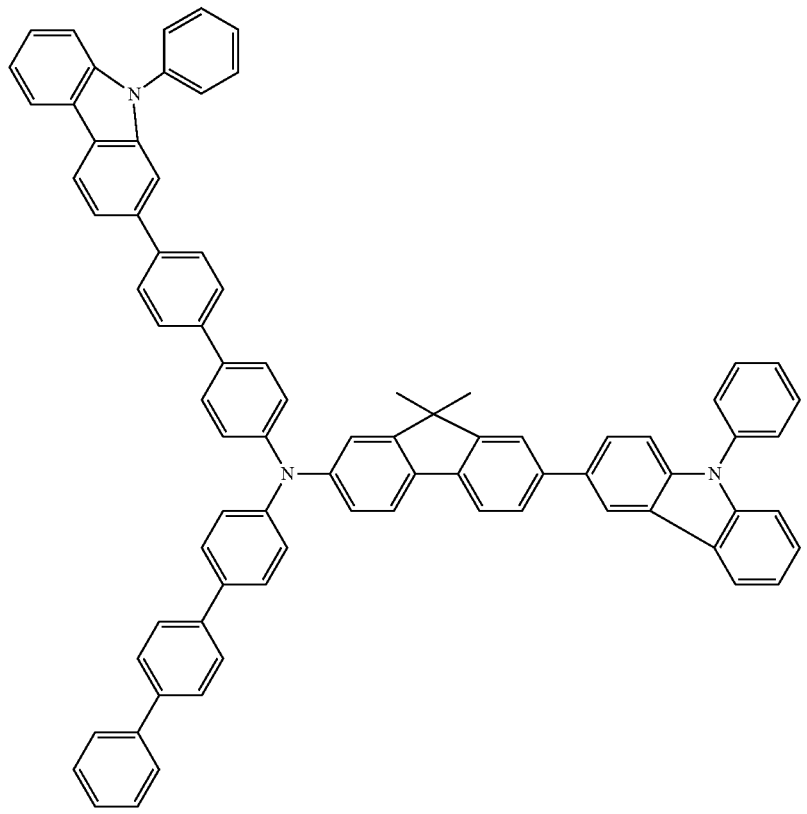
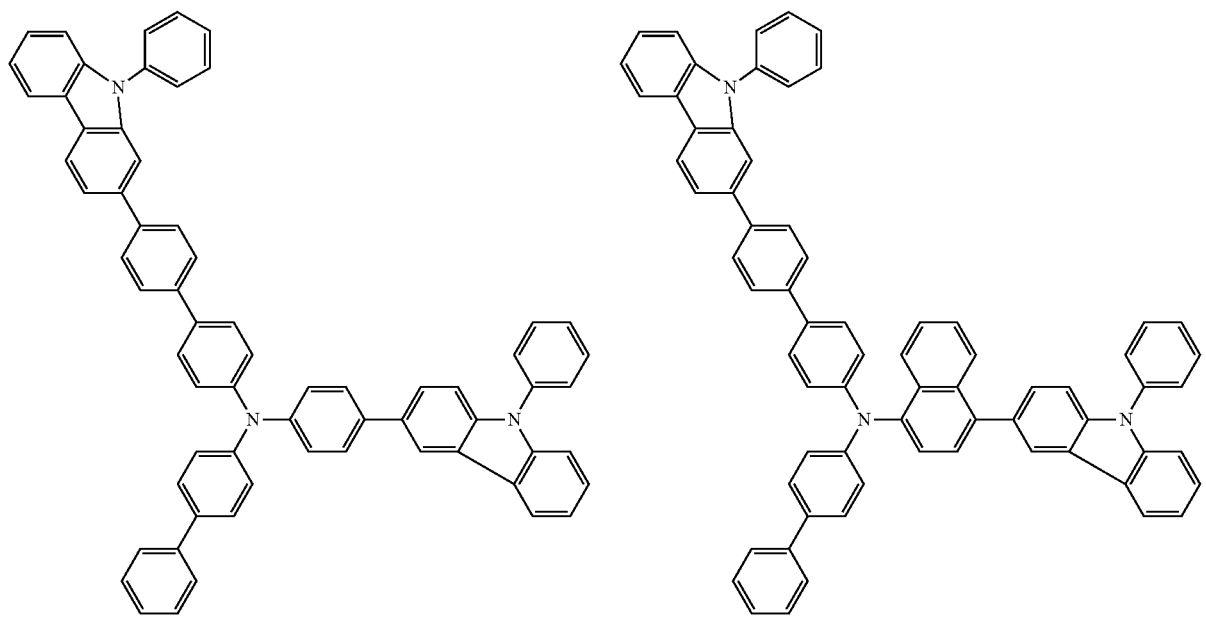

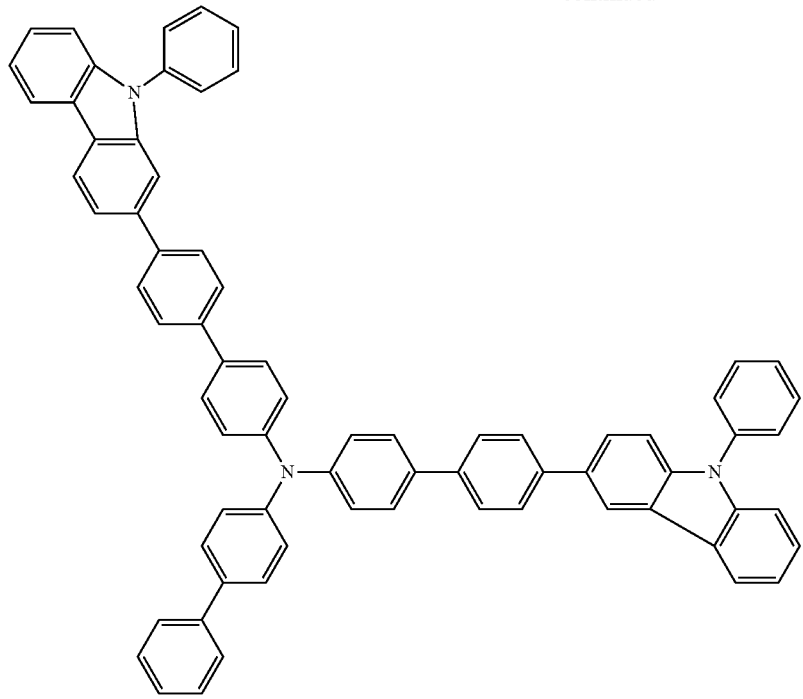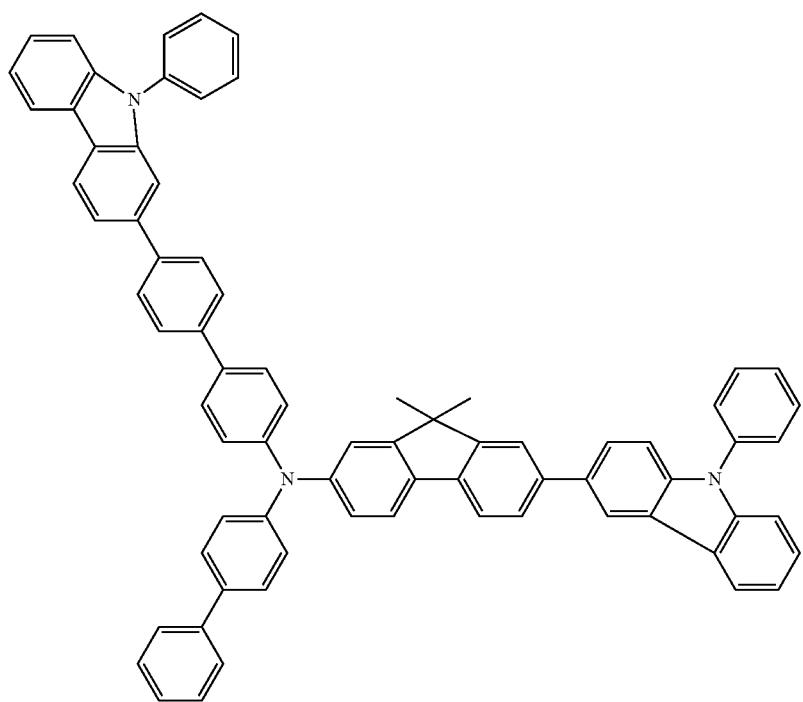

-continued
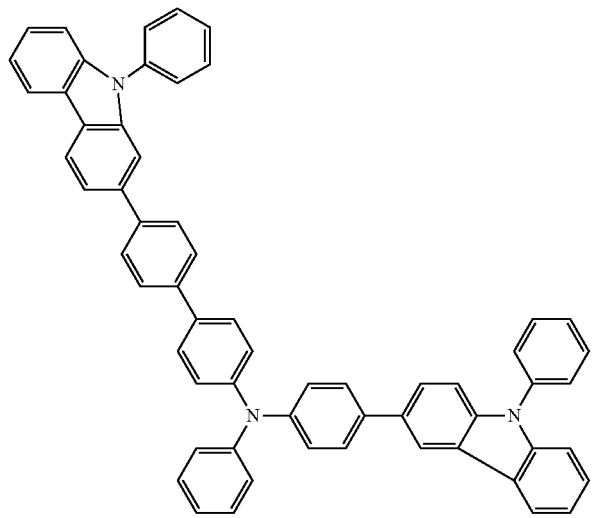
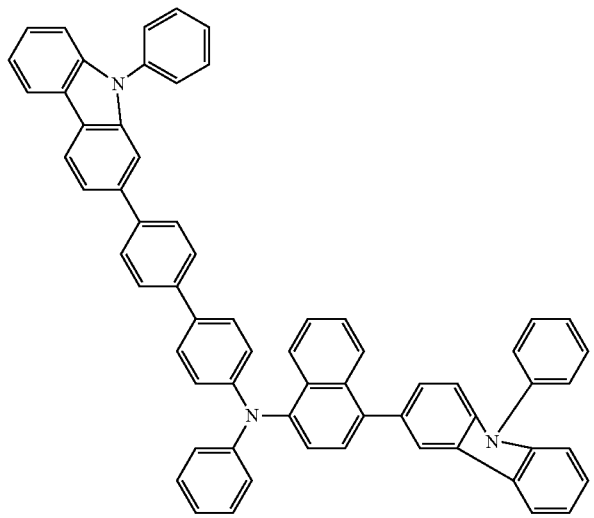
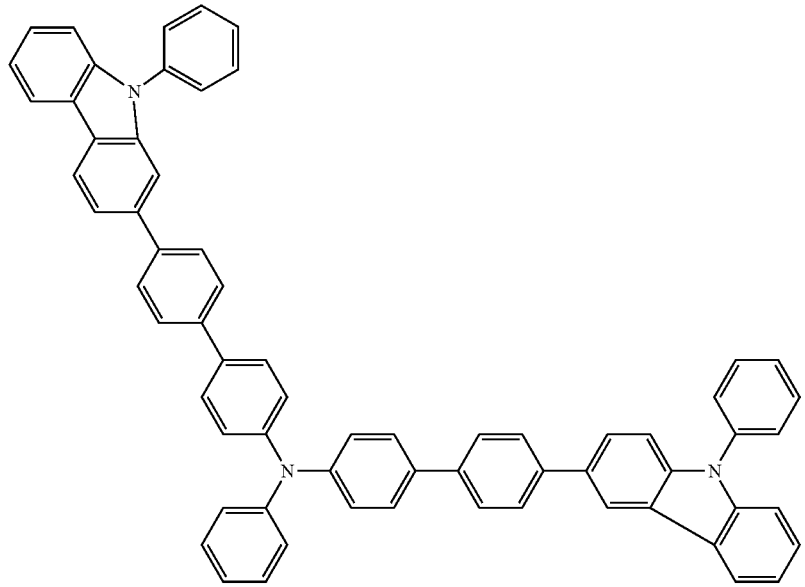
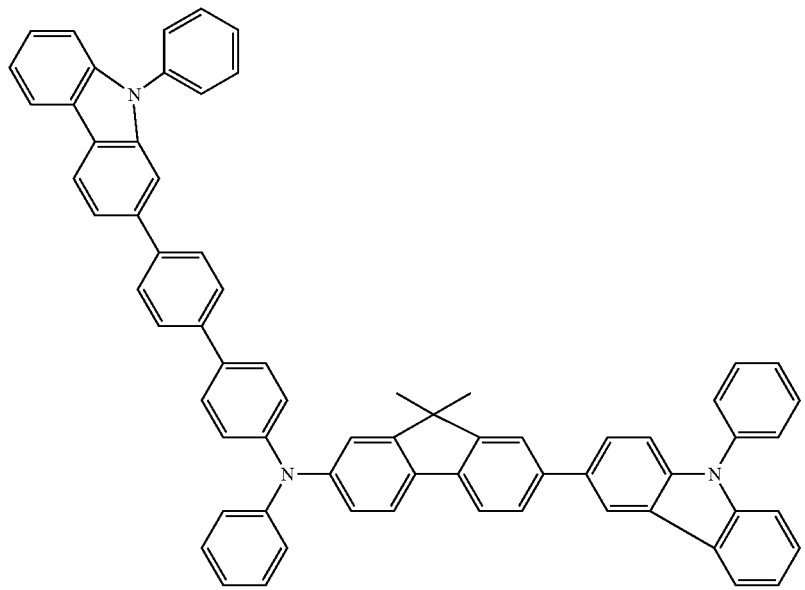

-continued
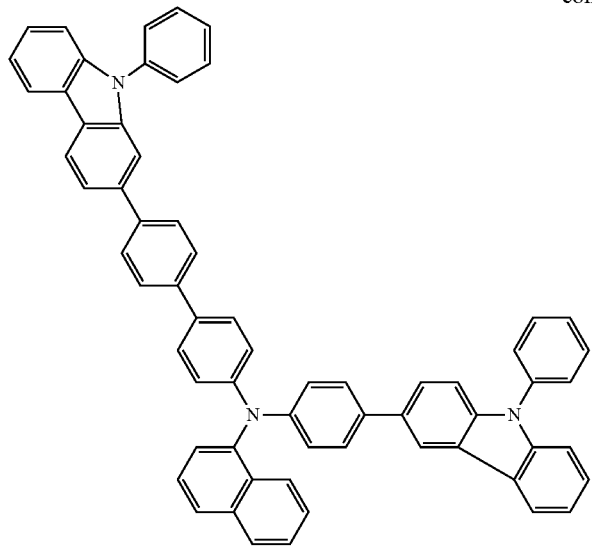
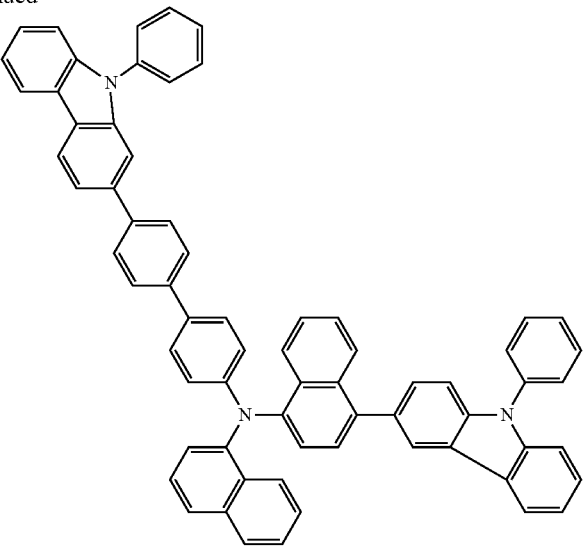
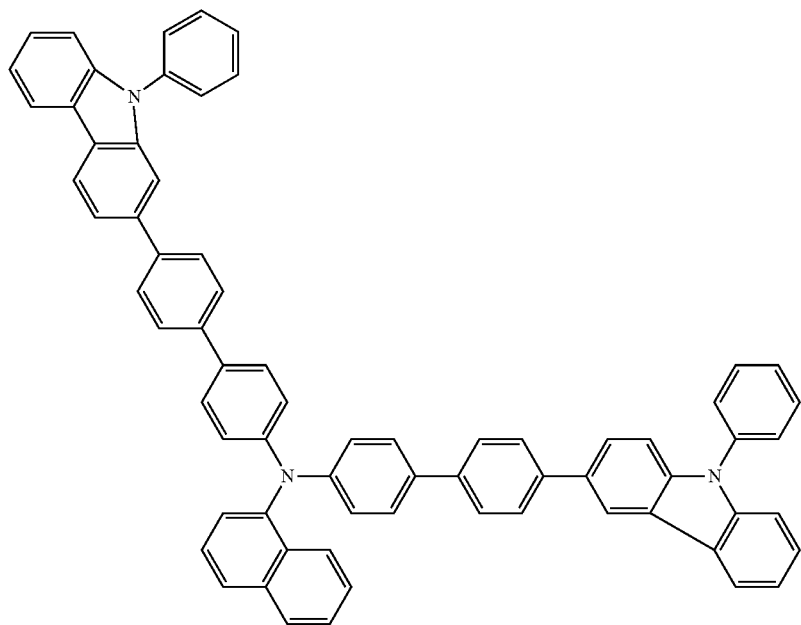

-continued
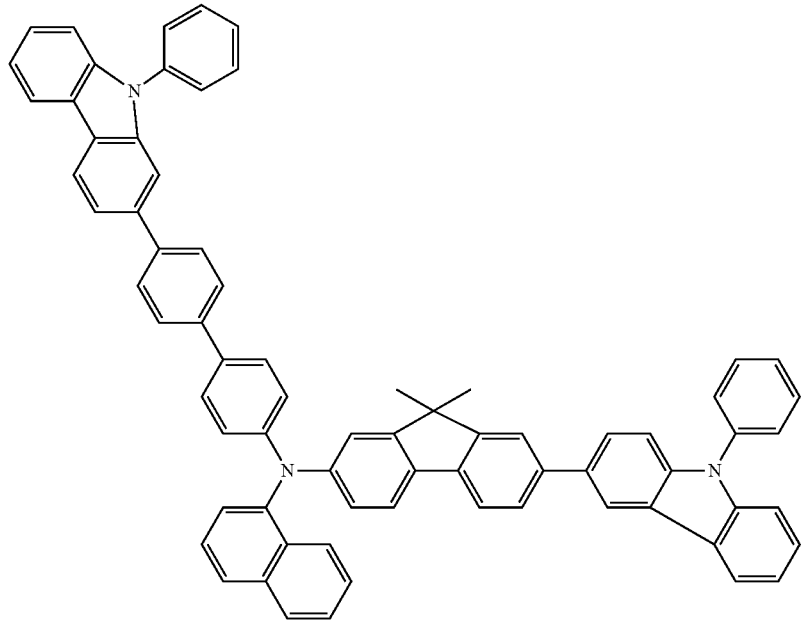
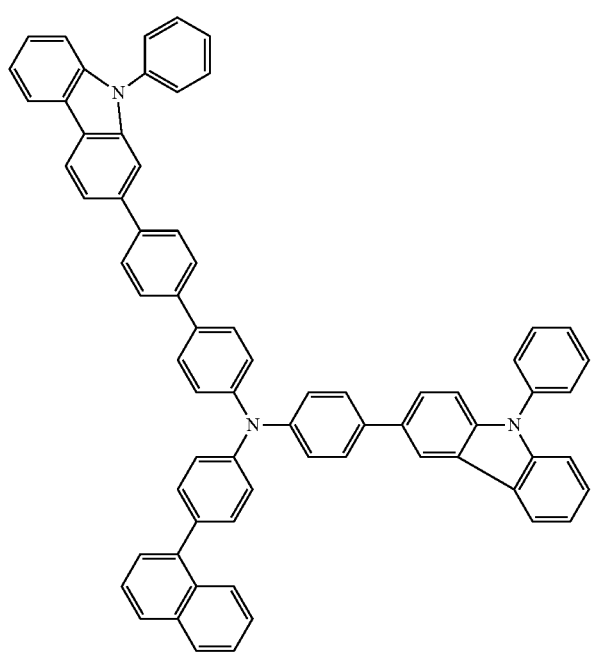
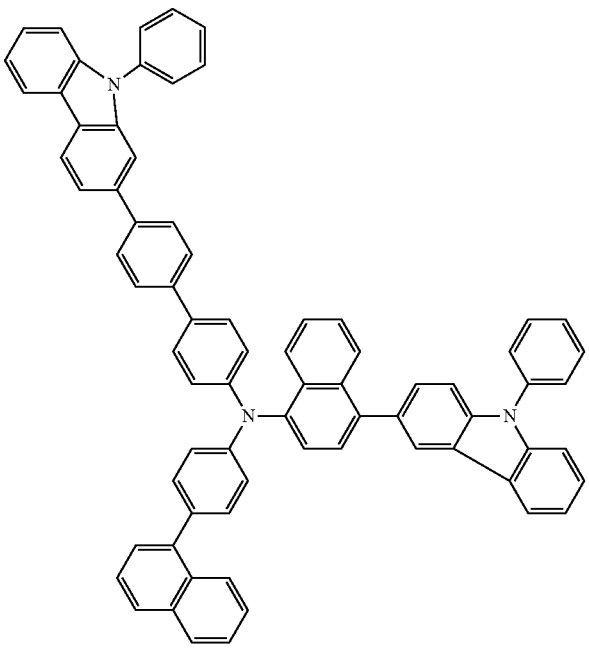

-continued
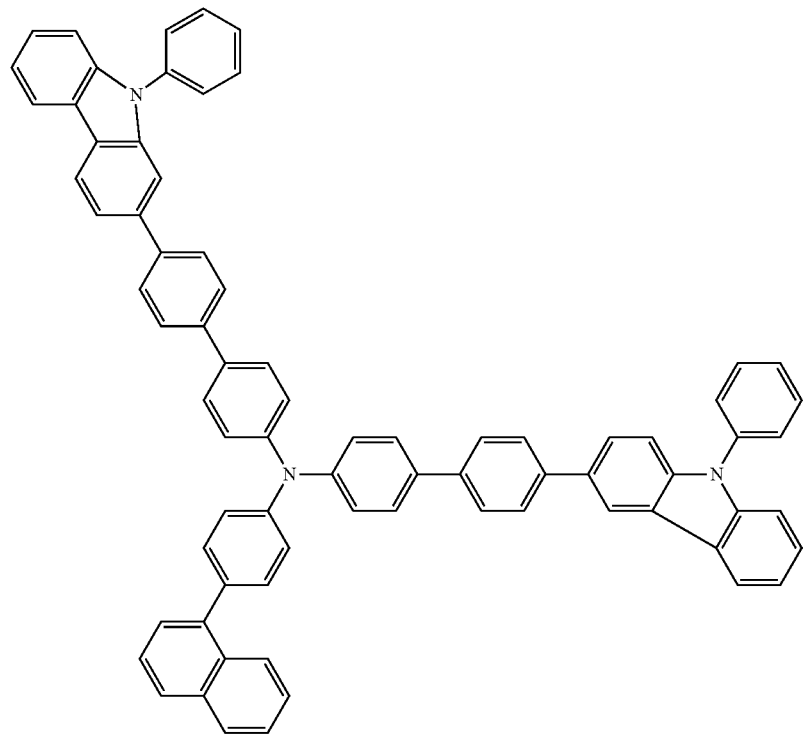
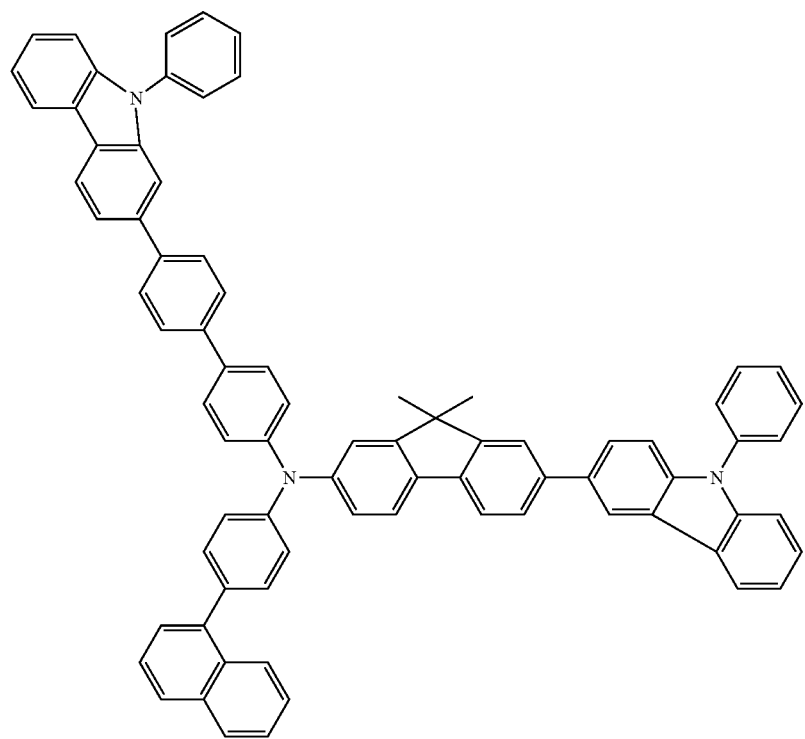

[Chem. 16]
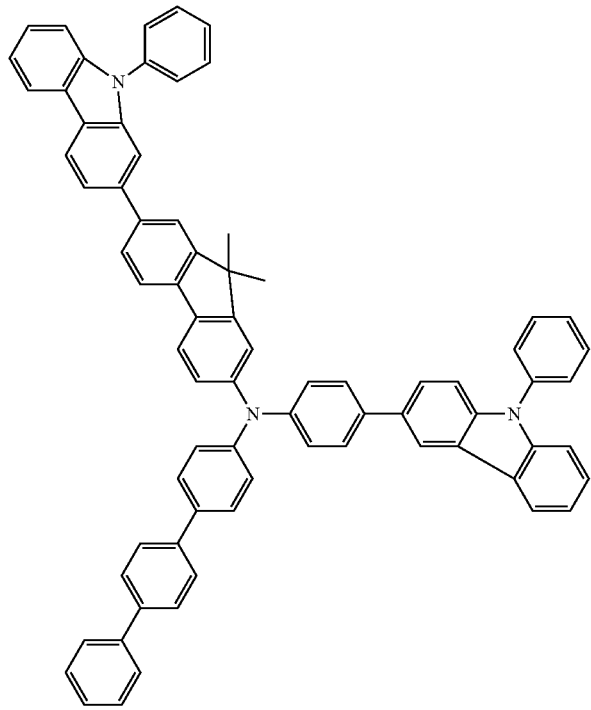
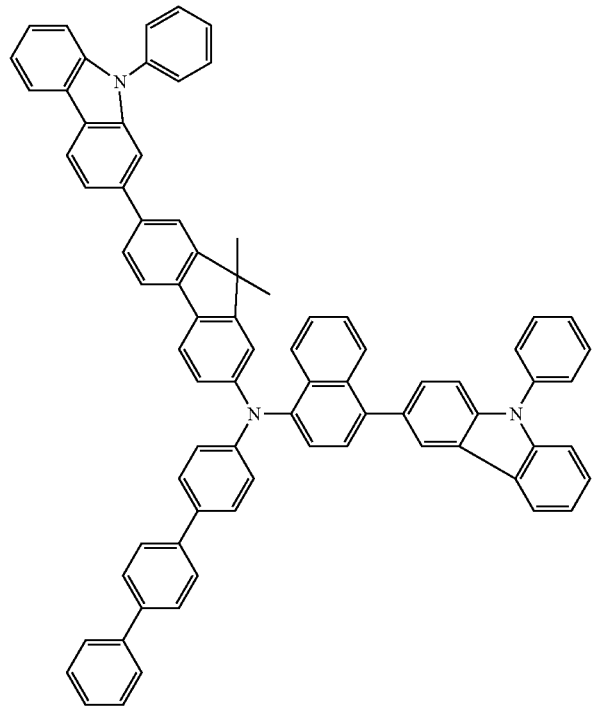
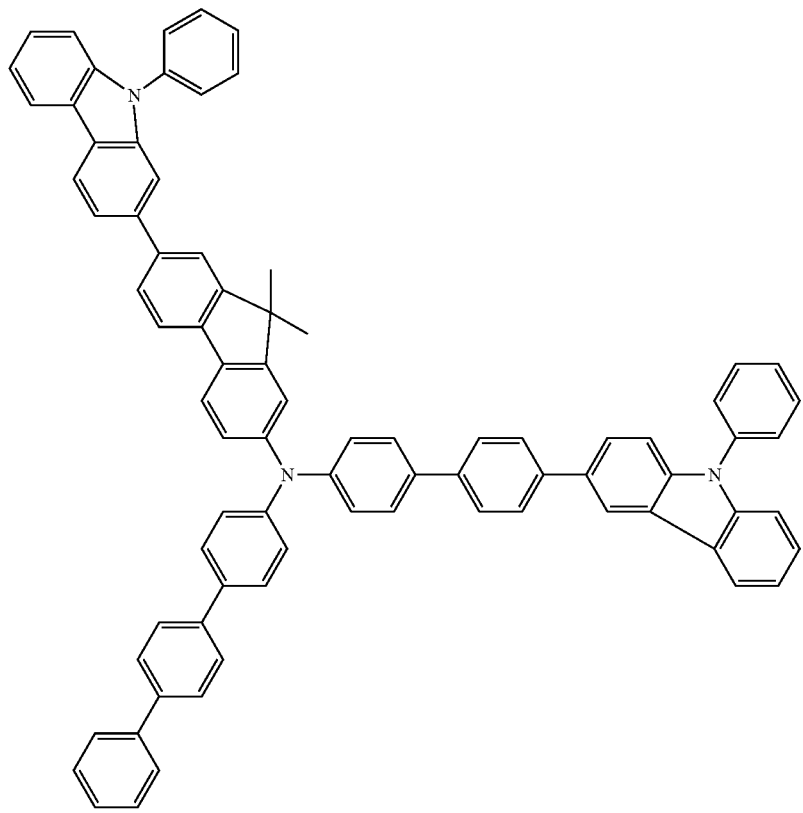

-continued
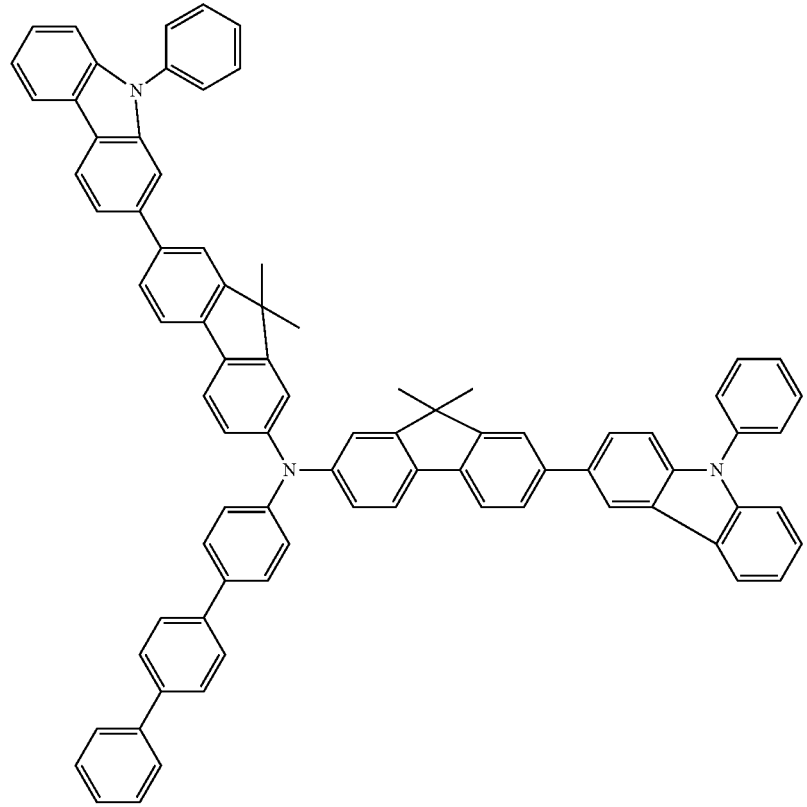
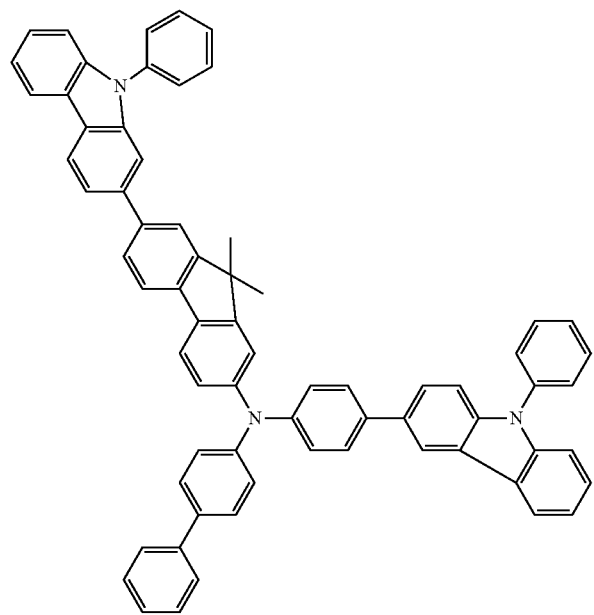

-continued
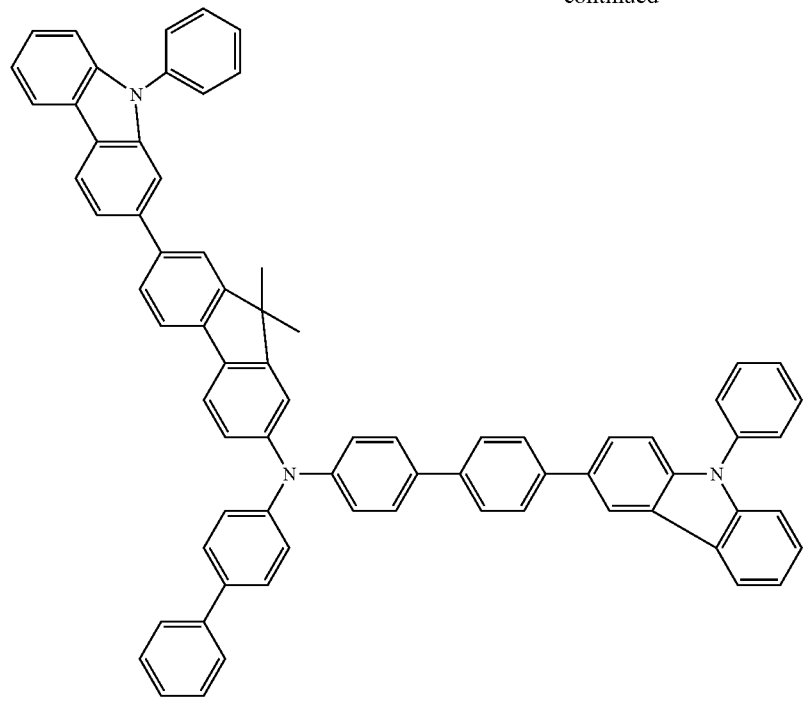
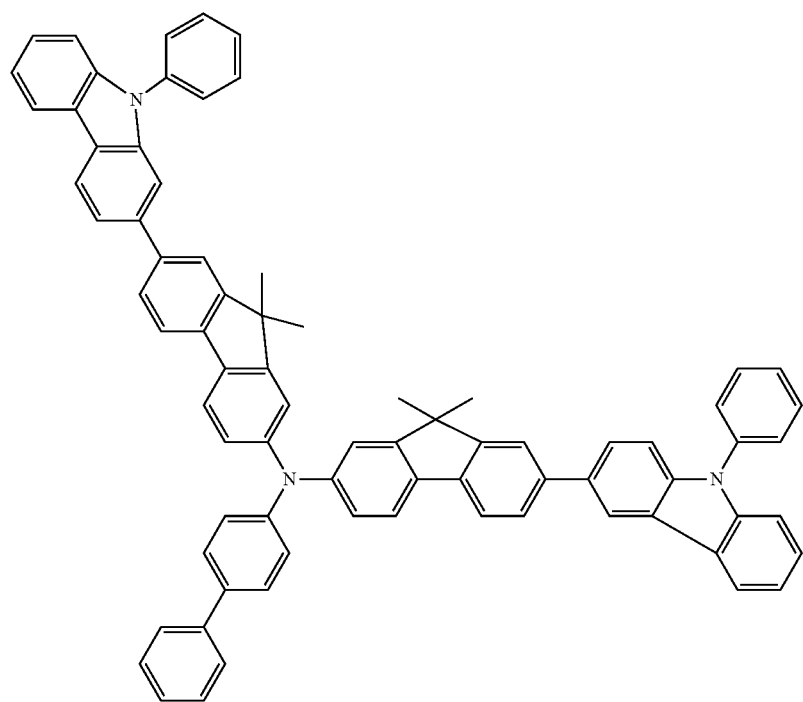

-continued
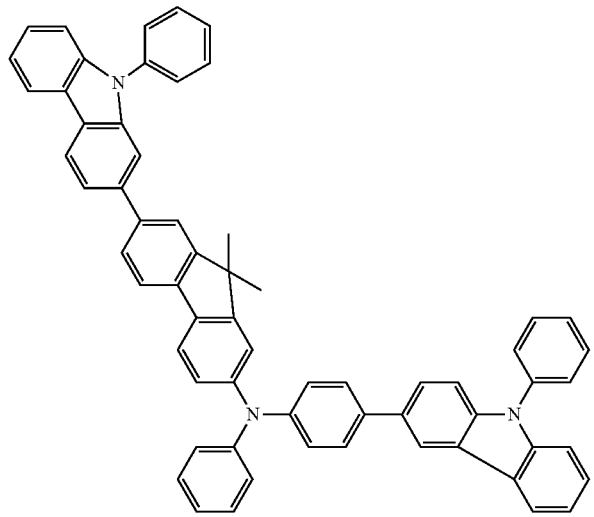
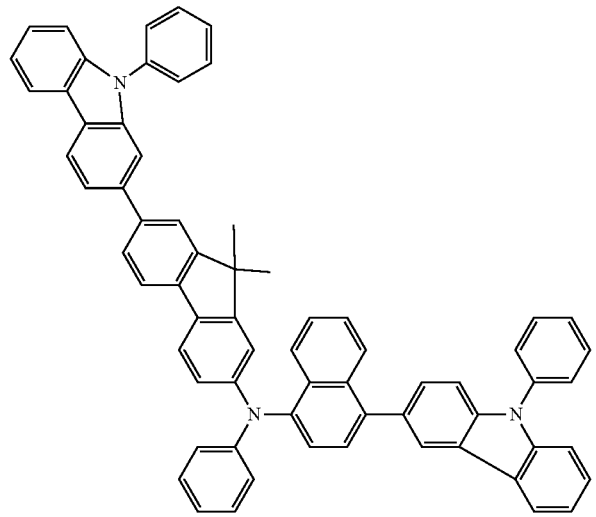
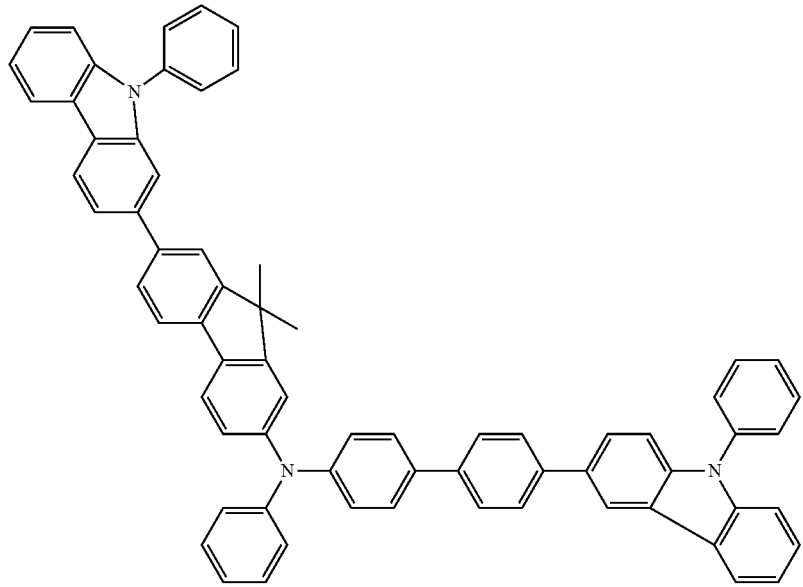
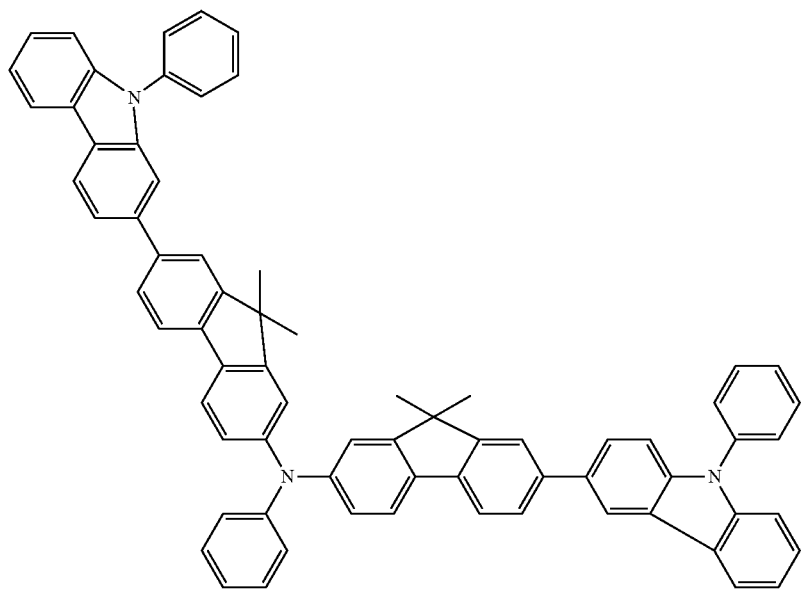

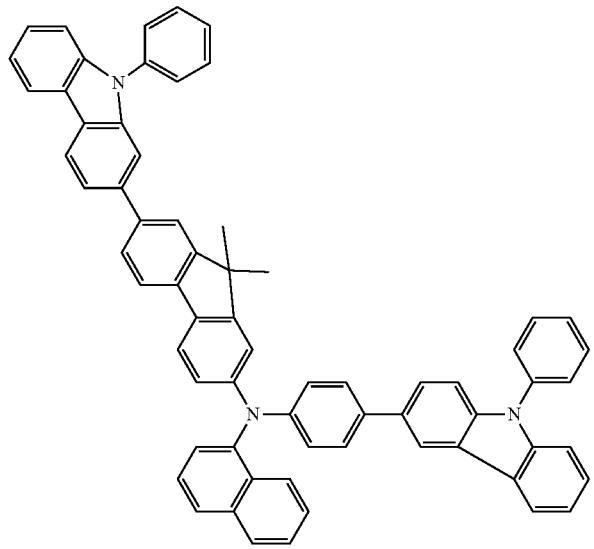
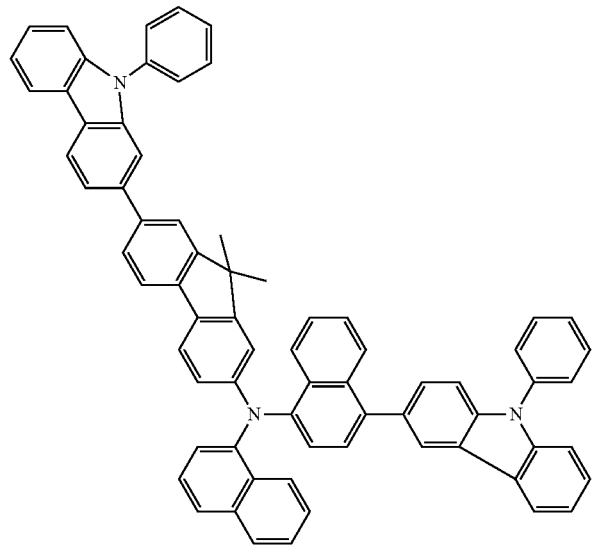
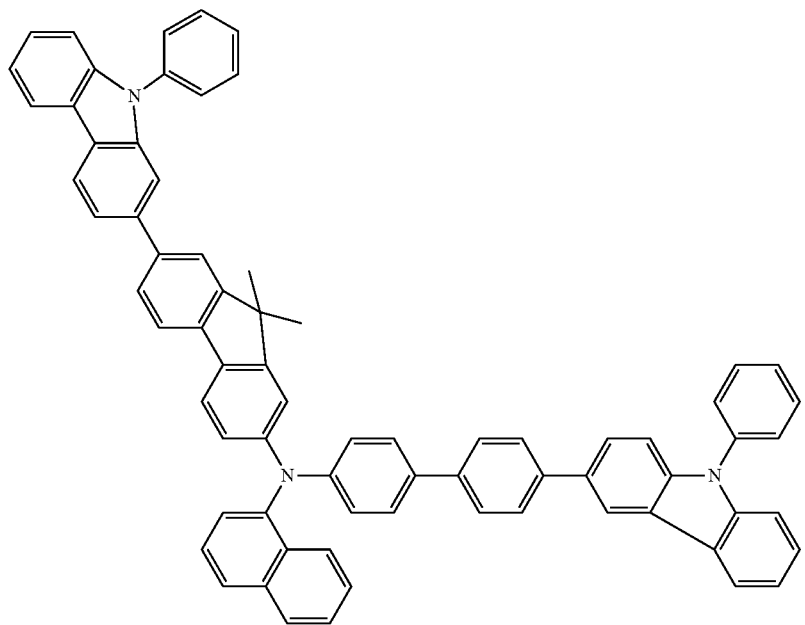

-continued
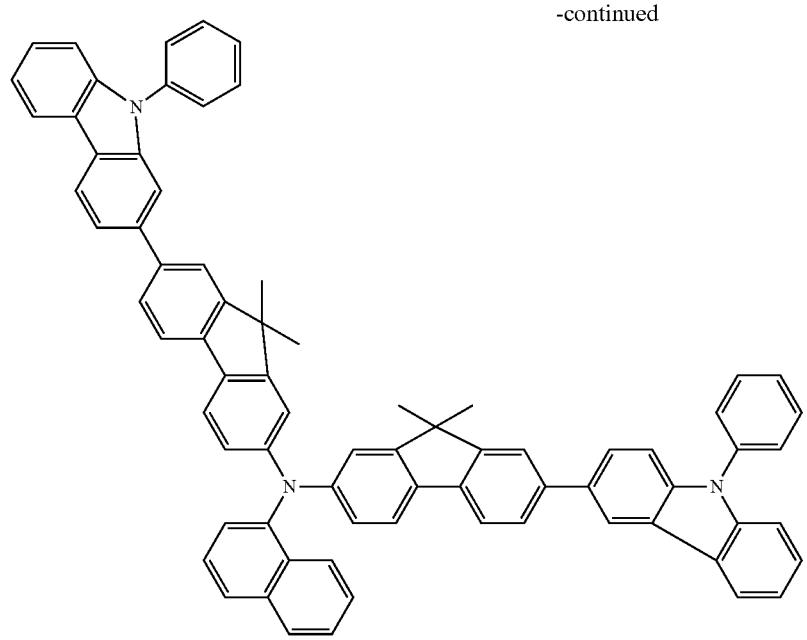
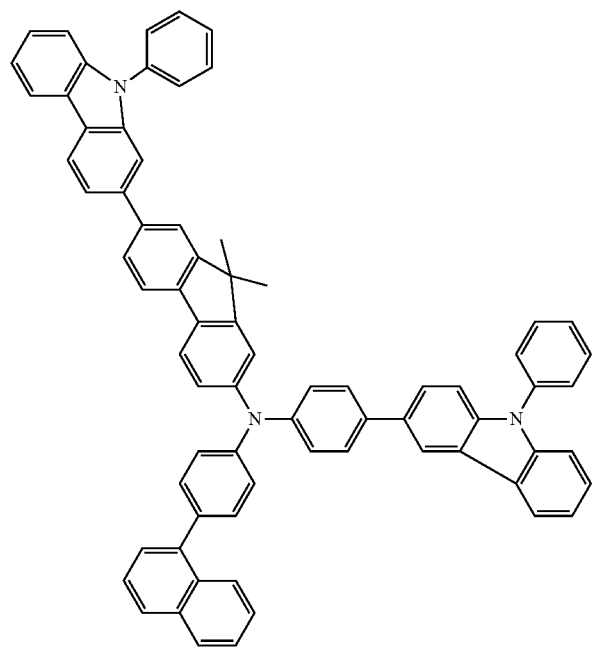
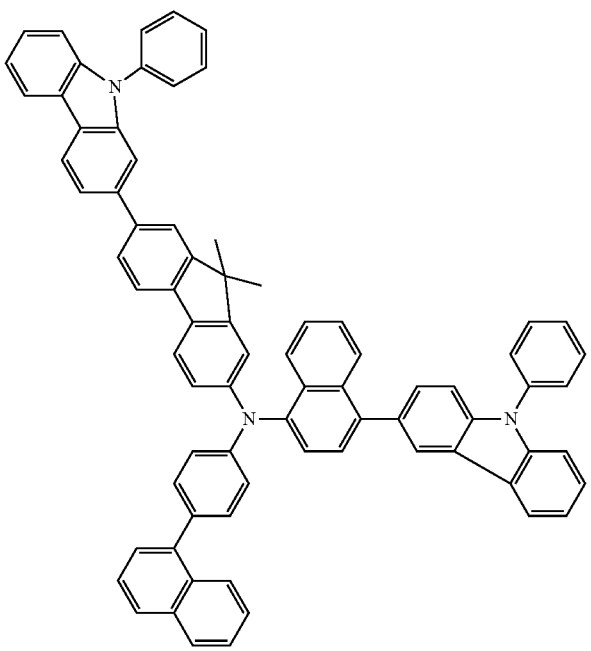

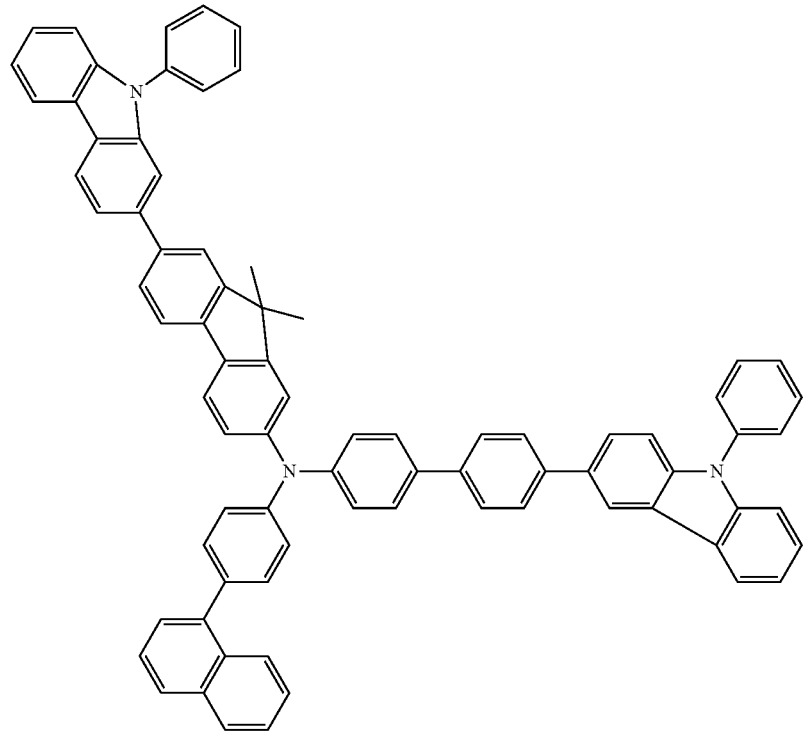
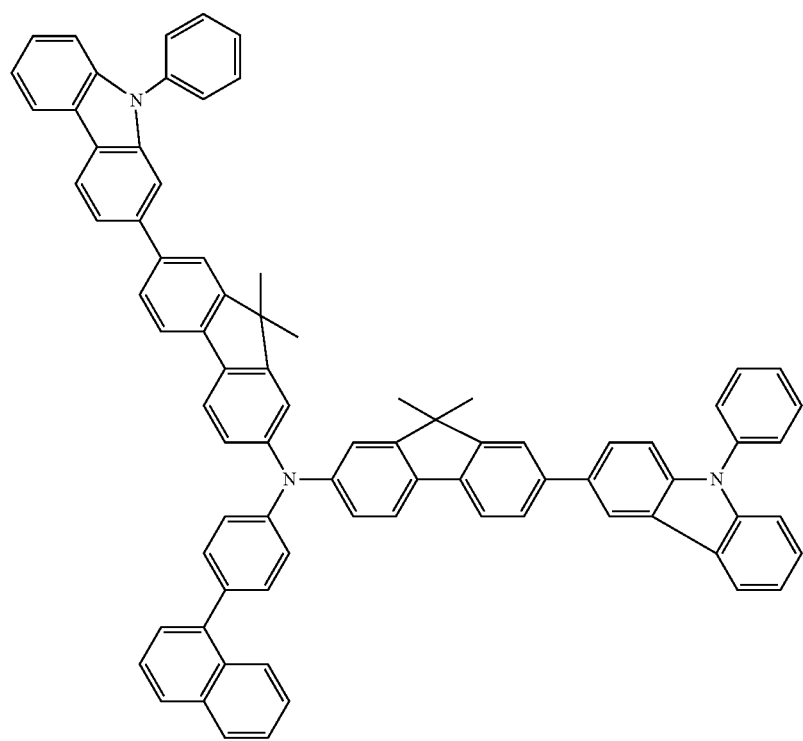

[Chem. 17]
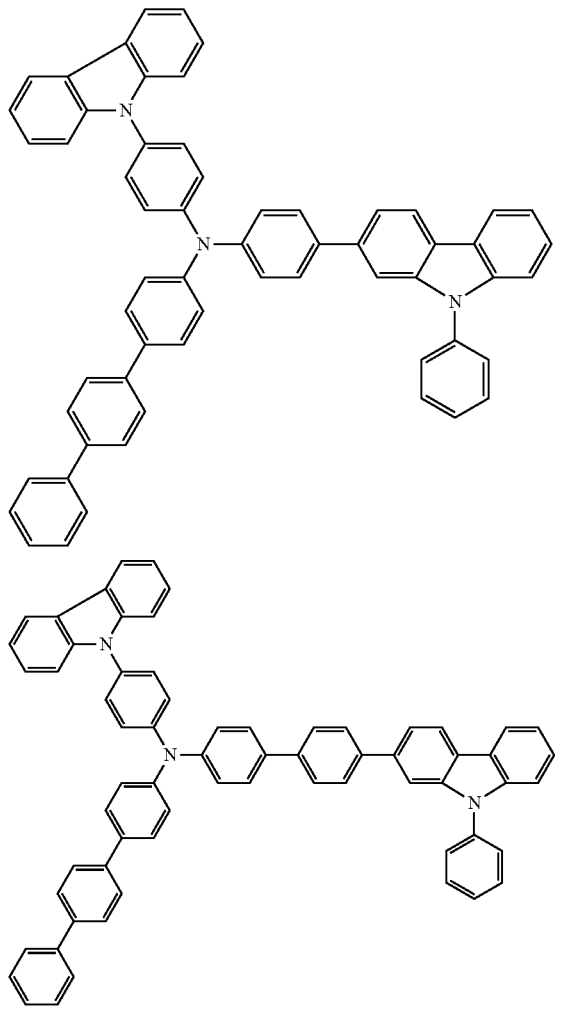
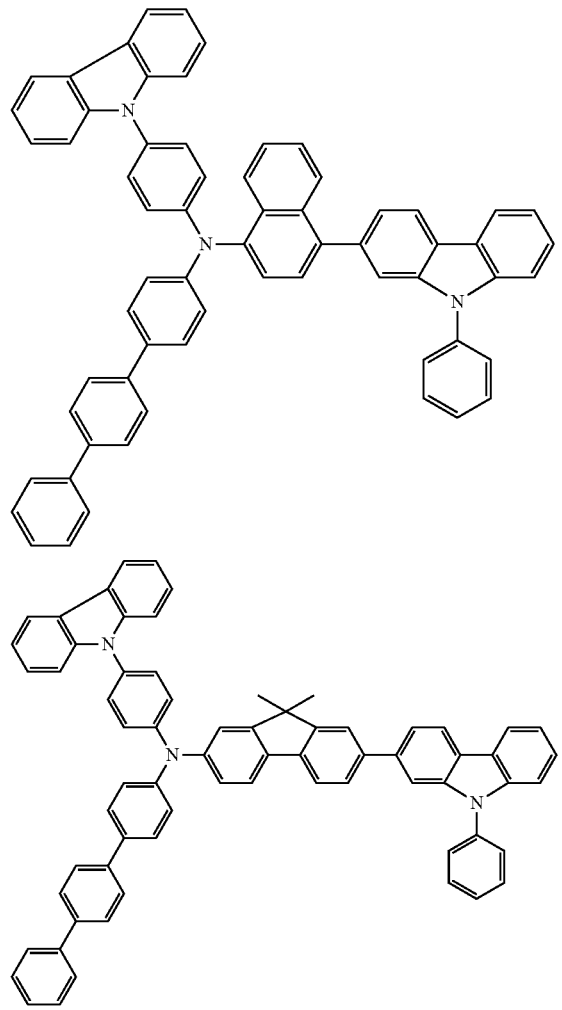
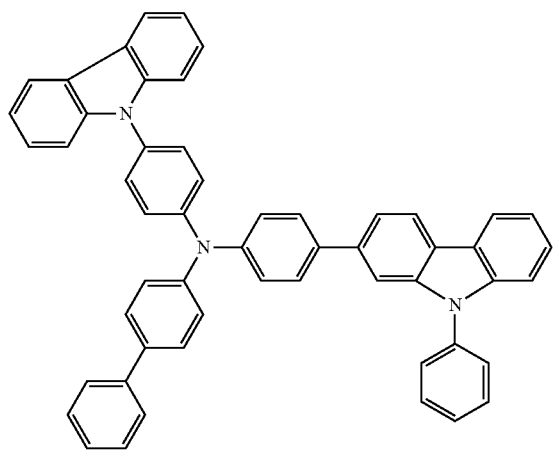
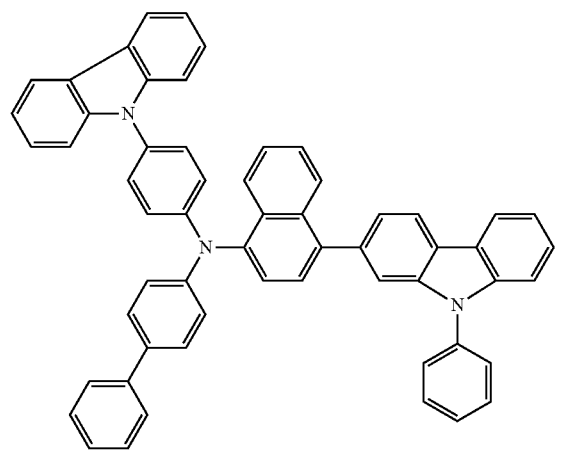

91
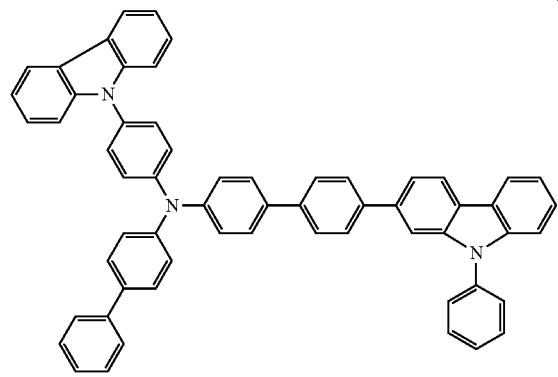
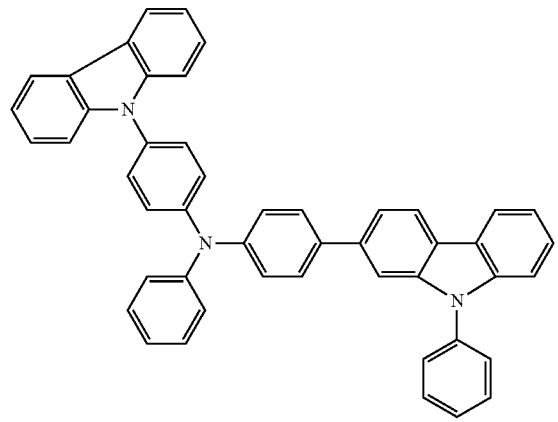
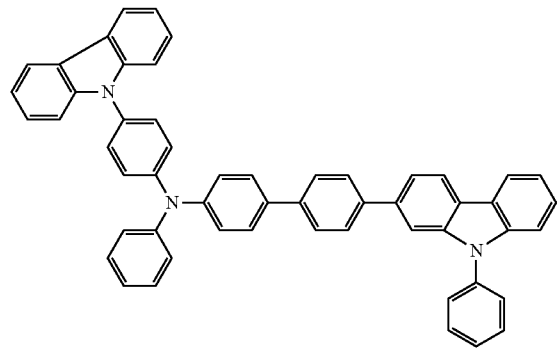
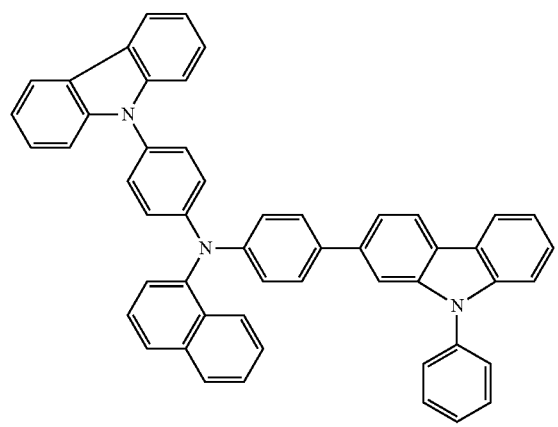
-continued
92
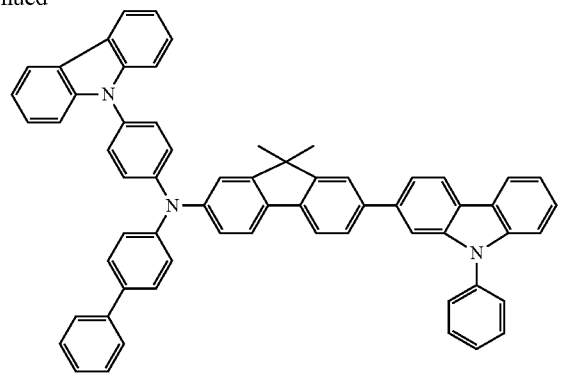
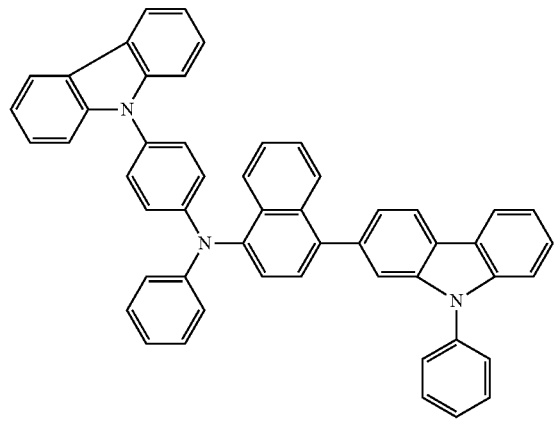
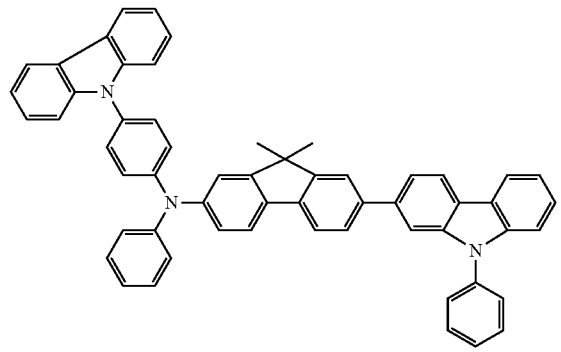
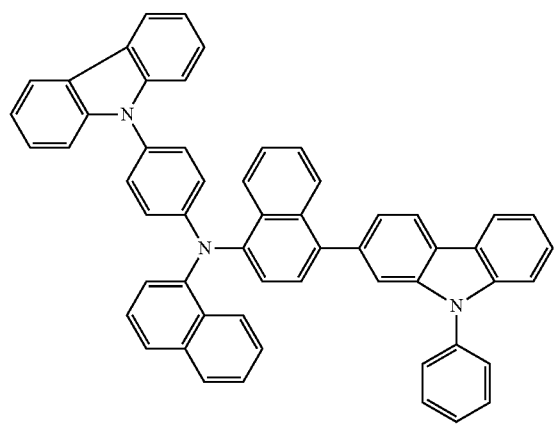

93 94
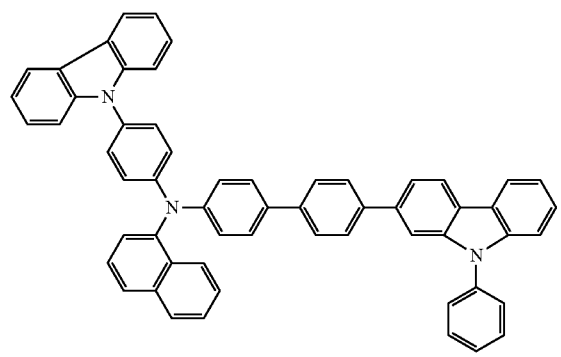
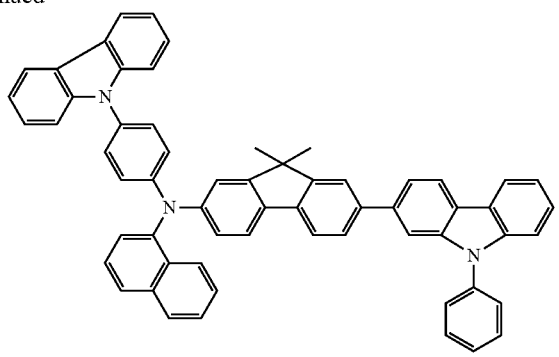
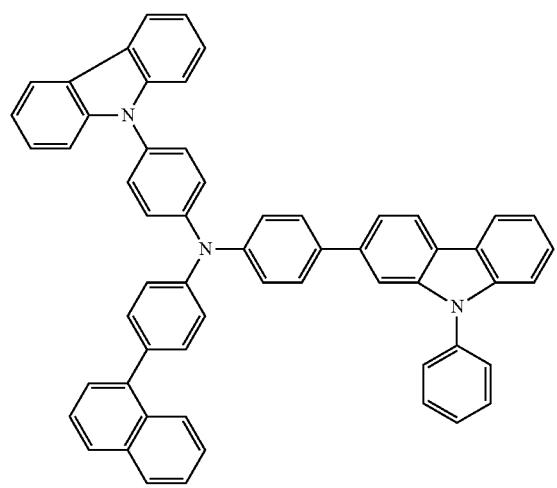
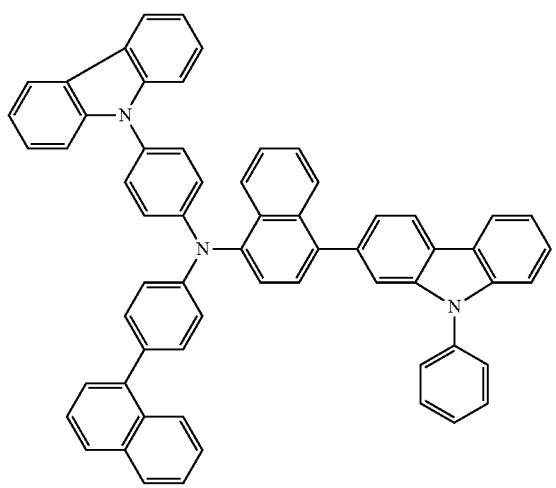
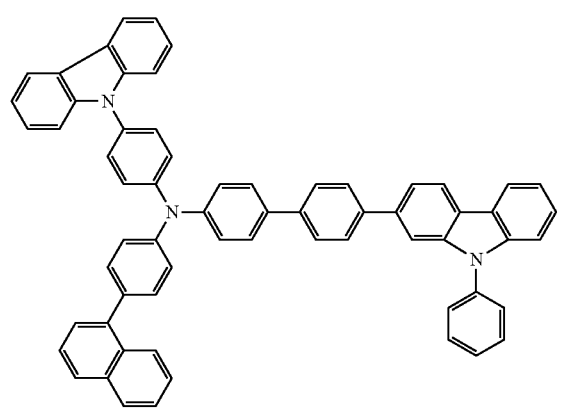
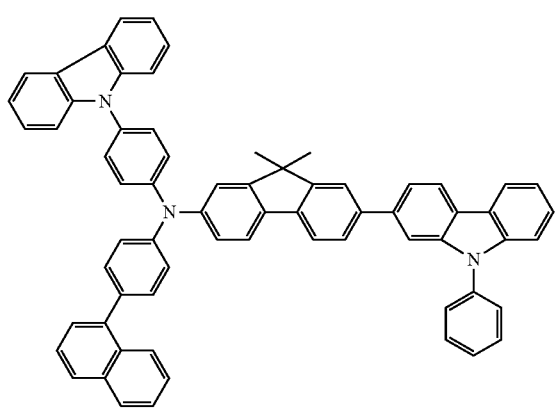

[Chem. 18]
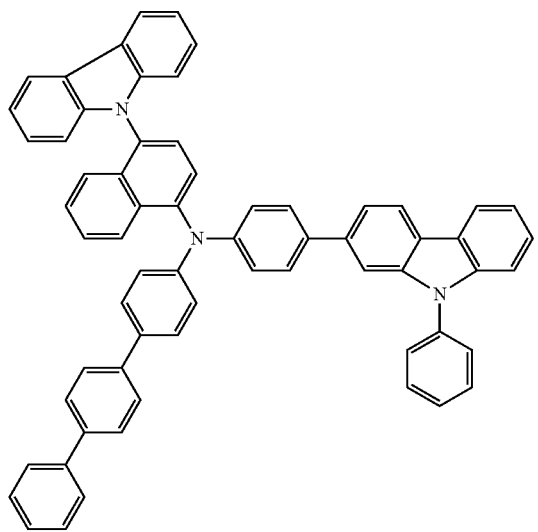
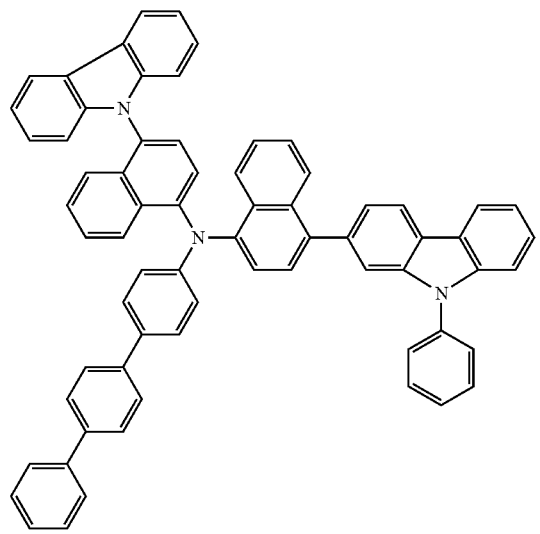
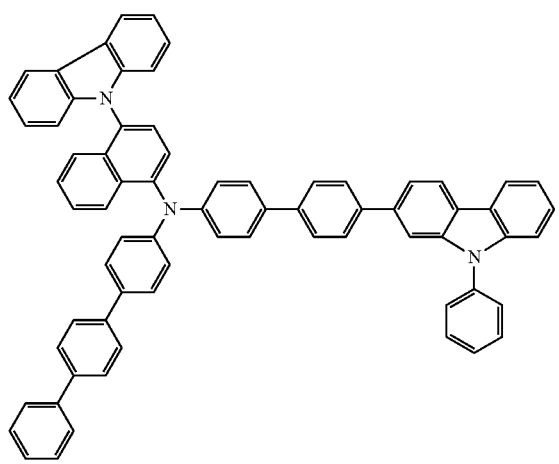
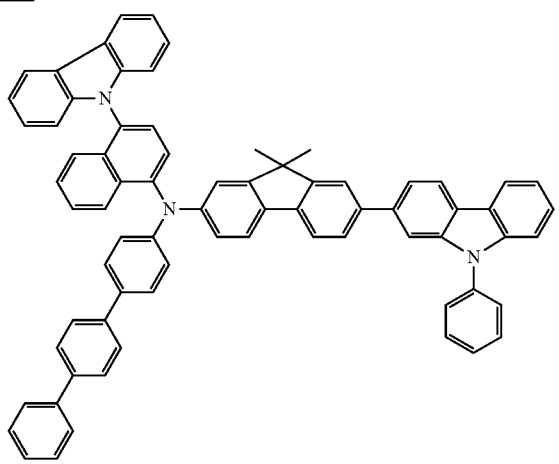
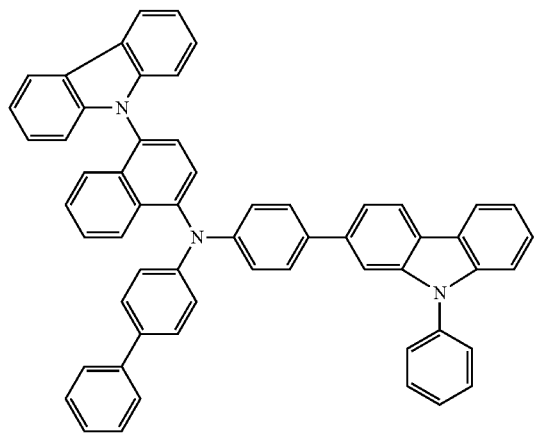
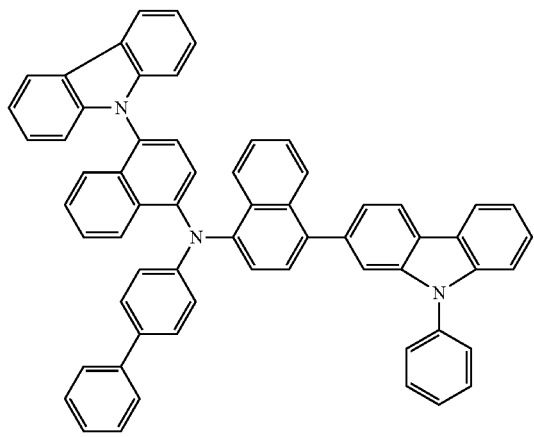

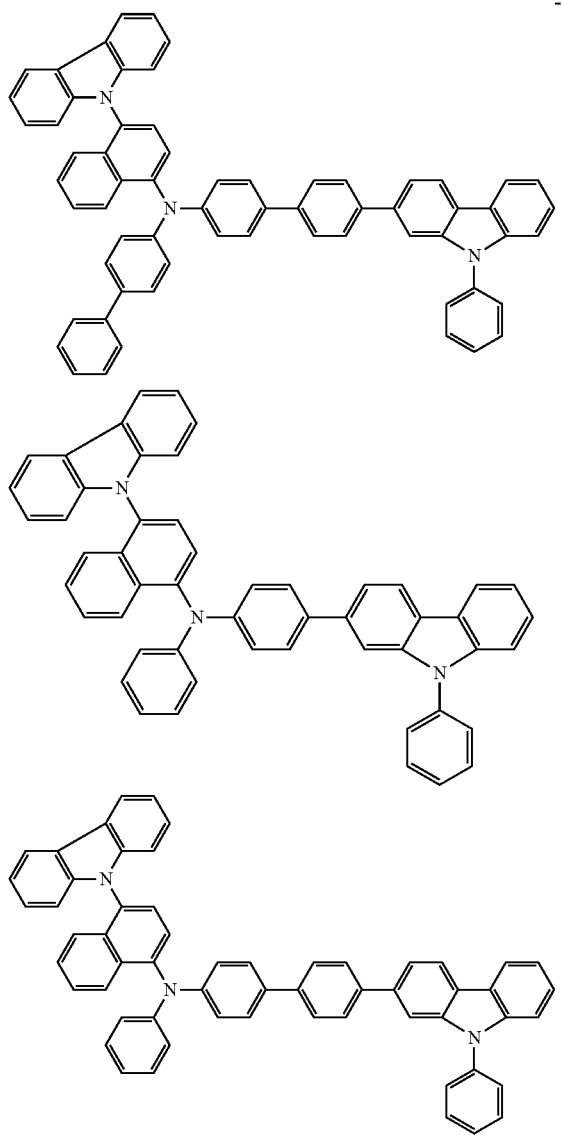
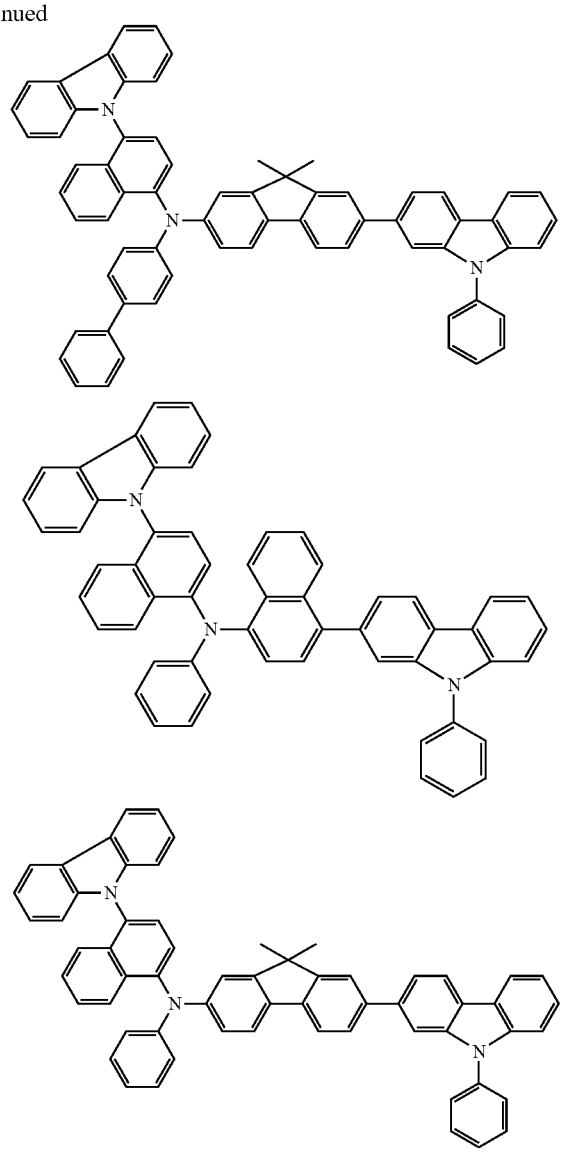
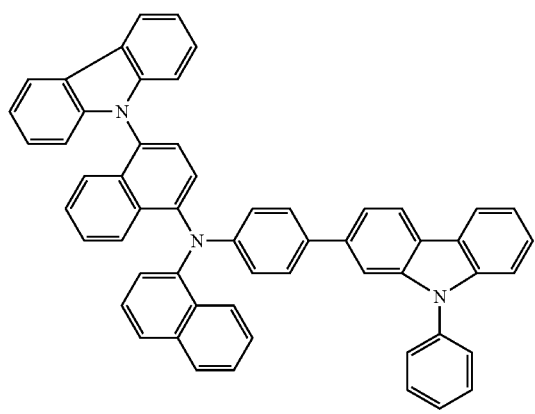
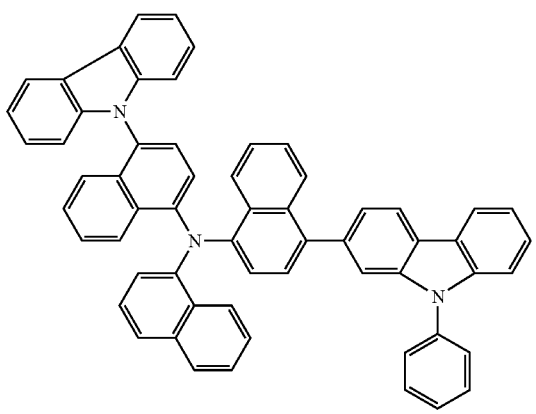

-continued
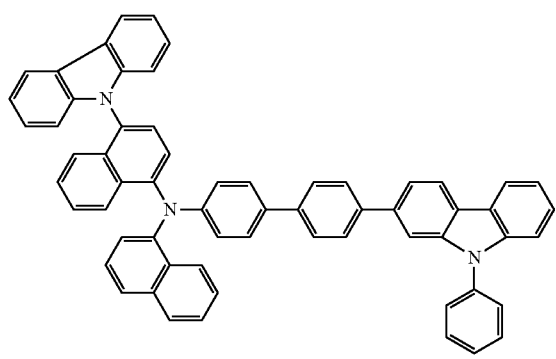
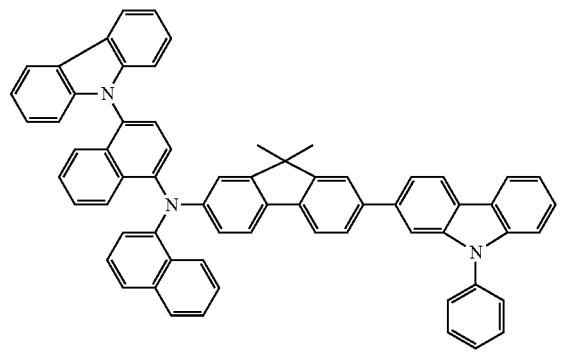
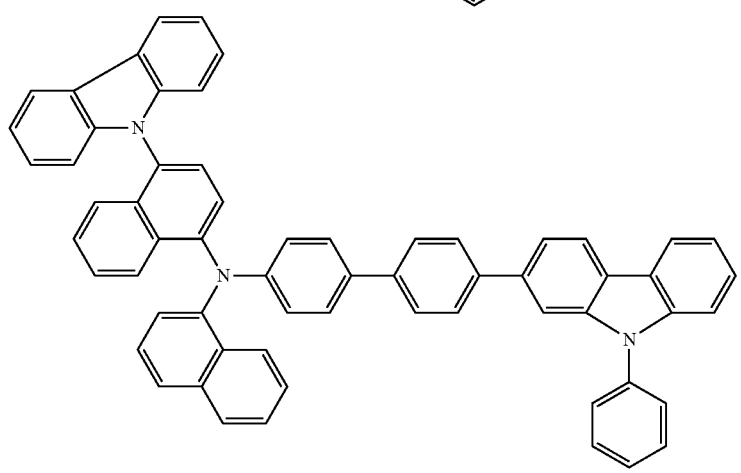
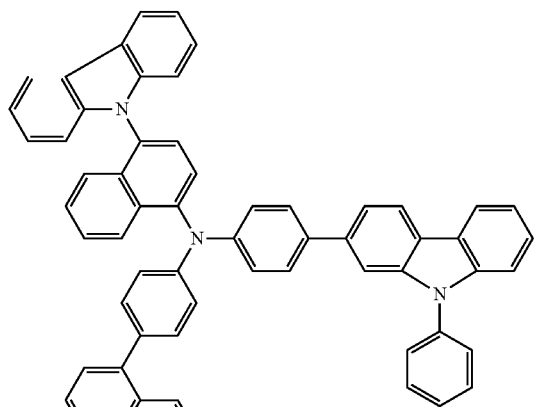
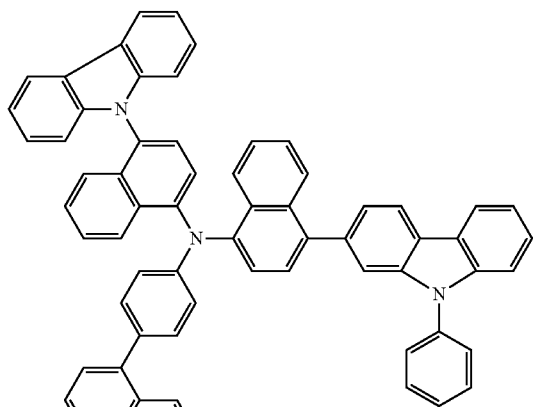
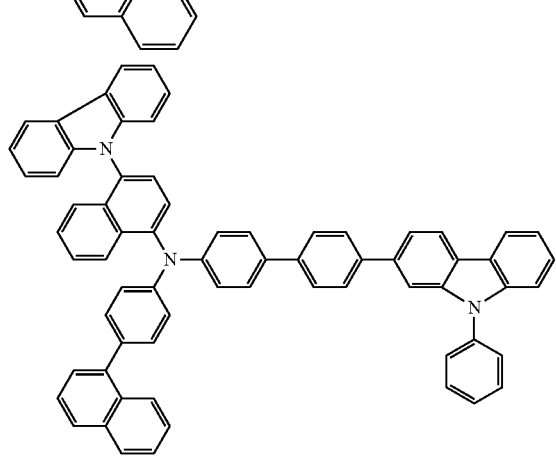
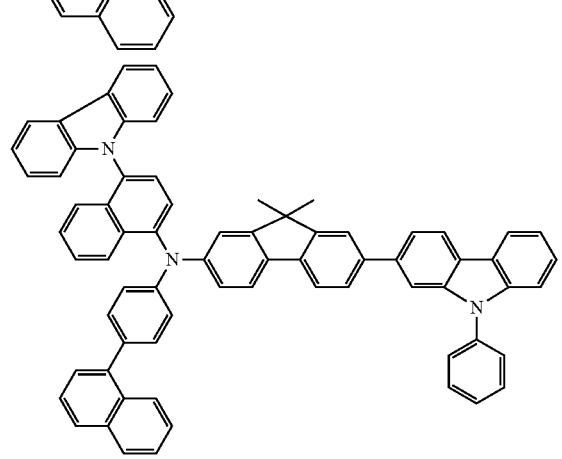

[Chem. 19]
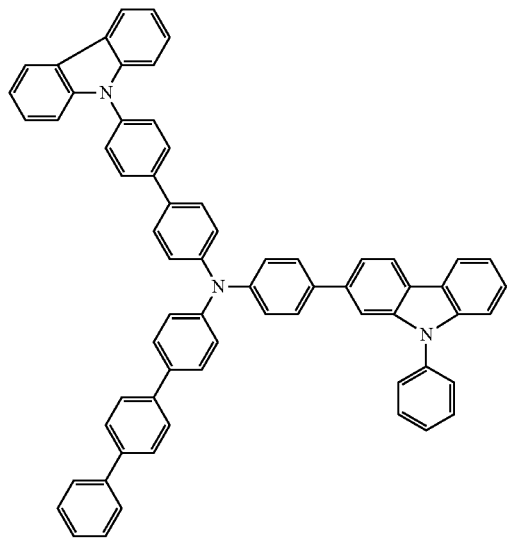
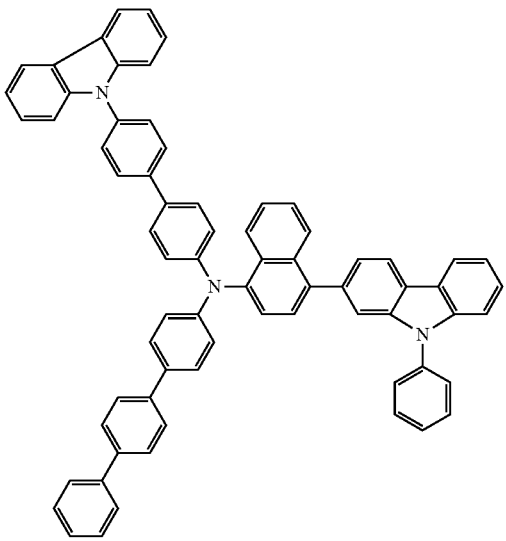
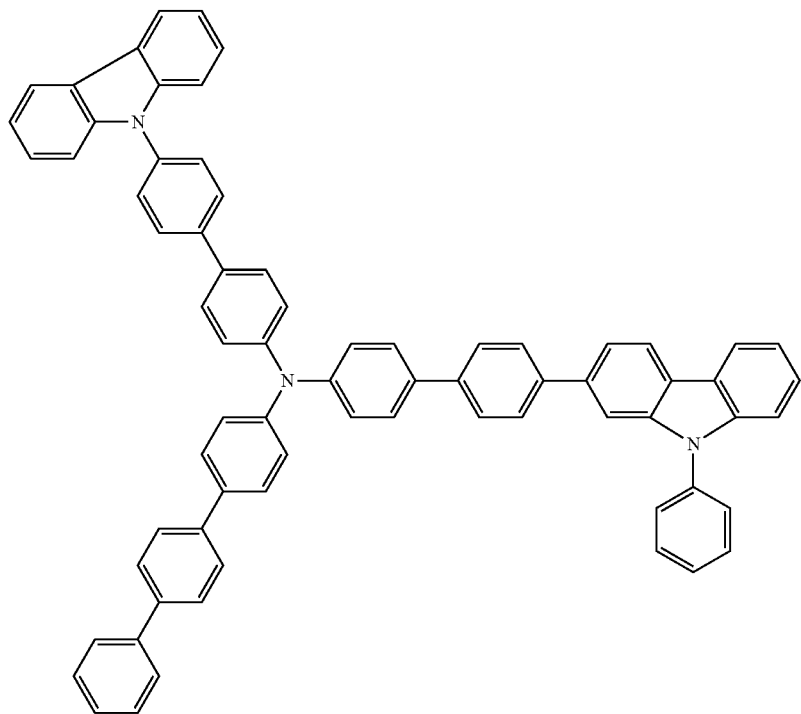

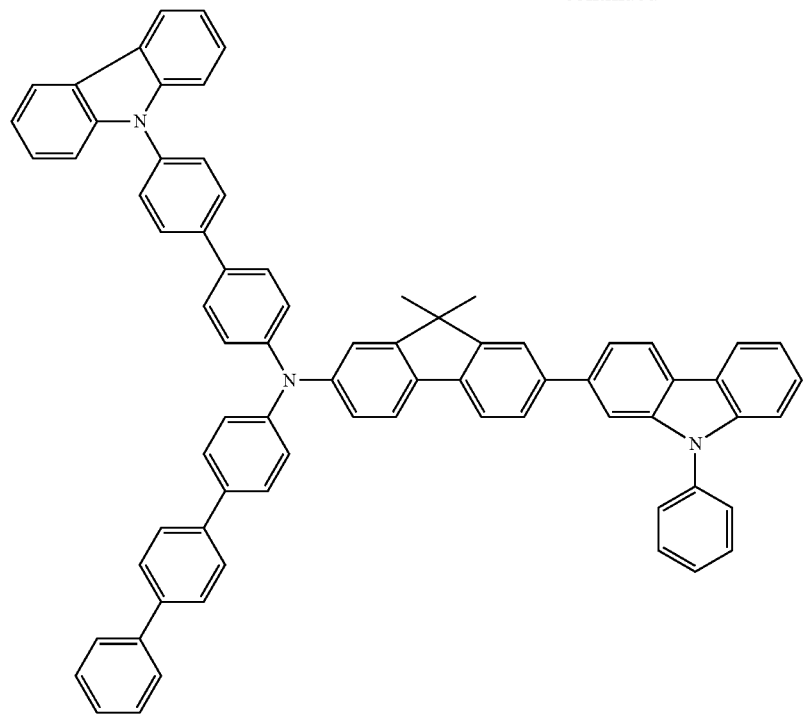
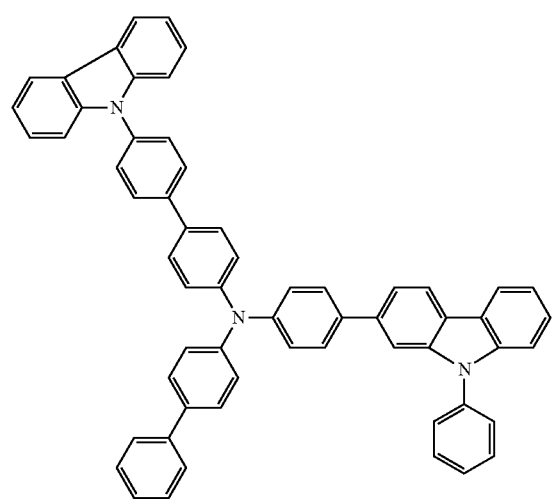
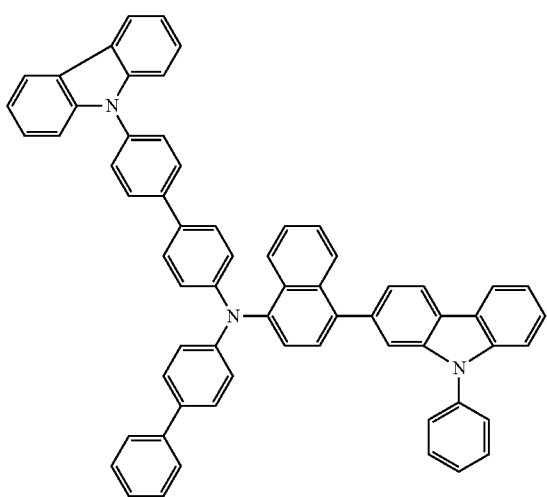

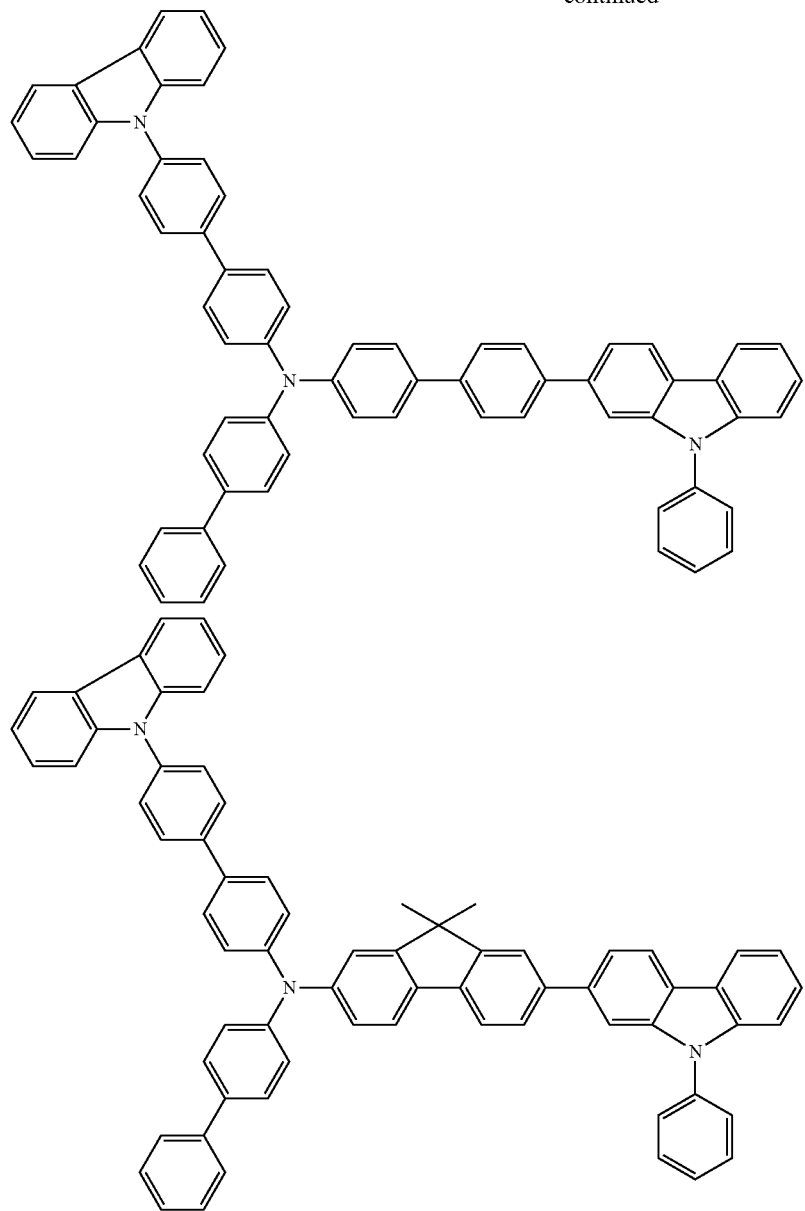
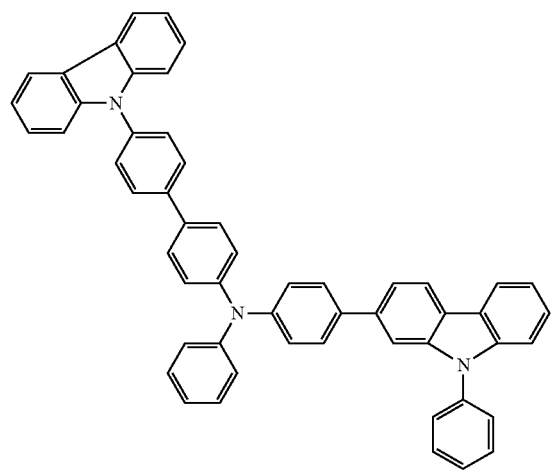
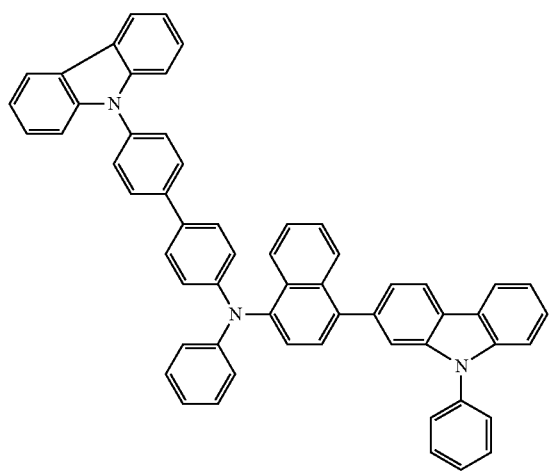

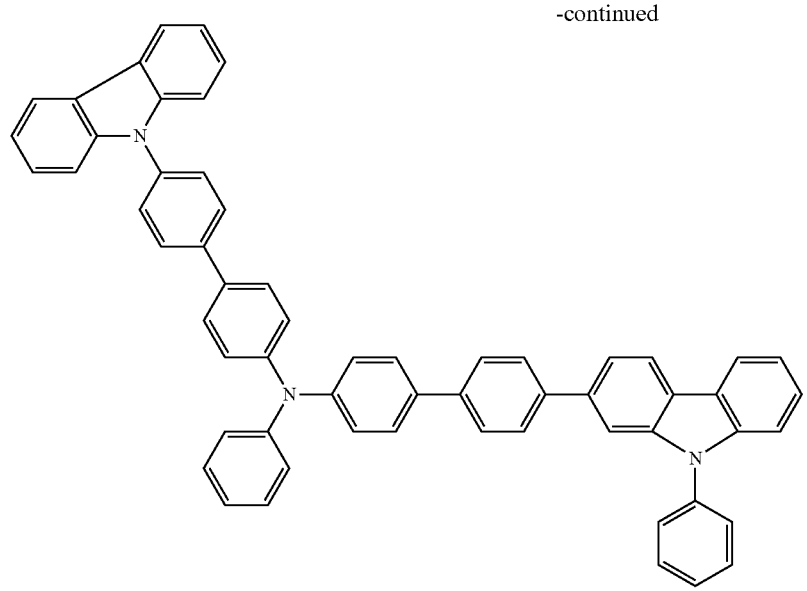
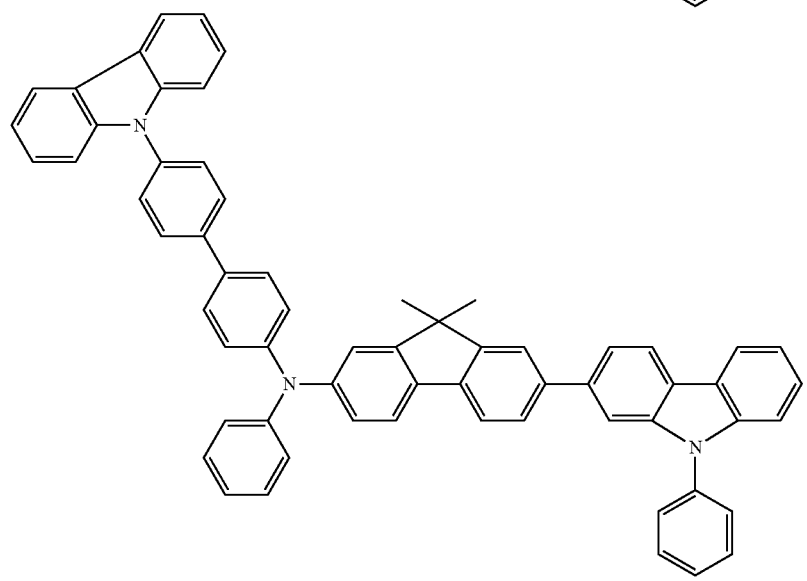
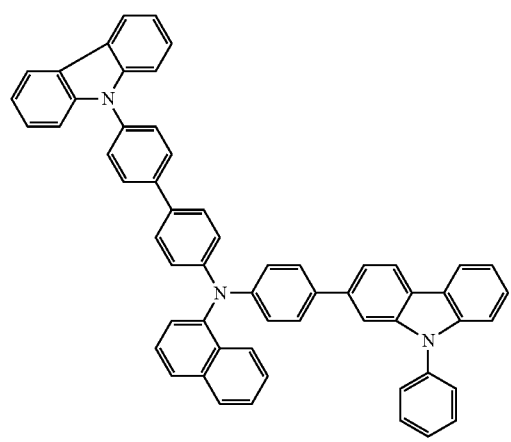
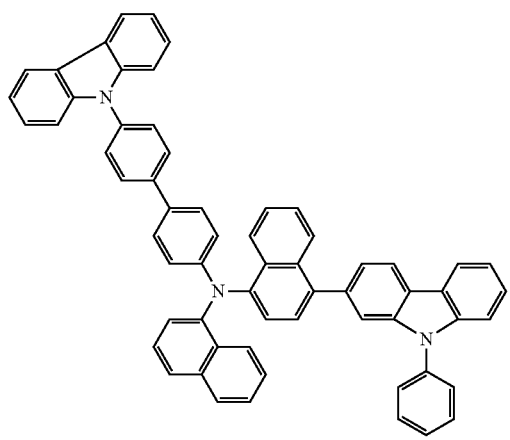

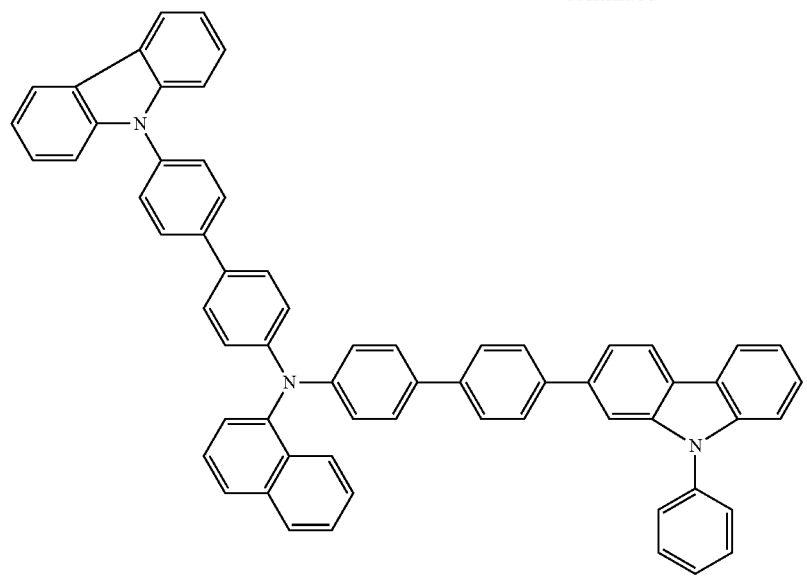
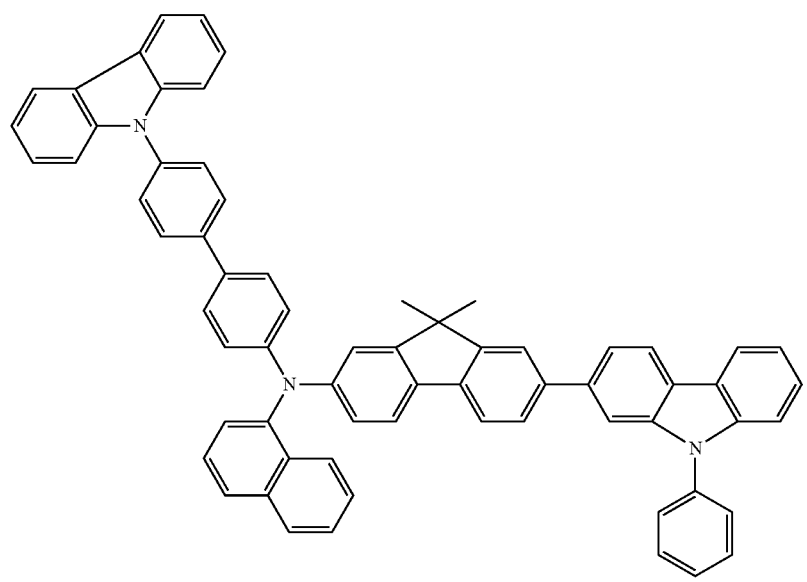
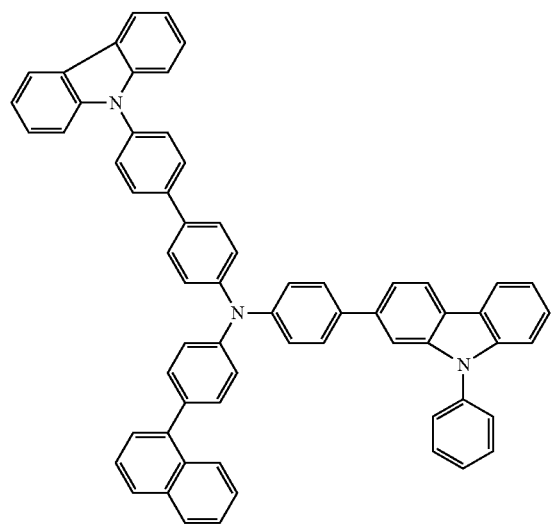
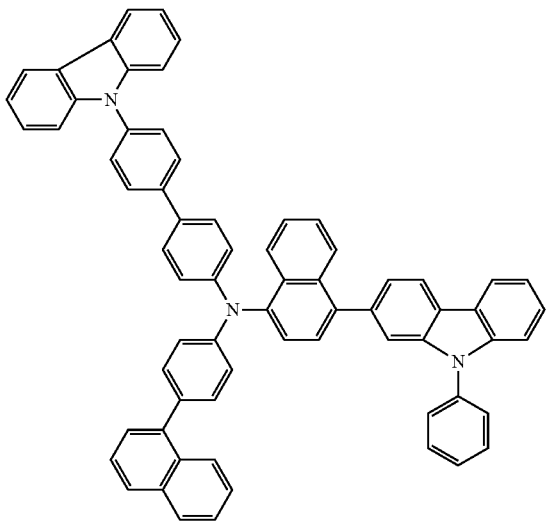

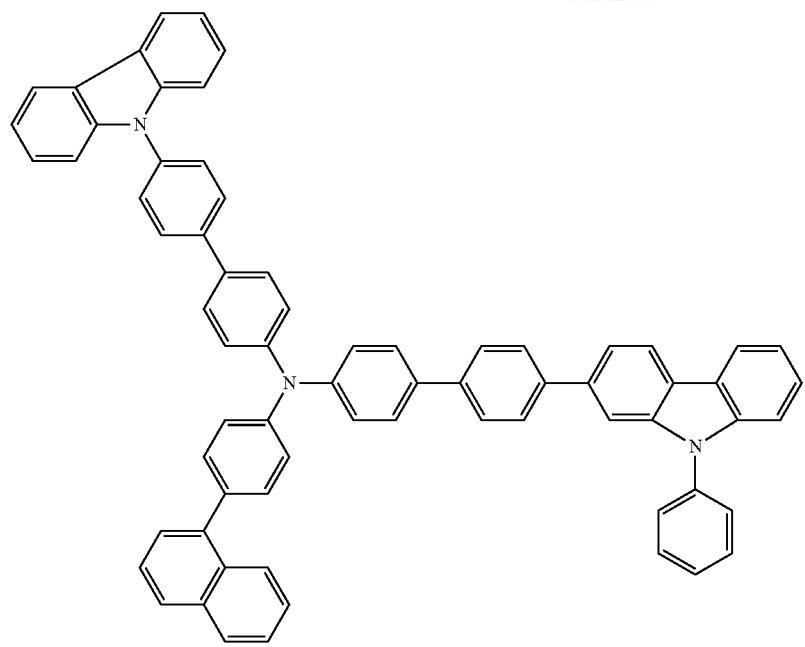
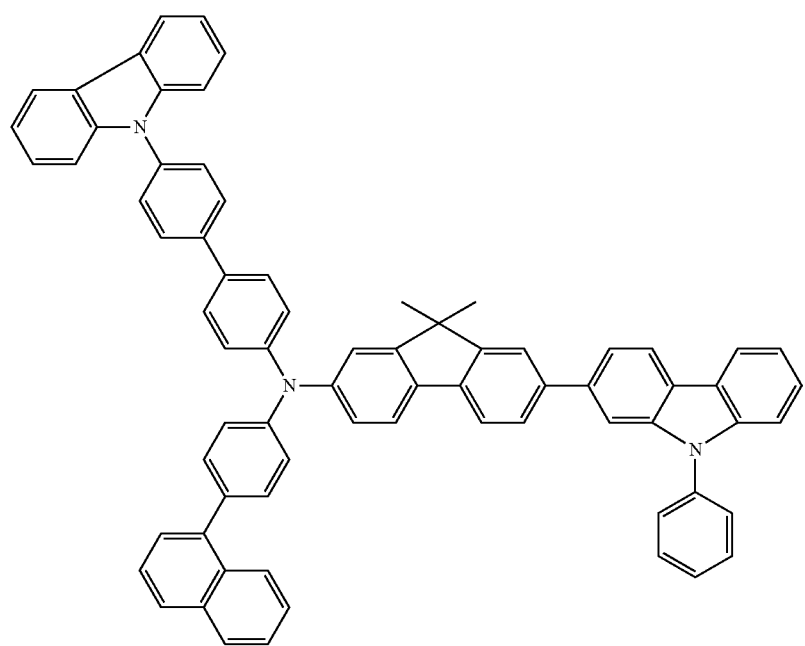

[Chem. 20]
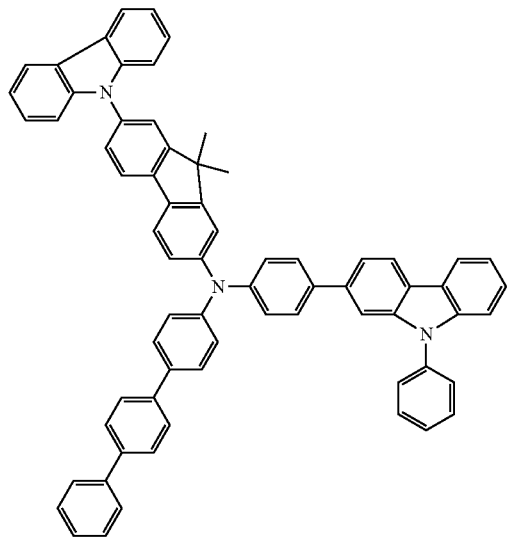
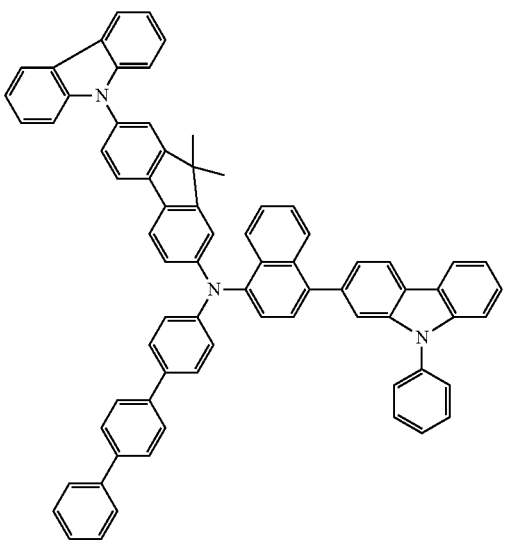
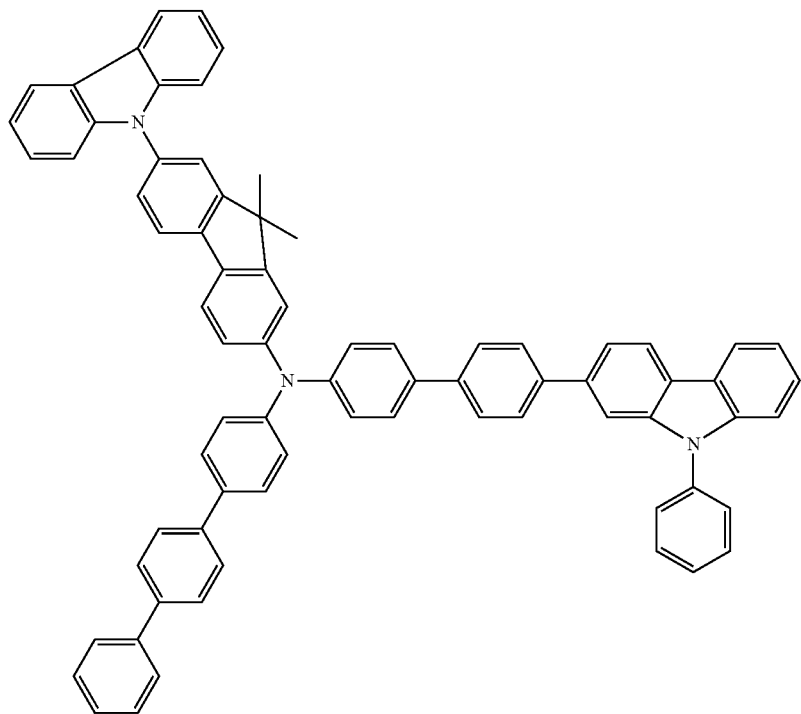

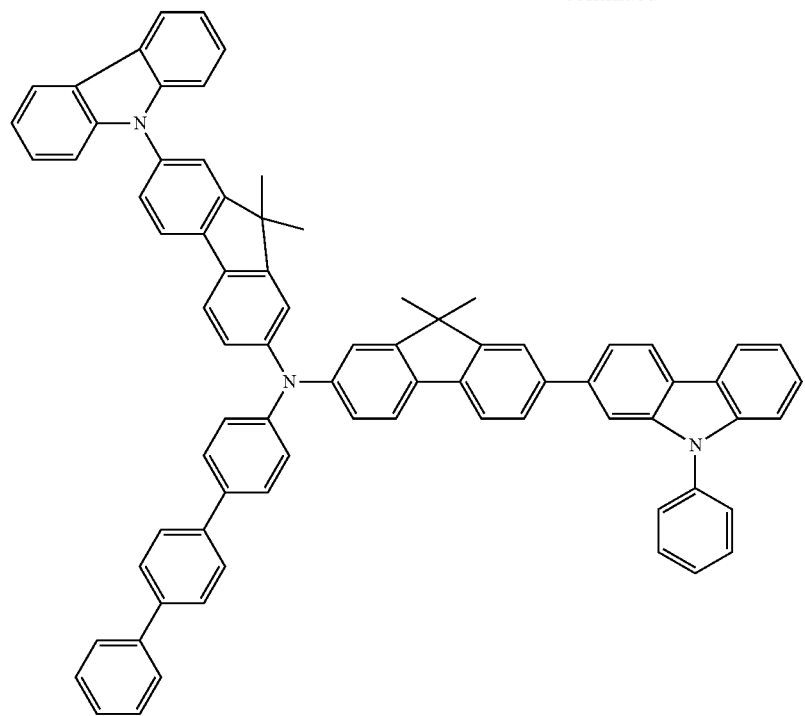
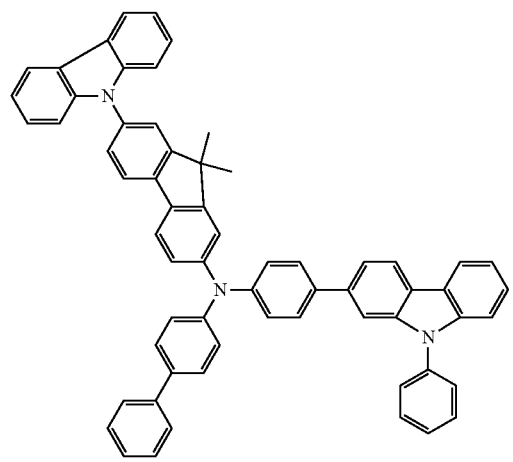
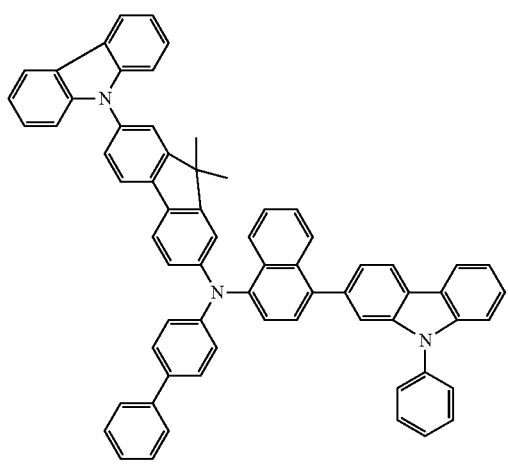

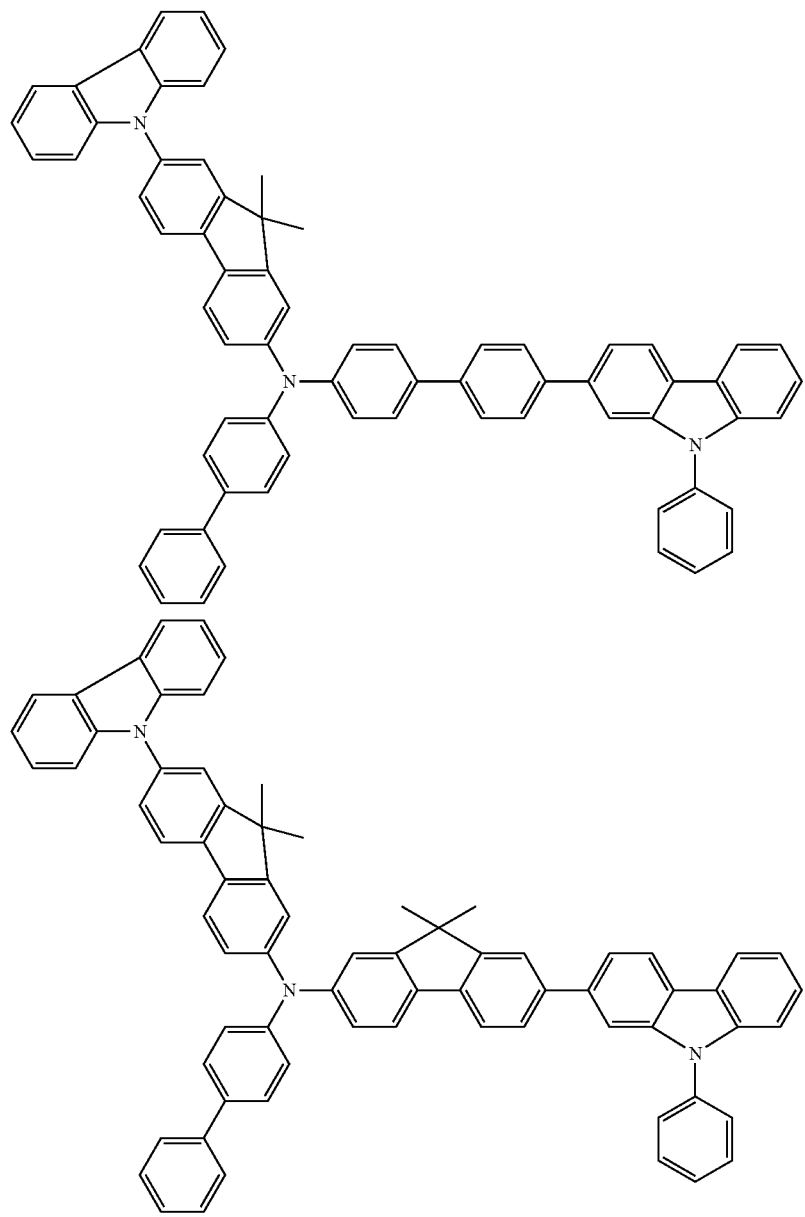
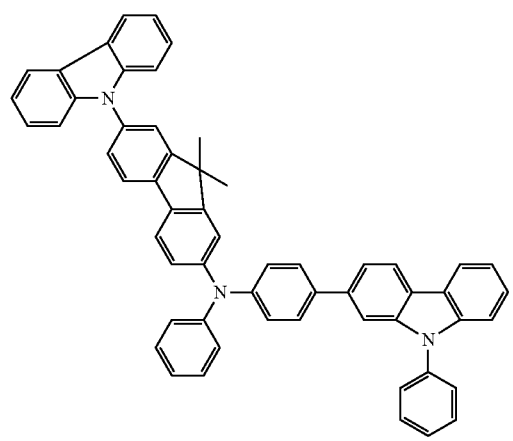
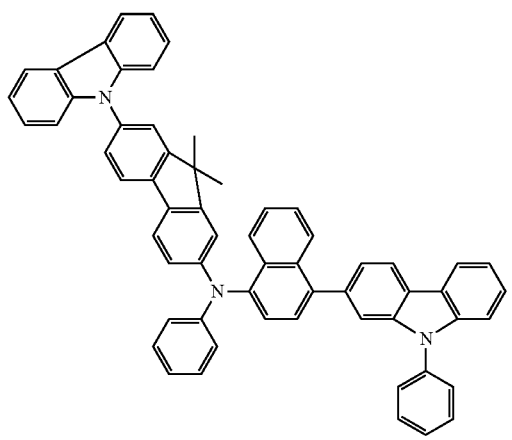

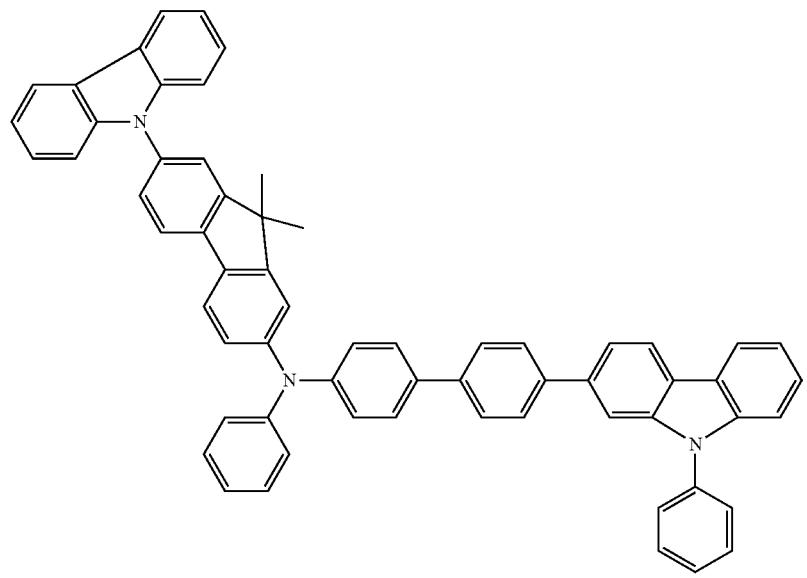
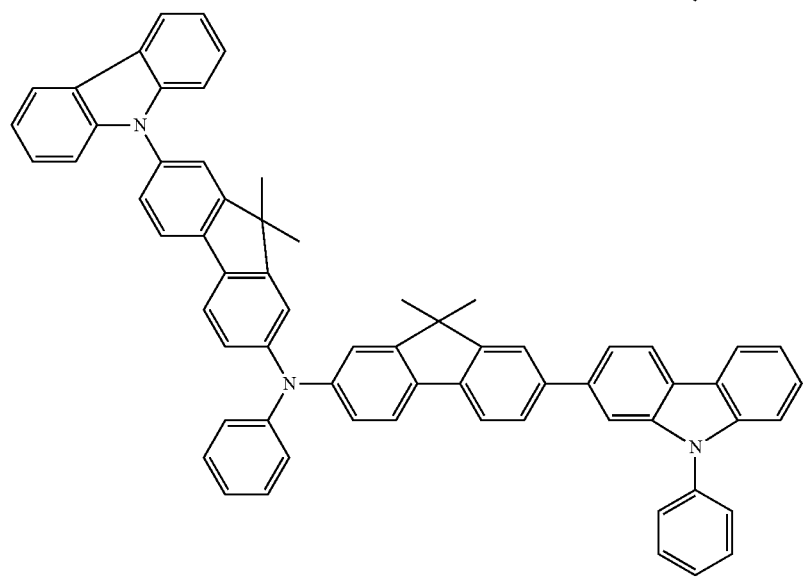
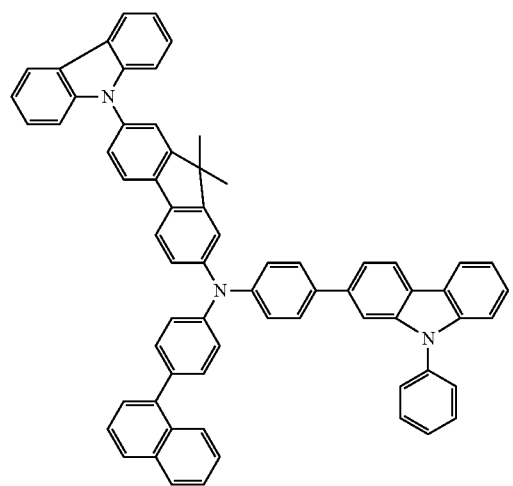
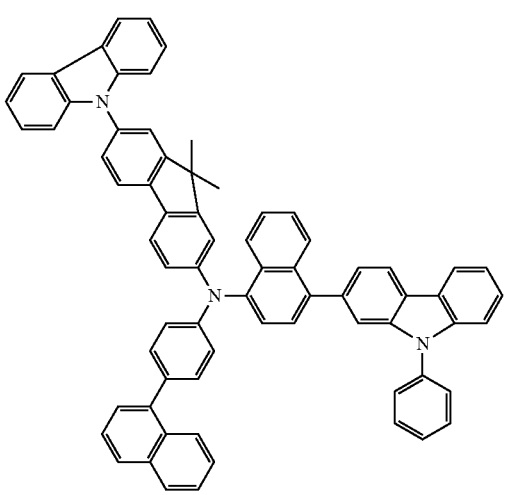

-continued
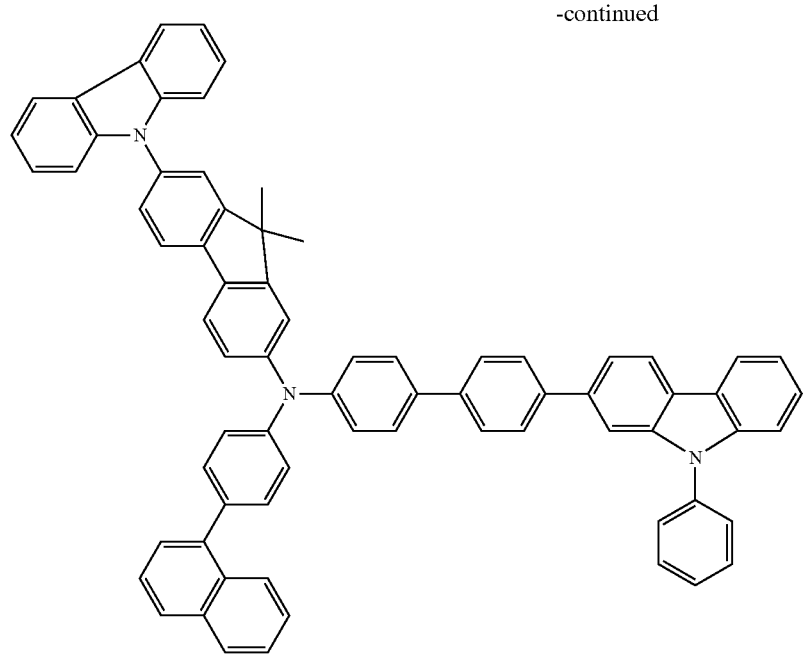
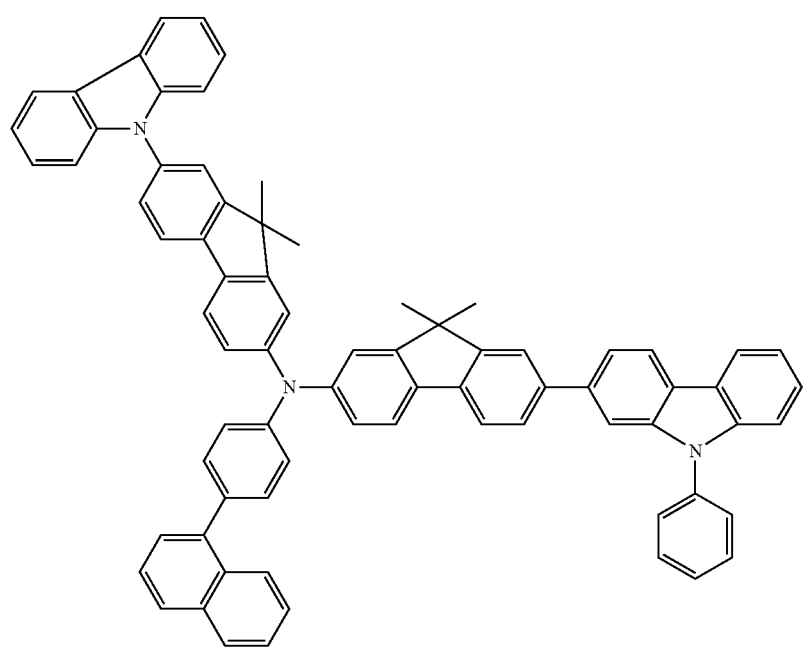

123
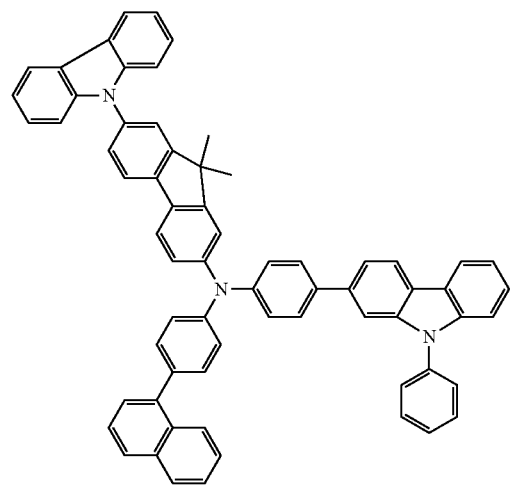
-continued
124
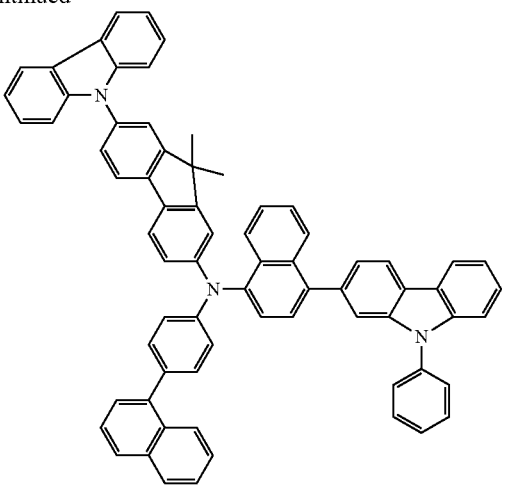
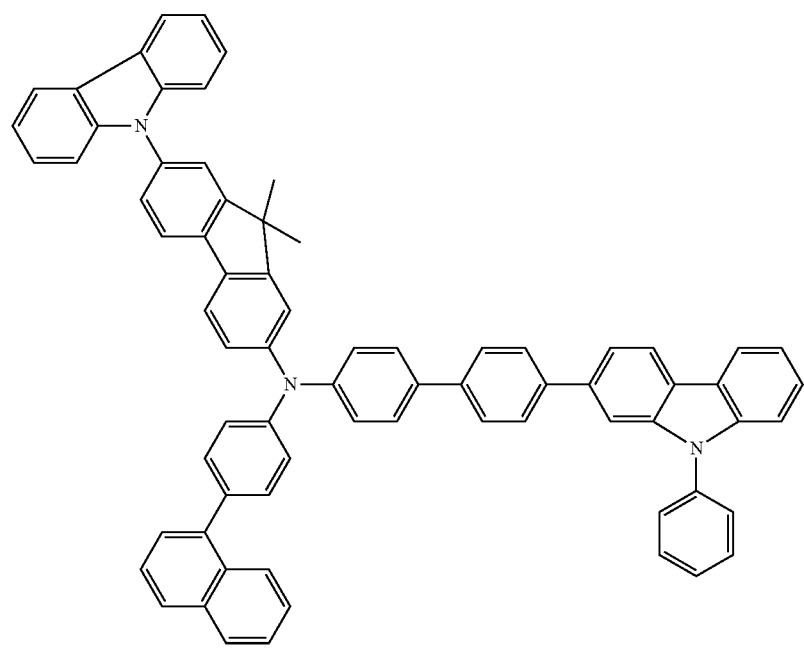

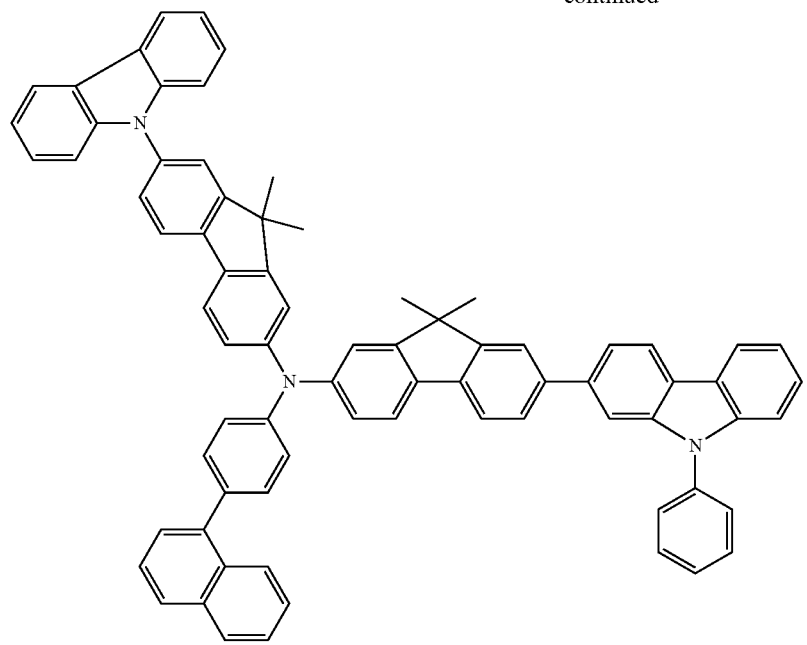
[Chem. 21]
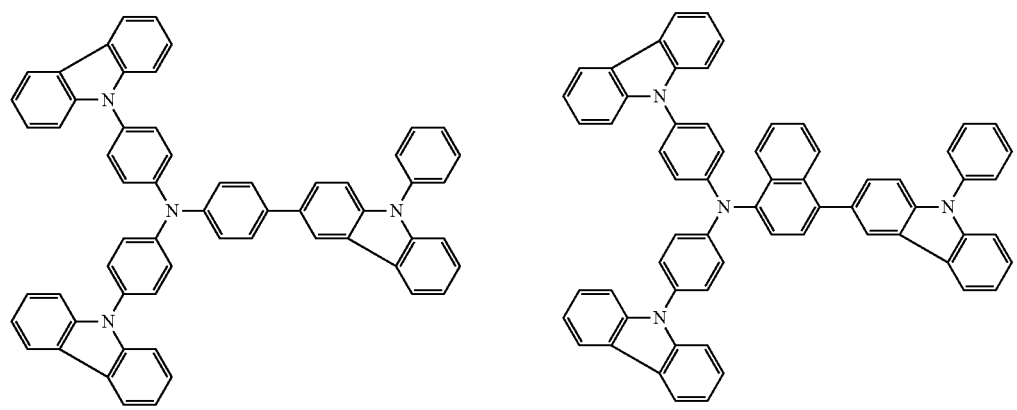
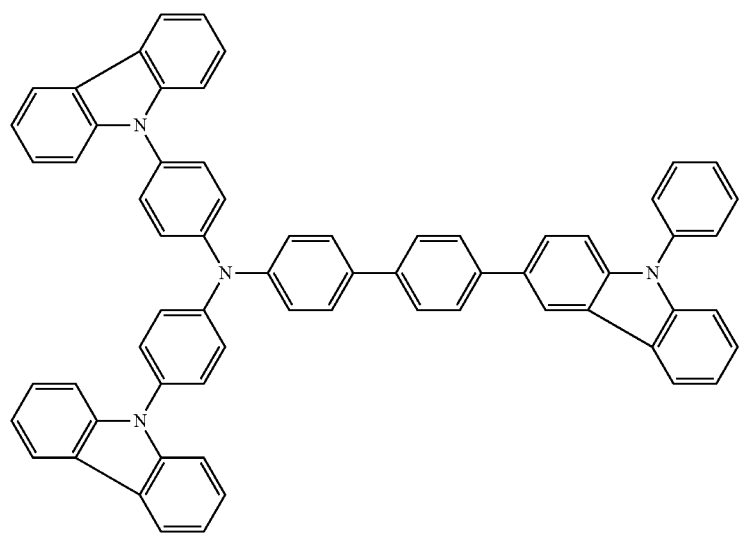

127
-continued
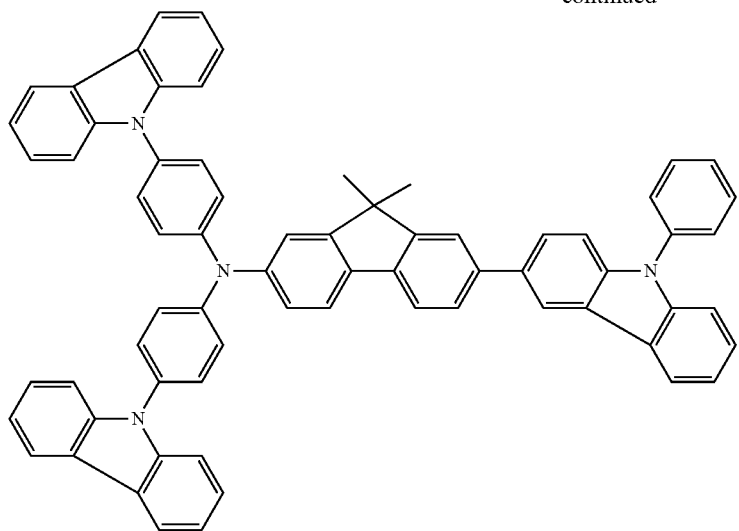
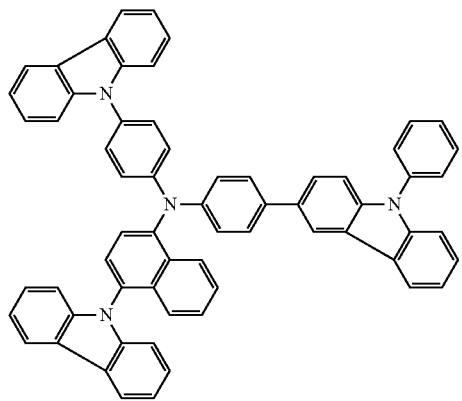
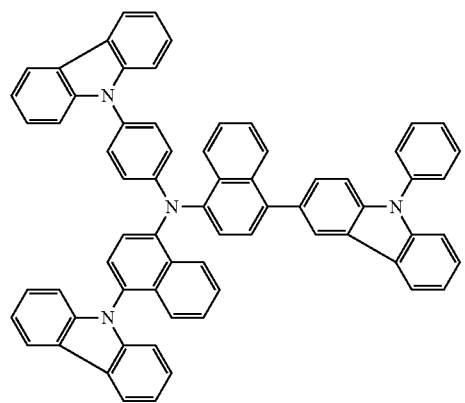
128
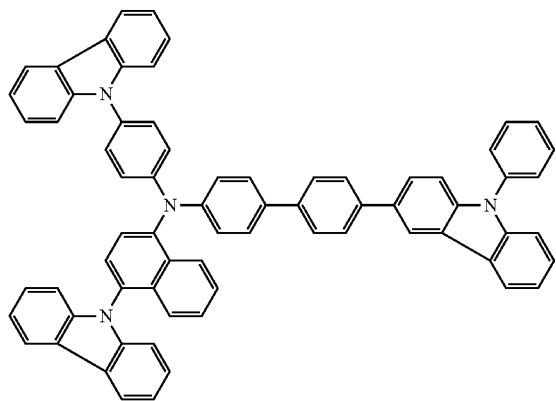
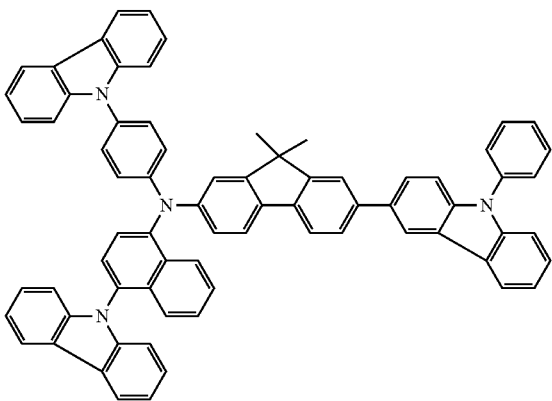

129
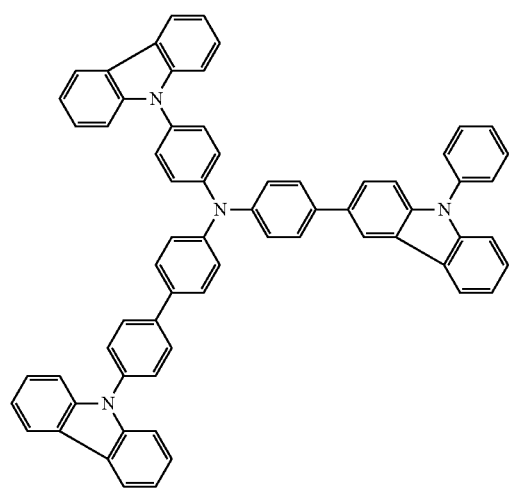
130
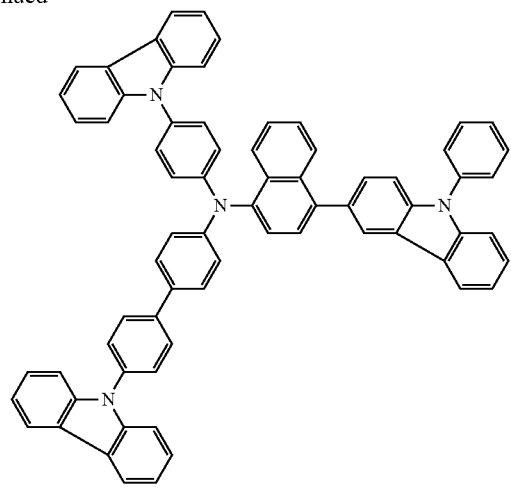
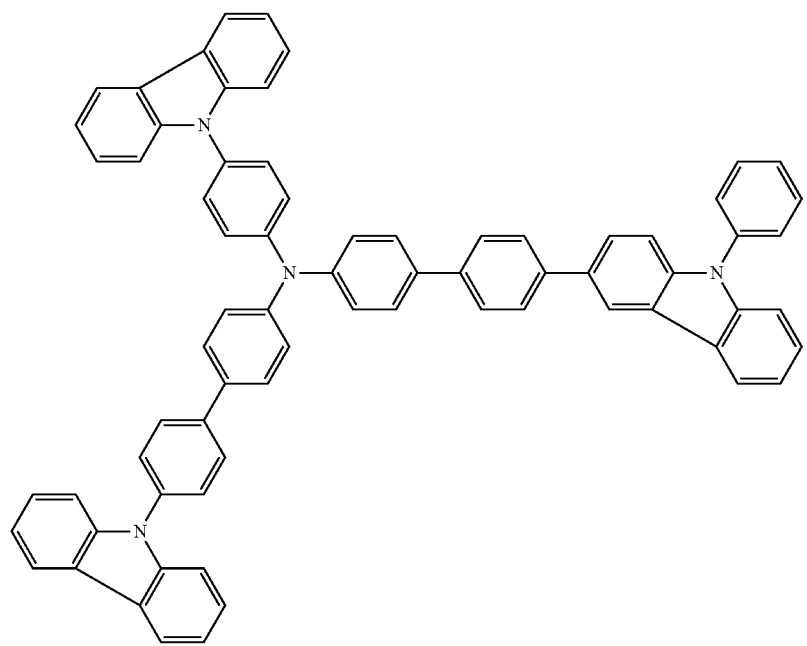

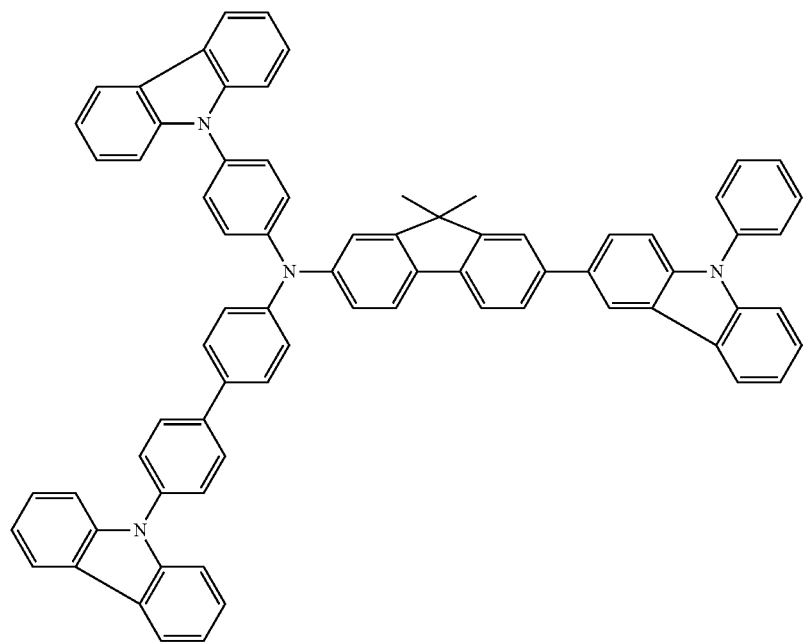
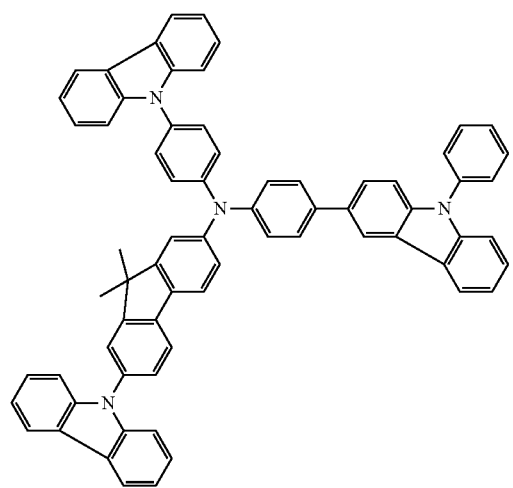
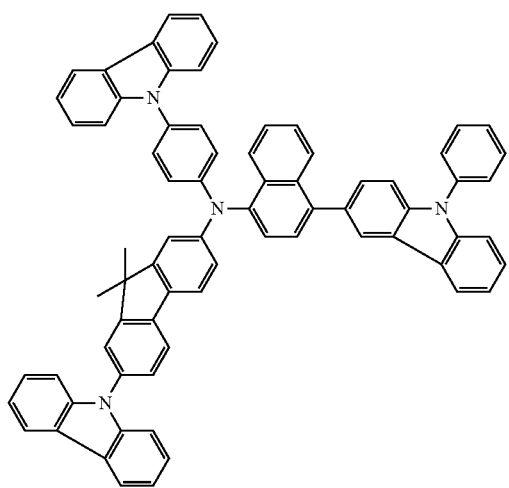

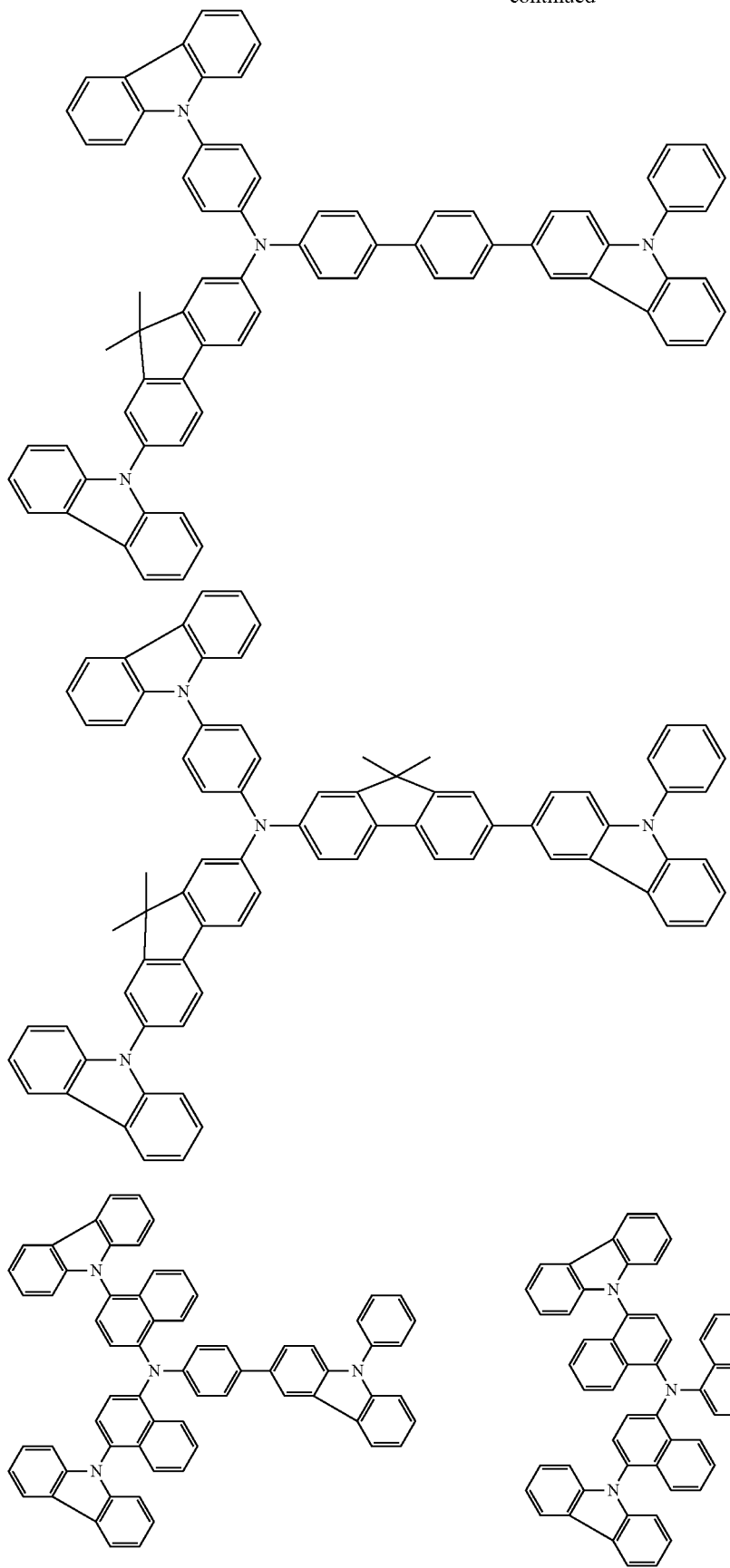

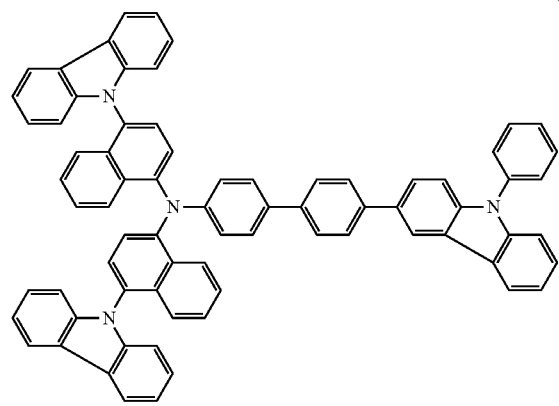
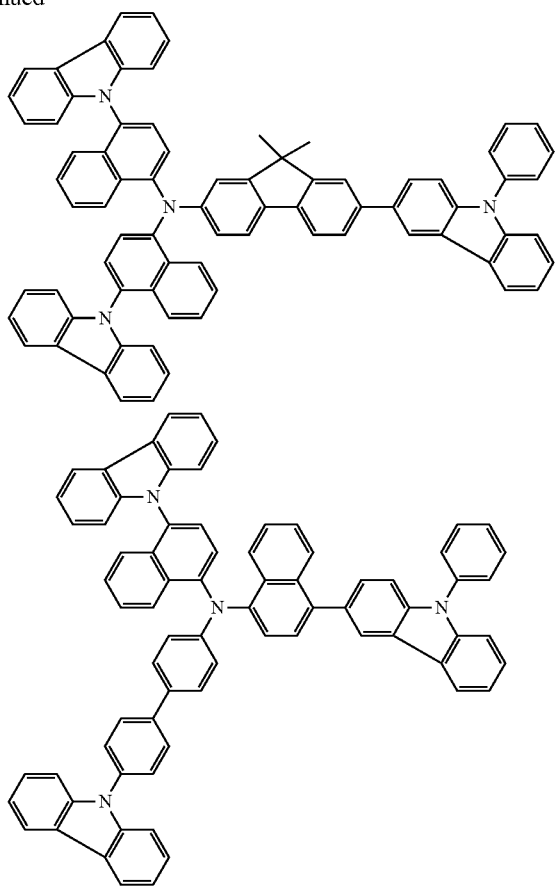
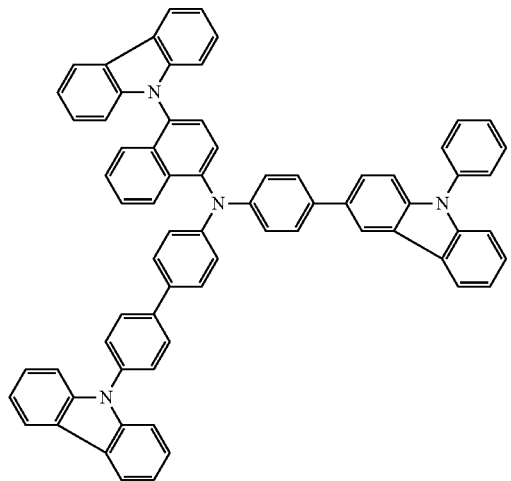
[Chem. 22]
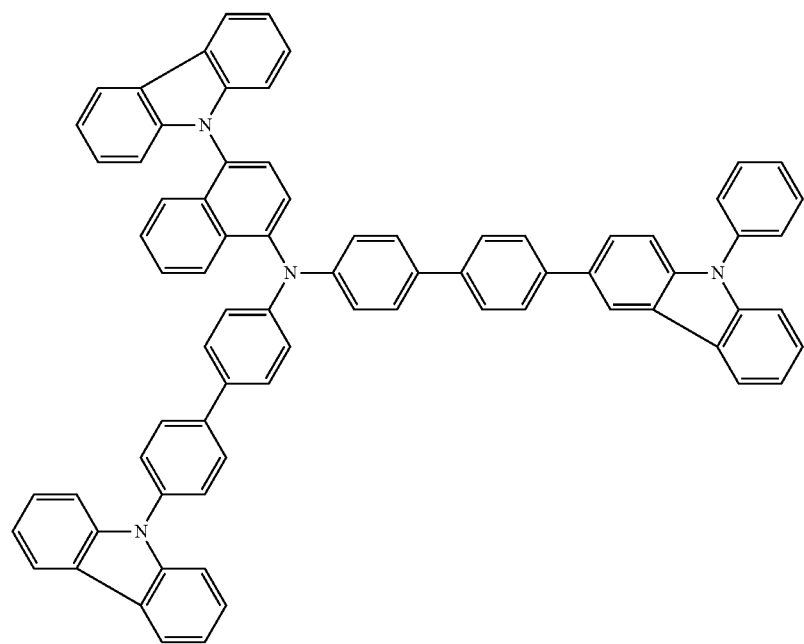

-continued
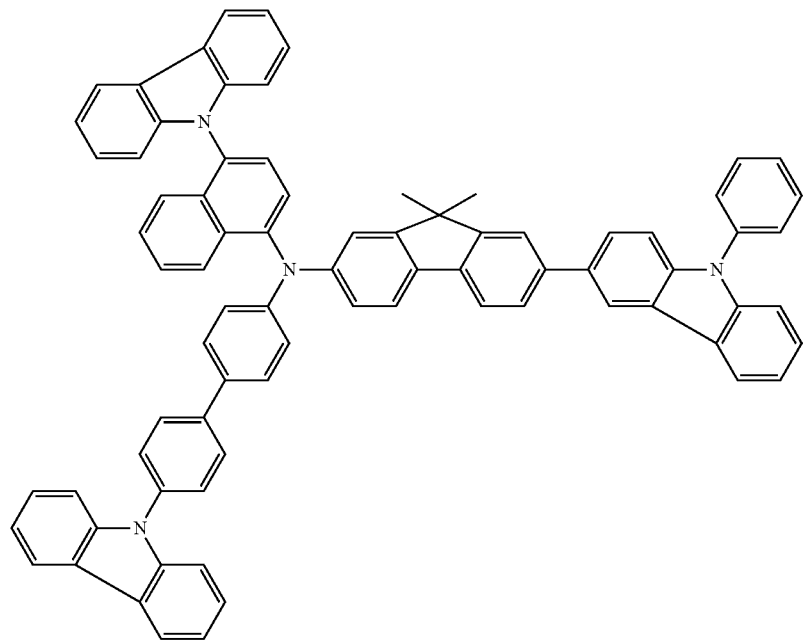
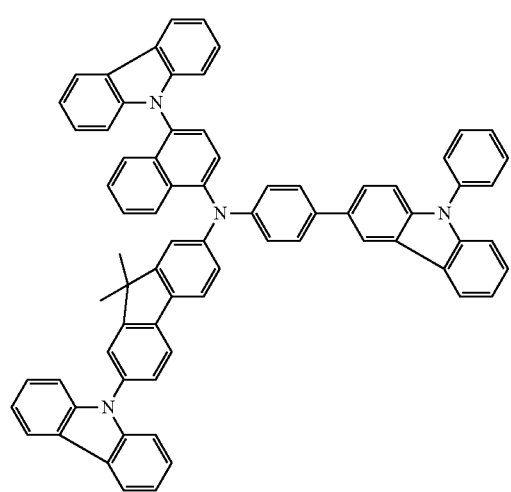
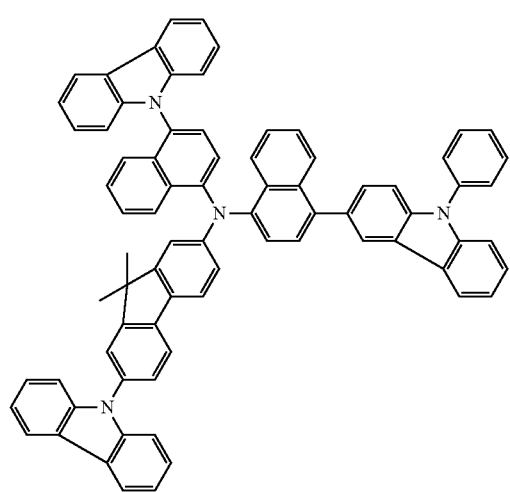

-continued
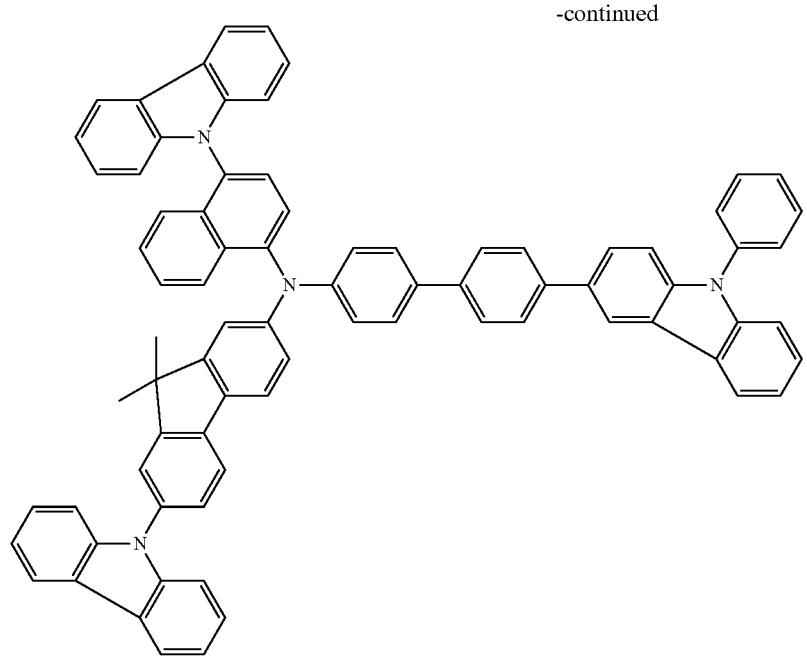
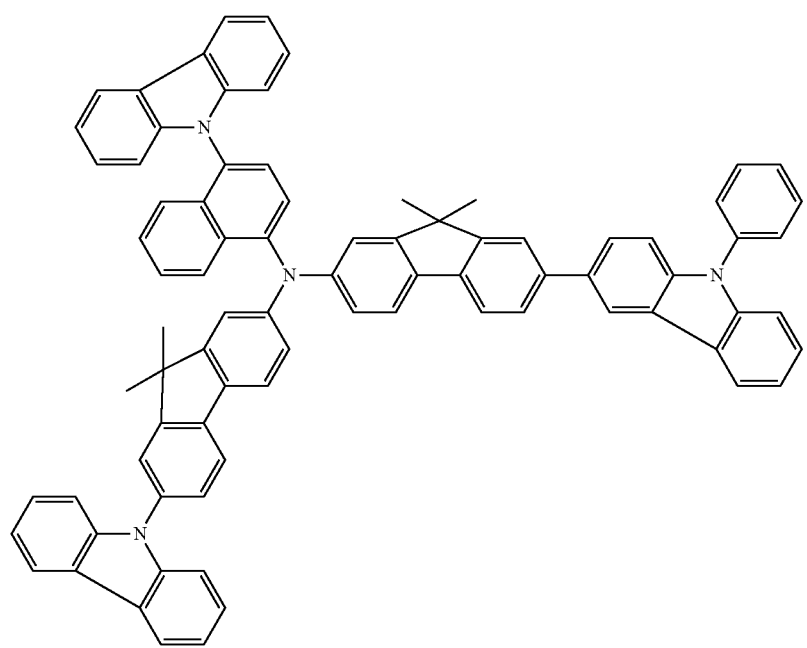

141 142
-continued
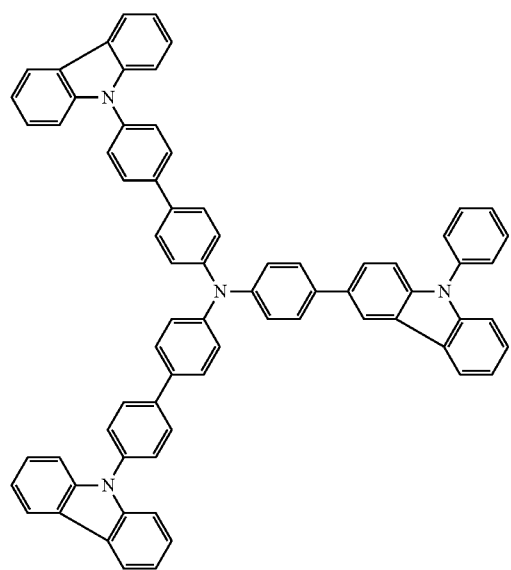 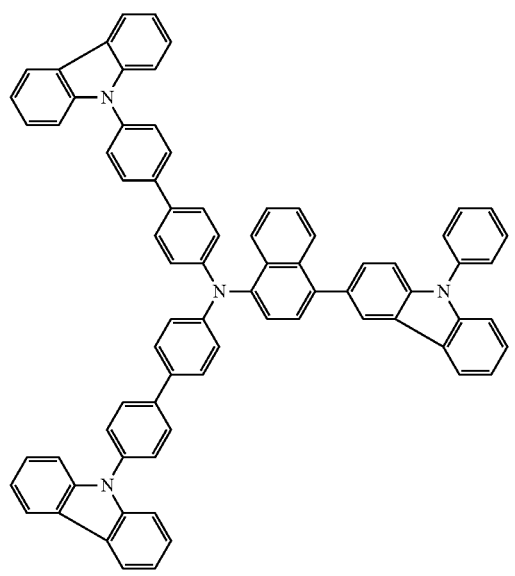
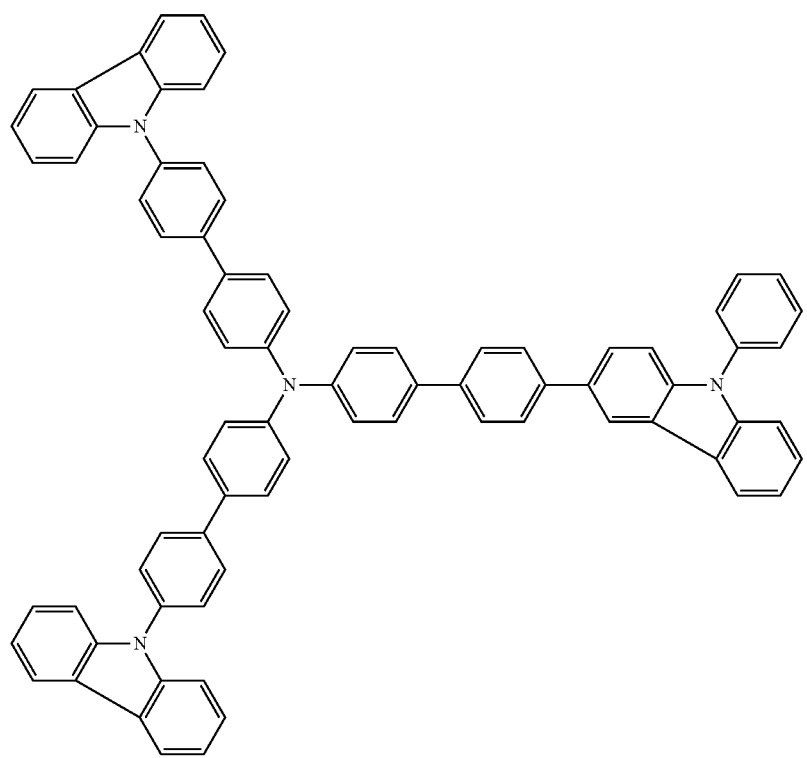

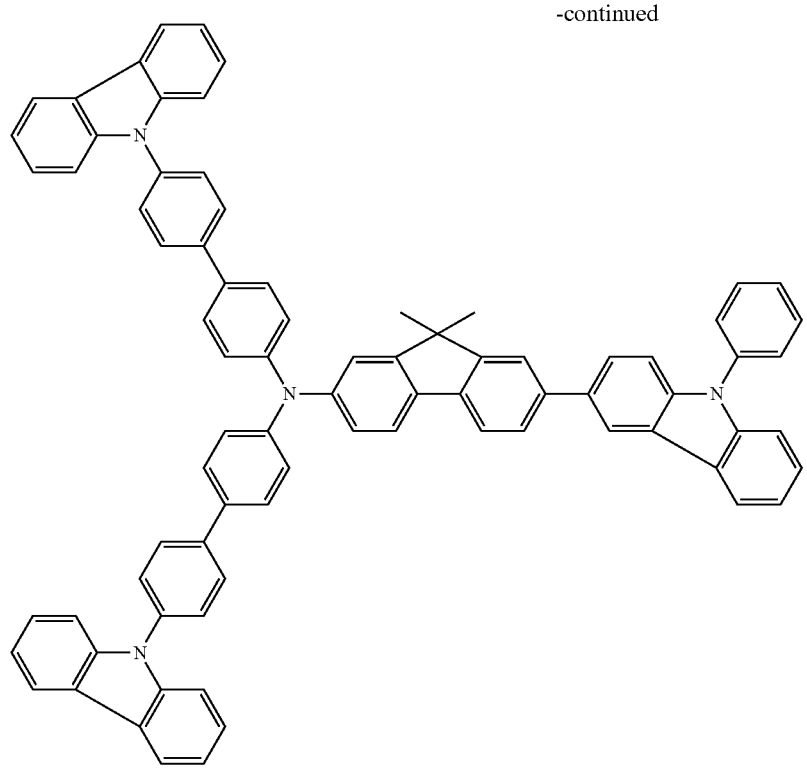
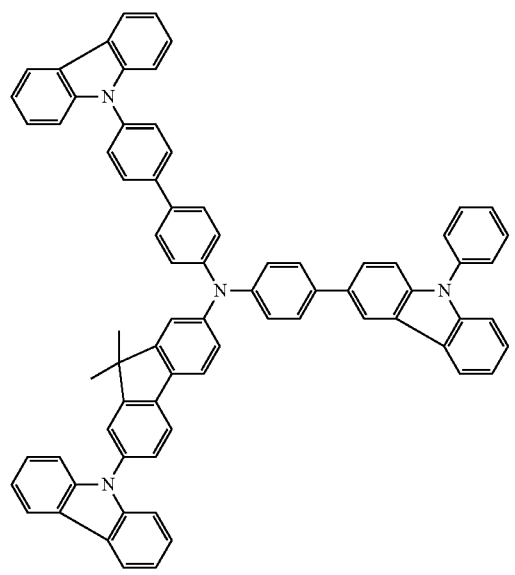
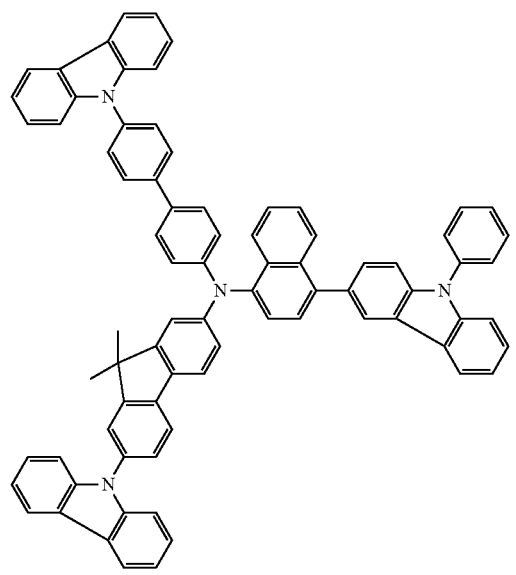

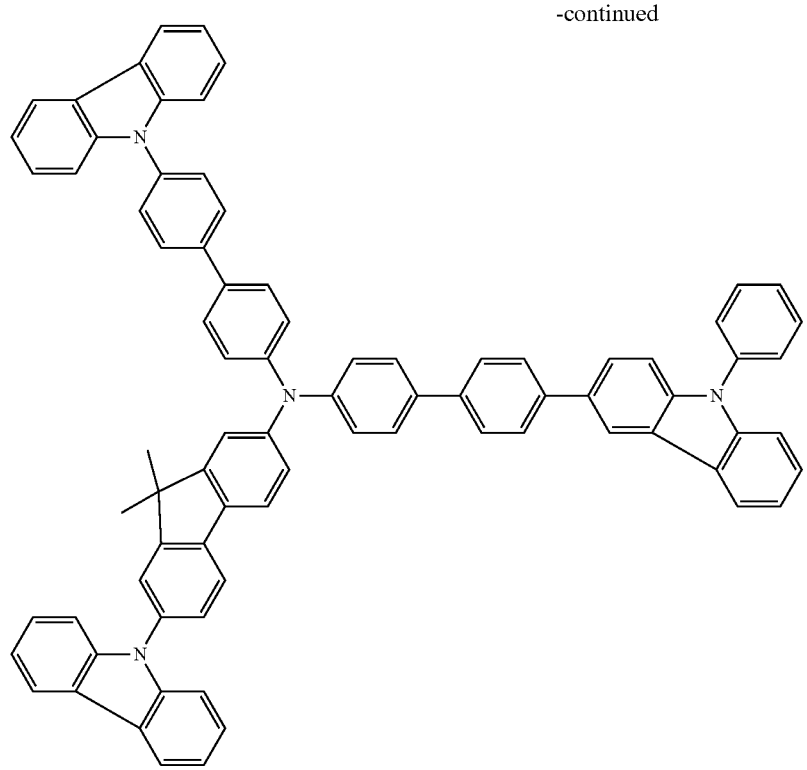
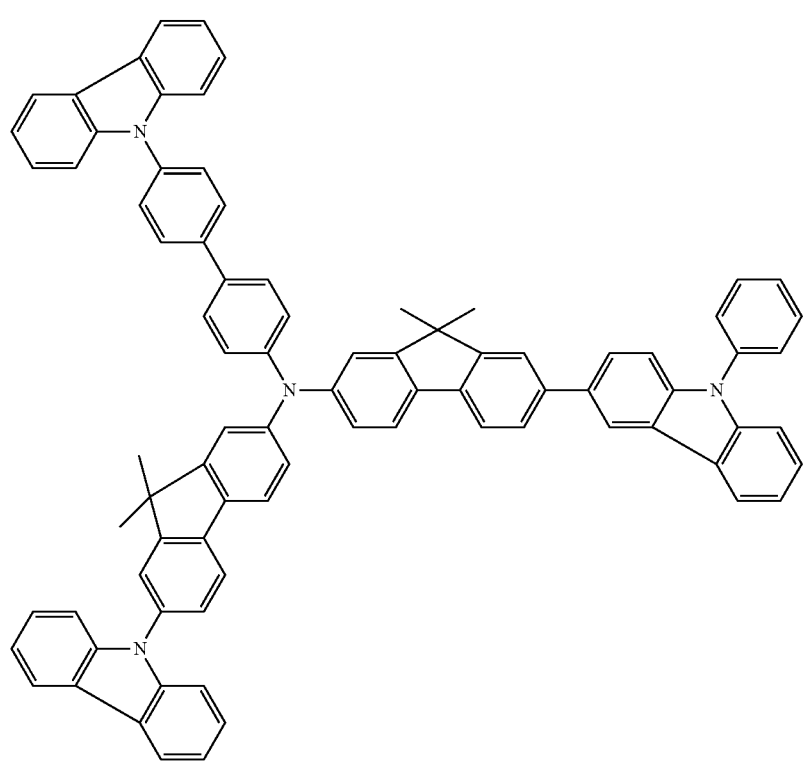

147
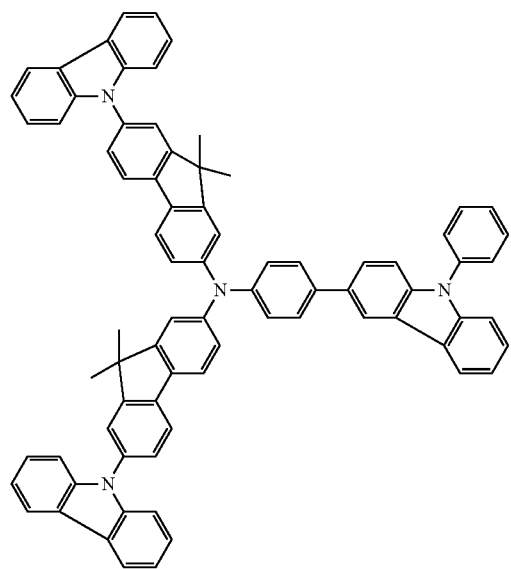
-continued
148
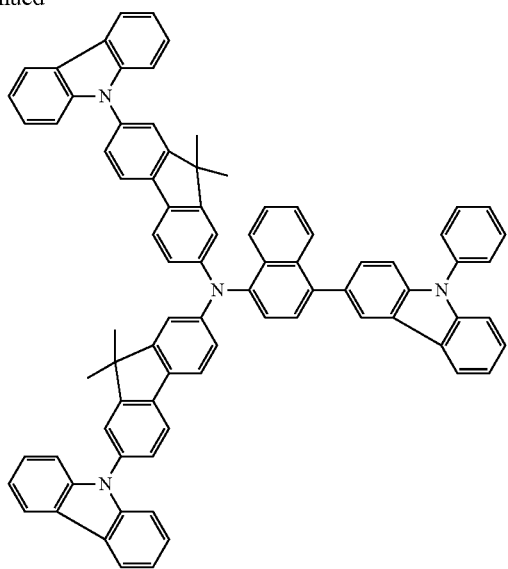
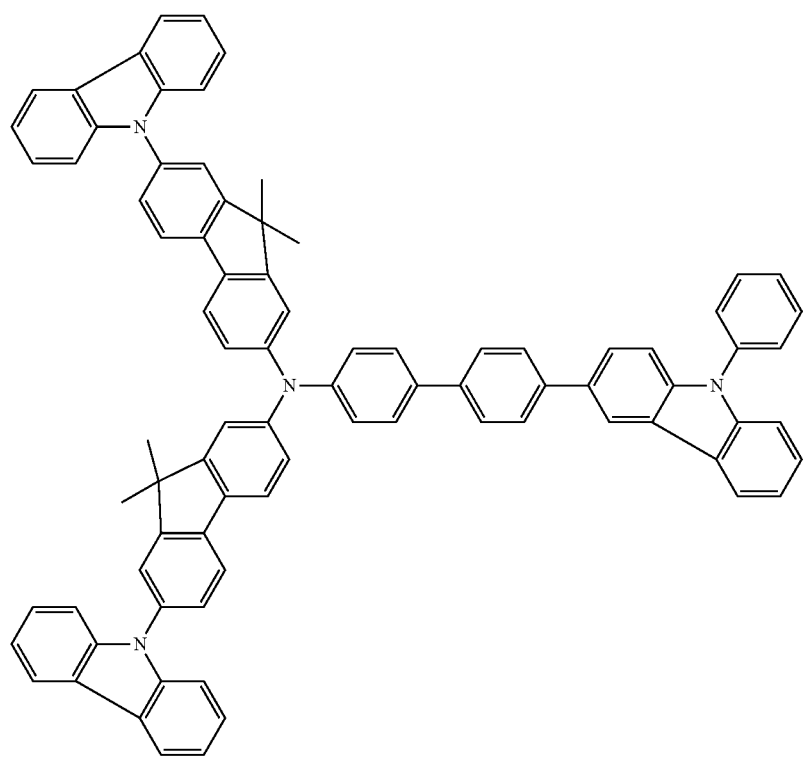

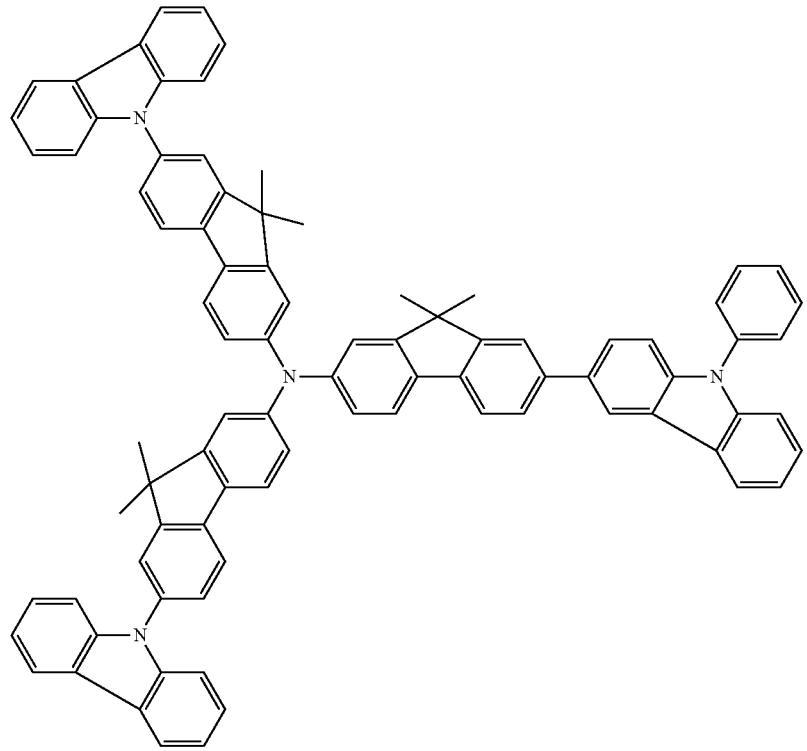
[Chem. 23]
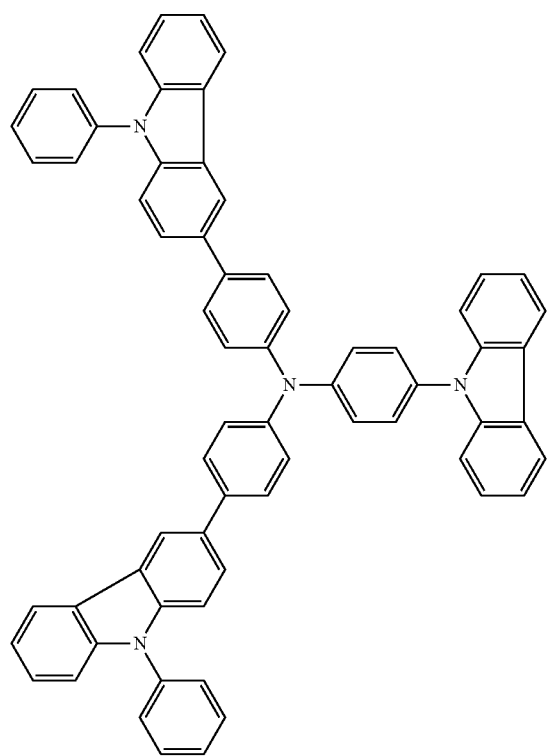
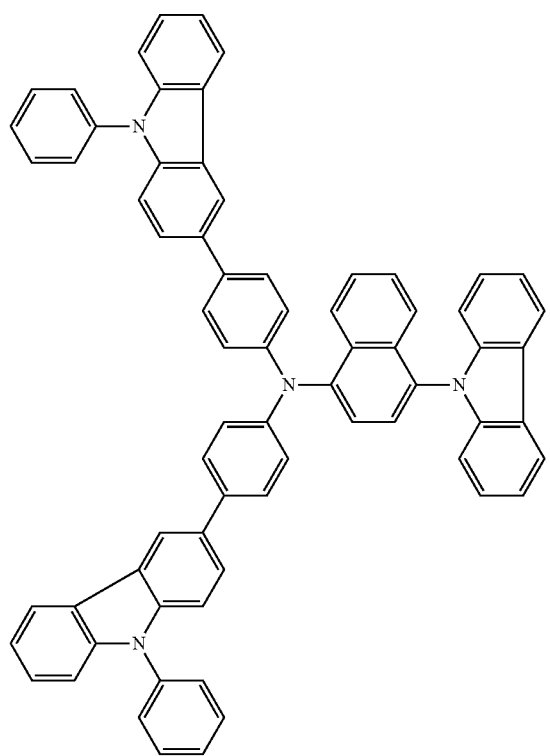

-continued
| 151 | 152 |
|---|---|
| 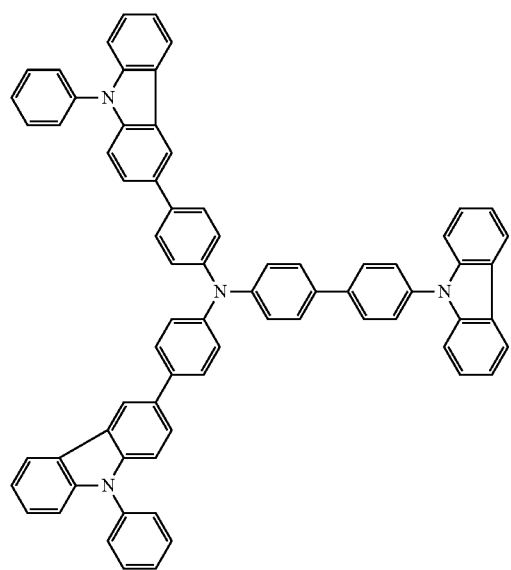 | 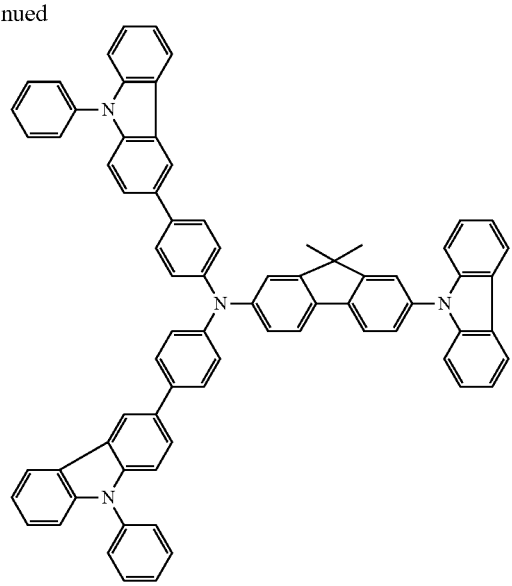 |
| 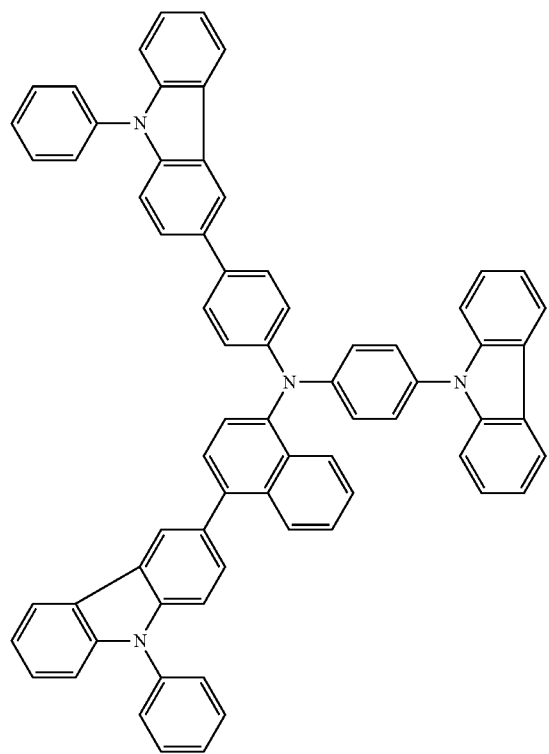 |  |

153
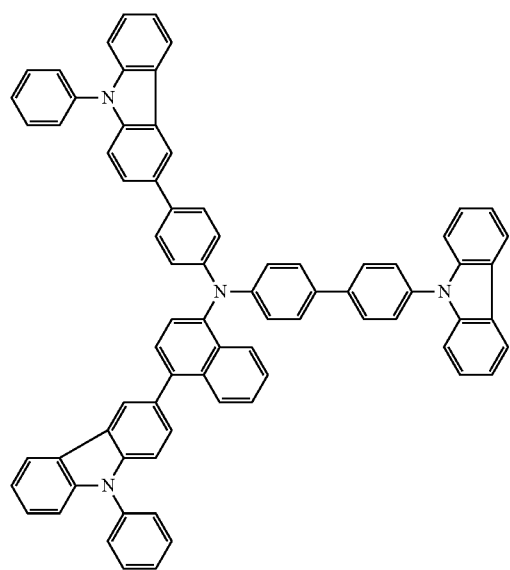
154
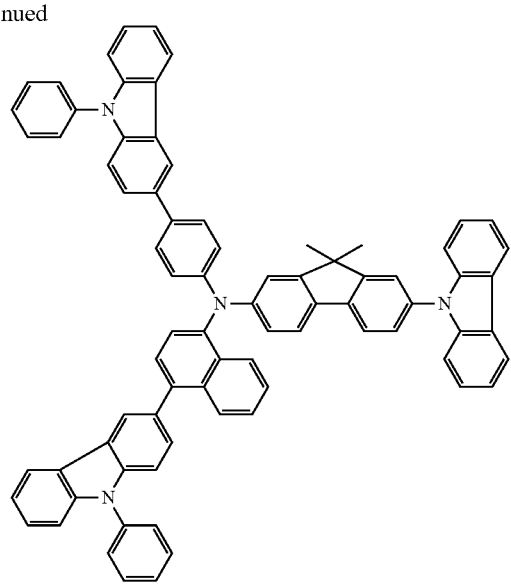
-continued
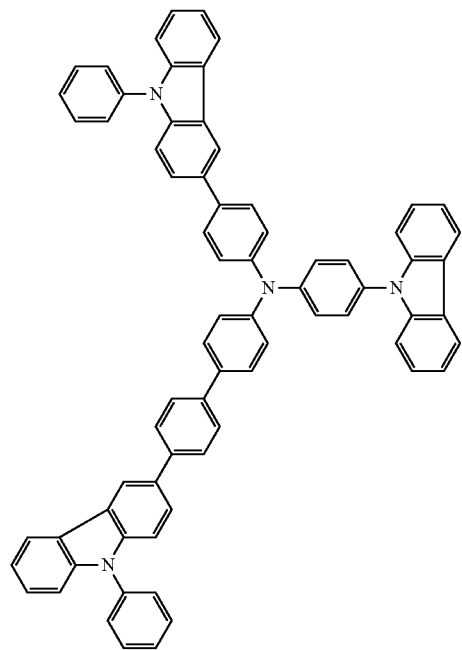
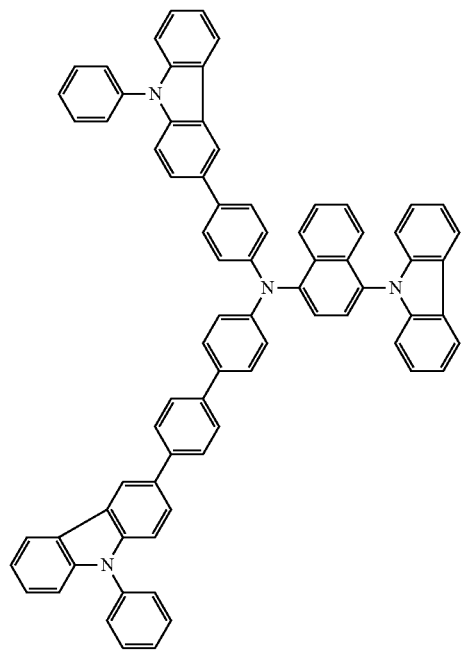

-continued
155
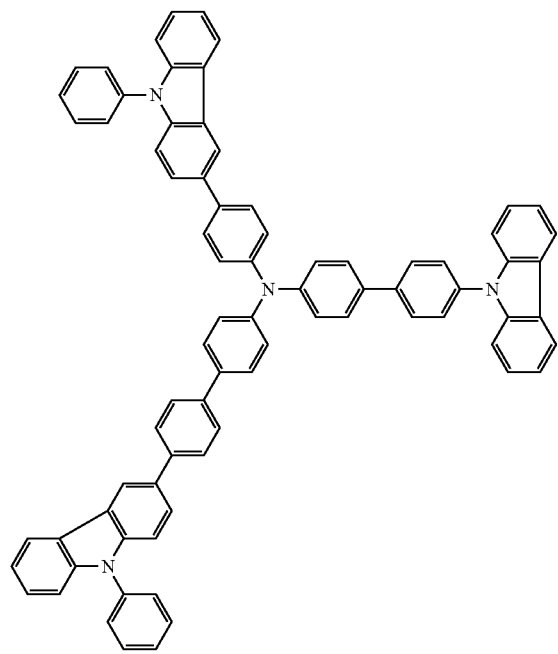
156
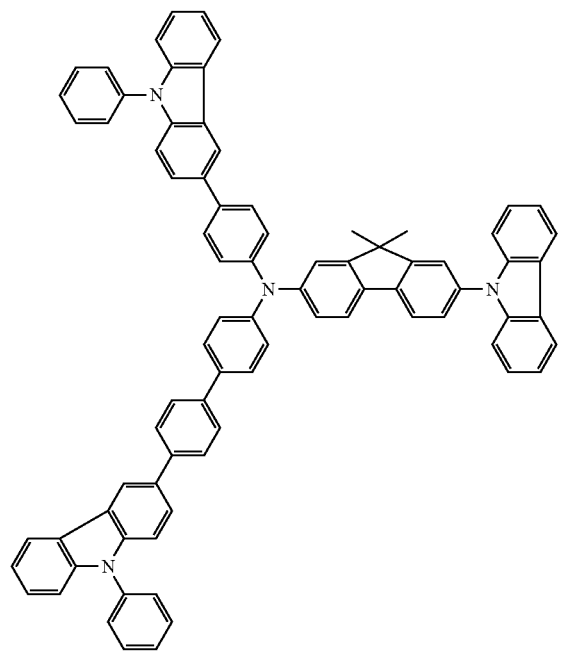
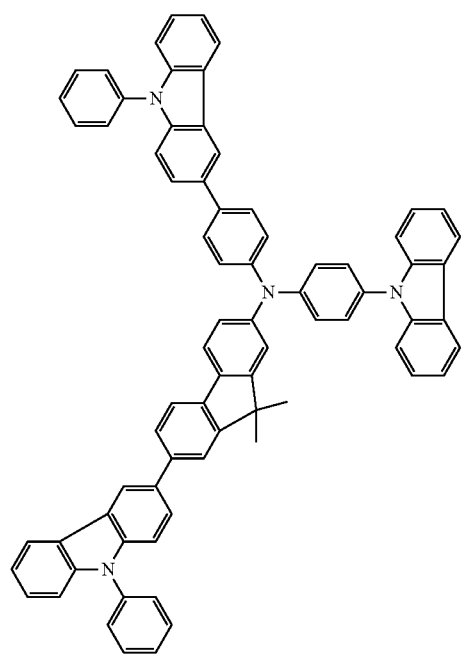
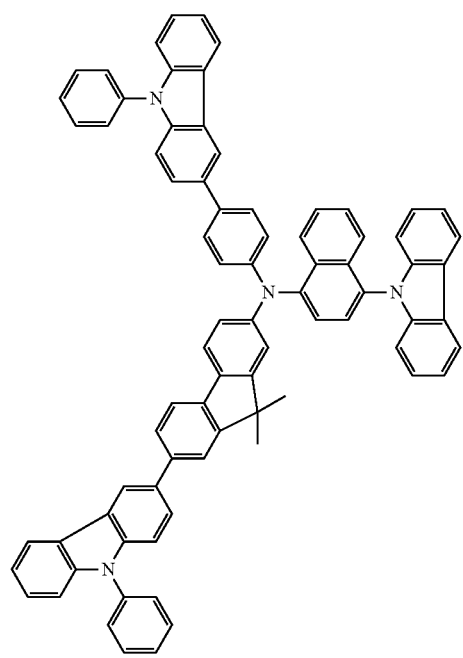

-continued
157
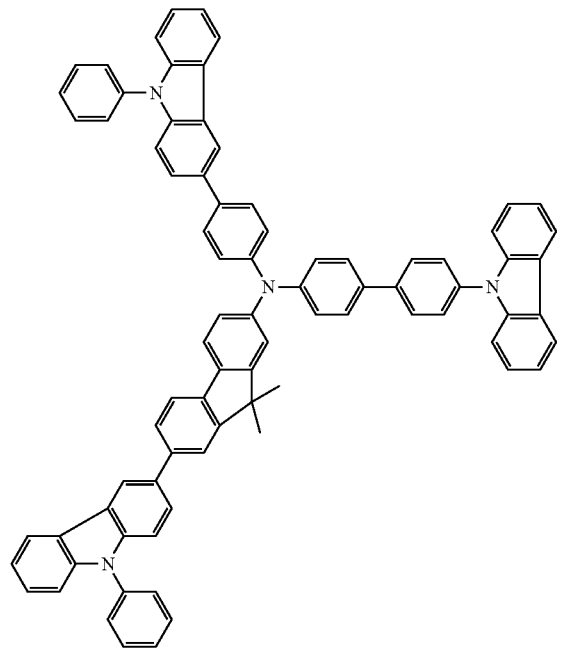
158
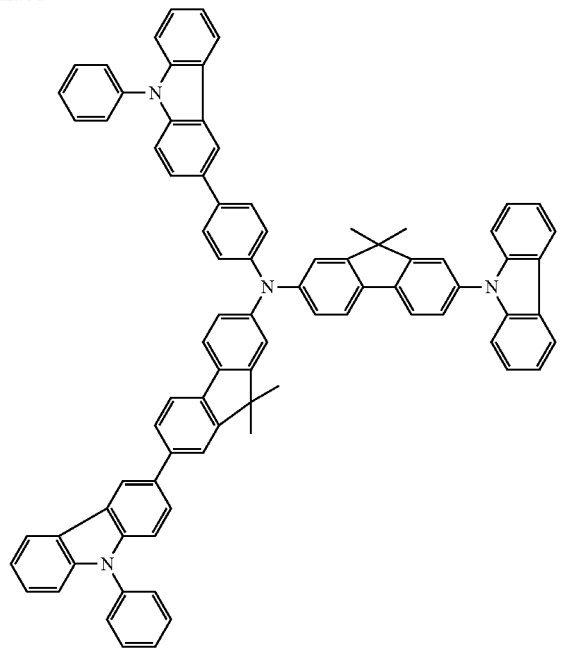
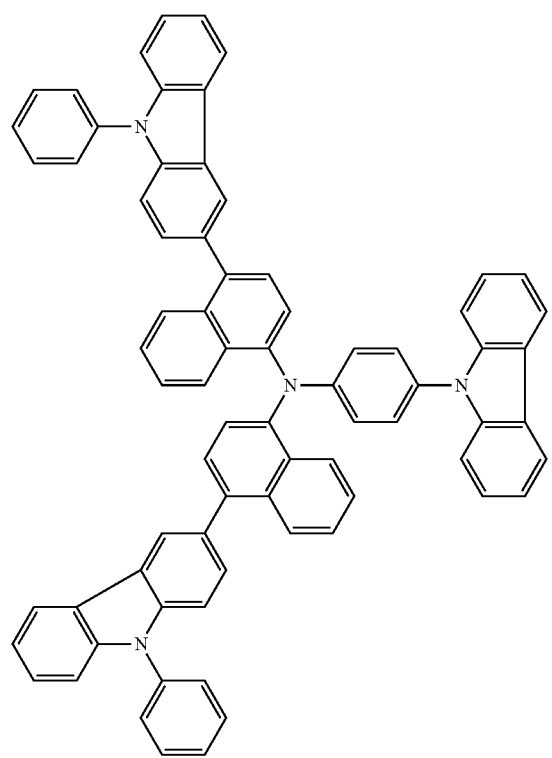
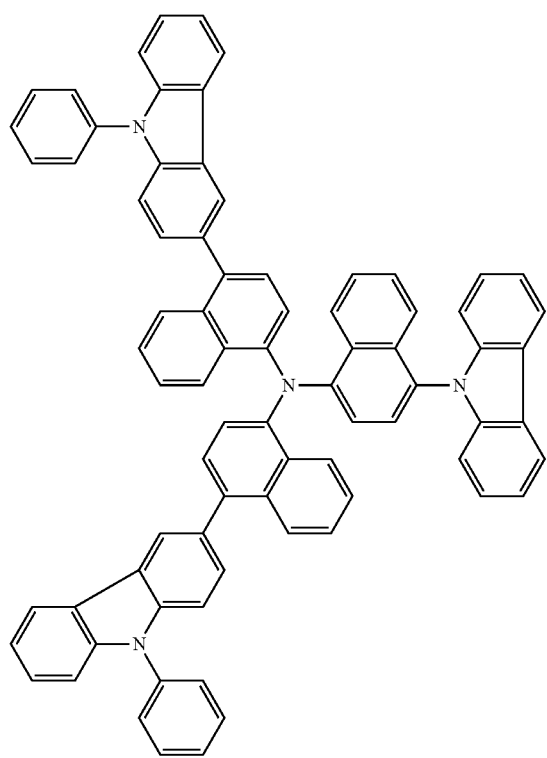

-continued
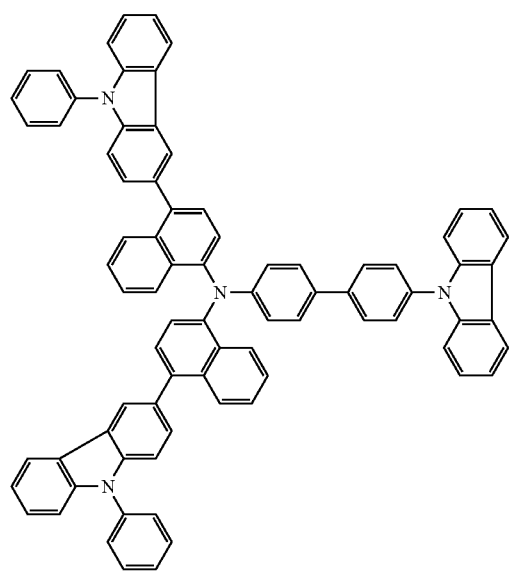
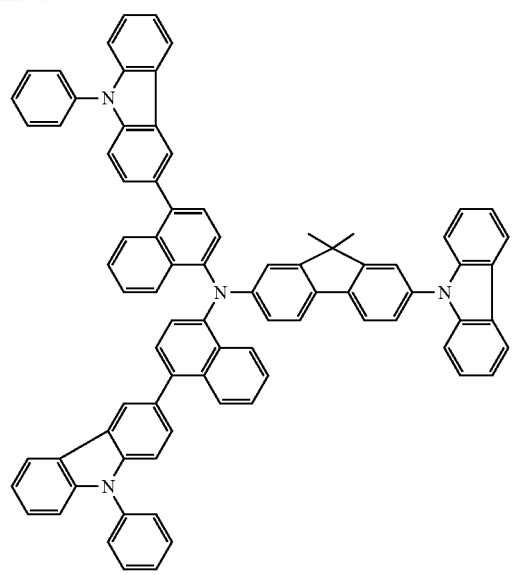
[Chem. 24]
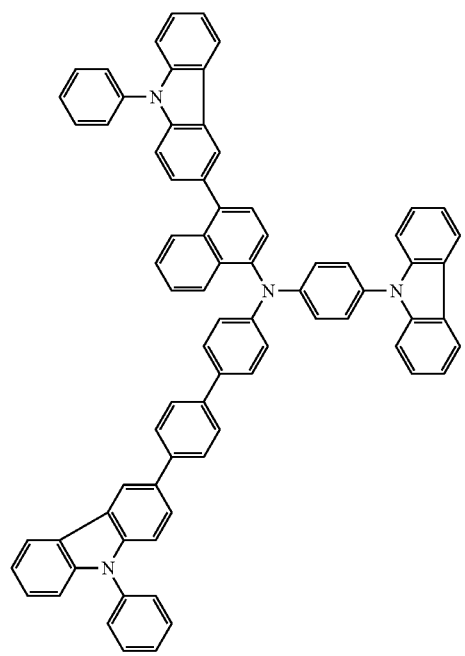
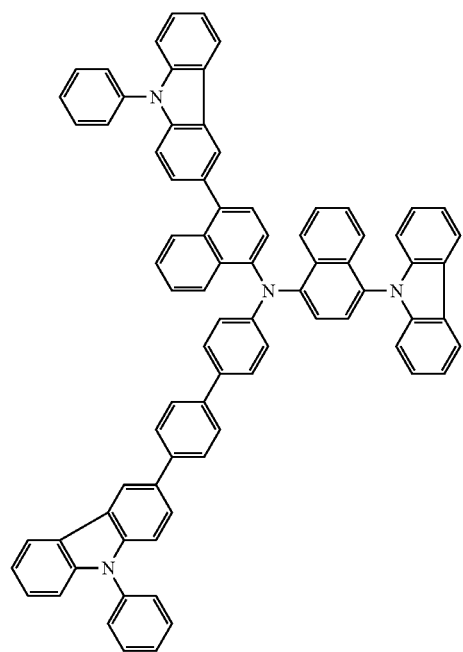

161
162
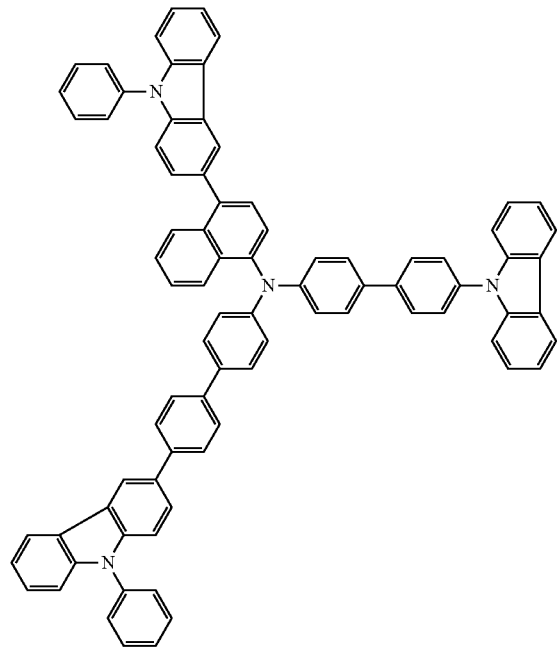
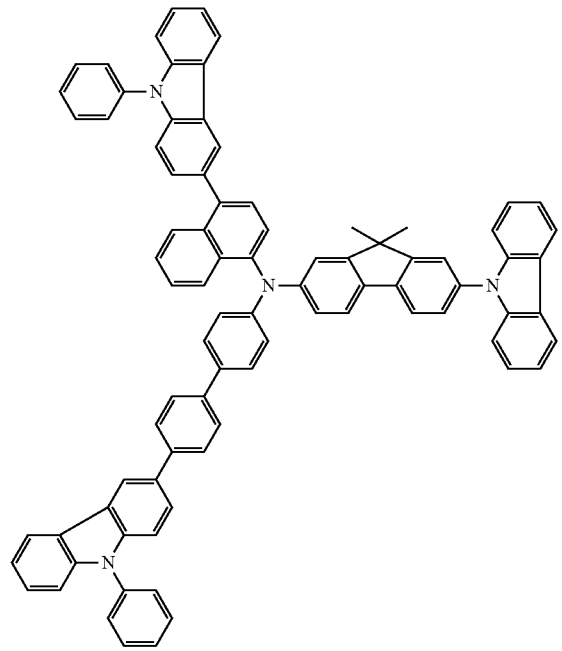
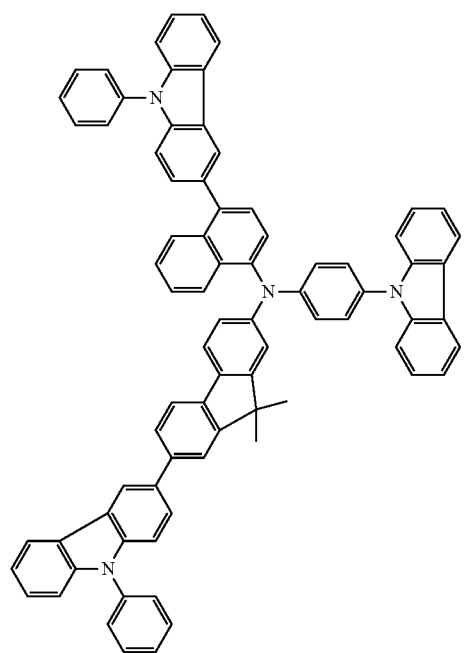
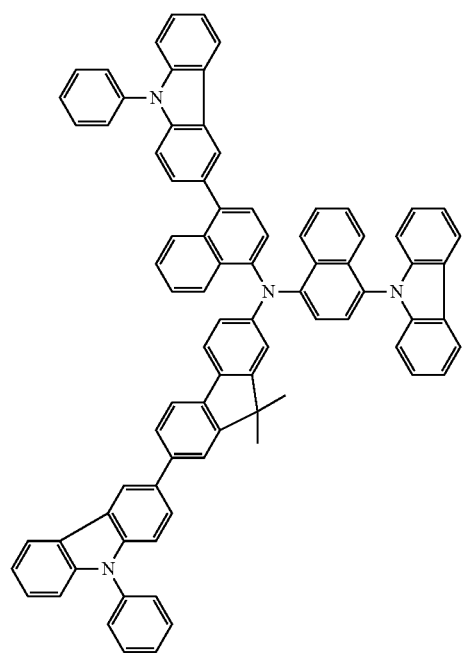

163
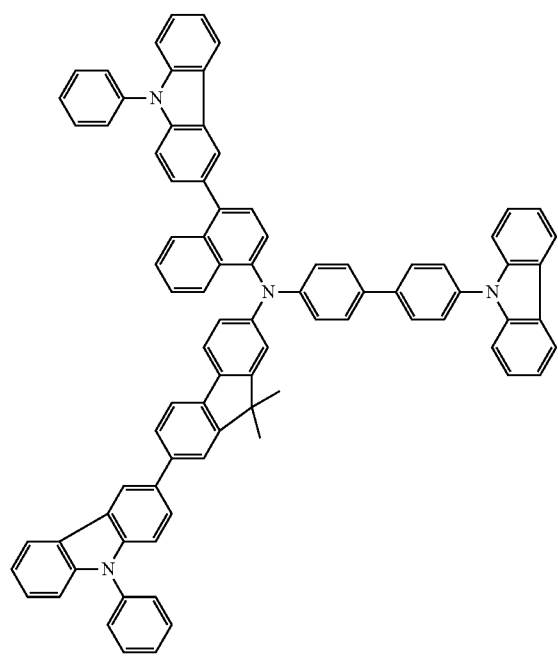
164
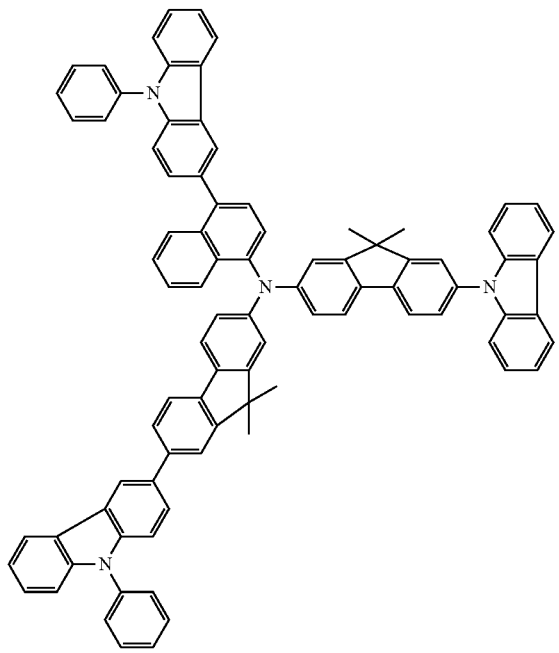
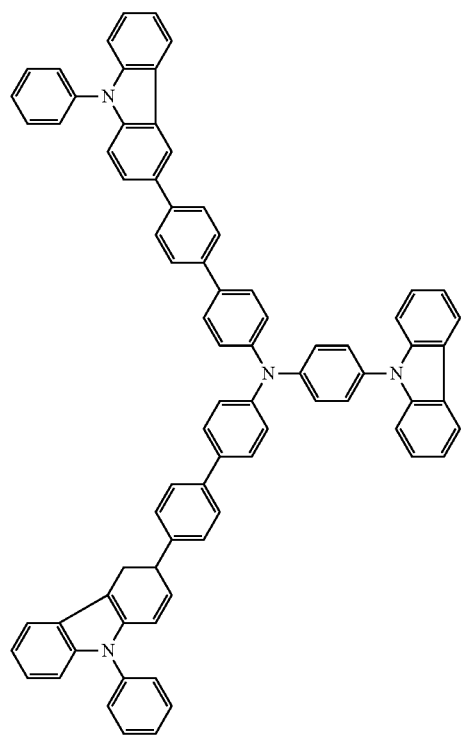
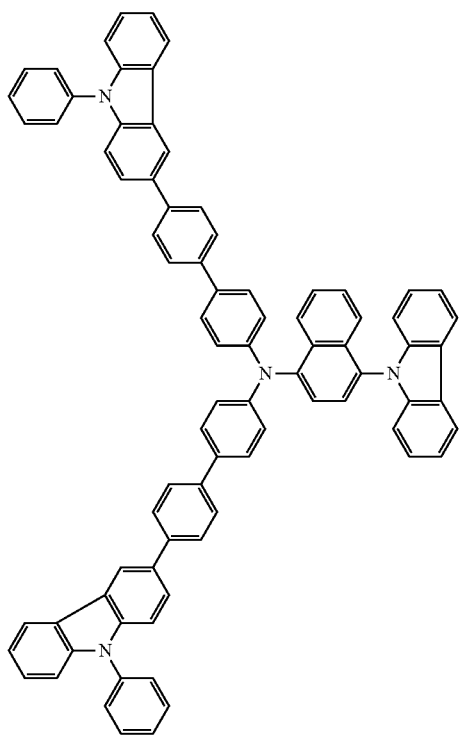

165
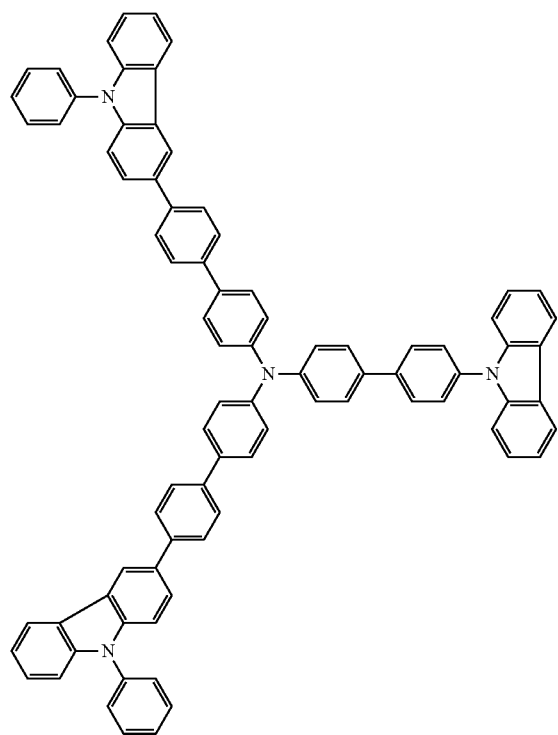
166
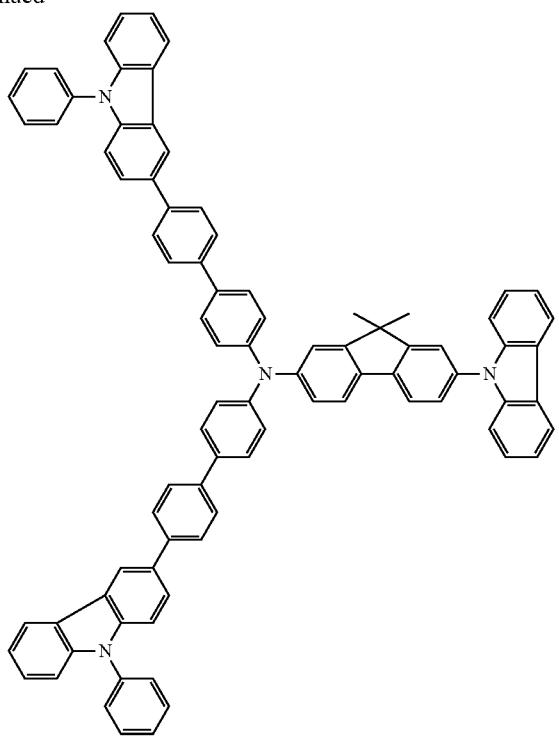
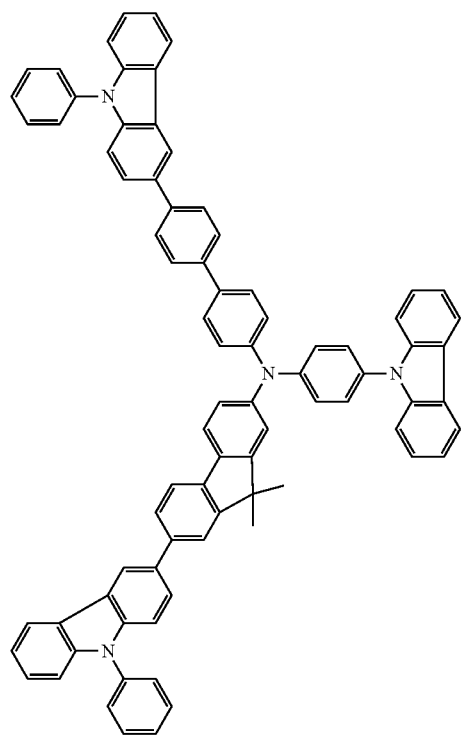
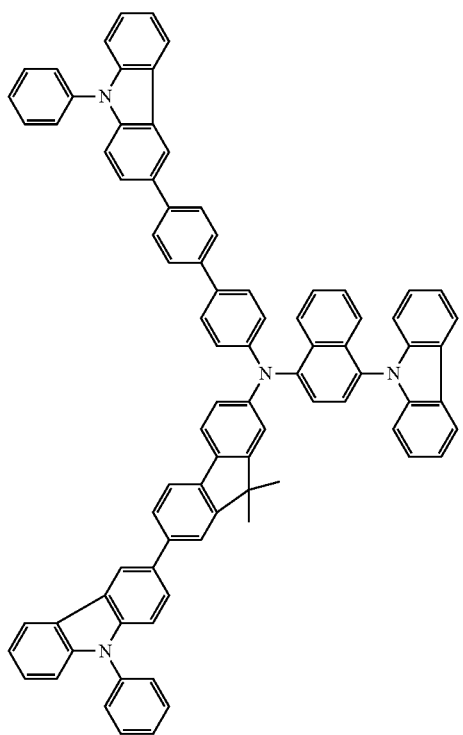

-continued
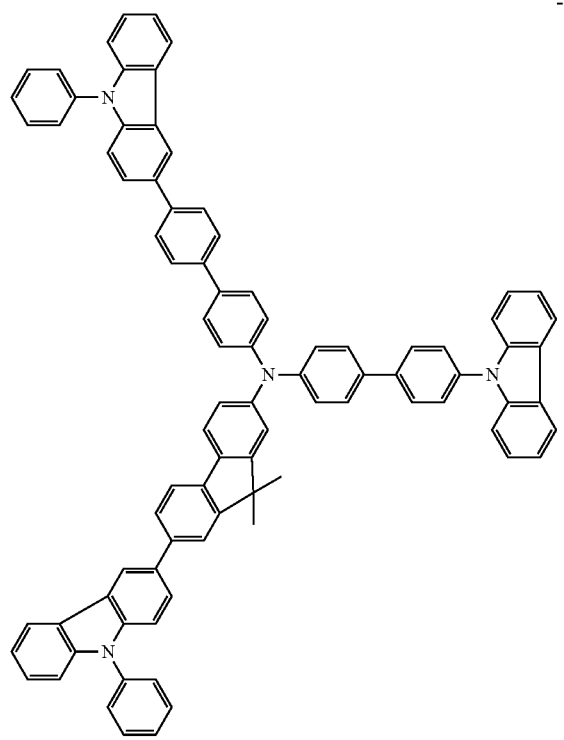
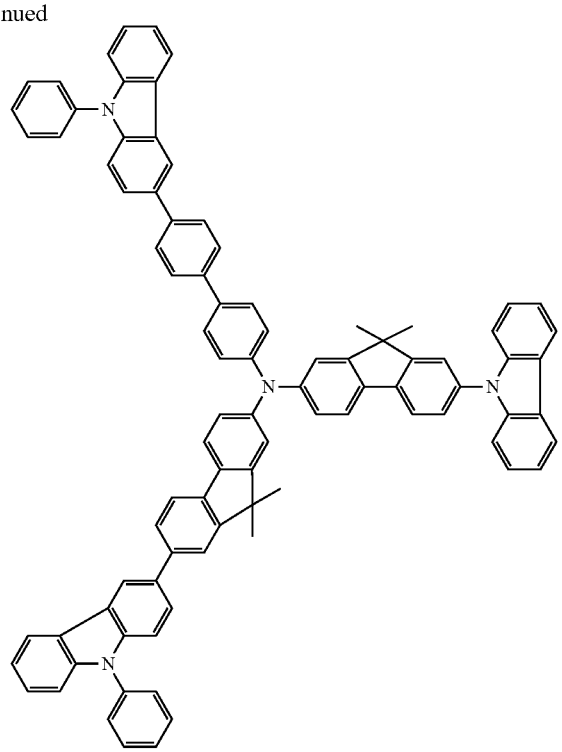
[Chem. 25]
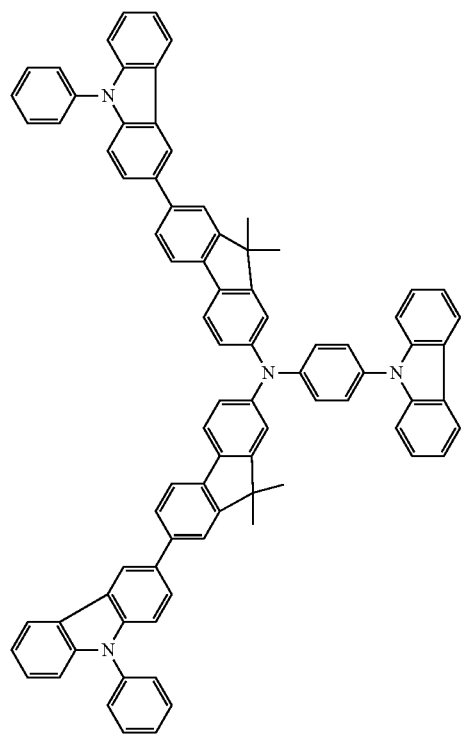
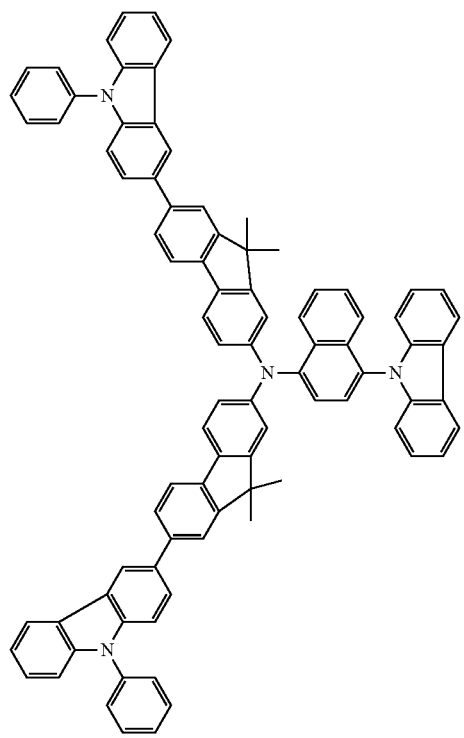

-continued
169
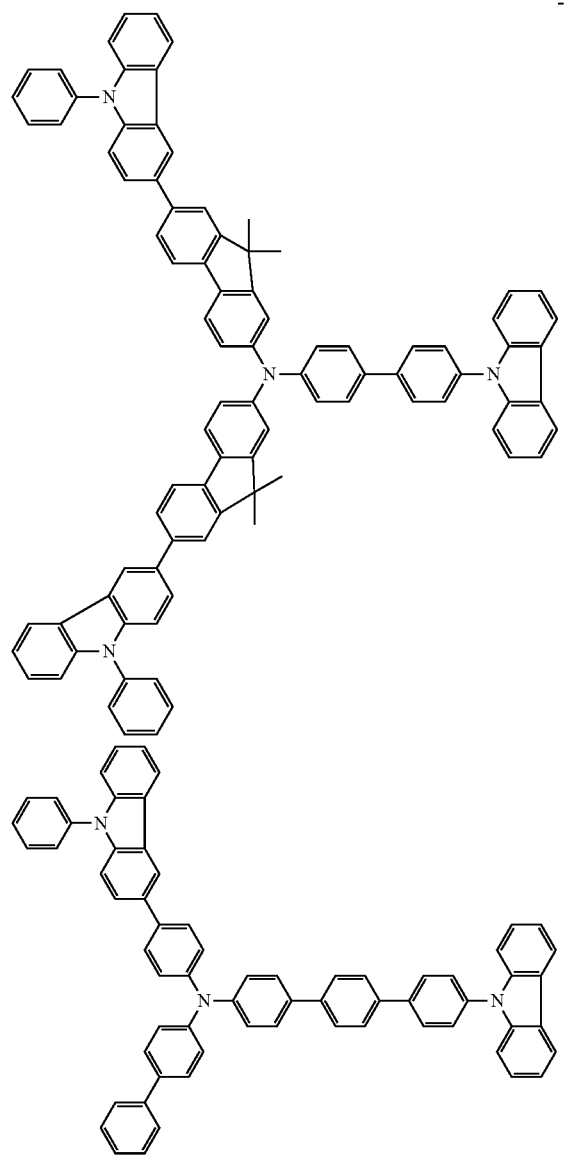
170
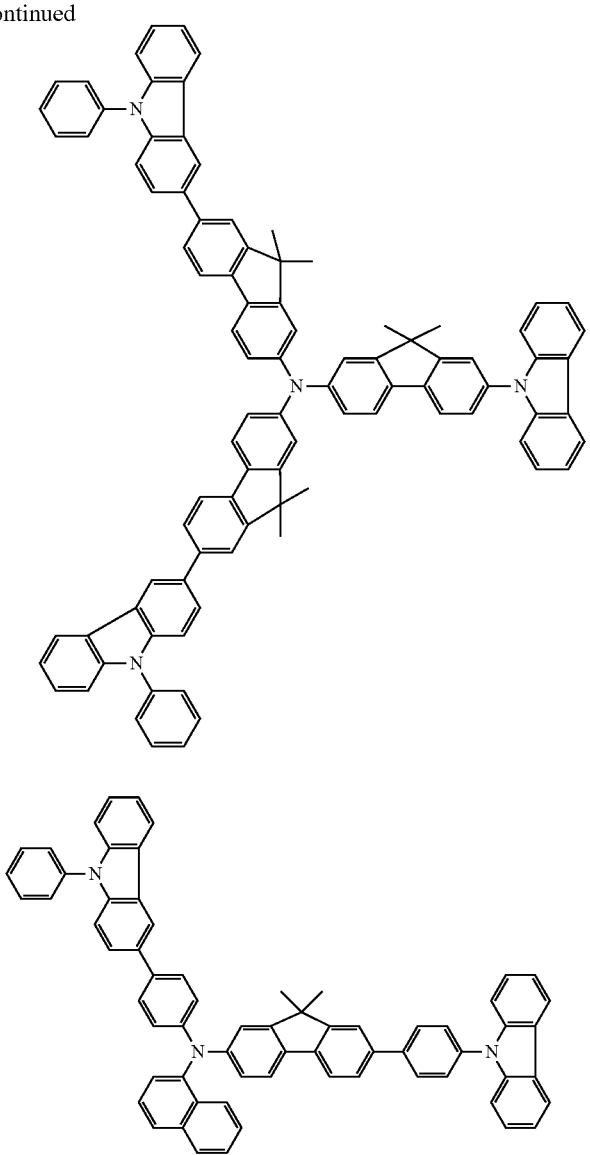
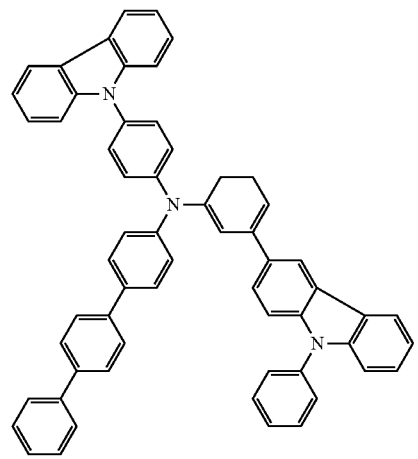
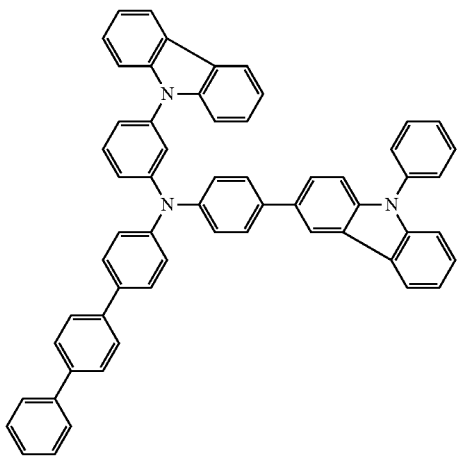

-continued
| 171 | 172 |
|---|---|
| 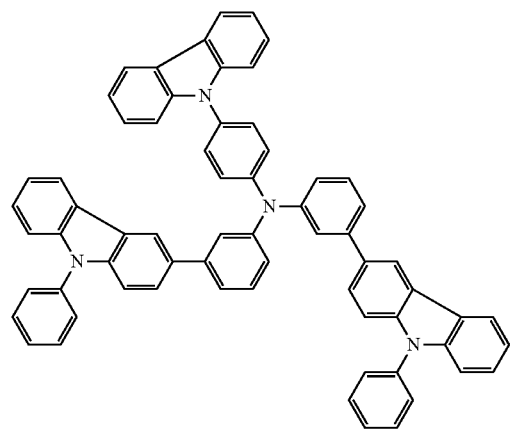 | 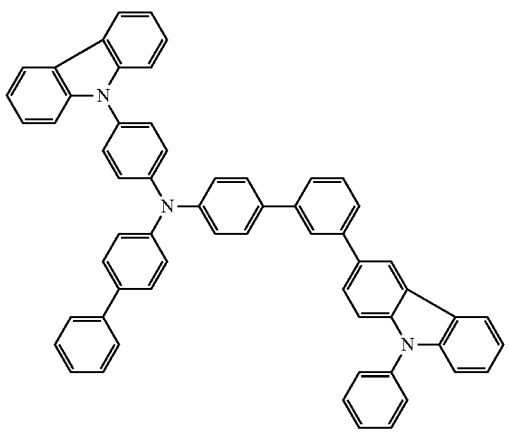 |
| 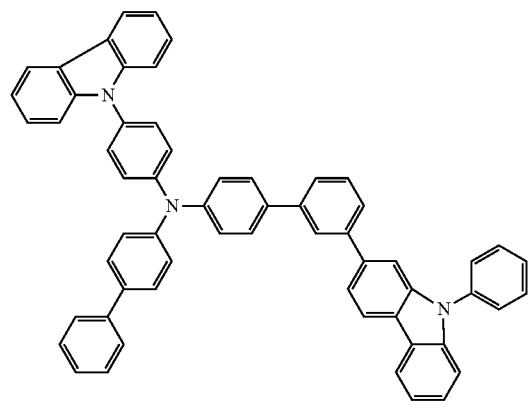 | 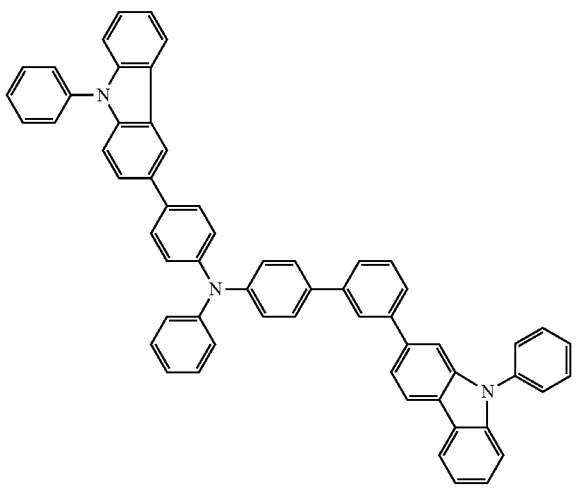 |
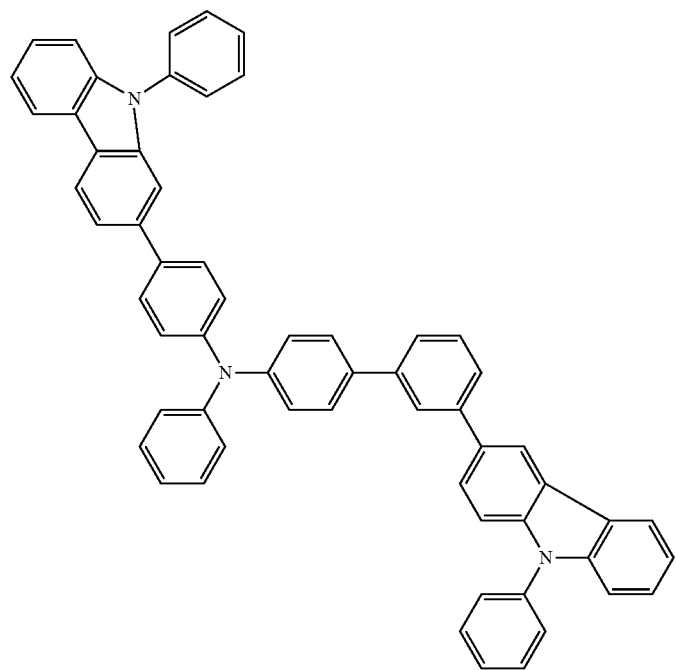

[Chem. 26]
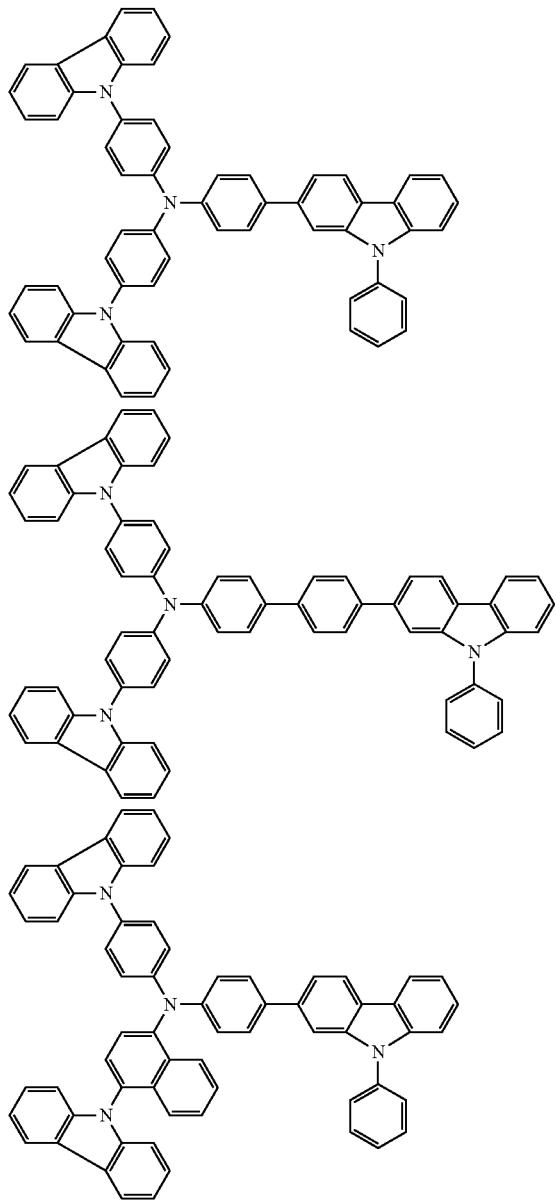
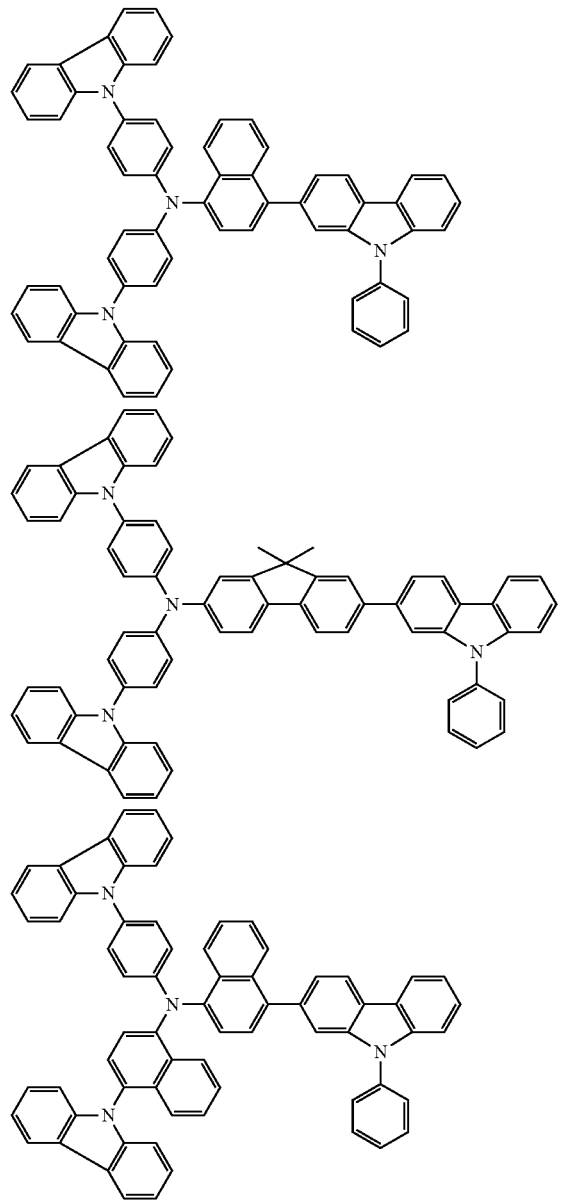
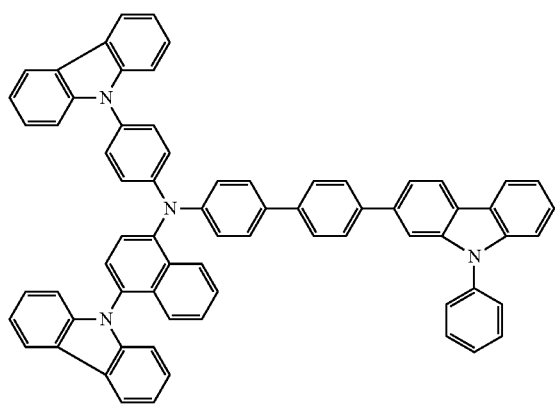
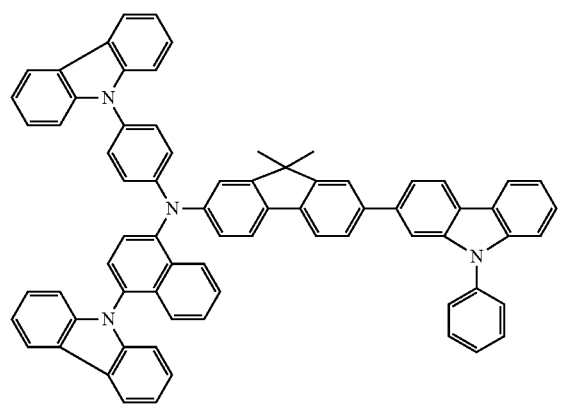

175
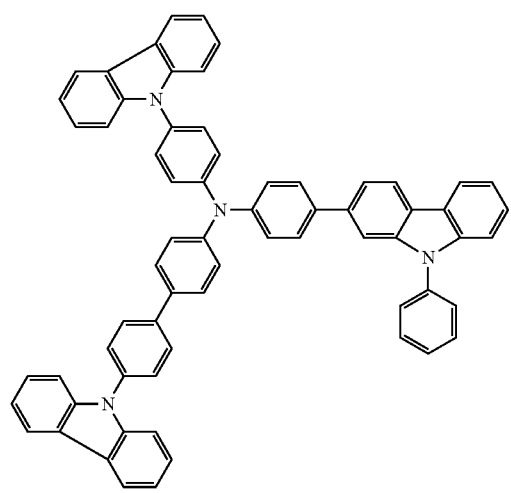
176
-continued
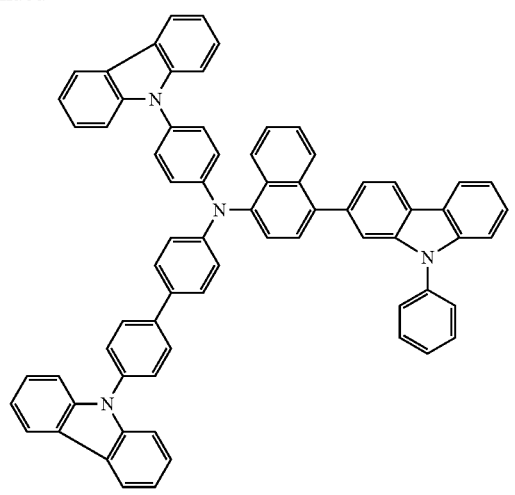
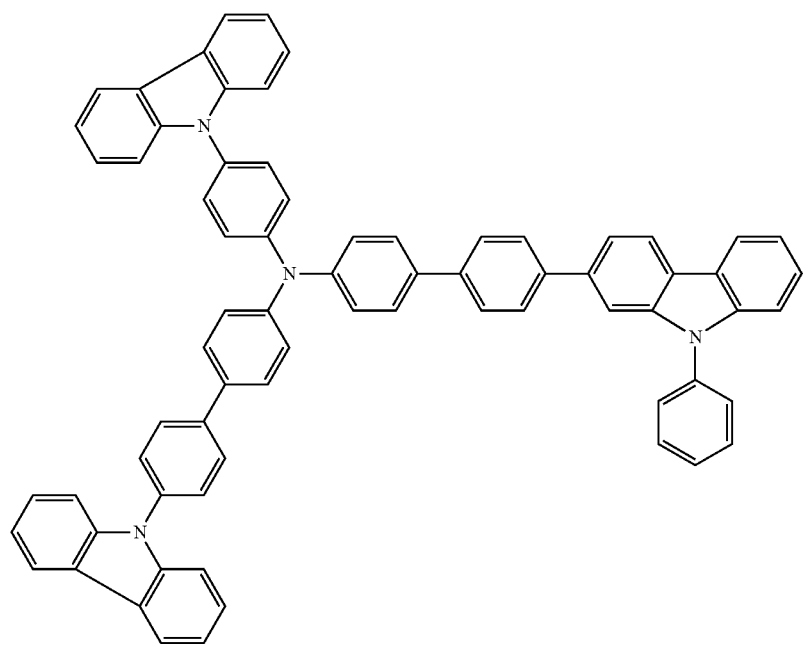

-continued
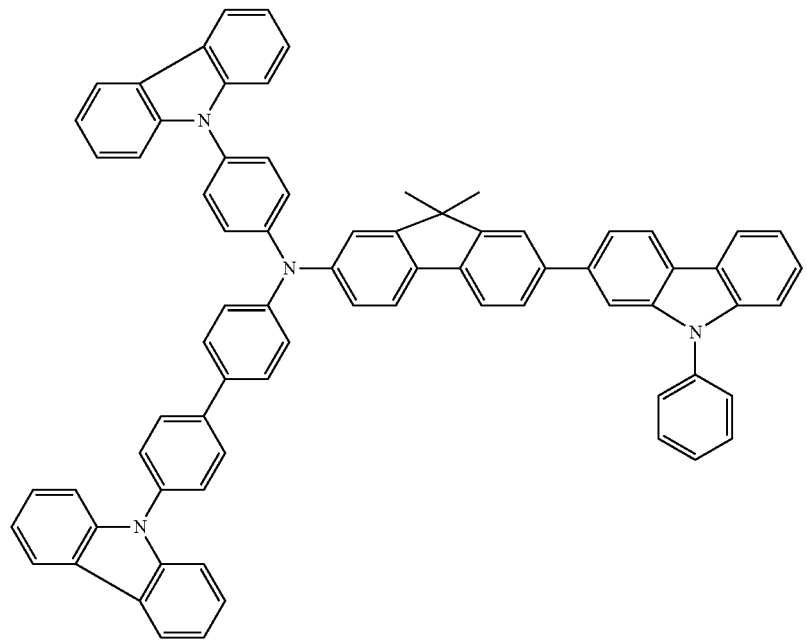
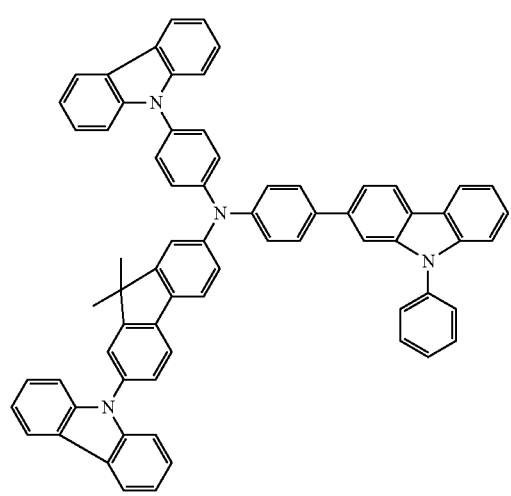
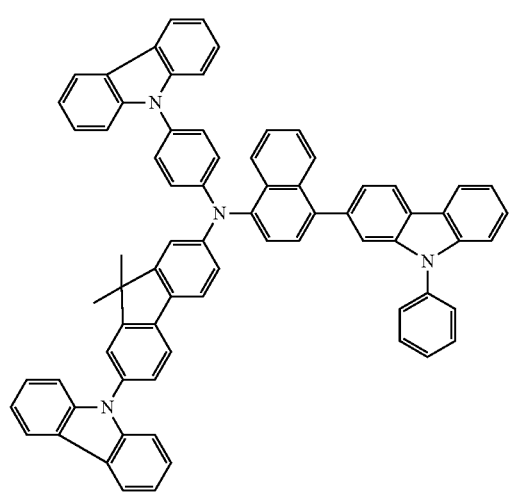

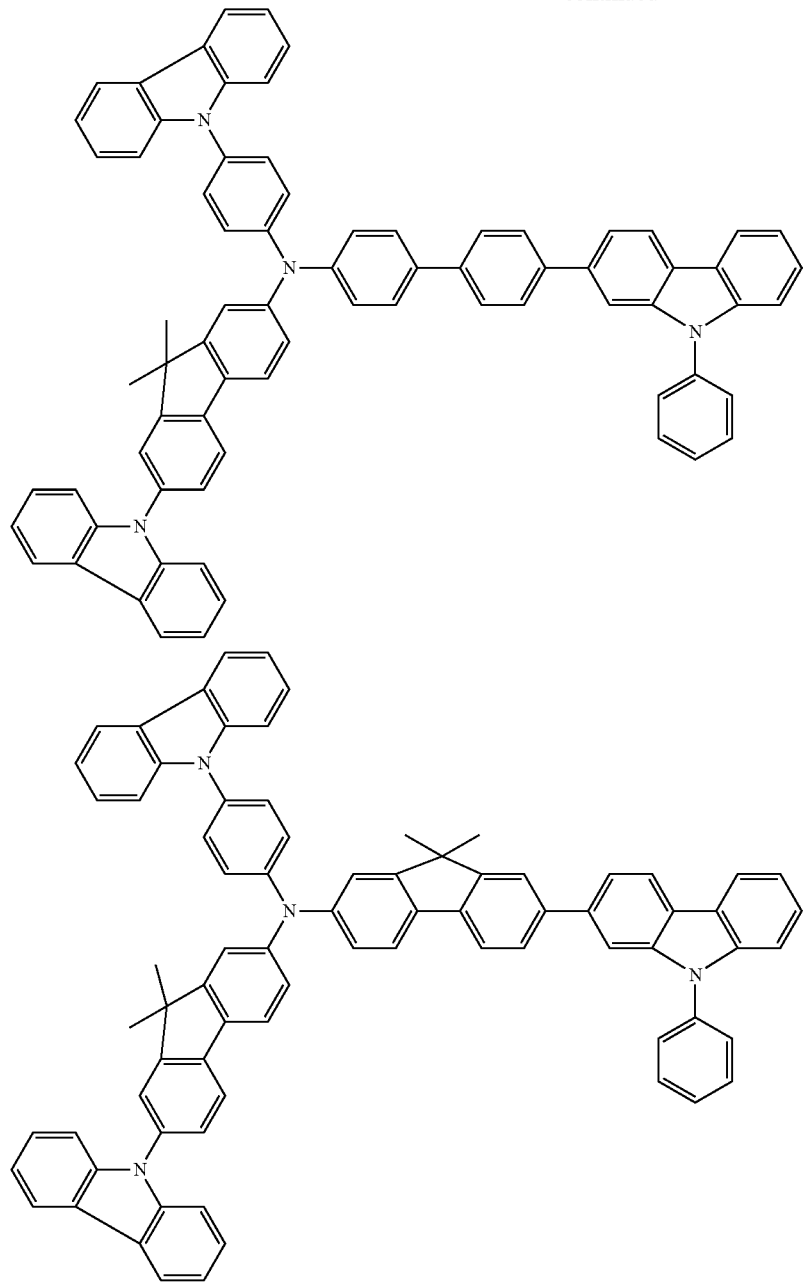
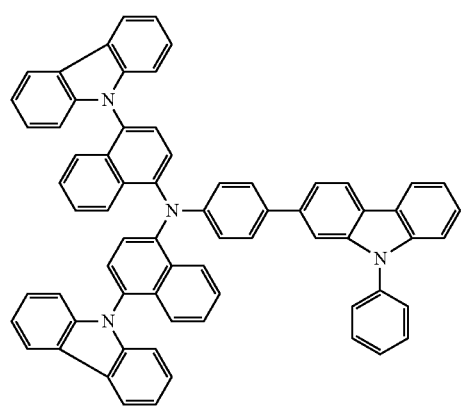
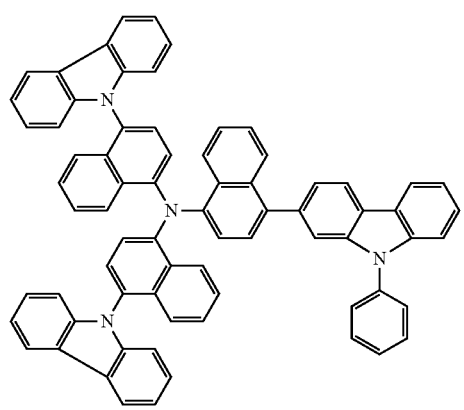

181
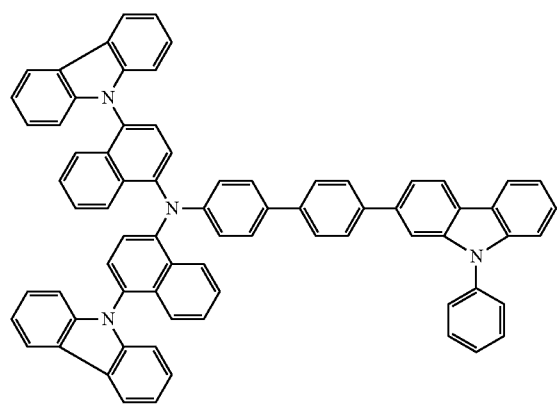
182
-continued
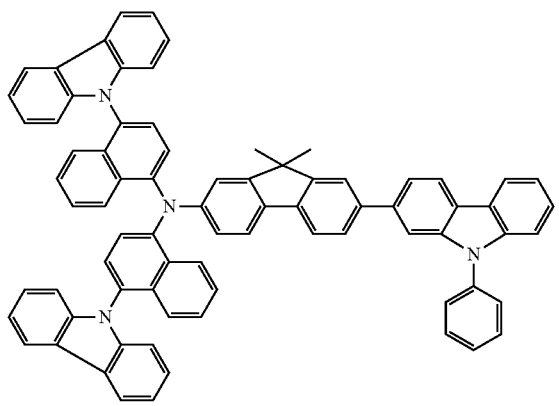
[Chem. 27]
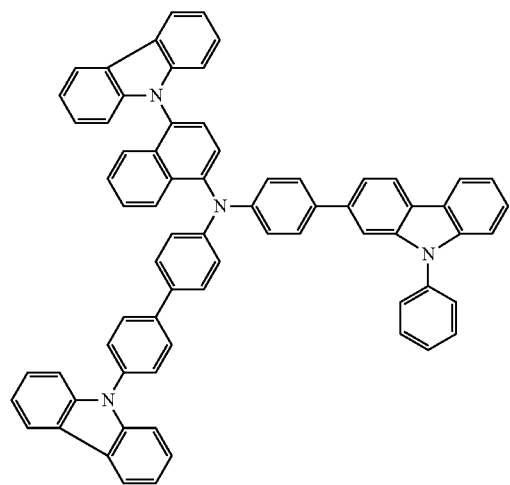
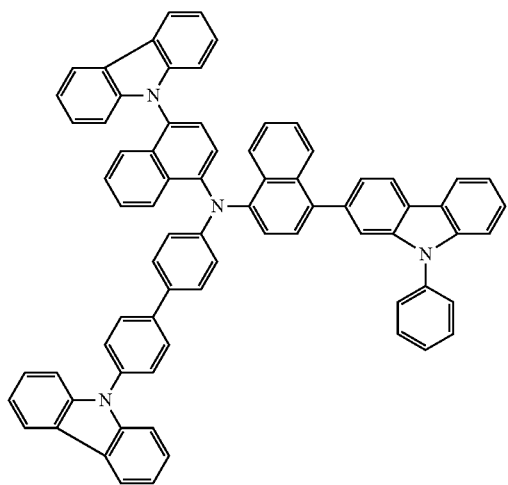
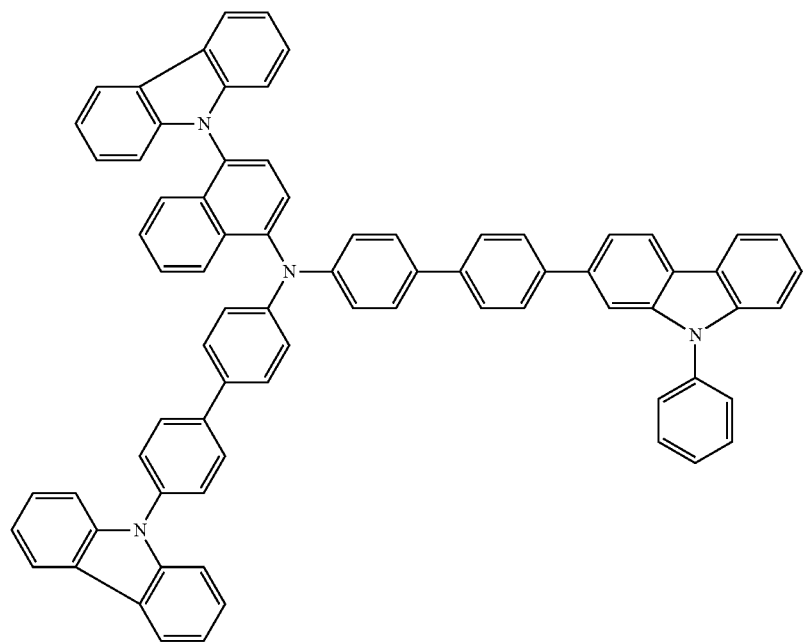

183
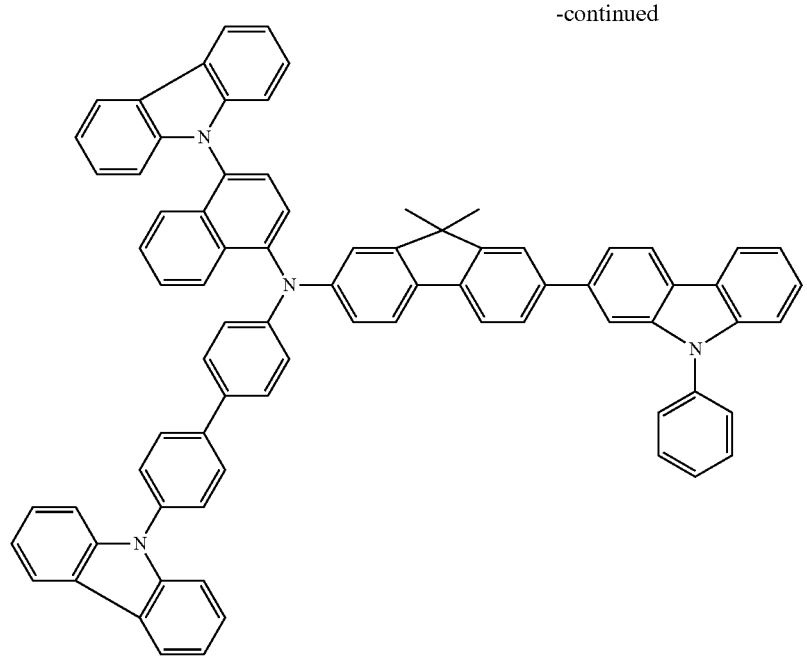
-continued
184
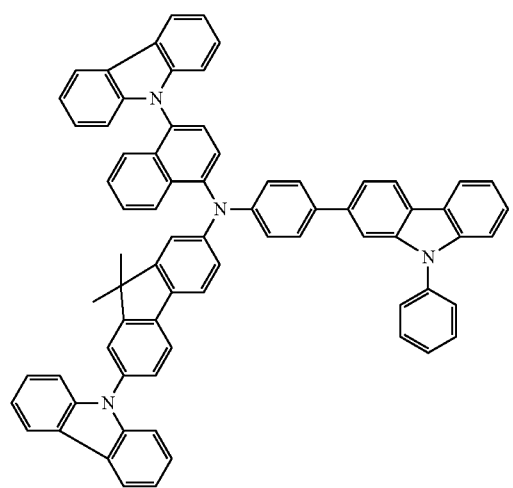
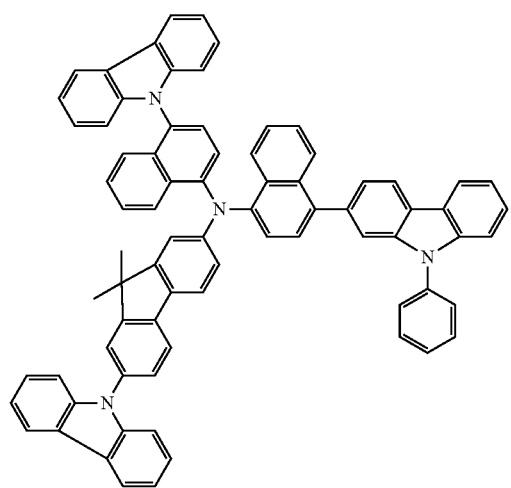

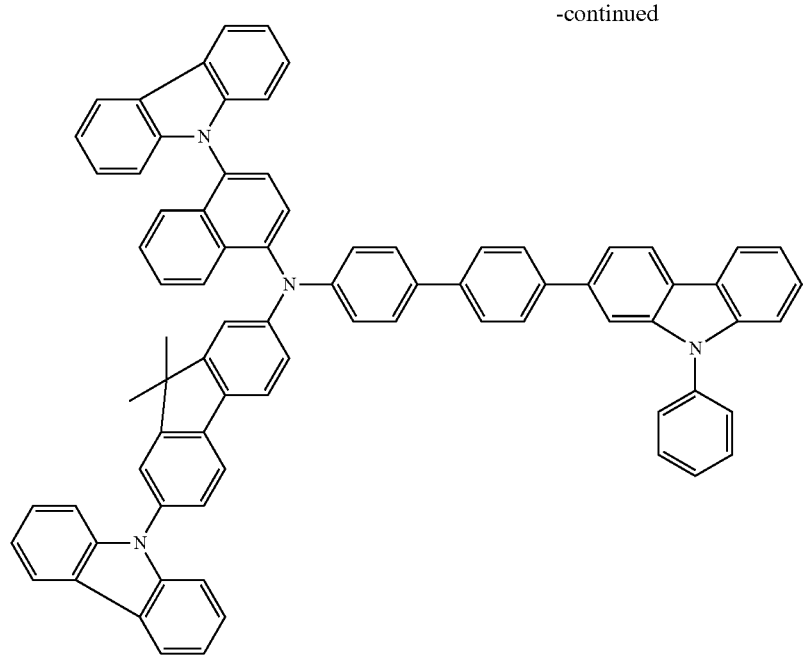
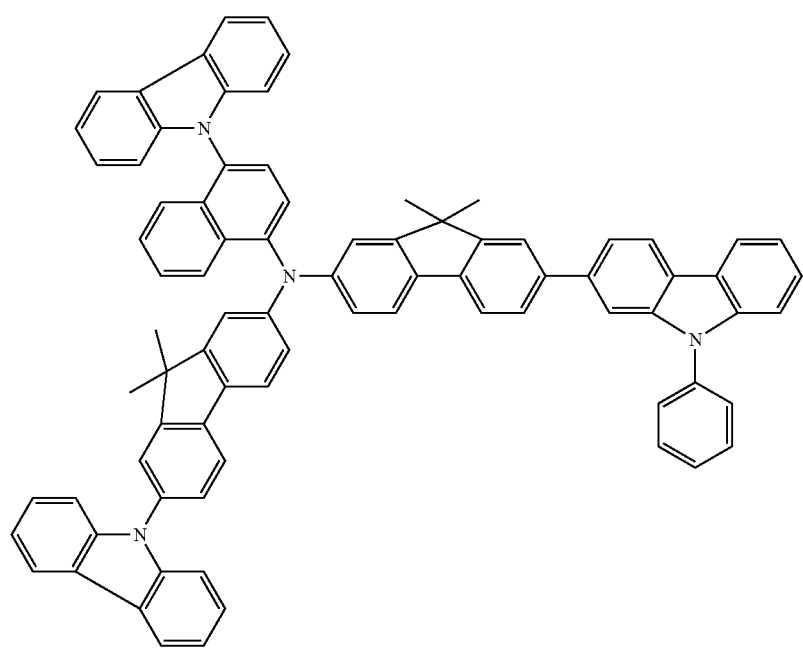

187
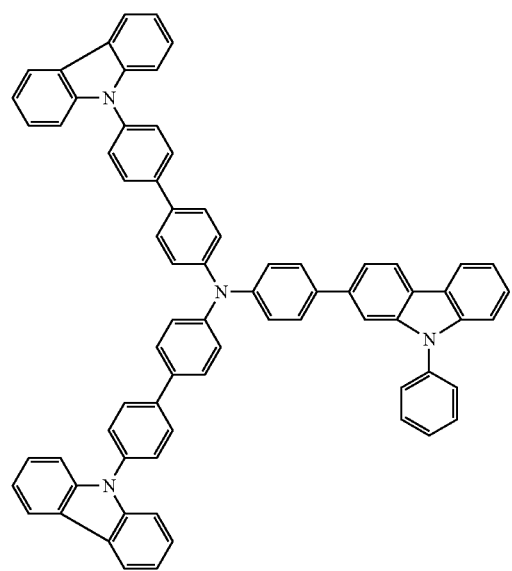
188
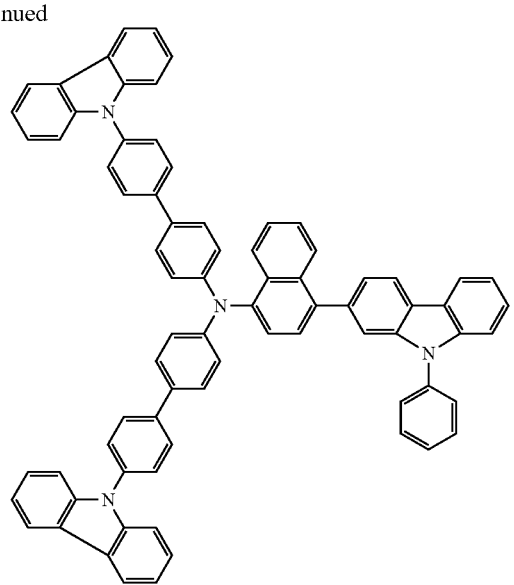
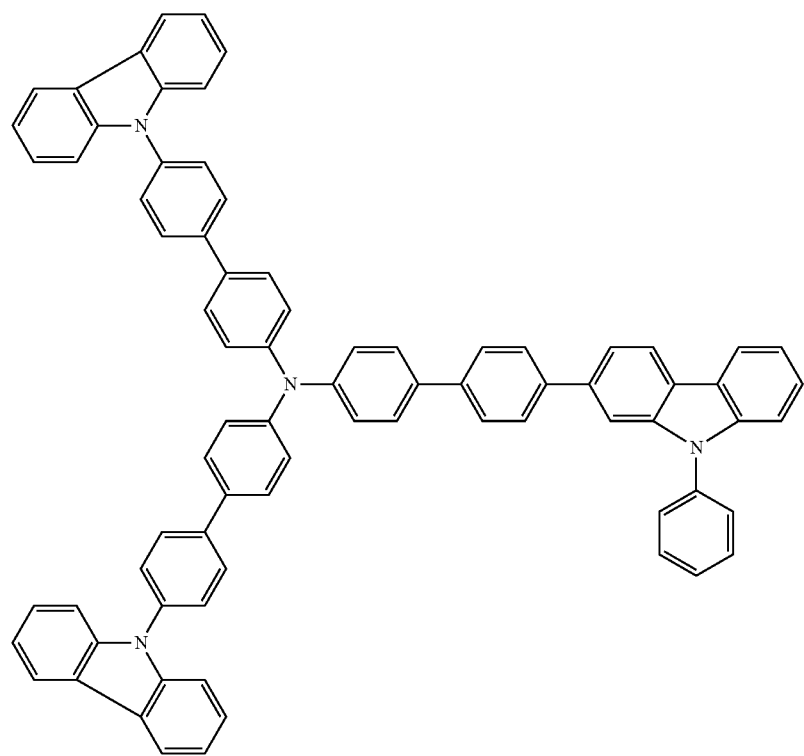

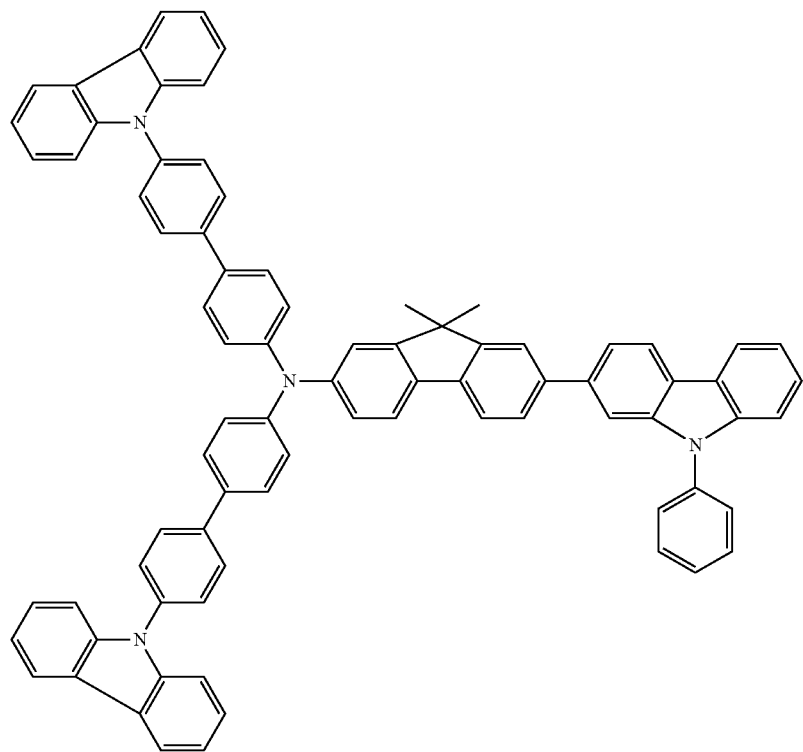
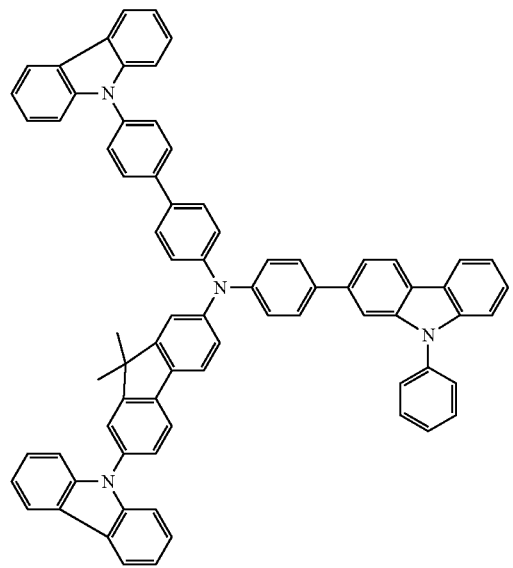
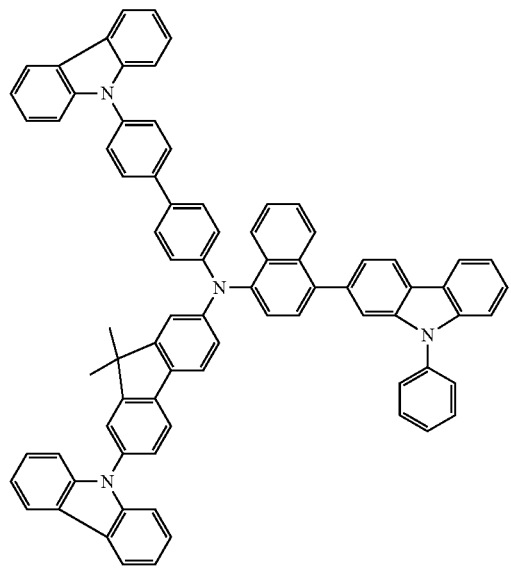

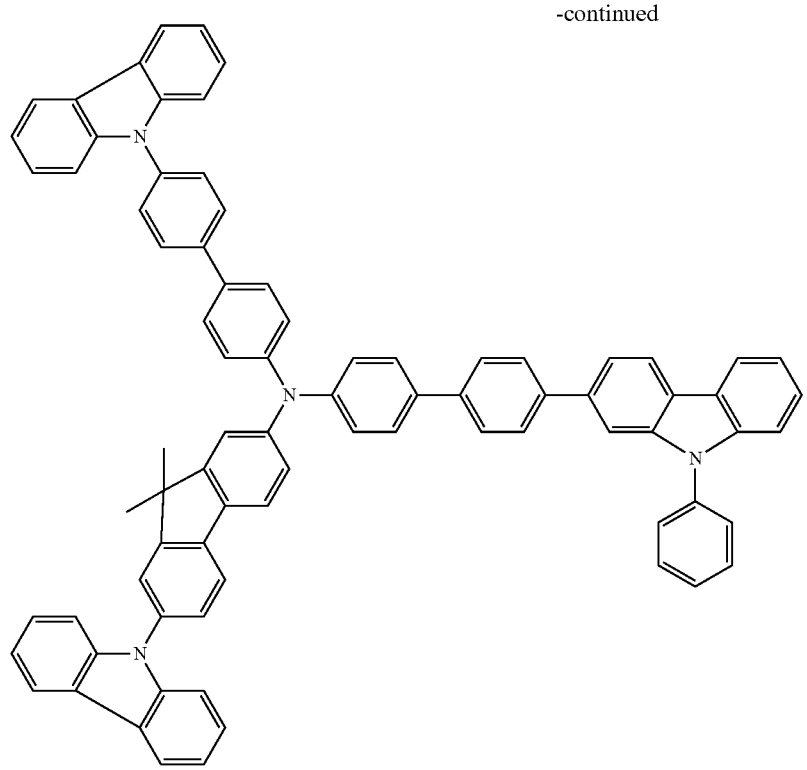
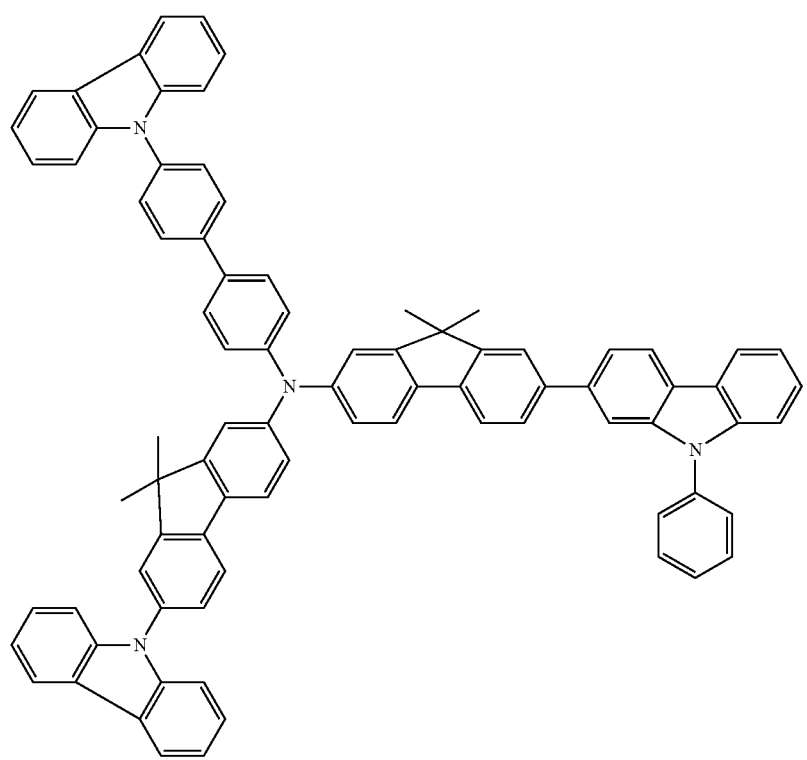

193
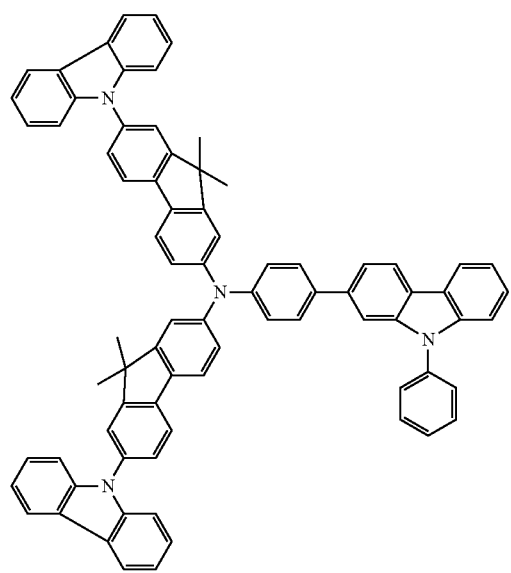
194
-continued
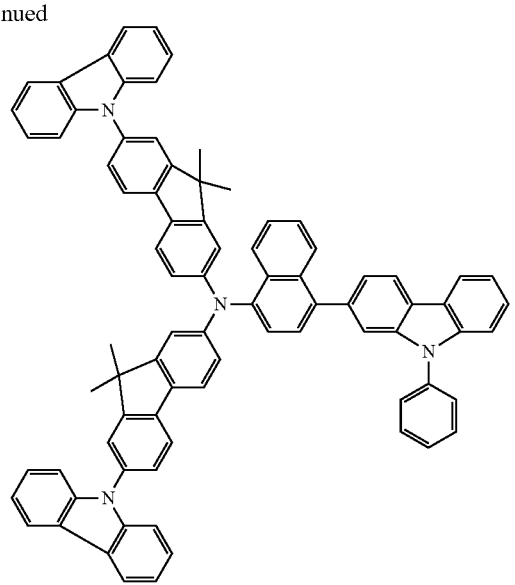
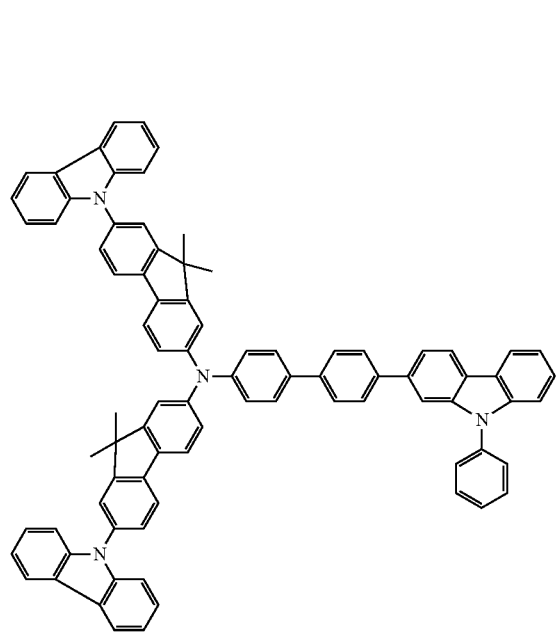
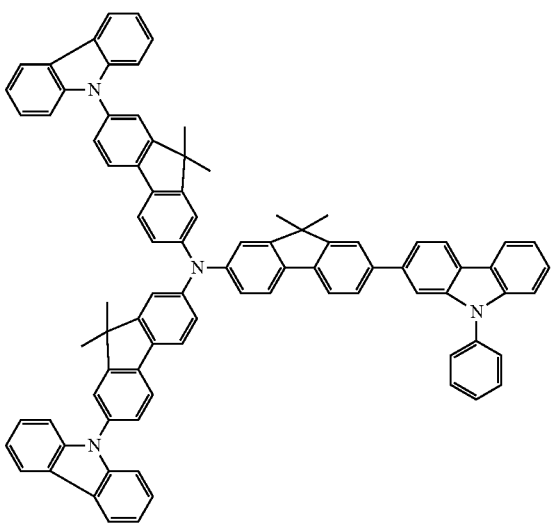

[Chem. 28]
195
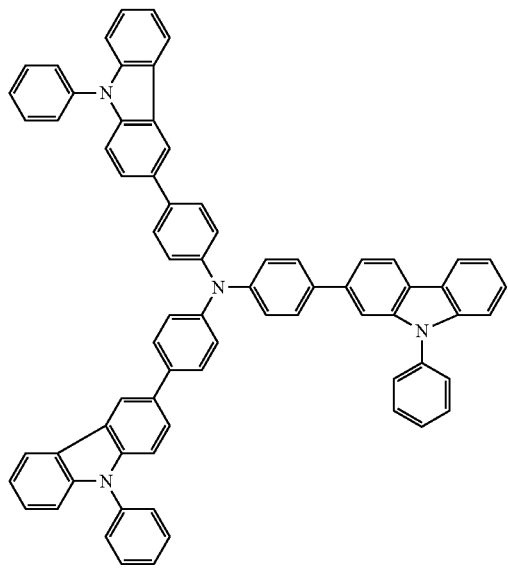
196
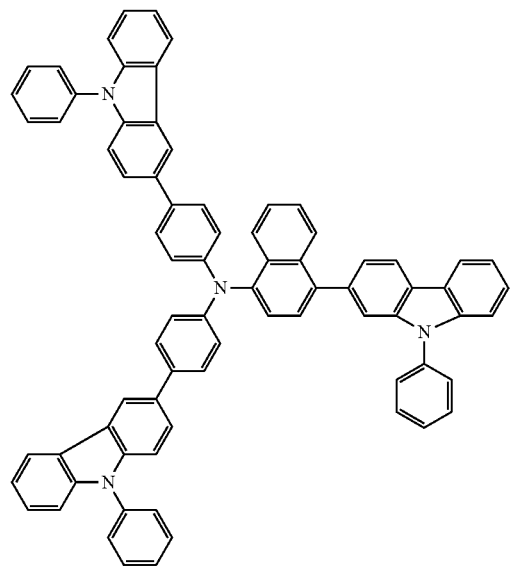
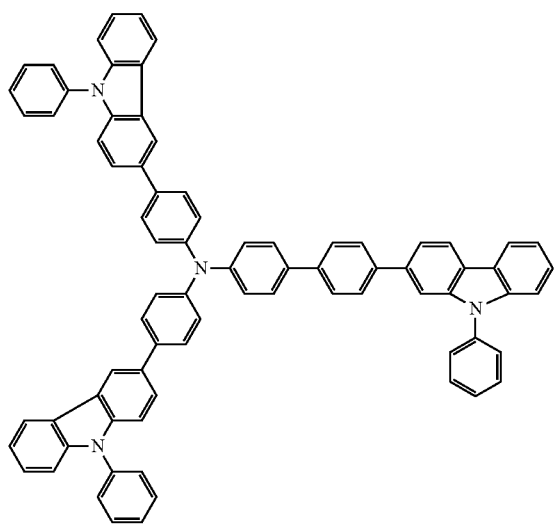
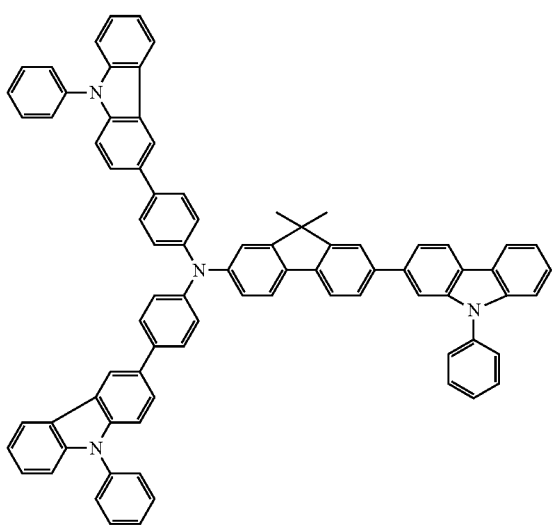

197
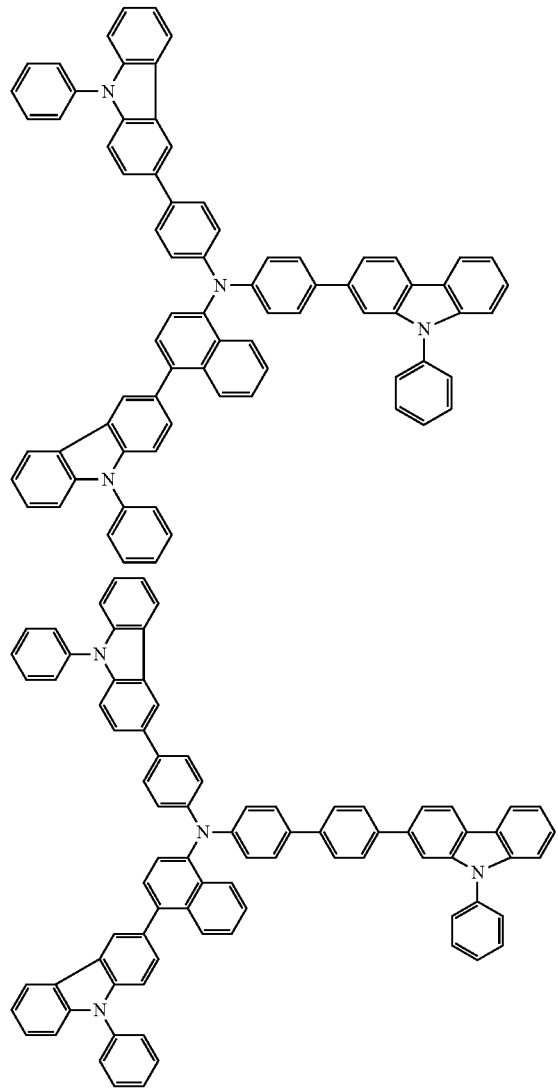
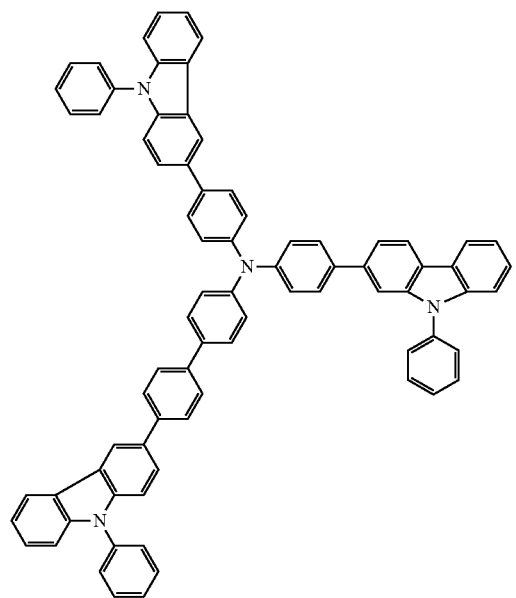
198
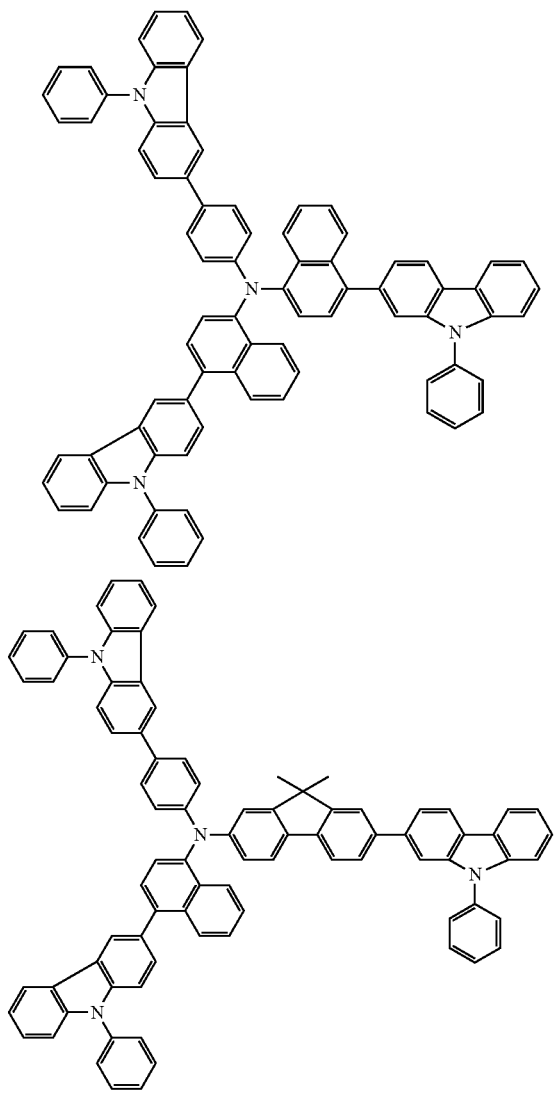
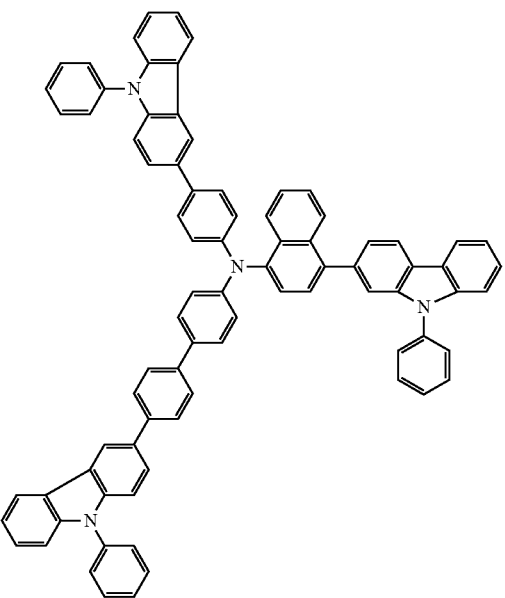

199
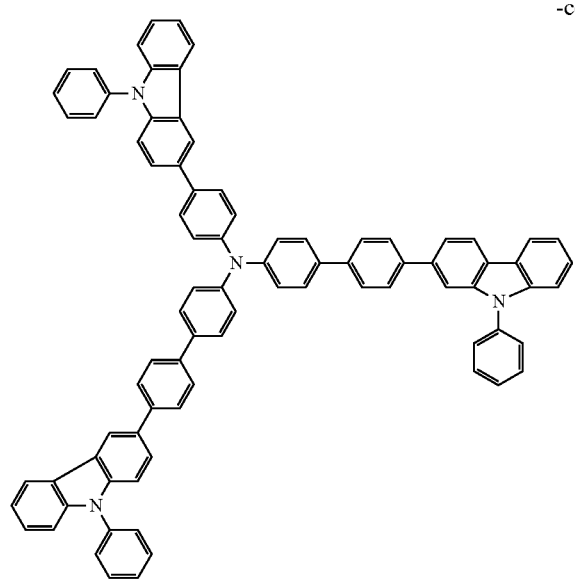
200
-continued
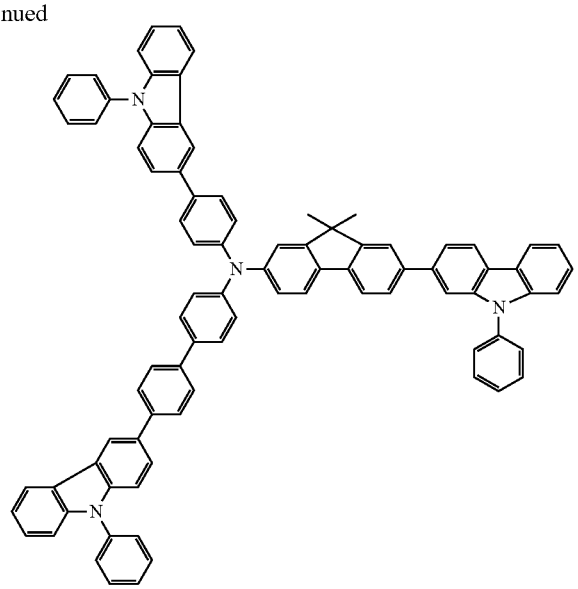
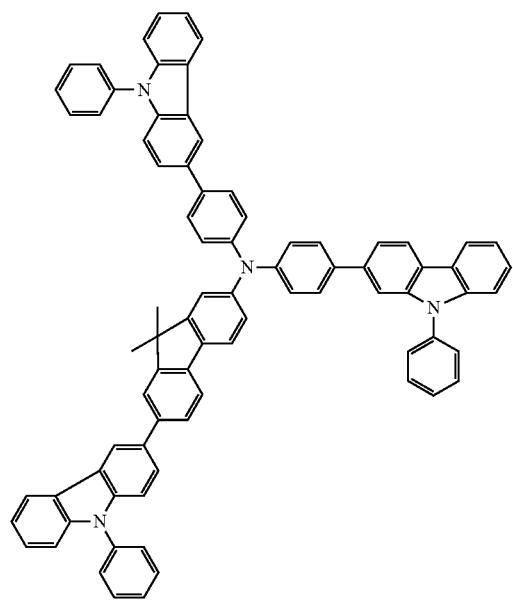
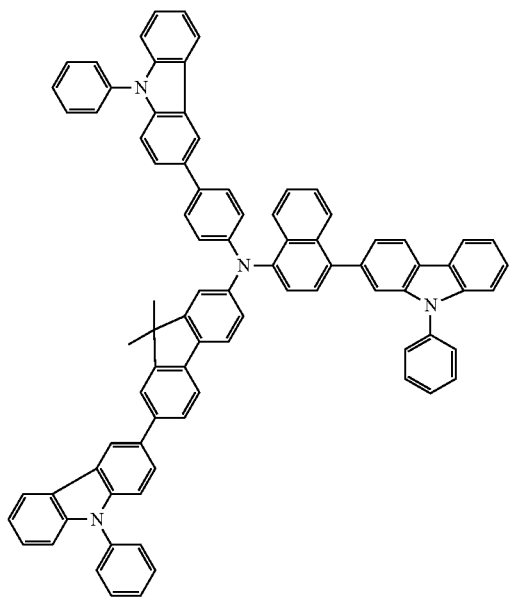

-continued
201
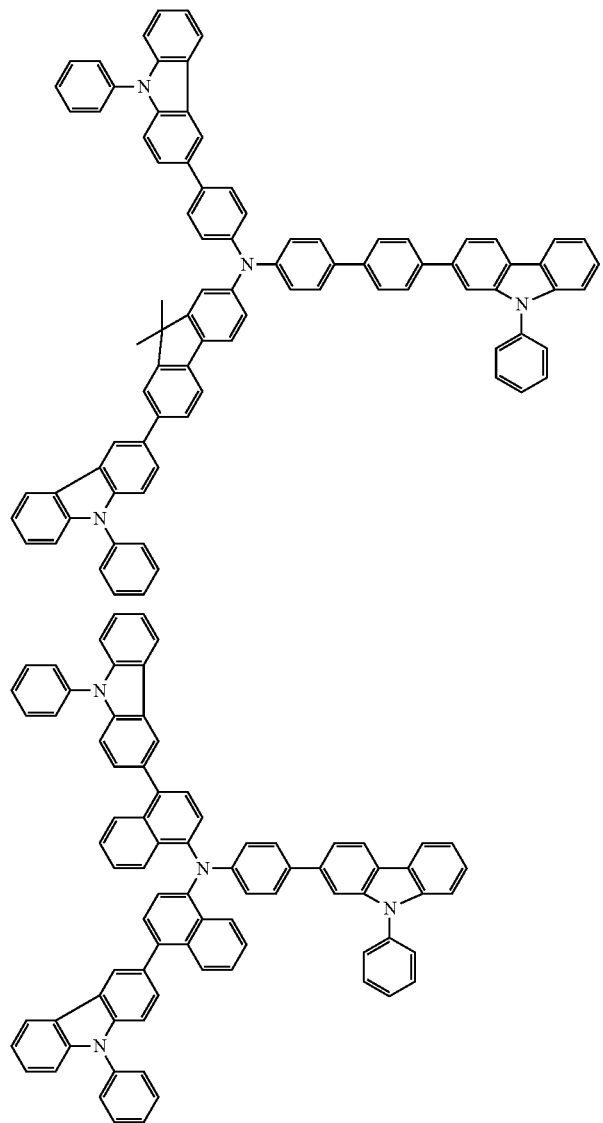
202
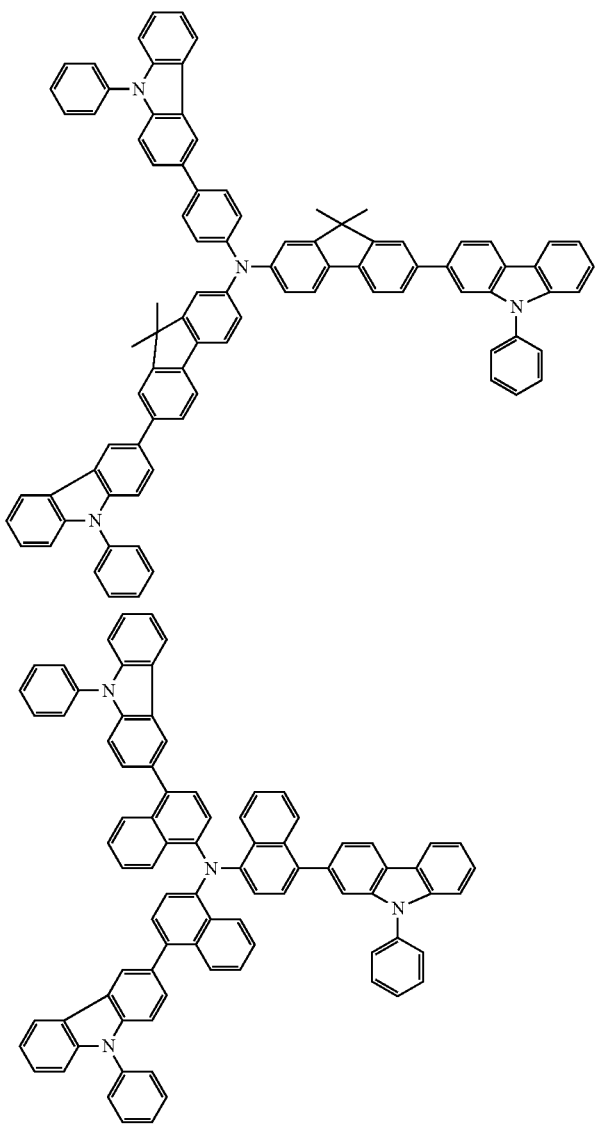
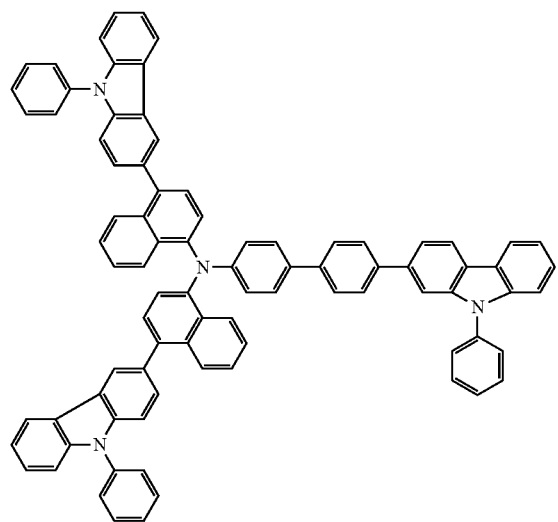
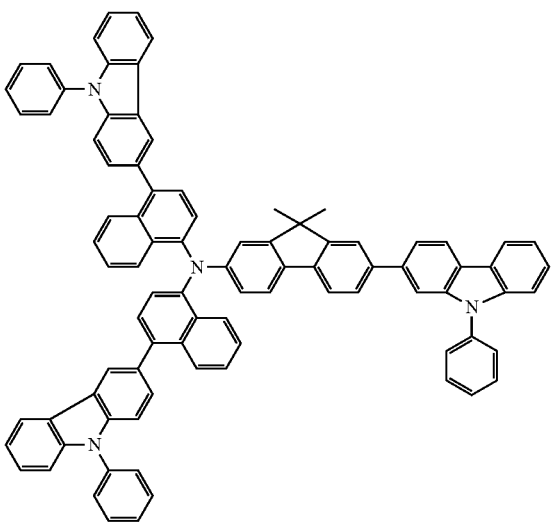

[Chem. 29]
203
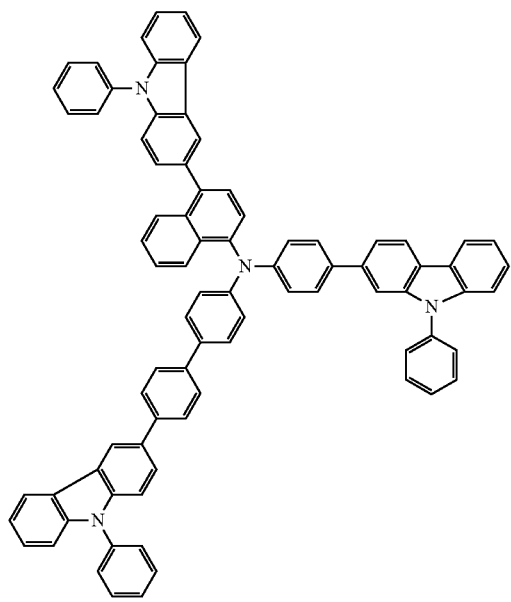
204
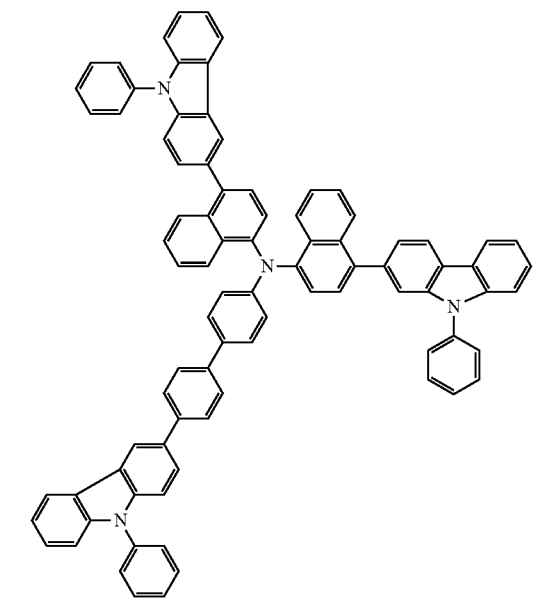
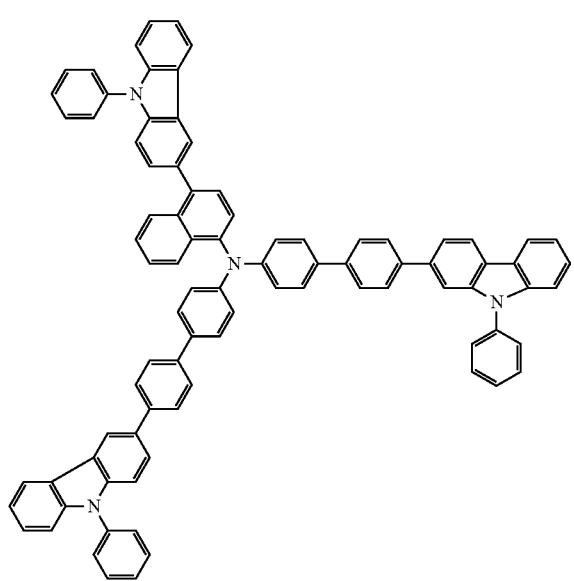
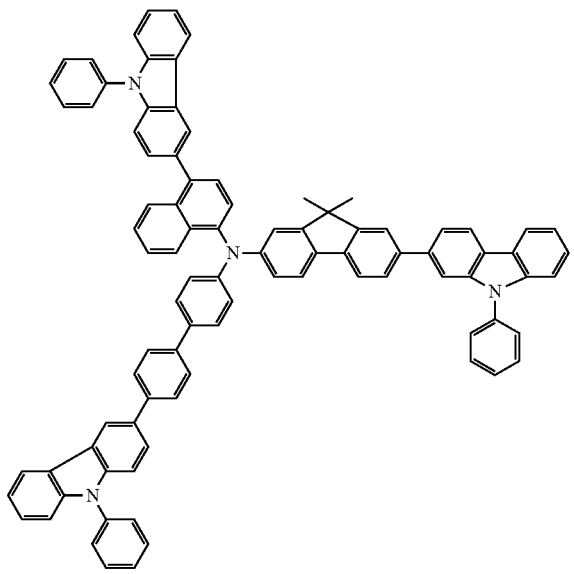

205
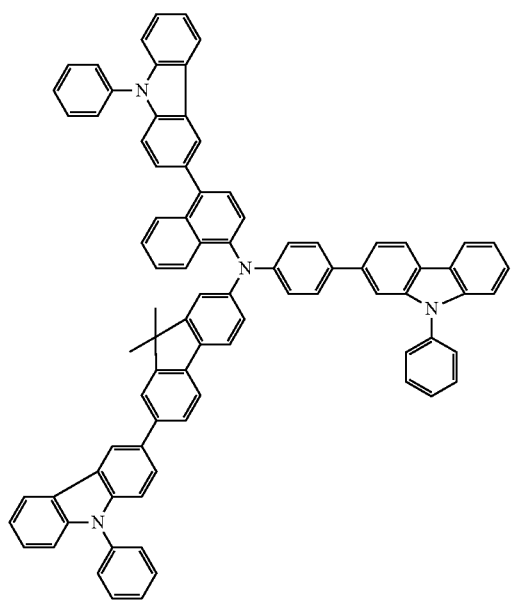
206
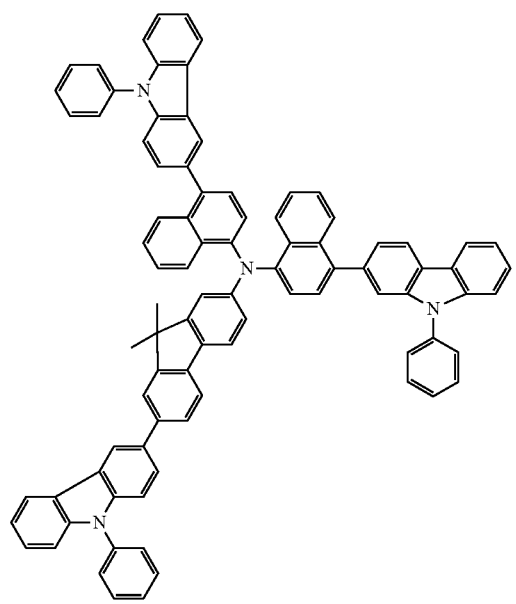
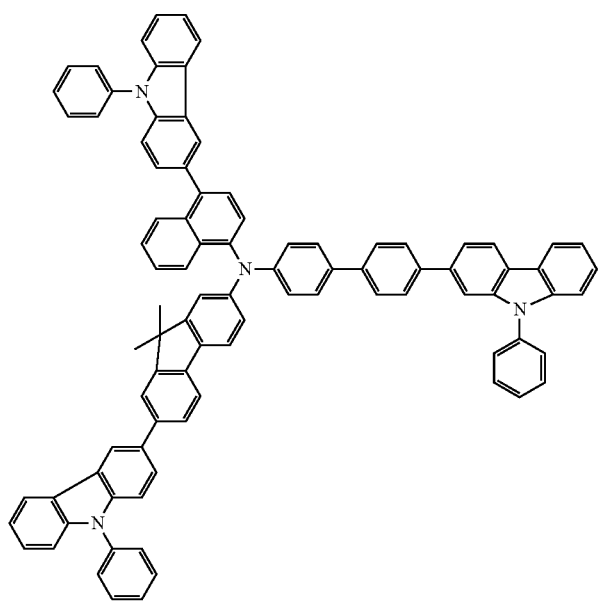
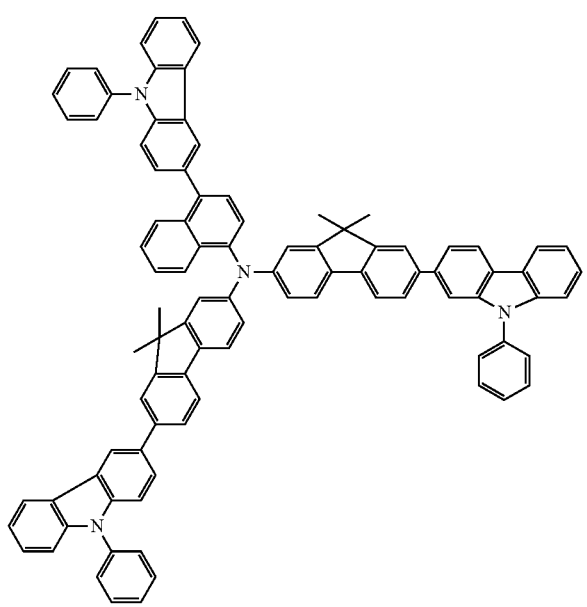

207
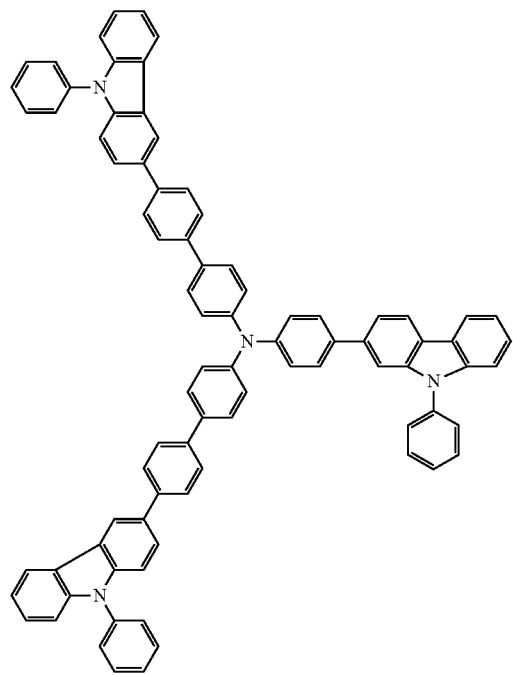
208
-continued
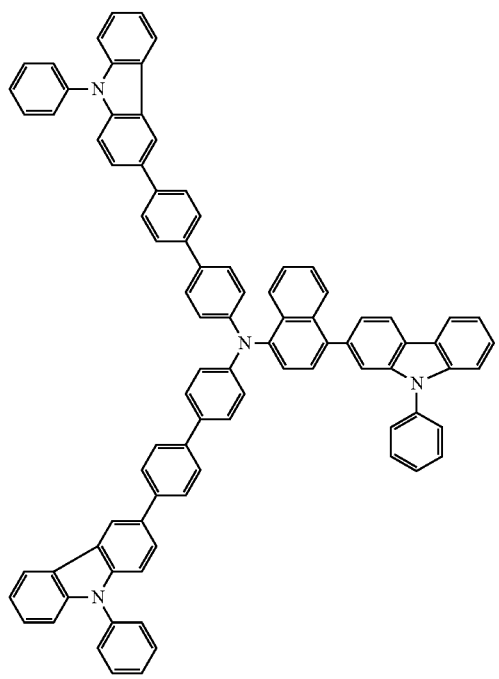
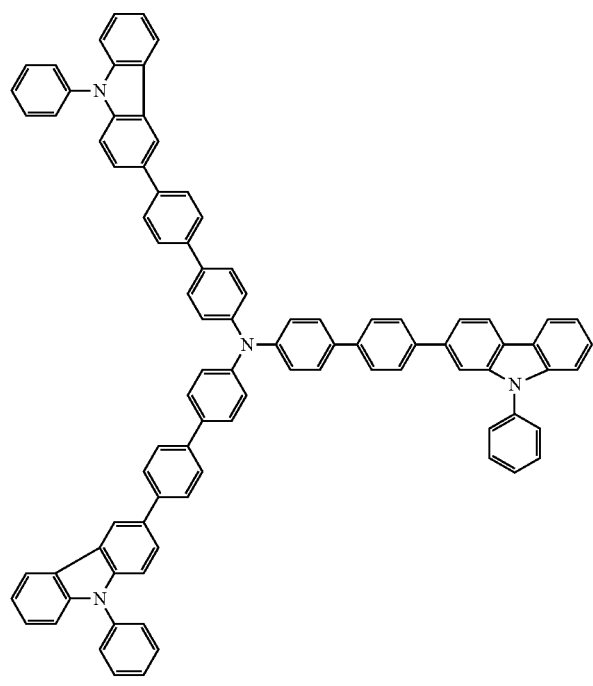
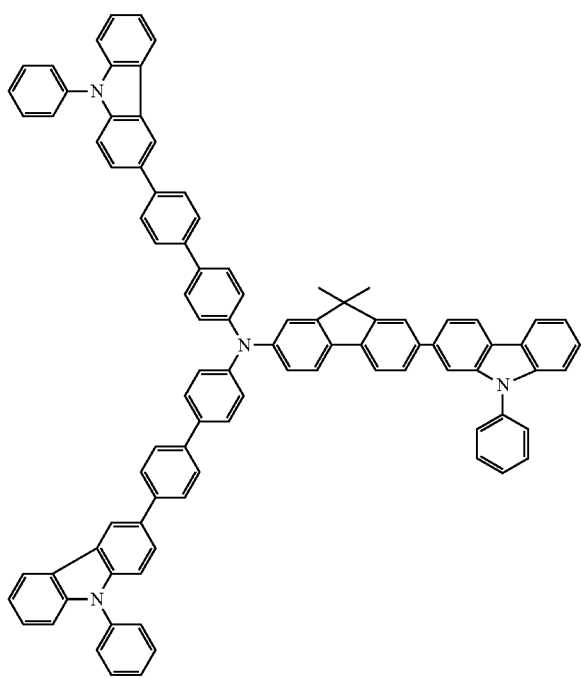

209
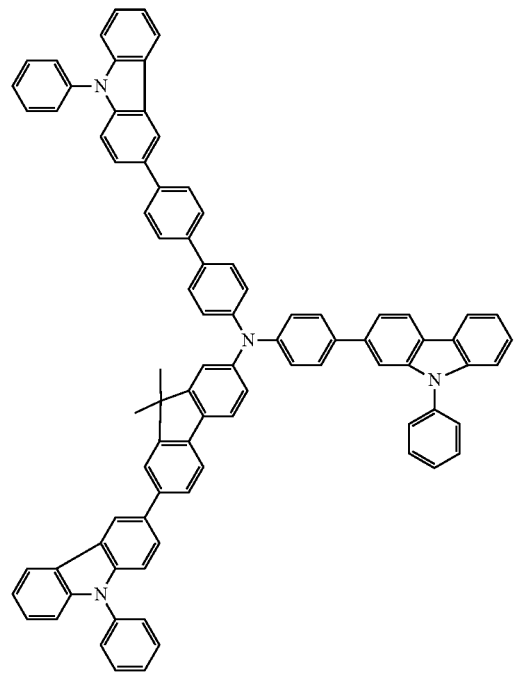
210
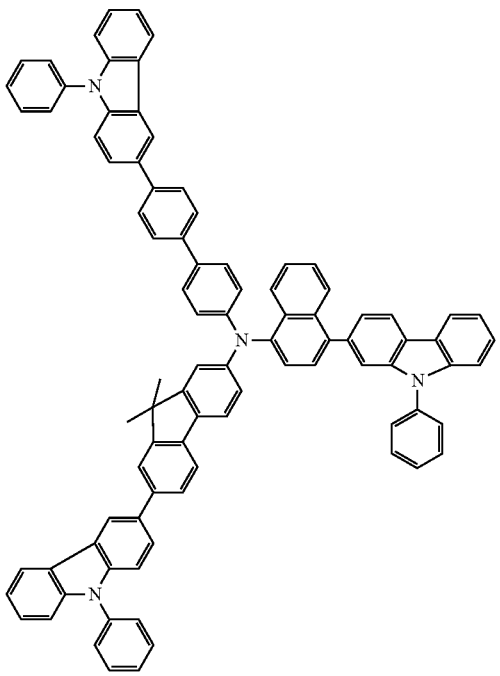
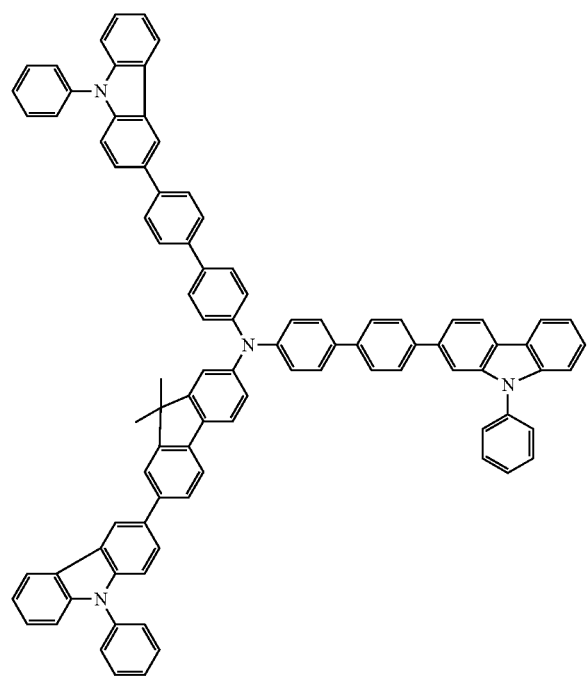
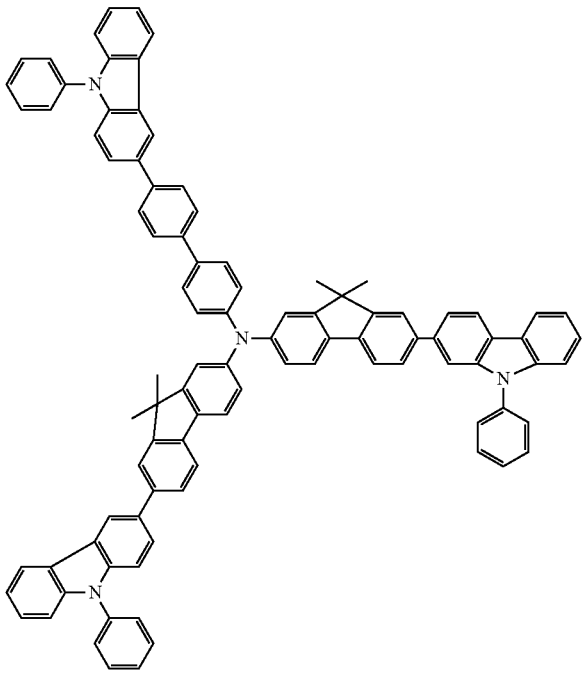

-continued
211
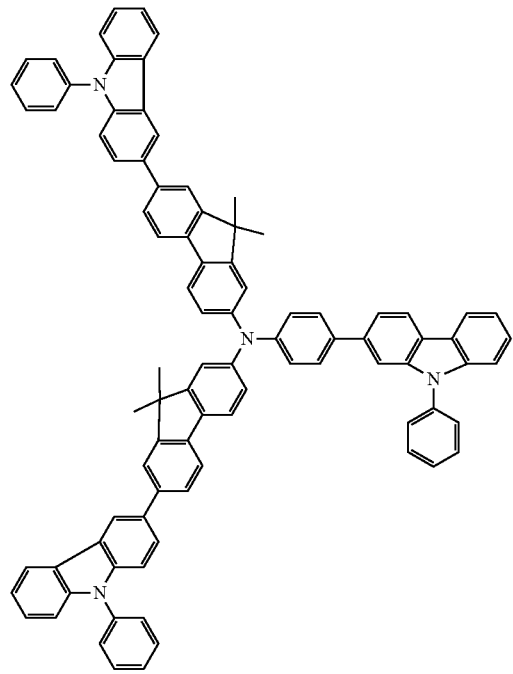
212
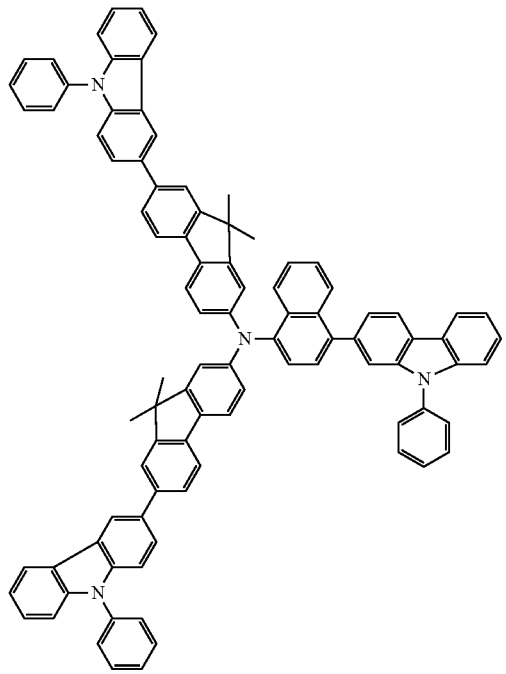
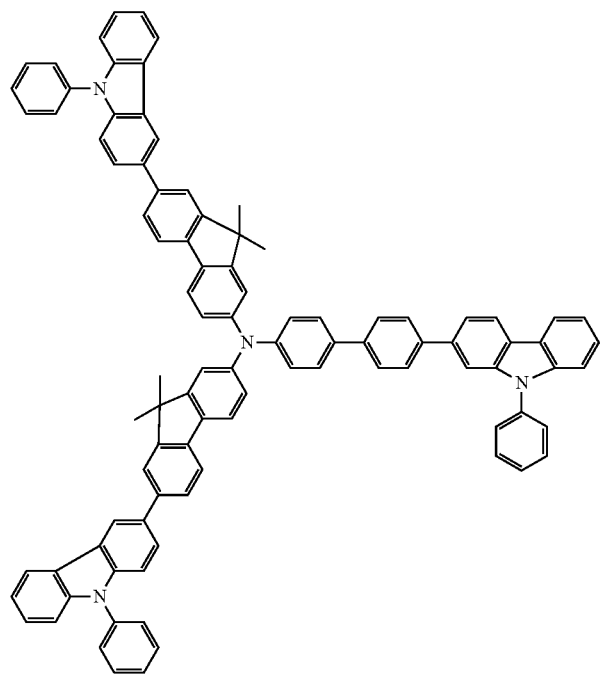
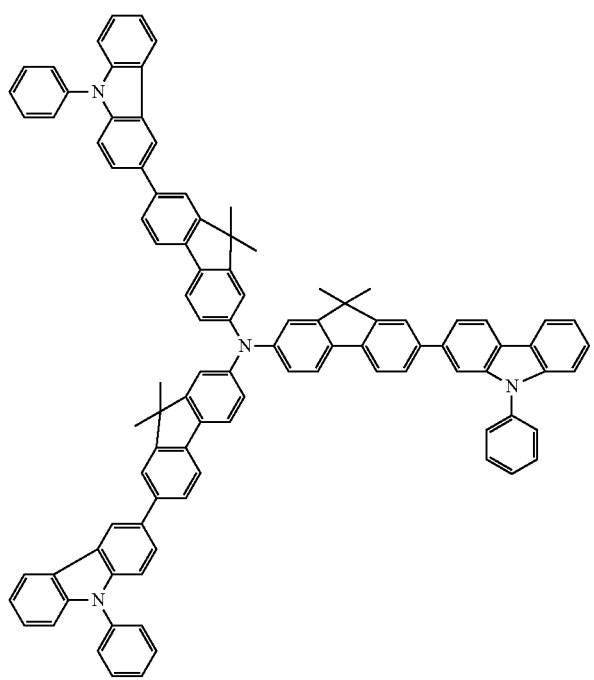

[Chem. 30]
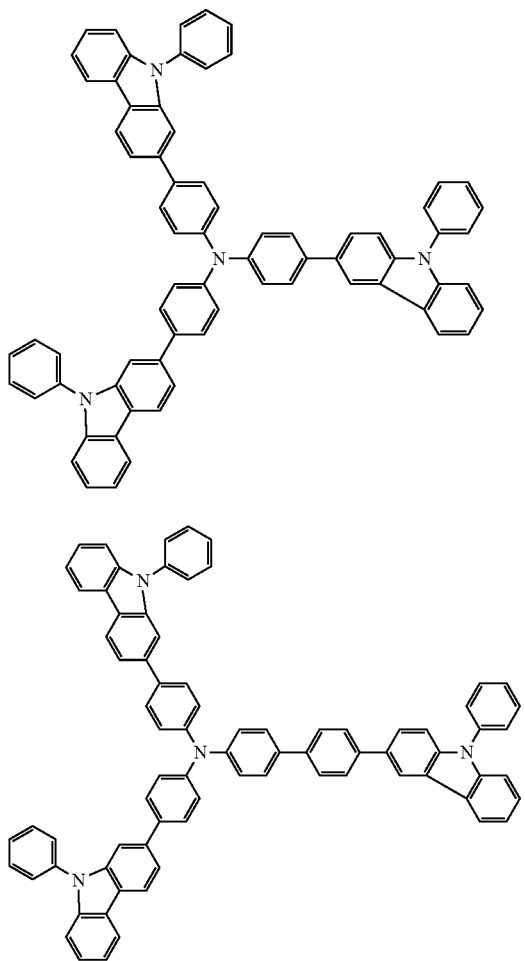
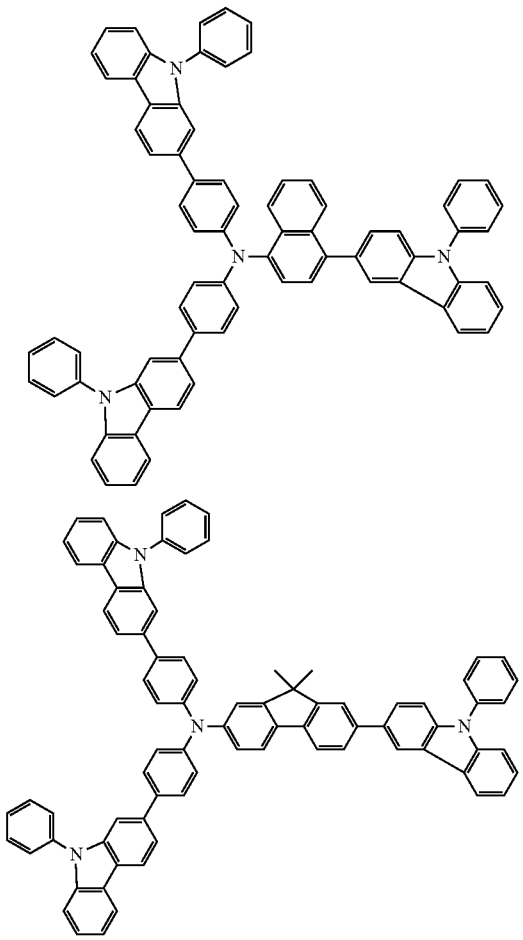
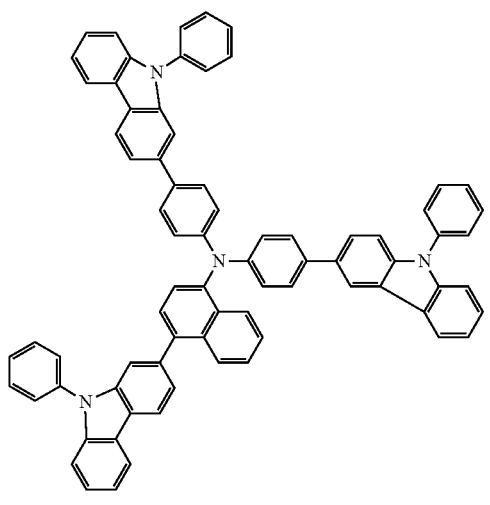
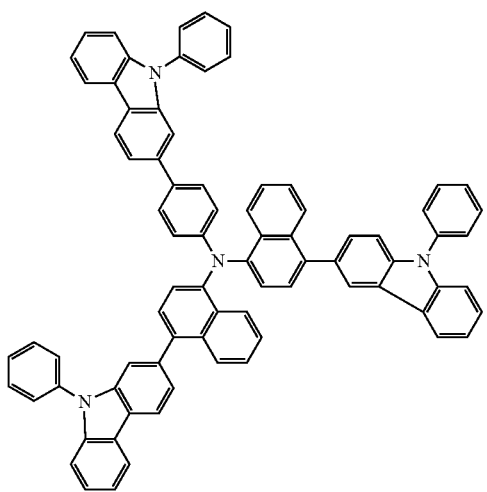

-continued
215
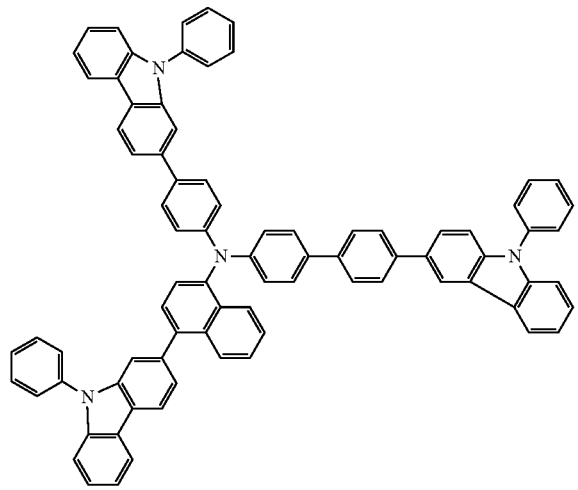
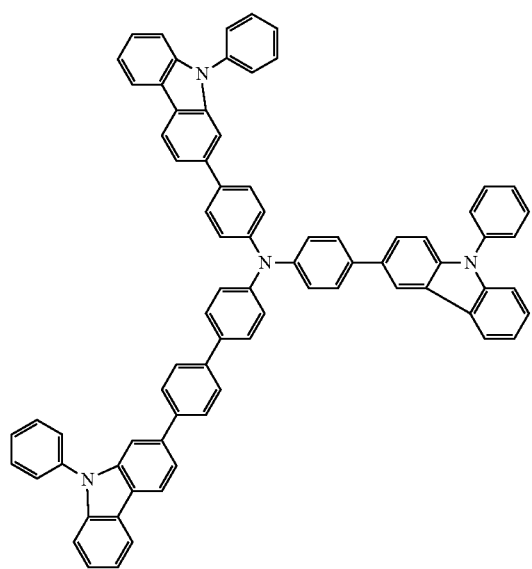
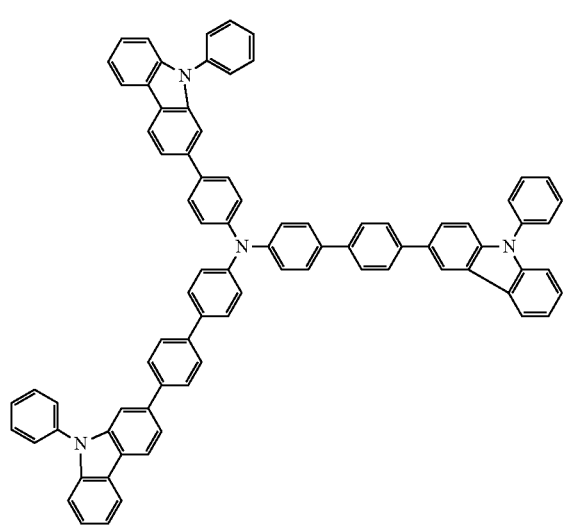
216
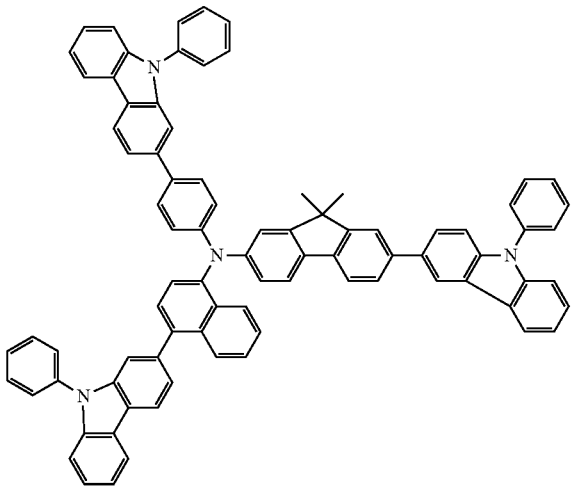
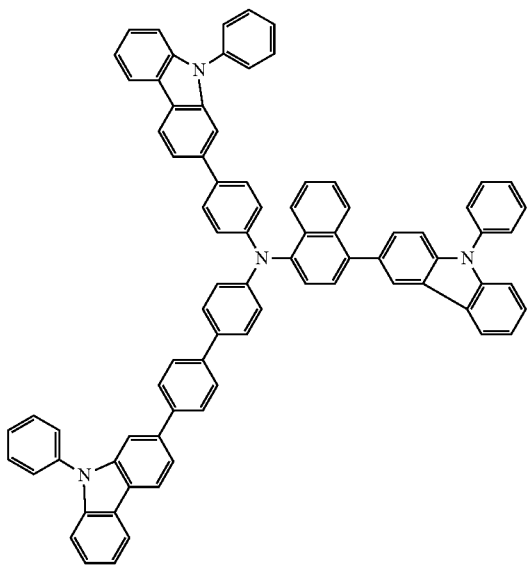
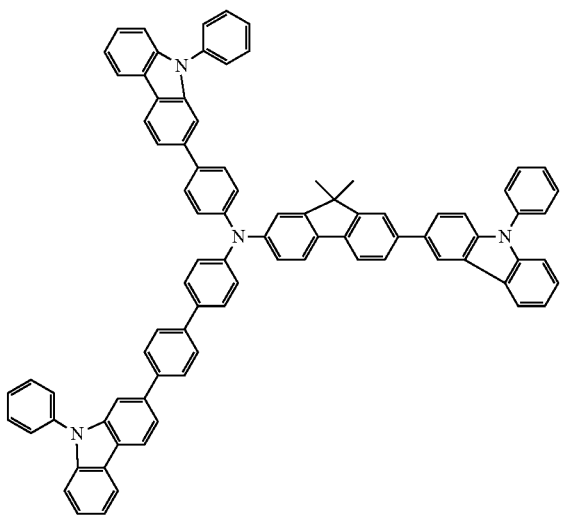

-continued
217
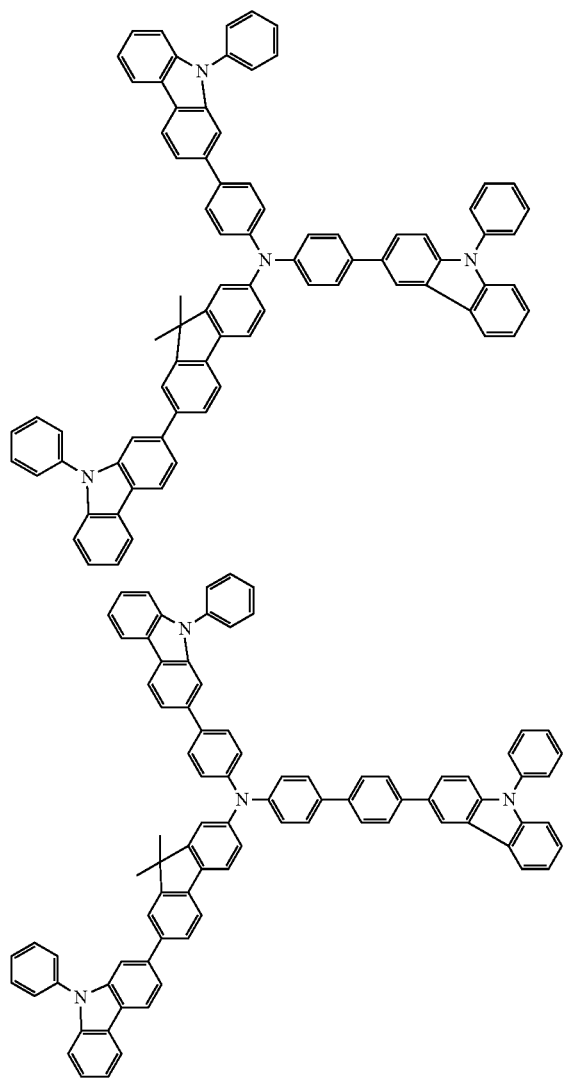
218
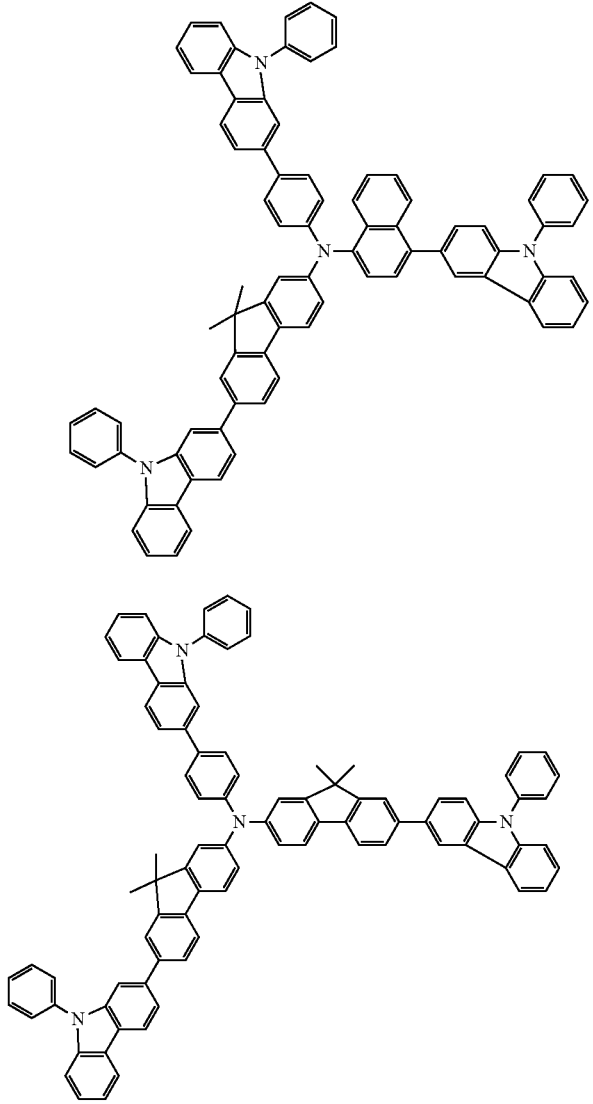
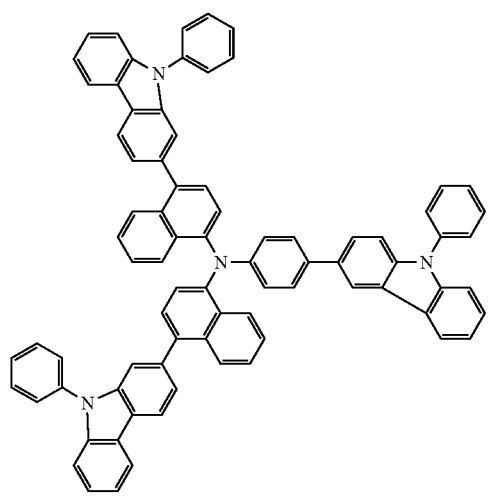
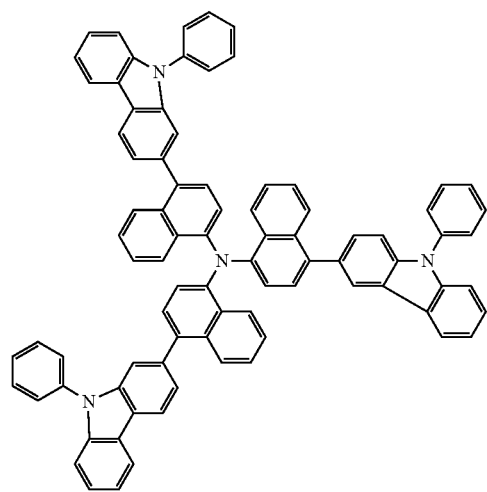

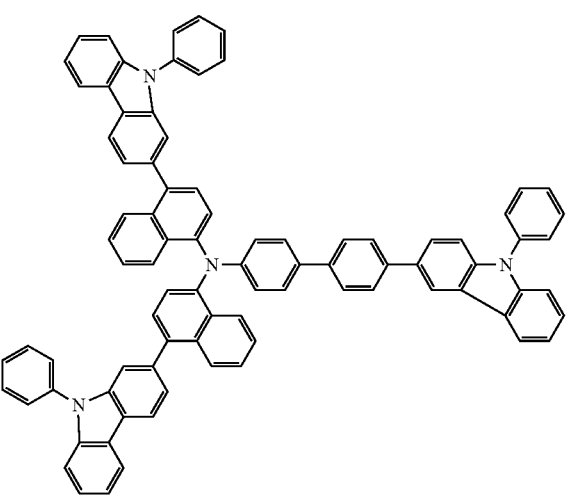
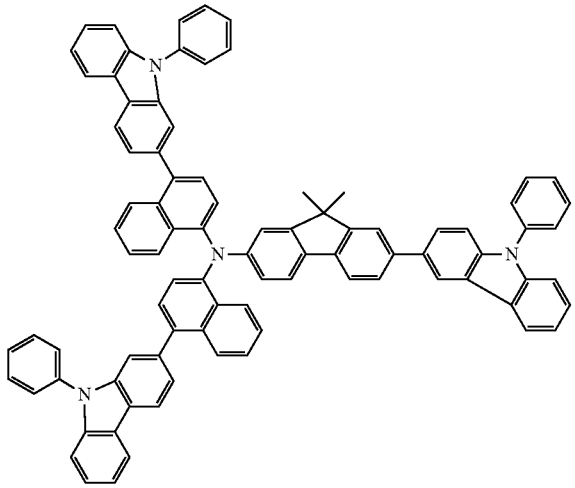
[Chem. 31]
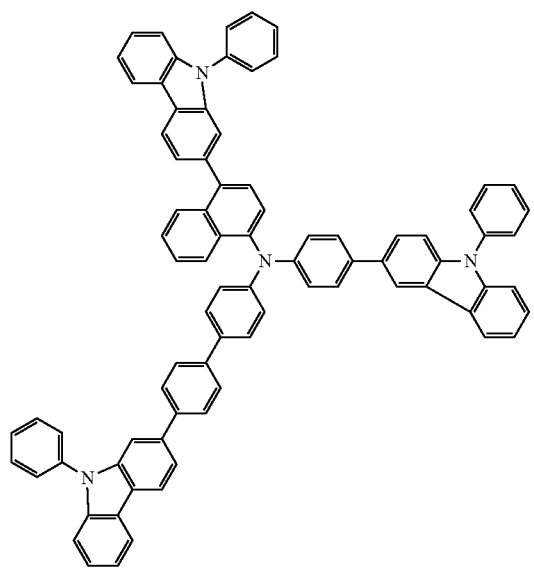
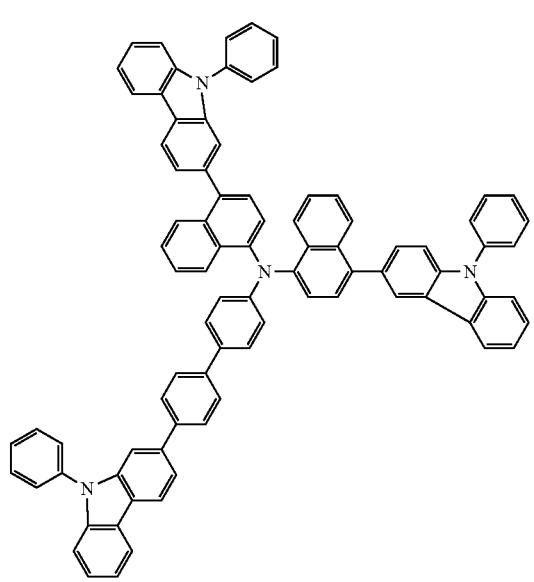
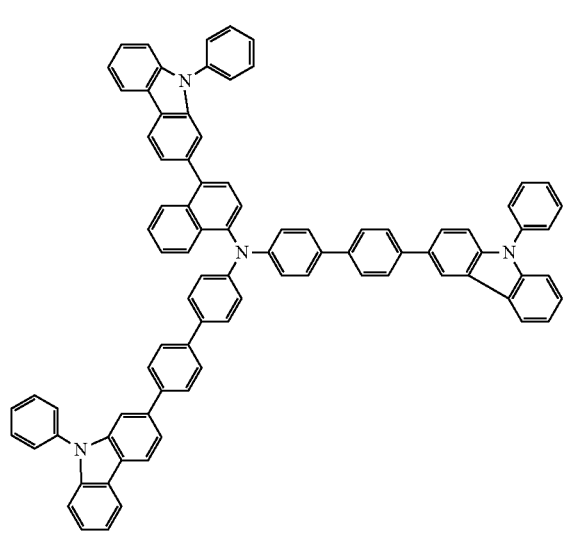
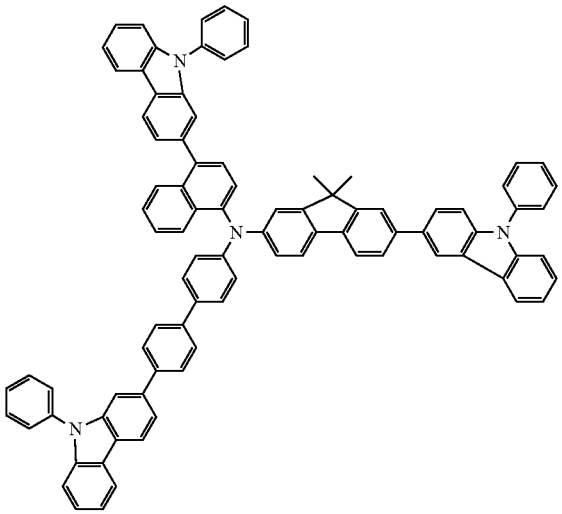

221 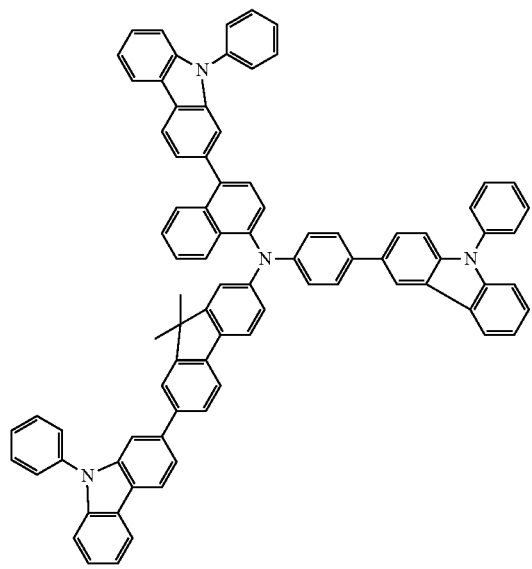 222 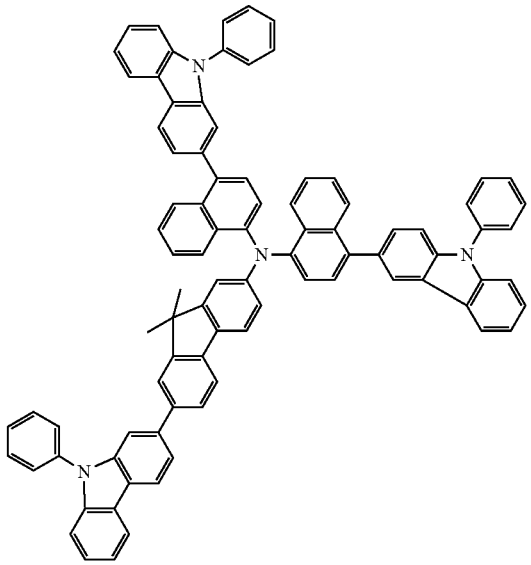
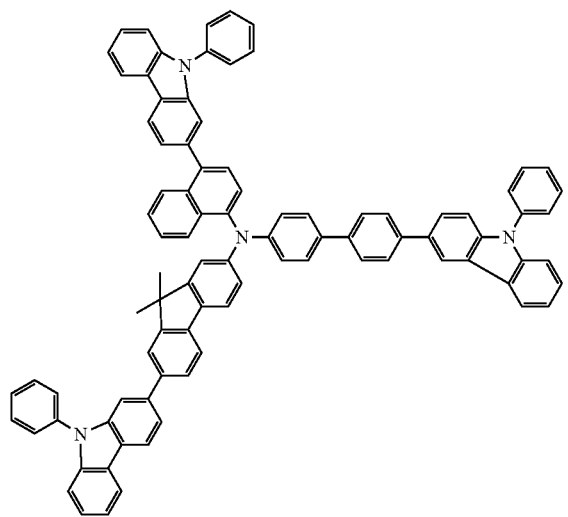 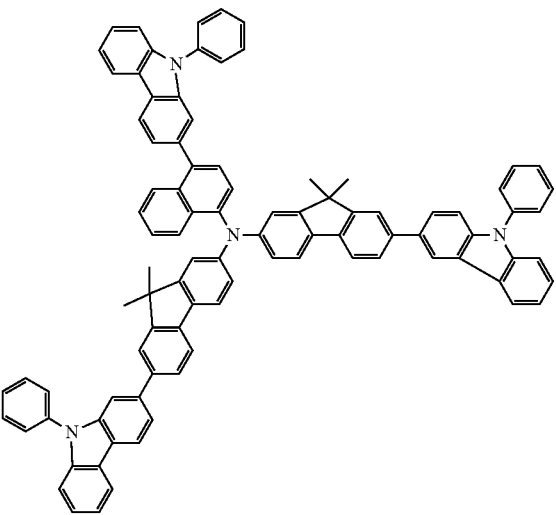

-continued
223
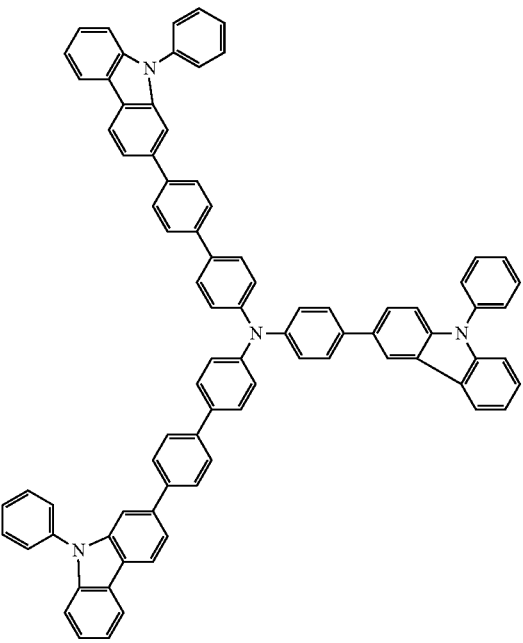
224
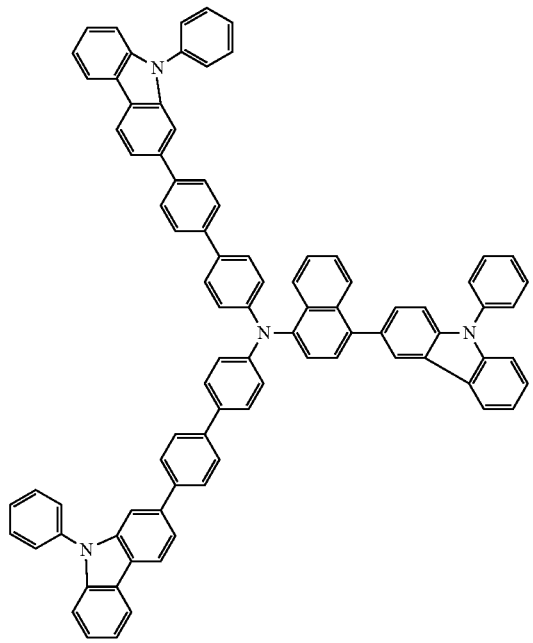
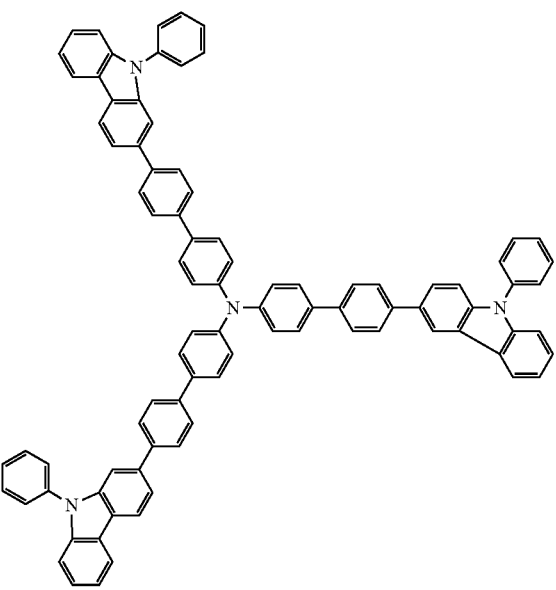
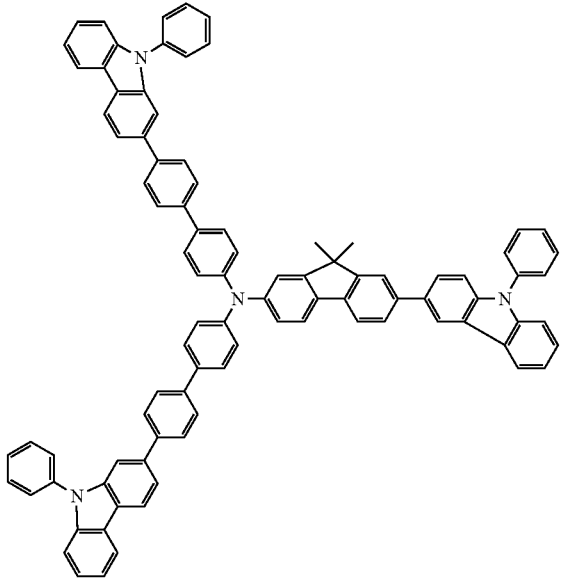

-continued
225
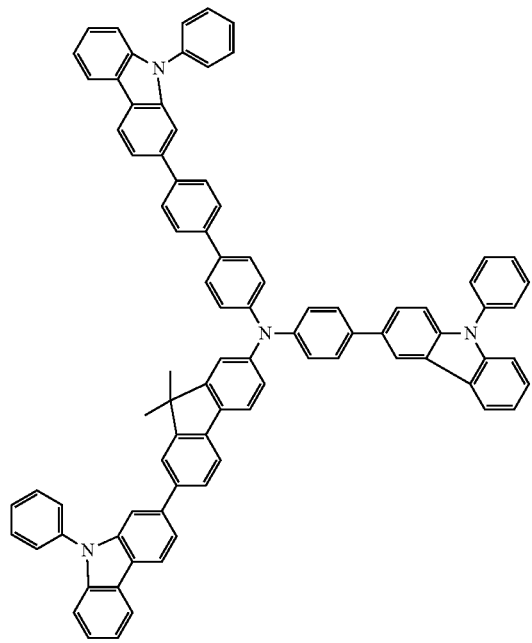
226
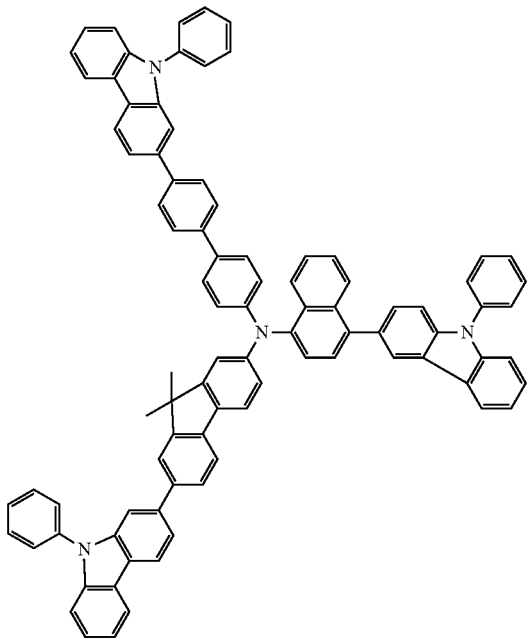
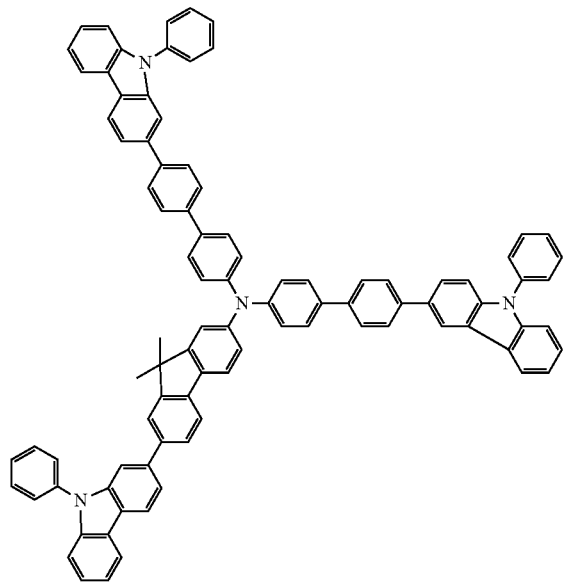
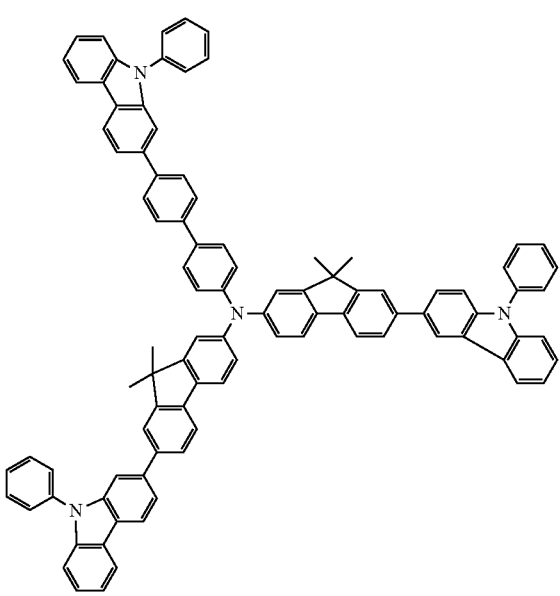

227
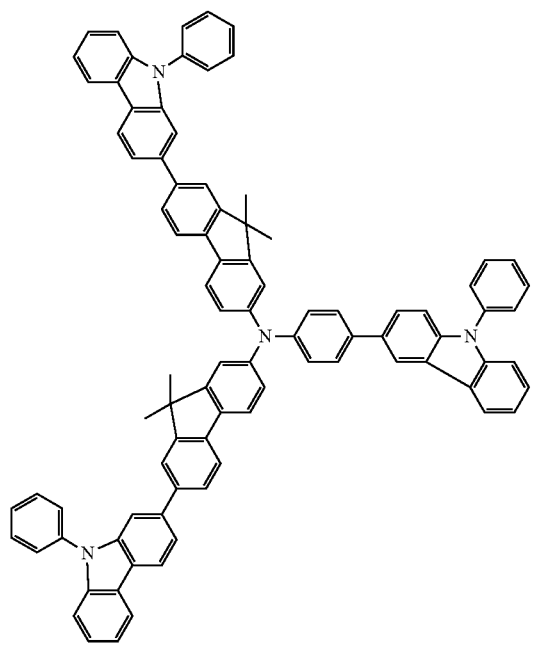
228
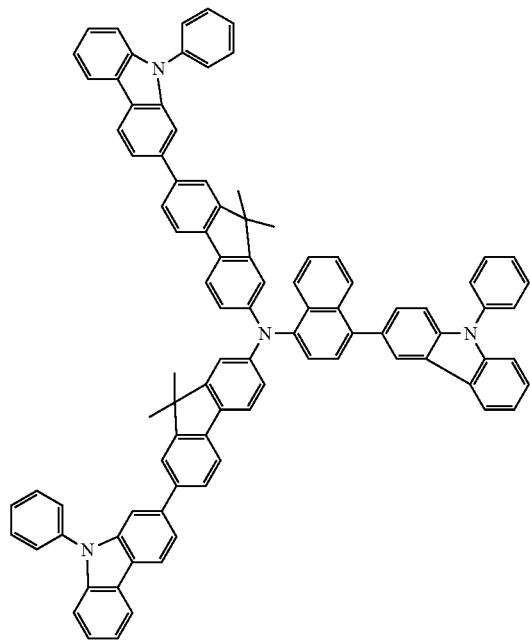
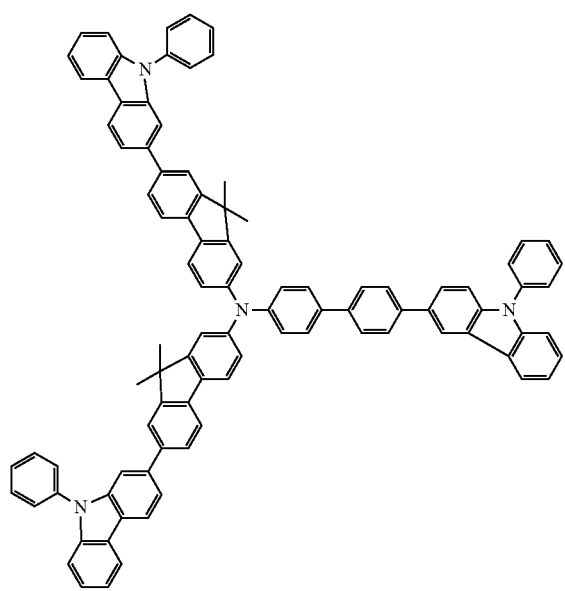
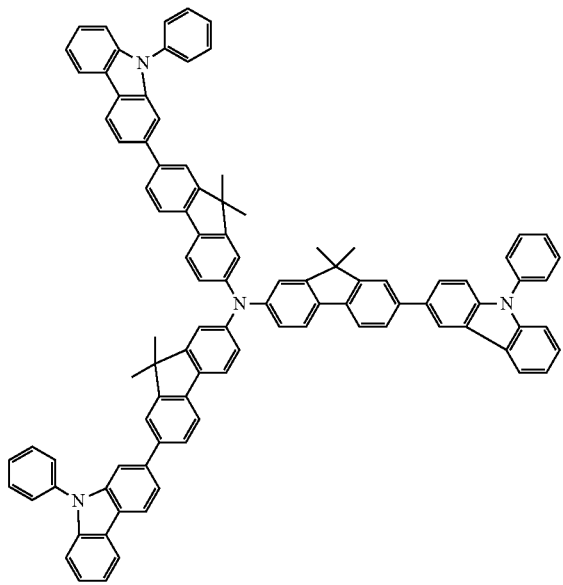

[Chem. 32]
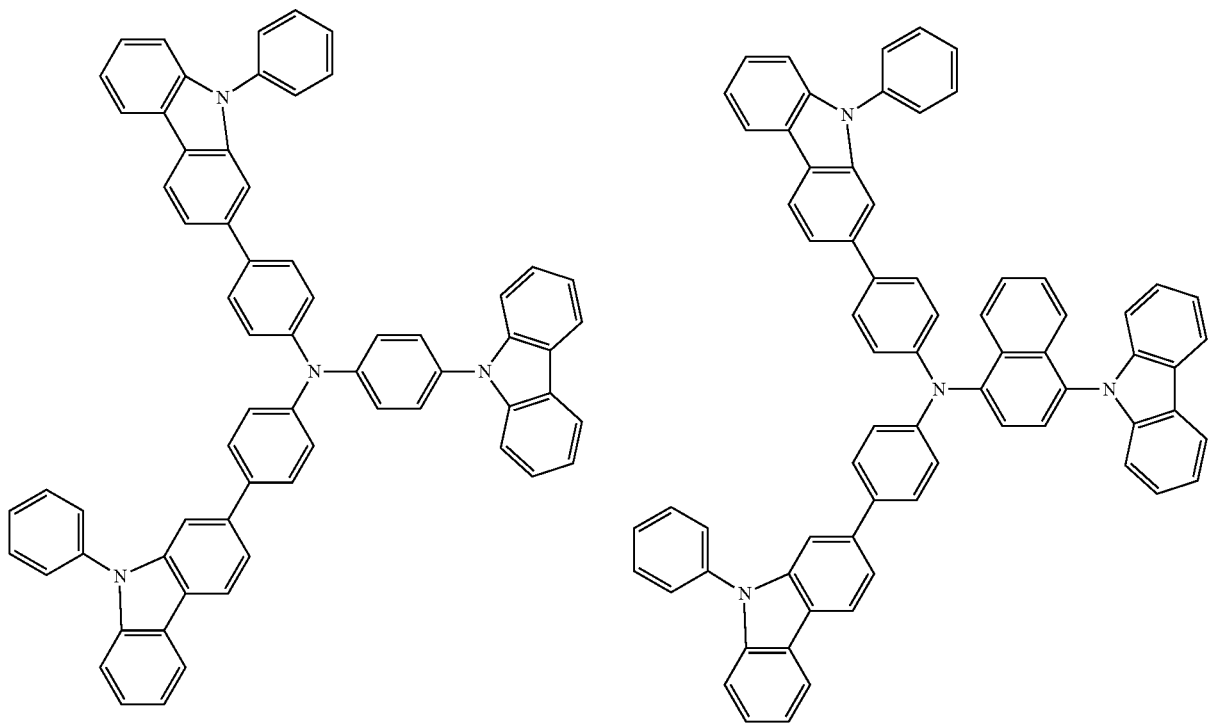
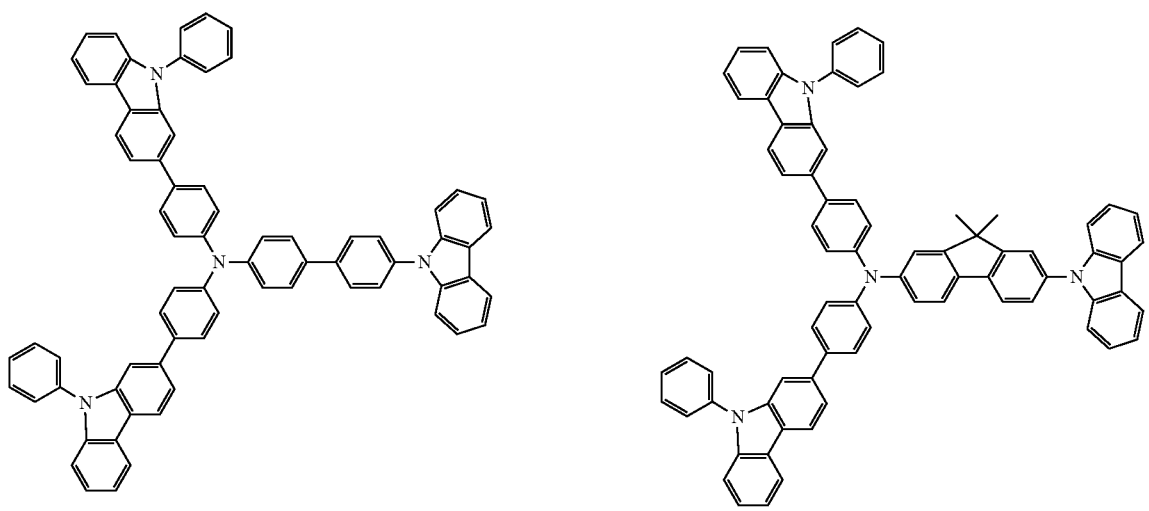

231 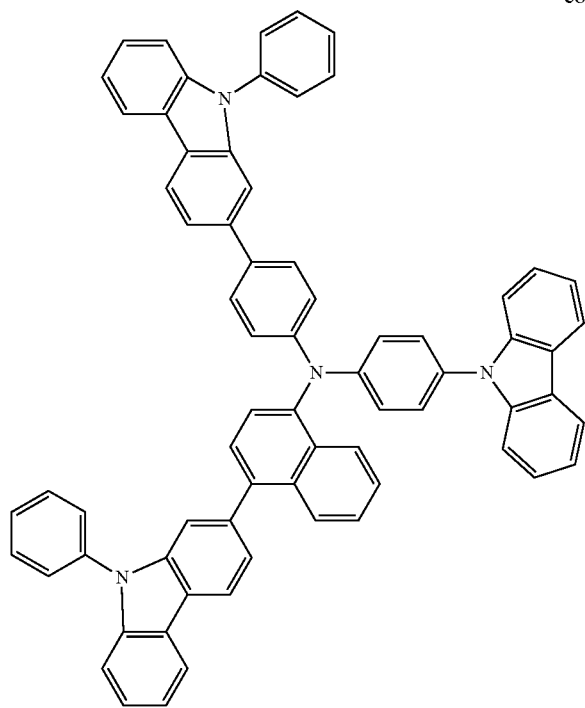 232 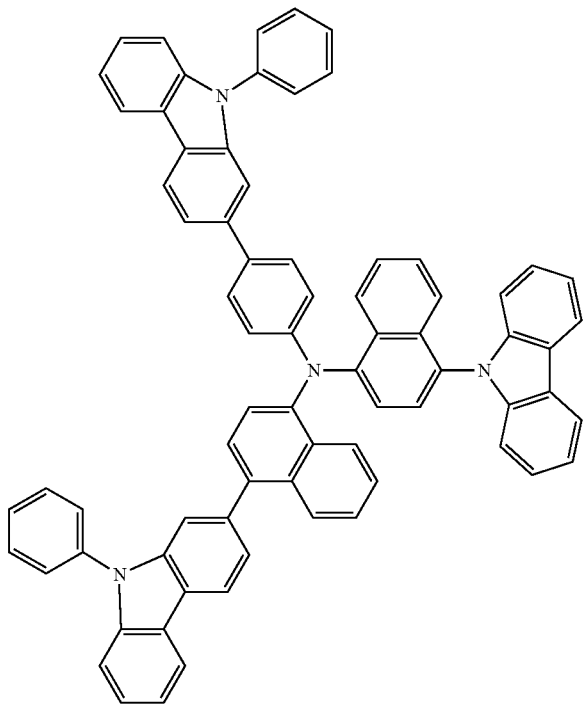
-continued
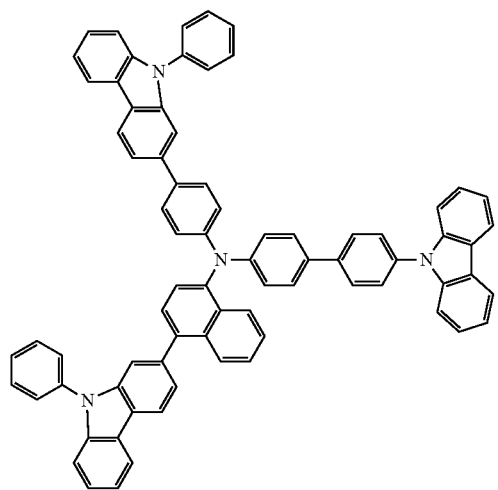 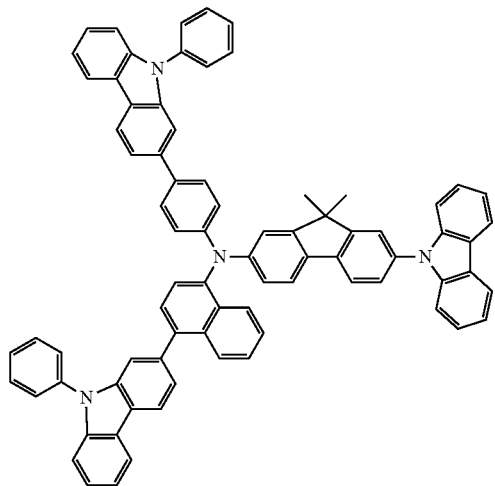

-continued
233
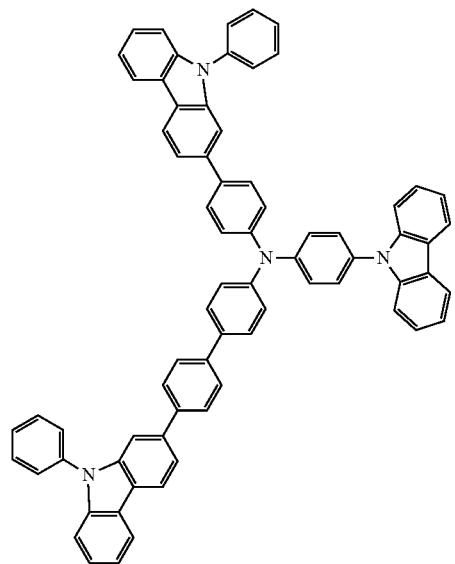
234
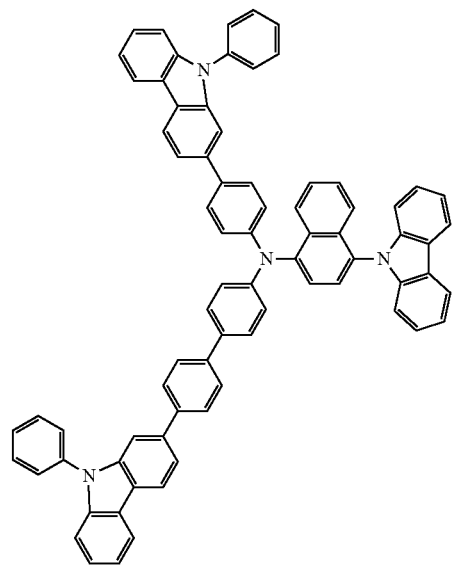
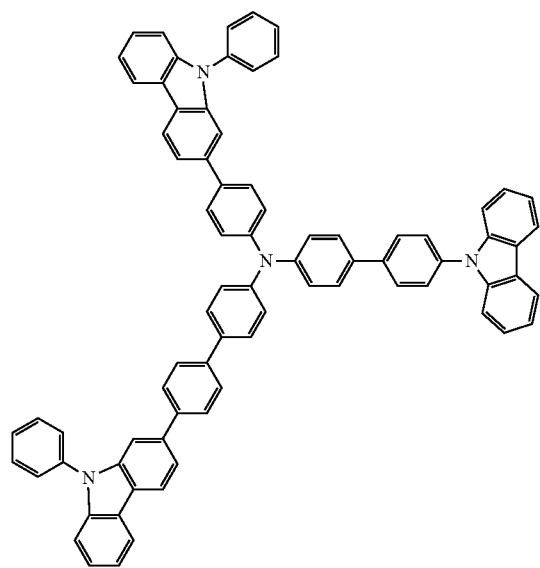
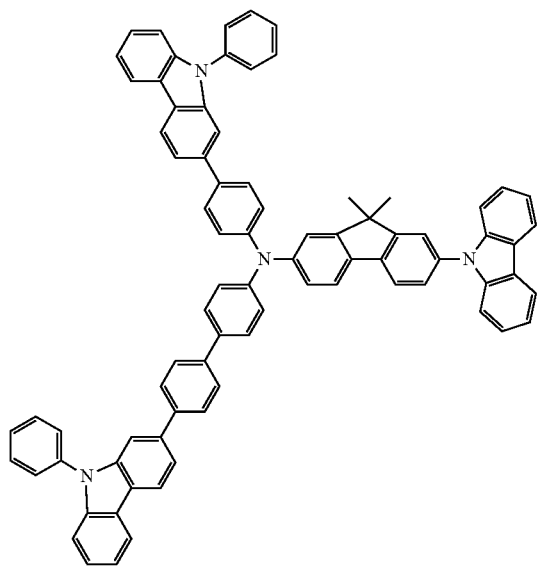

235
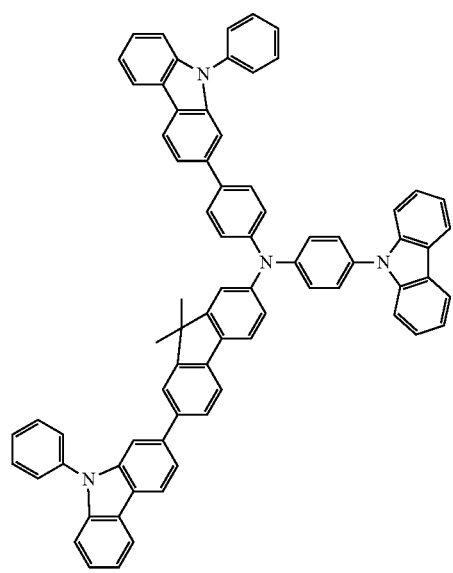
236
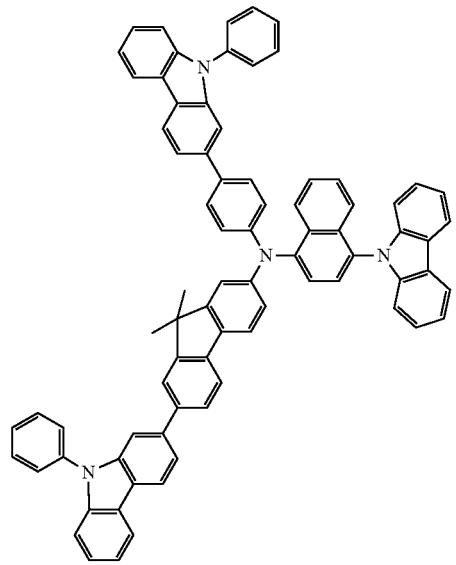
-continued
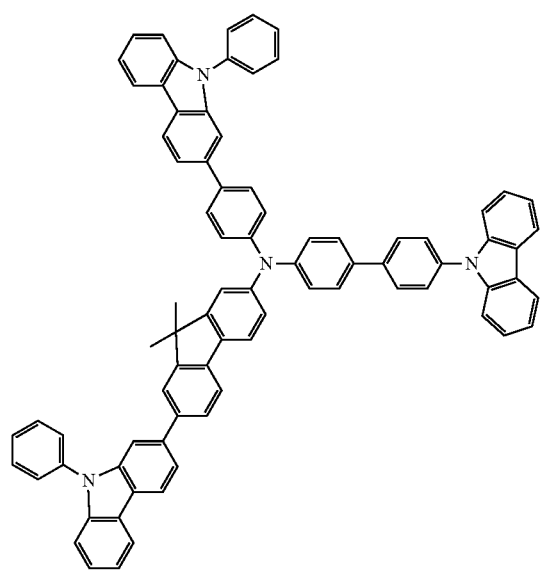
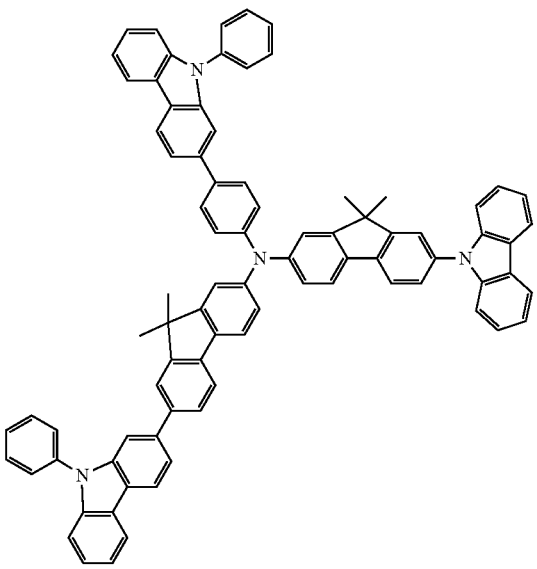

237 238
-continued
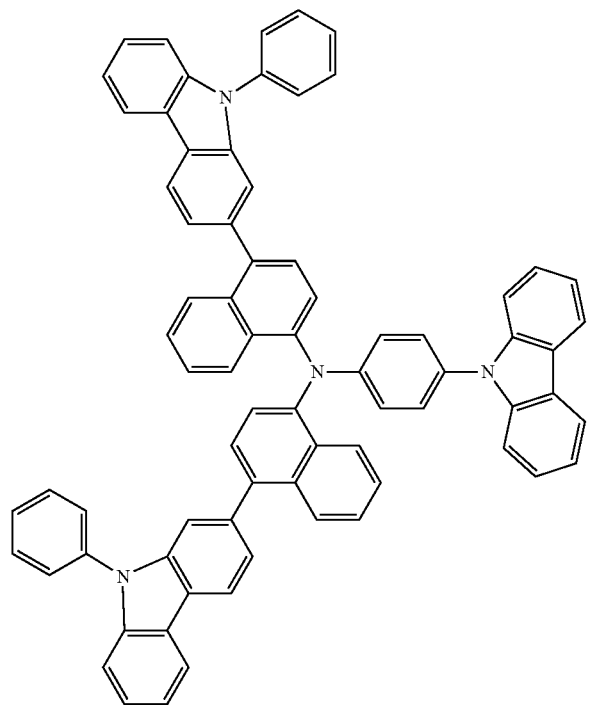
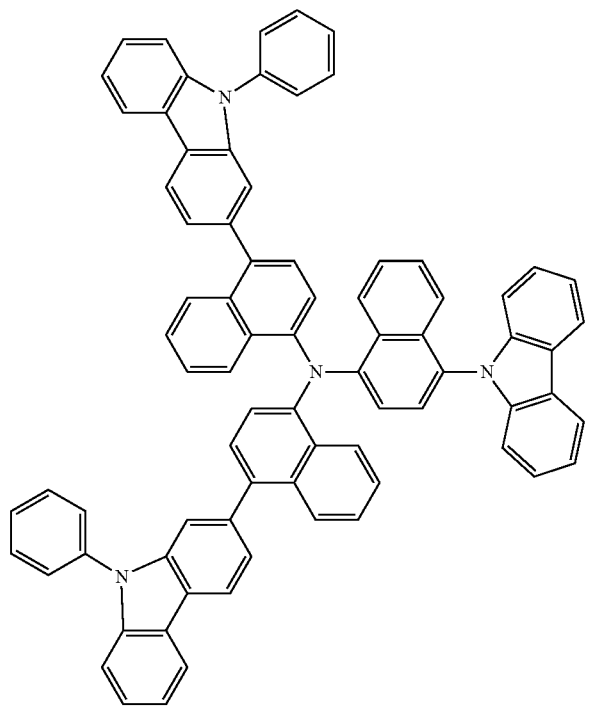
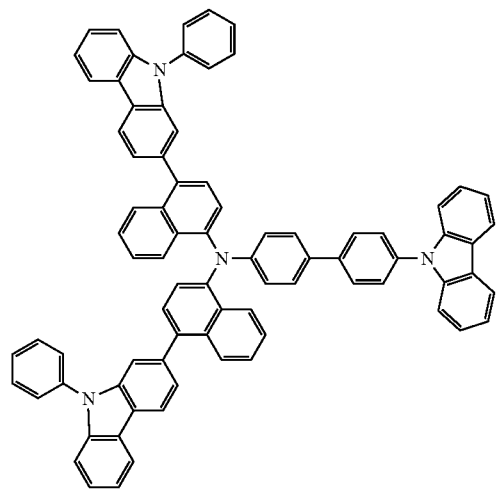
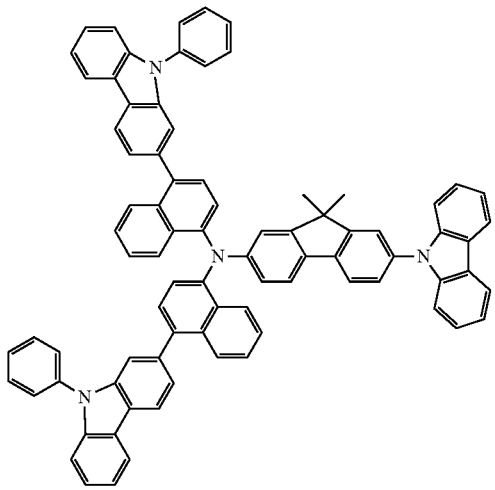

-continued
[Chem. 33]
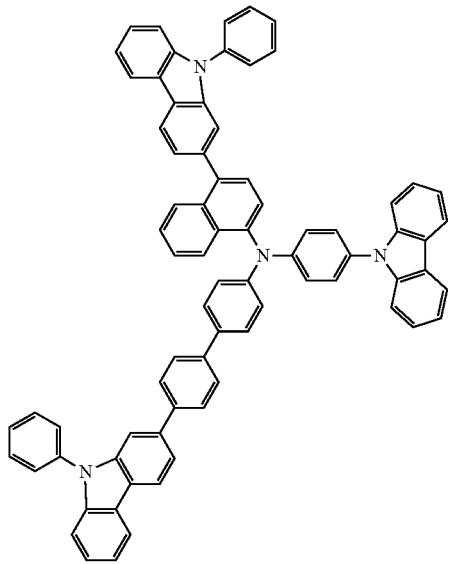
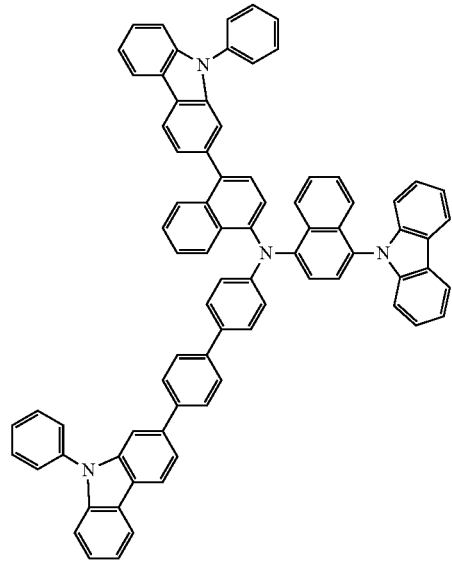
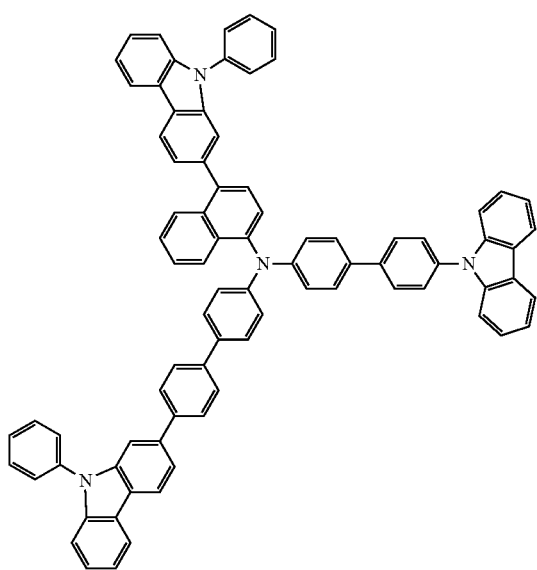
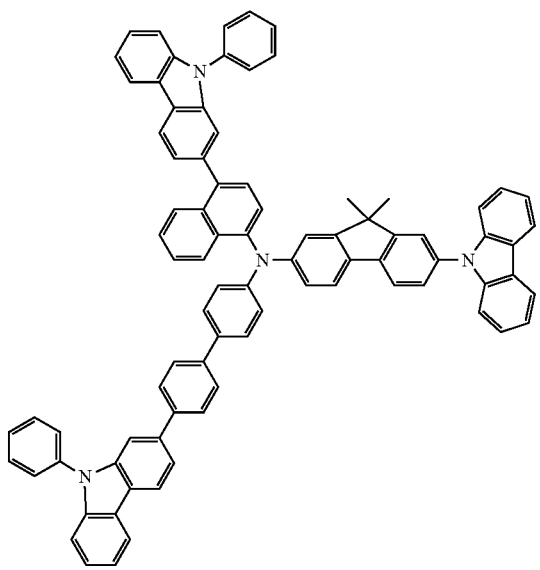

-continued
| 241 | 242 |
|---|---|
| 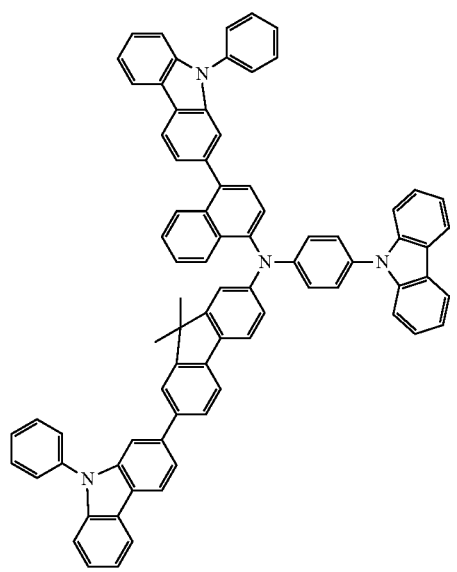 | 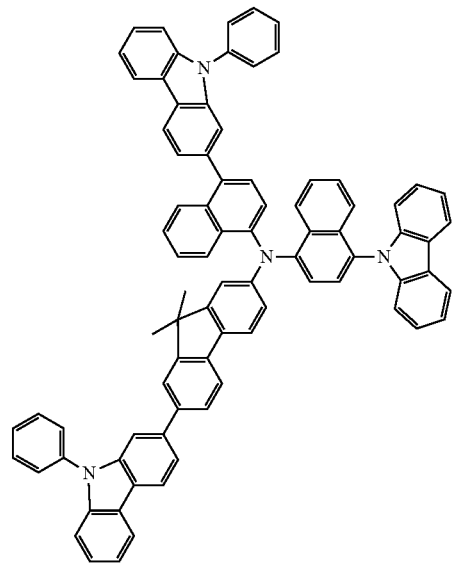 |
| 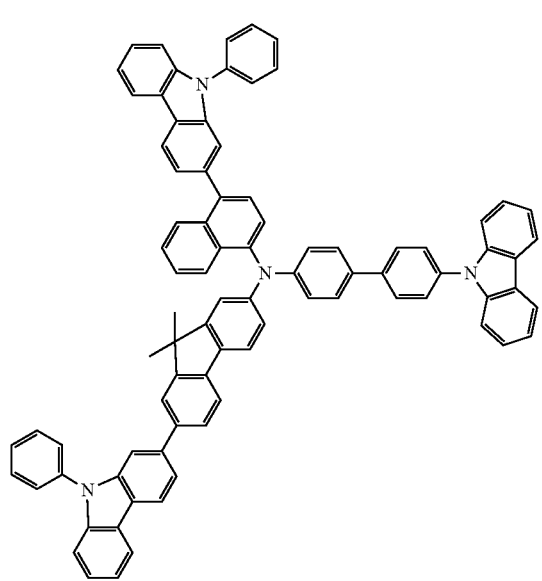 | 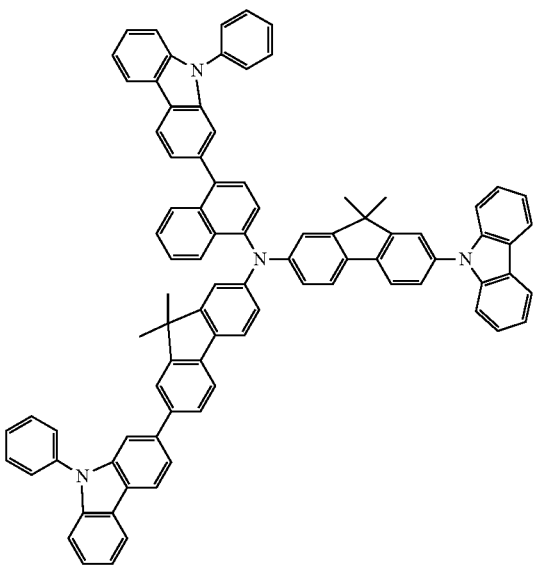 |

243
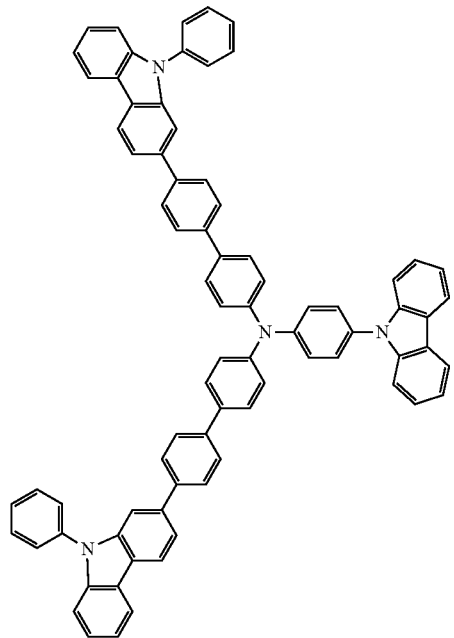
244
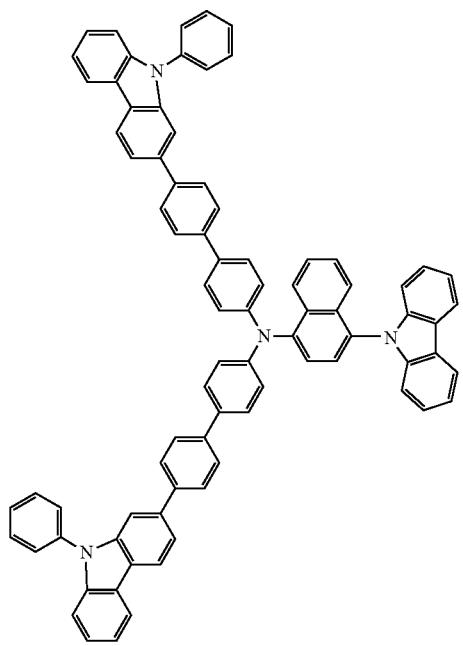
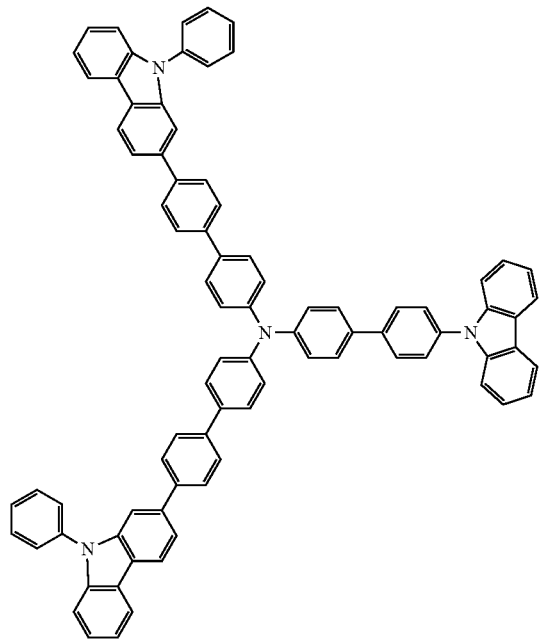
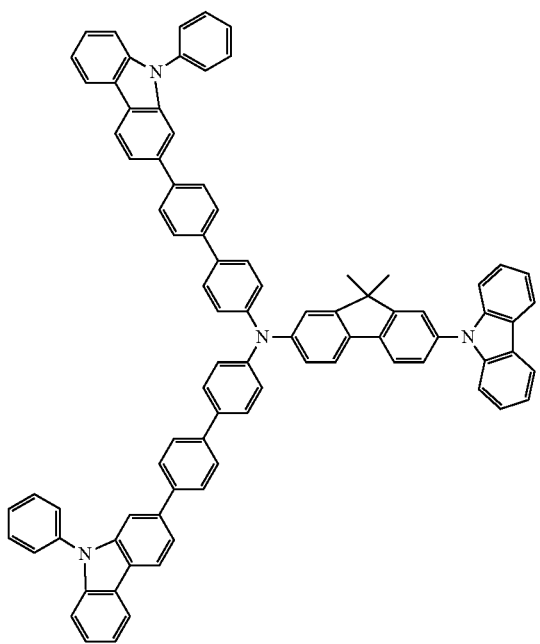

-continued
245
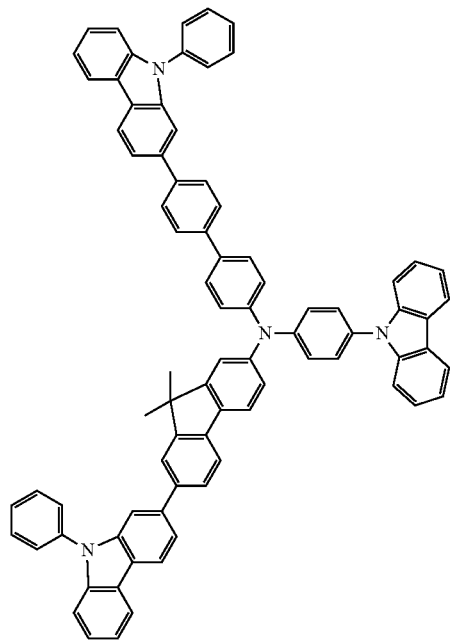
246
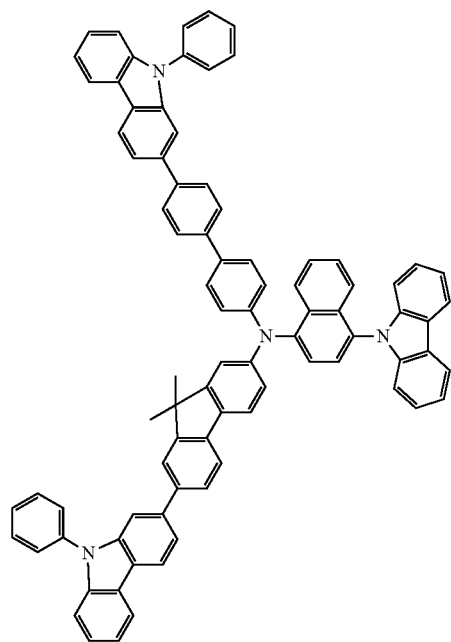
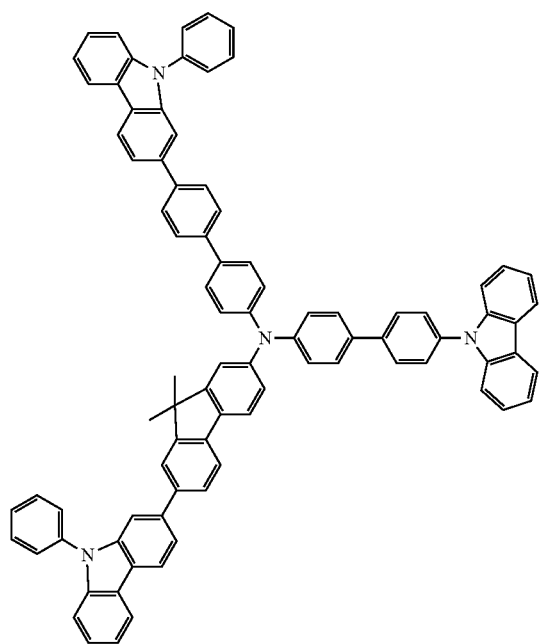
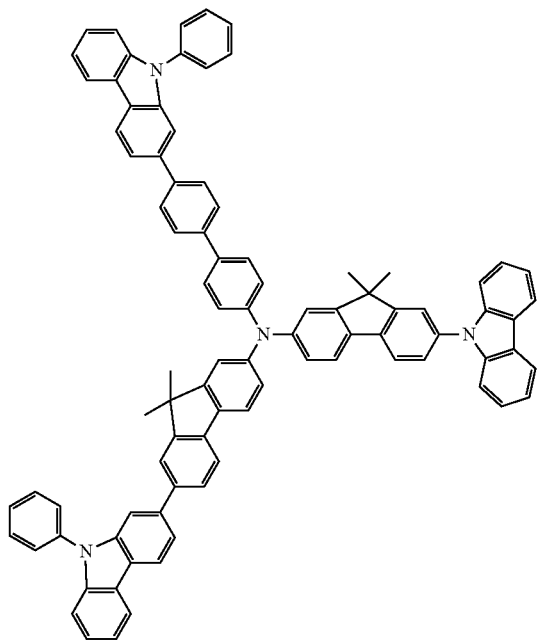

247
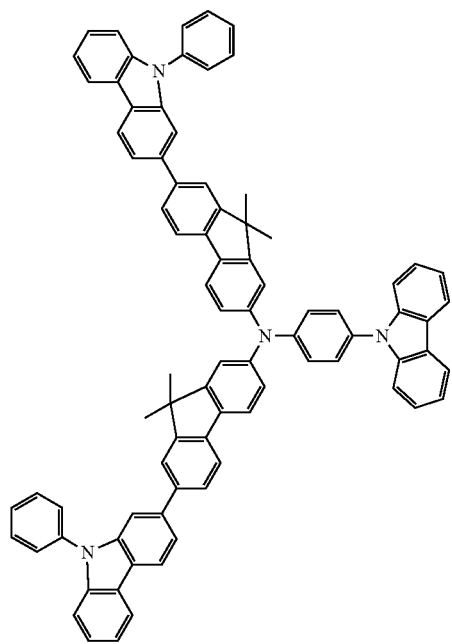
248
-continued
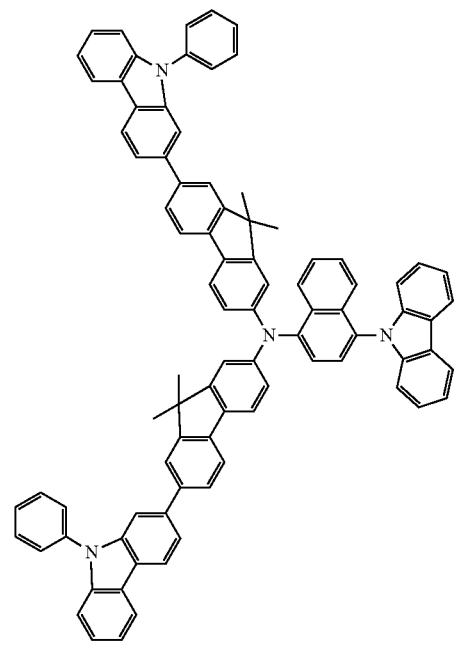
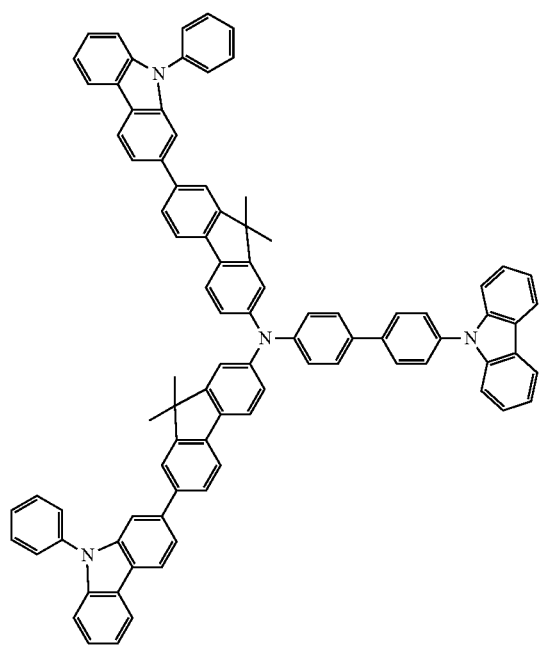
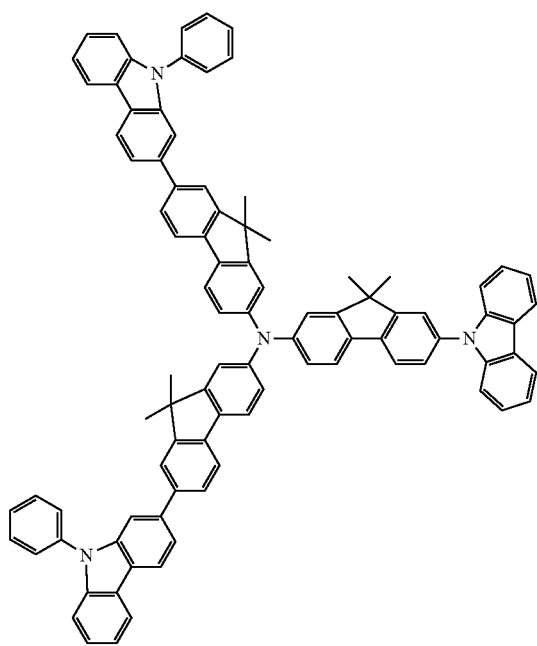

[Chem. 34]
-continued
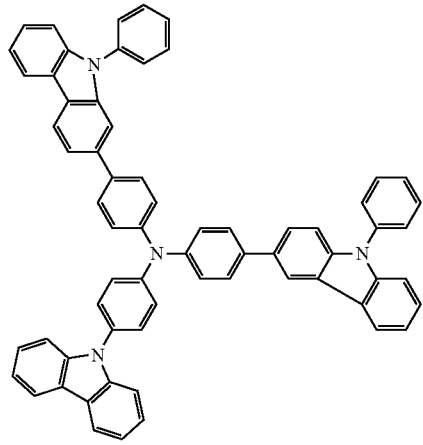
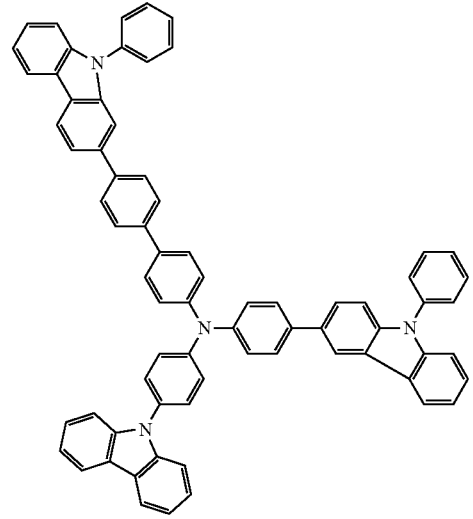
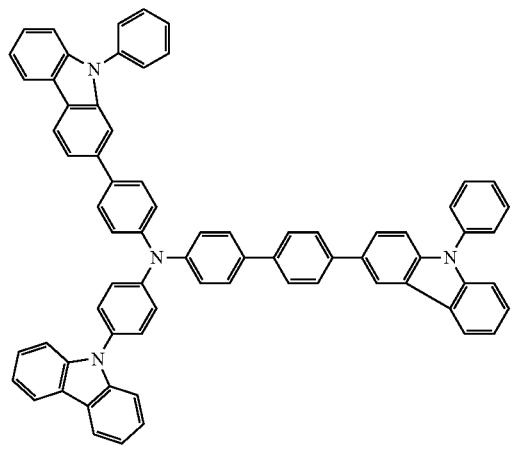
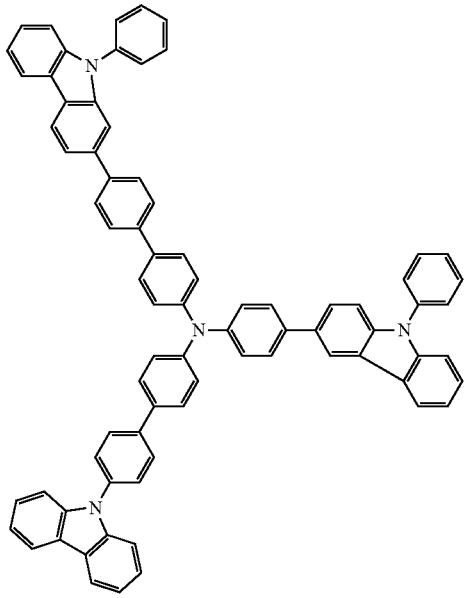
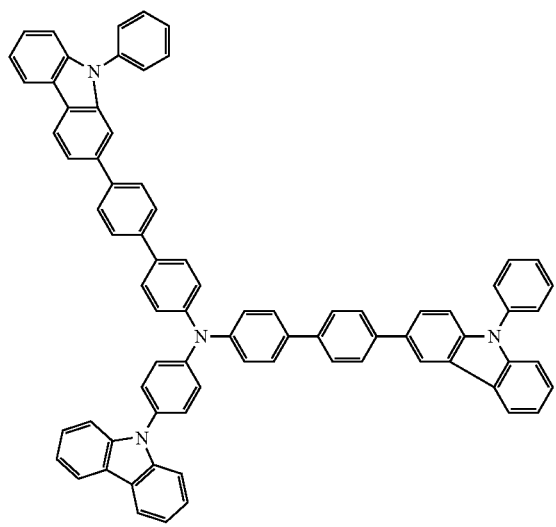
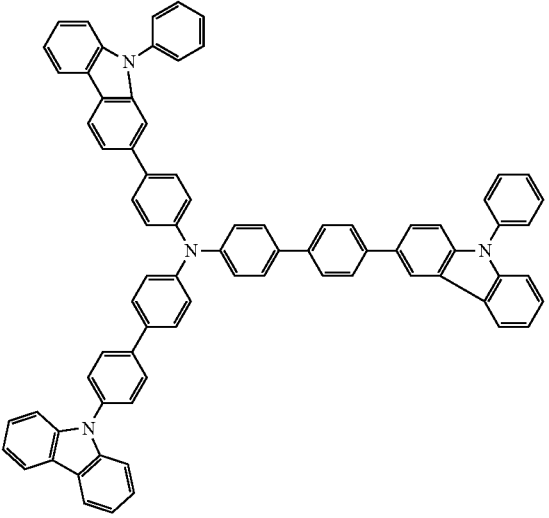

251
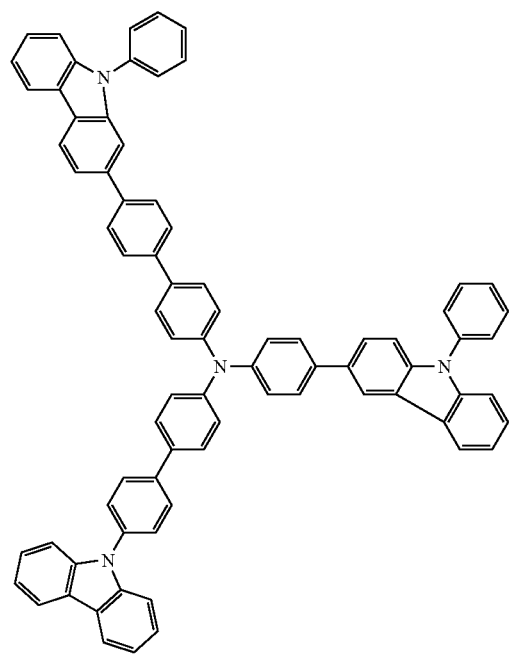
252
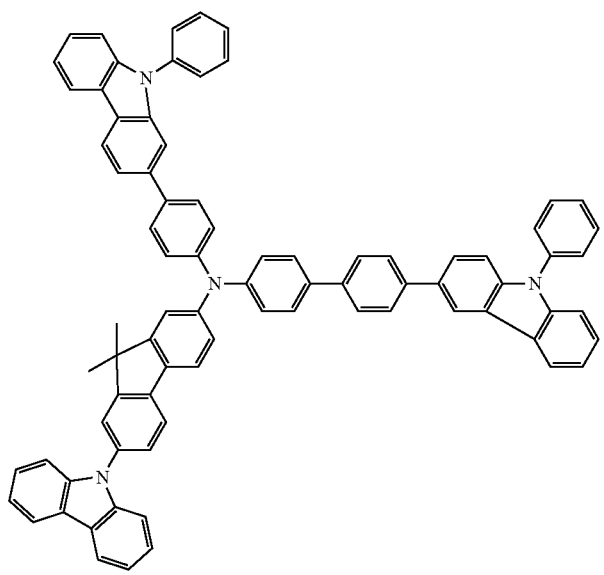
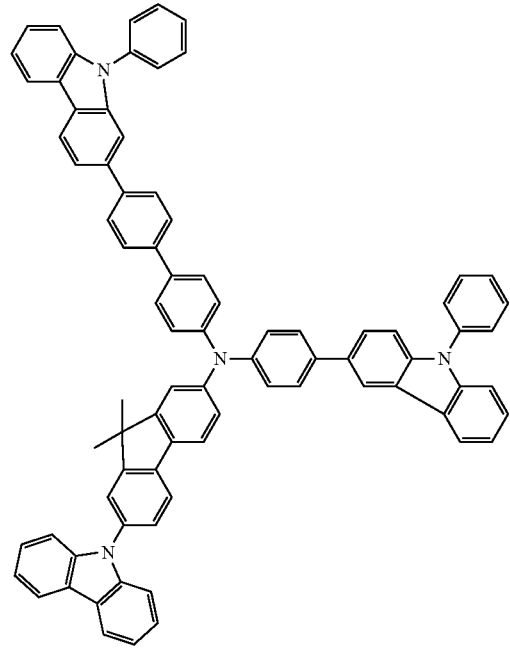
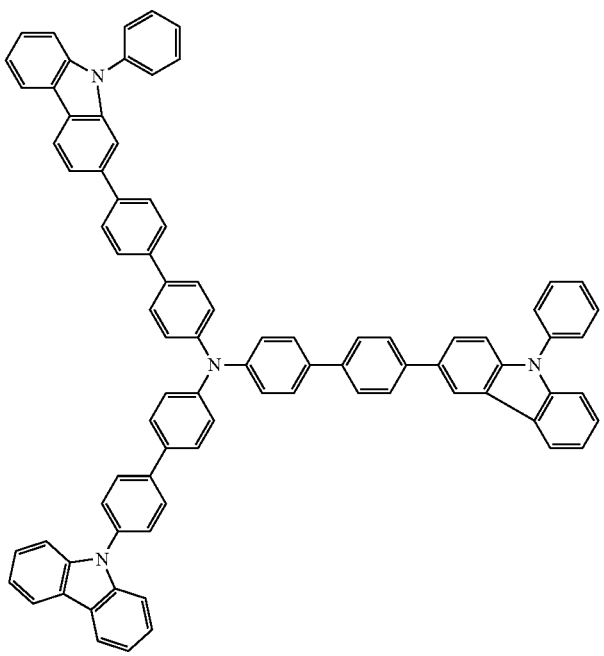

253
254
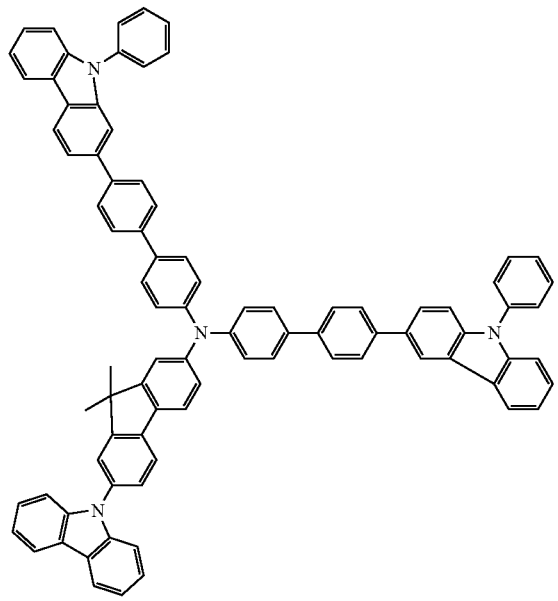
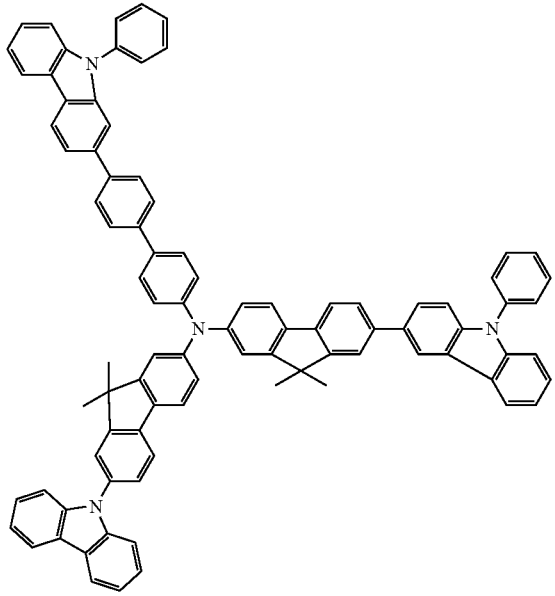
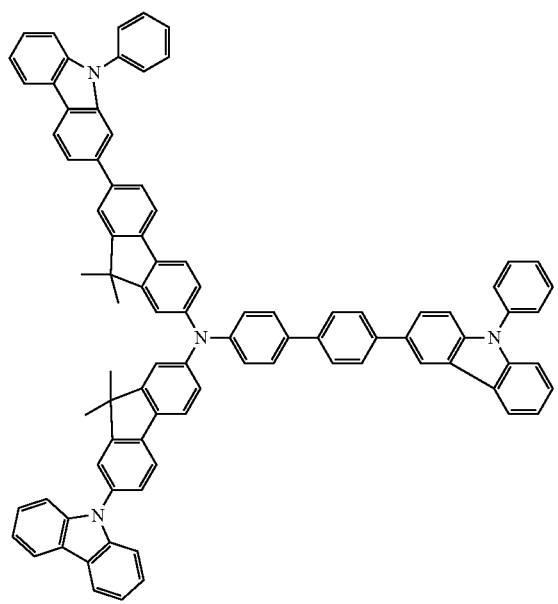
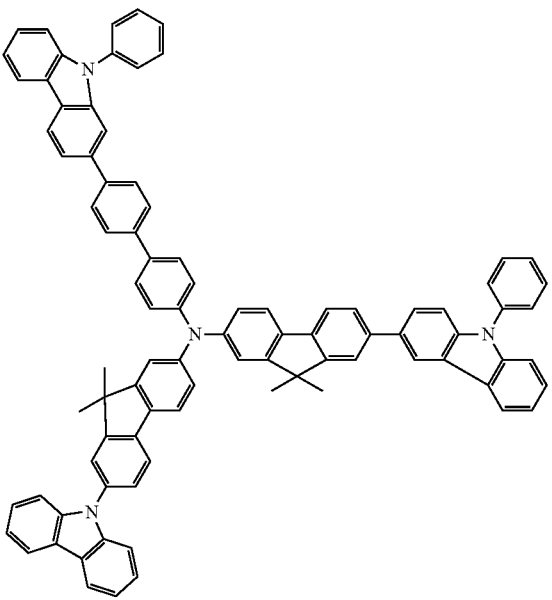

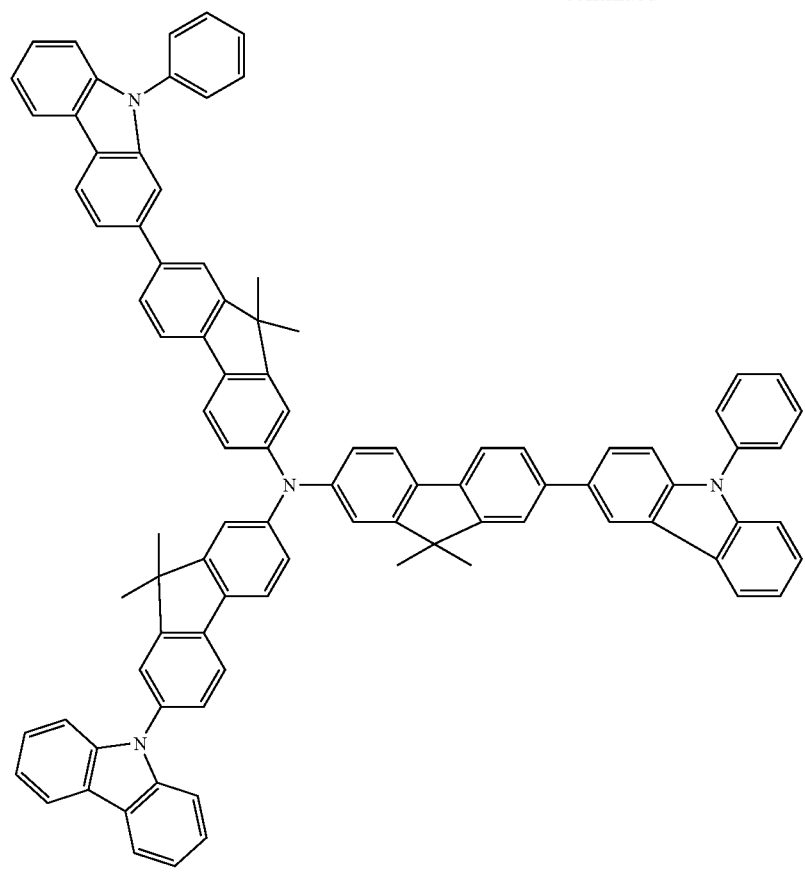
[Chem. 35]
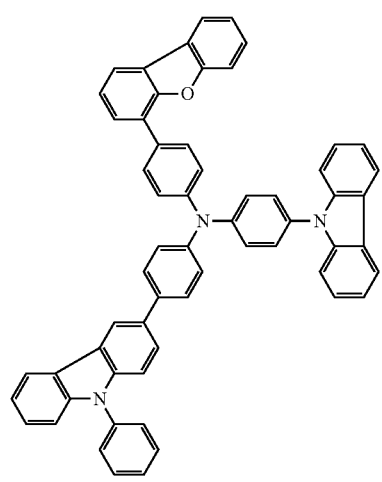
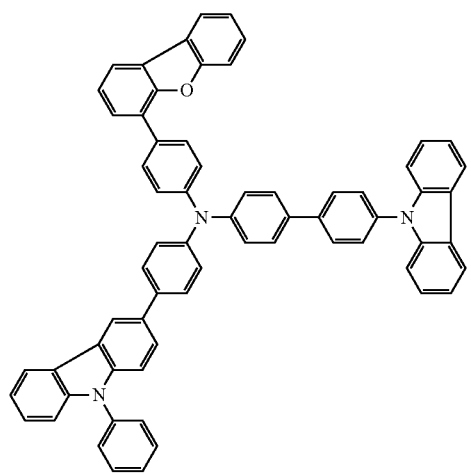

-continued
257
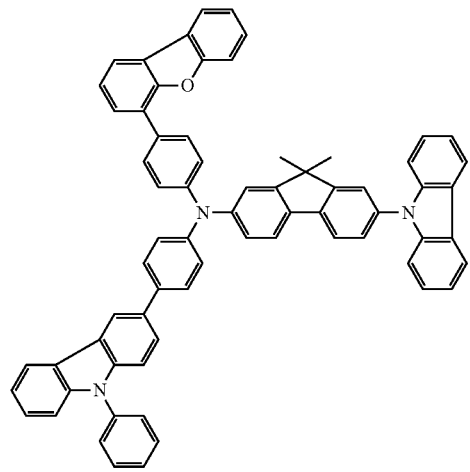
258
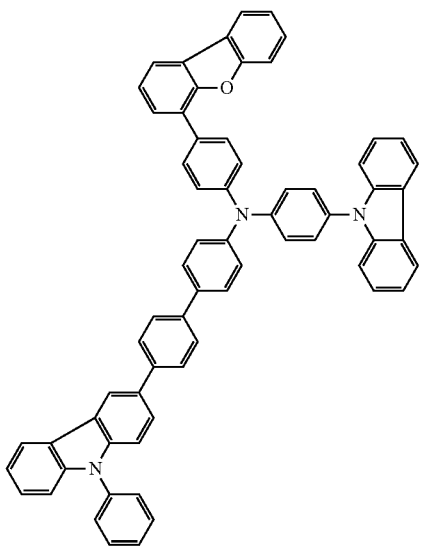
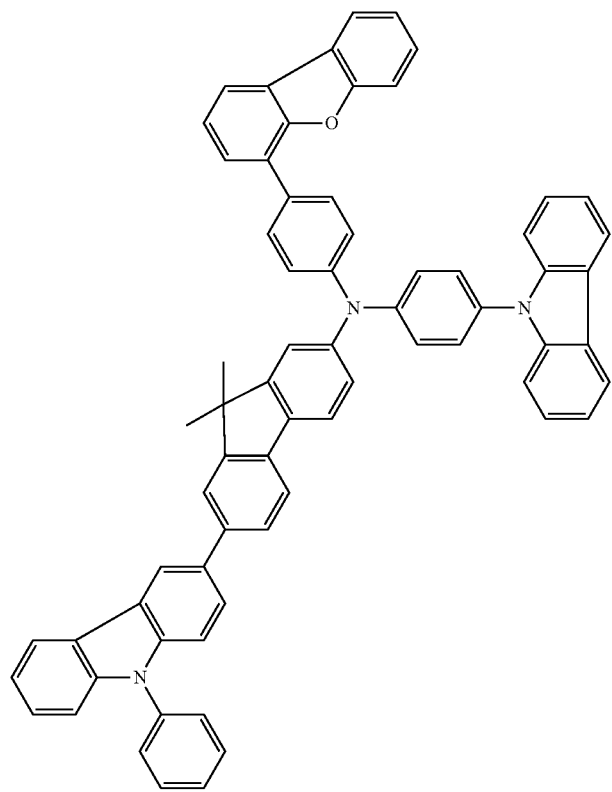
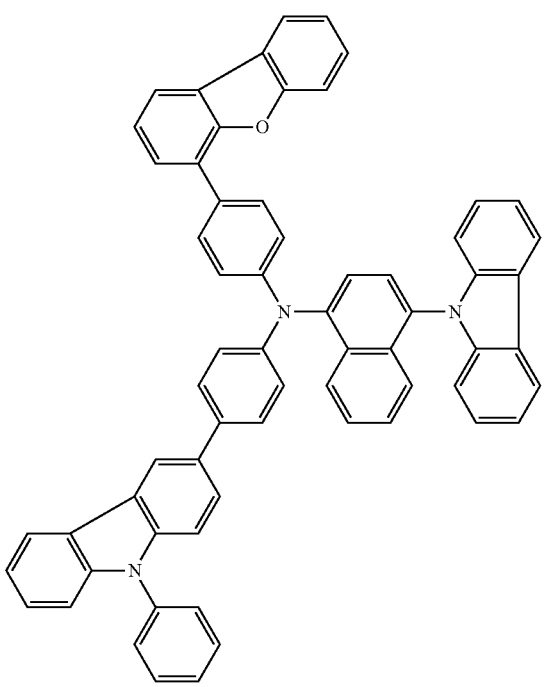

| 259 | 260 |
|---|---|
| 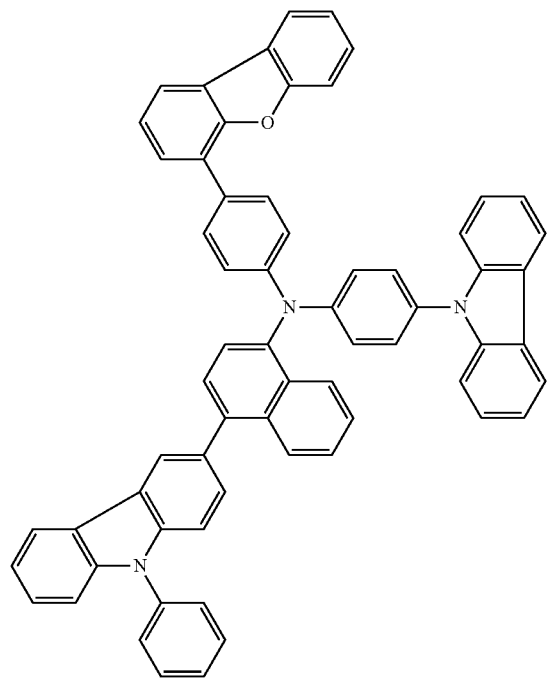 | 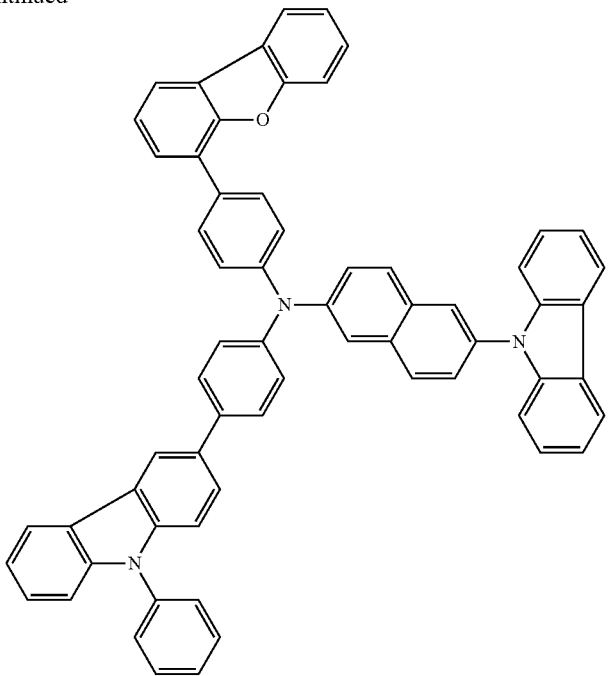 |
| 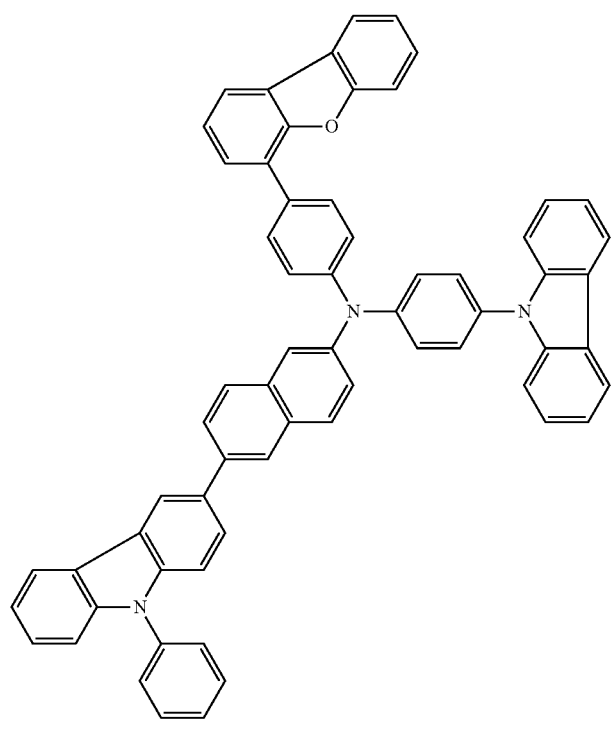 | 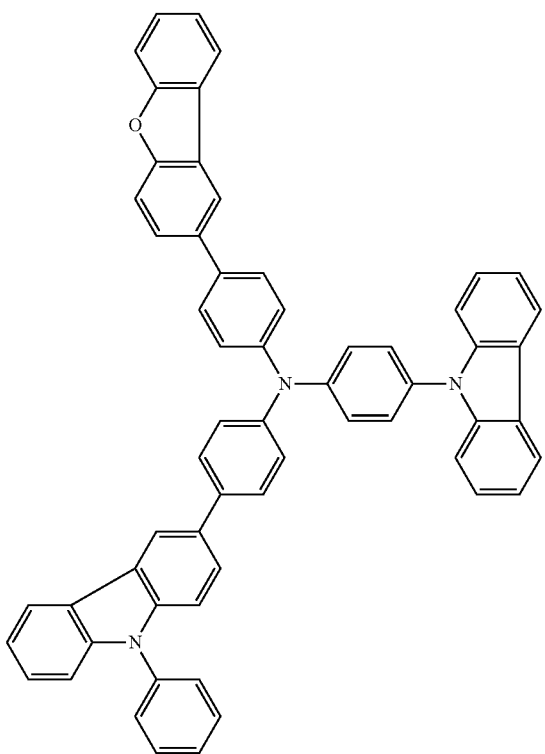 |

261
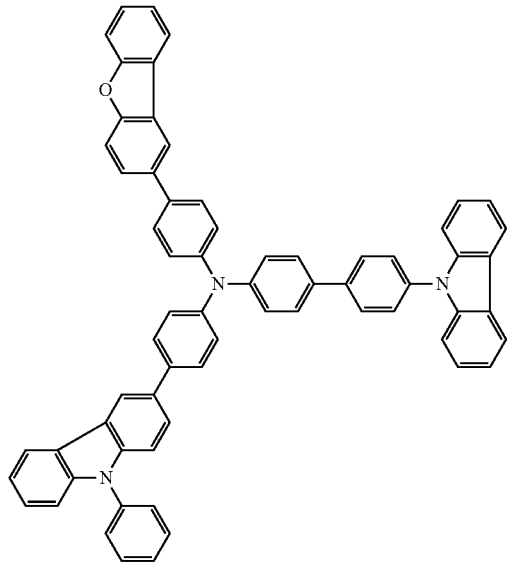
262
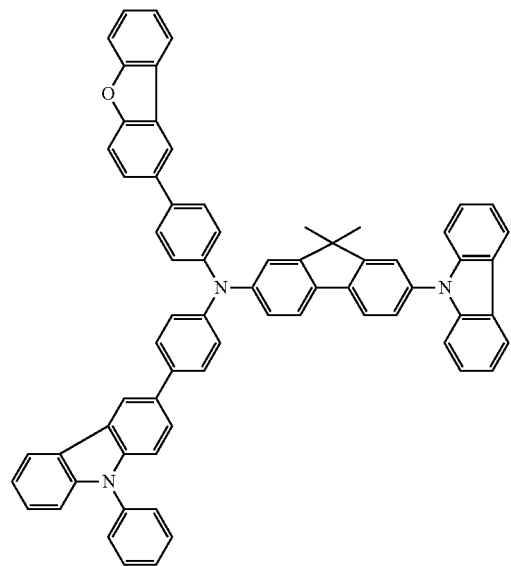
-continued
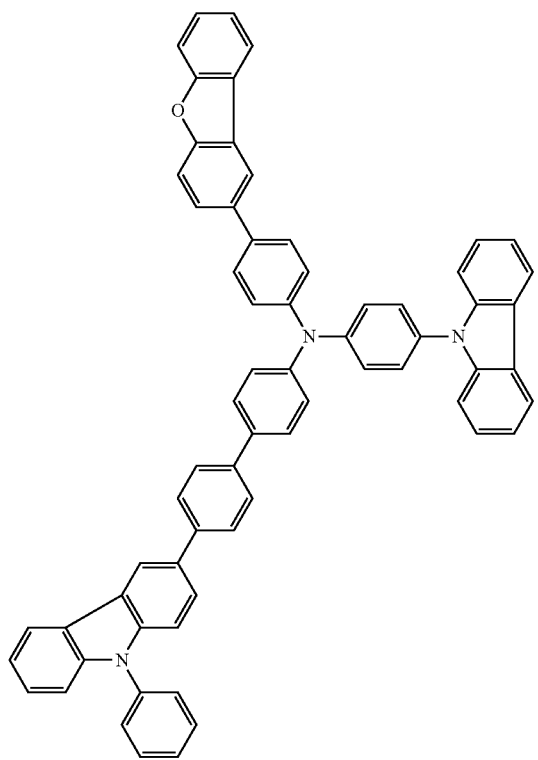
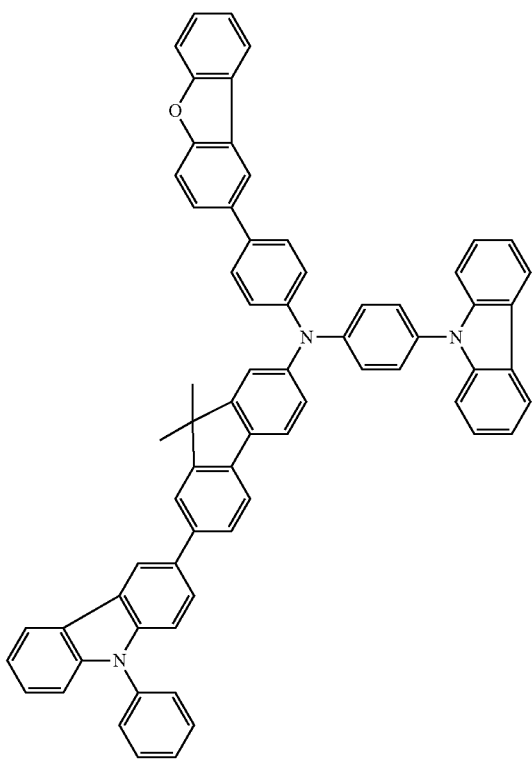

263
-continued
264
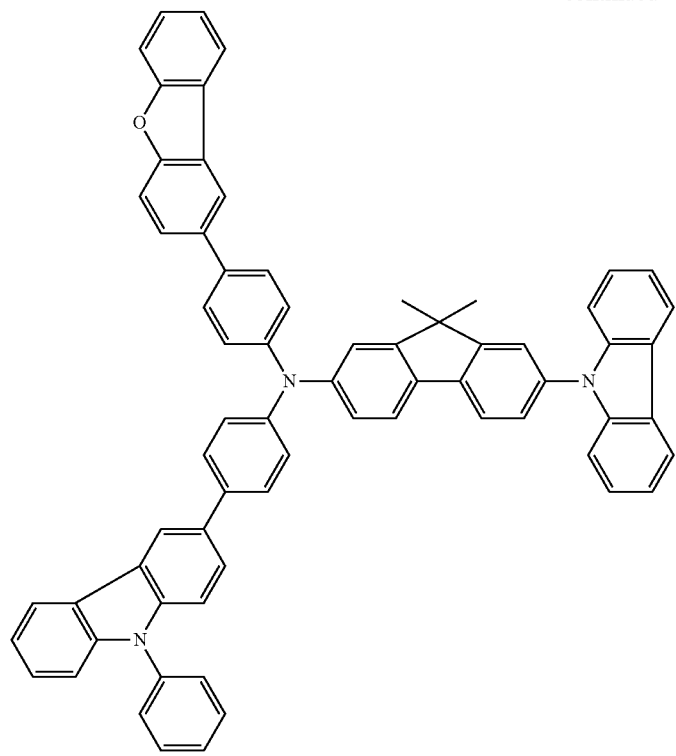
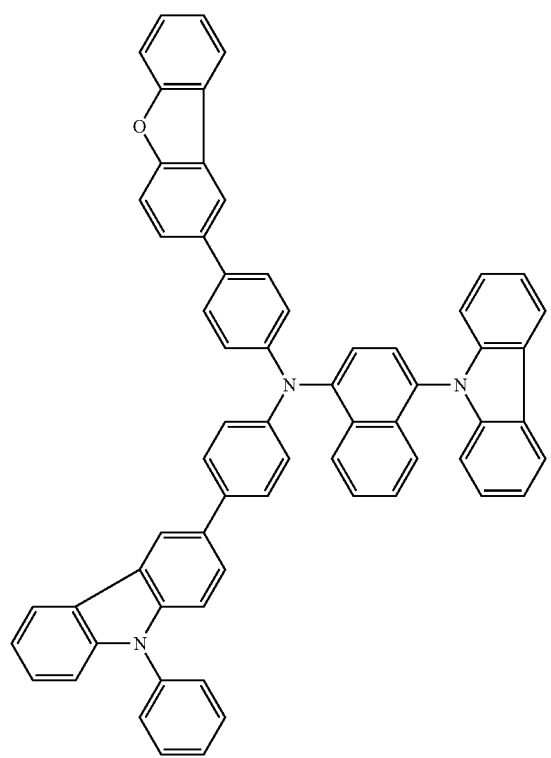
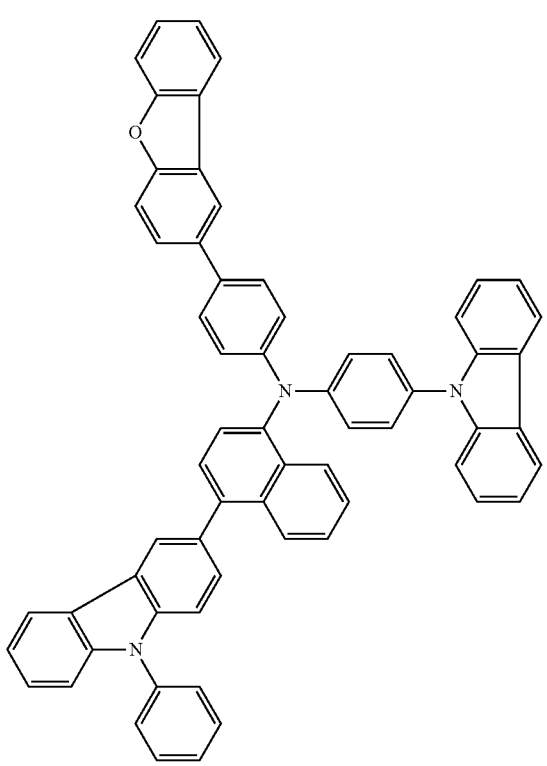

-continued
265
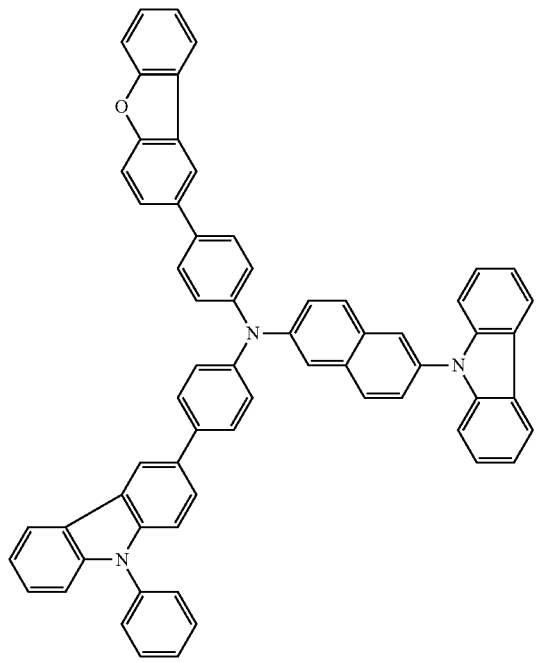
266
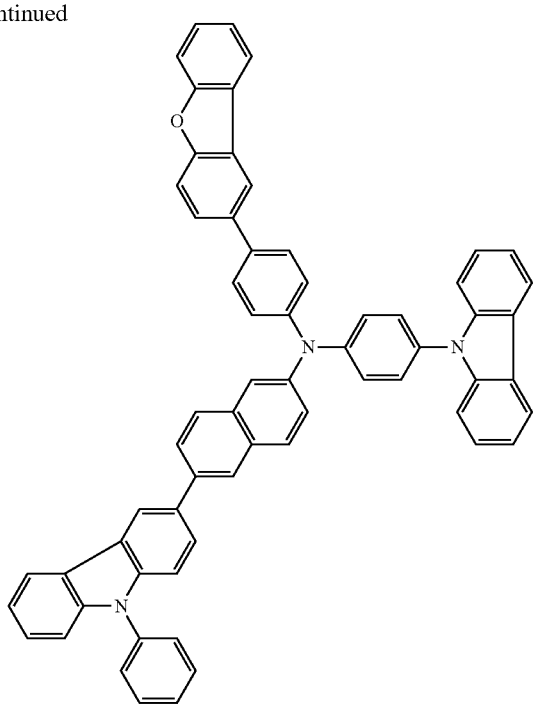
[Chem. 36]
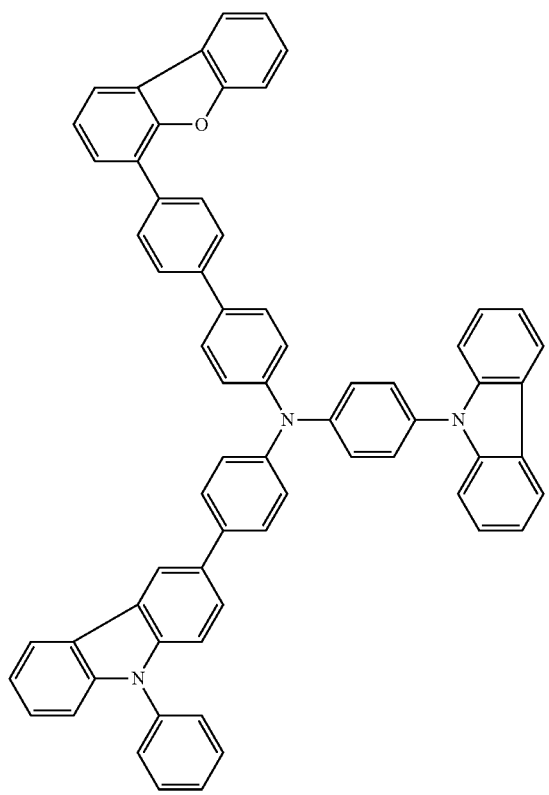
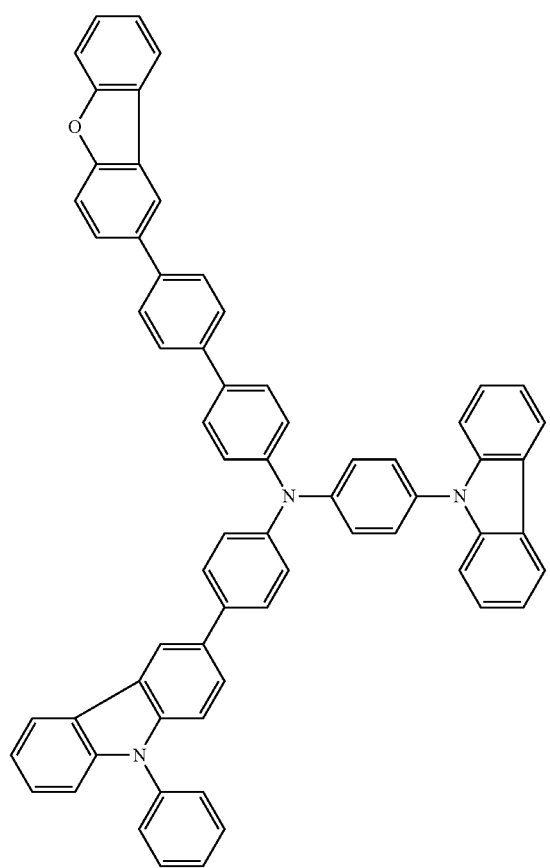

-continued
267
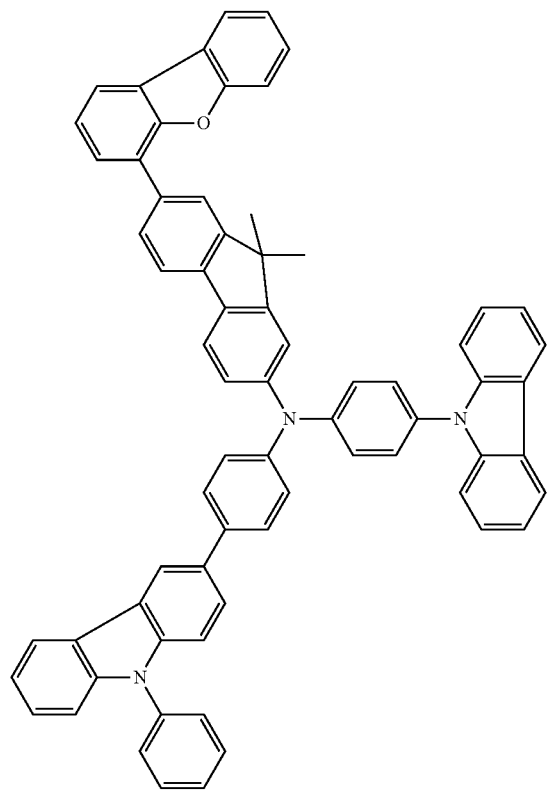
268
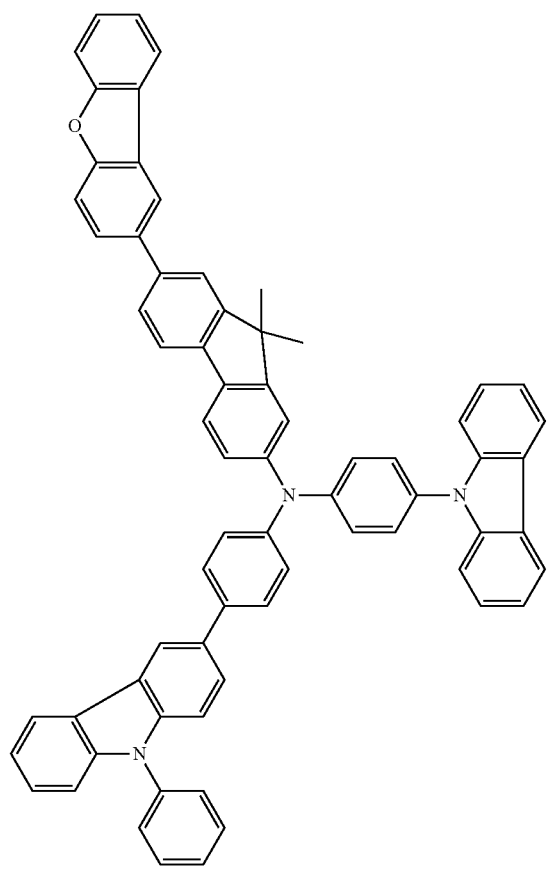
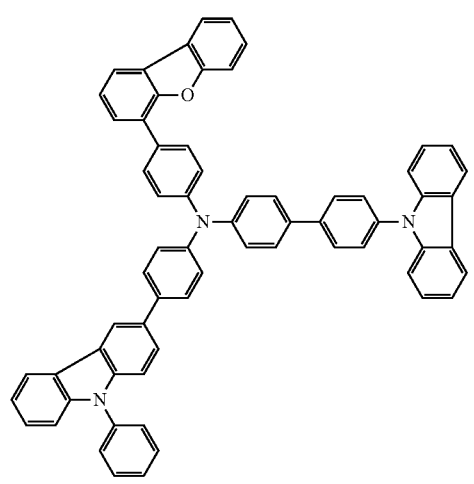
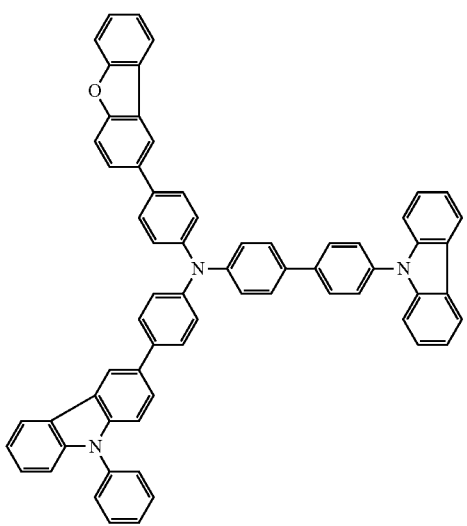

269
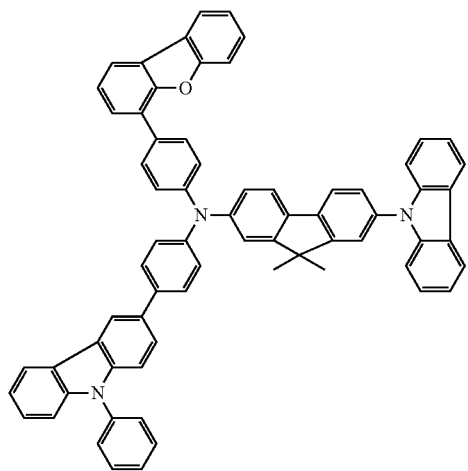
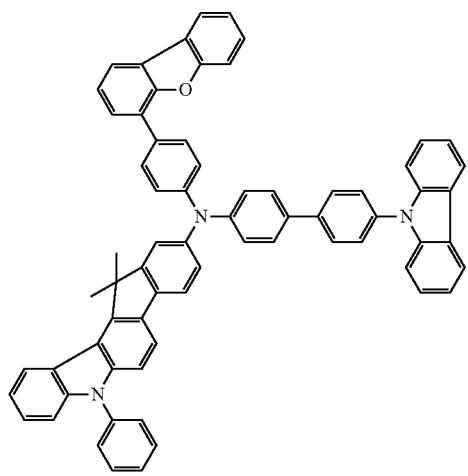
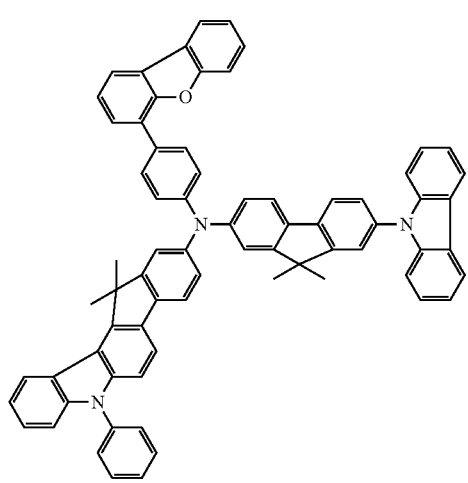
270
-continued
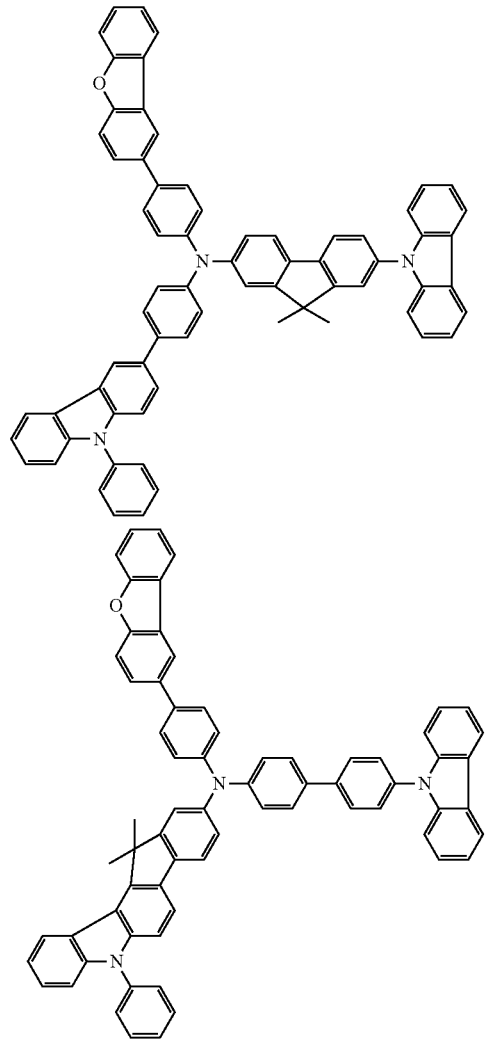
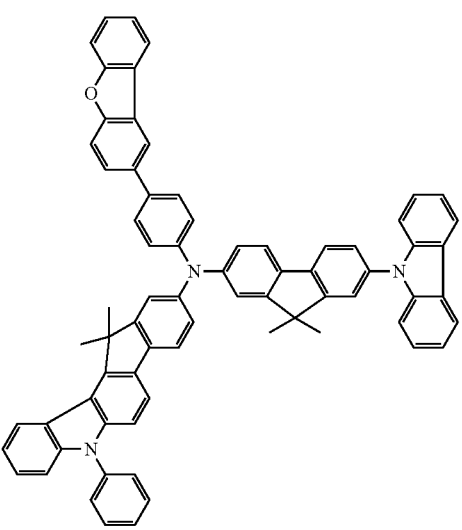

271
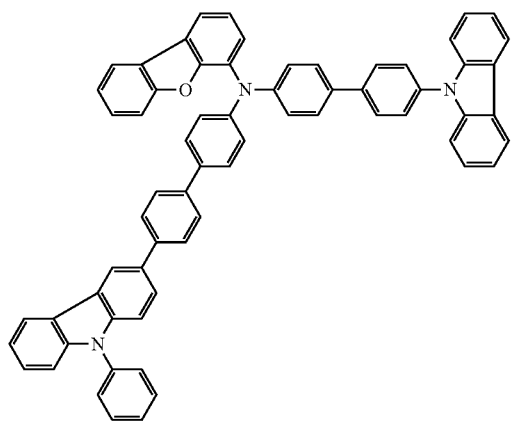
272
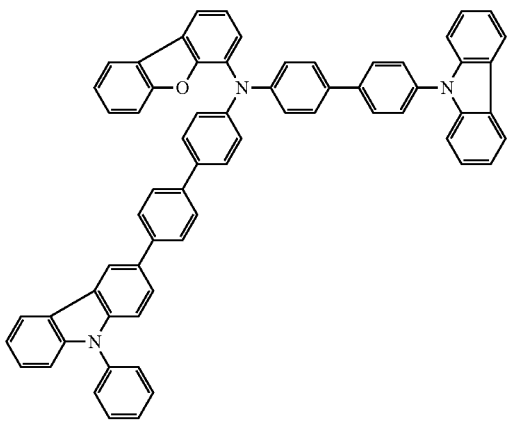
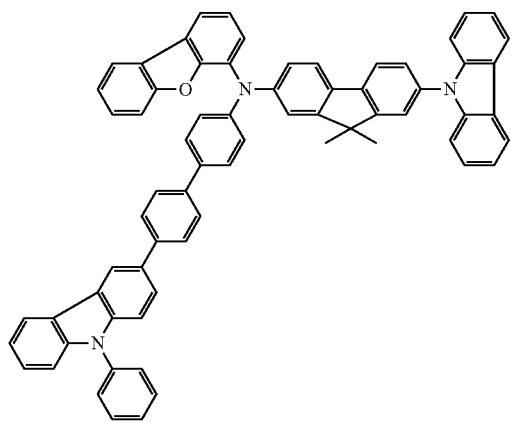
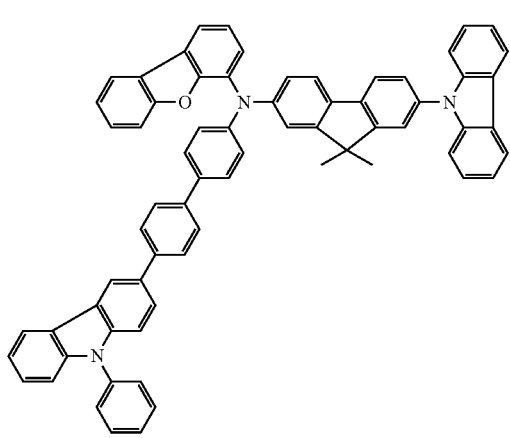
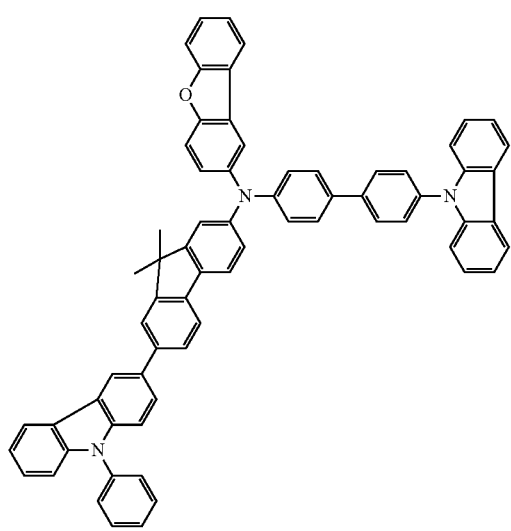
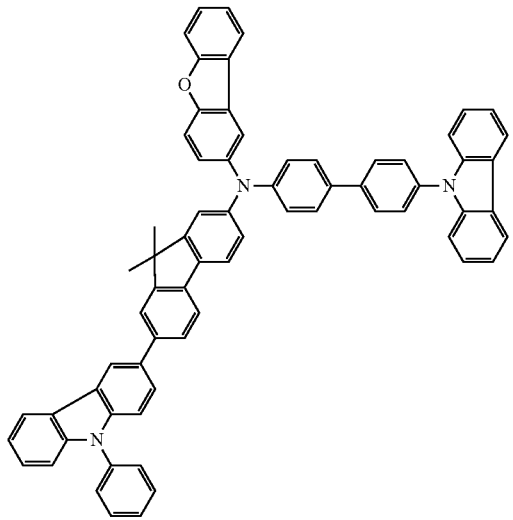

-continued
273
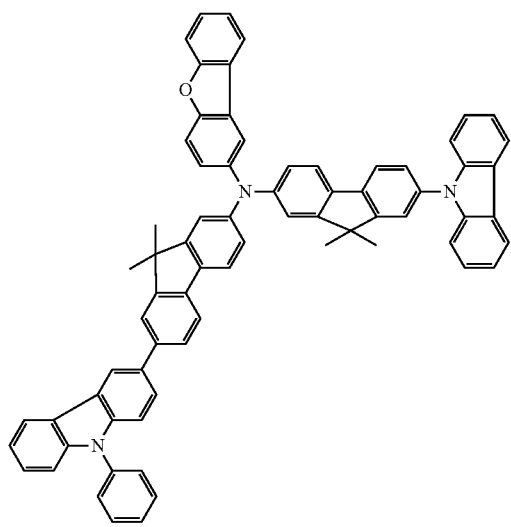
274
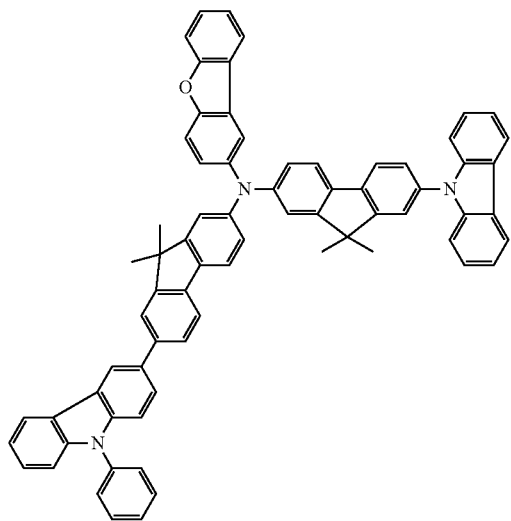
[Chem. 37]
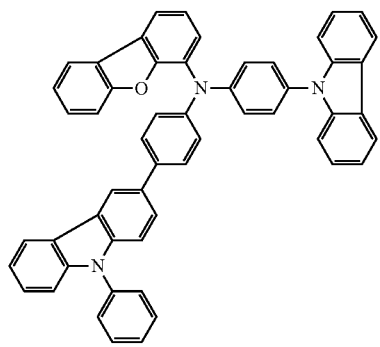
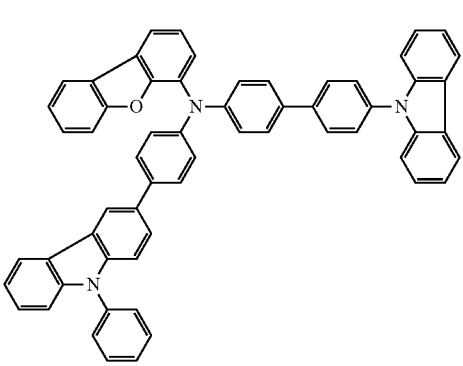
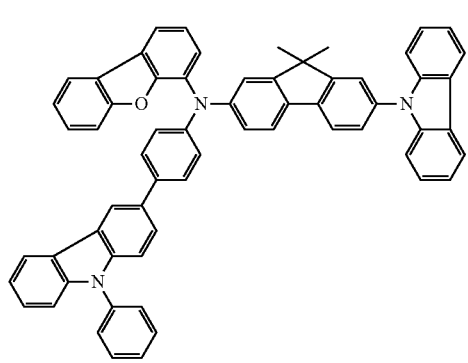
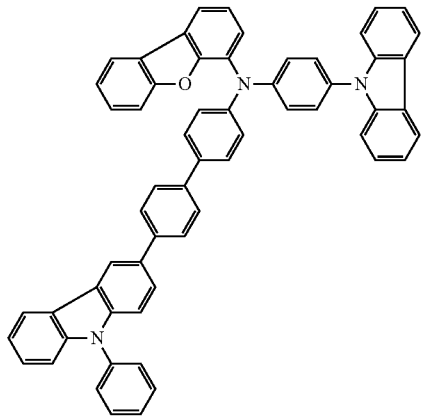

-continued
275
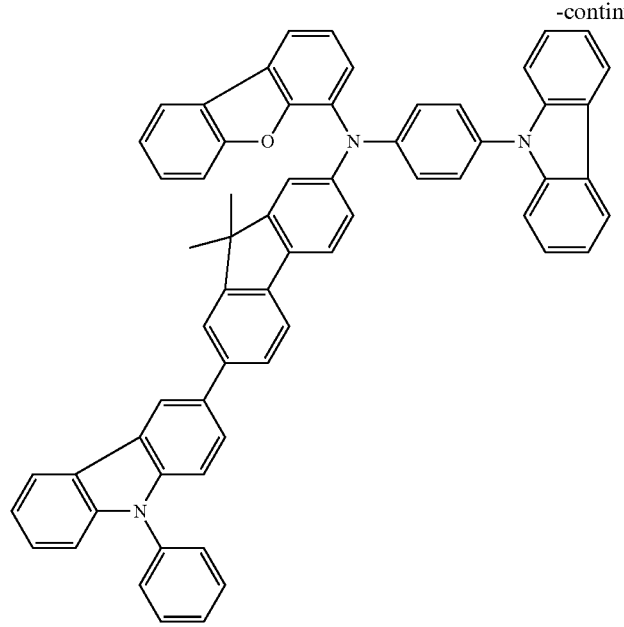
276
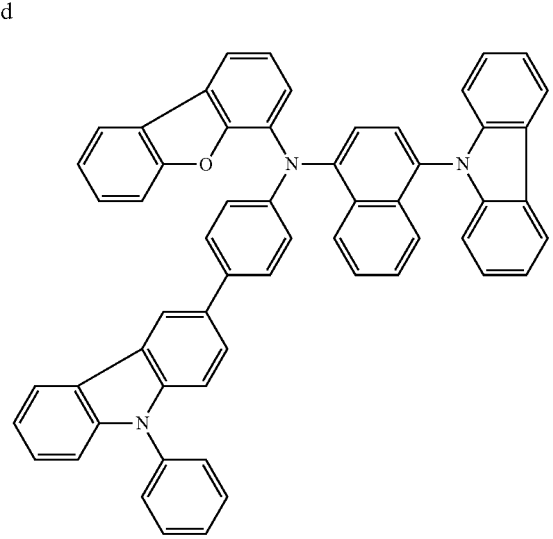
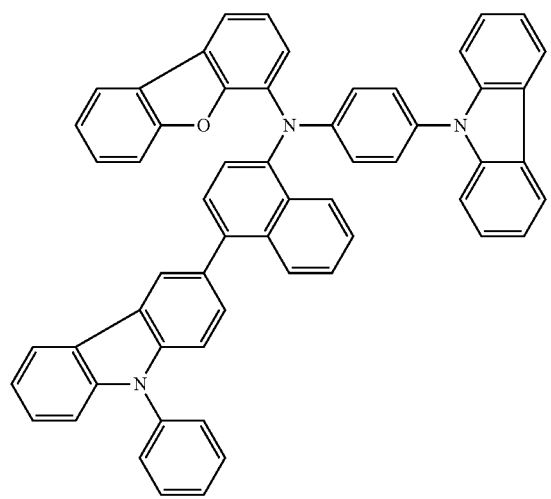
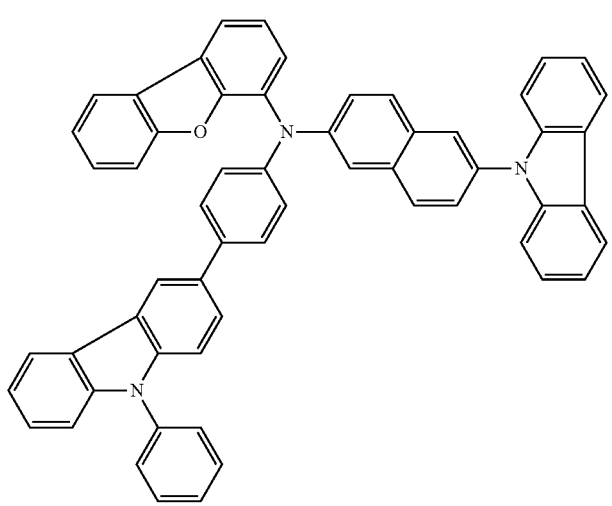

277
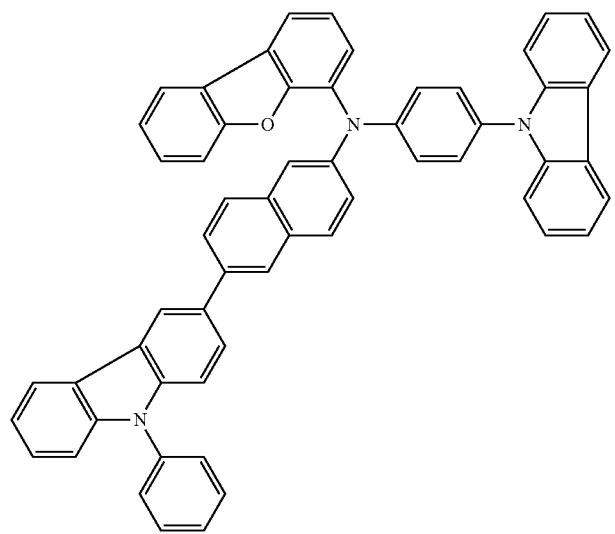
278
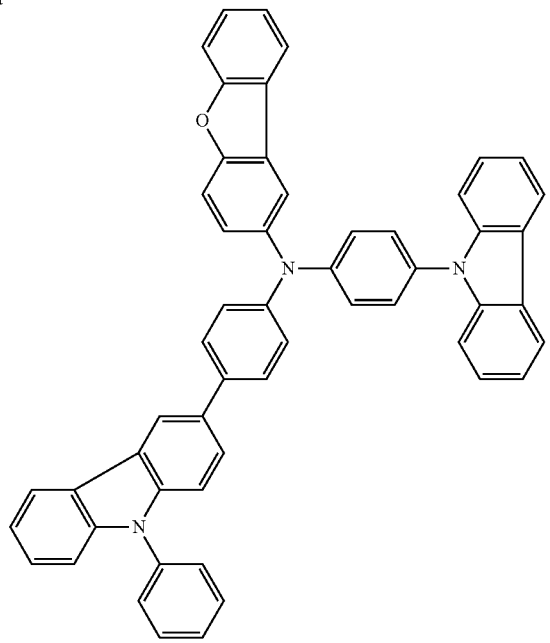
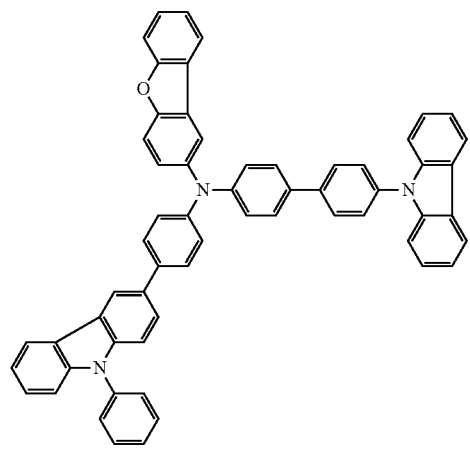
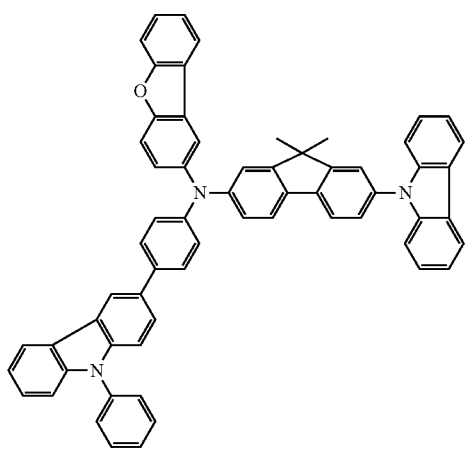

-continued
279
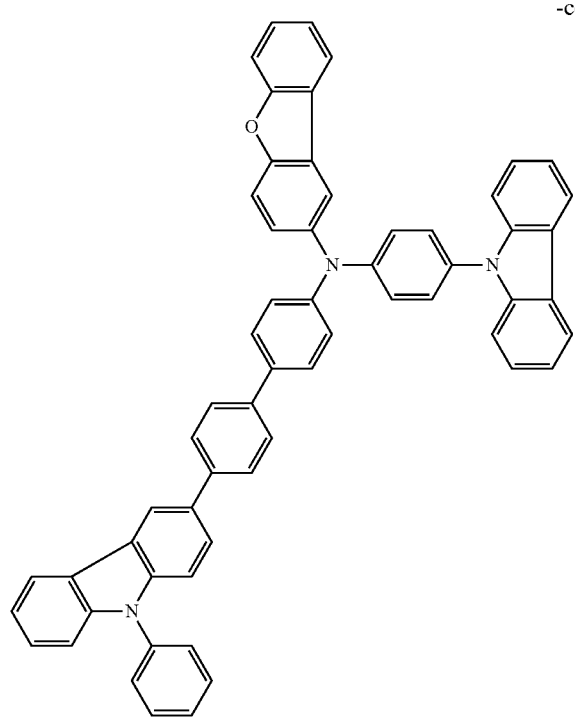
280
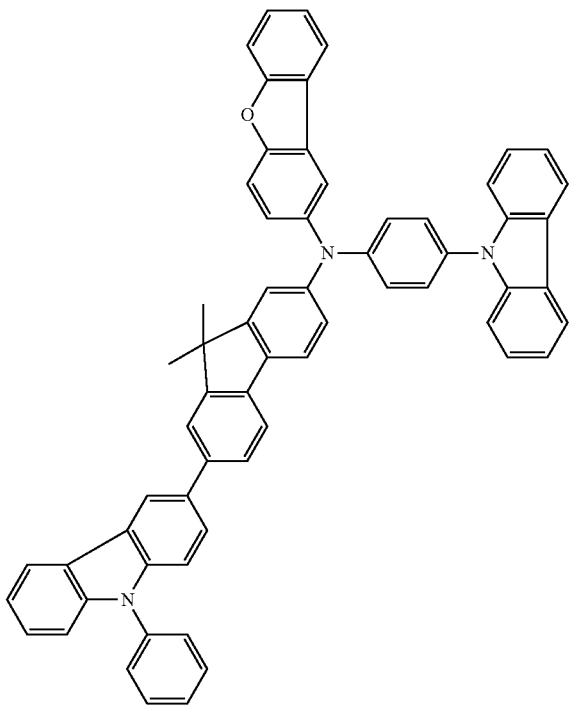
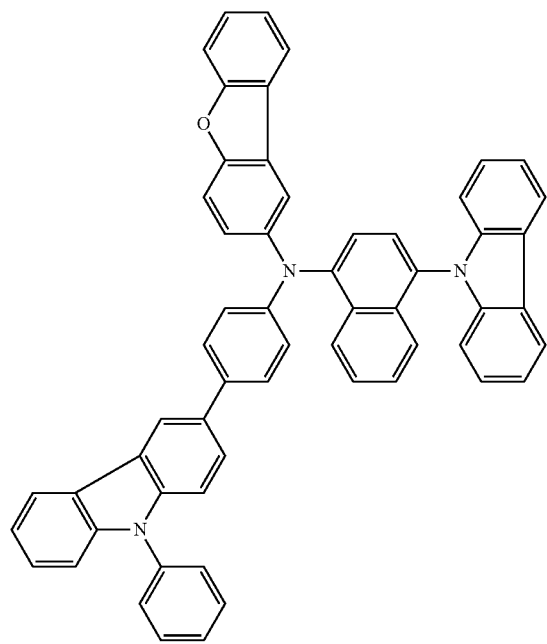
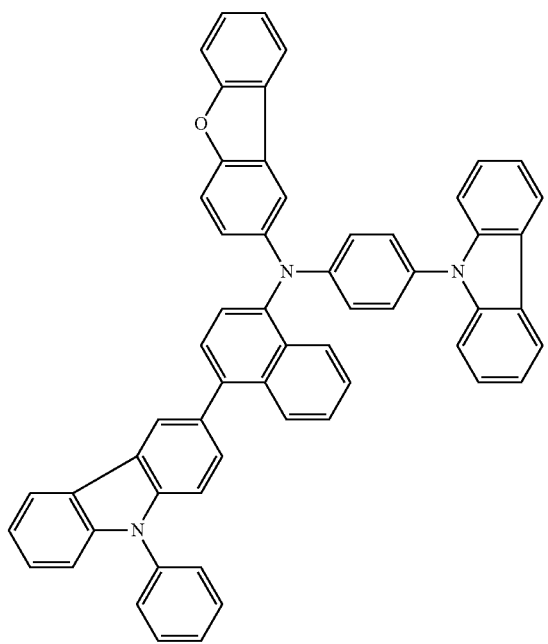

-continued
281 282
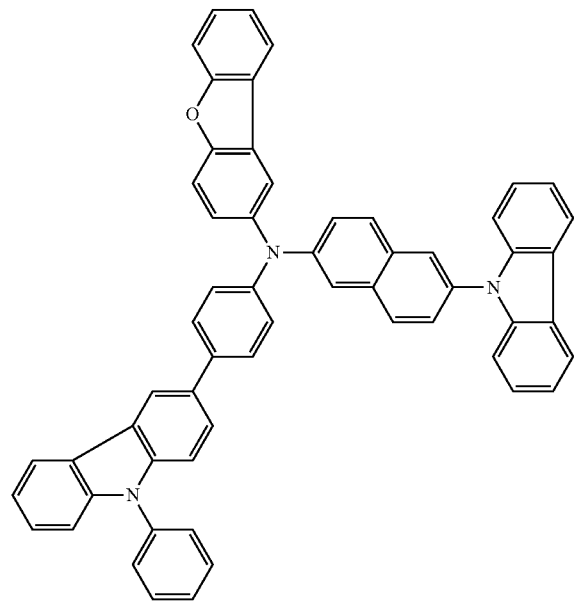 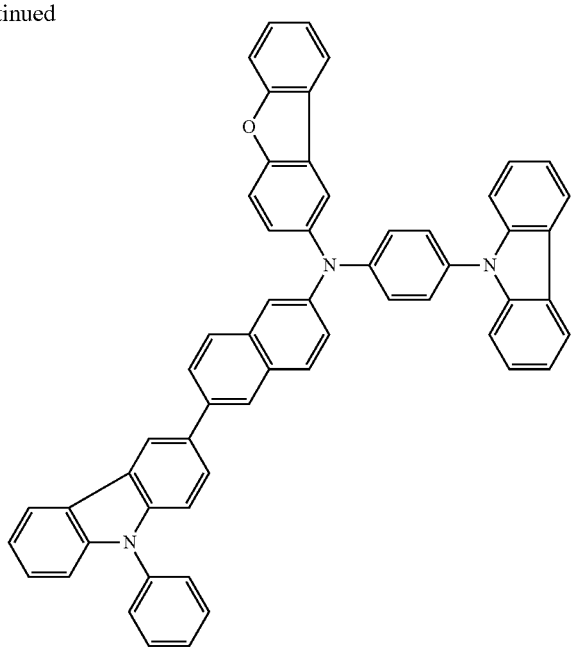
[Chem. 38]
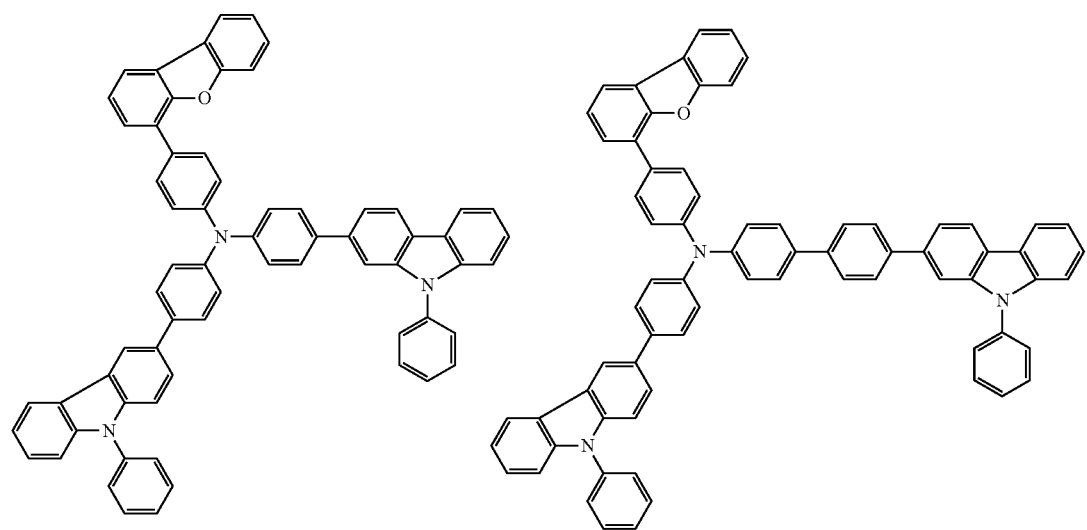

283
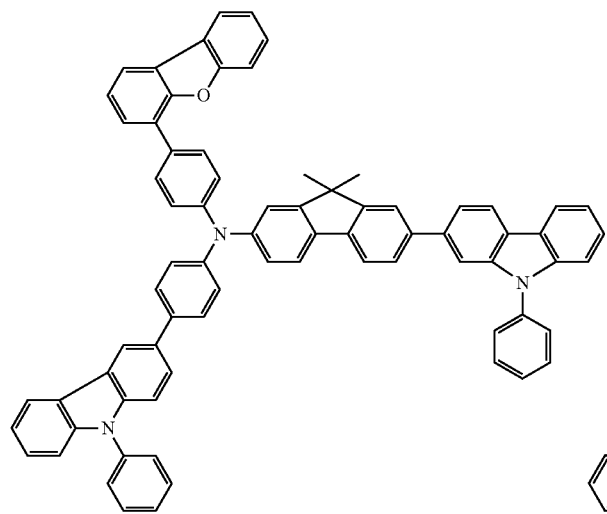
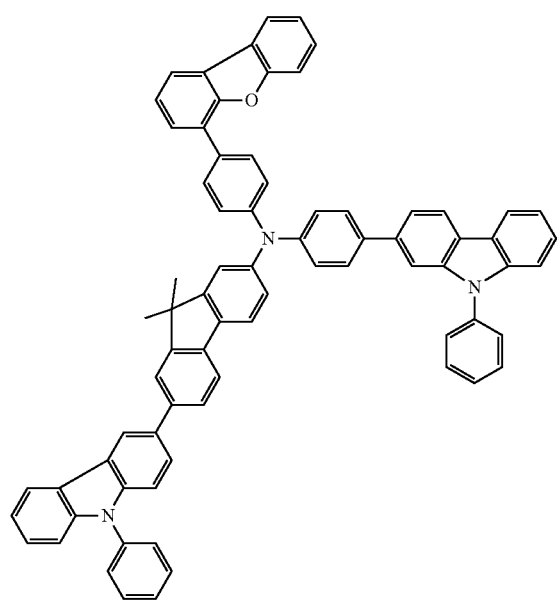
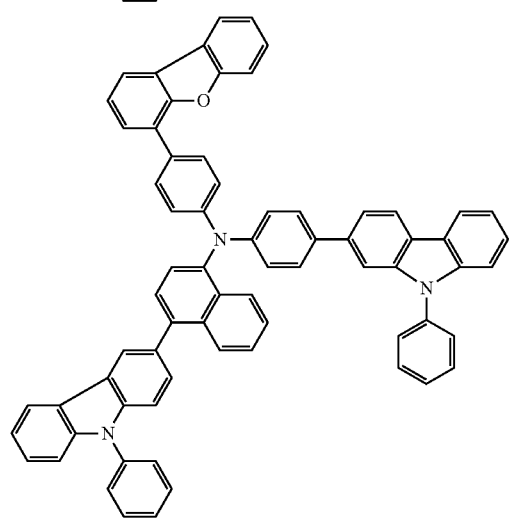
284
-continued
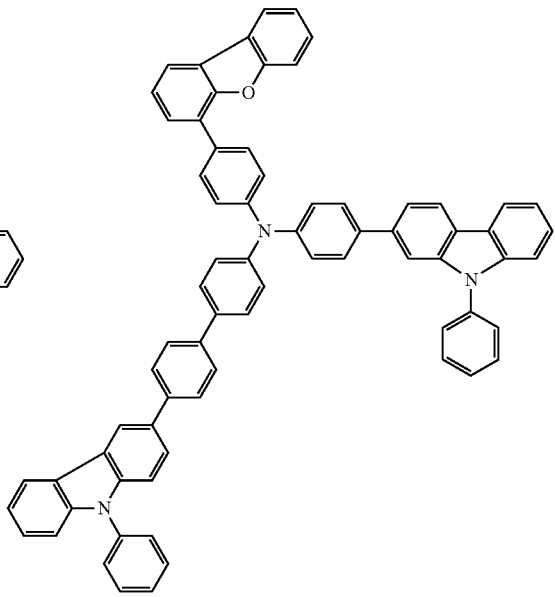
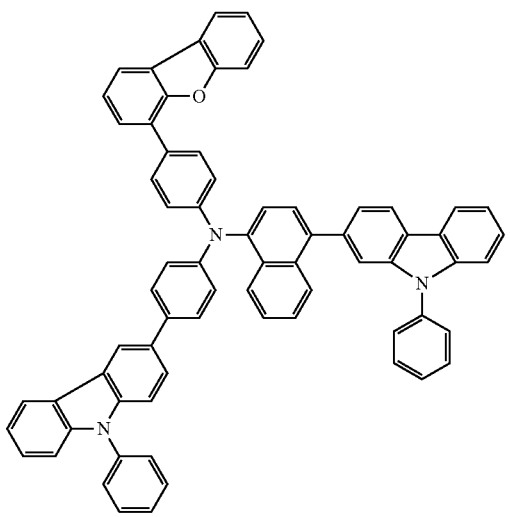
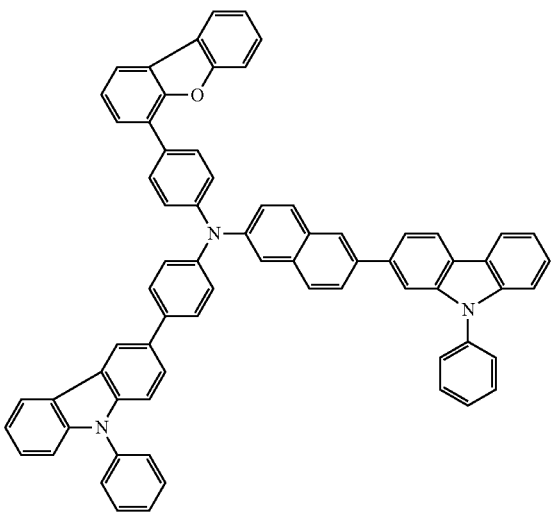

285
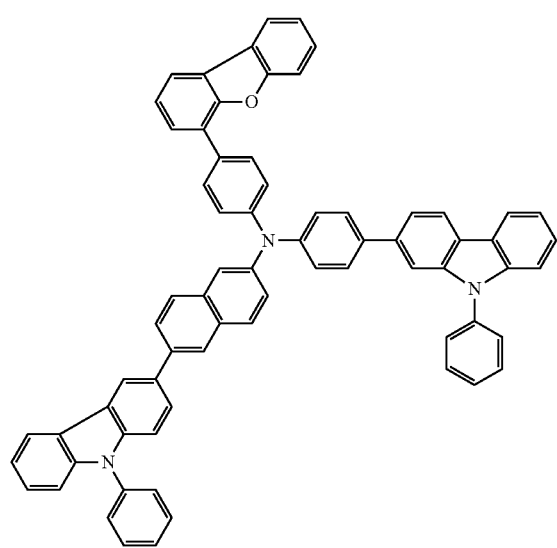
286
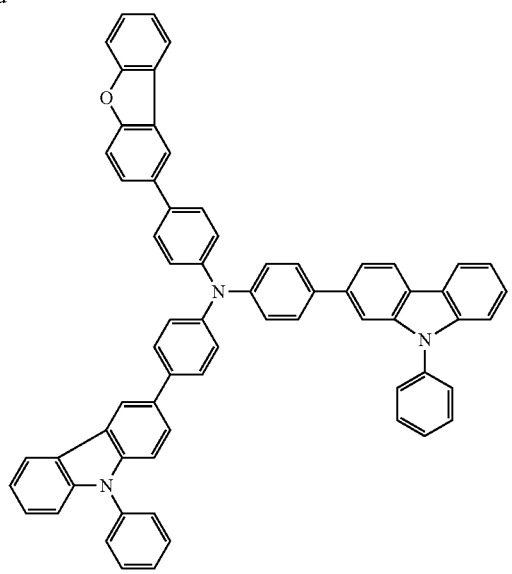
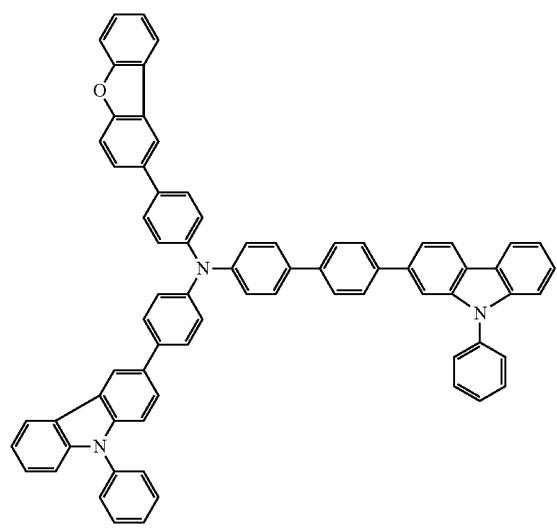
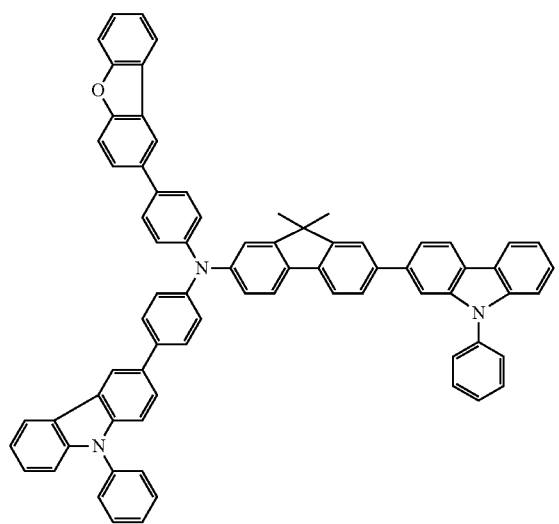

287
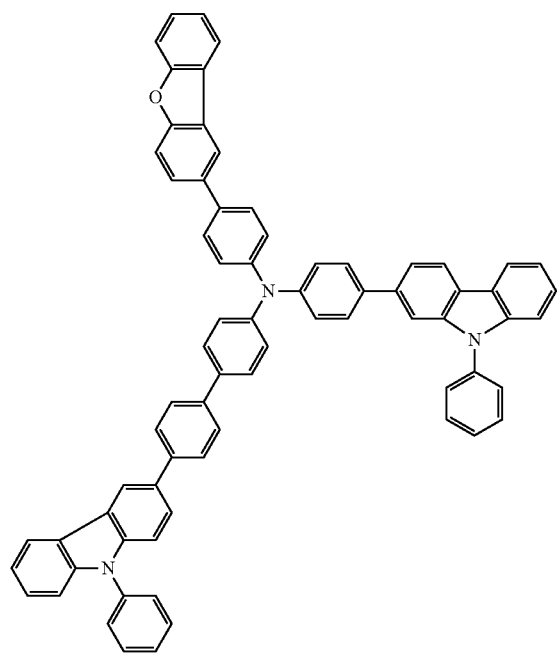
288
-continued
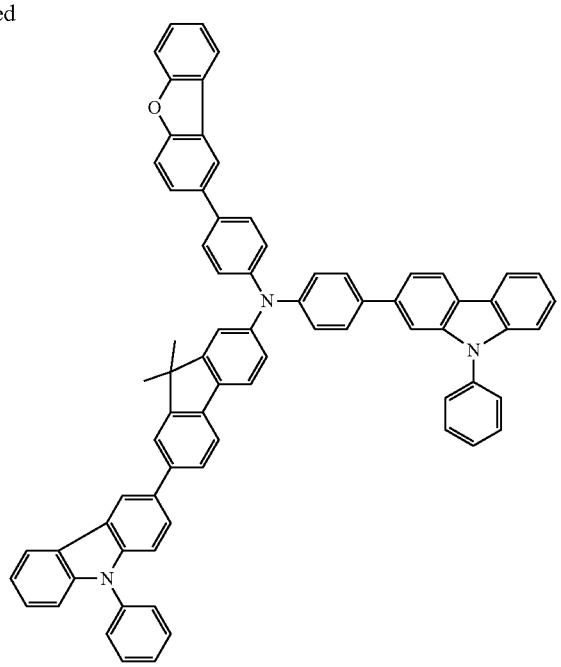
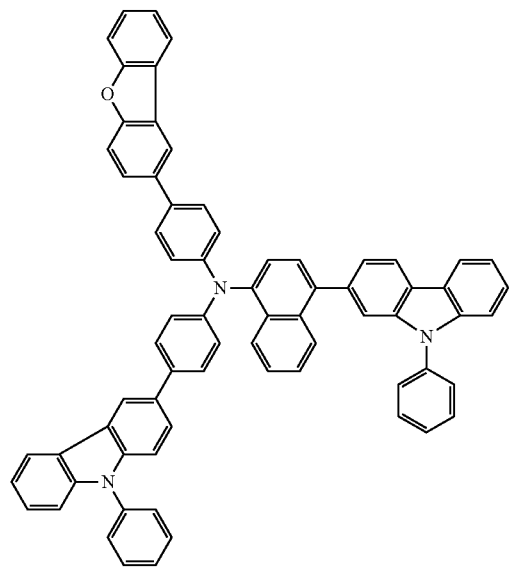
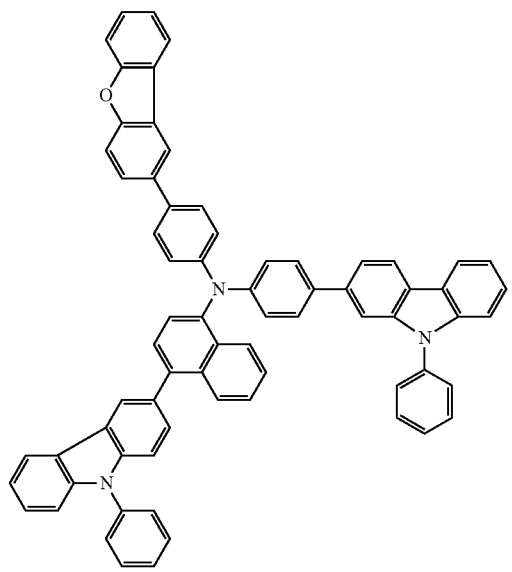

289
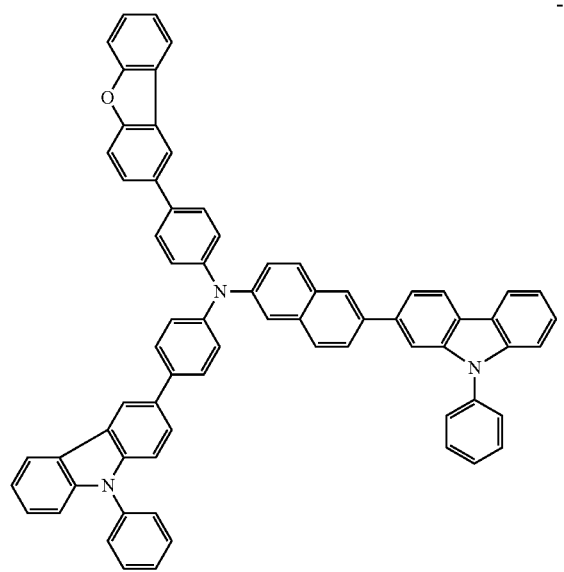
290
-continued
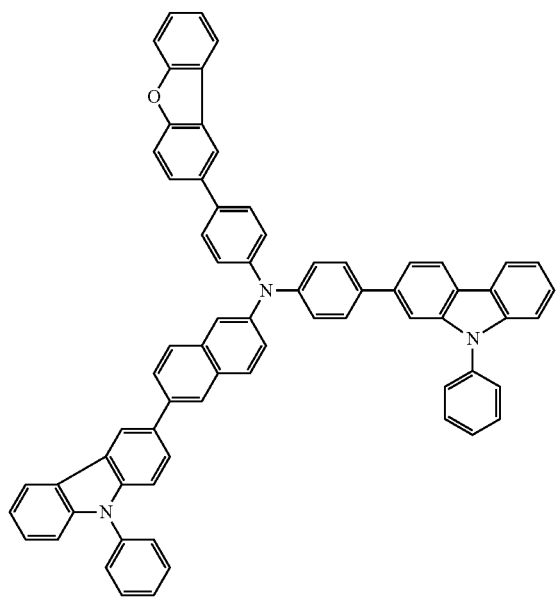
[Chem. 39]
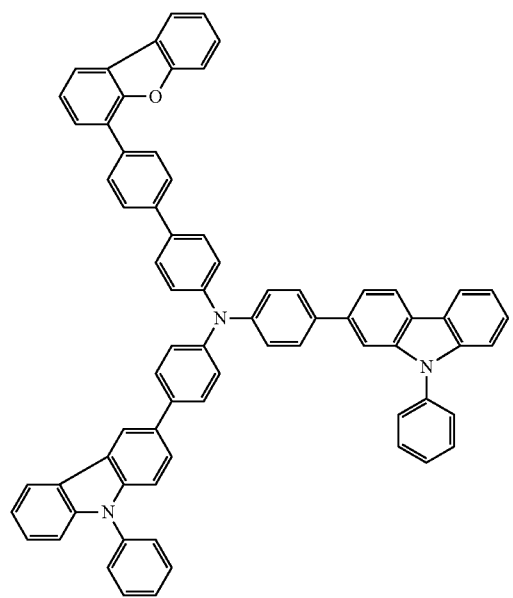
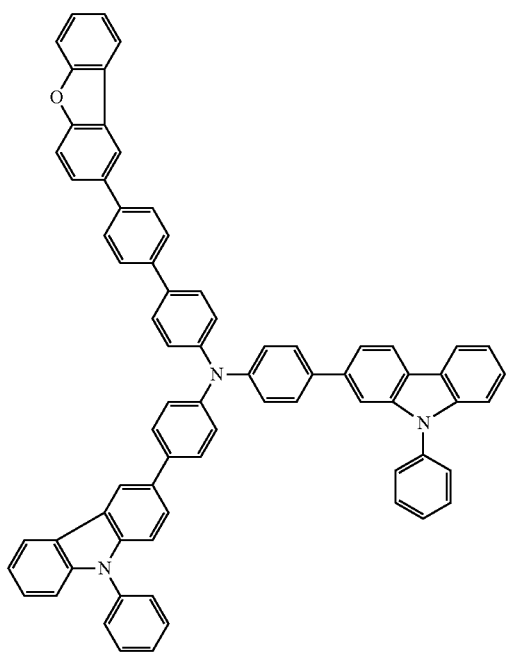

-continued
291
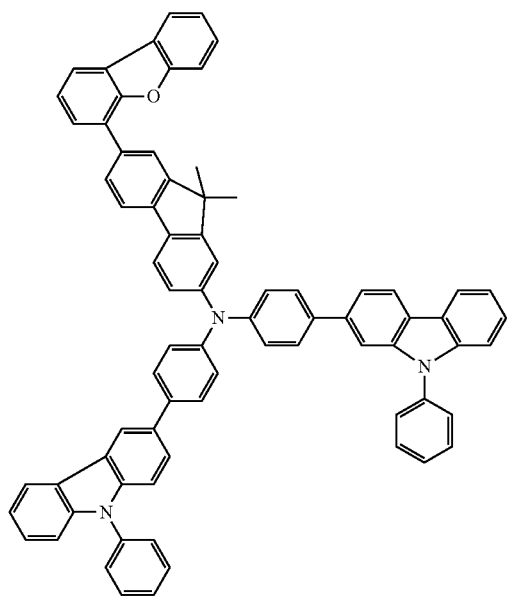
292
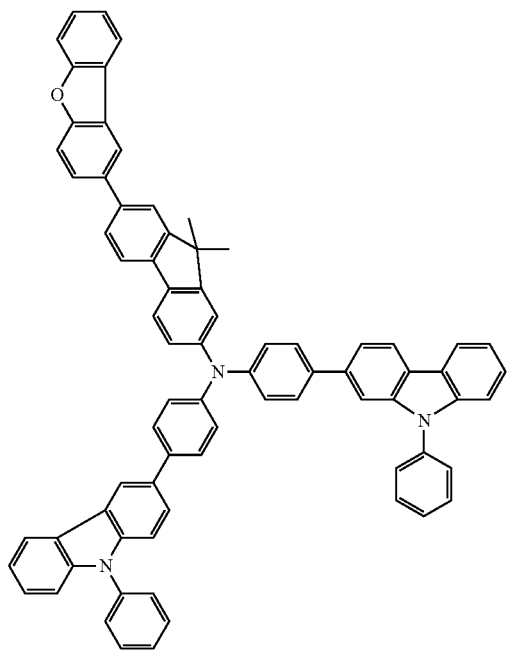
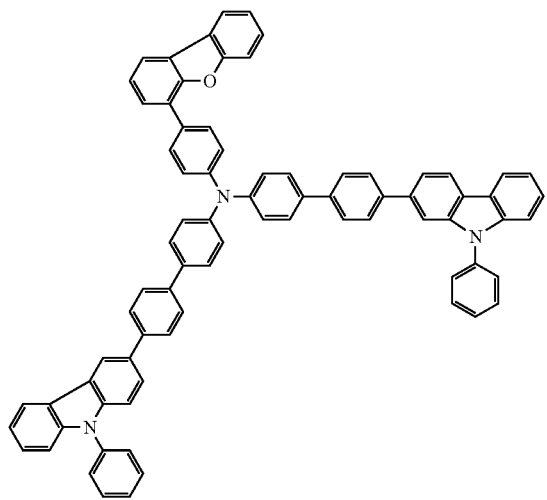
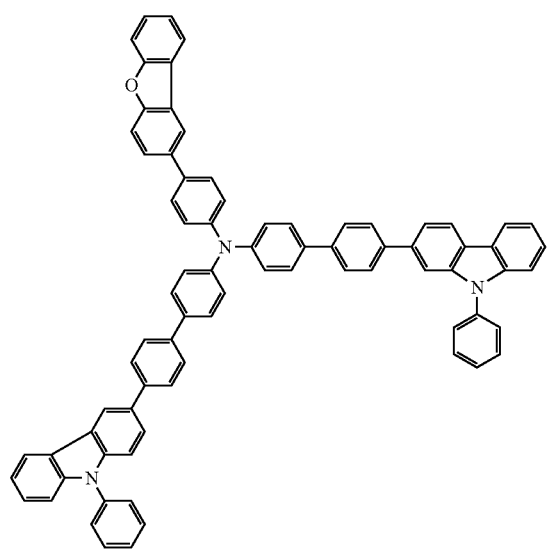

293
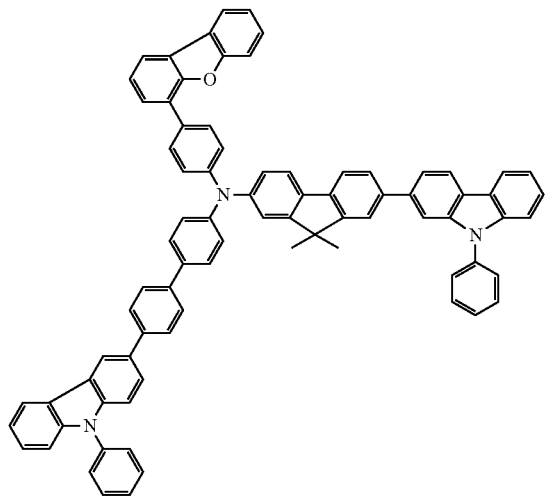
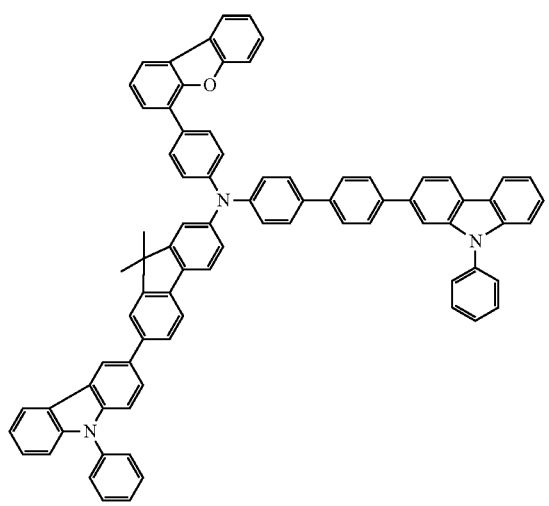
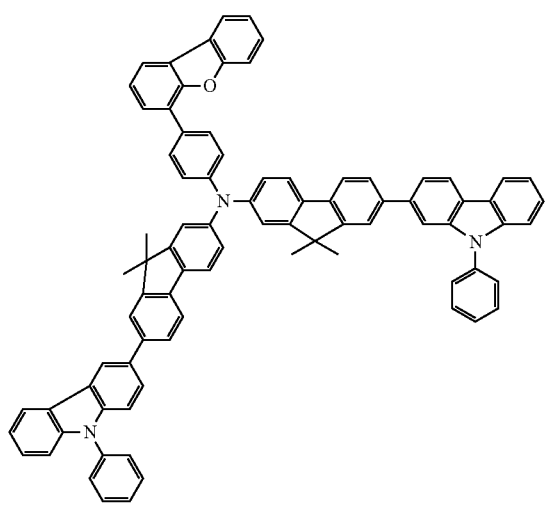
294
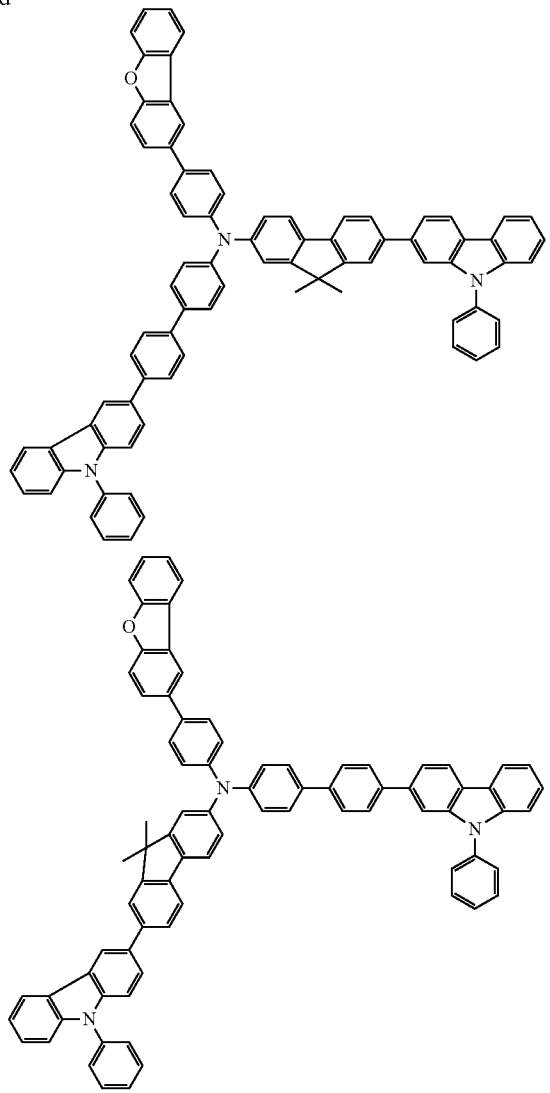
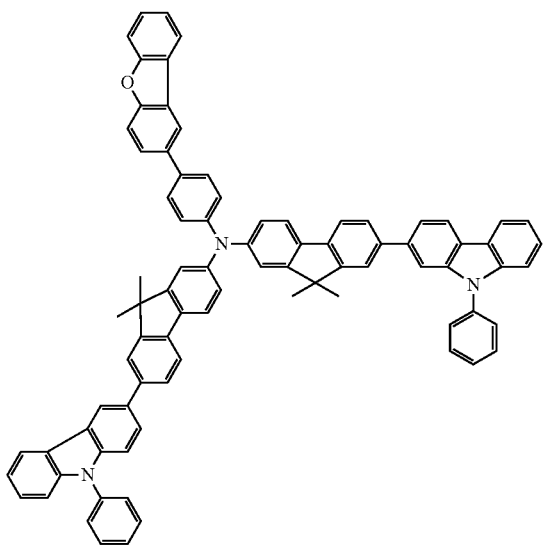

295
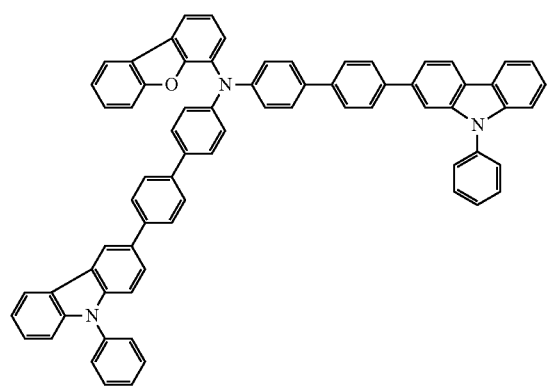
296
-continued
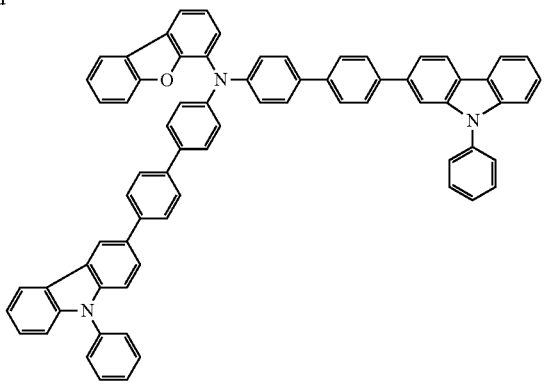
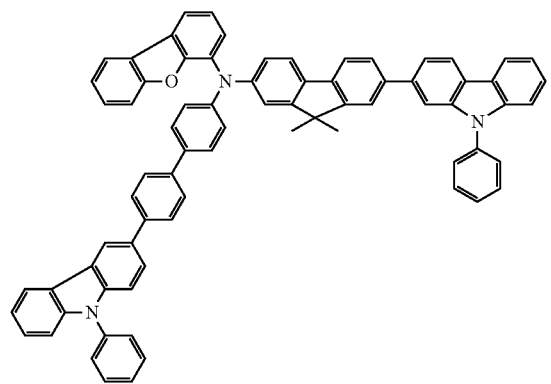
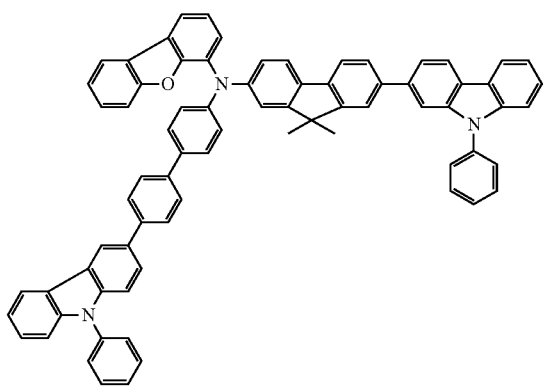
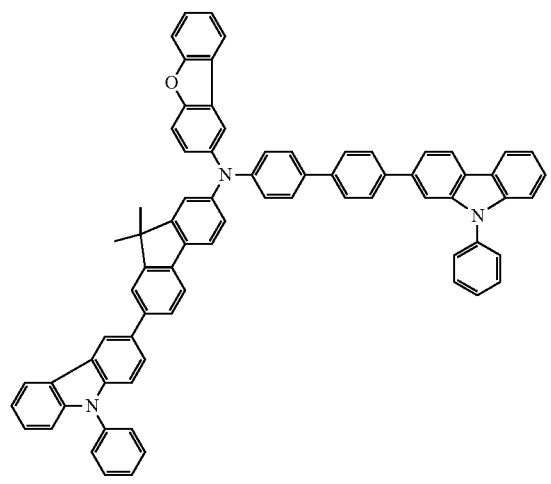
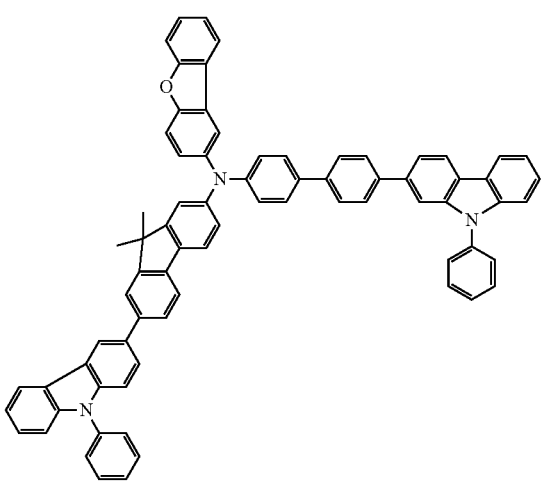

-continued
297
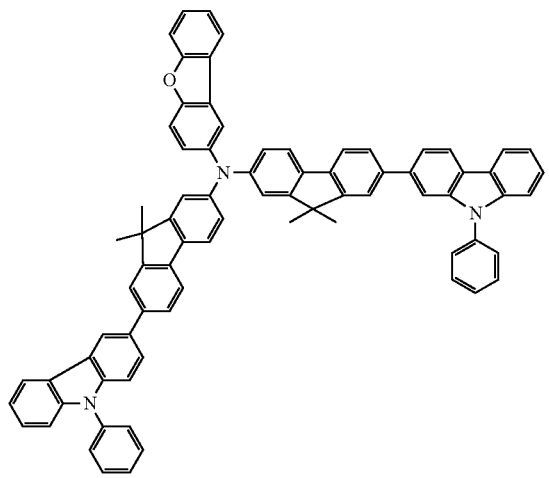
298
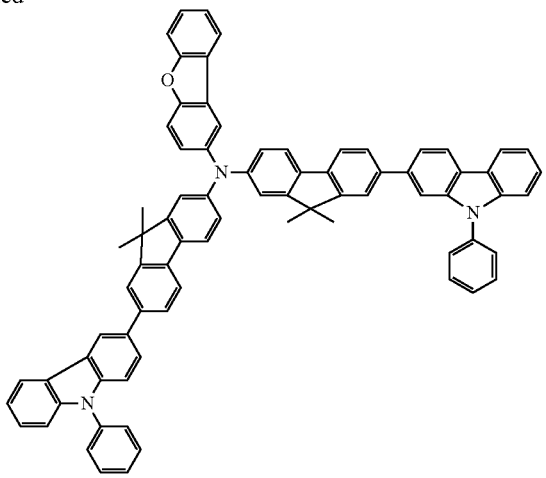
[Chem. 40]
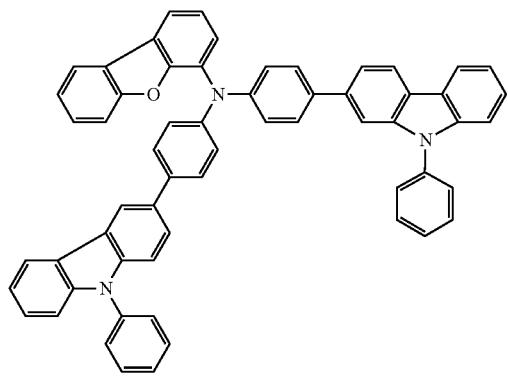
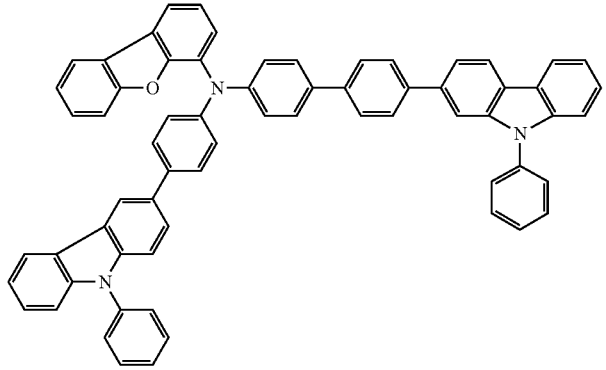
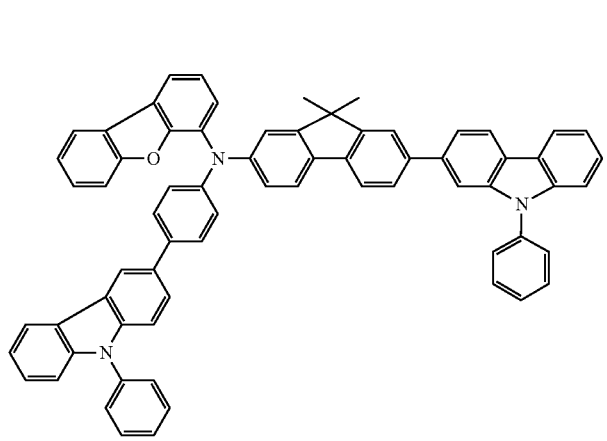
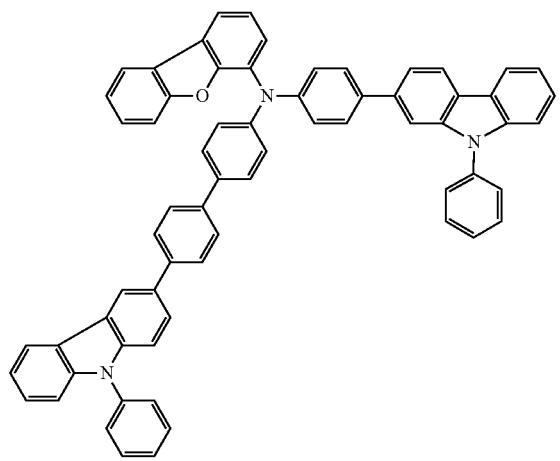

299
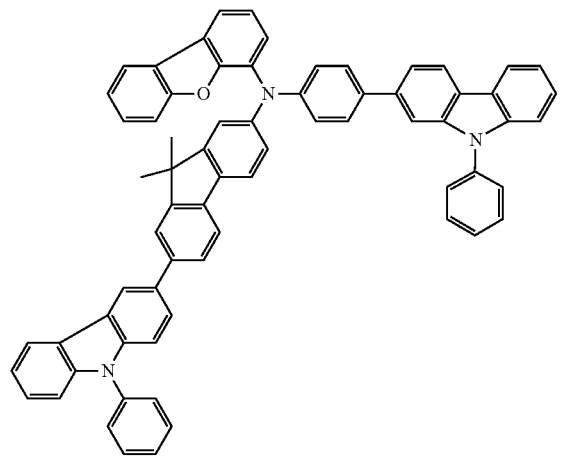
300
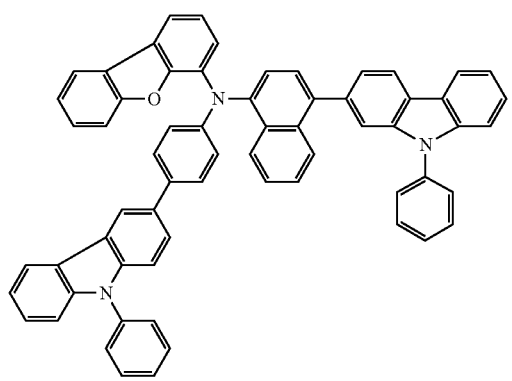
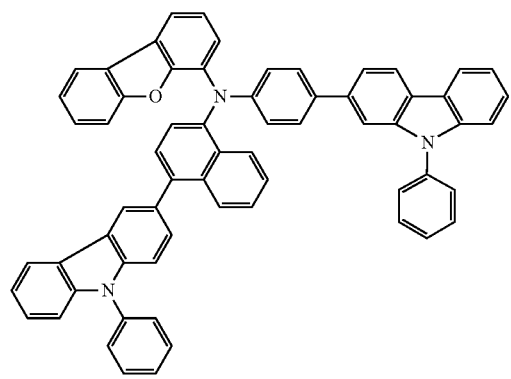
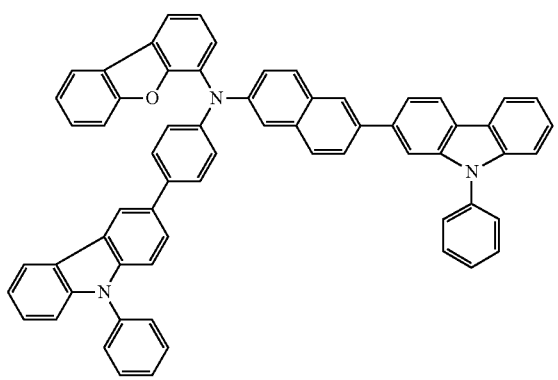
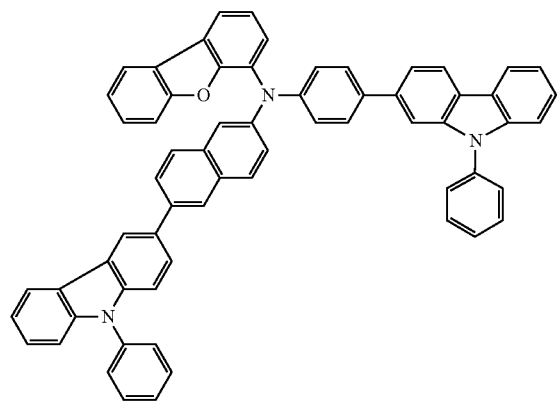
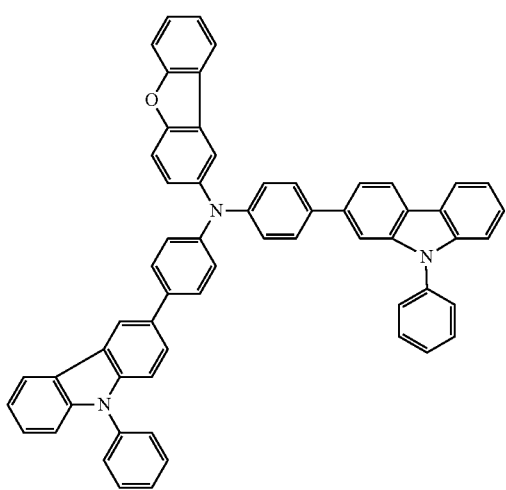

-continued
| 301 | 302 |
|---|---|
| 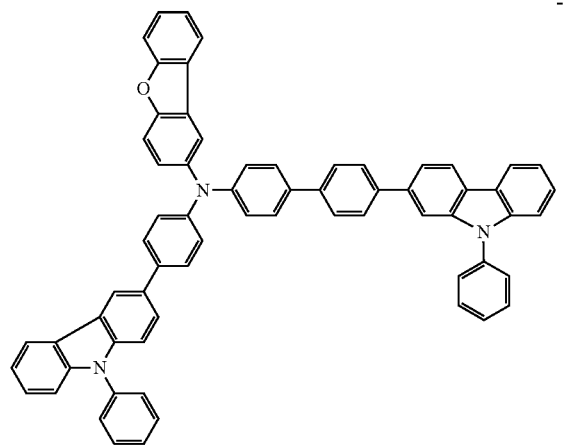 | 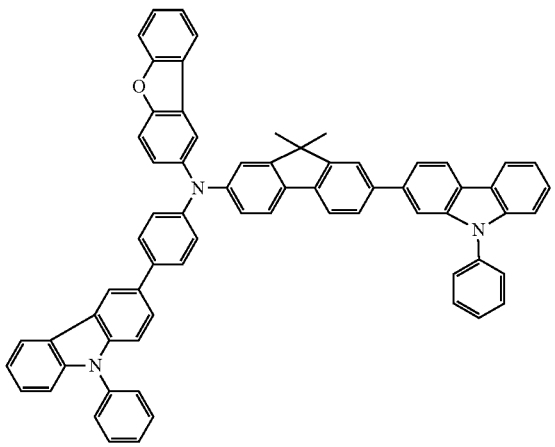 |
| 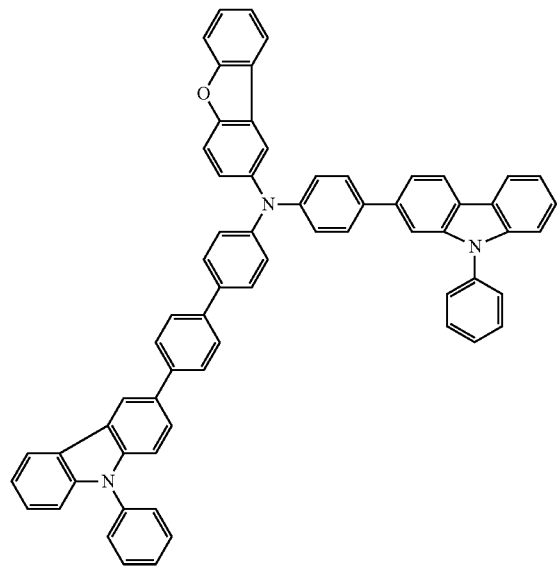 | 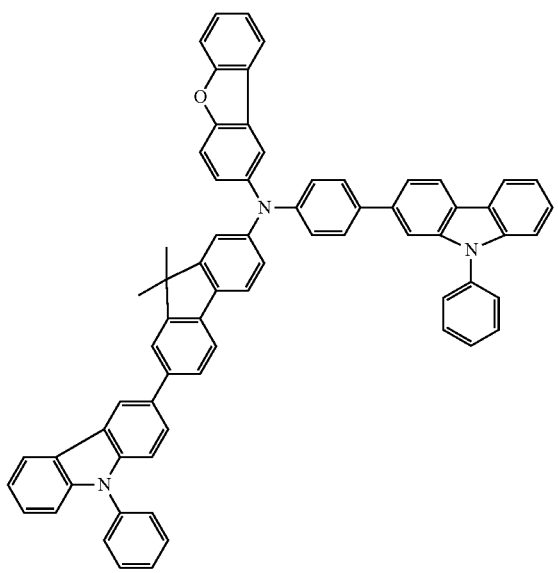 |
| 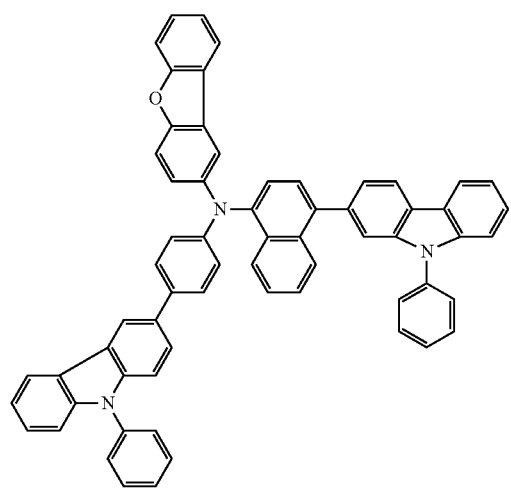 | 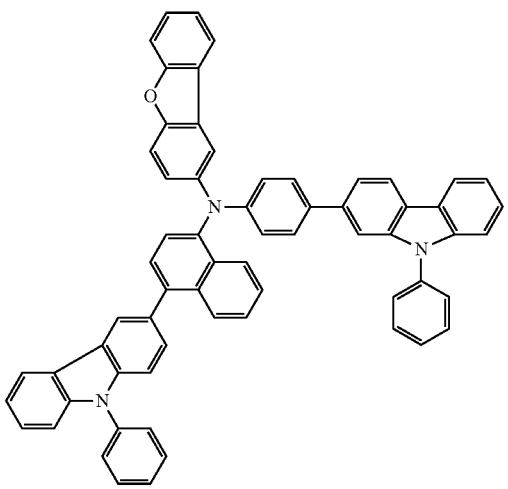 |

303
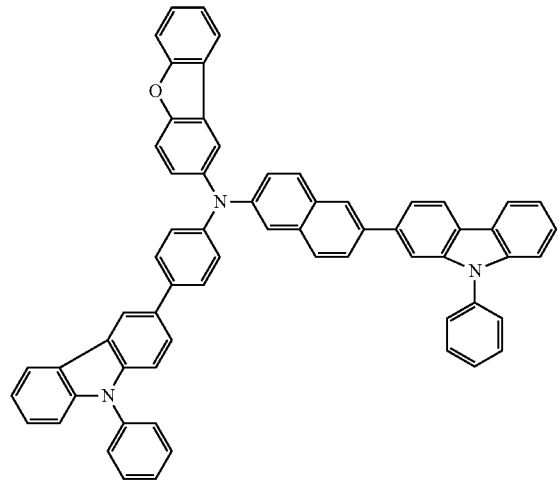
304
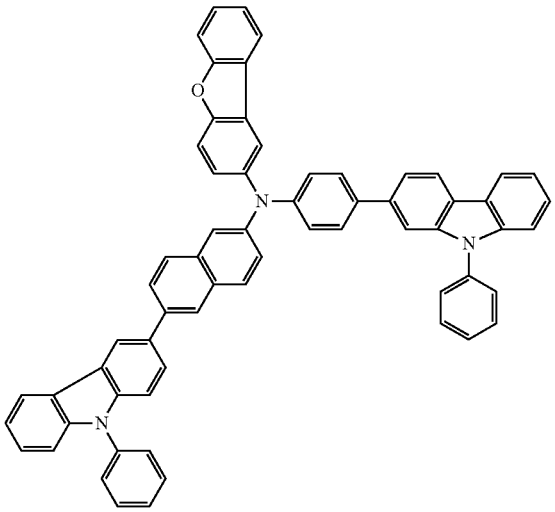
[Chem. 41]
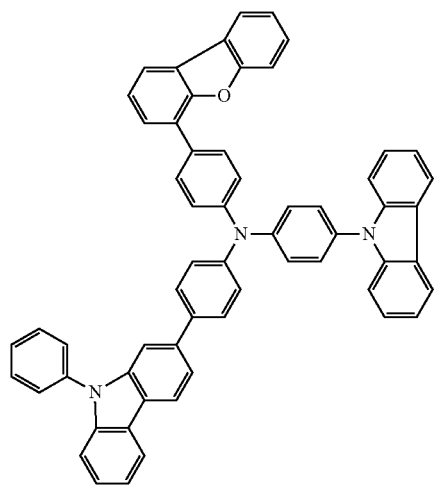
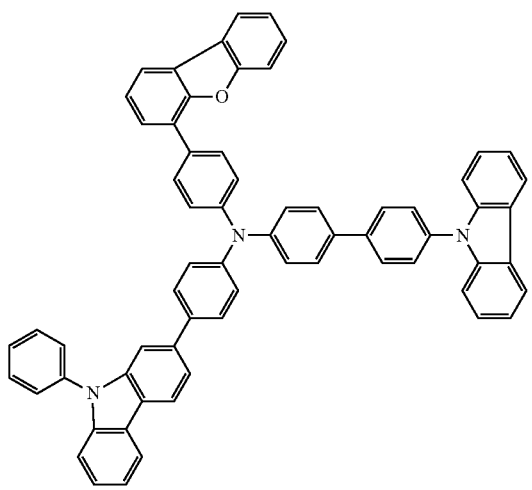
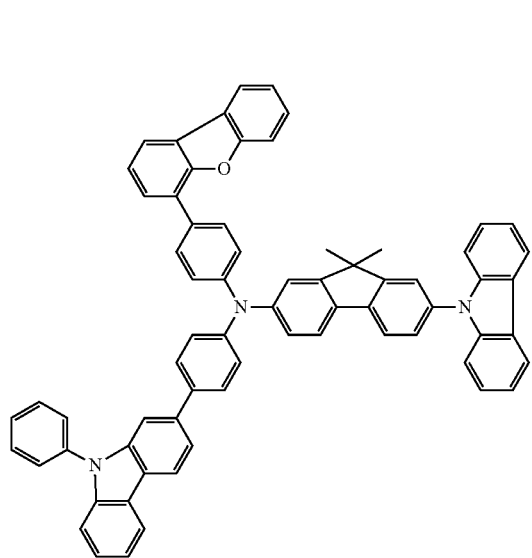
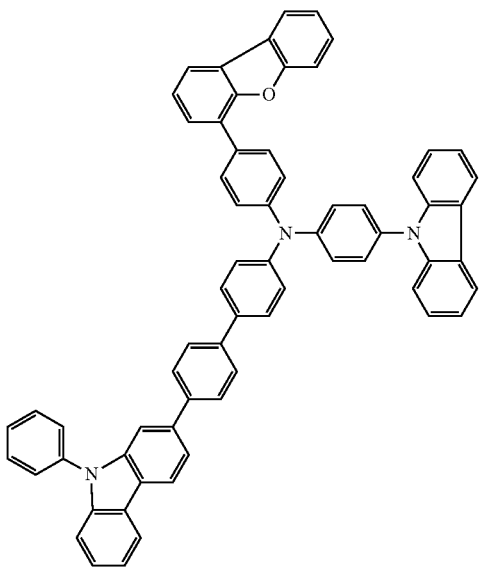

| 305 | 306 |
|---|---|
| 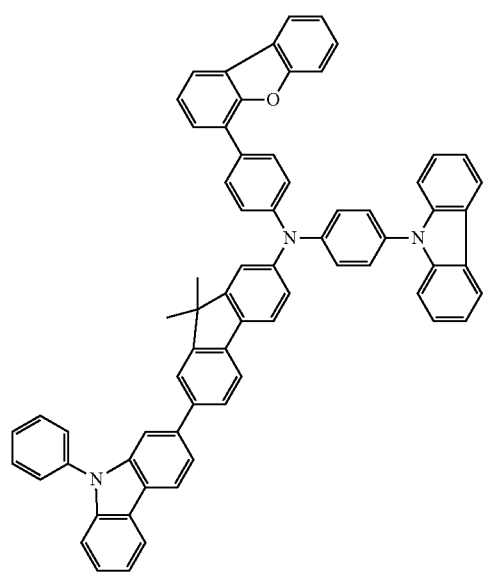 | 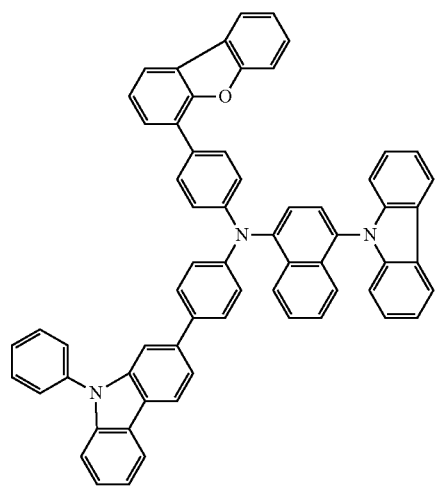 |
| 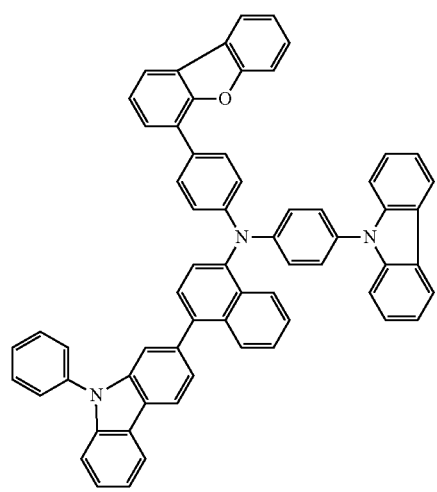 | 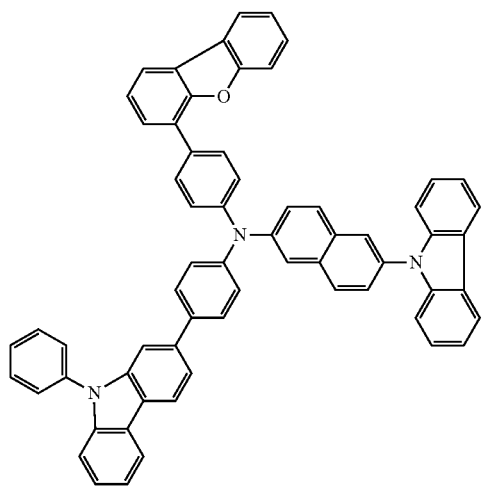 |
| 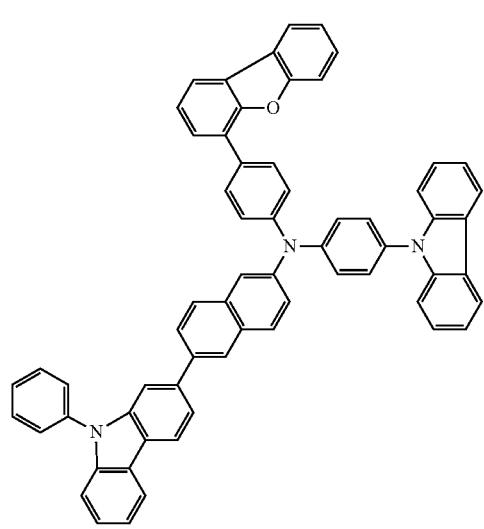 | 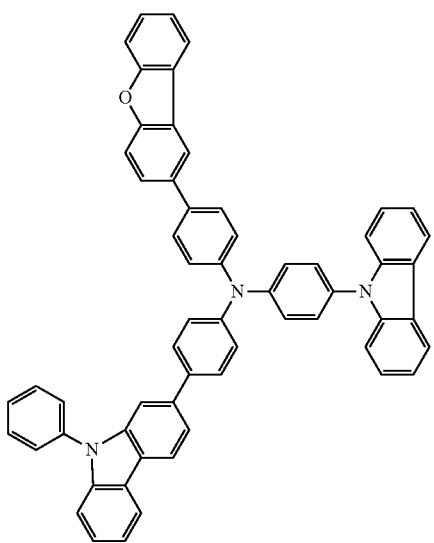 |

307
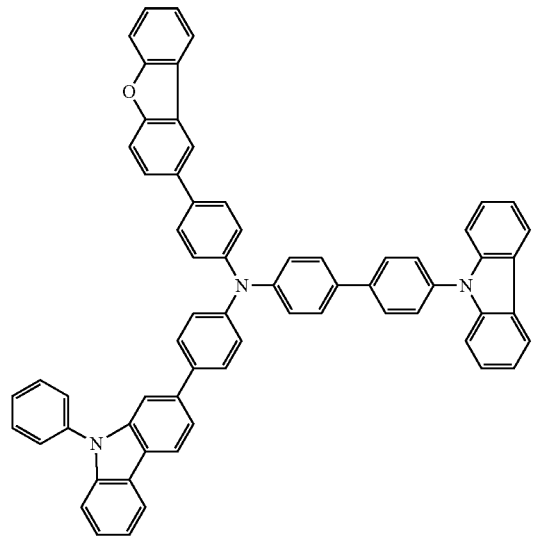
308
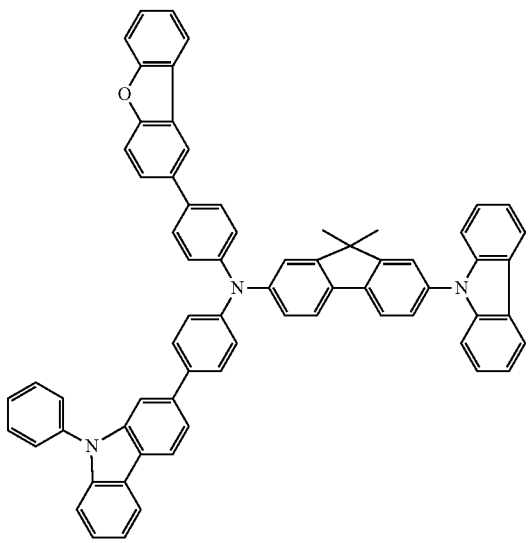
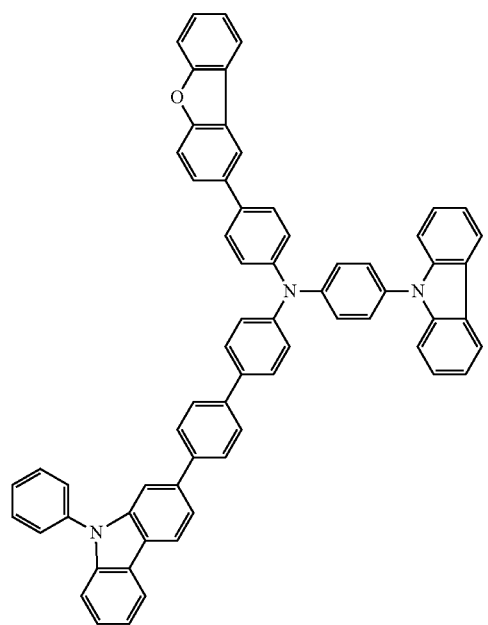
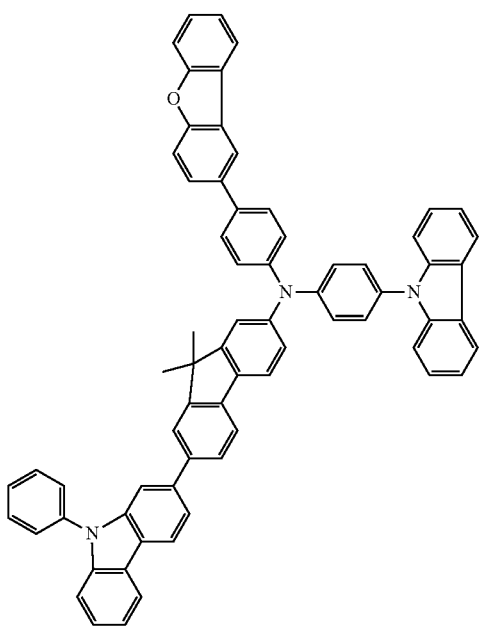

-continued
309
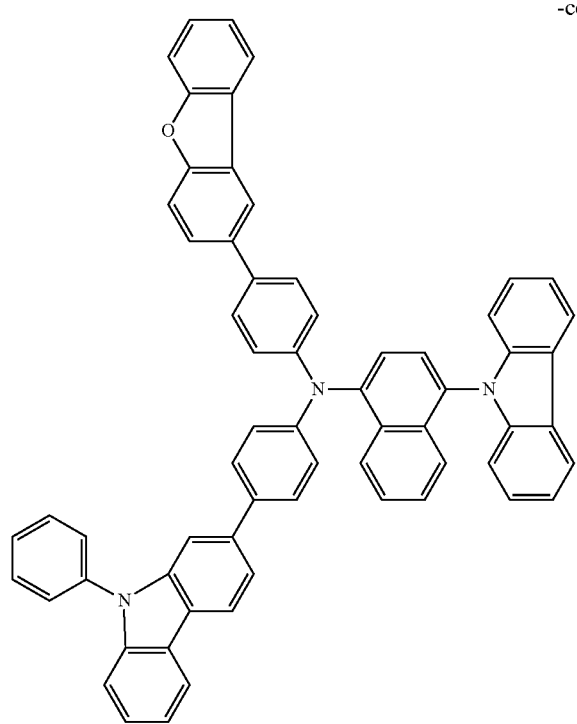
310
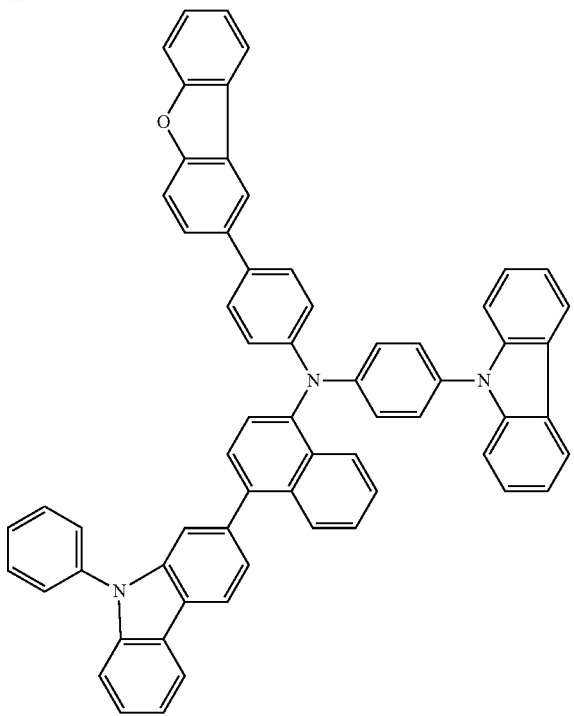
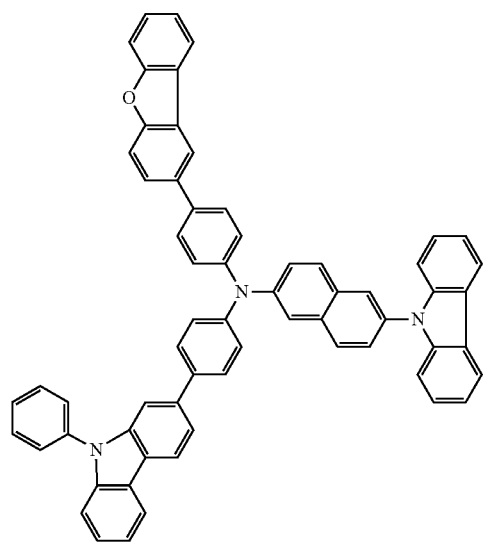
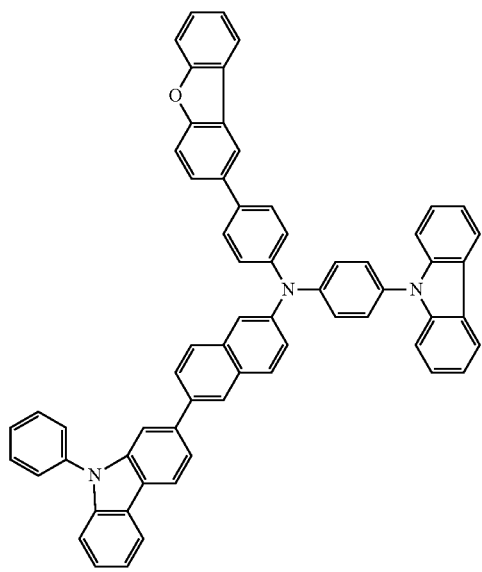

311
[Chem. 42]
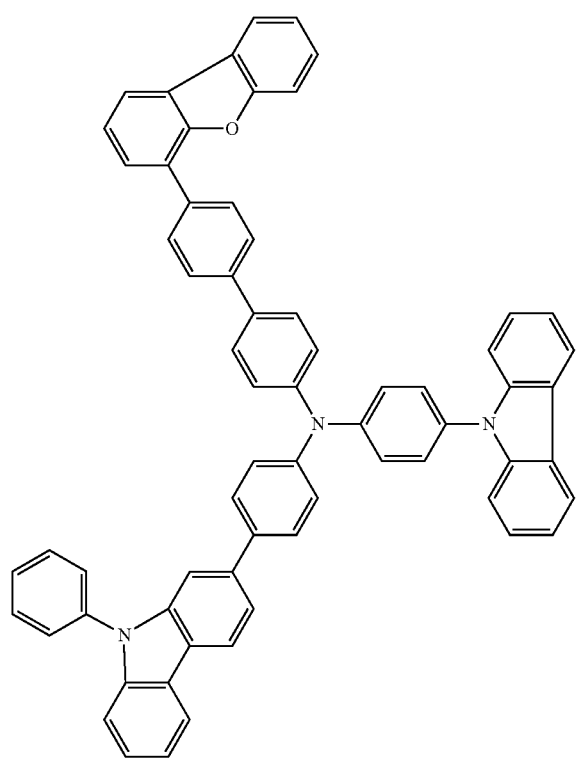
312
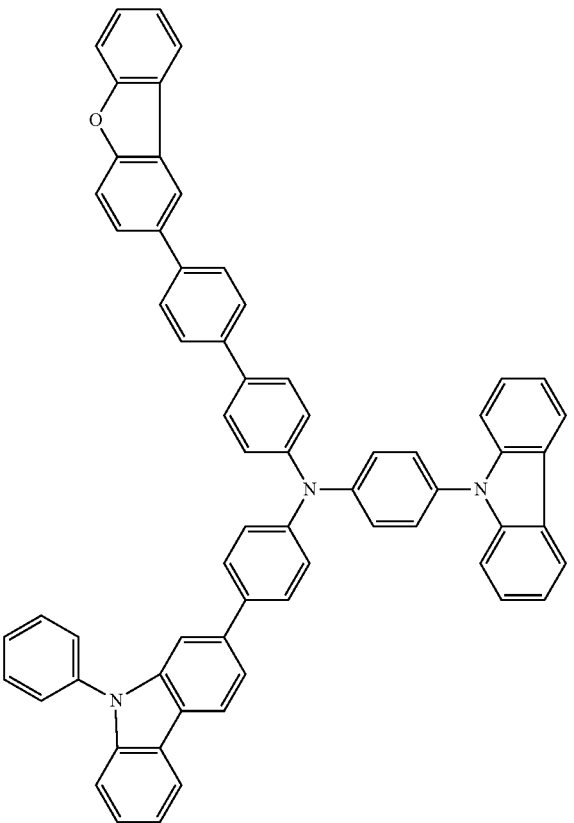
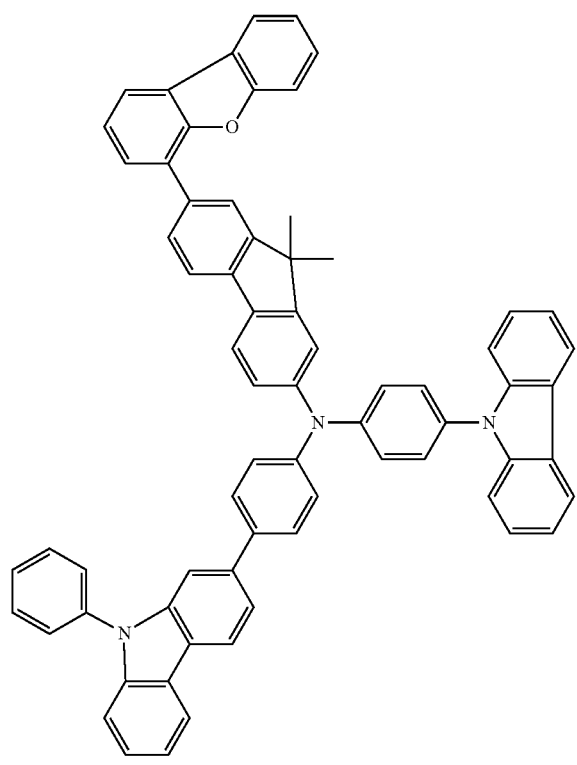
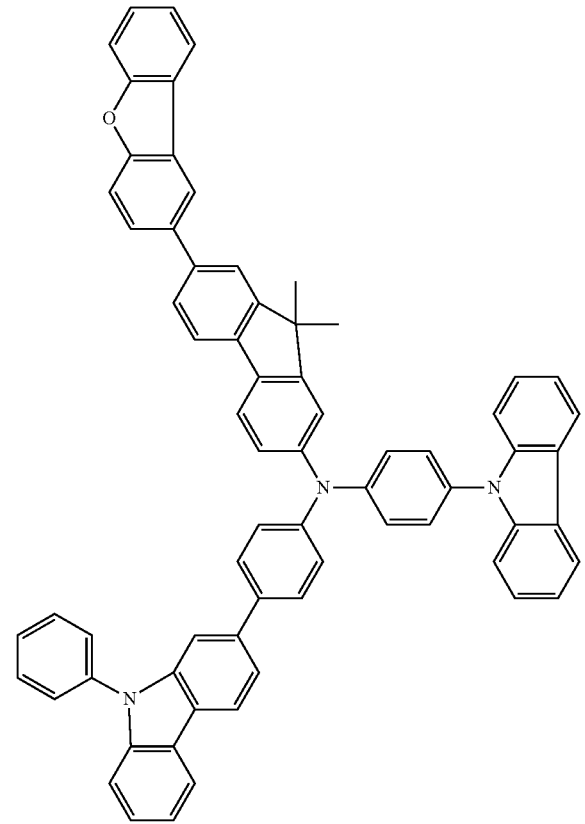

313 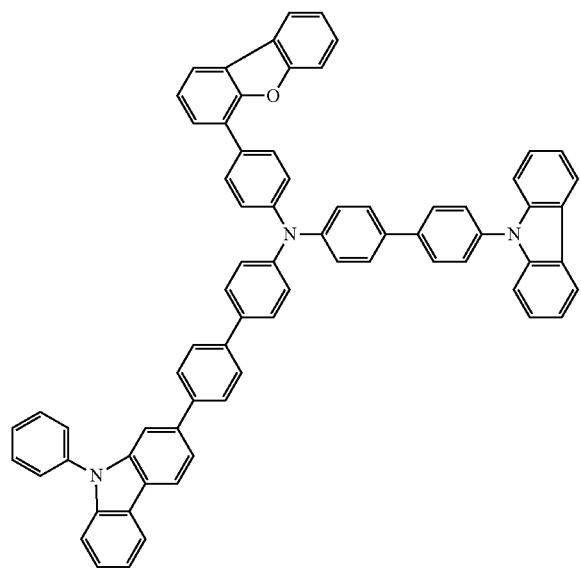
314 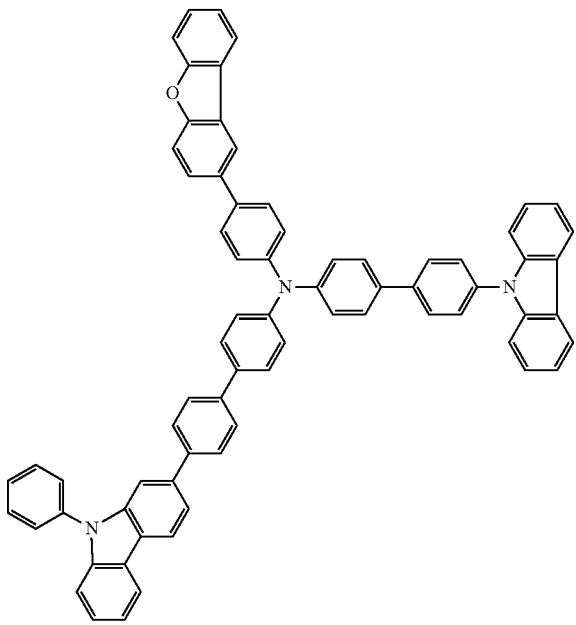
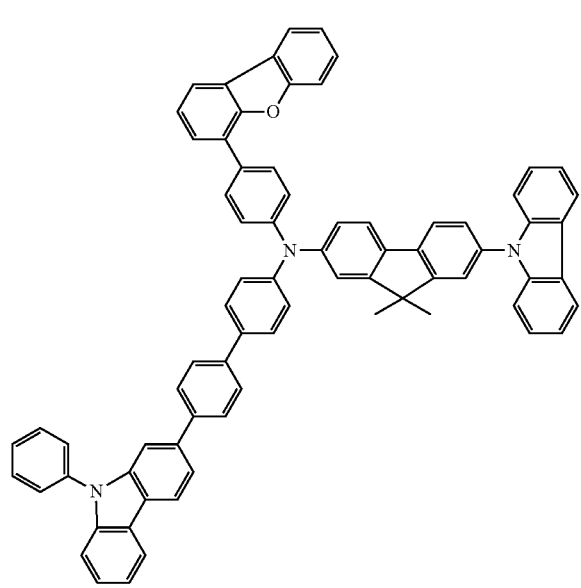
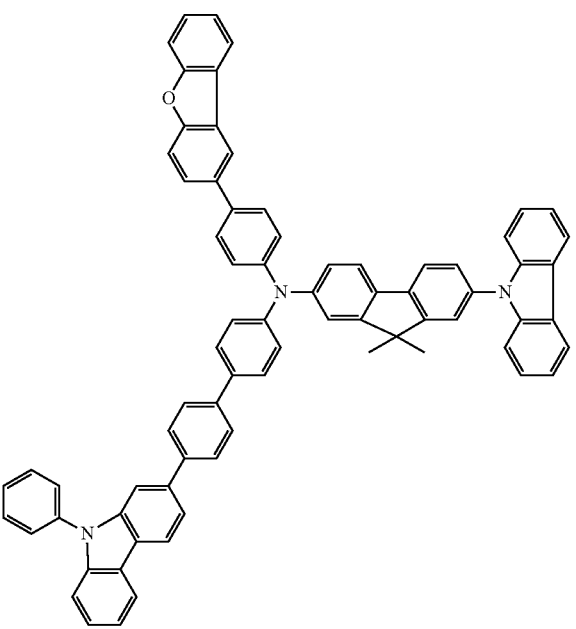

-continued
| 315 | 316 |
|---|---|
| 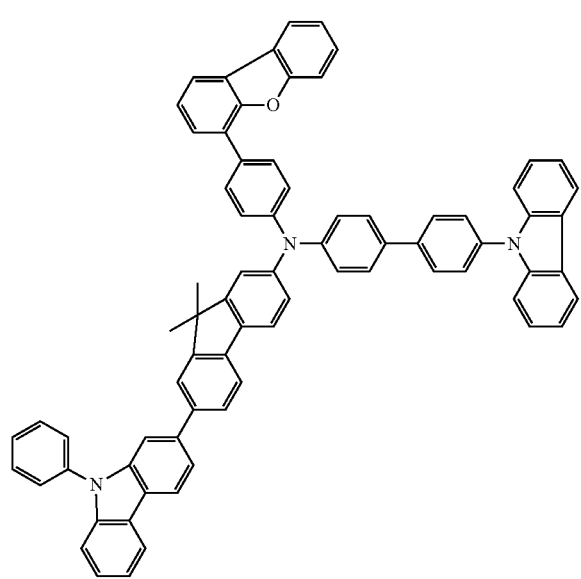 | 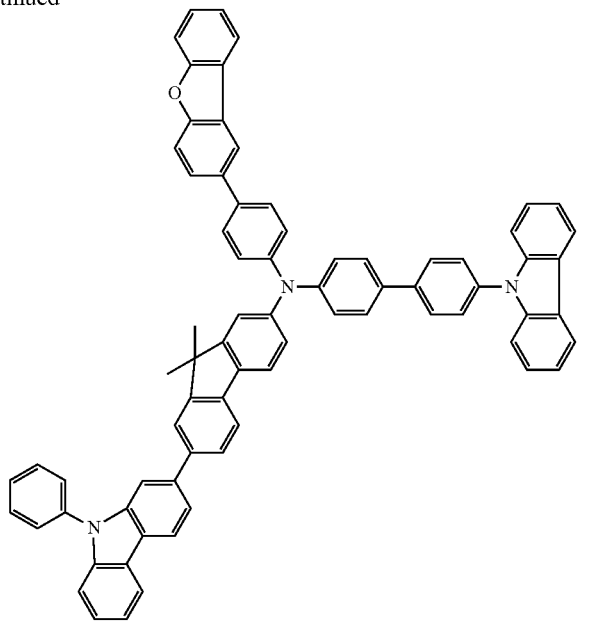 |
| 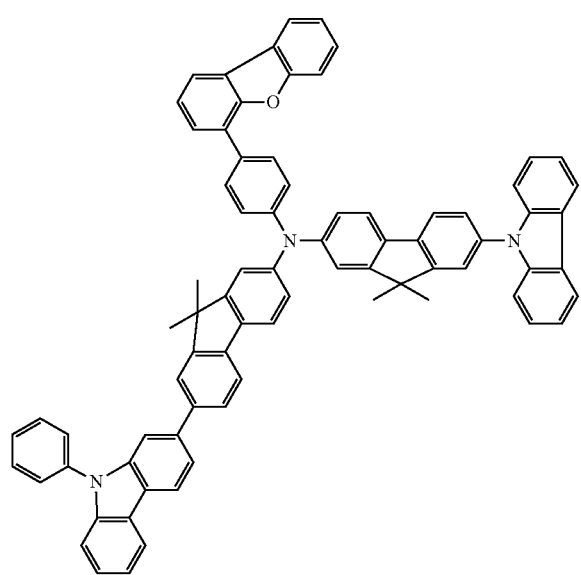 | 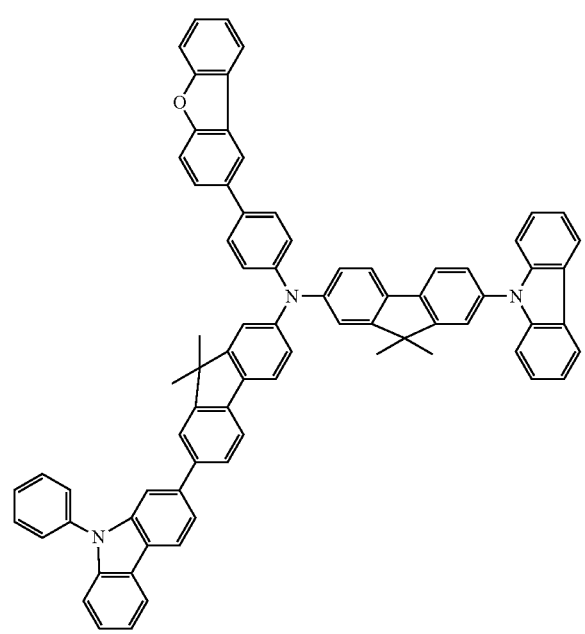 |
| 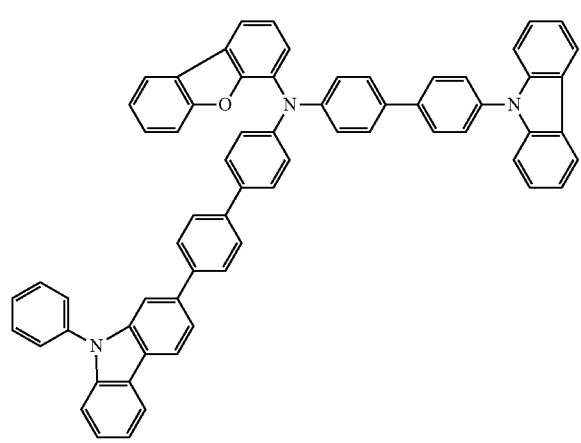 | 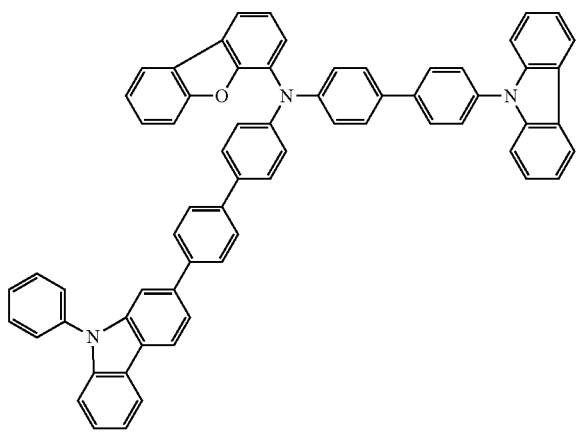 |

-continued
| 317 | 318 |
|---|---|
| 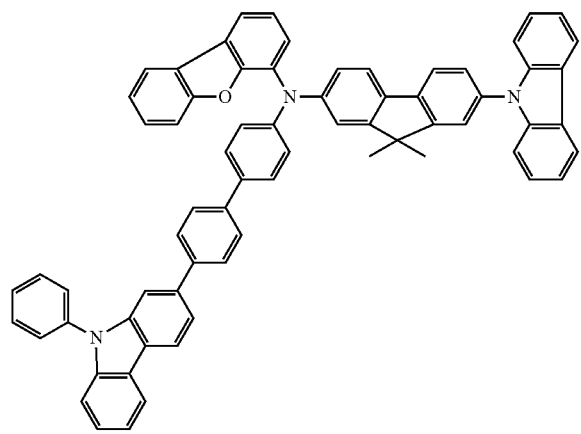 | 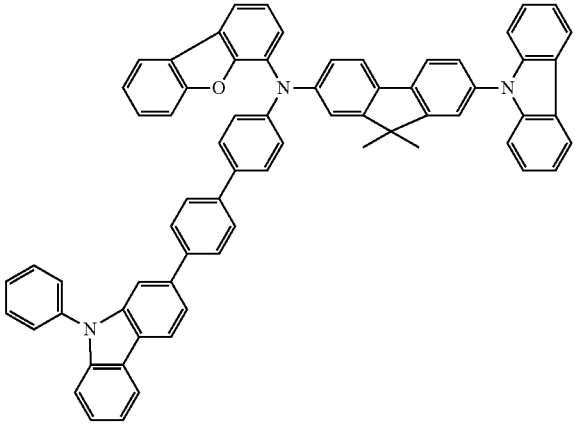 |
| 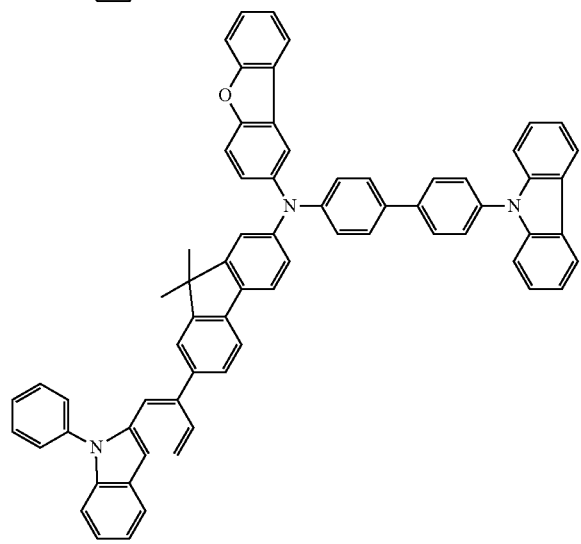 | 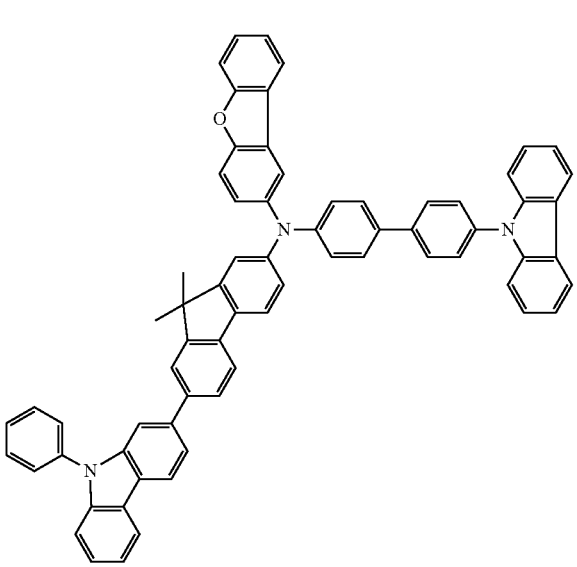 |
| 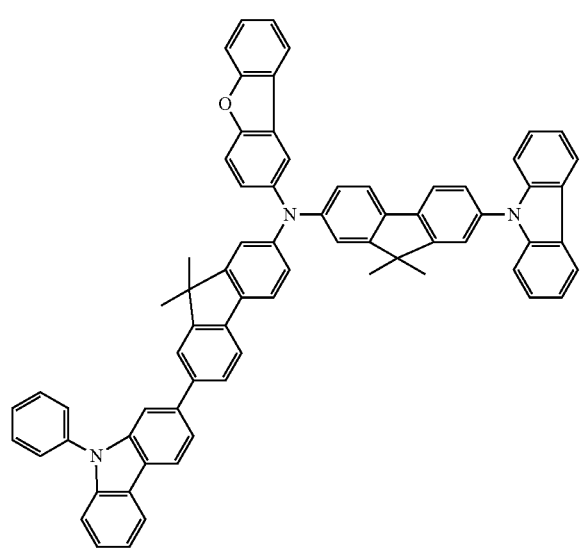 | 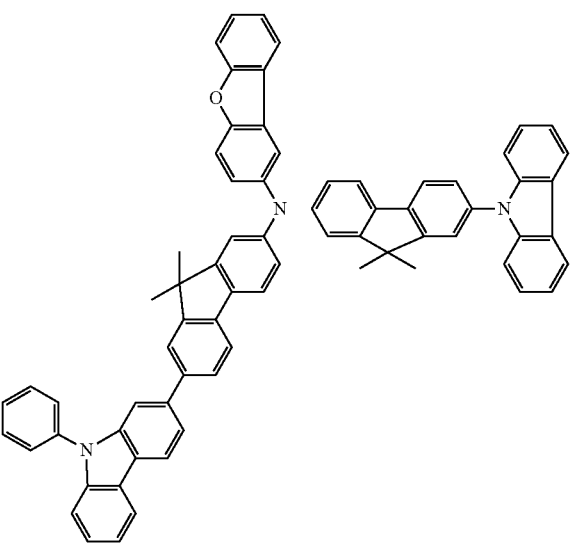 |

[Chem. 43]
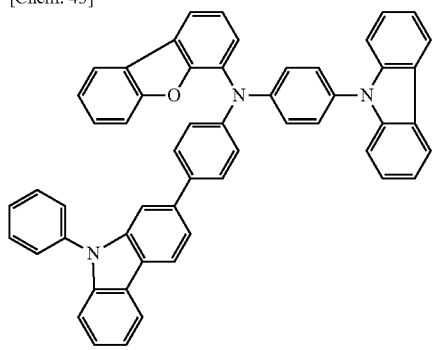
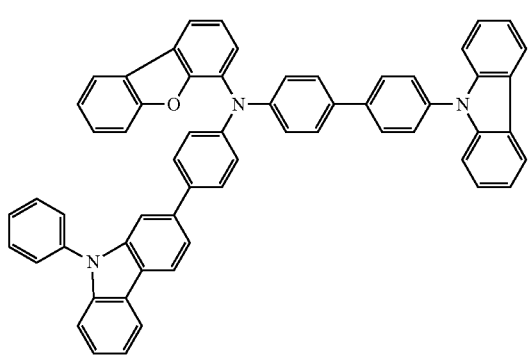
-continued
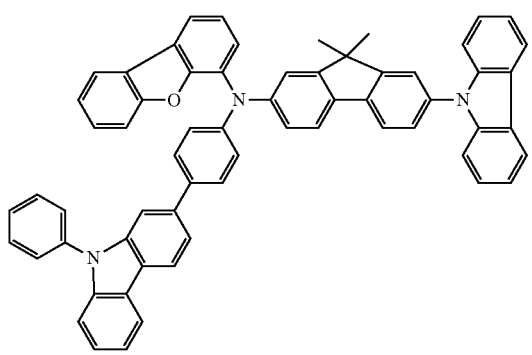
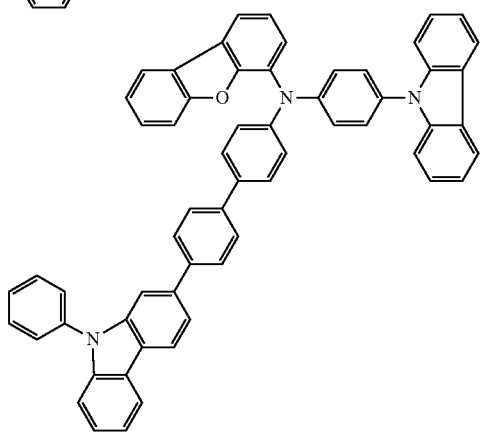
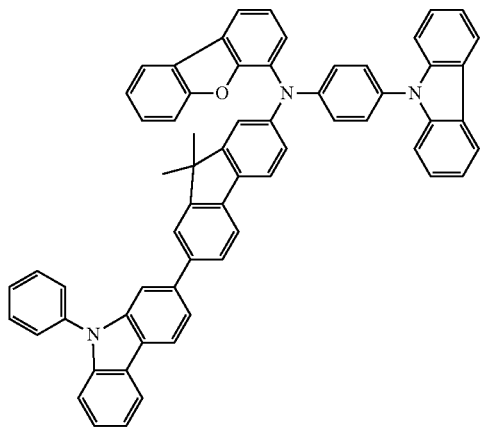
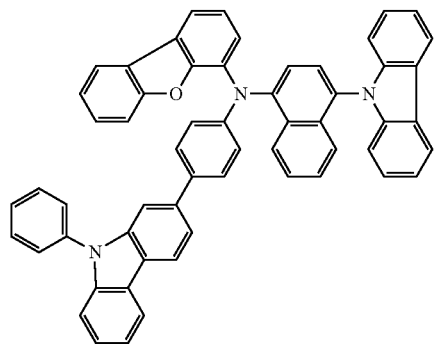
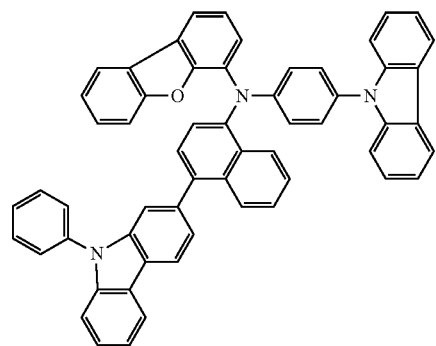
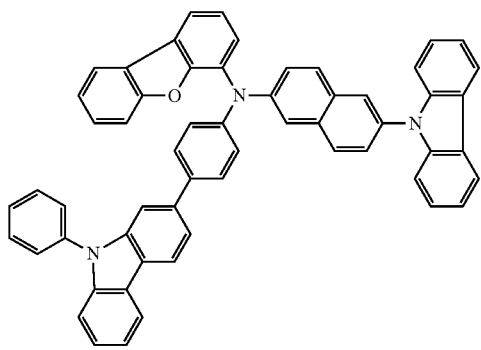

-continued
| 321 | 322 |
|---|---|
| 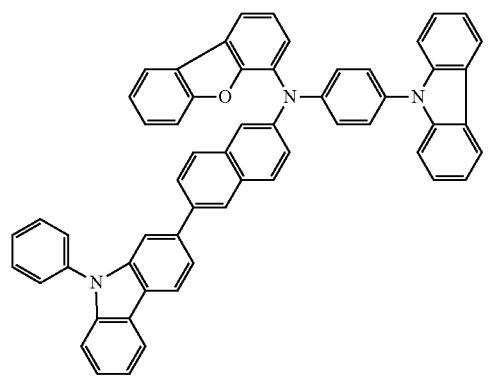 | 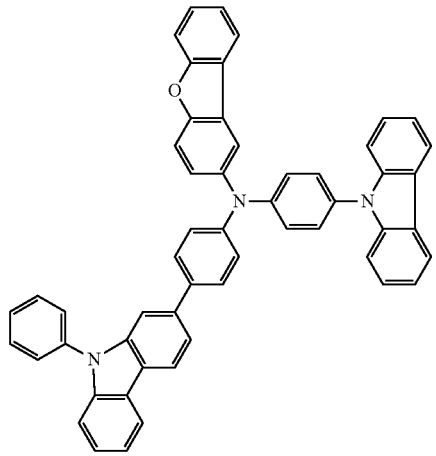 |
| 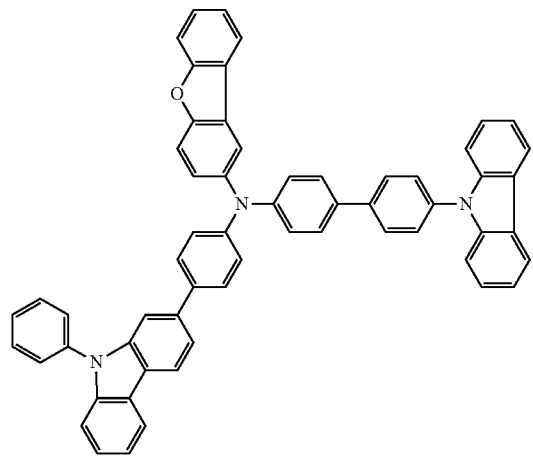 | 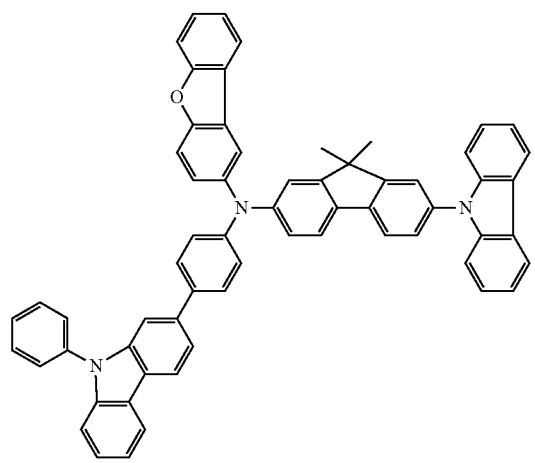 |
| 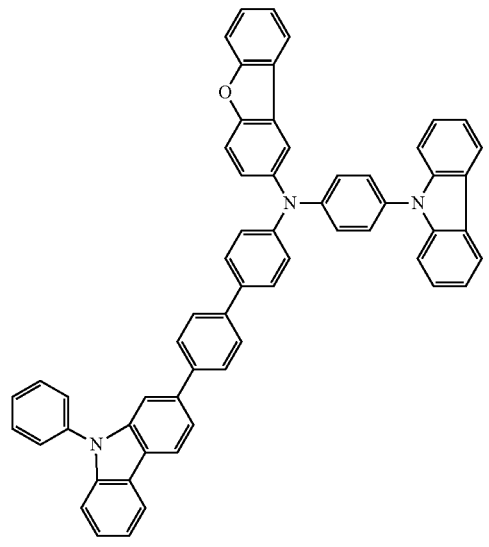 | 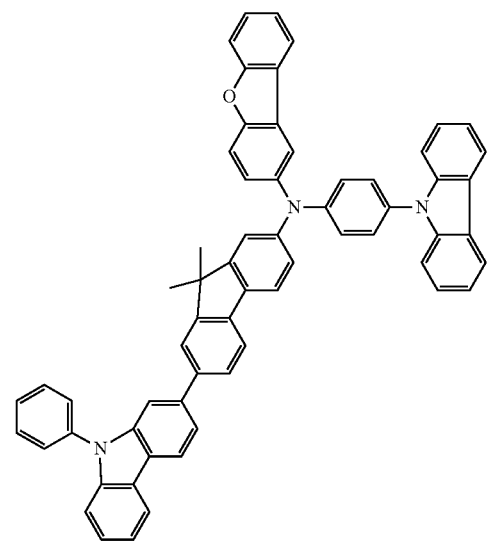 |

323 324
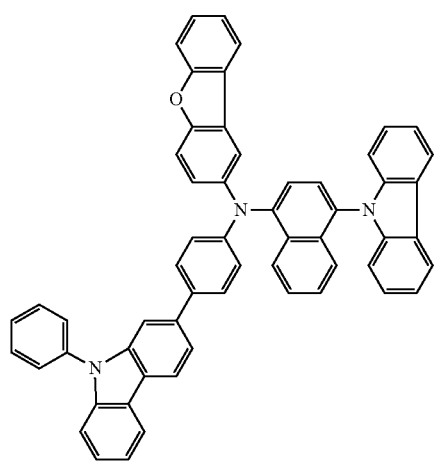 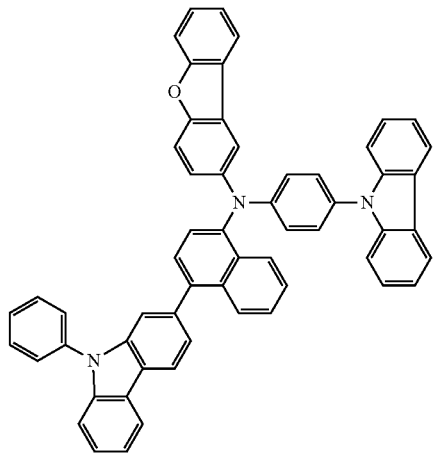
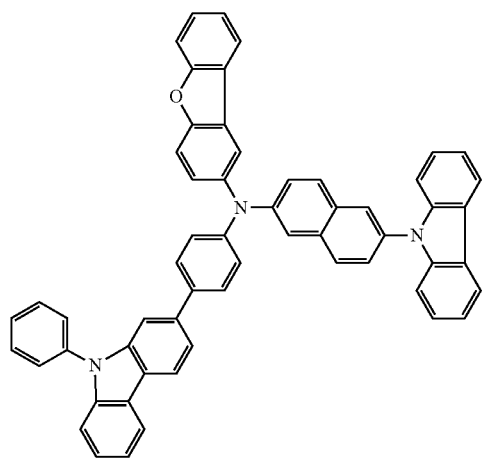 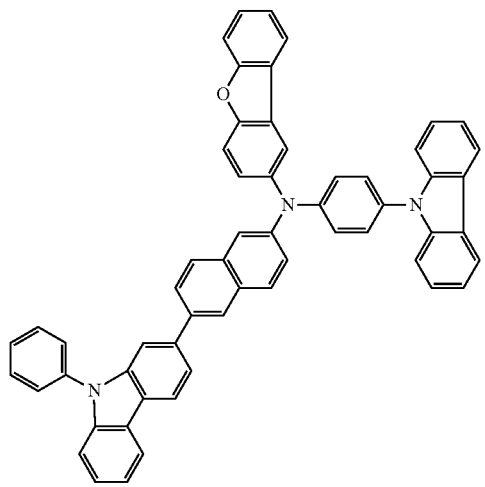
[Chem. 44]
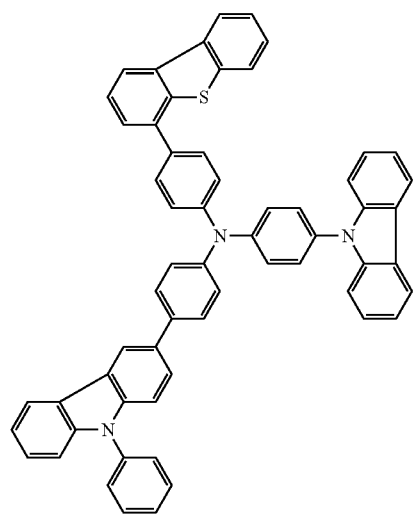 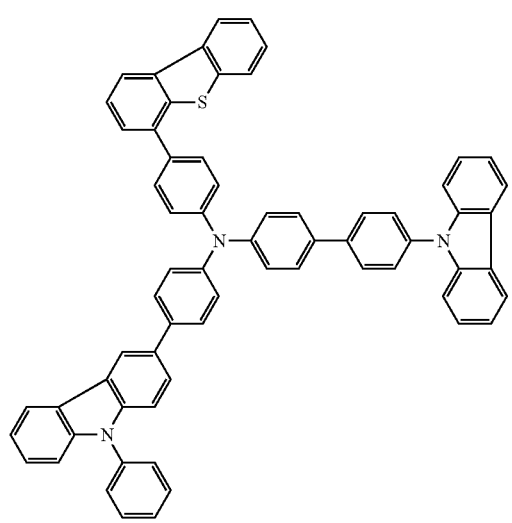

325
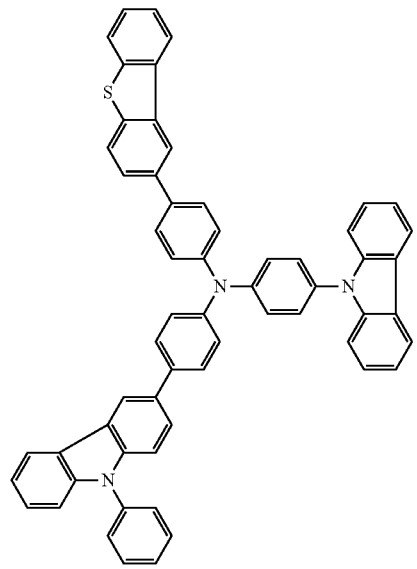
326
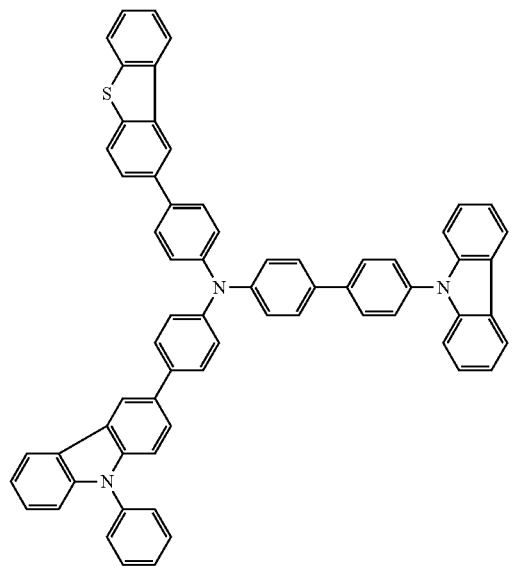
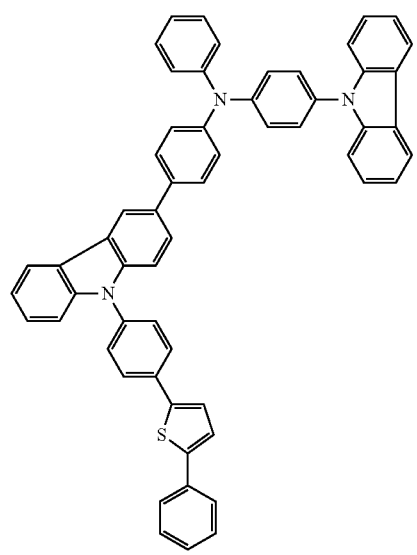
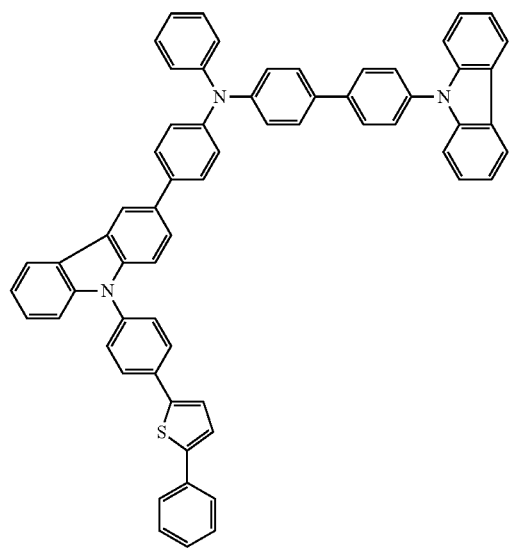

327
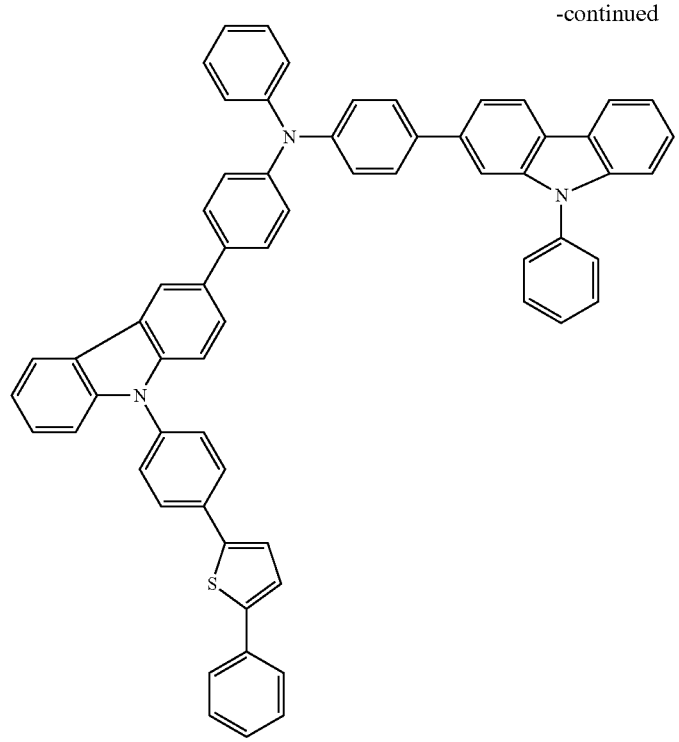
[Chem. 45]
328
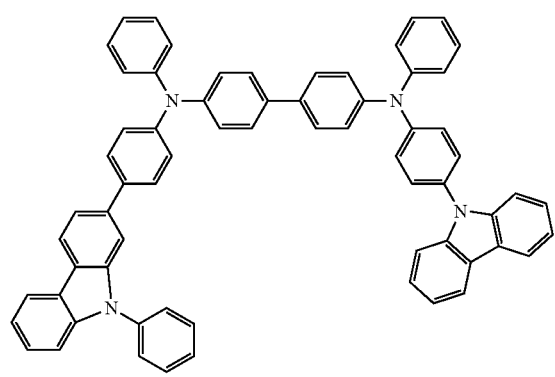
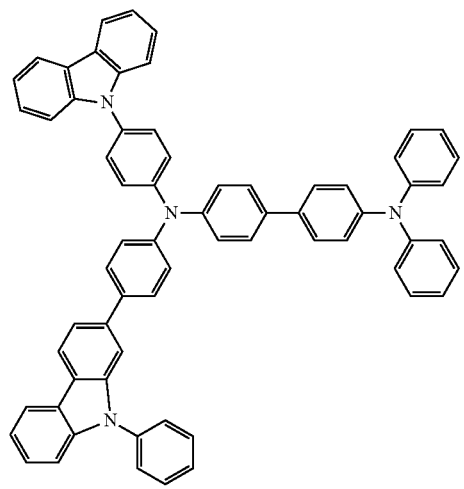

-continued
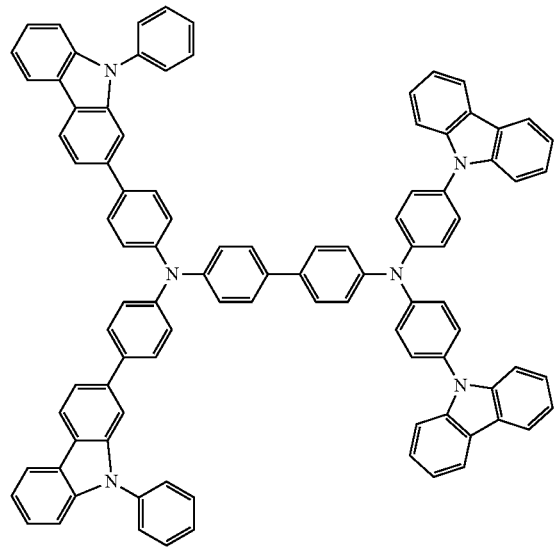
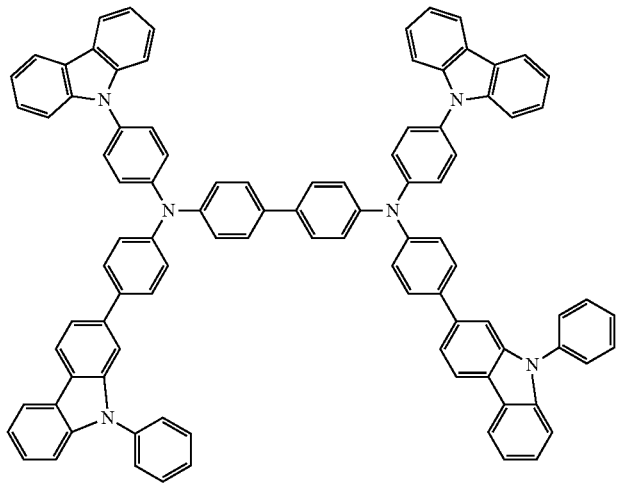
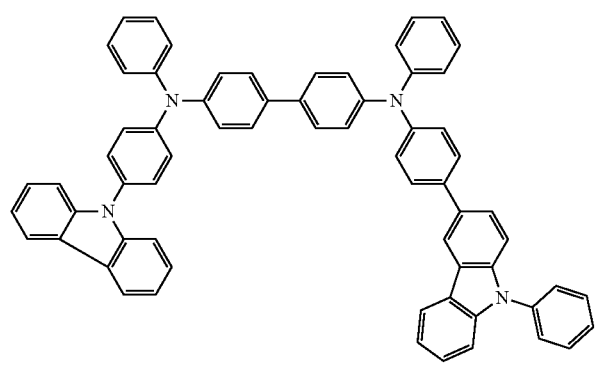
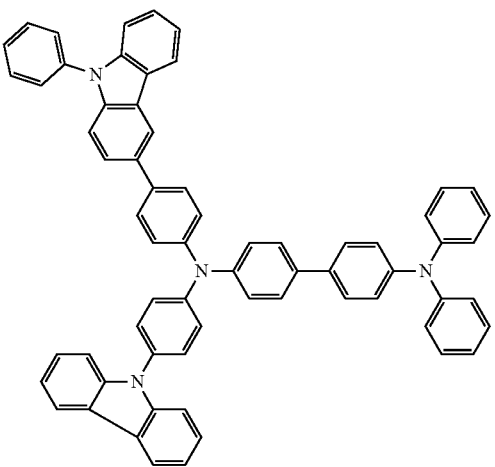
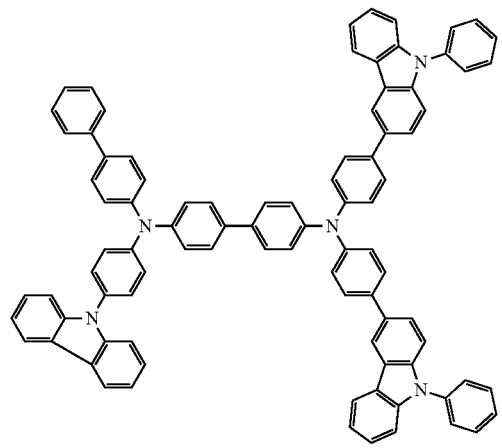
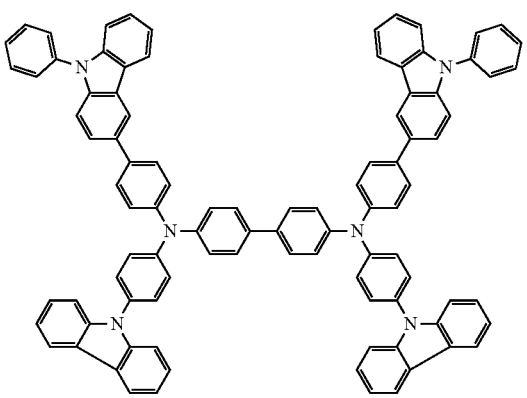

331
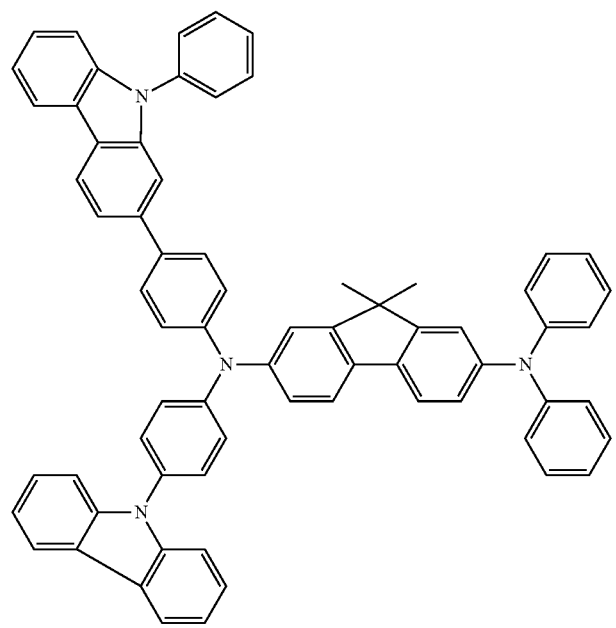
332
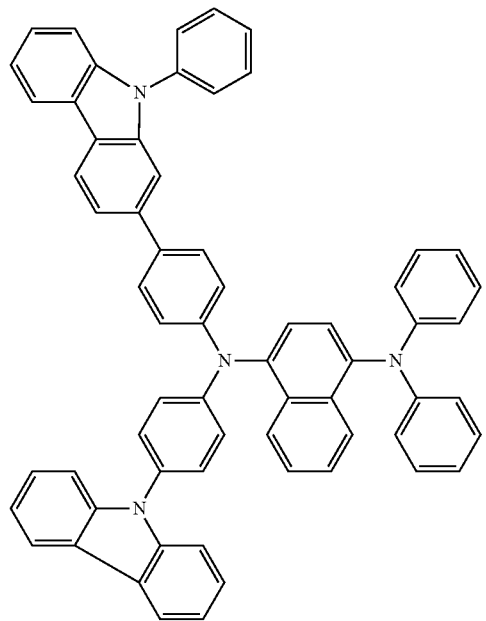
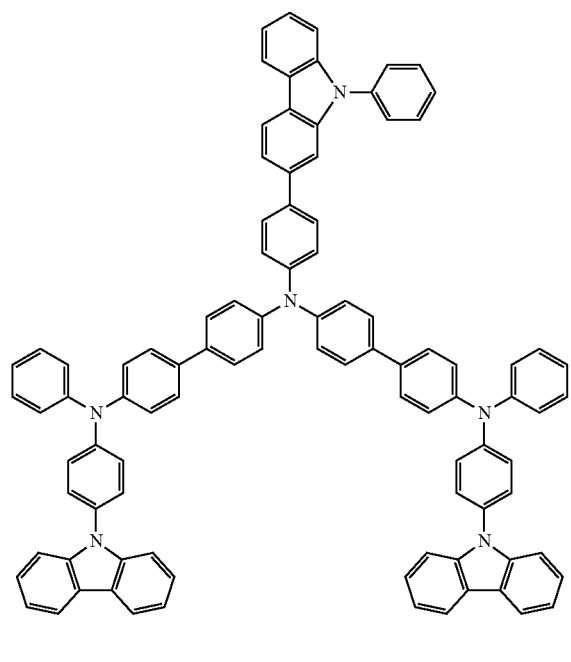
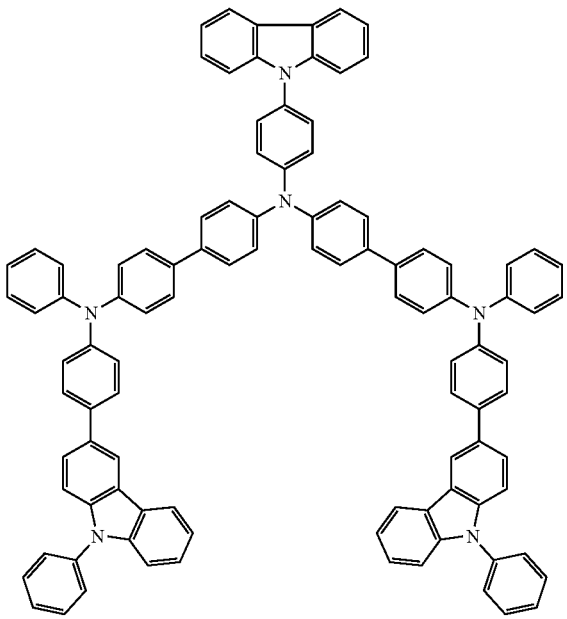

-continued
333
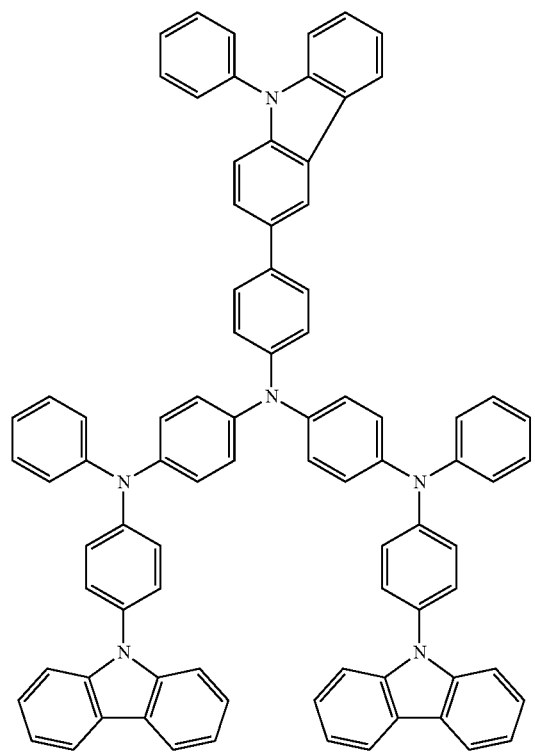
334
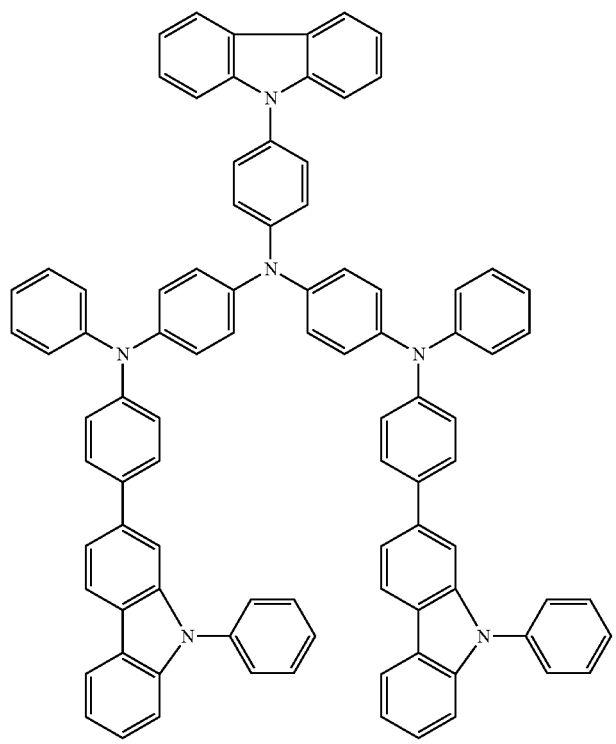
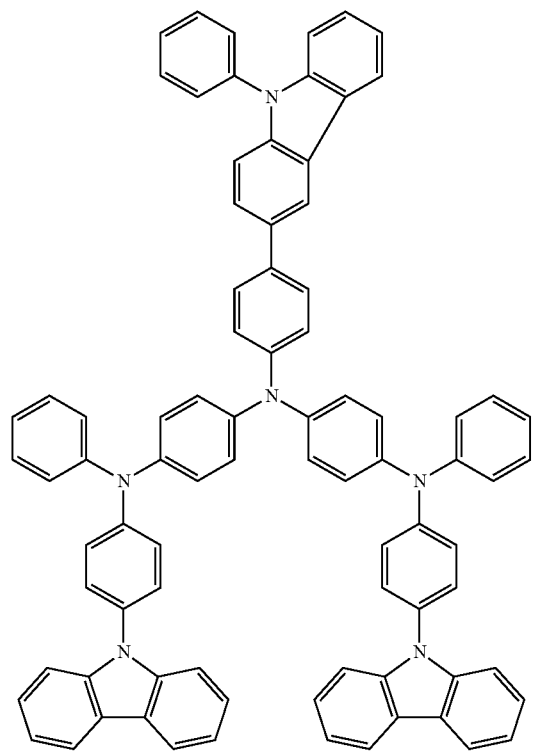
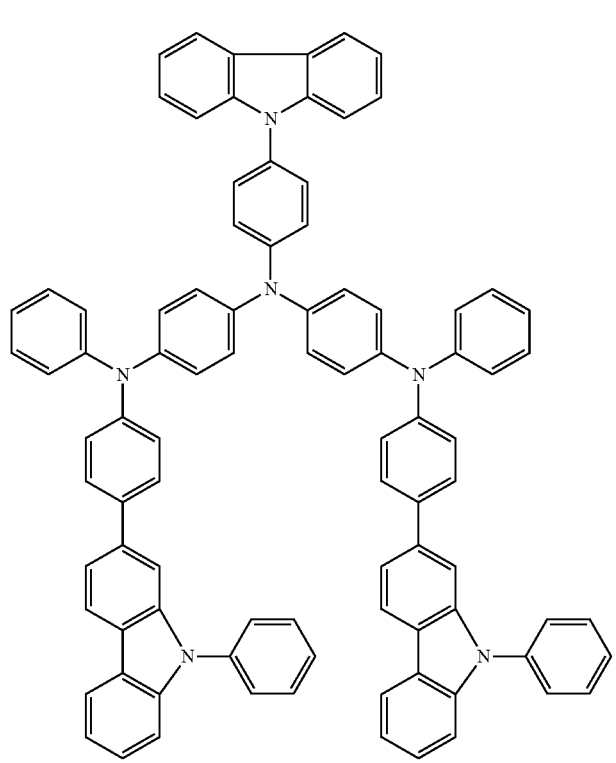

335
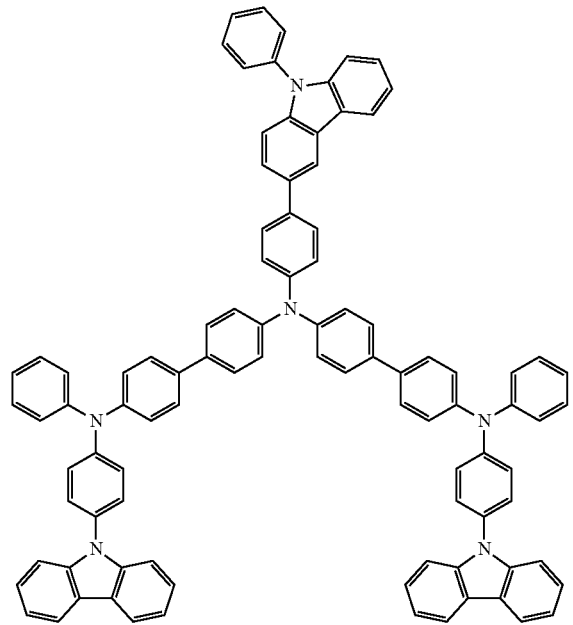
336
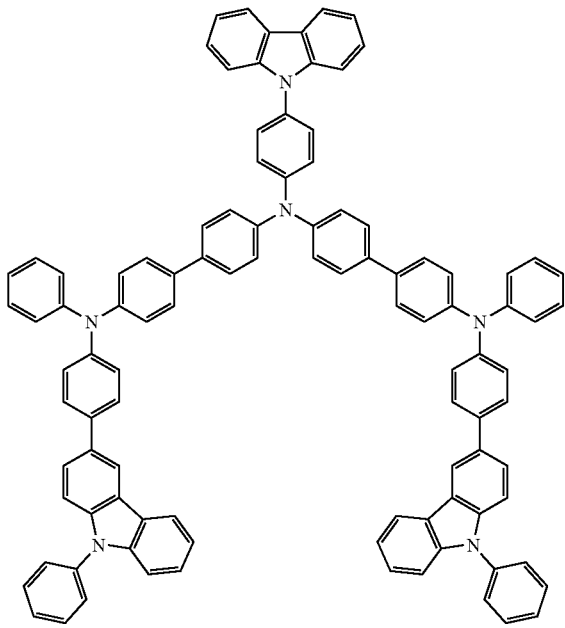
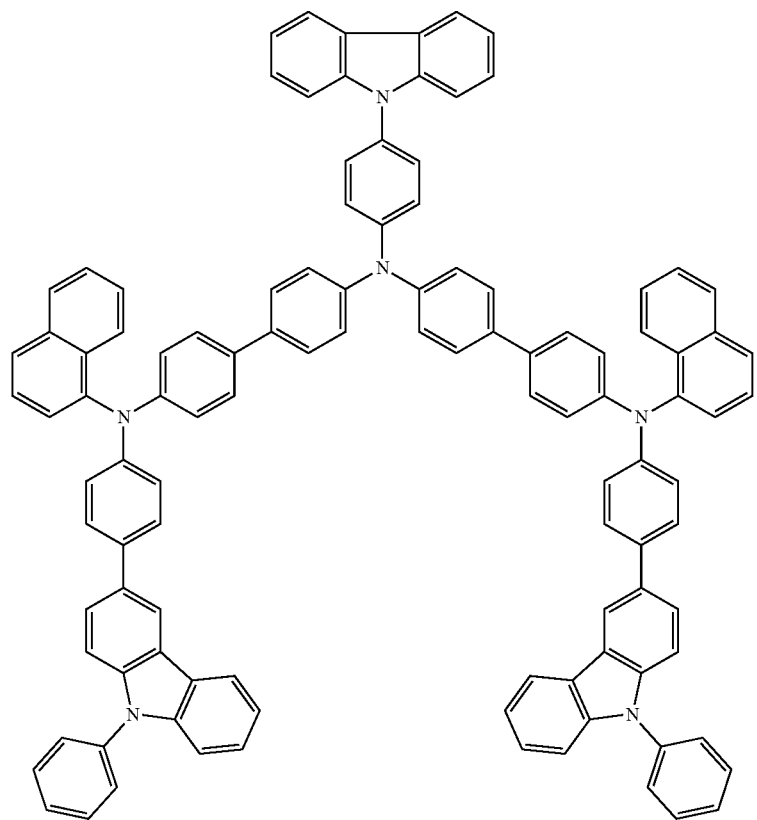

337
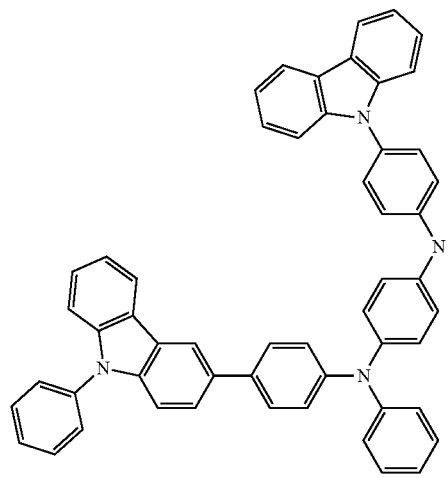
338
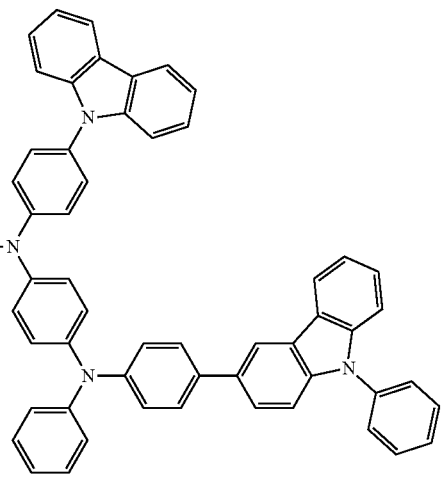
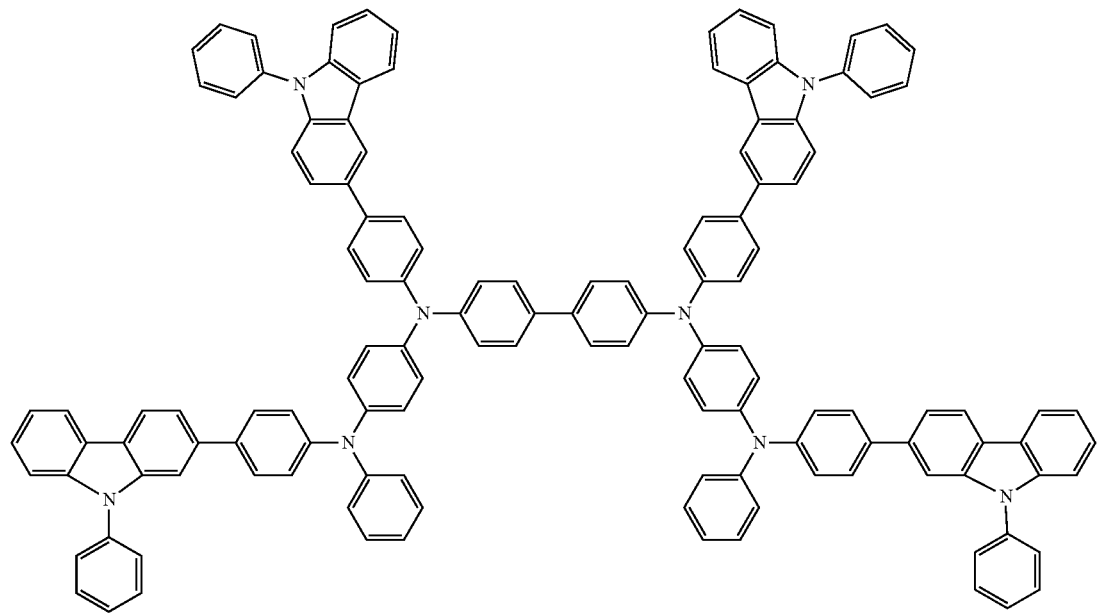

339
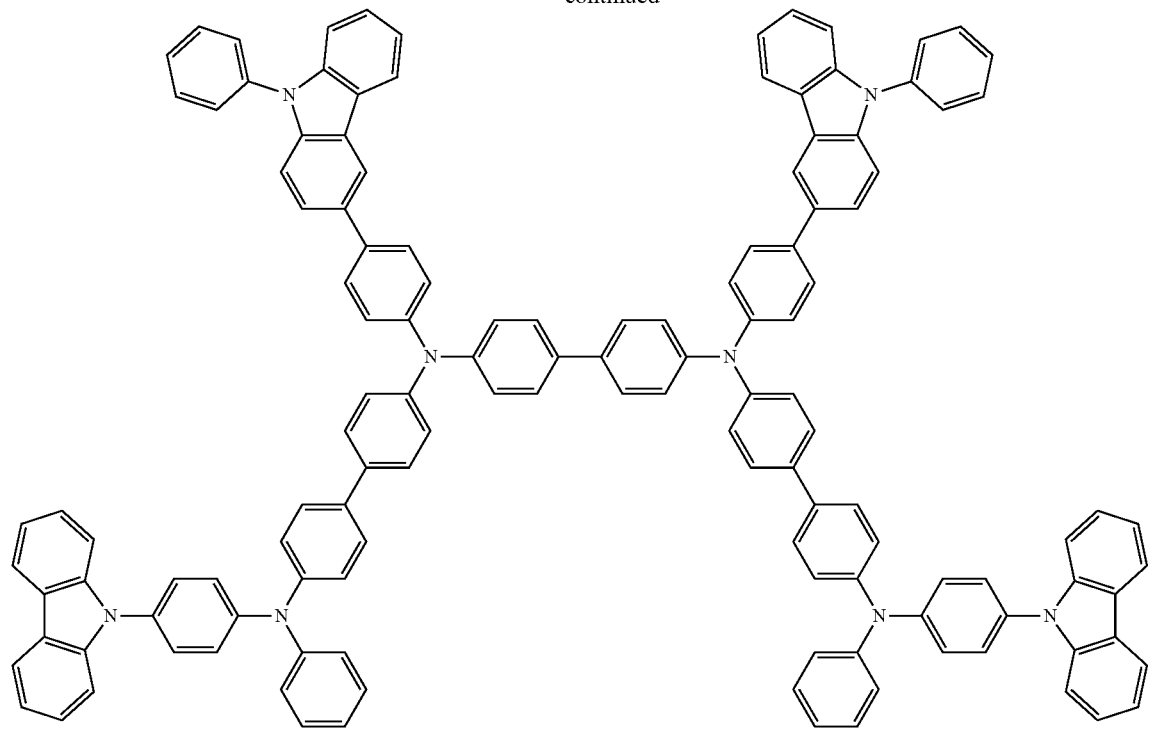
340
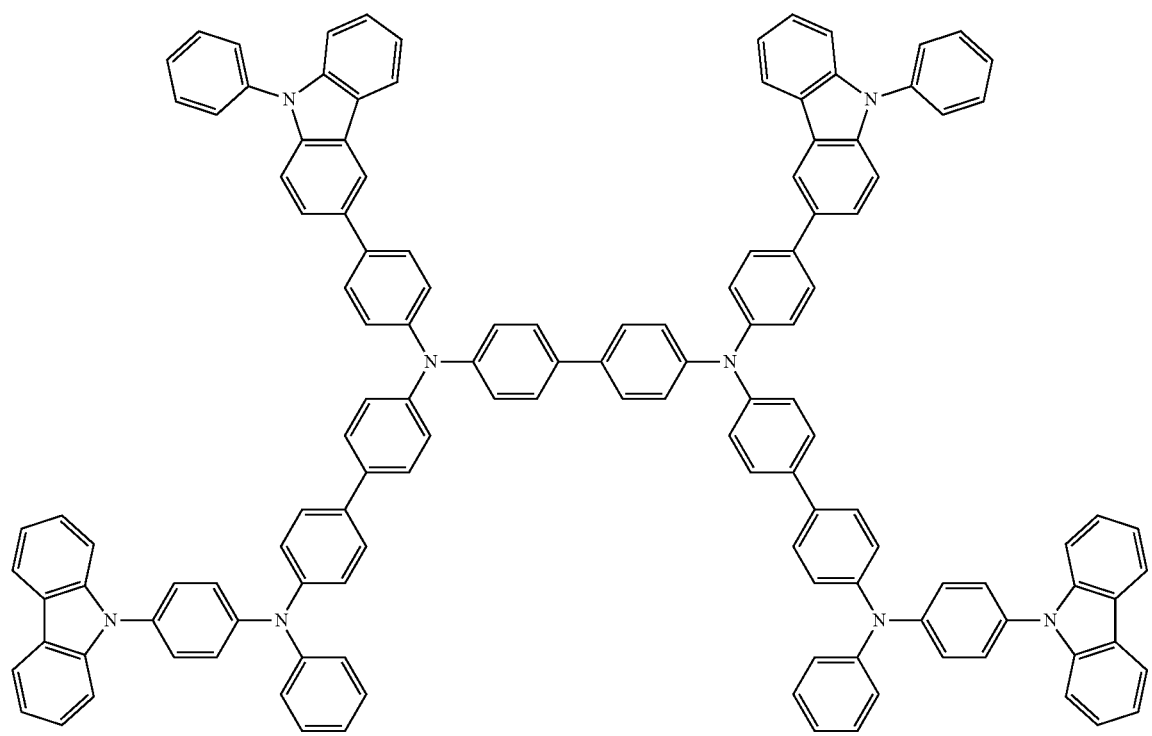

| 341 | 342 |
|---|---|
-continued
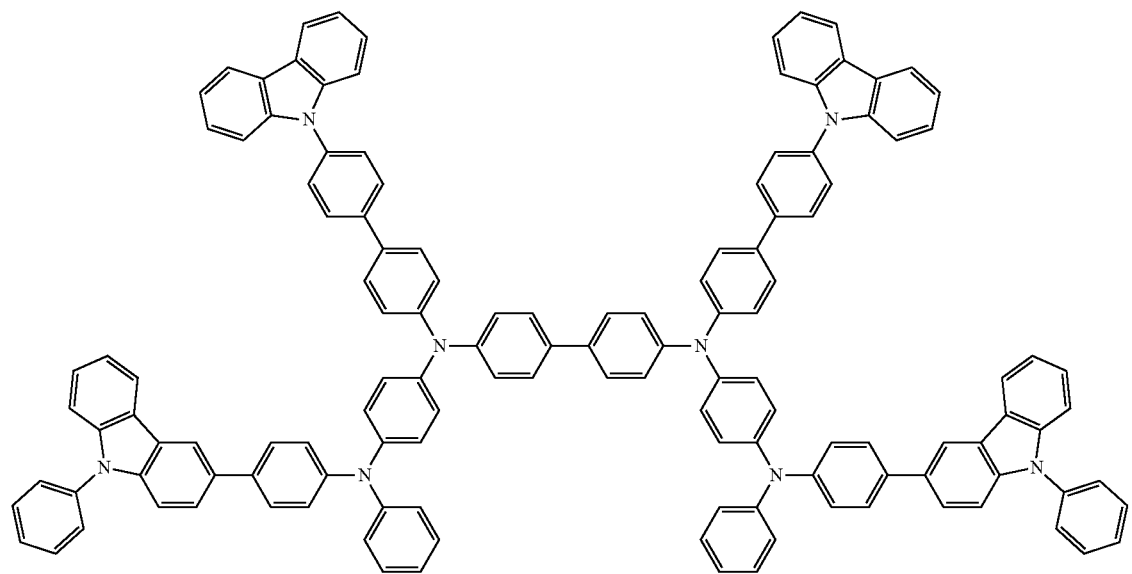
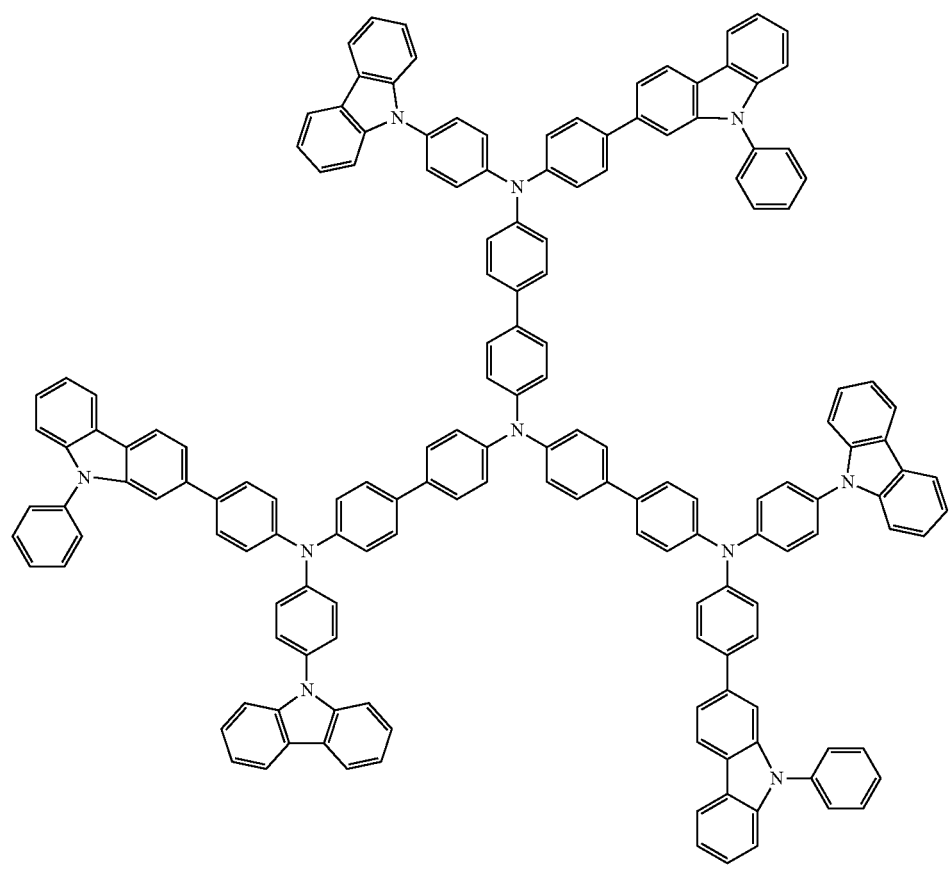

-continued
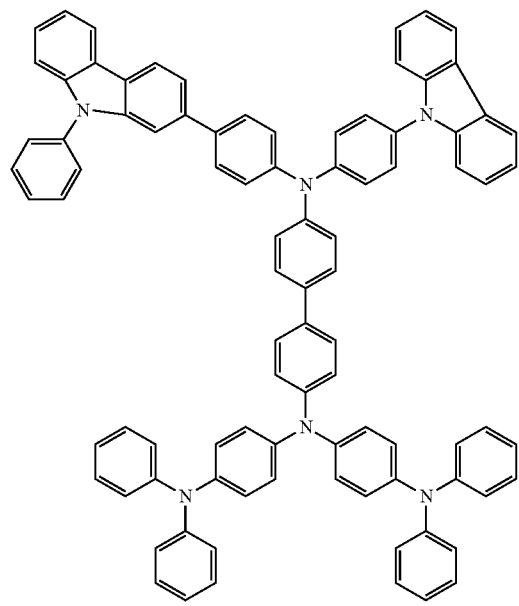
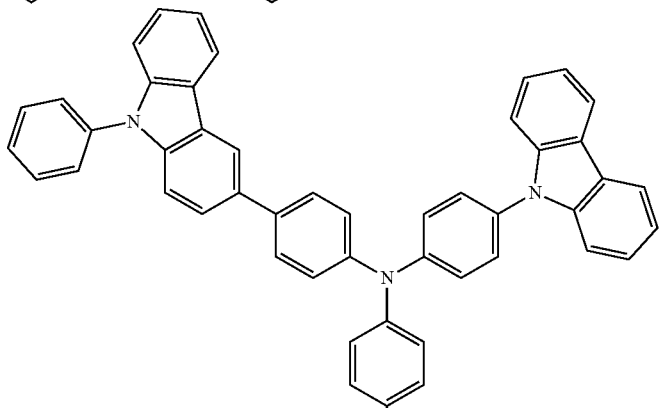
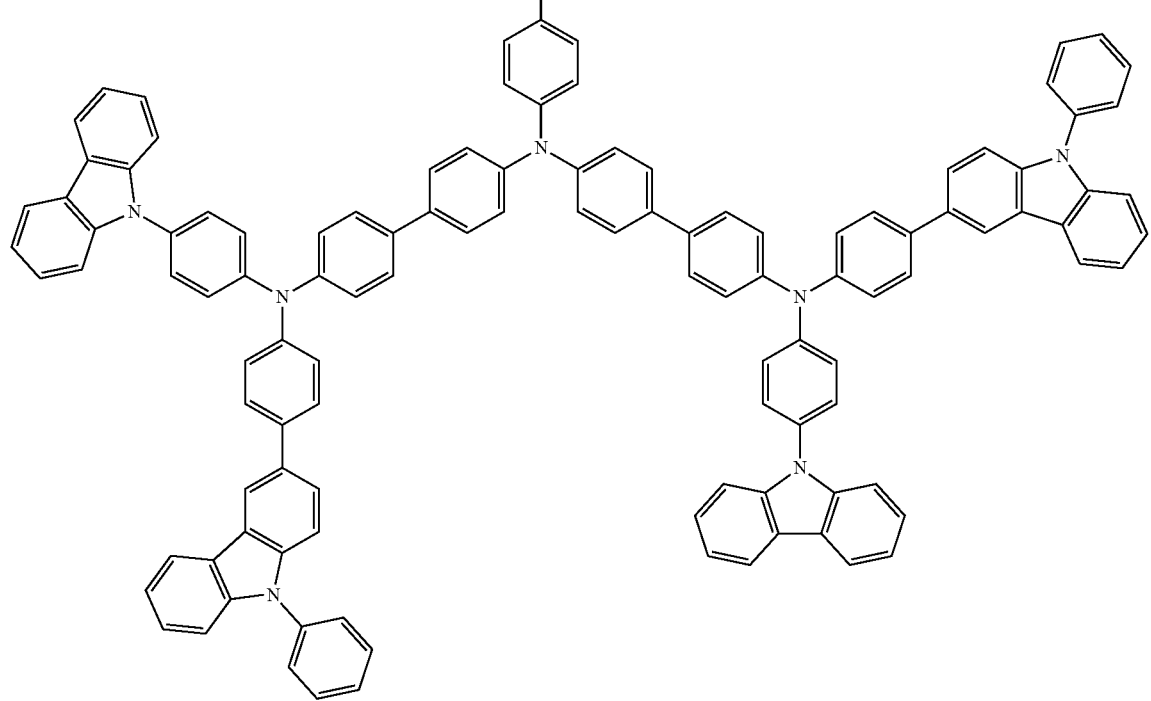

-continued

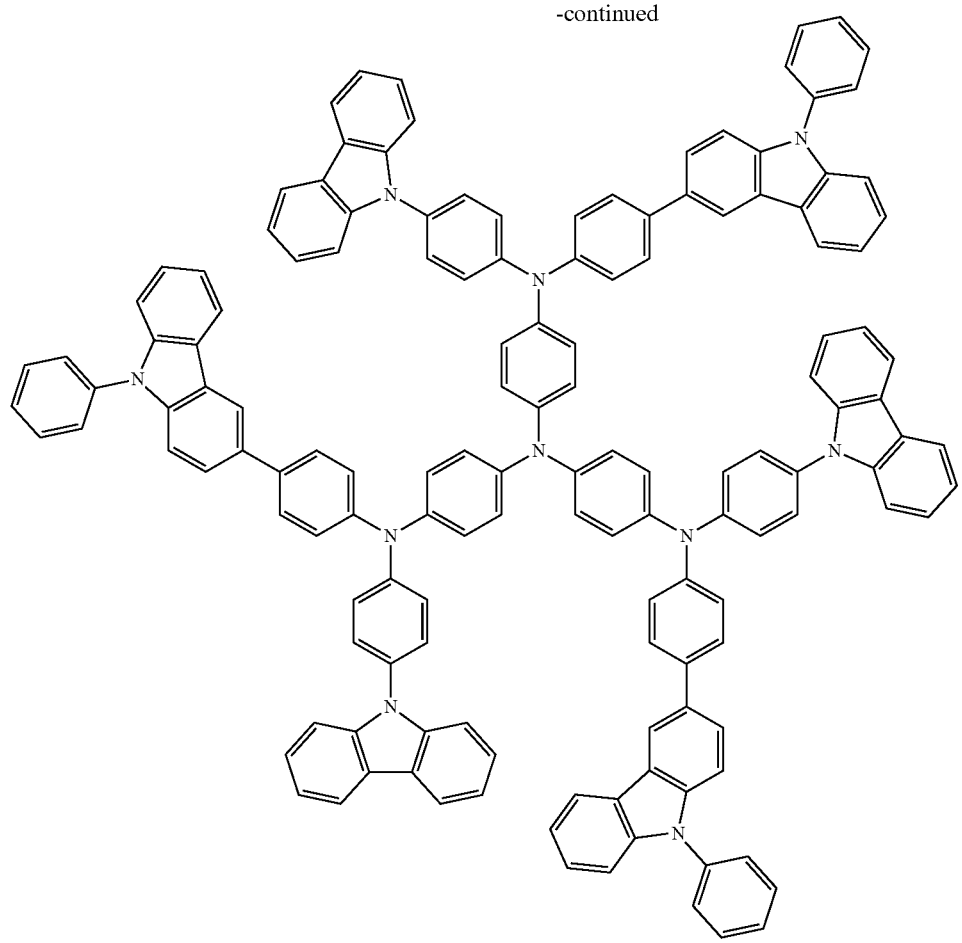

The aromatic amine derivative of the present invention hardly crystallizes, and is preferably used as a material for an organic EL device, in particular, as a hole transporting material for an organic EL device. An organic EL device using the aromatic amine derivative of the present invention has low driving voltage and a long lifetime.

Next, a method of producing the aromatic amine derivative of the present invention is described.

The method of producing the aromatic amine derivative of the present invention is not particularly limited, and is, for example, as described below.

(Production Method)

First, a method of producing the amine derivative represented by the formula (9) having the substituent A represented by the formula (1) and the substituent B represented by the formula (2) is described.

First, compounds that produce a substituent A represented by the formula (1) [such as 3-(N-phenyl) carbazolylboronic acid and 4-iodobromobenzene] are caused to react with each other in the presence of a catalyst [such as tetrakis(triphenylphosphine)palladium (0)] in a solvent [such as toluene] and an aqueous solution of an alkaline compound [such as sodium carbonate] at 50 to 150° C. Thus, a halide is obtained. The reactions are preferably performed under an atmosphere of an inert gas such as argon.

Next, halides that produce a substituent B represented by the formula (2) [such as carbazole and 4-iodobromobenzene] are caused to react with each other in the presence of catalysts [such as copper iodide (CuI) and an amine such as trans-1,2-cyclohexanediamine] in a solvent [such as 1,4-dioxane] and an alkaline compound [such as tripotassium phosphate] at 50 to 150° C. Thus, a halide is obtained. The reaction is preferably performed under an atmosphere of an inert gas such as argon.

A halide for producing the substituent A represented by the formula (1) and a compound for producing an amino group [such as acetamide] are caused to react with each other at a proper ratio [of, for example, 1:0.8 to 1.2] in the presence of catalysts [a metal halide such as copper iodide and an amine such as N,N'-dimethylethylenediamine] and an alkaline substance [such as potassium carbonate] in a solvent [such as xylene] at 50 to 250° C. After that, a halide for producing the substituent B represented by the formula (2) is further caused to react with the resultant at a proper ratio [of, for example, 1:0.8 to 1.2]. After that, the resultant is subjected to a reaction in the presence of an alkaline substance [such as potassium hydroxide] and water in a solvent [such as xylene] at 50 to 250° C. Thus, an intermediate X is synthesized. The reactions are each preferably performed under an atmosphere of an inert gas such as argon.

A halogenated aryl [such as 4-bromo-p-terphenyl] is separately provided as an intermediate Y.

Next, the intermediate X and the intermediate Y are caused to react with each other in the presence of catalysts [such as t-butoxy sodium and tris(dibenzylideneacetone)

dipalladium (0)] in a solvent [such as dry toluene] at 0 to 150° C. Thus, the aromatic amine derivative of the present invention can be synthesized. The reaction is preferably performed under an atmosphere of an inert gas such as argon.

After the completion of the reaction, the reaction product is cooled to room temperature, and then water is added to filtrate the product. The filtrate is extracted with a solvent such as toluene, and is then dried with a drying agent such as anhydrous magnesium sulfate. The dried product is desolvated under reduced pressure so as to be concentrated. The resultant coarse product is subjected to column purification, and is then recrystallized with a solvent such as toluene. The crystal is separated by filtration, and is then dried. Thus, the aromatic amine derivative of the present invention that has been purified is obtained.

In order that a plurality of formulae (1) may be introduced into the aromatic amine derivative represented by the formula (9), upon synthesis of the intermediate X, halides that produce a structure represented by the formula (1) as a halide has only to be caused to react with each other sequentially in accordance with the quantity to be introduced. Next, the intermediate X (amine body including a plurality of formulae (1)) and the intermediate Y (halide of the formula (2)) are caused to react with each other in the same manner as in the foregoing. Thus, the aromatic amine derivative of the present invention into which a plurality of formulae (1) and (2) have been introduced can be synthesized. The reactions are preferably performed under an atmosphere of an inert gas such as argon.

The formula (1) and the formula (2) can each be introduced alone or in plurality. Further, the formulae can be introduced in an arbitrary combination. A target product can be obtained by causing an amine compound (intermediate X) obtained as a result of the introduction and an arbitrary halide (intermediate Y) to react with each other. The order in which the halides are caused to reach with each other and the manner in which the halides are combined can be determined in consideration of, for example, reactivity and ease of purification.

In addition, the formulae (10) to (13) can each be synthesized in the same manner as in the synthesis of the monoamine by changing the [halide] into the [halide including the formula (1) and the formula (2)] in the synthesis of a known amine compound.

In addition, individual, similar synthesis methods described in known technologies (JP 2003-171366 A, WO 2006/114921 A1, WO 2006/073054 A1, WO 2007/125714 A1, and WO 2008/062636 A1) may each be employed for any such synthesis as described above.

Hereinafter, the organic EL device of the present invention is described.

The organic EL device of the present invention is an organic electroluminescence device having an organic thin-film layer formed of one or more layers including at least a light emitting layer, the organic thin-film layer being interposed between a cathode and an anode, in which at least one layer of the organic thin-film layer contains the aromatic amine derivative of the present invention.

The organic EL device of the present invention is preferably such that the organic thin-film layer has a hole transporting layer and/or a hole injecting layer, and the aromatic amine derivative of the present invention is incorporated into the hole transporting layer and/or the hole injecting layer.

In addition, it is preferred that: the organic thin-film layer have a hole transporting zone including at least a hole transporting layer and a hole injecting layer; and the aromatic amine derivative of the present invention be incorporated into a layer out of direct contact with the light emitting layer in the hole transporting zone.

Further, the aromatic amine derivative of the present invention is preferably incorporated as a main component into the hole transporting layer and/or the hole injecting layer.

The organic EL device of the present invention is preferably such that the light emitting layer contains a styrylamine compound and/or an arylamine compound.

The aromatic amine derivative of the present invention is particularly preferably used in an organic EL device that emits blue light.

Typical examples of the construction of the organic EL device of the present invention may include the following constructions:

(1) anode/light emitting layer/cathode;
(2) anode/hole injecting layer/light emitting layer/cathode;
(3) anode/light emitting layer/electron injecting layer/cathode;
(4) anode/hole injecting layer/light emitting layer/electron injecting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/hole injecting layer/hole transporting layer/light emitting layer/electron injecting layer/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting layer/hole transporting layer/light emitting layer/insulating layer/cathode;
and
(13) anode/insulating layer/hole injecting layer/hole transporting layer/light emitting layer/electron injecting layer/cathode.

Of those, the construction (8) is preferably used in ordinary cases. However, the construction is not limited to the foregoing.

(Transparent Substrate)

The organic EL device of the present invention is produced by laminating a plurality of layers having various layer constructions as described above on a light-transmissive substrate. Here, the light-transmissive substrate is a substrate which supports the organic EL device. It is preferred that the substrate be a flat substrate in which a transmittance of light of 50% or more in the visible light region where the wavelength is 400 to 700 nm.

Specifically, examples include a glass plate and a polymer plate. Examples of the glass plate include soda-lime glass, glass containing barium and strontium, lead glass, aluminosilicate glass, borosilicate glass, barium borosilicate glass, and quartz. Further, examples of the polymer plate include polycarbonate, acrylic, polyethylene terephthalate, polyether sulfide, and polysulfone.

<Anode>

A material having a work function larger than 4 eV is suitable as a conductive material to be used in the anode of the organic EL device of the present invention, and any one of, for example, the following materials is used: carbon, aluminum, vanadium, iron, cobalt, nickel, tungsten, silver, gold, platinum, and palladium, and alloys thereof; metal oxides such as tin oxide and indium oxide to be used in an ITO substrate and an NESA substrate; and organic conductive resins such as polythiophene and polypyrrole.

<Cathode>

A material having a work function smaller than 4 eV is suitable as a conductive substance to be used in the cathode. Examples include, but not limited to, magnesium, calcium, tin, lead, titanium, yttrium, lithium, ruthenium, manganese, aluminum, lithium fluoride, and alloys thereof. Representative examples of the alloys include, but not limited to, magnesium/silver, magnesium/indium, and lithium/aluminum. A ratio of the alloy components is controlled by, for example, the temperature of a vapor deposition source, an atmosphere, and a degree of vacuum, and an appropriate ratio is selected for the ratio. The anode and the cathode may each be formed of a layer construction having two or more layers, as required.

The cathode can be produced by forming a thin film of the conductive substance in accordance with a method such as vapor deposition or sputtering.

Here, when light emitted from the light emitting layer is obtained through the cathode, it is preferred that the cathode have a transmittance of more than 10% with respect to the emitted light. It is also preferred that the sheet resistivity of the cathode be several hundred Ω/□ or less. In addition, the thickness of the cathode is generally 10 nm to 1 μm, preferably 50 nm to 200 nm.

<Insulating Layer>

Defects in pixels are liable to be formed in organic EL devices due to leak and short circuit because an electric field is applied to ultra-thin films. In order to prevent the formation of the defects, it is preferred that a thin-film layer having insulating property be inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide, and a mixture or a laminate of those materials may be used.

<Light Emitting Layer>

The light emitting layer of the organic EL device has a combination of the following functions (1) to (3).

(1) The injecting function: the function that allows holes to be injected from the anode or the hole injecting layer and electrons to be injected from the cathode or the electron injecting layer when an electric field is applied.

(2) The transporting function: the function of transporting injected charges (i.e., electrons and holes) by the force of the electric field.

(3) The light emitting function: the function of providing the field for recombination of electrons and holes and leading the recombination to the emission of light.

Although the ease with which a hole is injected and the ease with which an electron is injected may differ from each other, and transporting abilities represented by the mobilities of a hole and an electron may vary in extent, one of the charges is preferably transferred.

Examples of a host material or a doping material which can be used in the light emitting layer in the present invention include, but not limited to, fused aromatic compounds and derivatives thereof, such as naphthalene, phananthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl) anthracene, and 1,4-bis(9'-ethynylanthracenyl)benzene, organic metal complexes such as tris(8-quinolinolato)aluminum and bis-(2-methyl-8-quinolinolato)-4-(phenylphenolinato)aluminum, a triarylamine derivative, a styrylamine derivative, a stilbene derivative, a coumarin derivative, a pyrane derivative, an oxazone derivative, a benzothiazole derivative, a benzoxazole derivative, a benzimidazole derivative, a pyrazine derivative, a cinnamate derivative, a diketopyrrolopyrrole derivative, an acridone derivative, and quinacridone derivative.

In the present invention, a light emitting material formed of a pyrene-based derivative and an amine compound, or any other known metal complex compound may be incorporated into the light emitting layer.

The metal complex compound is preferably a metal complex compound containing at least one metal selected from Ir, Ru, Pd, Pt, Os, and Re. The ligands of the complex preferably have at least one skeleton selected from a phenylpyridine skeleton, a bipyridyl skeleton, and a phenanthroline skeleton.

Specific examples of such metal complex compound include tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, octaethyl platinum porphyrin, octaphenyl platinum porphyrin, octaethyl palladium porphyrin, and octaphenyl palladium porphyrin. However, the metal complex compound is not limited thereto. An appropriate metal complex compound is selected in terms of a requested luminescent color, a device performance, and a relationship with a host compound.

In addition, a phosphorescent dopant or a fluorescent dopant may be used in the light emitting layer of the organic EL device of the present invention.

The phosphorescent dopant is a compound capable of emitting light from a triplet exciton. The dopant, which is not particularly limited as long as light is emitted from a triplet exciton, is preferably a metal complex containing at least one metal selected from the group consisting of Ir, Ru, Pd, Pt, Os, and Re, more preferably a porphyrin metal complex or an orthometalated metal complex. A porphyrin platinum complex is preferred as the porphyrin metal complex. One kind of phosphorescent dopant may be used alone, or two or more kinds of phosphorescent dopants may be used in combination.

There are various ligands for forming an orthometalated metal complex. Preferred examples of the ligands include 2-phenylpyridine derivatives, 7,8-benzoquinoline derivatives, 2-(2-thienyl)pyridine derivatives, 2-(1-naphthyl)pyridine derivatives, and 2-phenylquinoline derivatives. Each of those derivatives may have a substituent as required. A fluorinated compound or the above-mentioned derivative having a trifluoromethyl group is particularly preferred as a blue-based dopant. The metal complex may further include a ligand other than the above-mentioned ligands such as acetylacetonato or picric acid as an auxiliary ligand.

The content of the phosphorescent dopant in the light emitting layer is not particularly limited, and can be appropriately selected in accordance with the purpose. The content is, for example, 0.1 to 70 mass %, more preferably 1 to 30 mass %. When the content of the phosphorescent dopant is less than 0.1 mass %, the intensity of emitted light is weak, and an effect of the incorporation of the compound is not sufficiently exerted. When the content exceeds 70 mass a phenomenon called concentration quenching becomes remarkable, and device performance reduces. Further, the light emitting layer may contain a hole transporting material, an electron transporting material, and a polymer binder as required.

Further, the light emitting layer has a thickness of preferably 5 to 50 nm, more preferably 7 to 50 nm, most preferably 10 to 50 nm. When the thickness is less than 5 nm, the light emitting layer becomes difficult to form, and chromaticity may become difficult to adjust. When the thickness exceeds 50 nm, the driving voltage may increase.

The fluorescent dopant is preferably a compound selected from, for example, an amine-based compound, an aromatic compound, a chelate complex such as a tris(8-quinolinolato) aluminum complex, a coumarin derivative, a tetraphenylbutadiene derivative, a bisstyrylarylene derivative, and an oxadiazole derivative in accordance with a requested luminescent color. An arylamine compound and an aryldiamine compound are particularly preferred examples of such compound; out of those compounds, a styrylamine compound, a styryldiamine compound, an aromatic amine compound, or an aromatic diamine compound is more preferred, and a fused polycyclic amine derivative is still more preferred. One kind of those fluorescent dopants may be used alone, or two or more kinds thereof may be used in combination.

The organic EL device of the present invention preferably contains at least one of a styrylamine and an arylamine as the fluorescent dopant. A compound represented by the following general formula (50) is preferably used as at least one of the styrylamine compound and the arylamine.

[Chem. 47]

(50)

In the general formula (50), $Ar_{27}$ to $Ar_{29}$ each represent a substituted or unsubstituted aromatic group having 6 to 40 ring carbon atoms, and u represents an integer of 1 to 4, in particular, u preferably represents an integer of 1 or 2. One of $Ar_{27}$ to $Ar_{29}$ may represent a group containing a styryl group. When one of $Ar_{27}$ and $Ar_{28}$ has a styryl group, at least one of $Ar_{28}$ and $Ar_{29}$ is preferably substituted with a styryl group.

Here, examples of the aromatic group having 6 to 40 ring carbon atoms include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzothiophenyl group, an oxadiazolyl group, a diphenylanthranyl group, an indolyl group, a carbazolyl group, a pyridyl group, a benzoquinolyl group, a fluoranthenyl group, an acenaphthofluoranthenyl group, a stilbene group, a perylenyl group, a chrysenyl group, a picenyl group, a triphenylenyl group, a rubicenyl group, a benzoanthracenyl group, a phenylanthracenyl group, a bisanthracenyl group, and arylene groups represented by the following general formulae (C) and (D). Of those, preferred are a naphthyl group, an anthranyl group, a chrysenyl group, a pyrenyl group, and an arylene group represented by the general formula (D).

[Chem. 48]

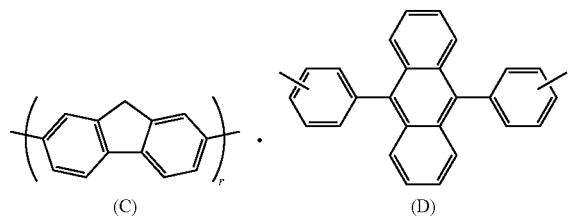

In the general formula (C), r represents an integer of 1 to 3.

It should be noted that preferred examples of the substituent which is substituted for the aromatic group and arylene group include an alkyl group having 1 to 6 carbon atoms (such as an ethyl group, a methyl group, an i-propyl group, an n-propyl group, an s-butyl group, a t-butyl group, a pentyl group, a hexyl group, a cyclopentyl group, or a cyclohexyl group), an alkoxy group having 1 to 6 carbon atoms (such as an ethoxy group, a methoxy group, an i-propoxy group, an n-propoxy group, an s-butoxy group, a t-butoxy group, a pentoxy group, a hexyloxy group, a cyclopentoxy group, or a cyclohexyloxy group), an aryl group having 5 to 40 carbon atoms, an amino group substituted by an aryl group having 5 to 40 carbon atoms, an ester group having an aryl group having 5 to 40 carbon atoms, an ester group having an alkyl group having 1 to 6 carbon atoms, a cyano group, a nitro group, and a halogen atom.

The light emitting material contained in the light emitting layer is not particularly limited, and examples of the host materials include polycyclic aromatic compounds such as an anthracene compound, a phenanthrene compound, a fluoranthene compound, a tetracene compound, a triphenylene compound, a chrysene compound, a pyrene compound, a coronene compound, a perylene compound, a phthaloperylene compound, a naphthaloperylene compound, a naphthacene compound, and a pentacene compound, oxadiazole, bisbenzoxazoline, bisstyryl, cyclopentadiene, a quinoline metal complex, a tris(8-hydroxyquinolinato)aluminum complex, a tris(4-methyl-8-quinolinato)aluminum complex, a tris(5-phenyl-8-quinolinato)aluminum complex, an aminoquinoline metal complex, a benzoquinoline metal complex, tri-(p-terphenyl-4-yl)amine, a 1-aryl-2,5-di(2-thienyl)pyrrole derivative, pyran, quinacridone, rubrene, a distyrylbenzene derivative, a distyrylarylene derivative, a porphyrin derivative, a stilbene derivative, a pyrazoline derivative, a coumarin-based dye, a pyran-based dye, a phthalocyanine-based dye, a naphthalocyanine-based dye, a croconium-based dye, a squalium-based dye, an oxobenzanthracene-based dye, a fluorescein-based dye, a rhodamine-based dye, a pyrylium-based dye, a perylene-based dye, a stilbene-based dye, a polythiophene-based dye, a rare-earth complex-based fluorescent substance, a rare-earth-based phosphorescent complex (such as an Ir complex), and polymer materials such as conductive polymers including polyvinylcarbazole, polysilane, and polyethylenedioxidethiophene (PEDOT). Those compounds may be used alone, or a mixture of two or more kinds thereof may be used.

As the host material to be used in combination with the compounds of the present invention, an anthracene derivative represented by the following formula (51) is preferred.

[Chem. 49]

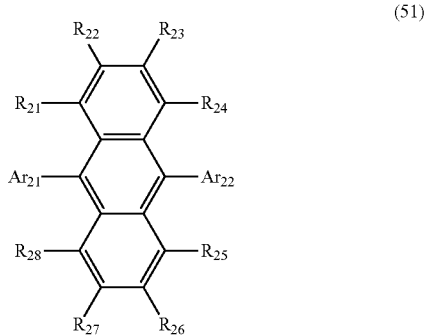

(51)

In the general formula (51), $A_{21}$ and $A_{22}$ each independently represent a substituted or unsubstituted aromatic group having 6 to 60 carbon atoms, and $R_{21}$ to $R_{28}$ each independently represent a hydrogen atom, a substituted or unsubstituted aromatic group having 6 to 50 carbon atoms, a substituted or unsubstituted aromatic heterocyclic group having 5 to 50 atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms, a substituted or unsubstituted arylthio group having 5 to 50 atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxy group.

A known light emitting material, doping material, hole injecting material, or electron injecting material can be used in the plurality of layers as required. Reductions in the luminance and lifetime of the organic EL device due to quenching can be prevented by providing the organic thin-film layers with a multilayer structure. A light emitting material, a doping material, a hole injecting material, and an electron injecting material can be used in combination as required. In addition, the doping material enables the achievement of improvements in emission luminance and luminous efficiency, and of the emission of red or blue light. In addition, each of the hole injecting layer, the light emitting layer, and the electron injecting layer may be formed of a layer construction having two or more layers. At that time, in the case of the hole injecting layer, a layer into which a hole is injected from an electrode is referred to as "hole injecting layer," and a layer that receives the hole from the hole injecting layer and transports the hole to the light emitting layer is referred to as "hole transporting layer." Similarly, in the case of the electron injecting layer, a layer into which an electron is injected from an electrode is referred to as "electron injecting layer," and a layer that receives the electron from the electron injecting layer and transports the electron to the light emitting layer is referred to as "electron transporting layer." Each of those layers is selected and used in consideration of various factors such as the energy level of a material therefor, its heat resistance, and its adhesiveness with an organic layer or a metal electrode.

<Hole Injecting Layer and Hole Transporting Layer>

The hole injecting/transporting layer are layers which help injection of holes into the light emitting layer and transports the holes to the light emitting region. The layers each exhibit a great mobility of holes and, in general, have an ionization energy as small as 5.7 eV or less. As such hole injecting/transporting layer, a material which transports holes to the light emitting layer under an electric field of a smaller strength is preferred. A material which exhibits, for example, a mobility of holes of at least $10^{-4}$ cm$^2$/V·sec under application of an electric field of $10^4$ to $10^6$ V/cm is preferred.

As described above, the aromatic amine derivative of the present invention is particularly preferably used in the hole injecting/transporting layer.

When the aromatic amine derivative of the present invention is used in the hole transporting zone, the aromatic amine derivative of the present invention may be used alone or as a mixture with any other material for forming the hole injecting/transporting layer.

The other material which can be used as a mixture with the aromatic amine derivative of the present invention for forming the hole injecting/transporting layer is not particularly limited as long as the material has the preferred property. The material can be arbitrarily selected from materials which are conventionally used as hole transporting materials in photoconductive materials and known materials which are used for hole injecting/transporting layers in organic EL devices. In the present invention, a material that has a hole transporting ability and can be used in a hole transporting zone is referred to as "hole transporting material."

Specific examples of the other material for a hole injecting/transporting layer than the aromatic amine derivative of the present invention include, but not limited to, a phthalocyanine derivative, a naphthalocyanine derivative, an acceptor material, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Of the hole injecting materials that can be used in the organic EL device of the present invention, more effective hole injecting materials are an aromatic tertiary amine derivative, a phthalocyanine derivative, and an acceptor material.

Examples of the aromatic tertiary amine derivative include, but not limited to, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1, 1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, and an oligomer or a polymer having one of the aromatic tertiary amine skeletons.

Examples of the phthalocyanine (Pc) derivative include, but not limited to, phthalocyanine derivatives such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, and GaPc-O-GaPc, and naphthalocyanine derivatives.

The acceptor material is an easily reducible organic compound. The ease with which the compound is reduced can be measured in terms of its reduction potential. In the present invention, when a saturated calomel electrode (SCE) is used as a reference electrode, a reduction potential of –0.8

V or more is preferred, and a compound having a reduction potential larger than that of tetracyanoquinodimethane (TCNQ) (about 0 V) is particularly preferred.

The easily reducible organic compound is preferably an organic compound having an electron-withdrawing substituent. Specific examples thereof include quinoid derivatives, pyrazine derivatives, arylborane derivatives, and imide derivatives. The quinoid derivatives include, but not limited to, a quinodimethane derivative, a thiopyrane dioxide derivative, a thioxanthene dioxide derivative, and a quinone derivative.

In the organic EL device of the present invention, a hexaazatriphenylene compound represented by the following formula (A) is particularly preferably used as the acceptor material.

[Chem. 50]

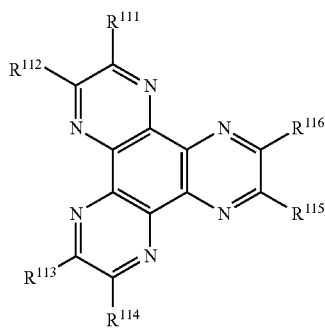

(A)

In the formula (A), $R^{111}$ to $R^{116}$ each independently represent a cyano group, —CONH$_2$, a carboxyl group, or —COOR$^{117}$ (where $R^{117}$ represents an alkyl group having 1 to 20 carbon atoms), or $R^{111}$ and $R^{112}$, $R^{113}$ and $R^{114}$, or $R^{115}$ and $R^{116}$ are bonded to each other to represent a group represented by —CO—O—CO—.

A nitrogen-containing heterocyclic derivative represented by the following formula disclosed in JP 3571977 B as well as the foregoing compound can be used as the acceptor material.

[Chem. 51]

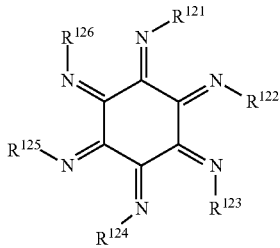

In the formula, $R^{121}$ to $R^{126}$ each represent any one of a substituted or unsubstituted alkyl group, a substituted or unsubstituted aryl group, a substituted or unsubstituted aralkyl group, and a substituted or unsubstituted heterocyclic group, provided that $R^{121}$ to $R^{126}$ may be identical to or different from one another, and $R^{121}$ and $R^{122}$, $R^{123}$ and $R^{124}$, $R^{125}$ and $R^{126}$, $R^{121}$ and $R^{126}$, $R^{122}$ and $R^{123}$, or $R^{124}$ and $R^{125}$ may form a fused ring.

The organic EL device of the present invention is preferably obtained by forming a layer containing any such aromatic tertiary amine derivative, phthalocyanine derivative, and/or acceptor material such as the hole transporting layer or the hole injecting layer between the light emitting layer and the anode.

The acceptor material can be used by being incorporated into the hole transporting zone, or can be used by being laminated in the hole transporting zone. The material is preferably used in a layer laminated on the anode side to contact the hole injecting layer or the hole transporting layer.

<Electron Injecting Layer and Electron Transporting Layer>

The electron injecting/transporting layer is a layer which helps injection of electrons into the light emitting layer, transports the electrons to the light emitting region, and exhibits a great mobility of electrons. Further, the adhesion improving layer is an electron injecting layer including a material exhibiting particularly improved adhesion with the cathode.

In addition, it is known that, in an organic EL device, emitted light is reflected by an electrode (cathode in this case), and hence emitted light directly extracted from an anode and emitted light extracted via the reflection by the electrode interfere with each other. The thickness of an electron transporting layer is appropriately selected from the range of several nanometers to several micrometers in order that the interference effect may be effectively utilized. In particular, when the thickness of the electron transporting layer is large, an electron mobility is preferably at least $10^{-5}$ cm$^2$/V·s or more upon application of an electric field of $10^4$ to $10^6$ V/cm in order to avoid an increase in voltage.

Specific examples of the material to be used for the electron injecting layer include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the material is not limited thereto. In addition, an electron-accepting substance can be added to the hole injecting material or an electron-donating substance can be added to the electron injecting material to thereby sensitize the hole injecting material or the electron injecting material, respectively.

In the organic EL device of the present invention, more effective electron injecting materials are a metal complex compound and a nitrogen-containing five-membered ring derivative.

Examples of the metal complex compound include, but not limited to, 8-hydroxyquinolinatolithium, bis(8-hydroxyquinolinato) zinc, bis(8-hydroxyquinolinato) copper, bis(8-hydroxyquinolinato)manganese, tris(8-hydroxyquinolinato) aluminum, tris(2-methyl-8-hydroxyquinolinato)aluminum, tris(8-hydroxyquinolinato)gallium, bis(10-hydroxybenzo[h] quinolinato) beryllium, bis(10-hydroxybenzo[h]quinolinato) zinc, bis(2-methyl-8-quinolinato)chlorogallium, bis(2-methyl-8-quinolinato) (o-cresolato)gallium, bis(2-methyl-8-quinolinato) (1-naphtholato)aluminum, and bis(2-methyl-8-quinolinato) (2-naphtholato)gallium.

Examples of the nitrogen-containing five-membered ring derivative preferably include, an oxazole derivative, a thiazole derivative, an oxadiazole derivative, a thiadiazole derivative, and a triazole derivative. Specific examples of the derivative include, but not limited to, 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)] benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene.

In the organic EL device of the present invention, the nitrogen-containing five-membered ring derivative is particularly preferably a benzimidazole derivative represented by any one of the following formulae (21) to (23).

[Chem. 52]

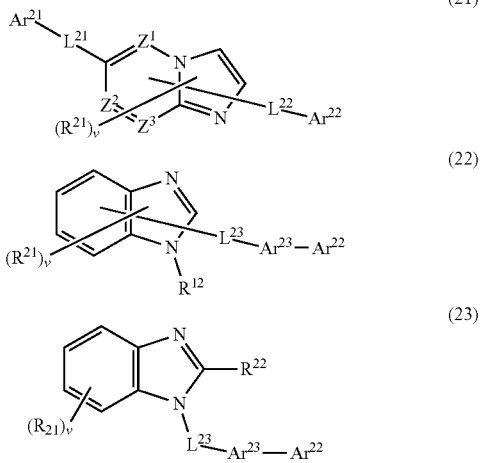

In the formulae (21) to (23), $Z^1$, $Z^2$, and $Z^3$ each independently represent a nitrogen atom or a carbon atom.

$R^{21}$ and $R^{22}$ each independently represent a substituted or unsubstituted aryl group having 6 to 50 carbon atoms, a substituted or unsubstituted heteroaryl group having 3 to 50 carbon atoms, an alkyl group having 1 to 20 carbon atoms, an alkyl group having 1 to 20 carbon atoms and substituted with a halogen atom, or an alkoxy group having 1 to 20 carbon atoms.

v represents an integer of 0 to 5, and when v represents an integer of 2 or more, a plurality of $R^{21}$'s may be identical to or different from each other. In addition, a plurality of $R^{21}$'s adjacent to each other may be bonded to each other to form a substituted or unsubstituted aromatic hydrocarbon ring.

$Ar^{21}$ represents a substituted or unsubstituted aryl group having 6 to 50 carbon atoms, or a substituted or unsubstituted heteroaryl group having 3 to 50 carbon atoms.

$Ar^{22}$ represents a hydrogen atom, an alkyl group having 1 to 20 carbon atoms, an alkyl group having 1 to 20 carbon atoms and substituted with a halogen atom, an alkoxy group having 1 to 20 carbon atoms, a substituted or unsubstituted aryl group having 6 to 50 carbon atoms, or a substituted or unsubstituted heteroaryl group having 3 to 50 carbon atoms.

It should be noted that one of $Ar^{21}$ and $Ar^{22}$ represents a substituted or unsubstituted fused ring group having 10 to 50 carbon atoms, or a substituted or unsubstituted heterofused ring group having 9 to 50 ring atoms.

$Ar^{23}$ represents a substituted or unsubstituted arylene group having 6 to 50 carbon atoms, or a substituted or unsubstituted heteroarylene group having 3 to 50 carbon atoms.

$L^{21}$, $L^{22}$, and $L^{23}$ each independently represent a single bond, a substituted or unsubstituted arylene group having 6 to 50 carbon atoms, a substituted or unsubstituted heterofused ring group having 9 to 50 ring atoms, or a substituted or unsubstituted fluorenylene group.

In the organic EL device of the present invention, a light emitting material, a doping material, a hole injecting material, or an electron injecting material may be incorporated into the layer containing the aromatic amine derivative of the present invention.

In addition, the surface of the organic EL device obtained by the present invention can be provided with a protective layer, or the entirety of the device can be protected with silicone oil, a resin, or the like from the viewpoint of an improvement in the stability of the device against a temperature, a humidity, an atmosphere, or the like.

At least one surface of the organic EL device of the present invention is desirably made sufficiently transparent in the luminous wavelength region of the device in order that the device may be caused to efficiently emit light. In addition, its substrate is also desirably transparent. A transparent electrode is set with the conductive material by a method such as vapor deposition or sputtering so that predetermined translucency may be secured. The light transmittance of the electrode on a light emitting surface is desirably set to 10% or more. A glass substrate and a transparent resin film are each available as the substrate, though the substrate is not limited as long as the substrate has mechanical and thermal strengths, and has transparency. Examples of the transparent resin film include polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyetherimide, polyimide, and polypropylene.

Any one of dry film forming methods such as vacuum deposition, sputtering, plasma, and ion plating, and wet film forming methods such as spin coating, dipping, and flow coating is applicable to the formation of each layer of the organic EL device of the present invention. The thickness of each layer is not particularly limited, but must be set to an appropriate thickness. An excessively large thickness requires an increased applied voltage for obtaining certain optical output, resulting in poor efficiency. An excessively small thickness causes a pin hole or the like, with the result that sufficient emission luminance cannot be obtained even when an electric field is applied. In general, the thickness is in the range of preferably 5 nm to 10 µm, or more preferably 10 nm to 0.2 µm.

In the case of a wet film forming method, a material of which each layer is formed is dissolved or dispersed into an appropriate solvent such as ethanol, chloroform, tetrahydrofuran, or dioxane, to thereby form a thin film. At that time, any one of the above solvents may be used.

An organic EL material-containing solution containing the aromatic amine derivative of the present invention as an organic EL material and a solvent can be used as a solution suitable for such wet film forming method. In addition, an appropriate resin or additive may be used in each of the organic thin-film layers for, for example, improving film formability or preventing a pin hole in the layer.

Examples of the resin which may be used include: insulating resins such as polystyrene, polycarbonate, polyallylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole. Examples of the additive include an antioxidant, a UV absorber, and a plasticizer.

<Method of Producing Organic EL Device>

The anode, the light emitting layer, the hole injecting/transporting layer as required, and the electron injecting/transporting layer as required are formed by means of the various materials and the layer formation methods listed in the foregoing, and the cathode is further formed. Thus, the organic EL device can be produced. Further, the organic EL device may also be produced by forming the above-mentioned layers in the order reverse to the order described above, i.e., the cathode being formed in the first step and the anode in the last step.

Hereinafter, an example of producing an organic EL device having a configuration in which an anode, a hole injecting layer, a light emitting layer, an electron injecting layer, and a cathode are formed successively on a light-transmissive substrate is described.

First, on a suitable light-transmissive substrate, a thin film made of a material for the anode is formed by a method such as vapor deposition or sputtering so that the thickness of the formed thin film is 1 µm or less, preferably in the range of 10 to 200 nm. Thus, an anode is produced. Then, a hole injecting layer is formed on the anode. The hole injecting layer can be formed in accordance with the vacuum vapor deposition process, the spin coating process, the casting process, the LB process, or the like, as described above. The vacuum vapor deposition process is preferred because a uniform film can be easily obtained and the possibility of formation of pin holes is small. When the hole injecting layer is formed in accordance with the vacuum vapor deposition process, in general, it is preferred that the conditions be suitably selected from the following ranges: the temperature of the source of the deposition: 50 to 450° C.; the degree of vacuum: $10^{-7}$ to $10^{-3}$ Torr; the rate of deposition: 0.01 to 50 nm/s; the temperature of the substrate: −50 to 300° C.; and the thickness of the film: 5 nm to 5 µm, although the conditions of the vacuum vapor deposition are different depending on the compound to be used (material for the hole injecting layer) and the crystal structure and the recombination structure of the target hole injecting layer.

The organic EL device of the present invention can find use in: flat luminous bodies for the flat panel displays of wall-hung televisions and the like; light sources for the backlights, measuring gauges, and the like of copying machines, printers, and liquid crystal displays; display boards; and marker lamps. In addition, the material of the present invention can be used not only in an organic EL device but also in the fields of, for example, an electrophotographic photosensitive member, a photoelectric converter, a solar cell, and an image sensor.

EXAMPLES

Hereinafter, the present invention is specifically described by way of examples. However, the present invention is not limited by these examples as long as the gist of the present invention is not deviated.

Synthesis Example 1 (Synthesis of Intermediate 1)

In a stream of argon, 47 g of 4-bromobiphenyl, 23 g of iodine, 9.4 g of periodic acid dihydrate, 42 mL of water, 360 mL of acetic acid, and 11 mL of sulfuric acid were loaded into a 1,000-mL three-necked flask, and the mixture was stirred at 65° C. for 30 minutes and was then subjected to a reaction at 90° C. for 6 hours. The reactant was poured into ice water, followed by filtering. The resultant was washed with water, and then washed with methanol, whereby 67 g of a white powder were obtained. Main peaks having ratios m/z of 358 and 360 were obtained with respect to $C_{12}H_8BrI=359$ by a field desorption mass spectrometry (hereinafter, referred to as FD-MS) analysis, so the powder was identified as the Intermediate 1.

Synthesis Example 2 (Synthesis of Intermediate 2)

A reaction was performed in the same manner as in Synthesis Example 1 except that 2-bromo-9,9-dimethylfluorene was used instead of 4-bromobiphenyl. As a result, 61 g of a white powder were obtained. Main peaks having ratios m/z of 398 and 400 were obtained with respect to $C_{15}H_{12}BrI=399$ by FD-MS analysis, so the powder was identified as the Intermediate 2.

Synthesis Example 3 (Synthesis of Intermediate 3)

17.7 g of 9-phenylcarbazole, 6.03 g of potassium iodide, 7.78 g of potassium iodate, 5.9 mL of sulfuric acid, and ethanol were loaded, and then the mixture was subjected to a reaction at 75° C. for 2 hours.

After the resultant had been cooled, clean water and ethyl acetate were added to perform separation and extraction. After that, the organic layer was washed with baking soda water and clean water, and was then concentrated. The resultant coarse product was purified by silica gel chromatography (toluene), and then the resultant solid was dried under reduced pressure. Thus, 21.8 g of a white solid were obtained. The solid was identified as the Intermediate 3 by FD-MS analysis.

Synthesis Example 4 (Synthesis of Intermediate 4)

In a stream of argon, dry toluene and dry ether were added to 13.1 g of the Intermediate 3, and then the mixture was cooled to −45° C. 25 mL of a solution (1.58 M) of n-butyllithium in hexane were dropped to the mixture, and then the temperature was increased to −5° C. over 1 hour while the mixture was stirred. The mixture was cooled to −45° C. again, and then 25 mL of boronic acid triisopropyl ester were slowly dropped to the mixture. After that, the mixture was subjected to a reaction for 2 hours.

After the temperature of the resultant had been returned to room temperature, a 10% diluted hydrochloric acid solution was added to the resultant, and then the mixture was stirred so that an organic layer was extracted. After having been washed with a saturated salt solution, the organic layer was dried with anhydrous magnesium sulfate and separated by filtration. After that, the separated product was concentrated. The resultant solid was purified by silica gel chromatography (toluene), and then the resultant solid was washed with n-hexane and dried under reduced pressure. Thus, 7.10 g of a solid were obtained. The solid was identified as the Intermediate 4 by FD-MS analysis.

Synthesis Example 5 (Synthesis of Intermediate 5)

Under an argon atmosphere, 300 mL of toluene and 150 mL of an aqueous solution of sodium carbonate having a concentration of 2 M were added to 28.3 g of 4-iodobromobenzene, 30.1 g of the Intermediate 4, 2.31 g of tetrakis(triphenylphosphine)palladium (0), and then the mixture was heated for 10 hours while being refluxed.

Immediately after the completion of the reaction, the resultant was filtered, and then the aqueous layer was removed. The organic layer was dried with sodium sulfate, and was then concentrated. The residue was purified by silica gel column chromatography. Thus, 20.2 g of a white crystal were obtained. The crystal was identified as the Intermediate 5 by FD-MS analysis.

Synthesis Example 6 (Synthesis of Intermediate 6)

A reaction was performed in the same manner as in Synthesis Example 5 except that the Intermediate 1 were used instead of 4-iodobromobenzene. Thus, 23.6 g of a white powder were obtained. The powder was identified as the Intermediate 6 by FD-MS analysis.

Synthesis Example 7 (Synthesis of Intermediate 7)

Under an argon atmosphere, 2 mL of trans-1,2-cyclohexanediamine and 300 mL of 1,4-dioxane were added to 28.3 g of 4-iodobromobenzene, 16.7 g of carbazole, 0.2 g of copper iodide (CuI), 42.4 g of tripotassium phosphate, and then the mixture was stirred at 100° C. for 20 hours.

After the completion of the reaction, 300 mL of water were added to the resultant. After that, the mixture was subjected to liquid separation, and then the aqueous layer was removed. The organic layer was dried with sodium sulfate, and was then concentrated. The residue was purified by silica gel column chromatography. Thus, 18.3 g of a white crystal were obtained (in 57.% yield). The resultant was identified as the Intermediate 7 by FD-MS analysis.

Synthesis Example 8 (Synthesis of Intermediate 8)

A reaction was performed in the same manner as in Synthesis Example 7 except that 35.9 g of the Intermediate 1 were used instead of 4-iodobromobenzene. Thus, 24.1 g of a white powder were obtained. The powder was identified as the Intermediate 8 by FD-MS analysis.

Synthesis Example 9 (Synthesis of Intermediate 9)

A reaction was performed in the same manner as in Synthesis Example 7 except that 39.9 g of the Intermediate 2 were used instead of the 4-iodobromobenzene. Thus, 24.1 g of a white powder were obtained. The powder was identified as the Intermediate 9 by FD-MS analysis.

Synthesis Example 10 (Synthesis of Intermediate 10)

In a stream of argon, 5.9 g of acetamide, 39.8 g of the Intermediate 5, 2.70 g of copper iodide, 40.8 g of potassium carbonate, and diethylbenzene were loaded, and then the mixture was subjected to a reaction at 175° C. for 19 hours. Further, 39.8 g of the Intermediate 8 were loaded into the resultant, and then the mixture was subjected to a reaction at 175° C. for 19 hours.

After the resultant had been cooled, clean water was added so that the resultant was filtered. The residue was washed with acetone, methanol, and clean water three times each. Thus, 32.5 g of an acetamide body of the Intermediate 10 were obtained.

32.5 g of the acetamide body of the Intermediate 10, 26.3 g of potassium hydroxide, 25 mL of clean water, and diethylbenzene were loaded, and then the mixture was subjected to a reaction at 175° C. for 5 hours.

After the resultant had been cooled, clean water was added so that the resultant was filtered. The residue was washed with acetone, methanol, and clean water three times each, and was then purified with a short column (toluene). The resultant solid was washed with n-hexane and dried under reduced pressure. Thus, 19.2 g of a white solid were obtained. The solid was identified as the Intermediate 10 by FD-MS analysis.

Synthesis Example 11 (Synthesis of Intermediate 11)

Reactions were performed in the same manner as in Synthesis Example 10 except that 32.2 g of the Intermediate 7 were used instead of the Intermediate 8. Thus, 15.2 g of a white powder were obtained. The powder was identified as the Intermediate 11 by FD-MS analysis.

Synthesis Example 12 (Synthesis of Intermediate 12)

Reactions were performed in the same manner as in Synthesis Example 10 except that 47.4 g of the Intermediate 6 were used instead of the Intermediate 5. Thus, 24.8 g of a white powder were obtained. The powder was identified as the Intermediate 12 by FD-MS analysis.

Synthesis Example 13 (Synthesis of Intermediate 13)

Reactions were performed in the same manner as in Synthesis Example 10 except that: 47.4 g of the Intermediate 6 were used instead of the Intermediate 5; and 32.2 g of the Intermediate 7 were used instead of the Intermediate 8. Thus, 21.8 g of a white powder were obtained. The powder was identified as the Intermediate 13 by FD-MS analysis.

Synthesis Example 14 (Synthesis of Intermediate 14)

Reactions were performed in the same manner as in Synthesis Example 10 except that 36.9 g of the Intermediate 3 were used instead of the Intermediate 5. Thus, 16.4 g of a white powder were obtained. The powder was identified as the Intermediate 14 by FD-MS analysis.

Synthesis Example 15 (Synthesis of Intermediate 15)

Reactions were performed in the same manner as in Synthesis Example 10 except that: 36.9 g of the Intermediate 3 were used instead of the Intermediate 5; and 32.2 g of the Intermediate 7 were used instead of the Intermediate 8. Thus, 20.3 g of a white powder were obtained. The powder was identified as the Intermediate 15 by FD-MS analysis.

Synthesis Example 16 (Synthesis of Intermediate 16)

Reactions were performed in the same manner as in Synthesis Example 10 except that 43.8 g of the Intermediate 9 were used instead of the Intermediate 8. Thus, 22.4 g of a white powder were obtained. The powder was identified as the Intermediate 16 by FD-MS analysis.

Synthesis Example 17 (Synthesis of Intermediate 17)

Reactions were performed in the same manner as in Synthesis Example 10 except that: 39.8 g of the Intermediate 6 were used instead of the Intermediate 5; and 43.8 g of the Intermediate 9 were used instead of the Intermediate 8. Thus, 24.8 g of a white powder were obtained. The powder was identified as the Intermediate 17 by FD-MS analysis.

Synthesis Example 18 (Synthesis of Intermediate 18)

In a stream of argon, 4.7 g of aniline, 36.0 g of the Intermediate 1, 10 g of t-butoxy sodium (manufactured by Hiroshima Wako Ltd.), 1.6 g of bis(triphenylphosphine) palladium (II) chloride (manufactured by TOKYO CHEMICAL INDUSTRY CO., LTD.), and 500 mL of xylene were loaded and subjected to a reaction at 130° C. for 24 hours.

After the resultant had been cooled, 1,000 mL of water were added to the resultant, and then the mixture was filtrated with celite. The filtrate was extracted with toluene, and was then dried with anhydrous magnesium sulfate. The dried product was concentrated under reduced pressure. The resultant coarse product was subjected to column purification, and was then recrystallized with toluene. The crystal was taken by filtration, and was then dried. As a result, 6.9 g of a pale yellow powder were obtained. The powder was identified as the Intermediate 18 by FD-MS analysis.

Synthesis Example 19 (Synthesis of Intermediate 19)

A reaction was performed in the same manner as in Synthesis Example 18 except that 16.8 g of N,N'-diphenylbenzidine was used instead of aniline. As a result, 7.3 g of a white powder were obtained. The powder was identified as the Intermediate 19 by FD-MS analysis.

Synthesis Example 20 (Synthesis of Intermediate 20)

Under an argon atmosphere, 600 mL of dry tetrahydrofuran were added to 78.0 g of dibenzofuran, and then the mixture was cooled to −30° C. 300 mL of a solution of n-butyllithium in hexane (1.65 M) were dropped to the mixture, and then the temperature of the whole was increased to room temperature over 1 hour while the whole was stirred. After having been stirred at room temperature for 5 hours, the resultant was cooled to −60° C., and then 60 mL of 1,2-dibromoethane were dropped to the resultant over 1 hour.

After having been stirred at room temperature for 15 hours, the mixture was poured into 1,000 mL of ice water, and then the organic layer was extracted with dichloromethane. The organic layer was washed with a saturated salt solution, and was then dried with anhydrous magnesium sulfate. The dried product was separated by filtration, and was then concentrated. The resultant solid was purified by silica gel chromatography (toluene), washed with tetrahydrofuran and methanol, and dried under reduced pressure. As a result, 70 g of a solid were obtained. The solid was identified as the Intermediate 20 by FD-MS analysis.

Synthesis Example 21 (Synthesis of Intermediate 21)

Under an argon atmosphere, 300 mL of toluene and 150 mL of an aqueous solution of sodium carbonate having a concentration of M were added to 28.3 g of 4-iodobromobenzene, 22.3 g of dibenzofuran-4-boronic acid, and 2.31 g of tetrakis(triphenylphosphine)palladium (0), and then the mixture was heated while being refluxed for 10 hours.

Immediately of ter the completion of the reaction, the resultant was filtrated, and then the aqueous layer was removed. The organic layer was dried with sodium sulfate, and was then concentrated. The residue was purified by silica gel column chromatography. Thus, 26.2 g of a white crystal were obtained. The crystal was identified as the Intermediate 21 by FD-MS analysis.

Synthesis Example 22 (Synthesis of Intermediate 22)

Under a nitrogen atmosphere, 1 L of acetic acid were added to 150 g of dibenzofuran, and then the whole was dissolved under heat. 188 g of bromine were dropped to the solution while water cooling occasionally. After that, the mixture was stirred for 20 hours under air cooling. The precipitated crystal was separated by filtration, and was then sequentially washed with acetic acid and water. The washed crystal was dried under reduced pressure. The resultant crystal was purified by distillation under reduced pressure, and was then repeatedly recrystallized with methanol several times. Thus, 66.8 g of solid were obtained. The solid was identified as the Intermediate 22 by FD-MS analysis.

Synthesis Example 23 (Synthesis of Intermediate 23)

Under an argon atmosphere, 400 mL of anhydrous tetrahydrofuran were added to 24.7 g of the Intermediate 22, and then 63 mL of a solution of n-butyllithium in hexane having a concentration of 1.6 M were added to the mixture during the stirring of the mixture at −40° C. The reaction solution was stirred for 1 hour while being heated to 0° C. The reaction solution was cooled to −78° C. again, and then a solution of 26.0 g of trimethyl borate in 50 mL of anhydrous tetrahydrofuran was dropped to the solution. The reaction solution was stirred at room temperature for 5 hours. 200 mL of 1N hydrochloric acid were added to the solution, and then the mixture was stirred for 1 hour. After that, the aqueous layer was removed. The organic layer was dried with magnesium sulfate, and then the solvent was removed by distillation under reduced pressure. The resultant solid was washed with toluene. Thus, 15.2 g of solid were obtained. The solid was identified as the Intermediate 23 by FD-MS analysis.

Synthesis Example 24 (Synthesis of Intermediate 24)

A reaction was performed in the same manner as in Synthesis Example 21 except that 22.3 g of the Intermediate 23 were used instead of the dibenzofuran-4-boronic acid. Thus, 23.1 g of a white powder were obtained. The powder was identified as the Intermediate 24 by FD-MS analysis.

Synthesis Example 25 (Synthesis of Intermediate 25)

A reaction was performed in the same manner as in Synthesis Example 5 except that 30.1 g of 9-phenylcarbazole-2-boronic acid were used instead of the Intermediate 4. Thus, 20.0 g of a white powder were obtained. The powder was identified as the Intermediate 25 by FD-MS analysis.

Synthesis Example 26 (Synthesis of Intermediate 26)

A reaction was performed in the same manner as in Synthesis Example 10 except that 20.0 g of the Intermediate 25 were used instead of the Intermediate 8. Thus, 10.5 g of a white powder were obtained. The powder was identified as the Intermediate 26 by FD-MS analysis.

Synthesis Example 27 (Synthesis of Intermediate 27)

Under an argon atmosphere, 1,000 mL of toluene and 500 mL of an aqueous solution of sodium carbonate having a concentration of 2M were added to 120.0 g (399 mmol) of 1-bromo-3-fluoro-4-iodobenzene, 72.7 g (479 mmol) of 2-methoxyphenyl boronic acid, and 9.2 g (7.96 mmol) of tetrakis(triphenylphosphine)palladium(0), and then the mixture was heated while being refluxed for 10 hours.

Immediately after the completion of the reaction, the resultant was filtrated, and then the aqueous layer was removed. The organic layer was dried with sodium sulfate, and was then concentrated. The residue was purified by silica gel column chromatography. Thus, 89.6 g of a white crystal of 4-bromo-2-fluoro-2'-methoxybiphenyl were obtained (in 80% yield).

Under an argon atmosphere, 900 mL of dichloromethane were added to 89.6 g (319 mmol) of 4-bromo-2-fluoro-2'-methoxybiphenyl, and then the mixture was stirred under ice cooling. 95.9 g (382 mmol) of boron tribromide were added dropwise to the mixture, and then the whole was stirred at room temperature for 12 hours. After the completion of the reaction, 200 mL of water were added to the resultant, and then the mixture was stirred for 1 hour. After that, the aqueous layer was removed. The organic layer was dried with magnesium sulfate, and was then concentrated. The residue was purified by silica gel column chromatography. Thus, 68.1 g of a white crystal of 4-bromo-2-fluoro-2'-hydroxybiphenyl were obtained (in 70% yield).

1,500 mL of N-methylpyrrolidone were added to 68.1 g (255 mmol) of 4-bromo-2-fluoro-2'-hydroxybiphenyl and 70.4 g (510 mmol) of potassium carbonate, and then the mixture was stirred at 180° C. for 3 hours. After the completion of the reaction, water was added to the resultant, and then extraction with toluene was performed. The organic layer was dried with sodium sulfate, and was then concentrated. The residue was recrystallized from toluene so as to be purified. Thus, 44.2 g of a white crystal were obtained (in 60% yield). The crystal was identified as the Intermediate 27 by FD-MS analysis.

Synthesis Example 28 (Synthesis of Intermediate 28)

Under an argon atmosphere, 350 mL of toluene and 170 mL of an aqueous solution of sodium carbonate having a concentration of 2 M were added to 34.2 g (138 mmol) of the Intermediate 27, 26.0 g (166 mmol) of 4-chlorophenylboronic acid, 3.2 g (2.77 mmol) of tetrakis(triphenylphosphine)palladium(0), and then the mixture was heated for 12 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 23.1 g of a white crystal were obtained (in 60% yield). The crystal was identified as the Intermediate 28 by FD-MS analysis.

Synthesis Embodiment 1 (Synthesis of Compound H1)

In a stream of argon, 6.5 g of the Intermediate 10, 3.1 g of 4-bromo-p-terphenyl, 1.3 g of t-butoxy sodium (manufactured by Hiroshima Wako Ltd.), 46 mg of tris(dibenzylideneacetone)dipalladium(0) (manufactured by Sigma-Aldrich, Inc), 21 mg of tri-t-butylphosphine, and 50 mL of dry toluene were, and then the mixture was subjected to a reaction at 80° C. for 8 hours.

After having been cooled, 500 mL of water were added, and then the mixture was subjected to celite filtration. The filtrate was extracted with toluene and dried with anhydrous magnesium sulfate. The dried product was concentrated under reduced pressure, and then the resultant coarse product was subjected to column purification. The purified product was recrystallized with toluene, and then the recrystallized product was taken by filtration. After that, the resultant was dried. Thus, 6.1 g of a pale yellow powder were obtained. The powder was identified as the Compound H1 by FD-MS analysis.

Synthesis Embodiment 2 (Synthesis of Compound H2)

A reaction was performed in the same manner as in Synthesis Embodiment 1 except that 5.8 g of the Intermediate 11 were used instead of the Intermediate 10. Thus, 4.8 g of a pale yellow powder were obtained. The powder was identified as the Compound H2 by FD-MS analysis.

Synthesis Embodiment 3 (Synthesis of Compound H3)

A reaction was performed in the same manner as in Synthesis Embodiment 1 except that 7.3 g of the Intermediate 12 were used instead of the Intermediate 10. Thus, 5.9 g of a pale yellow powder were obtained. The powder was identified as the Compound H3 by FD-MS analysis.

Synthesis Embodiment 4 (Synthesis of Compound H4)

A reaction was performed in the same manner as in Synthesis Embodiment 1 except that 6.5 g of the Intermediate 13 were used instead of the Intermediate 10. Thus, 4.3 g of a pale yellow powder were obtained. The powder was identified as the Compound H4 by FD-MS analysis.

Synthesis Embodiment 5 (Synthesis of Compound H5)

A reaction was performed in the same manner as in Synthesis Embodiment 1 except that 2.3 g of the 4-bromobiphenyl were used instead of the 4-bromo-p-terphenyl. Thus, 3.5 g of a pale yellow powder were obtained. The powder was identified as the Compound H5 by FD-MS analysis.

Synthesis Embodiment 6 (Synthesis of Compound H6)

A reaction was performed in the same manner as in Synthesis Embodiment 1 except that: 5.7 g of the Intermediate 11 were used instead of the Intermediate 10; and 2.1 g of 1-bromonaphthalene were used instead of 4-bromo-p-terphenyl. Thus, 3.2 g of a pale yellow powder were obtained. The powder was identified as the Compound H6 by FD-MS analysis.

Synthesis Embodiment 7 (Synthesis of Compound H7)

A reaction was performed in the same manner as in Synthesis Embodiment 1 except that: 7.3 g of the Intermediate 12 were used instead of the Intermediate 10; and 2.1 g of 1-bromonaphthalene were used instead of 4-bromo-p-terphenyl. Thus, 3.9 g of a pale yellow powder were obtained. The powder was identified as the Compound H7 by FD-MS analysis.

Synthesis Embodiment 8 (Synthesis of Compound H8)

A reaction was performed in the same manner as in Synthesis Embodiment 1 except that: 6.5 g of the Intermediate 13 were used instead of the Intermediate 10; and 2.3 g of 4-bromobiphenyl were used instead of 4-bromo-p-terphenyl. Thus, 4.5 g of a pale yellow powder were obtained. The powder was identified as the Compound H8 by FD-MS analysis.

Synthesis Embodiment 9 (Synthesis of Compound H9)

A reaction was performed in the same manner as in Synthesis Embodiment 1 except that: 5.8 g of the Intermediate 11 were used instead of the Intermediate 10; and 4.0 g of the Intermediate 5 were used instead of 4-bromo-p-terphenyl. Thus, 4.2 g of a pale yellow powder were obtained. The powder was identified as the Compound H9 by FD-MS analysis.

Synthesis Embodiment 10 (Synthesis of Compound H10)

A reaction was performed in the same manner as in Synthesis Embodiment 1 except that 4.0 g of the Intermediate 5 were used instead of 4-bromo-p-terphenyl. Thus, 3.7 g of a pale yellow powder were obtained. The powder was identified as the Compound H10 by FD-MS analysis.

Synthesis Embodiment 11 (Synthesis of Compound H11)

A reaction was performed in the same manner as in Synthesis Embodiment 1 except that 6.9 g of the Intermediate 16 were used instead of the Intermediate 10. Thus, 4.7 g of a pale yellow powder were obtained. The powder was identified as the Compound H11 by FD-MS analysis.

Synthesis Embodiment 12 (Synthesis of Compound H12)

A reaction was performed in the same manner as in Synthesis Embodiment 1 except that 7.7 g of the Intermediate 17 were used instead of the Intermediate 10. Thus, 4.9 g of a pale yellow powder were obtained. The powder was identified as the Compound H12 by FD-MS analysis.

Synthesis Embodiment 13 (Synthesis of Compound H13)

A reaction was performed in the same manner as in Synthesis Embodiment 1 except that: 7.3 g of the Intermediate 12 were used instead of the Intermediate 10; and 2.0 g of 4,4'-diiodobiphenyl were used instead of 4-bromo-p-terphenyl. Thus, 3.3 g of a pale yellow powder were obtained. The powder was identified as the Compound H13 by FD-MS analysis.

Synthesis Embodiment 14 (Synthesis of Compound H14)

A reaction was performed in the same manner as in Synthesis Embodiment 1 except that: 5.8 g of the Intermediate 11 were used instead of the Intermediate 10; and 2.7 g of the Intermediate 18 were used instead of 4-bromo-p-terphenyl. Thus, 3.6 g of a pale yellow powder were obtained. The powder was identified as the Compound H14 by FD-MS analysis.

Synthesis Embodiment 15 (Synthesis of Compound H15)

A reaction was performed in the same manner as in Synthesis Embodiment 1 except that 1.6 g of tris(4-bromophenyl)amine were used instead 4-bromo-p-terphenyl. Thus, 2.3 g of a pale yellow powder were obtained. The powder was identified as the Compound H15 by FD-MS analysis.

Synthesis Embodiment 16 (Synthesis of Compound H16)

A reaction was performed in the same manner as in Synthesis Embodiment 1 except that: 6.5 g of the Intermediate 13 were used instead of the Intermediate 10; and 6.5 g of the Intermediate 19 were used instead of 4-bromo-p-terphenyl. Thus, 3.6 g of a pale yellow powder were obtained. The powder was identified as the Compound H16 by FD-MS analysis.

Synthesis Embodiment 17 (Synthesis of Compound H17)

A reaction was performed in the same manner as in Synthesis Embodiment 1 except that: 5.8 g of the Intermediate 11 were used instead of the Intermediate 10; and 3.2 g of the Intermediate 21 were used instead of 4-bromo-p-terphenyl. Thus, 5.7 g of a pale yellow powder were obtained. The powder was identified as the Compound H17 by FD-MS analysis.

Synthesis Embodiment 18 (Synthesis of Compound H18)

A reaction was performed in the same manner as in Synthesis Embodiment 1 except that: 5.8 g of the Intermediate 11 were used instead of the Intermediate 10; and 3.2 g of the Intermediate 24 were used instead of 4-bromo-p-terphenyl. Thus, 4.8 g of a pale yellow powder were obtained. The powder was identified as the Compound H18 by FD-MS analysis.

Synthesis Embodiment 19 (Synthesis of Compound H19)

A reaction was performed in the same manner as in Synthesis Embodiment 1 except that 3.2 g of the Intermediate 21 were used instead of 4-bromo-p-terphenyl. Thus, 6.3 g of a pale yellow powder were obtained. The powder was identified as the Compound H19 by FD-MS analysis.

Synthesis Embodiment 20 (Synthesis of Compound H20)

A reaction was performed in the same manner as in Synthesis Embodiment 1 except that 3.2 g of the Intermediate 24 were used instead of 4-bromo-p-terphenyl. Thus, 5.9 g of a pale yellow powder were obtained. The powder was identified as the Compound H₂O by FD-MS analysis.

Synthesis Embodiment 21 (Synthesis of Compound H21)

A reaction was performed in the same manner as in Synthesis Embodiment 1 except that: 6.9 g of the Intermediate 16 were used instead of the Intermediate 10; and 3.2 g of the Intermediate 21 were used instead of 4-bromo-p-terphenyl. Thus, 6.3 g of a pale yellow powder were obtained. The powder was identified as the Compound H21 by FD-MS analysis.

Synthesis Embodiment 22 (Synthesis of Compound H22)

A reaction was performed in the same manner as in Synthesis Embodiment 1 except that: 6.9 g of the Intermediate 16 were used instead of the Intermediate 10; and 3.2 g of the Intermediate 24 were used instead of 4-bromo-p-terphenyl. Thus, 6.0 g of a pale yellow powder were obtained. The powder was identified as the Compound H22 by FD-MS analysis.

Synthesis Embodiment 23 (Synthesis of Compound H23)

A reaction was performed in the same manner as in Synthesis Embodiment 1 except that: 5.8 g of the Intermediate 11 were used instead of the Intermediate 10; and 2.5 g of the Intermediate 20 were used instead of 4-bromo-p-terphenyl. Thus, 4.5 g of a pale yellow powder were obtained. The powder was identified as the Compound H23 by FD-MS analysis.

Synthesis Embodiment 24 (Synthesis of Compound H24)

A reaction was performed in the same manner as in Synthesis Embodiment 1 except that: 5.8 g of the Intermediate 11 were used instead of the Intermediate 10; and 2.5 g of the Intermediate 22 were used instead of 4-bromo-p-terphenyl. Thus, 4.0 g of a pale yellow powder were obtained. The powder was identified as the Compound H24 by FD-MS analysis.

Synthesis Embodiment 25 (Synthesis of Compound H25)

A reaction was performed in the same manner as in Synthesis Embodiment 1 except that 2.5 g of the Intermediate 20 were used instead of 4-bromo-p-terphenyl. Thus, 4.2 g of a pale yellow powder were obtained. The powder was identified as the Compound H25 by FD-MS analysis.

Synthesis Embodiment 26 (Synthesis of Compound H26)

A reaction was performed in the same manner as in Synthesis Embodiment 1 except that: 2.5 g of the Intermediate 22 were used instead of 4-bromo-p-terphenyl. Thus, 4.3 g of a pale yellow powder were obtained. The powder was identified as the Compound H26 by FD-MS analysis.

Synthesis Embodiment 27 (Synthesis of Compound H27)

A reaction was performed in the same manner as in Synthesis Embodiment 1 except that: 6.9 g of the Intermediate 16 were used instead of the Intermediate 10; and 2.5 g of the Intermediate 20 were used instead of 4-bromo-p-terphenyl. Thus, 5.0 g of a pale yellow powder were obtained. The powder was identified as the Compound H27 by FD-MS analysis.

Synthesis Embodiment 28 (Synthesis of Compound H28)

A reaction was performed in the same manner as in Synthesis Embodiment 1 except that: 6.9 g of the Intermediate 16 were used instead of the Intermediate 10; and 2.5 g of the Intermediate 22 were used instead of 4-bromo-p-terphenyl. Thus, 4.7 g of a pale yellow powder were obtained. The powder was identified as the Compound H28 by FD-MS analysis.

Synthesis Embodiment 29 (Synthesis of Compound H29)

A reaction was performed in the same manner as in Synthesis Embodiment 1 except that: 6.5 g of the Intermediate 26 were used instead of the Intermediate 10; and 2.3 g of 4-bromobiphenyl were used instead of 4-bromo-p-terphenyl. Thus, 5.7 g of a pale yellow powder were obtained. The powder was identified as the Compound H29 by FD-MS analysis.

Synthesis Embodiment 30 (Synthesis of Compound H30)

A reaction was performed in the same manner as in Synthesis Embodiment 1 except that 6.5 g of the Intermediate 26 were used instead of the Intermediate 10. Thus, 6.1 g of a pale yellow powder were obtained. The powder was identified as the Compound H30 by FD-MS analysis.

Synthesis Embodiment 31 (Synthesis of Compound H31)

A reaction was performed in the same manner as in Synthesis Embodiment 1 except that: 6.5 g of the Intermediate 26 were used instead of the Intermediate 10; and 3.2 g of the Intermediate 21 were used instead of 4-bromo-p-terphenyl. Thus, 6.3 g of a pale yellow powder were obtained. The powder was identified as the Compound H31 by FD-MS analysis.

Synthesis Embodiment 32 (Synthesis of Compound H32)

A reaction was performed in the same manner as in Synthesis Embodiment 1 except that: 6.5 g of the Interme-

Synthesis Embodiment 33 (Synthesis of Compound H33)

A reaction was performed in the same manner as in Synthesis Embodiment 1 except that: 6.5 g of the Intermediate 26 were used instead of the Intermediate 10; and 2.5 g of the Intermediate 20 were used instead of 4-bromo-p-terphenyl. Thus, 5.9 g of a pale yellow powder were obtained. The powder was identified as the Compound H33 by FD-MS analysis.

Synthesis Embodiment 34 (Synthesis of Compound H34)

A reaction was performed in the same manner as in Synthesis Embodiment 1 except that: 6.5 g of the Intermediate 26 were used instead of the Intermediate 10; and 2.5 g of the Intermediate 22 were used instead of 4-bromo-p-terphenyl. Thus, 4.3 g of a pale yellow powder were obtained. The powder was identified as the Compound H34 by FD-MS analysis.

Synthesis Embodiment 35 (Synthesis of Compound H35)

A reaction was performed in the same manner as in Synthesis Embodiment 1 except that: 5.8 g of the Intermediate 11 were used instead of the Intermediate 10; and 1.6 g of bromobenzene were used instead of 4-bromo-p-terphenyl. Thus, 4.6 g of a pale yellow powder were obtained. The powder was identified as the Compound H35 by FD-MS analysis.

Synthesis Embodiment 36 (Synthesis of Compound H36)

A reaction was performed in the same manner as in Synthesis Embodiment 1 except that 1.6 g of bromobenzene were used instead of 4-bromo-p-terphenyl. Thus, 5.0 g of a pale yellow powder were obtained. The powder was identified as the Compound H36 by FD-MS analysis.

Synthesis Embodiment 37 (Synthesis of Compound H37)

A reaction was performed in the same manner as in Synthesis Embodiment 1 except that: 6.9 g of the Intermediate 16 were used instead of the Intermediate 10; and 1.6 g of bromobenzene were used instead of 4-bromo-p-terphenyl. Thus, 5.4 g of a pale yellow powder were obtained. The powder was identified as the Compound H37 by FD-MS analysis.

Synthesis Embodiment 38 (Synthesis of Compound H38)

A reaction was performed in the same manner as in Synthesis Embodiment 1 except that: 5.8 g of the Intermediate 11 were used instead of the Intermediate 10; and 2.3 g of 4-bromophenyl were used instead of 4-bromo-p-terphenyl. Thus, 5.0 g of a pale yellow powder were obtained. The powder was identified as the Compound H38 by FD-MS analysis.

Synthesis Embodiment 39 (Synthesis of Compound H39)

A reaction was performed in the same manner as in Synthesis Embodiment 1 except that: 6.9 g of the Intermediate 16 were used instead of the Intermediate 10; and 2.3 g of 4-bromophenyl were used instead of 4-bromo-p-terphenyl. Thus, 5.8 g of a pale yellow powder were obtained. The powder was identified as the Compound H39 by FD-MS analysis.

Synthesis Embodiment 40 (Synthesis of Compound H40)

A reaction was performed in the same manner as in Synthesis Embodiment 1 except that 2.1 g of 1-bromonaphthalene were used instead of 4-bromo-p-terphenyl. Thus, 5.3 g of a pale yellow powder were obtained. The powder was identified as the Compound H40 by FD-MS analysis.

Synthesis Embodiment 41 (Synthesis of Compound H41)

A reaction was performed in the same manner as in Synthesis Embodiment 1 except that: 6.9 g of the Intermediate 16 were used instead of the Intermediate 10; and 2.1 g of 1-bromonaphthalene were used instead of 4-bromo-p-terphenyl. Thus, 5.4 g of a pale yellow powder were obtained. The powder was identified as the Compound H41 by FD-MS analysis.

Synthesis Embodiment 42 (Synthesis of Compound H42)

A reaction was performed in the same manner as in Synthesis Embodiment 1 except that: 5.8 g of the Intermediate 11 were used instead of the Intermediate 10; and 3.2 g of the Intermediate 7 were used instead of 4-bromo-p-terphenyl. Thus, 5.6 g of a pale yellow powder were obtained. The powder was identified as the Compound H42 by FD-MS analysis.

Synthesis Embodiment 43 (Synthesis of Compound H43)

A reaction was performed in the same manner as in Synthesis Embodiment 1 except that: 6.5 g of the Intermediate 26 were used instead of the Intermediate 10; and 1.6 g of bromobenzene were used instead of 4-bromo-p-terphenyl. Thus, 4.9 g of a pale yellow powder were obtained. The powder was identified as the Compound H43 by FD-MS analysis.

Synthesis Embodiment 44 (Synthesis of Compound H44)

A reaction was performed in the same manner as in Synthesis Embodiment 1 except that: 6.5 g of the Intermediate 26 were used instead of the Intermediate 10; and 2.1 g of 1-bromonaphthalene were used instead of 4-bromo-p-terphenyl. Thus, 5.3 g of a pale yellow powder were obtained. The powder was identified as the Compound H44 by FD-MS analysis.

Synthesis Embodiment 45 (Synthesis of Compound H45)

A reaction was performed in the same manner as in Synthesis Embodiment 1 except that: 6.5 g of the Intermediate 13 were used instead of the Intermediate 10; and 3.2 g of the Intermediate 7 were used instead of 4-bromo-p-terphenyl. Thus, 6.3 g of a pale yellow powder were obtained. The powder was identified as the Compound H45 by FD-MS analysis.

Synthesis Embodiment 46 (Synthesis of Compound H46)

A reaction was performed in the same manner as in Synthesis Embodiment 1 except that 3.2 g of the Intermediate 7 were used instead of 4-bromo-p-terphenyl. Thus, 6.1 g of a pale yellow powder were obtained. The powder was identified as the Compound H46 by FD-MS analysis.

Synthesis Embodiment 47 (Synthesis of Compound H47)

A reaction was performed in the same manner as in Synthesis Embodiment 1 except that: 6.9 g of the Intermediate 16 were used instead of the Intermediate 10; and 3.2 g of the Intermediate 7 were used instead of 4-bromo-p-terphenyl. Thus, 6.3 g of a pale yellow powder were obtained. The powder was identified as the Compound H47 by FD-MS analysis.

Synthesis Embodiment 48 (Synthesis of Compound H48)

A reaction was performed in the same manner as in Synthesis Embodiment 1 except that: 6.5 g of the Intermediate 26 were used instead of the Intermediate 10; and 3.2 g of the Intermediate 7 were used instead of 4-bromo-p-terphenyl. Thus, 6.0 g of a pale yellow powder were obtained. The powder was identified as the Compound H48 by FD-MS analysis.

Synthesis Embodiment 49 (Synthesis of Compound H49)

A reaction was performed in the same manner as in Synthesis Embodiment 1 except that: 5.8 g of the Intermediate 11 were used instead of the Intermediate 10; and 2.8 g of the Intermediate 28 were used instead of 4-bromo-p-terphenyl. Thus, 5.7 g of a pale yellow powder were obtained. The powder was identified as the Compound H49 by FD-MS analysis.

Synthesis Embodiment 50 (Synthesis of Compound H50)

A reaction was performed in the same manner as in Synthesis Embodiment 1 except that 2.8 g of the Intermediate 28 were used instead of 4-bromo-p-terphenyl. Thus, 6.4 g of a pale yellow powder were obtained. The powder was identified as the Compound H50 by FD-MS analysis.

Synthesis Embodiment 51 (Synthesis of Compound H51)

A reaction was performed in the same manner as in Synthesis Embodiment 1 except that: 6.9 g of the Intermediate 16 were used instead of the Intermediate 10; and 2.8 g of the Intermediate 28 were used instead of 4-bromo-p-terphenyl. Thus, 5.3 g of a pale yellow powder were obtained. The powder was identified as the Compound H51 by FD-MS analysis.

Synthesis Embodiment 52 (Synthesis of Compound H52)

A reaction was performed in the same manner as in Synthesis Embodiment 1 except that: 6.5 g of the Intermediate 26 were used instead of the Intermediate 10; and 2.8 g of the Intermediate 28 were used instead of 4-bromo-p-terphenyl. Thus, 6.3 g of a pale yellow powder were obtained. The powder was identified as the Compound H52 by FD-MS analysis.

Synthesis Embodiment 53 (Synthesis of Compound H53)

A reaction was performed in the same manner as in Synthesis Embodiment 1 except that: 5.8 g of the Intermediate 11 were used instead of the Intermediate 10; and 2.5 g of the Intermediate 27 were used instead of 4-bromo-p-terphenyl. Thus, 5.3 g of a pale yellow powder were obtained. The powder was identified as the Compound H53 by FD-MS analysis.

Synthesis Embodiment 54 (Synthesis of Compound H54)

A reaction was performed in the same manner as in Synthesis Embodiment 1 except that 2.5 g of the Intermediate 27 were used instead of 4-bromo-p-terphenyl. Thus, 5.3 g of a pale yellow powder were obtained. The powder was identified as the Compound H54 by FD-MS analysis.

Synthesis Embodiment 55 (Synthesis of Compound H55)

A reaction was performed in the same manner as in Synthesis Embodiment 1 except that: 6.9 g of the Intermediate 16 were used instead of the Intermediate 10; and 2.5 g of the Intermediate 27 were used instead of 4-bromo-p-terphenyl. Thus, 5.8 g of a pale yellow powder were obtained. The powder was identified as the Compound H55 by FD-MS analysis.

Synthesis Embodiment 56 (Synthesis of Compound H56)

A reaction was performed in the same manner as in Synthesis Embodiment 1 except that: 6.5 g of the Intermediate 26 were used instead of the Intermediate 10; and 2.5 g of the Intermediate 27 were used instead of 4-bromo-p-terphenyl. Thus, 5.0 g of a pale yellow powder were obtained. The powder was identified as the Compound H56 by FD-MS analysis.

The Intermediates 1 to 28 synthesized in Synthesis Examples 1 to 28 described in the foregoing and the Compounds H1 to H56 each serving as the aromatic amine derivative of the present invention synthesized in Synthesis Embodiments 1 to 56 are as shown below.

[Chem. 53]
Intermediate1
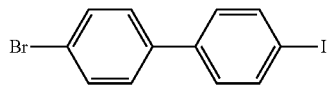
Intermediate2
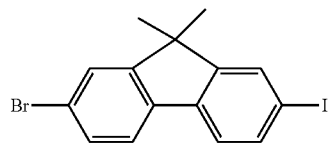
Intermediate3
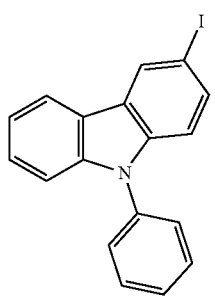
Intermediate4
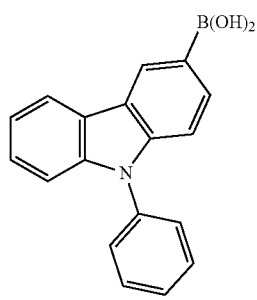
Intermediate5
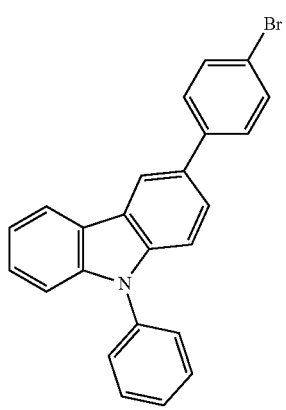
Intermediate6
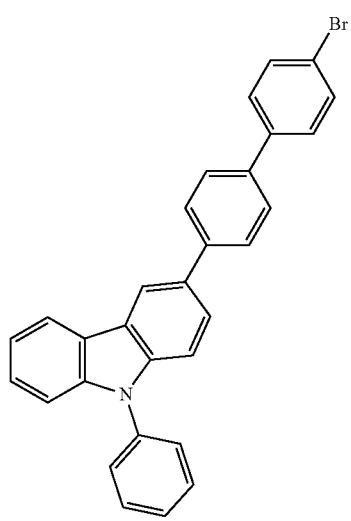
Intermediate7
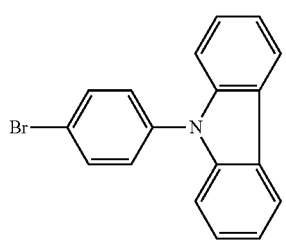
Intermediate8
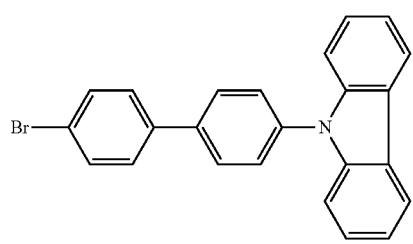

-continued
Intermediate9
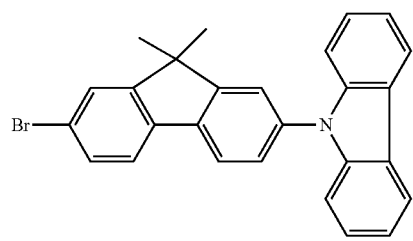
Intermediate10
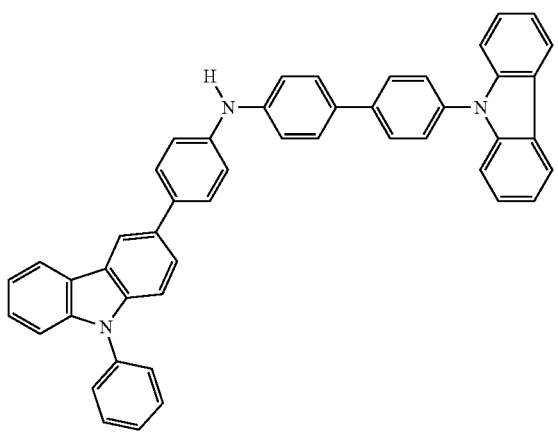
Intermediate11
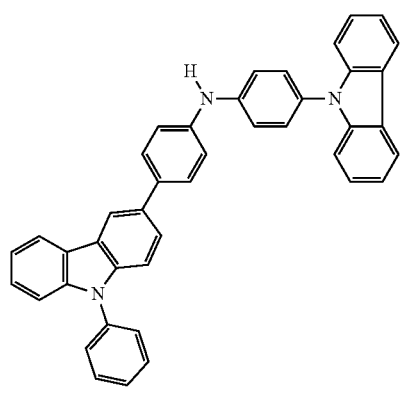
Intermediate12
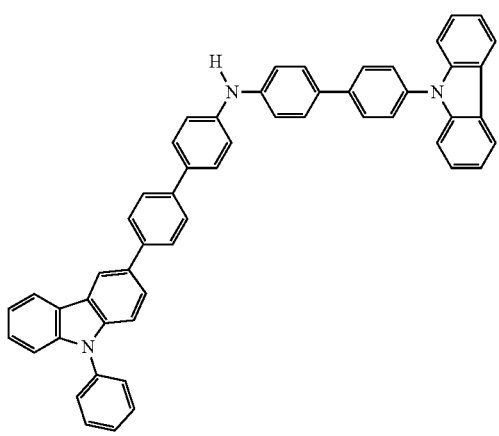
Intermediate13
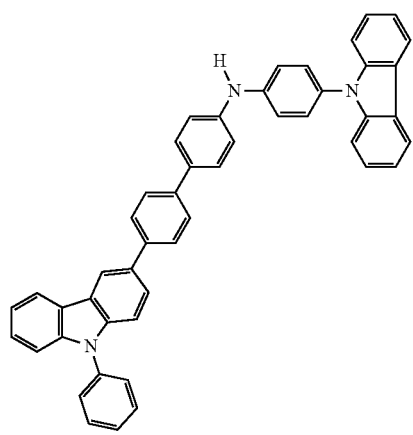
Intermediate14
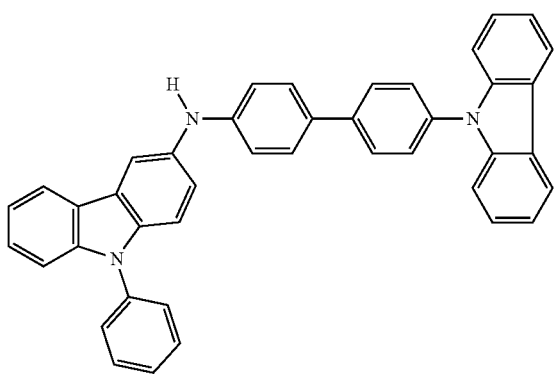

-continued
Intermediate15
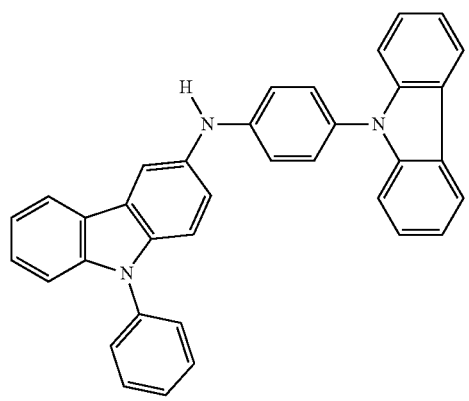
Intermediate16
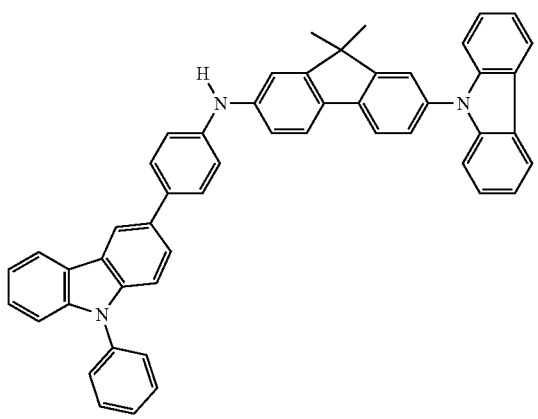
Intermediate17
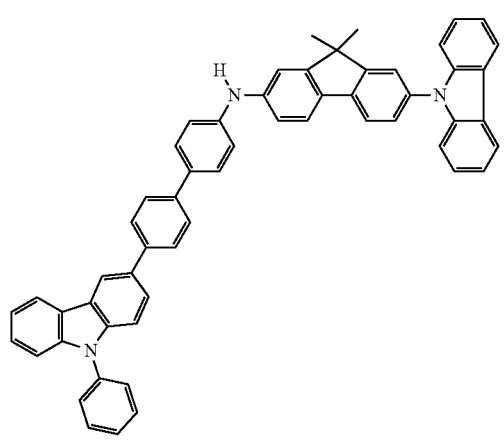
[Chem. 54]
Intermediate18
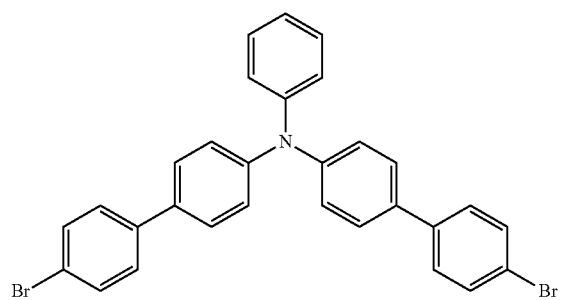
Intermediate19
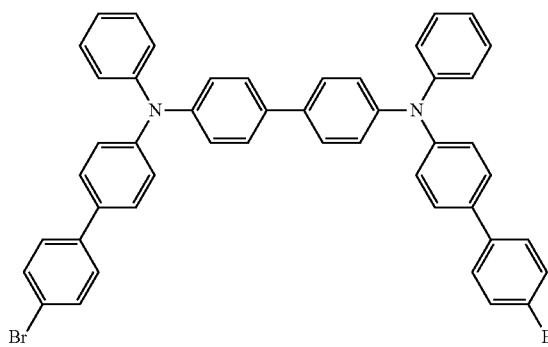
Intermediate20
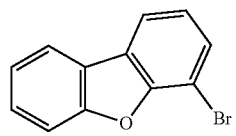
Intermediate21
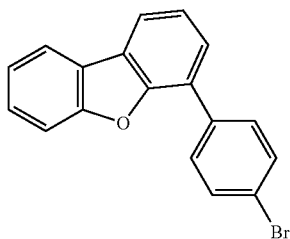

-continued
Intermediate22
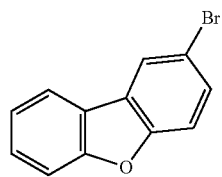
Intermediate23
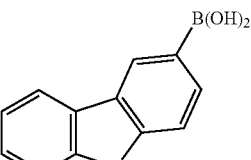
Intermediate24
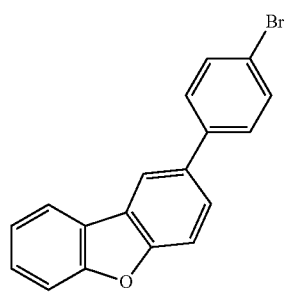
Intermediate25
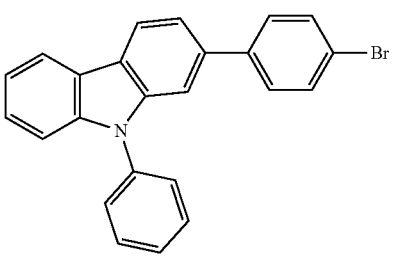
Intermediate26
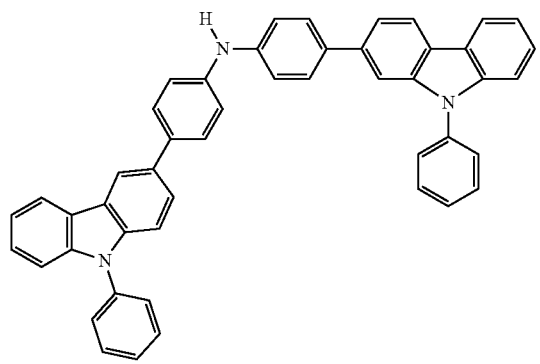
Intermediate27
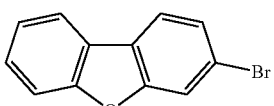
Intermediate28
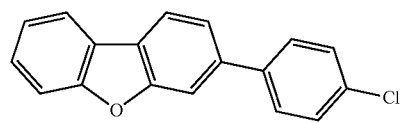
[Chem. 55]
H1
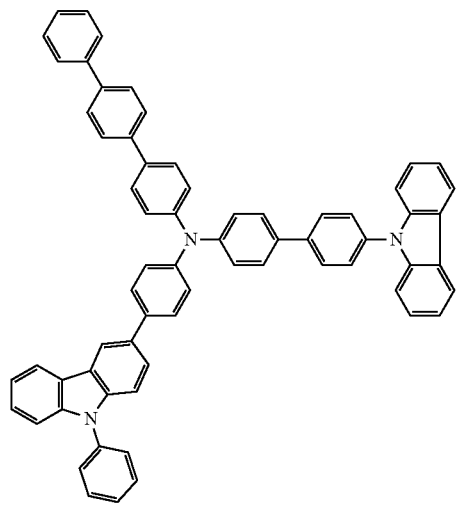
H2
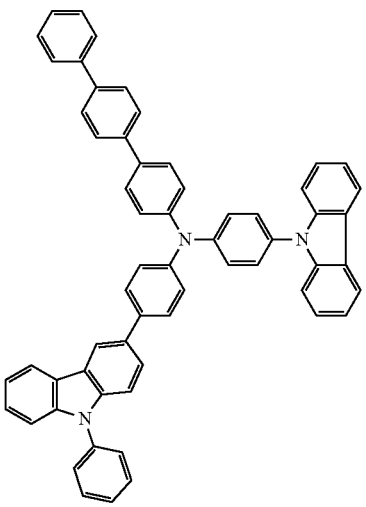

-continued
H3
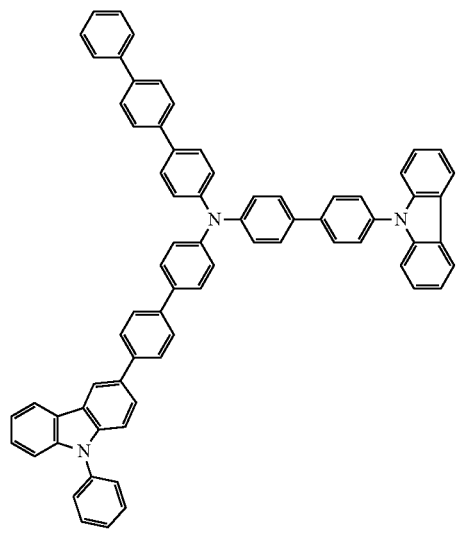
H4
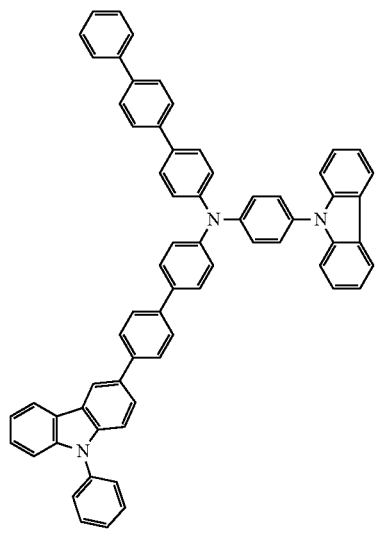
H5
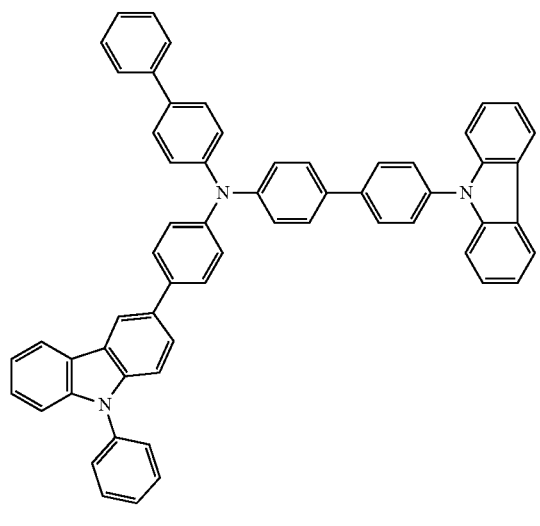
H6
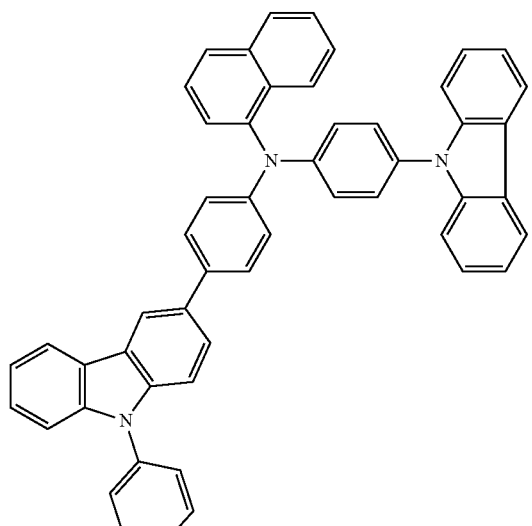
H7
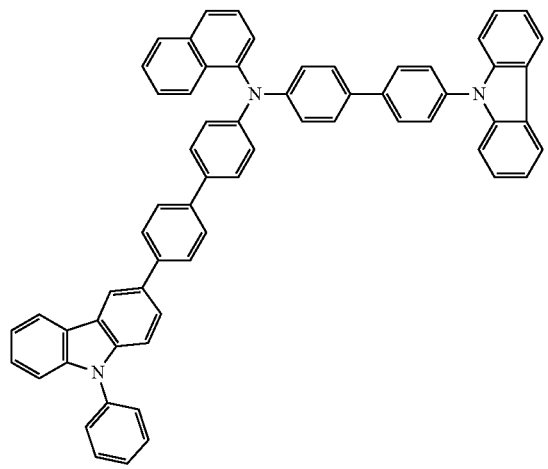
H8
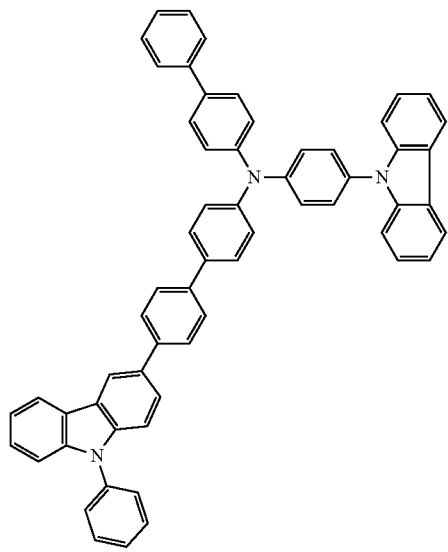

H9
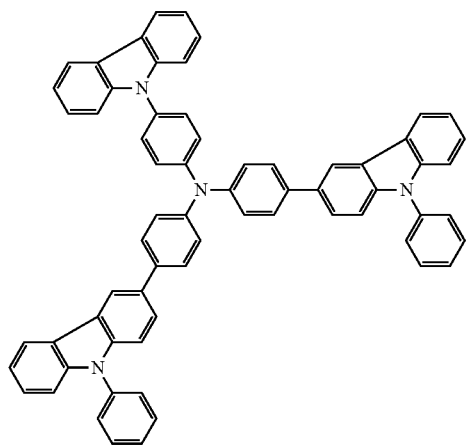
H10
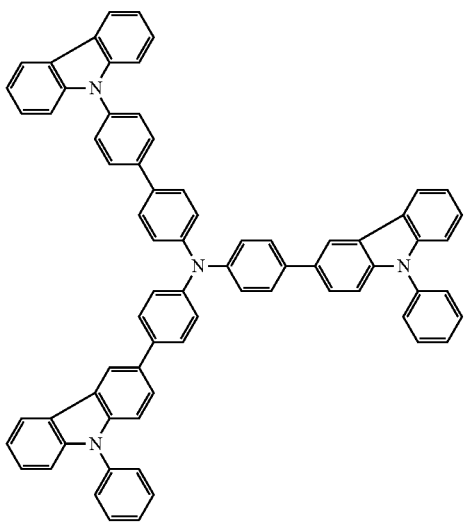
H11
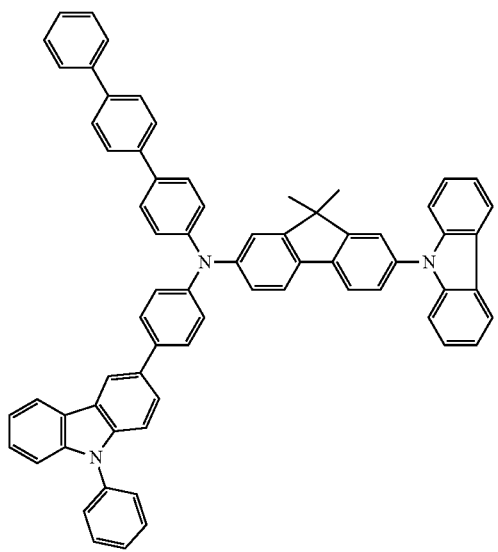
H12
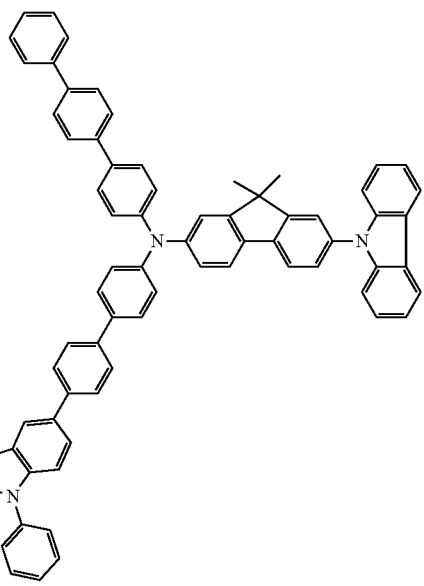
[Chem. 56]
H13
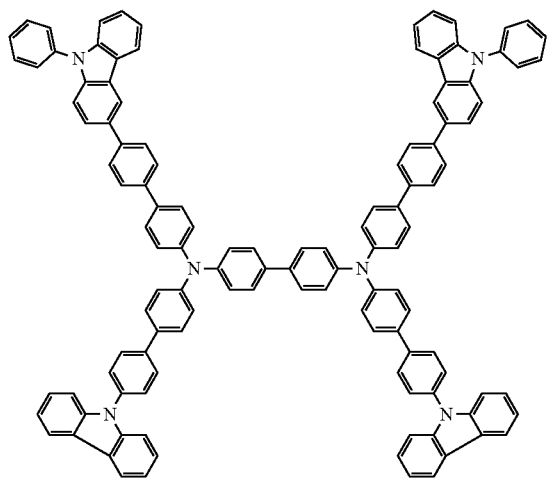

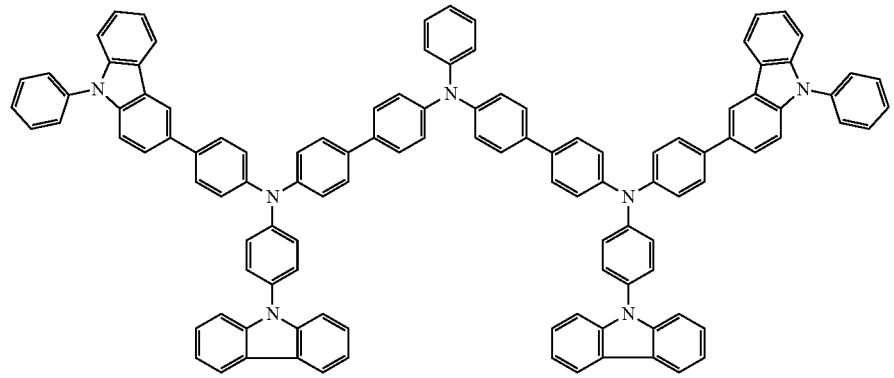
H14
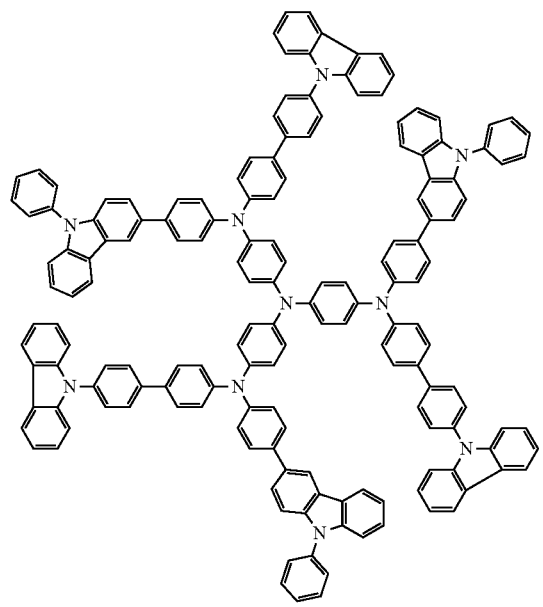
H15
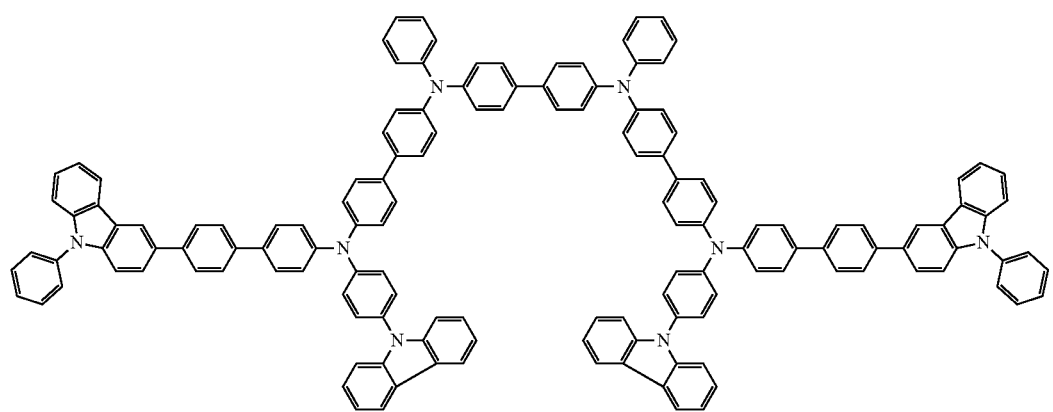
H16

[Chem. 57]
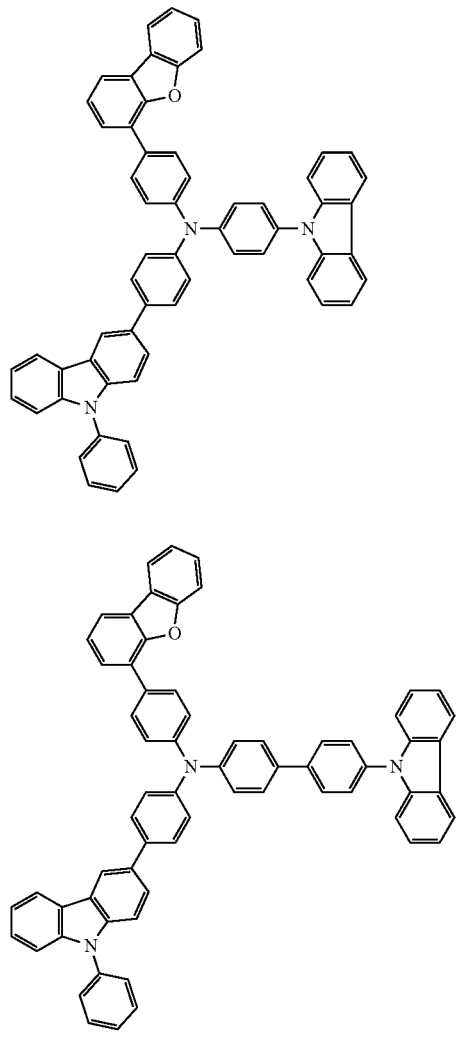
H17
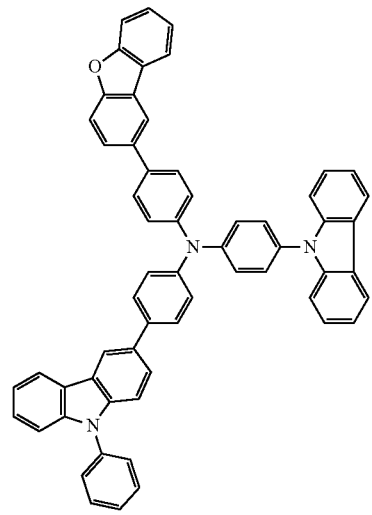
H18
H19
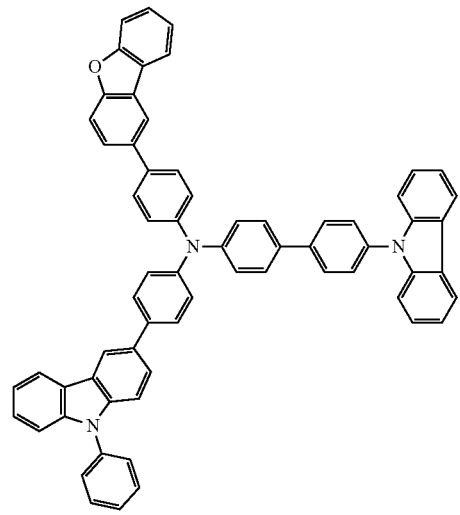
H20
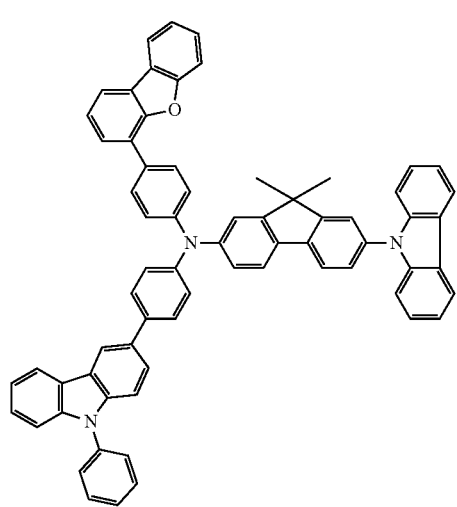
H21

-continued
| 391 | 392 |
|---|---|
| H22 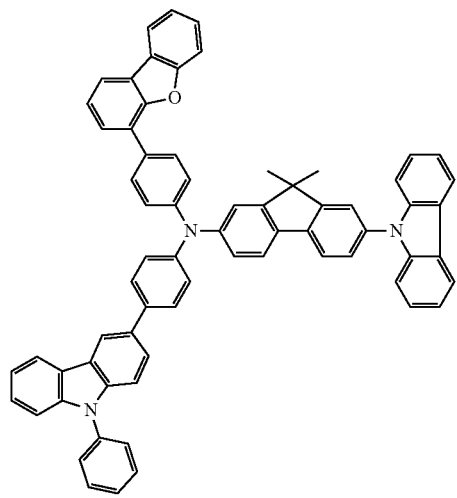 | H23 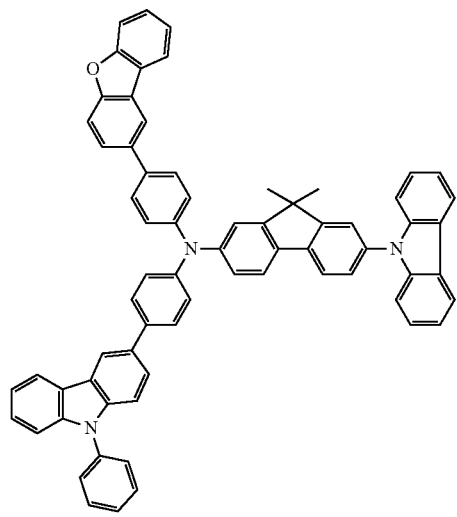 |
| H24 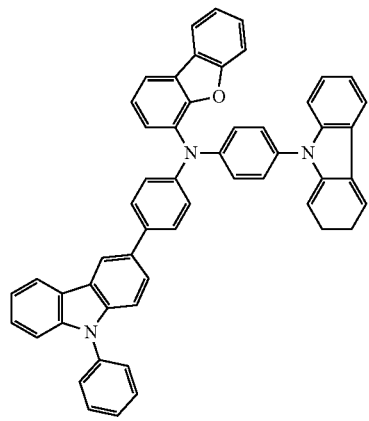 | H25 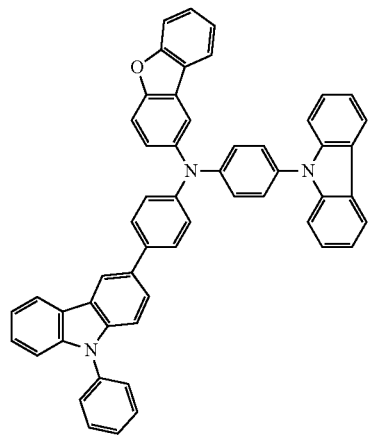 |
| H25 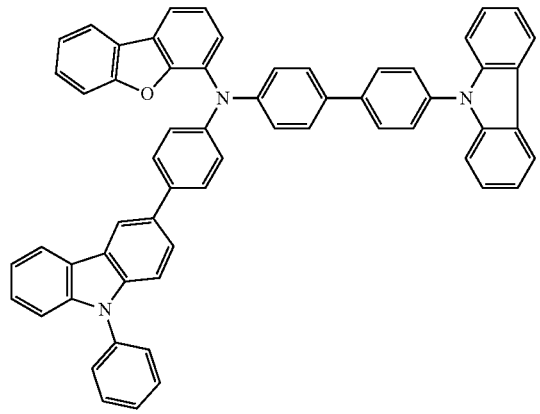 | H26 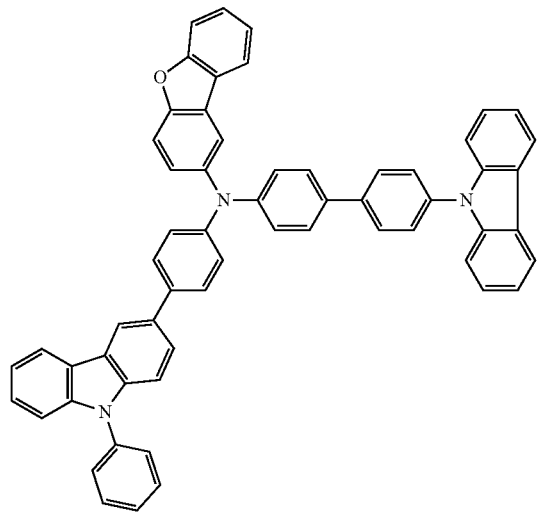 |

-continued
H27
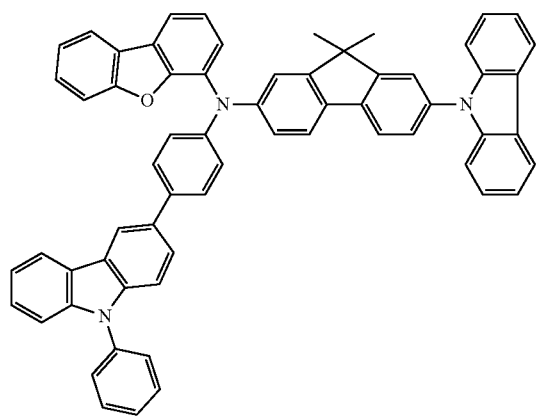
H28
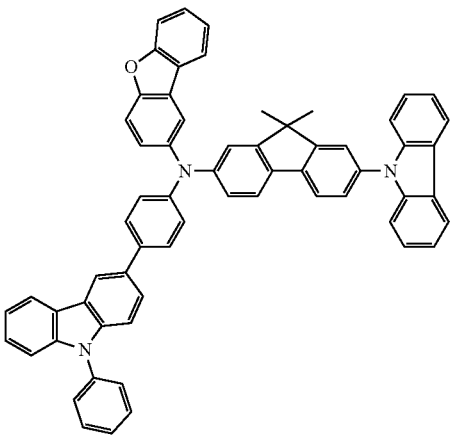
[Chem. 58]
H29
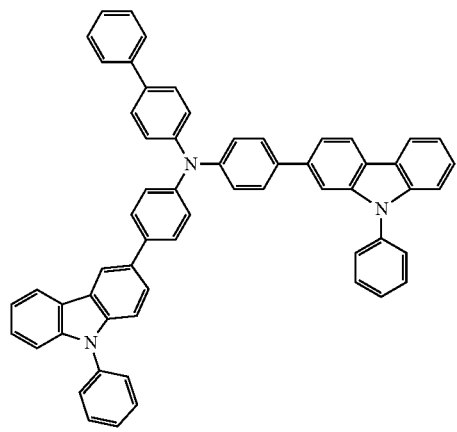
H30
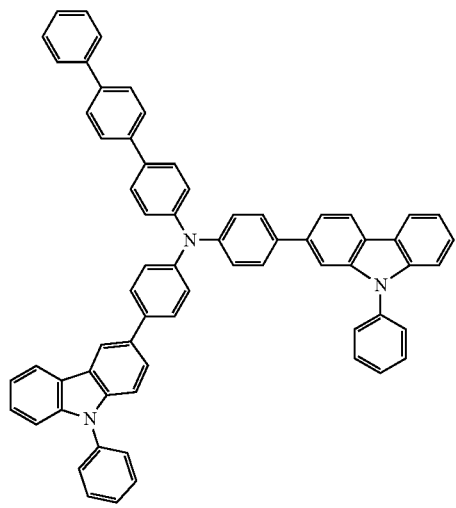
H31
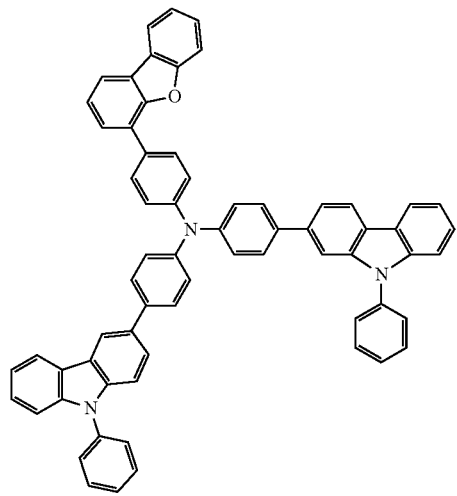
H32
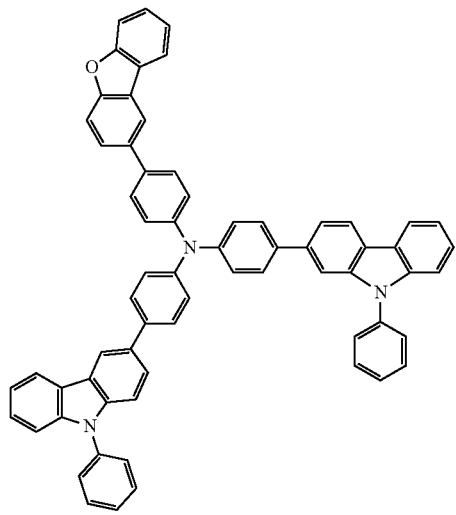

-continued
H33
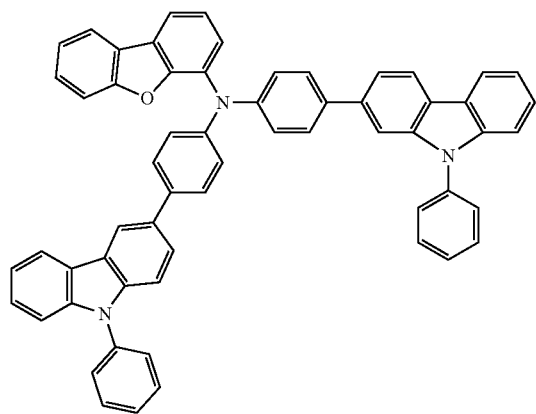
H34
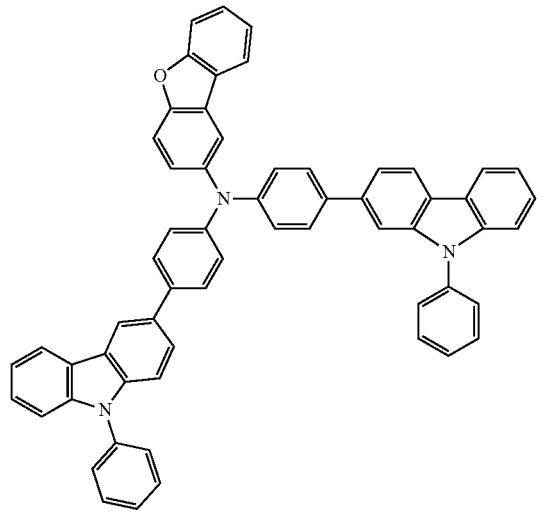
[Chem. 59]
H35
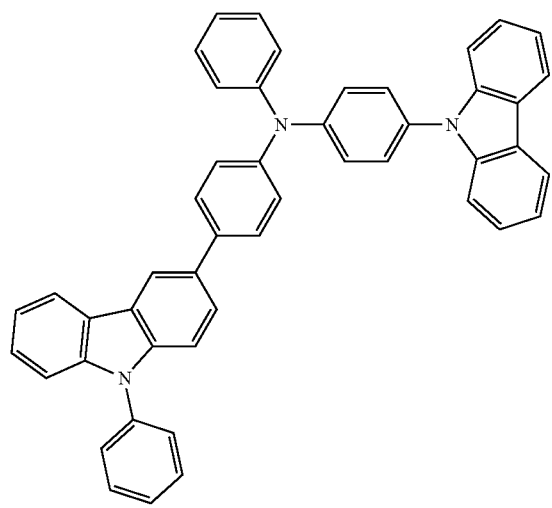
H36
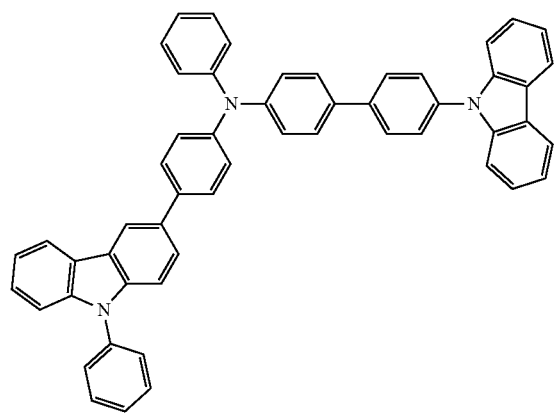
H37
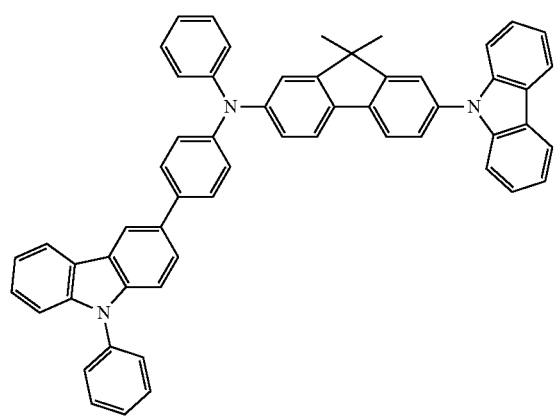
H38
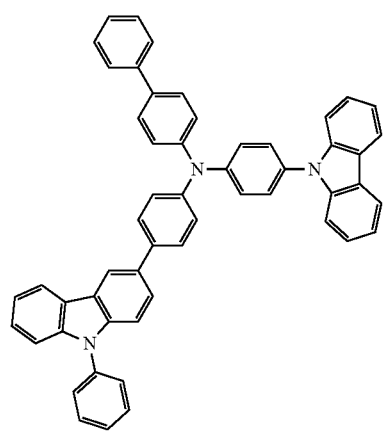

-continued
H39
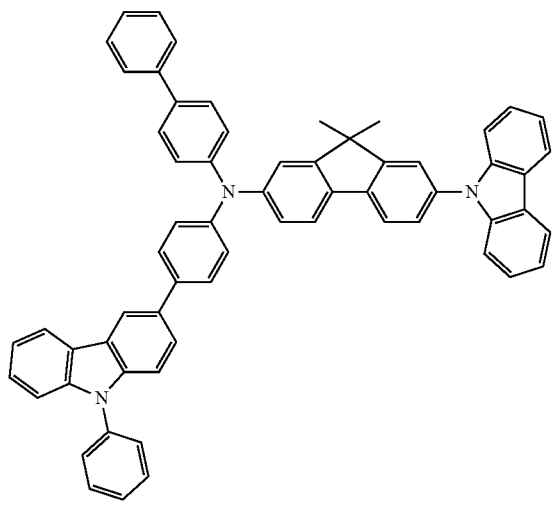
H40
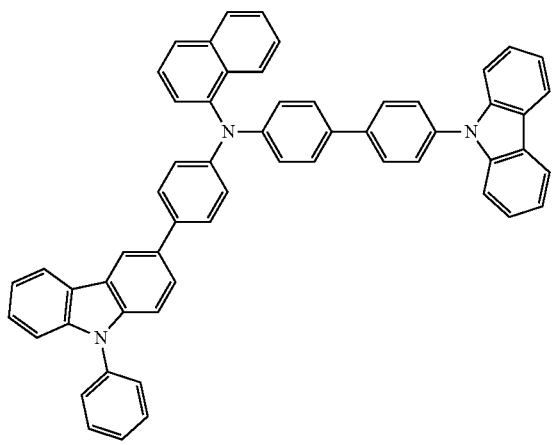
H41
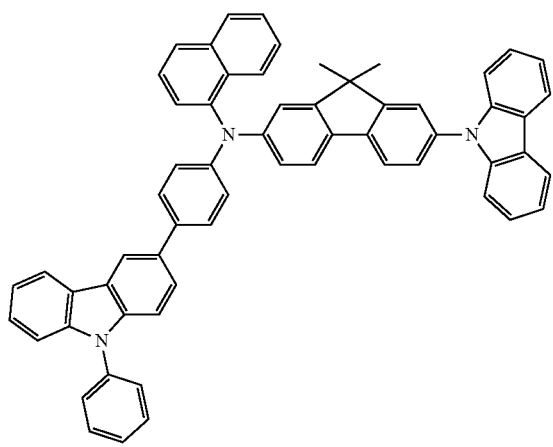
H42
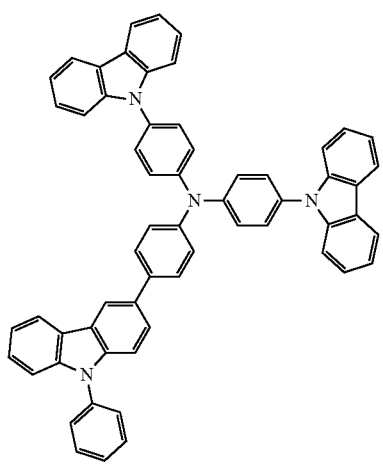
H43
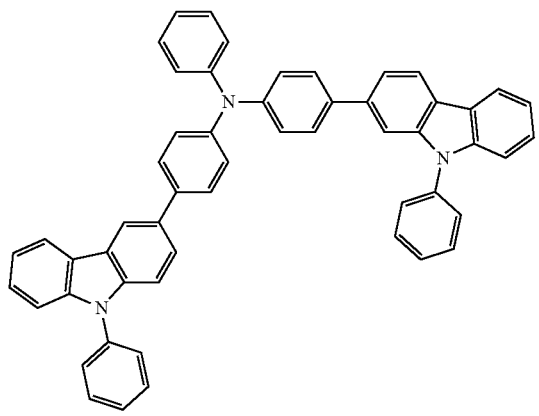
H44
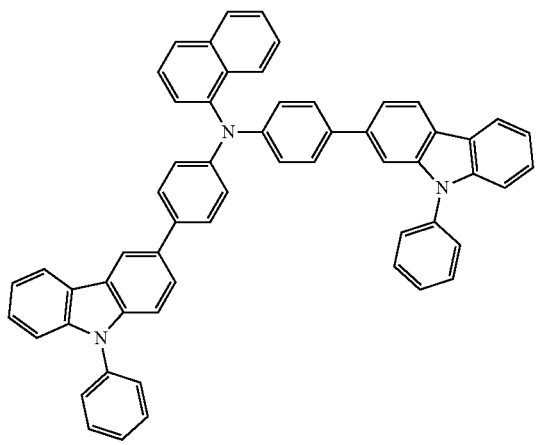

[Chem. 60]
H45 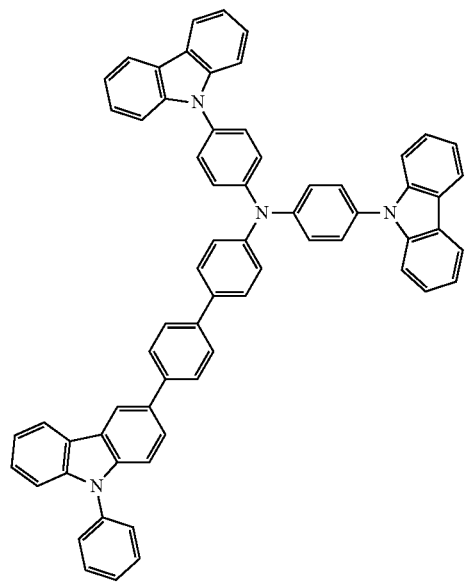
H46 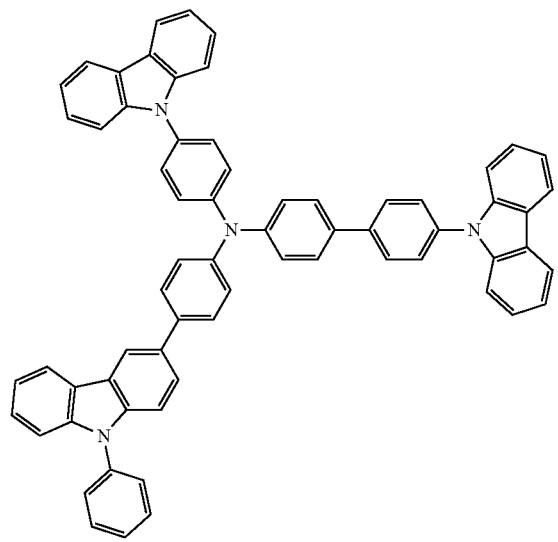
H47 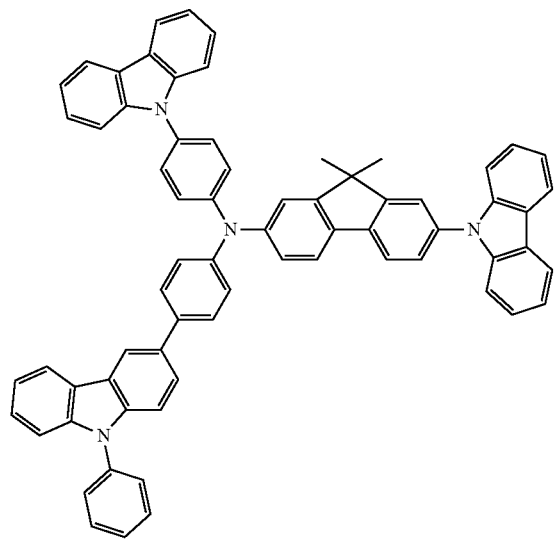
H48 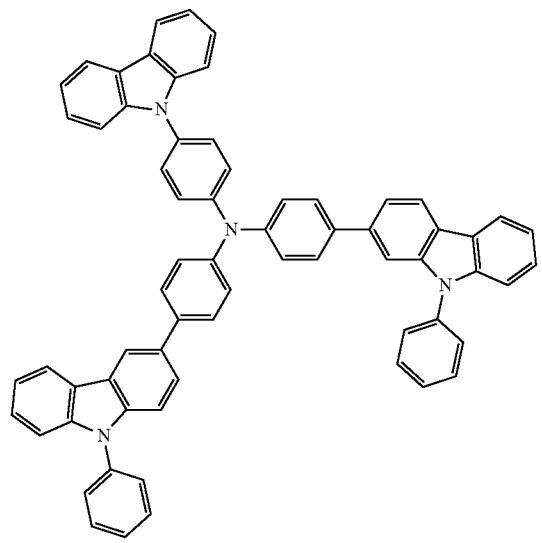

-continued
401 H49
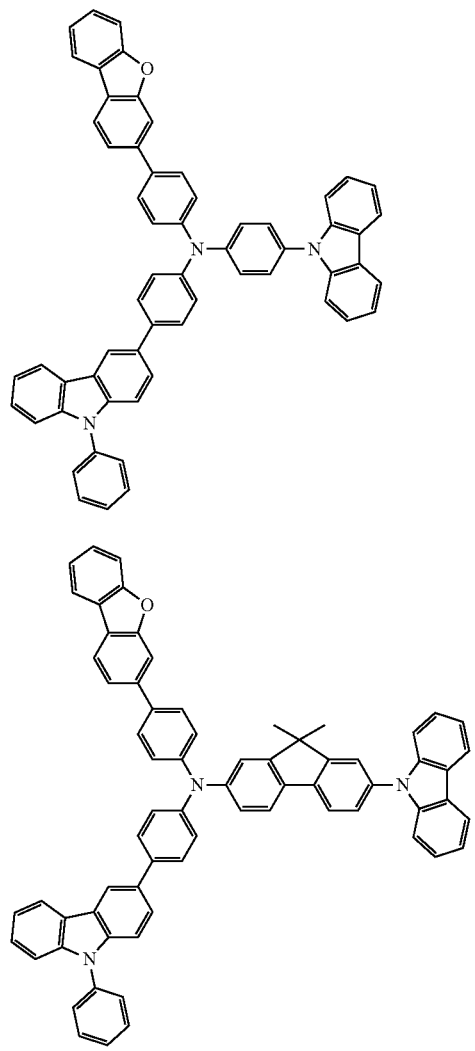
402 H50
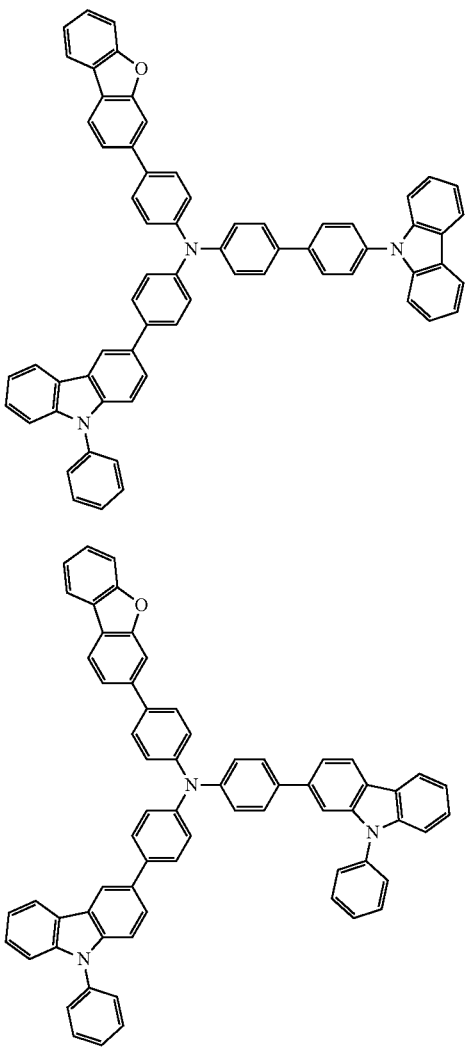
H51
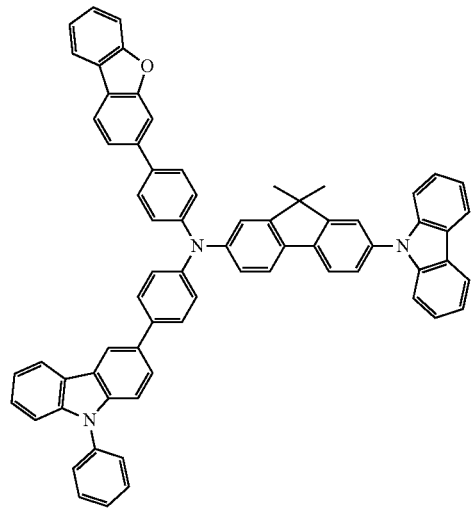
H52
H53
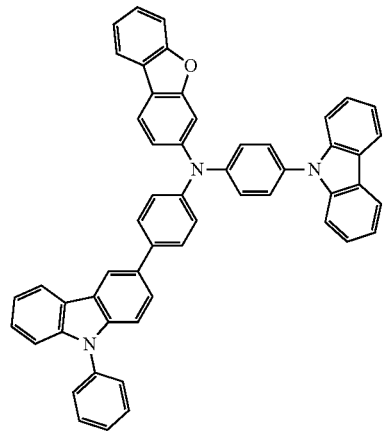
H54
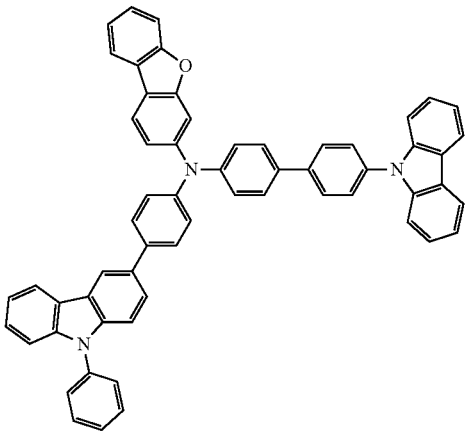

-continued

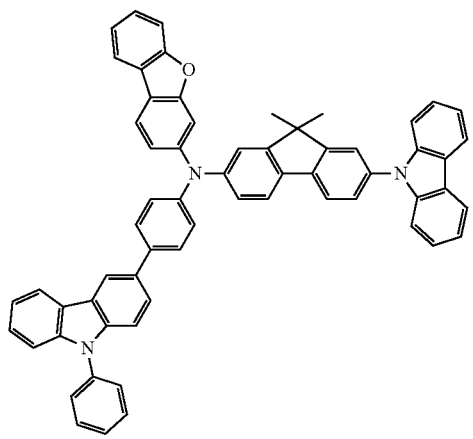
H55

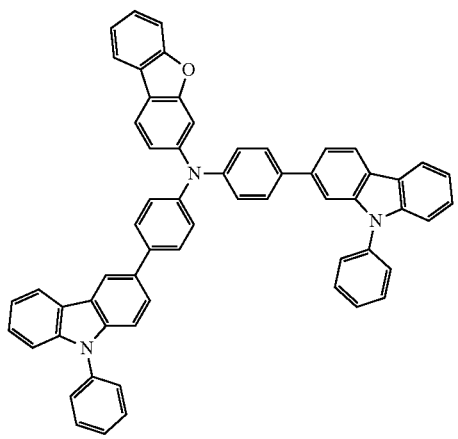
H56

Example 1 (Production of Organic EL Device)

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes. After that, the substrate was subjected to UV ozone cleaning for 30 minutes.

The glass substrate with the transparent electrode line after the cleaning was mounted on a substrate holder of a vacuum vapor deposition device. First, the following compound H232 was deposited from vapor on the surface on the side where the transparent electrode line was formed so as to cover the transparent electrode. Then, the H232 film having a thickness of 60 nm was formed as the hole injecting layer. The Compound H1 serving as a hole transporting material was deposited from vapor and formed into a hole transporting layer having a thickness of 20 nm on the H232 film. Further, the following compound EM1 was deposited from vapor and formed into a light emitting layer having a thickness of 40 nm. Simultaneously with this formation, the following amine compound D1 having a styryl group, as a light emitting molecule, was deposited from vapor in such a manner that a weight ratio between EM1 and D1 was 40:2.

The following Alq was formed into a film having a thickness of 10 nm on the resultant film. The film functions as an electron injecting layer. After that, Li serving as a reduction-causing dopant (Li source: manufactured by SAES Getters) and Alq were subjected to co-vapor deposition. Thus, an Alq:Li film (having a thickness of 10 nm) was formed as an electron injecting layer (cathode). Metal Al was deposited from vapor onto the Alq:Li film to form a metal cathode. Thus, an organic EL device was formed.

Next, the luminescent color of the resultant organic EL device was observed. Further, the driving voltage of the device and the half lifetime of its light emission when the device was driven with a DC constant current at an initial luminance of 5,000 cd/m² and room temperature was measured. Table 1 shows the results.

[Chem. 61]

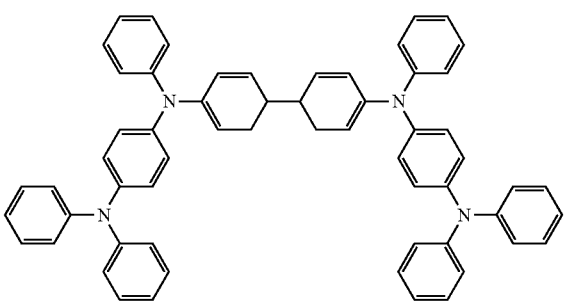
H232

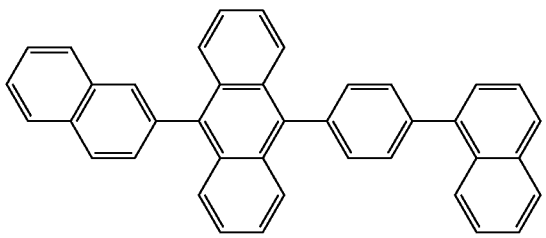
EM1

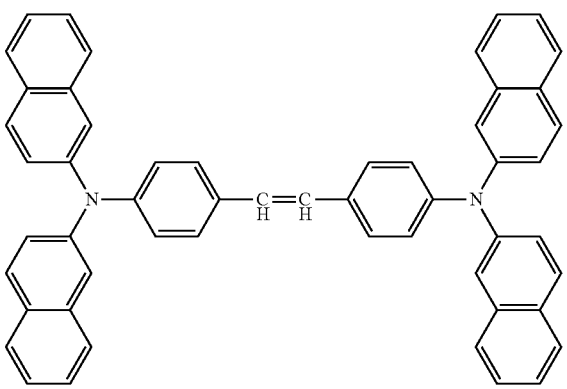
D1

-continued

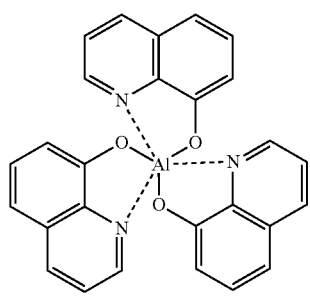

Alq

Examples 2 to 29 (Production of Organic EL Device)

Each organic EL device was produced in the same manner as in Example 1 except that the respective compounds shown in Table 1 were used as hole transporting materials instead of the Compound H1.

In the same manner as in Example 1, the luminescent color of the resultant organic EL device was observed, and the driving voltage of the device and the half lifetime of its light emission when the device was driven with a DC constant current at an initial luminance of 5,000 cd/m² and room temperature was measured. Table 1 shows the results.

Example 30 (Production of Organic EL Device)

An organic EL device was produced in the same manner as in Example 1 except that the following arylamine compound D2 was used instead of the amine compound D1 having a styryl group. Here, Me represents a methyl group.

In addition, in the same manner as in Example 1, the luminescent color of the resultant organic EL device was observed, and the driving voltage of the device and the half lifetime of its light emission when the device was driven with a DC constant current at an initial luminance of 5,000 cd/m² and room temperature was measured. Table 1 shows the results.

[Chem. 62]

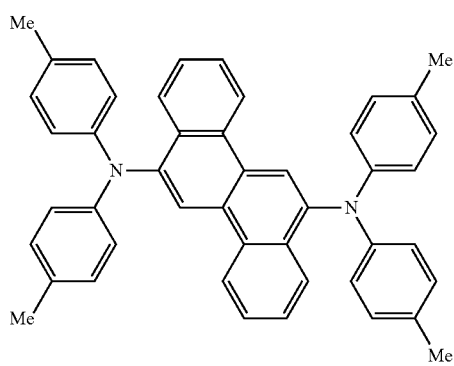

D2

Example 31 (Production of Organic EL Device)

An organic EL device was produced in the same manner as in Example 1 except that the following imidazole compound (ET1) was used as an electron transporting material instead of Alq.

In addition, in the same manner as in Example 1, the luminescent color of the resultant organic EL device was observed, and the driving voltage of the device and the half lifetime of its light emission when the device was driven with a DC constant current at an initial luminance of 5,000 cd/m² and room temperature was measured. Table 1 shows the results.

[Chem. 63]

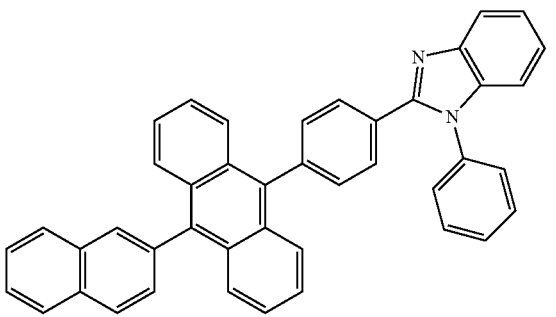

ET1

Example 32 (Production of Organic EL Device)

An organic EL device was produced in the same manner as in Example 1 except that the following acceptor compound (C-1) was formed into a film having a thickness of 10 nm instead of H232, and then the Compound H1 was formed into a film having a thickness of 70 nm.

In addition, in the same manner as in Example 1, the luminescent color of the resultant organic EL device was observed, and the driving voltage of the device and the half lifetime of its light emission when the device was driven with a DC constant current at an initial luminance of 5,000 cd/m² and room temperature was measured. Table 1 shows the results.

[Chem. 64]

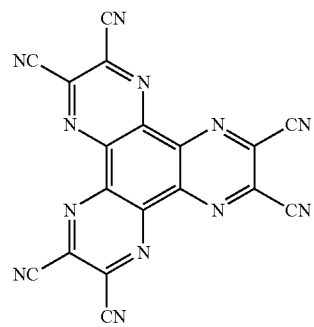

C-1

Comparative Examples 1 to 5

Organic EL devices were each produced in the same manner as in Example 1 except that the following Comparative Compounds 1 to 5 shown in Table 1 was used as a hole transporting material instead of the Compound H1.

In addition, in the same manner as in Example 1, the luminescent color of the resultant organic EL device was observed, and the driving voltage of the device and the half lifetime of its light emission when the device was driven with a DC constant current at an initial luminance of 5,000 cd/m² and room temperature was measured. Table 1 shows the results.
[Chem. 65]
Comparative Compound 1
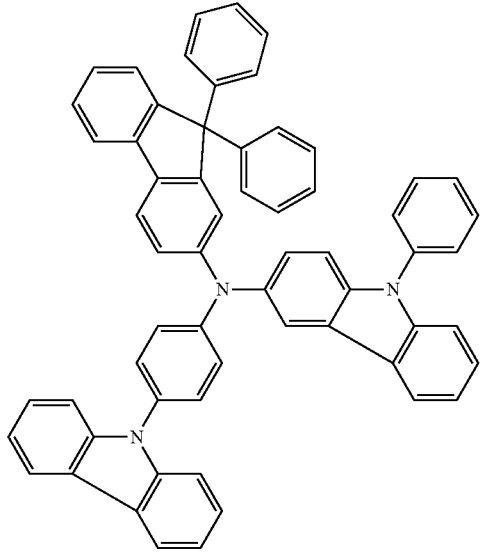
Comparative Compound 2
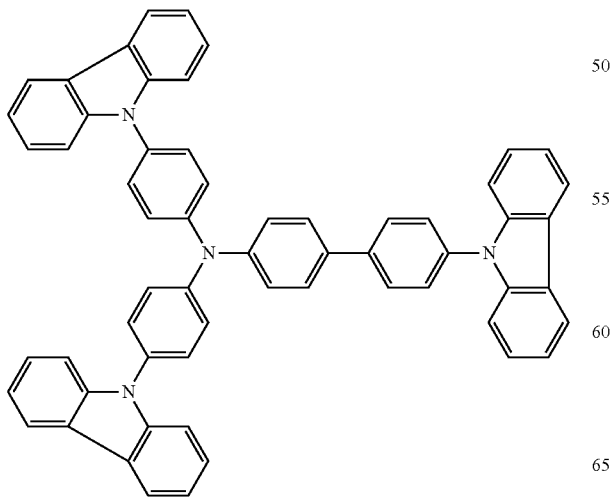
Comparative Compound 3
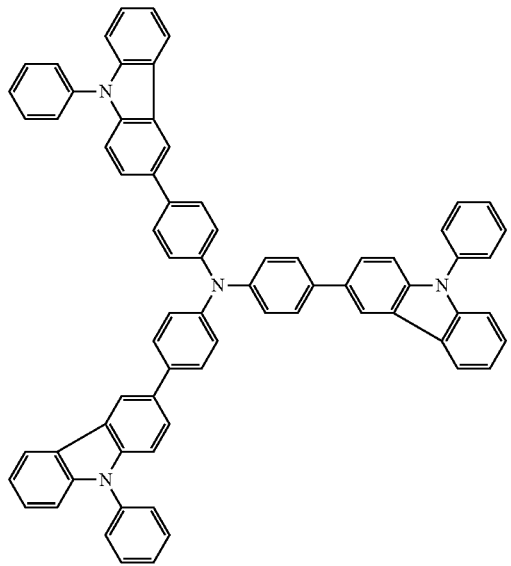
Comparative Compound 4
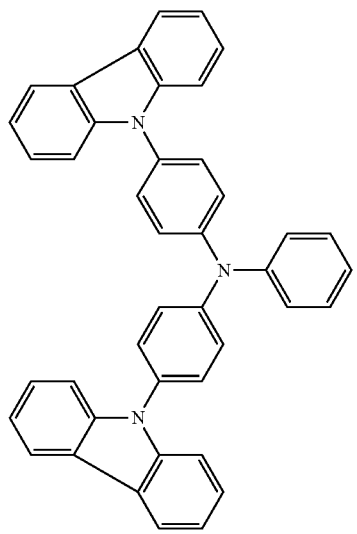
Comparative Compound 5
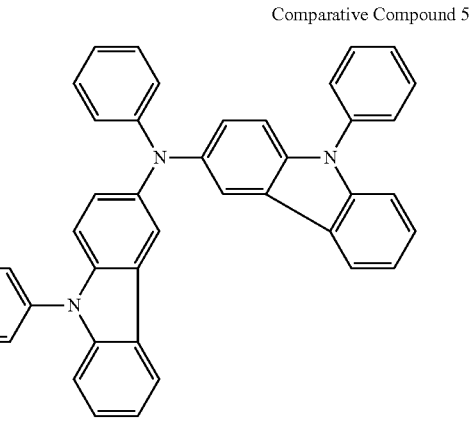

Comparative Example 6

An organic EL device was produced in the same manner as in Example 11 except that the Comparative Compound 1 was used as a hole transporting material instead of the Compound H1.

In addition, in the same manner as in Example 1, the luminescent color of the resultant organic EL device was observed, and the driving voltage of the device and the half lifetime of its light emission when the device was driven with a DC constant current at an initial luminance of 5,000 cd/m² and room temperature was measured. Table 1 shows the results.

Comparative Example 7

An organic EL device was produced in the same manner as in Example 12 except that the Comparative Compound 1 was used as a hole transporting material instead of the Compound H1.

In addition, in the same manner as in Example 1, the luminescent color of the resultant organic EL device was observed, and the driving voltage of the device and the half lifetime of its light emission when the device was driven with a DC constant current at an initial luminance of 5,000 cd/m² and room temperature was measured. Table 1 shows the results.

Comparative Example 8

An organic EL device was produced in the same manner as in Example 13 except that the Comparative Compound 1 was used as a hole transporting material instead of the Compound H1.

In addition, in the same manner as in Example 1, the luminescent color of the resultant organic EL device was observed, and the driving voltage of the device and the half lifetime of its light emission when the device was driven with a DC constant current at an initial luminance of 5,000 cd/m² and room temperature was measured. Table 1 shows the results.

TABLE 1

|  |  | Hole transporting material | Luminescent color | Driving voltage (V) | Half lifetime (Hour) |
|---|---|---|---|---|---|
| Example | 1 | H1 | Blue | 6.8 | 390 |
|  | 2 | H2 | Blue | 6.8 | 370 |
|  | 3 | H3 | Blue | 6.8 | 420 |
|  | 4 | H4 | Blue | 7.0 | 390 |
|  | 5 | H17 | Blue | 7.0 | 410 |
|  | 6 | H18 | Blue | 7.0 | 370 |
|  | 7 | H29 | Blue | 6.8 | 380 |
|  | 8 | H30 | Blue | 6.8 | 420 |
|  | 9 | H31 | Blue | 6.8 | 400 |
|  | 10 | H32 | Blue | 6.8 | 370 |
|  | 11 | H5 | Blue | 6.8 | 380 |
|  | 12 | H6 | Blue | 6.8 | 370 |
|  | 13 | H7 | Blue | 6.9 | 370 |
|  | 14 | H8 | Blue | 7.0 | 370 |
|  | 15 | H9 | Blue | 6.7 | 380 |
|  | 16 | H10 | Blue | 6.7 | 400 |
|  | 17 | H11 | Blue | 6.8 | 400 |
|  | 18 | H12 | Blue | 6.9 | 400 |
|  | 19 | H35 | Blue | 6.8 | 350 |
|  | 20 | H36 | Blue | 6.8 | 360 |
|  | 21 | H37 | Blue | 6.7 | 360 |
|  | 22 | H38 | Blue | 6.8 | 350 |
|  | 23 | H39 | Blue | 6.7 | 360 |
|  | 24 | H40 | Blue | 6.8 | 340 |
|  | 25 | H41 | Blue | 6.7 | 340 |
|  | 26 | H42 | Blue | 7.0 | 320 |
|  | 27 | H43 | Blue | 6.6 | 400 |
|  | 28 | H44 | Blue | 6.6 | 400 |
|  | 29 | H49 | Blue | 6.8 | 380 |
|  | 30 | H1 | Blue | 6.9 | 380 |
|  | 31 | H1 | Blue | 6.5 | 370 |
|  | 32 | H1 | Blue | 6.5 | 310 |
| Comparative Example | 1 | Comparative Compound 1 | Blue | 7.8 | 150 |
|  | 2 | Comparative Compound 2 | Blue | 6.8 | 150 |
|  | 3 | Comparative Compound 3 | Blue | 6.7 | 120 |
|  | 4 | Comparative Compound 4 | Blue | 7.0 | 80 |
|  | 5 | Comparative Compound 5 | Blue | 7.9 | 90 |
|  | 6 | Comparative Compound 1 | Blue | 7.9 | 120 |
|  | 7 | Comparative Compound 1 | Blue | 7.2 | 140 |
|  | 8 | Comparative Compound 1 | Blue | 7.2 | 80 |

As is apparent from the results of Table 1, the organic EL device of each of Examples 1 to 32 using the aromatic amine derivative of the present invention has low driving voltage and a long half lifetime as compared with the organic EL device of each of Comparative Examples 1 to 8 using the aromatic amine derivative of Comparative Compounds 1 to 5.

INDUSTRIAL APPLICABILITY

As described above in detail, the molecules of the aromatic amine derivative of the present invention hardly crystallize, and the incorporation of the derivative into an organic thin-film layer improves a yield upon production of an organic EL device and can realize an organic EL device having low driving voltage and a long lifetime. Accordingly, the derivative is extremely useful as an organic EL device having high practicality.

The invention claimed is:

1. An aromatic amine derivative represented by formula (9):

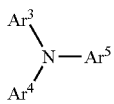

(9)

wherein:

Ar³ is a substituent A represented by formula (3) or formula (4);

Ar⁴ is a substituent B represented by formula (1);

Ar⁵ is a substituted or unsubstituted aryl group having 6 to 25 ring carbon atoms;

the substituent A and the substituent B are different from each other in a position at which L¹ or L³ is bonded to a carbazole structure;

411

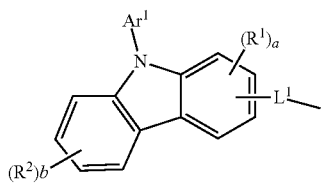

(1)

wherein:

L¹ is a substituted or unsubstituted arylene group having 6 to 25 ring carbon atoms;

a substituent which L¹ may have is a linear or branched alkyl group having 1 to 15 carbon atoms, a cycloalkyl group having 3 to 15 ring carbon atoms, a trialkylsilyl group having linear or branched alkyl groups each having 1 to 15 carbon atoms, a triarylsilyl group having aryl groups each having 6 to 25 ring carbon atoms, an alkylarylsilyl group having a linear or branched alkyl group having 1 to 15 carbon atoms and an aryl group having 6 to 25 ring carbon atoms, an aryl group having 6 to 25 ring carbon atoms, a halogen atom, or a cyano group;

Ar¹ is a substituted or unsubstituted aryl group having 6 to 25 ring carbon atoms;

a substituent which Ar¹ may have is a linear or branched alkyl group having 1 to 15 carbon atoms, a cycloalkyl group having 3 to 15 ring carbon atoms, a trialkylsilyl group having linear or branched alkyl groups each having 1 to 15 carbon atoms, a triarylsilyl group having aryl groups each having 6 to 25 ring carbon atoms, an alkylarylsilyl group having a linear or branched alkyl group having 1 to 15 carbon atoms and an aryl group having 6 to 25 ring carbon atoms, an aryl group having 6 to 25 ring carbon atoms, a halogen atom, or a cyano group;

a is an integer of 0 to 3 and b is an integer of 0 to 4; and

R¹ and R² are each independently a linear or branched alkyl group having 1 to 15 carbon atoms, a cycloalkyl group having 3 to 15 ring carbon atoms, a trialkylsilyl group having linear or branched alkyl groups each having 1 to 15 carbon atoms, a triarylsilyl group having aryl groups each having 6 to 25 ring carbon atoms, an alkylarylsilyl group having a linear or branched alkyl group having 1 to 15 carbon atoms and an aryl group having 6 to 25 ring carbon atoms, an aryl group having 6 to 25 ring carbon atoms, a halogen atom, or a cyano group, and a plurality of R¹'s to R²'s adjacent to each other may be bonded to each other to form a saturated or unsaturated, divalent group that forms a ring;

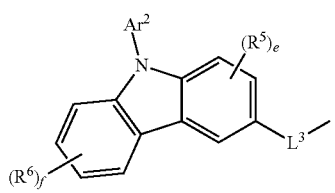

(3)

412
-continued

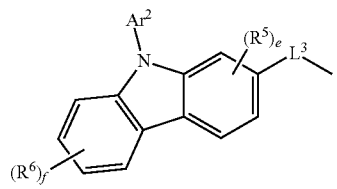

(4)

wherein:

L³ is defined the same as L¹;

Ar² is defined the same as Ar¹;

R⁵ and R⁶ are defined the same as R¹ and R²;

e is an integer of 0 to 3; and f is an integer of 0 to 4.

2. The aromatic amine derivative according to claim 1, wherein the substituted or unsubstituted aryl group having 6 to 25 ring carbon atoms for Ar⁵ is selected from the group consisting of a phenyl group, a 2-methylphenyl group, a 3-methylphenyl group, a 4-methylphenyl group, a 4-ethylphenyl group, a biphenyl group, a 4-methylbiphenyl group, a 4-ethylbiphenyl group, a 4-cyclohexylbiphenyl group, an anthracenyl group, a naphthacenyl group, a terphenyl group, a triphenylyl group, a 3,5-dichlorophenylyl group, a naphthyl group, a 5-methylnaphthyl group, a phenanthryl group, a chrysenyl group, a benzophenanthryl group, a terphenyl group, a benzanthranyl group, a benzochrysenyl group, a pentacenyl group, a picenyl group, a pentaphenyl group, a pyrenyl group, a benzopyrenyl group, a chrysenyl group, a fluorenyl group, a 9,9-dimethylfluorenyl group, an indenyl group, an acenaphthylenyl group, a fluoranthenyl group, and a perylenyl group.

3. The aromatic amine derivative according to claim 1, wherein L¹ is represented by formula (5):

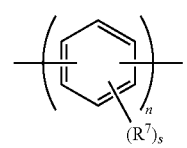

(5)

wherein:

R⁷ is a linear or branched alkyl group having 1 to 15 carbon atoms, a cycloalkyl group having 3 to 15 ring carbon atoms, a trialkylsilyl group having linear or branched alkyl groups each having 1 to 15 carbon atoms, a triarylsilyl group having aryl groups each having 6 to 25 ring carbon atoms, an alkylarylsilyl group having a linear or branched alkyl group having 1 to 15 carbon atoms and an aryl group having 6 to 25 ring carbon atoms, an aryl group having 6 to 25 ring carbon atoms, a halogen atom, or a cyano group, and a plurality of R⁷'s adjacent to each other may be bonded to each other to form a ring;

n and s are each independently an integer of 0 to 4; and when n is 2 to 4, R⁷'s on different benzene rings may be identical to or different from each other, and respective R⁷'s present on benzene rings adjacent to each other may be bonded to each other to form a ring.

4. The aromatic amine derivative according to claim 1, wherein $L^1$ is represented by any one of formulae (6) to (8):

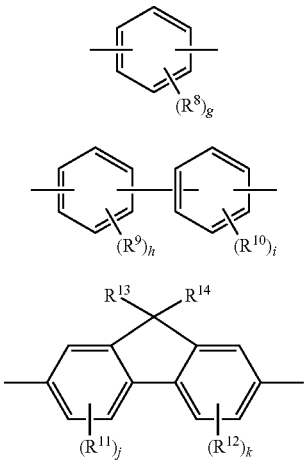

wherein:
$R^8$ to $R^{12}$ are each independently a linear or branched alkyl group having 1 to 15 carbon atoms, a cycloalkyl group having 3 to 15 ring carbon atoms, a trialkylsilyl group having linear or branched alkyl groups each having 1 to 15 carbon atoms, a triarylsilyl group having aryl groups each having 6 to 25 ring carbon atoms, an alkylarylsilyl group having a linear or branched alkyl group having 1 to 15 carbon atoms and an aryl group having 6 to 25 ring carbon atoms, an aryl group having 6 to 25 ring carbon atoms, a halogen atom, or a cyano group, and a plurality of $R^8$'s to $R^{12}$'s adjacent to each other may be bonded to each other to form a saturated or unsaturated ring;

$R^{13}$ and $R^{14}$ are each independently a linear or branched alkyl group having 1 to 15 carbon atoms or a cycloalkyl group having 3 to 15 ring carbon atoms; and g, h, and i are each independently an integer of 0 to 4, and j and k are each independently an integer of 0 to 3.

5. The aromatic amine derivative according to claim 1, wherein:
$Ar^5$ is a substituted or unsubstituted aryl group represented by formula (14):

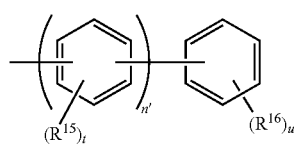

wherein:
$R^{15}$ and $R^{16}$ are each independently a halogen atom, a linear or branched alkyl group having 1 to 15 carbon atoms, a linear or branched alkenyl group having 2 to 15 carbon atoms, an aryl group having 6 to 25 ring carbon atoms, or a heteroaryl group having 5 to 25 ring atoms, a plurality of $R^{15}$'s or $R^{16}$'s adjacent to each other, or $R^{15}$ and $R^{16}$ may be bonded to each other to form a ring; and n' is an integer of 0 to 3, t is an integer of 0 to 4, and u is an integer of 0 to 5.

6. The aromatic amine derivative according to claim 1, wherein:
$Ar^5$ is a substituted or unsubstituted aryl group represented by formula (15):

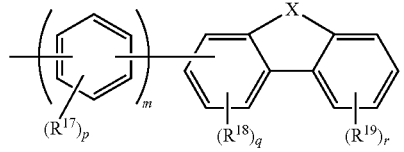

wherein:
X is an oxygen atom or a sulfur atom;
$R^{17}$, $R^{18}$, and $R^{19}$ are each independently a linear or branched alkyl group having 1 to 15 carbon atoms, a linear or branched alkenyl group having 2 to 15 carbon atoms, a cycloalkyl group having 3 to 15 ring carbon atoms, an aryl group having 6 to 25 ring carbon atoms, a heteroaryl group having 5 to 25 ring atoms, a triarylalkyl group having aryl groups each having 6 to 25 ring carbon atoms, a trialkylsilyl group having alkyl groups each having 1 to 15 carbon atoms, a triarylsilyl group having aryl groups each having 6 to 25 ring carbon atoms, an alkylarylsilyl group having an alkyl group having 1 to 15 carbon atoms and an aryl group having 6 to 25 ring carbon atoms, a halogen atom, or a cyano group, and a plurality of $R^{17}$'s, $R^{18}$'s, or $R^{19}$'s adjacent to each other, or $R^{18}$ and $R^{19}$ may be bonded to each other to form a ring;

m is an integer of 1 to 4, and when m is 2 to 4, $R^{17}$'s on different benzene rings may be identical to or different from each other, and respective $R^{17}$'s present on benzene rings adjacent to each other may be bonded to each other to form a ring; and q is an integer of 0 to 3, r and p are each independently an integer of 0 to 4, and when m is 2 to 4, p's that specify the numbers of $R^{17}$'s on the different benzene rings may have the same value or may have different values.

7. The aromatic amine derivative according to claim 6, wherein formula (15) is represented by formula (16):

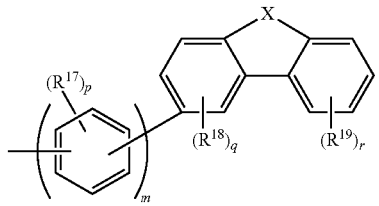

wherein X, $R^{17}$ to $R^{19}$, m, p, q, and r are the same as those of formula (15).

8. A material for an organic electroluminescence device comprising the aromatic amine derivative according to claim 1.

9. A hole transporting material for an organic electroluminescence device comprising the aromatic amine derivative according to claim 1.

10. An organic electroluminescence device comprising an organic thin-film layer formed of one or more layers including at least a light emitting layer, the organic thin-film layer being interposed between a cathode and an anode, wherein at least one layer of the organic thin-film layer comprises the aromatic amine derivative according to claim 1.

11. The organic electroluminescence device according to claim 10, comprising a hole transporting layer and/or a hole injecting layer in the organic thin-film layer, wherein the hole transporting layer and/or the hole injecting layer comprises the aromatic amine derivative.

12. The organic electroluminescence device according to claim 10, wherein the light emitting layer comprises a styrylamine compound and/or an arylamine compound.

13. The organic electroluminescence device according to claim 10, comprising at least an electron transporting layer in the organic thin-film layer, wherein the electron transporting layer comprises a nitrogen-containing heterocyclic derivative represented by any one of formulae (21) to (23):

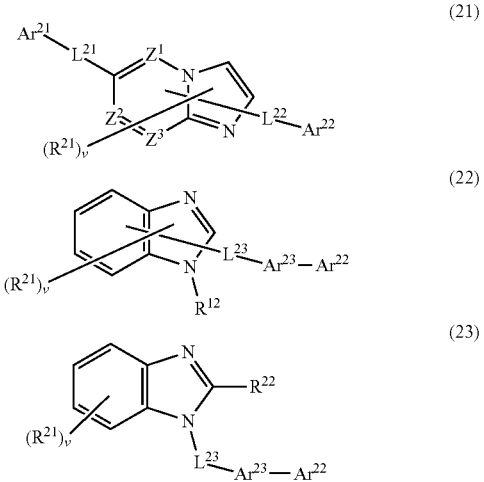

wherein:
$Z^1$, $Z^2$, and $Z^3$ are each independently a nitrogen atom or a carbon atom;

$R^{12}$, $R^{21}$ and $R^{22}$ are each independently a substituted or unsubstituted aryl group having 6 to 50 carbon atoms, a substituted or unsubstituted heteroaryl group having 3 to 50 carbon atoms, or an alkyl group having 1 to 20 carbon atoms, which may be substituted by a halogen atom or an alkoxy group having 1 to 20 carbon atoms;

v is an integer of 0 to 5, and when v is an integer of 2 or more, a plurality of $R^{21}$'s may be identical to or different from each other, and a plurality of $R^{21}$'s adjacent to each other may be bonded to each other to form a substituted or unsubstituted aromatic hydrocarbon ring;

$Ar^{21}$ is a substituted or unsubstituted aryl group having 6 to 50 carbon atoms or a substituted or unsubstituted heteroaryl group having 3 to 50 carbon atoms;

$Ar^{22}$ is a hydrogen atom, an alkyl group having 1 to 20 carbon atoms, an alkyl group having 1 to 20 carbon atoms and substituted with a halogen atom, an alkoxy group having 1 to 20 carbon atoms, a substituted or unsubstituted aryl group having 6 to 50 carbon atoms, or a substituted or unsubstituted heteroaryl group having 3 to 50 carbon atoms, provided that one of $Ar^{21}$ and $Ar^{22}$ is a substituted or unsubstituted fused ring group having 10 to 50 carbon atoms or a substituted or unsubstituted fused heterocyclic ring group having 9 to 50 ring atoms;

$Ar^{23}$ is a substituted or unsubstituted arylene group having 6 to 50 carbon atoms or a substituted or unsubstituted heteroarylene group having 3 to 50 carbon atoms; and $L^{21}$, $L^{22}$, and $L^{23}$ are each independently a single bond, a substituted or unsubstituted arylene group having 6 to 50 carbon atoms, a substituted or unsubstituted fused heterocyclic ring group having 9 to 50 ring atoms, or a substituted or unsubstituted fluorenylene group.

14. The organic electroluminescence device according to claim 11, wherein a layer containing an acceptor material is joined to the hole transporting layer and/or the hole injecting layer.

* * * * *